(12) United States Patent
Tabas et al.

(10) Patent No.: US 9,771,430 B2
(45) Date of Patent: Sep. 26, 2017

(54) METHOD OF TREATING A METABOLIC DISORDER INDUCED BY OBESITY IN A SUBJECT IN NEED THEREOF BY ADMINISTERING MK2/3 INHIBITORS

(71) Applicant: THE TRUSTEES OF COLUMBIA UNIVERSITY IN THE CITY OF NEW YORK, New York, NY (US)

(72) Inventors: Ira Tabas, New City, NY (US); Lale Ozcan, Edgewater, NJ (US)

(73) Assignee: THE TRUSTEES OF COLUMBIA UNIVERSITY IN THE CITY OF NEW YORK, New York, NY (US)

(*) Notice: Subject to any disclaimer, the term of this patent is extended or adjusted under 35 U.S.C. 154(b) by 0 days.

(21) Appl. No.: 14/197,173

(22) Filed: Mar. 4, 2014

(65) Prior Publication Data

US 2014/0314789 A1    Oct. 23, 2014

Related U.S. Application Data

(63) Continuation-in-part of application No. PCT/US2012/053552, filed on Aug. 31, 2012.

(60) Provisional application No. 61/676,091, filed on Jul. 26, 2012, provisional application No. 61/676,152, filed on Jul. 26, 2012, provisional application No. 61/621,407, filed on Apr. 6, 2012, provisional application No. 61/618,551, filed on Mar. 30, 2012, provisional application No. 61/530,851, filed on Sep. 2, 2011.

(51) Int. Cl.
| | |
|---|---|
| *A61K 31/00* | (2006.01) |
| *C12N 9/99* | (2006.01) |
| *C07K 16/40* | (2006.01) |
| *A01K 67/027* | (2006.01) |
| *C07K 14/705* | (2006.01) |
| *C12N 9/12* | (2006.01) |
| *A61K 31/47* | (2006.01) |
| *A61K 31/472* | (2006.01) |
| *C12N 15/113* | (2010.01) |
| *G01N 33/50* | (2006.01) |

(52) U.S. Cl.
CPC .......... *C07K 16/40* (2013.01); *A01K 67/0275* (2013.01); *A61K 31/47* (2013.01); *A61K 31/472* (2013.01); *C07K 14/705* (2013.01); *C12N 9/1205* (2013.01); *C12N 15/1137* (2013.01); *G01N 33/5023* (2013.01); *A01K 2207/05* (2013.01); *A01K 2207/25* (2013.01); *A01K 2217/075* (2013.01); *A01K 2217/15* (2013.01); *A01K 2227/105* (2013.01); *A01K 2267/0362* (2013.01); *G01N 2333/91215* (2013.01); *G01N 2500/10* (2013.01); *G01N 2800/04* (2013.01)

(58) Field of Classification Search
CPC ...................................................... C07K 16/40
See application file for complete search history.

(56) References Cited

U.S. PATENT DOCUMENTS

| | | | |
|---|---|---|---|
| 5,096,815 | A | 3/1992 | Ladner et al. |
| 5,198,346 | A | 3/1993 | Ladner et al. |
| 5,223,409 | A | 6/1993 | Ladner et al. |
| 5,283,317 | A | 2/1994 | Saifer et al. |
| 5,386,019 | A | 1/1995 | Danishefsky et al. |
| 5,712,171 | A | 1/1998 | Zambias et al. |
| 6,828,327 | B2 | 12/2004 | Kuo et al. |
| 7,205,298 | B2 | 4/2007 | Kuo et al. |
| 7,294,504 | B1 | 11/2007 | Wang |
| 7,422,896 | B1 | 9/2008 | Wang |
| 7,989,472 | B2 | 8/2011 | Kim et al. |
| 8,039,484 | B2 | 10/2011 | Ge et al. |
| 8,071,143 | B2 | 12/2011 | Hayes et al. |
| 8,143,269 | B2 | 3/2012 | Whitten et al. |
| 2002/0173478 | A1 | 11/2002 | Gewirtz |
| 2003/0079235 | A1 | 4/2003 | Craig et al. |
| 2004/0018176 | A1 | 1/2004 | Tolentino et al. |
| 2004/0086973 | A1 | 5/2004 | Duecker |

(Continued)

FOREIGN PATENT DOCUMENTS

| | | |
|---|---|---|
| CN | 101506208 A | 8/2009 |
| EP | 1815867 A1 | 8/2007 |

(Continued)

OTHER PUBLICATIONS

Fyhrquist et al., 2010, J. Investig, Dermatol., 130: 342-344.*

(Continued)

*Primary Examiner* — Gyan Chandra
(74) *Attorney, Agent, or Firm* — Wilmer Cutler Pickering Hale and Dorr LLP

(57) ABSTRACT

The present invention relates to methods of treating or preventing a metabolic disorder in a subject, methods of treating or preventing coronary artery disease in a subject with a metabolic disorder, as well as methods of reducing hepatic glucose production in a subject. Such methods include, but are not limited to, the administration to the subject of inhibitors or activators of CaMKII, IP3Rs, calcineurin, p38, MK2/3, HDAC4, Dach1, Dach2, or any combination thereof. The invention also provides methods of identifying a compound that inhibits the activity of CaMKII, IP3Rs, calcineurin, p38, MK2/3, HDAC4, Dach1 or Dach2, or reduces the activity and/or activation of CaMKII, IP3Rs, calcineurin, p38, MK2/3, HDAC4, Dach1 or Dach, or activates CaMKII, IP3Rs, calcineurin, p38, MK2/3, HDAC4, Dach1 or Dach2.

7 Claims, 256 Drawing Sheets
(104 of 256 Drawing Sheet(s) Filed in Color)

(56) References Cited

U.S. PATENT DOCUMENTS

| | | |
|---|---|---|
| 2004/0127511 A1 | 7/2004 | Anderson et al. |
| 2004/0171659 A1* | 9/2004 | Medicherla ........ A61K 31/4439 |
| | | 514/369 |
| 2007/0072204 A1 | 3/2007 | Hannon et al. |
| 2007/0298999 A1 | 12/2007 | Wang |
| 2008/0255121 A1 | 10/2008 | Tagashira et al. |
| 2008/0312313 A1 | 12/2008 | Carballido Herrera et al. |
| 2009/0099178 A1 | 4/2009 | Bhagwat et al. |
| 2009/0156523 A1 | 6/2009 | Cho et al. |
| 2010/0056494 A1 | 3/2010 | Winzeler et al. |
| 2010/0069502 A1 | 3/2010 | Cohen |
| 2010/0113563 A1 | 5/2010 | Wang |
| 2010/0285033 A1 | 11/2010 | Bayer |

FOREIGN PATENT DOCUMENTS

| | | |
|---|---|---|
| WO | WO-91/05058 | 4/1991 |
| WO | WO-93/20242 | 10/1993 |
| WO | WO-94/07507 | 4/1994 |
| WO | WO-94/18318 | 8/1994 |
| WO | WO-95/18972 A1 | 7/1995 |
| WO | WO-96/22529 A1 | 7/1996 |
| WO | WO-99/07409 | 2/1999 |
| WO | WO-99/20624 | 4/1999 |
| WO | WO-99/32619 A1 | 7/1999 |
| WO | WO-00/01846 | 1/2000 |
| WO | WO-00/44895 | 8/2000 |
| WO | WO-00/44914 | 8/2000 |
| WO | WO-01/29058 A1 | 4/2001 |
| WO | WO-01/36646 | 5/2001 |
| WO | WO-2004/053107 | 6/2004 |
| WO | WO-2007008982 A2 | 1/2007 |
| WO | WO-2008/025512 | 3/2008 |
| WO | WO-2011/097079 A1 | 8/2011 |
| WO | WO-2013/033657 A2 | 3/2013 |

OTHER PUBLICATIONS

Mourey et al, JPET 333: 797-807, 2010.*
Abu-Farha, M. et al., "Proteomics analysis of human obesity reveals the epigenetic factor HDAC4 as a potential target for obesity," PLoS One, vol. 8, No. 9, e75342, 17 pages (Sep. 2013).
Accili, D. and Arden, K.C., "FoxOs at the crossroads of cellular metabolism, differentiation, and transformation," Cell, vol. 117, pp. 421-426 (May 14, 2004).
Achard, C. S. and Laybutt, D. R., "Lipid-induced endoplasmic reticulum stress in liver cells results in two distinct outcomes: adaptation with enhanced insulin signaling or insulin resistance," Diabetes—Insulin—Glucagon—Gastrointestinal, Endocrinology, vol. 153, No. 5, pp. 2164-2177 (May 2012).
Akagi, K. et al., "Cre-mediated somatic site-specific recombination in mice," Nucleic Acids Research, vol. 25, No. 9, pp. 1781-1788 (1997).
Altarejos, J. Y. and Montminy, M., "CREB and the CRTC co-activators: sensors for hormonal and metabolic signals," Nat. Rev. Mol. Cell Biol., vol. 12, No. 3, pp. 141-151, 27 pages (Mar. 2011).
Ang, E. S. et al., "Calcium/calmodulin-dependent kinase activity is required for efficient induction of osteoclast differentiation and bone resorption by receptor activator of nuclear factor kappa B ligand (RANKL)," Journal of Cellular Physiology, vol. 212, No. 3, pp. 787-795 (Sep. 2007).
Asada, S. et al., "Mitogen-activated protein kinases, Erk and p38, phosphorylate and regulate Foxo1," Cellular Signaling, vol. 19, No. 3, pp. 519-527 (Mar. 2007).
Asim, R. et al., "Suppressive effects of black seed oil on ovalbumin induced acute lung remodeling in E3 rats," Swiss Med. Wkly., vol. 140, No. w13128, pp. 1-7 (2010).
Ayala, J. E. et al., "Conservation of an insulin response unit between mouse and human glucose-6-phosphatase catalytic subunit gene promoters: transcription factor FKHR binds the insulin response sequence," Diabetes, vol. 48, pp. 1885-1889 (Sep. 1999).

Backs, J. et al., "CaM kinase II selectively signals to histone deacetylase 4 during cardiomyocyte hypertrophy," The Journal of Clinical Investigation, vol. 116, No. 7, pp. 1853-1864 (Jul. 2006).
Backs, J. et al., "The delta isoform of CaM kinase II is required for pathological cardiac hypertrophy and remodeling after pressure overload," Proc. Natl. Acad. Sci. USA, vol. 106, No. 7, pp. 2342-2347 (Feb. 17, 2009).
Backs, J. et al., "The gamma isoform of CaM kinase II controls mouse egg activation by regulating cell cycle resumption," Proc. Natl. Acad. Sci. USA, vol. 107, No. 1, pp. 81-86 (Jan. 5, 2010).
Barthel, A. et al., "Differential regulation of endogenous glucose-6-phosphatase and phosphoenolpyruvate carboxykinase gene expression by the forkhead transcription factor FKHR in H4IIE-hepatoma cells," Biochemical and Biophysical Research Communications, vol. 285, No. 4, pp. 897-902 (Jul. 27, 2001).
Bass, Brenda L., "The short answer," Nature, vol. 411, pp. 428-429 (May 24, 2001).
Beausoleil, S.A. et al., "A probability-based approach for high-throughput protein phosphorylation analysis and site localization," Nature Biotechnology, vol. 24, No. 10, pp. 1285-1292 (Oct. 2006).
Bird, G. S. et al., "Sulfhydryl reagents and cAMP-dependent kinase increase the sensitivity of the inositol 1,4,5- trisphosphate receptor in hepatocytes," The Journal of Biological Chemistry, vol. 268, No. 24, pp. 17917-17923 (Aug. 25, 1993).
Blanquet, P. R., "Identification of two persistently activated neurotrophin-regulated pathways in rat hippocampus," Neuroscience, vol. 95, No. 3, pp. 705-719 (Dec. 2000).
Bligh, E. G. and Dyer, W. J., "A rapid method of total lipid extraction and purification," Canadian Journal of Biochemistry and Physiology, vol. 37, pp. 911-917 (1959).
Blondelle, S. E. and Houghten, R. A., "Novel antimicrobial compounds identified using synthetic combinatorial library technology," TIBTECH, vol. 14, pp. 60-65 (Feb. 1996).
Bock, L. C. et al., "Selection of single-stranded DNA molecules that bind and inhibit human thrombin," Nature, vol. 355, pp. 564-566 (Feb. 1992).
Bomfeldt, K. E. and Tabas, I., "Insulin resistance, hyperglycemia, and atherosclerosis," Cell Metabolism, vol. 14, pp. 575-585 (Nov. 2, 2011).
Brenner, S. and Lerner, R. A., "Encoded combinatorial chemistry," Proc. Natl. Acad. Sci. USA, vol. 89, pp. 5381-5383 (Jun. 1992).
Bromati, C. R. et al., "UPR induces transient burst of apoptosis in islets of early lactating rats through reduced AKT phosphorylation via ATF4/CHOP stimulation of TRB3 expression," Am. J. Physiol. Regul. Integr. Comp. Physiol., vol. 300, pp. R92-R100 (2011).
Brown, M. S. and Goldstein, J. L., "Selective versus total insulin resistance: a pathogenic paradox," Cell Metabolism, vol. 7, pp. 95-96 (Feb. 2008).
Brozinick, J. T. et al., "Defective signaling through Akt-2 and -3 but not Akt-1 in insulin-resistant human skeletal muscle: potential role in insulin resistance," Diabetes, vol. 52, pp. 935-941 (Apr. 2003).
Brunet, A. et al., "Akt promotes cell survival by phosphorylating and inhibiting a Forkhead transcription factor," Cell, vol. 96, No. 6, pp. 857-868 (Mar. 19, 1999).
Buchholz, M. and Ellenrieder, V., "An emerging role for Ca2+/calcineurin/NFAT signaling in cancerogenesis," Cell Cycle, vol. 6, No. 1, pp. 16-19 (Jan. 2007).
Bunin, B. A. et al., "The combinatorial synthesis and chemical and biological evaluation of a 1,4-benzodiazepine library," Proc. Natl. Acad. Sci., vol. 91, pp. 4708-4712 (May 1994).
Burgess, S. C. et al., "Cytosolic phosphoenolpyruvate carboxykinase does not solely control the rate of hepatic gluconeogenesis in the intact mouse liver," Cell Metab., vol. 5, No. 4, pp. 313-320, 15 pages (Apr. 2007).
Bygrave, F. L. and Benedetti, A., "Calcium: its modulation in liver by cross-talk between the actions of glucagon and calcium-mobilizing agonists," Biochem. J., vol. 296, Part 1, pp. 1-14 (1993).
Cantin, G. T. et al., "Optimizing TiO2-based phosphopeptide enrichment for automated multidimensional liquid chromatography coupled to tandem mass spectrometry," Anal. Chem., vol. 79, No. 12, pp. 4666-4673, 18 pages (Jun. 2007).

(56) References Cited

OTHER PUBLICATIONS

Cao, W. et al., "p38 Mitogen-activated protein kinase plays a stimulatory role in hepatic gluconeogenesis," J. Biol. Chem., vol. 280, No. 52, pp. 42731-42737 (Dec. 30, 2005).
Chiacchiera, F. and Simone, C., "The AMPK-FoxO3A axis as a target for cancer treatment," Cell Cycle, vol. 9, No. 6, pp. 1091-1096 (Mar. 15, 2010).
Cho, H. et al., "Insulin resistance and a diabetes mellitus-like syndrome in mice lacking the protein kinase Akt2 (PKB beta)," Science, vol. 292, pp. 1728-1731 (Jun. 1, 2001).
Christian, R. B. et al., "Simplified Methods for Construction, Assessment and Rapid Screening of Peptide Libraries in Bacteriophage," J. Mol. Biol., vol. 227, pp. 711-718 (1992).
Clyne, C. D. et al., "The effects of KN62, a Ca2+/calmodulin-dependent protein kinase II inhibitor, on adrenocortical cell aldosterone production," Endocrine Research, vol. 21, No. 1-2, pp. 259-265 (1995).
Cociorva, D. et al., "Validation of tandem mass spectrometry database search results using DTASelect, Current Protocols in Bioinformatics," Chapter 13, Unit 13.4, 14 pages (Jan. 1, 2007).
Corcoran, C. A. et al., "Genotoxic and endoplasmic reticulum stresses differentially regulate TRB3 expression," Cancer Biology & Therapy, vol. 4, No. 10, pp. 1063-1067, 6 pages (Oct. 2005).
Couchonnal, L. F. and Anderson, M. E., "The role of calmodulin kinase II in myocardial physiology and disease," Physiology, vol. 23, pp. 151-159 (2008).
Cruz, L. N. et al., "Regulation of multidrug resistance-associated protein 2 by calcium signaling in mouse liver," Hepatology, vol. 52, No. 1, pp. 327-337, 19 pages (Jul. 2010).
Cuadrado, A. and Nebreda, A. R., "Mechanisms and functions of p38 MAPK signaling," Biochem. J., vol. 429, No. 3, pp. 403-417 (Aug. 1, 2010).
Cunha, D. A. et al., "Death protein 5 and p53-upregulated modulator of apoptosis mediate the endoplasmic reticulum stress-mitochondrial dialog triggering lipotoxic rodent and human beta-cell apoptosis," Diabetes, vol. 61, pp. 2763-2775 (Nov. 2012).
Dallas, A. and Vlassov, A. V., "RNAi: A novel antisense technology and its therapeutic potential," Med. Sci. Monit., vol. 12, No. 4, pp. RA67-RA74, 9 pages (2006).
Dash, P. K. et al., "cAMP response element-binding protein is activated by Ca2+/calmodulin—as well as cAMP-dependent protein kinase," Proc. Natl. Acad. Sci. USA, vol. 88, pp. 5061-5065 (Jun. 1991).
Davis, R. J. et al., "Dach1 mutant mice bear no gross abnormalities in eye, limb, and brain development and exhibit postnatal lethality," Molecular and Cellular Biology, vol. 21, No. 5, pp. 1484-1490 (Mar. 2001).
Davis, R. J. et al., "Mouse Dach2 mutants do not exhibit gross defects in eye development or brain function," Genesis, vol. 44, No. 2, pp. 84-92 (Feb. 2006).
Delahunty, C. and Yates, J. R., III, "Protein identification using 2D-LC-MS/MS," Methods, vol. 35, No. 3, pp. 248-255 (Mar. 2005).
Dentin, R. et al., "Insulin modulates gluconeogenesis by inhibition of the coactivator TORC2," Nature, vol. 449, No. 7160, pp. 366-369, 5 pages (Sep. 20, 2007).
Devlin, J. J. et al., "Random Peptide Libraries: A Source of Specific Protein Binding Molecules," Science, vol. 249, pp. 404-406 (Jul. 27, 1990).
Du, K. et al., "TRB3: a tribbles homolog that inhibits Akt/PKB activation by insulin in liver," Science, vol. 300, pp. 1574-1577 (Jun. 6, 2003).
Elbashir, S. M. et al., "Duplexes of 21-nucleotide RNAs mediate RNA interference in cultured mammalian cells," Nature, vol. 411, pp. 494-498 (May 24, 2001).
Ellington, A. D. and Szostak, J. W., "Selection in vitro of single-stranded DNA molecules that fold into specific ligand-binding structures," Nature, vol. 355, pp. 850-852 (Feb. 27, 1992).
Eng, J. K. et al., "An approach to correlate tandem mass spectral data of peptides with amino acid sequences in a protein database," J. Am. Soc. Mass Spectrometry, vol. 5, pp. 976-989 (1994).
Engel, F. B. et al., "p38 MAP kinase inhibition enables proliferation of adult mammalian cardiomyocytes," Genes Dev., vol. 19, pp. 1175-1187 (2005).
Erb, E. et al., "Recursive deconvolution of combinatorial chemical libraries," Proc. Natl. Acad. Sci. USA, vol. 91, pp. 11422-11426 (Nov. 1994).
Erickson, J. R. et al., "Diabetic hyperglycaemia activates CaMKII and arrhythmias by O-linked glycosylation," Nature, vol. 502, 13 pages (Oct. 17, 2013).
Essers, M. A. et al., "FOXO transcription factor activation by oxidative stress mediated by the small GTPase Ral and JNK," The EMBO J., vol. 23, pp. 4802-4812 (2004).
European Search Report issued by the European Patent Office for Application No. 12829035.0 dated Jun. 1, 2015 (8 pages).
Ferris, C. D. et al., "Inositol trisphosphate receptor: phosphorylation by protein kinase C and calcium calmodulin-dependent protein kinases in reconstituted lipid vesicles," Proc. Natl. Acad. Sci. USA, vol. 88, pp. 2232-2235 (Mar. 1991).
Fodor, S. P. et al., "Light-Directed, Spatially Addressable Parallel Chemical Synthesis," Science, vol. 251, pp. 767-773 (Feb. 15, 1991).
Fowlkes, D. M. et al., "Multipurpose Vectors for Peptide Expression on the M13 Viral Surface," BioTechniques, vol. 13, No. 3, pp. 422-427 (1992).
Frescas, D. et al., "Nuclear trapping of the forkhead transcription factor FoxO1 via Sirt-dependent deacetylation promotes expression of glucogenetic genes," J. Biol. Chem., vol. 280, No. 21 pp. 20589-20595 (May 27, 2005).
Freshney, N. W. et al., "Interleukin-1 activates a novel protein kinase cascade that results in the phosphorylation of Hsp27," Cell vol. 78, No. 6, pp. 1039-1049 (Sep. 23, 1994).
Friedmann, N. and Rasmussen, H., "Calcium, manganese and hepatic gluconeogenesis," Biochim. Biophys. Acta., vol. 222, pp. 41-52 (Oct. 27, 1970).
Fu, S. et al., "Aberrant lipid metabolism disrupts calcium homeostasis causing liver endoplasmic reticulum stress in obesity," Nature, vol. 473, No. 7348, pp. 528-531, 10 pages (May 26, 2011).
Futatsugi, A. et al., "IP3 receptor types 2 and 3 mediate exocrine secretion underlying energy metabolism," Science, vol. 309, No. 5744, pp. 2232-2234 (Sep. 30, 2005).
Fyhrquist, N. et al., "MK2 Signaling: Lessons on Tissue Specificity in Modulation of Inflammation," Journal of Investigative Dermatology, vol. 130, pp. 342-344 (2010).
Gaestel, Matthias, "MAPKAP kinases—MKs—two's company, three's a crowd," Nat. Rev. Mol. Cell. Biol., vol. 7, No. 2, pp. 120-130 (Feb. 2006).
Gallop, M. A. et al., "Applications of Combinatorial Technologies to Drug Discovery. 1. Background and Peptide Combinatorial Libraries," Journal of Medicinal Chemistry, vol. 37, No. 9, pp. 1233-1251 (Apr. 29, 1994).
Greer, E. L. and Brunet, A., "FOXO transcription factors at the interface between longevity and tumor suppression," Oncogene, vol. 24, pp. 7410-7425 (2005).
Gregor, M. F. et al., "Endoplasmic reticulum stress is reduced in tissues of obese subjects after weight loss," Diabetes, vol. 58, pp. 693-700 (Mar. 2009).
Hall, R. K. et al., "The orphan receptors COUP-TF and HNF-4 serve as accessory factors required for induction of phosphoenolpyruvate carboxykinase gene transcription by glucocorticoids," Proc. Natl. Acad. Sci. USA, vol. 92, pp. 412-416 (Jan. 1995).
Hammad, E.-S. F. et al., "Morphological and biochemical observations on hepatic glycogen metabolism in genetically diabetic (db/db) mice," Diabete. Metab., vol. 8, No. 2, pp. 147-153 (Jun. 1982).
Hansen, John Bondo, "Towards selective Kir6.2/SUR1 potassium channel openers, medicinal chemistry and therapeutic perspectives," Curr. Med. Chem., vol. 13, No. 4, pp. 361-376 (2006).
Hansen, L. H. et al., "Glucagon-mediated Ca2+ signaling in BHK cells expressing cloned human glucagon receptors," Am. J. Physiol., vol. 274, pp. C1552-C1562 (1998).
Harano, Y. et al., "Phosphorylation of carnitine palmitoyltransferase and activation by glucagon in isolated rat hepatocytes," FEBS Lett., vol. 188, No. 2, pp. 267-272 (Sep. 1985).

(56) References Cited

OTHER PUBLICATIONS

Hemi, R. et al., "p38 mitogen-activated protein kinase-dependent transactivation of ErbB receptor family: a novel common mechanism for stress-induced IRS-1 serine phosphorylation and insulin resistance," Diabetes, vol. 60, pp. 1134-1145 (Apr. 2011).
Herzig, S. et al., "CREB Regulates Hepatic Gluconeogenesis via the Coactivator PGC-1," Nature, vol. 413, No. 6852, pp. 179-183 (Sep. 13, 2001).
Hogan, P. G. et al., "Transcriptional regulation by calcium, calcineurin, and NFAT," Genes Dev., vol. 17, pp. 2205-2232 (2003).
Houghten, R. A. et al., "Generation and Use of Synthetic Peptide Combinatorial Libraries for Basic Research and Drug Discovery," Nature, vol. 354, pp. 84-86, 5 pages (Nov. 7, 1991).
Houghten, R. A. et al., "The Use of Synthetic Peptide Combinatorial Libraries for the Identification of Bioactive Peptides," Biotechniques, vol. 13, No. 3, pp. 412-421, 12 pages (Sep. 1992).
Huang, X. et al., "A three-step protocol for lead optimization: quick identification of key conformational features and functional groups in the SAR studies of non-ATP competitive MK2 (MAPKAPK2) inhibitors," Bioorg. Med. Chem. Lett., vol. 22, No. 1, pp. 65-70 (Jan. 1, 2012).
Hudson, Peter J., "Recombinant antibody fragments," Curr. Opin. Biotechnol., vol. 9, pp. 395-402 (1998).
International Search Report and Written Opinion issued by the U. S. Patent and Trademark Office as International Searching Authority for International Application No. PCT/US2012/053552 dated Mar. 11, 2013 (15 pages).
Jagavelu, K. et al., "Systemic deficiency of the MAP kinase-activated protein kinase 2 reduces atherosclerosis in hypercholesterolemic mice," Circ. Res. vol. 101, pp. 1104-1112, 18 pages (2007).
Janeway, C. A. et al., "Immunobiology 5th edition: The Immune System in Health and Disease," Garland Publishing, 16 pages—Title, Copyright and Table of Contents only (2001).
Jansson, D. et al., "Glucose controls CREB activity in islet cells via regulated phosphorylation of TORC2," Proc. Natl. Acad. Sci. USA, vol. 105, No. 29, pp. 10161-10166 (Jul. 22, 2008).
Jayawickreme, C. K. et al., "Creation and functional screening of a multi-use peptide library," Proc. Natl. Acad. Sci. USA, vol. 91, pp. 1614-1618 (Mar. 1994).
Kalota, A. et al., "Progress in the Development of Nucleic Acid Therapeutics," Handb. Exp. Pharmacol., vol. 173, pp. 173-196 (2006).
Kase, H. et al., "K-252 compounds, novel and potent inhibitors of protein kinase C and cyclic nucleotide-dependent protein kinases," Biochem. Biophys. Res. Commun., vol. 142, No. 2, pp. 436-440 (Jan. 30, 1987).
Kay, B. K. et al., "An M13 Phage Library Displaying Random 38-Amino-Acid Peptides as a Source of Novel Sequences with Affinity to Selected targets," Gene, vol. 128, pp. 59-65 (1993).
Kerouz, N. J. et al., "Differential regulation of insulin receptor substrates-1 and -2 (IRS-1 and IRS-2) and phosphatidylinositol 3-kinase isoforms in liver and muscle of the obese diabetic (ob/ob) mouse," J. Clin. Invest., vol. 100, No. 12, pp. 3164-3172 (Dec. 1997).
Klover, P. J. and Mooney, R. A., "Hepatocytes: critical for glucose homeostasis," Int. J. Biochem. Cell Biol., vol. 36, No. 5, pp. 753-758 (May 2004).
Konner, A. C. and Bruning, J. C., "Selective insulin and leptin resistance in metabolic disorders," Cell Metab. vol. 16, pp. 144-152 (Aug. 8, 2012).
Kostenko, S. et al., "Physiological roles of mitogen-activated-protein-kinase-activated p38-regulated/activated protein kinase," World Journal of Biological Chemistry, vol. 2, No. 5, pp. 73-89 (May 26, 2011).
Kotlyarov, A. and Gaestal, M., "Is MK2 (mitogen-activated protein kinase-activated protein kinase 2) the key for understanding post-transcriptional regulation of gene expression?," Biochem. Soc. Trans., vol. 30, Part 6, pp. 959-963 (Nov. 2002).
Kraus-Friedmann, N. and Feng, L., "The role of intracellular Ca2+ in the regulation of gluconeogenesis," Metabolism, vol. 45, No. 3, pp. 389-403 (Mar. 1996).
Krook, A. et al., "Insulin-stimulated Akt kinase activity is reduced in skeletal muscle from NIDDM subjects," Diabetes, vol. 47, No. 8, pp. 1281-1286 (Aug. 1998).
Kwok, S. et al., "Genetically encoded probe for fluorescence lifetime imaging of CaMKII activity," Biochem. Biophys. Res. Commun., vol. 369, No. 2, pp. 519-525, 12 pages (May 2, 2008).
Ladiges, W. C. et al., "Pancreatic beta-cell failure and diabetes in mice with a deletion mutation of the endoplasmic reticulum molecular chaperone gene P58IPK," Diabetes, vol. 54, pp. 1074-1081 (Apr. 2005).
Lam, K. S. et al., "A new type of synthetic peptide library for identifying ligand-binding activity," Nature, vol. 354, pp. 82-84 (Nov. 7, 1991).
Leavens, K. F. and Birnbaum, M. J., "Insulin signaling to hepatic lipid metabolism in health and disease," Crit. Rev. Biochem. Mol. Biol., vol. 46, pp. 200-215 (2011).
Lenstra, J. A. et al., "Isolation of sequences from a random-sequence expression library that mimic viral epitopes," Journal of Immunological Methods, vol. 152, pp. 149-157 (1992).
Liang, F. et al., "Increased expression of dachshund homolog 1 in ovarian cancer as a predictor for poor outcome," Int. J. Gynecol. Cancer., vol. 22, No. 3, pp. 386-393 (Mar. 2012).
Lima, A. F. et al., "Acute exercise reduces insulin resistance-induced TRB3 expression and amelioration of the hepatic production of glucose in the liver of diabetic mice," J. Cell. Physiol., vol. 221, pp. 92-97 (Oct. 2009).
Lin, H. V. and Accili, D., "Hormonal regulation of hepatic glucose production in health and disease," Cell Metab., vol. 14, No. 1, pp. 9-19, 20 pages (Jul. 6, 2011).
Liu, H. et al., "A model for random sampling and estimation of relative protein abundance in shotgun proteomics," Anal. Chem., vol. 76, No. 14, pp. 4193-4201 (Jul. 15, 2004).
Liu, P. et al., "A highly efficient recombineering-based method for generating conditional knockout mutations," Genome Research, vol. 13, pp. 476-484 (2003).
Liu, Y. et al., "A fasting inducible switch modulates gluconeogenesis via activator/coactivator exchange," Nature, vol. 456, No. 7219, pp. 269-273, 16 pages (Nov. 13, 2008).
Lu, B. et al., "Automatic validation of phosphopeptide identifications from tandem mass spectra," Anal. Chem., vol. 79, No. 4, pp. 1301-1310, 24 pages (Feb. 15, 2007).
Lutzelburger, M. and Kjems, J., "Strategies to Identify Potential Therapeutic Target Sites in RNA," Handb. Exp. Pharmacol., vol. 173, pp. 243-259 (2006).
MacCoss, M. J. et al., "Shotgun identification of protein modifications from protein complexes and lens tissue," Proc. Natl. Acad. Sci. USA, vol. 99, No. 12, pp. 7900-7905 (Jun. 11, 2002).
Mannhold, Raimund, "Structure-Activity Relationships of KATP Channel Openers," Current Topics in Medicinal Chemistry, vol. 6, No. 10, pp. 1031-1047 (2006).
Marber, M. S. et al., "The p38 mitogen-activated protein kinase pathway-a potential target for intervention in infarction, hypertrophy, and heart failure," J. Mol. Cell Cardiol., vol. 51, No. 4, pp. 485-490, 12 pages (Oct. 2011).
Marques-da-Silva, A. C. et al., "Ca2+ dependence of gluconeogenesis stimulation by glucagon at different cytosolic NAD(+)-NADH redox potentials," Braz. J. Med. Biol. Res., vol. 30, No. 7, pp. 827-836 (Jul. 1997).
Matsumoto, M. et al., "Impaired regulation of hepatic glucose production in mice lacking the forkhead transcription factor Foxo1 in liver," Cell Metabolism, vol. 6, pp. 208-216 (Sep. 2007).
Matsumoto, M. et al., "Role of the insulin receptor substrate 1 and phosphatidylinositol 3-kinase signaling pathway in insulin-induced expression of sterol regulatory element binding protein 1c and glucokinase genes in rat hepatocytes," Diabetes, vol. 51, pp. 1672-1680 (Jun. 2002).
Mattheakis, L. C. et al., "An in vitro polysome display system for identifying ligands from very large peptide libraries," Proc. Natl. Acad. Sci. USA, vol. 91, pp. 9022-9026 (Sep. 1994).

(56) References Cited

OTHER PUBLICATIONS

Maynard, J. and Georgiou, G., "Antibody Engineering," Ann. Rev. Biomed. Eng., vol. 2, pp. 339-376 (2000).

McConnell, H. M. et al., "The Cytosensor Microphysiometer: Biological Applications of Silicon Technology," Science, vol. 257, pp. 1906-1912 (Sep. 25, 1992).

McDonald, W. H. et al., "MS1, MS2, and SQT-three unified, compact, and easily parsed file formats for the storage of shotgun proteomic spectra and identifications," Rapid Commun. Mass Spectrom., vol. 18, No. 18, pp. 2162-2168 (2004).

McManus, M. T. and Sharp, P. A., "Gene silencing in mammals by small interfering RNAs," Nature Review Genetics, vol. 3, pp. 737-747 (Oct. 2002).

Medynski, Dan, "Synthetic Peptide Combinatorial Libraries: Using Applied Molecular Evolution to Accelerate Drug Discovery is Now Within the Reach of Every Lab," BioTechnology, vol. 12, pp. 709-710 (1994).

Mine, T. et al., "Role of calcium fluxes in the action of glucagon on glucose metabolism in rat hepatocytes," Am. J. Physiol., vol. 265, No. 1, pp. G35-G42 (Jul. 1993).

Mosbach, Klaus, "Molecular Imprinting," Trends in Biochem. Sci. (TIBS), vol. 19, No. 9, pp. 9-14 (Jan. 1994).

Naimi, M. et al., "Nuclear forkhead box O1 controls and integrates key signaling pathways in hepatocytes," Endocrinology, vol. 148, No. 5, pp. 2424-2434 (2007).

Nakae, J. et al., "Regulation of insulin action and pancreatic beta-cell function by mutated alleles of the gene encoding forkhead transcription factor Foxo1," Nat. Genet., vol. 32, pp. 245-253 (Oct. 2002).

Nakae, J. et al., "The forkhead transcription factor Foxo1 (Fkhr) confers insulin sensitivity onto glucose-6-phosphatase expression," J. Clin. Invest., vol. 108, No. 9, pp. 1359-1367 (Nov. 2001).

Nodin, B. et al., "Discovery of dachshund 2 protein as a novel biomarker of poor prognosis in epithelial ovarian cancer," J. Ovarian Res., vol. 5, No. 1, pp. 1-10 (2012).

Ohlmeyer, M. H. J. et al., "Complex Synthetic Chemical Libraries Indexed with Molecular Tags," Proc. Natl. Acad. Sci. USA, vol. 90, pp. 10922-10926 (Dec. 1993).

Ohoka, N. et al., "TRB3, a novel ER stress-inducible gene, is induced via ATF4-CHOP pathway and is involved in cell death," The EMBO Journal, vol. 24, pp. 1243-1255 (2005).

Oldenburg, K. R. et al., "Peptide ligands for a sugar-binding protein isolated from a random peptide library," Proc. Natl. Acad. Sci. USA, vol. 89, pp. 5393-5397 (Jun. 1992).

Ostresh, J. M. et al., "'Libraries from libraries': Chemical transformation of combinatorial libraries to extend the range and repertoire of chemical diversity," Proc. Natl. Acad. Sci. USA, vol. 91, pp. 11138-11142 (Nov. 1994).

Ozcan, L. et al., "Calcium Signaling through CaMKII Regulates Hepatic Glucose Production in Fasting and Obesity," Cell Metabolism, vol. 15, No. 5, pp. 739-751 (May 2, 2012).

Ozcan, U. et al., "Endoplasmic reticulum stress links obesity, insulin action, and type 2 diabetes," Science, vol. 306, pp. 457-461 16 pages (Oct. 15, 2004).

Park, S. W. et al., "Sarco(endo)plasmic reticulum Ca2+-ATPase 2b is a major regulator of endoplasmic reticulum stress and glucose homeostasis in obesity," Proc. Natl. Acad. Sci. USA, vol. 107, No. 45, pp. 19320-19325 (Nov. 9, 2010).

Parmley, S. F. and Smith, G. P., "Filamentous fusion phage cloning vectors for the study of epitopes and design of vaccines," Adv. Exp. Med. Biol., vol. 251, pp. 215-218 (1989).

Patterson, R. L. et al., "Inositol 1,4,5-trisphosphate receptors as signal integrators," Annu. Rev. Biochem., vol. 73, pp. 437-465 (2004).

Peng, J. et al., "Evaluation of multidimensional chromatography coupled with tandem mass spectrometry (LC/LC-MS/MS) for large-scale protein analysis: the yeast proteome," J. Proteome. Res., vol. 2, No. 1, pp. 43-50 (2003).

Periasamy, Muthu, "Calcineurin and the heartbeat, an evolving story," J. Mol. Cell Cardiol., vol. 34, No. 3, pp. 259-262 (Mar. 2002).

Petersen, K. F. and Sullivan, J. T., "Effects of a novel glucagon receptor antagonist (Bay 27/9955) on glucagon-stimulated glucose production in humans," Diabetologia, vol. 44, pp. 2018-2024 (2001).

Pfleiderer, P. J. et al., "Modulation of vascular smooth muscle cell migration by calcium/calmodulin-dependent protein kinase II-delta 2," Am. J. Physiol. Cell Physiol., vol. 286, pp. C1238-C1245 (2004).

Pilkis, S. J. and Granner, D. K., "Molecular physiology of the regulation of hepatic gluconeogenesis and glycolysis," Annu. Rev. Physiol., vol. 54, pp. 885-909 (1992).

Puigserver, P. et al., "Insulin-regulated hepatic gluconeogenesis through FOXO1-PGC-1alpha interaction," Nature, vol. 423, No. 6939, pp. 550-555 (May 29, 2003).

Puthanveetil, P. et al., "The increase in cardiac pyruvate dehydrogenase kinase-4 after short-term dexamethasone is controlled by an Akt-p38-forkhead box other factor-1 signaling axis," Endocrinology, vol. 151, pp. 2306-2318 (2010).

Radziuk, J. and Pye, S., "Hepatic glucose uptake, gluconeogenesis and the regulation of glycogen synthesis," Diabetes Metab. Res. Rev., vol. 17, No. 4, pp. 250-272 (Jul.-Aug. 2001).

Raingeaud, J. et al., "MKK3- and MKK6-regulated gene expression is mediated by the p38 mitogen-activated protein kinase signal transduction pathway," Mol. Cell. Biol., vol. 16, No. 3, pp. 1247-1255 (Mar. 1996).

Rebar, E. J. and Pabo, C. O., "Zinc Finger Phage: Affinity Selection of Fingers with New DNA-Binding Specificities," Science, vol. 263, pp. 671-673 (Feb. 4, 1994).

Rhee, J. et al., "Regulation of hepatic fasting response by PPARgamma coactivator-1alpha (PGC-1): requirement for hepatocyte nuclear factor 4alpha in gluconeogenesis," Proc. Natl. Acad. Sci. USA, vol. 100, No. 7, pp. 4012-4017 (Apr. 1, 2003).

Rokita, A. G. and Anderson, M. E., "New therapeutic targets in cardiology: arrhythmias and Ca2+/calmodulin-dependent kinase II (CaMKII)," Circulation, vol. 126, pp. 2125-2139 (2012).

Rouse, J. et al., "A novel kinase cascade triggered by stress and heat shock that stimulates MAPKAP kinase-2 and phosphorylation of the small heat shock proteins," Cell, vol. 78, pp. 1027-1037 (Sep. 23, 1994).

Saad, M. J. et al., "Regulation of insulin receptor substrate-1 in liver and muscle of animal models of insulin resistance," J. Clin. Invest., vol. 90, pp. 1839-1849 (Nov. 1992).

Salmon, S. E. et al., "Discovery of biologically active peptides in random libraries: Solution-phase testing after staged orthogonal release from resin beads," Proc. Natl. Acad. Sci. USA, vol. 90, pp. 11708-11712 (Dec. 1993).

Saltiel, A. R. and Kahn, C. R., "Insulin signaling and the regulation of glucose and lipid metabolism," Nature, vol. 414, No. 6865, pp. 799-806 (Dec. 13, 2001).

Saltiel, Alan R., "New perspectives into the molecular pathogenesis and treatment of type 2 diabetes," Cell, vol. 104, pp. 517-529 (Feb. 23, 2001).

Samuel, V. T. and Shulman, G. I., "Mechanisms for insulin resistance: common threads and missing links," Cell, vol. 148, No. 5, pp. 852-871, 35 pages (Mar. 2, 2012).

Scott, J. K. and Smith, G. P., "Searching for Peptide Ligands with an Epitope Library," Science, vol. 249, No. 4967, pp. 386-390, 6 pages (Jul. 27, 1990).

Screaton, R. A. et al., "The CREB coactivator TORC2 functions as a calcium- and cAMP-sensitive coincidence detector," Cell, vol. 119, pp. 61-74 (Oct. 1, 2004).

Sen, G. L. and Blau, H. M., "A brief history of RNAi: the silence of the genes," The FASEB Journal, vol. 20, pp. 1293-1299 (2006).

Shea, Kenneth J., Molecular Imprinting of Synthetic Network Polymers: The De Novo synthesis of Macromolecular Binding and Catalytic Sites, TRIP, vol. 2, No. 5, pp. 166-173, 9 pages (May 1994).

Sheng, M. et al., "CREB: a Ca(2+)-regulated transcription factor phosphorylated by calmodulin-dependent kinases," Science, vol. 252, No. 5011, pp. 1427-1430 (Jun. 7, 1991).

(56) References Cited

OTHER PUBLICATIONS

Shiryaev, A and Moens, U., "Mitogen-activated protein kinase p38 and MK2, MK3 and MK5: ménage à trois or ménage à quatre?," Cell Signal, vol. 22, No. 8, pp. 1185-1192 (Aug. 2010).

Simon, R. J. et al., "Peptoids: A modular approach to drug discovery," Proc. Natl. Acad. Sci. USA, vol. 89, pp. 9367-9371 (Oct. 1992).

Singer, Harold A., "Ca2+/calmodulin-dependent protein kinase II Function in Vascular Remodeling," J. Physiol., vol. 590, No. 6, pp. 1349-1356 (2012).

Sjolander, S. and Urbaniczky, C., "Integrated fluid handling system for biomolecular interaction analysis," Analytical Chemistry, vol. 63, No. 20, pp. 2338-2345 (1991).

Sorensen, H. et al., "Immunoneutralization of endogenous glucagon reduces hepatic glucose output and improves long-term glycemic control in diabetic ob/ob mice," Diabetes, vol. 55, pp. 2843-2848 (Oct. 2006).

Staddon, J. M. and Hansford, R. G., "Evidence indicating that the glucagon-induced increase in cytoplasmic free Ca2+ concentration in hepatocytes is mediated by an increase in cyclic AMP concentration," Eur. J. Biochem., vol. 179, pp. 47-52 (1989).

Staudt, L. M. et al., "Cloning of a Lymphoid-Specific cDNA Encoding a Protein Binding the Regulatory Octamer DNA Motif," Science, vol. 241, pp. 577-580 (Jul. 29, 1988).

Streicher, J. M. et al., "MAPK-activated protein kinase-2 in cardiac hypertrophy and cyclooxygenase-2 regulation in heart," Circ. Res., vol. 106 pp. 1434-1443, 25 pages (2010).

Sugawara, H. et al., "Genetic evidence for involvement of type 1, type 2 and type 3 inositol 1,4,5-trisphosphate receptors in signal transduction through the B-cell antigen receptor," The EMBO J., vol. 16, No. 11, pp. 3078-3088 (1997).

Sugimura, M. et al., "DY-9760e, a novel calmodulin antagonist with cytoprotective action," Eur. J. Pharm., vol. 336, No. 1, pp. 99-106 (Oct. 1, 1997).

Sun, Z. et al., "Hepatic Hdac3 promotes gluconeogenesis by repressing lipid synthesis and sequestration," Nat. Med., vol. 18, No. 6, pp. 934-942, 22 pages (Jun. 2012).

Sundaram, K. et al., "DACH1 negatively regulates the human RANK ligand gene expression in stromal/preosteoblast cells," J. Cell Biochem., vol. 103, No. 6, pp. 1747-1759, 20 pages (Apr. 15, 2008).

Szabo, A. et al., "Surface plasmon resonance and its use in biomolecular interaction analysis (BIA)," Curr. Opin. Struct. Biol., vol. 5, No. 5, pp. 699-705 (Oct. 1995).

Szado, T. et al., "Phosphorylation of inositol 1,4,5-trisphosphate receptors by protein kinase B/AKT inhibits Ca2+ release and apoptosis," Proc. Natl. Acad. Sci. USA, vol. 105, No. 7, pp. 2427-2432 (Feb. 19, 2008).

Tabas, I. and Ron, D., "Integrating the mechanisms of apoptosis induced by endoplasmic reticulum stress," Nat. Cell Biol., vol. 13, No. 3, pp. 184-190, 17 pages (Mar. 2011).

Tabb, D. L. et al., "DTASelect and Contrast: tools for assembling and comparing protein identifications from shotgun proteomics," J. Proteome. Res., vol. 1, No. 1, pp. 21-26, 14 pages (2002).

Takao, K. et al., "Visualization of synaptic Ca2+/calmodulin-dependent protein kinase II activity in living neurons," J. Neurosci., vol. 25, No. 12, pp. 3107-3112 (Mar. 23, 2005).

Tanaka, J. et al., "Foxo1 links hyperglycemia to LDL oxidation and endothelial nitric oxide synthase dysfunction in vascular endothelial cells," Diabetes, vol. 58, pp. 2344-2354 (Oct. 2009).

Tang, H. and Goldman, D., "Activity-dependent gene regulation in skeletal muscle is mediated by a histone deacetylase (HDAC)-Dach2-myogenin signal transduction cascade," Proc. Natl. Acad. Sci. USA, vol. 103, No. 45, pp. 16977-16982 (Nov. 7, 2006).

Tang, H. et al., "A histone deacetylase 4/myogenin positive feedback loop coordinates denervation-dependent gene induction and suppression," Molecular Biology of the Cell, vol. 20, No. 4, pp. 1120-1131 (Feb. 15, 2009).

Timmins, J. M. et al., "Calcium/calmodulin-dependent protein kinase II links ER stress with Fas and mitochondrial apoptosis pathways," J. Clin. Invest., vol. 119, No. 10, pp. 2925-2941 (Oct. 2009).

Tokumitsu, H. et al., "STO-609, a Specific Inhibitor of the Ca2+/Calmodulin-dependent Protein Kinase Kinase," J. Biol. Chem., vol. 277, No. 18, pp. 15813-15818 (May 3, 2002).

Tovey, S. C. et al., "Regulation of inositol 1,4,5-trisphosphate receptors by cAMP independent of cAMP-dependent protein kinase," J. Biol. Chem., vol. 285, No. 17, pp. 12979-12989 (Apr. 23, 2010).

Tuerk, C. et al., "RNA pseudoknots that inhibit human immunodeficiency virus type 1 reverse transcriptase," Proc. Natl. Acad. Sci. USA, vol. 89, pp. 6988-6992 (Aug. 1992).

Unger, R. H. and Cherrington, A. D., "Glucagonocentric restructuring of diabetes: a pathophysiologic and therapeutic makeover," J. Clin. Invest., vol. 122, No. 1, pp. 4-12 (Jan. 2012).

Valera, A. et al., "Calcium-mobilizing effectors inhibit P-enolpyruvate carboxykinase gene expression in cultured rat hepatocytes," FEBS Lett., vol. 333, No. 3, pp. 319-324 (Nov. 1993).

Van der Horst, A. and Burgering, B. M., "Stressing the role of FoxO proteins in lifespan and disease," Nat. Rev. Mol. Cell Biol., vol. 8, No. 6, pp. 440-450 (Jun. 2007).

Volpe, P. and Alderson-Lang, B. H., "Regulation of inositol 1,4,5-trisphosphate-induced Ca2+ release. II. Effect of cAMP-dependent protein kinase," Am. J. Physiol., vol. 258, No. 6, Part 1, pp. C1086-C1091 (Jun. 1990).

Von Groote-Bidlingmaier, F. et al., "DYRK1 is a co-activator of FKHR (FOXO1a)-dependent glucose-6-phosphatase gene expression," Biochem. Biophys. Res. Commun., vol. 300, No. 3, pp. 764-769 (Jan. 17, 2003).

Wakelam, M. J. et al., "Activation of two signal-transduction systems in hepatocytes by glucagon," Nature, vol. 323, No. 6083, pp. 68-71 (Sep. 4-10, 1986).

Walter, P. and Ron, D., "The unfolded protein response: from stress pathway to homeostatic regulation," Science, vol. 334, No. 6059, pp. 1081-1086 (Nov. 25, 2011).

Wang, B. et al., "Characterization of a hormone-dependent module regulating energy balance," Cell, vol. 145, No. 4, pp. 596-606, 22 pages (May 13, 2011).

Wang, H. et al., "ATP-Sensitive Potassium Channel Openers and 2,3-Dimethyl-2-Butylamine Derivatives," Current Medicinal Chemistry, vol. 14, No. 2, pp. 133-155 (2007).

Wang, Y. et al., "Inositol-1,4,5-trisphosphate receptor regulates hepatic gluconeogenesis in fasting and diabetes," Nature, vol. 485, No. 7396, pp. 128-132, 11 pages (Apr. 8, 2012).

Wang, Y. et al., "The CREB coactivator CRTC2 links hepatic ER stress and fasting gluconeogenesis," Nature, vol. 460, No. 7254, pp. 534-537, 13 pages (Jul. 23, 2009).

Warming, S. et al., "Simple and highly efficient BAC recombineering using galK selection," Nucleic Acids Res., vol. 33, No. 4, e36, pp. 1-12 (2005).

Wehrens, X. H. T. et al., "Intracellular calcium release and cardiac disease," Annu. Rev. Physiol., vol. 67, pp. 69-98, 35 pages (2005).

Weismann, D. et al., "Knockdown of the gene encoding *Drosophila* tribbles homologue 3 (Trib3) improves insulin sensitivity through peroxisome proliferator-activated receptor-gamma (PPARgamma) activation in a rat model of insulin resistance," Diabetologia, vol. 54, No. 4, pp. 935-944, 18 pages (Apr. 2011).

Werner, T. and Nelson, P. J., "Joining high-throughput technology with in silico modelling advances genome-wide screening towards targeted discovery," Briefings in Functional Genomics and Proteomics, vol. 5, No. 1, pp. 32-36 (2006).

Wilkins, B. J. and Molkentin, J. D., "Calcium-calcineurin signaling in the regulation of cardiac hypertrophy," Biochem. Biophys. Res. Commun., vol. 322, No. 4, pp. 1178-1191 (Oct. 1, 2004).

Wu, J. et al., "ATF6alpha optimizes long-term endoplasmic reticulum function to protect cells from chronic stress," Dev. Cell, vol. 13, No. 3, pp. 351-364 (Sep. 2007).

Wu, K. et al., "DACH1 inhibits transforming growth factor-beta signaling through binding Smad4," J. Biol. Chem., vol. 278, No. 51, pp. 51673-51684 (Dec. 19, 2003).

(56) References Cited

OTHER PUBLICATIONS

Wu, Z. et al., "Transducer of regulated CREB-binding proteins (TORCs) induce PGC-1alpha transcription and mitochondrial biogenesis in muscle cells," Proc. Natl. Acad. Sci. USA, vol. 103, No. 39, pp. 14379-14384 (Sep. 26, 2006).

Wulff, Gunter, "9: Molecular Recognition in Polymers Prepared by Imprinting with Templates," Polymeric Reagents and Catalysts, ACS Symposium Series 308, 47 pages (Apr. 28-May 3, 1985).

Xu, T. et al., "ProLuCID, a fast and sensitive tandem mass spectra-based protein identification program," Mol. Cell Proteomics, vol. 5, No. 671, p. S174 (Oct. 28-Nov. 1, 2006).

Yan, W. et al., "Control of PERK eIF2alpha kinase activity by the endoplasmic reticulum stress-induced molecular chaperone P58IPK," Proc. Natl. Acad. Sci. USA, vol. 99, No. 25, pp. 15920-15925 (Dec. 10, 2002).

Yang, J. et al., "Polyomic profiling reveals significant hepatic metabolic alterations in glucagon-receptor (GCGR) knockout mice: implications on anti-glucagon therapies for diabetes," BMC Genomics, vol. 12, No. 281, pp. 1-14 (2011).

Weismann, D. et al., "Knockdown of the gene encoding *Drosophila* tribbles homologue 3 (Trib3) improves insulin sensitivity through peroxisome proliferator-activated receptor-gamma (PPAR-gamma) activation in a rat model of insulin resistance," Diabetologia, vol. 54, No. 4, pp. 935-944, 18 pages (Apr. 2011).

Yoon, Y. S. et al., "Suppressor of MEK null (SMEK)/protein phosphatase 4 catalytic subunit (PP4C) is a key regulator of hepatic gluconeogenesis," Proc. Natl. Acad. Sci. USA, vol. 107, No. 41, pp. 17704-17709, 6 pages (Oct. 12, 2010).

Yu, H. et al., "Structural basis for the binding of proline-rich peptides to SH3 domains," Cell, vol. 76, No. 5, pp. 933-945 (Mar. 11, 1994).

Zhang, T. et al., "CaMKIIdelta isoforms differentially affect calcium handling but similarly regulate HDAC/MEF2 transcriptional responses," J. Biol. Chem., vol. 282, No. 48, pp. 35078-35087 (Nov. 30, 2007).

Extended European Search Report issued by the European Patent Office for Application No. 12829035.0 dated Sep. 16, 2015 (11 pages).

Extended European Search Report issued by the European Patent Office for Patent Application No. 16163993.5 dated Aug. 29, 2016 (8 pages).

Ozcan et al., "Treatment of Obese Insulin-Resistant Mice With an Allosteric MAPKAPK2/3 Inhibitor Lowers Blood Glucose and Improves Insulin Sensitivity," Diabetes 64(10), 3396-405 (2016).

Hayashi, Y., "Metabolic impact of glucagon deficiency," Diabetes, Obesity and Metabolism 13:(Suppl. 1), pp. 151-157 (2011).

Vuguin and Charron, "Novel insight into glucagon receptor action: lessons from knockout and transgenic mouse models," Diabetes, Obesity and Metabolism 13:(Suppl. 1), pp. 144-150 (2011).

Wang et al. "InsP3 Receptor Regulates Hepatic Gluconeogenesis in Fasting and Diabetes," Author Manuscript (11 pages), Published in final edited form as: Nature 485(7396), pp. 128-132 (2012).

Wang et al., "A Hormone-Dependent Module Regulating Energy Balance," Cell 145, pp. 596-606 (2011).

Dobbs and Hehre, "Molecular orbital theory of the properties of inorganic and organometallic compounds. 6. Extended basis sets for second-row transition metals," J. Comp. Chem. 8, pp. 880-893 (1987).

Communication from European Patent Office dated Jul. 6, 2017 for European Patent Application No. 16163993.5 (5 pages).

\* cited by examiner

Hepatic CaMKIIγ deficiency → ↓ nuclear FoxO1 → ↓ GNG/HGP → ↓ hyperinsulinemia → ↓ mTORC1 → ↓ dyslipidemia

Figure 18

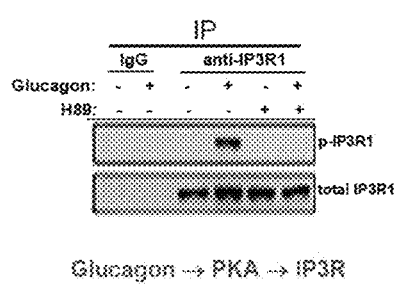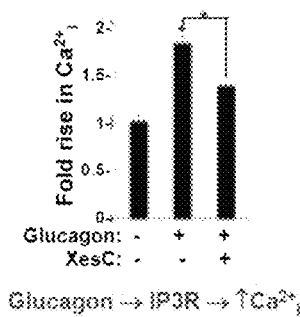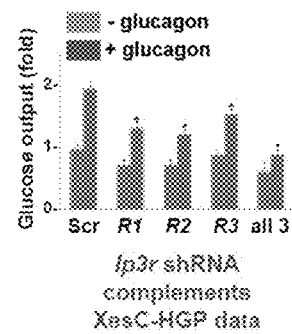
Figure 21J

A

| | Peptide | Site | Spectral Count # (KO) | Debunker Score (KO) | A Score (KO) | Spectral Count # (WT) | Debunker Score (WT) | A Score (WT) | Spectral Count # Ratio (KO/WT) |
|---|---|---|---|---|---|---|---|---|---|
| 1: | K.KASLQSQQEGPQSRS*PGSQFSK.W | S284 | 4 | 0.99 | 30.66 | 6 | 0.99 | 57.5 | - |
| 2: | K.WPAS*PGSHSNEKFDNWSTFRPR.T | S295 | 17 | 0.99 | 29.82 | 37 | 0.99 | 40.35 | 0.45 |
| 3: | R.TSSNASTSGRLS*PIMTEQNRLRDGDVHSLVYPPSAAK.M | S326 | 33 | 0.99 | 30.65 | 20 | 0.60 | 24.89 | 1.65 |
| 4: | K.ELLTSDS*PPHNRMSPVDPGVAGPNSK.V | S467 | 5 | 0.34 | 16.22 | 13 | 0.59 | 12.09 | 0.38 |
| 5: | K.ELLTSDSPPHNRMS*PVDPGVAGPNSR.V | S475 | 5 | 0.34 | 32.44 | 10 | 0.72 | 44.72 | 0.5 |
| 6: | R.SCT*VPLPR.P | T24 | 0 | 0 | 0 | 1 | 0.80 | 42.66 | - |
| 7: | R.SSWWRLNPEGKSGKS*PR.R | S246 | 2 | 0.99 | 16.23 | 5 | 0.99 | 10.49 | - |
| 8: | R.AAS*MDMNSKFAKSR.G | S353 | 3 | 0.99 | 45.45 | 1 | 0.99 | 31.85 | - |
| 9: | C.YSFAPPNTSLNS*PSPNYSK.Y | S413 | 0 | 0 | 0 | 1 | 0.31 | 14.42 | - |
| 10: | C.YSFAPPNTSLNSPS*PNYSK.Y | S415 | 0 | 0 | 0 | 1 | 0.92 | 11.56 | - |
| 11: | R.TLPHVVNTMPHTSAMNRLT*PVK.T | T553 | 2 | 0.99 | 37.41 | 1 | 0.36 | 12.03 | - |

```
  1 maeapqvvet dpdfeplprq rscT²⁴wplprp efhqsnsts
 41 spapsggaaa npdaaaslas asavstdfms nlslleesed
 81 farapgcvav aaaaaasrgl cgdfqgpeag cvhpappqpp
121 ptgplsqppp vppsaaaaag plagqprkts ssrnawgnl
161 syadlitkai essaekrltl sqiyewnrvks vpyfkdkgds
201 nssagwknsi rhnlslhskf irvqnegtgk sswwmlnpeg
241 gksgkS²⁴⁶prrr aaS²⁵³mdnnskf aksrgraakk kaslqsgqeg
281 pgdS²⁸⁴pgsqfs kwpaS²⁹⁵pgshs nddfdnwstf rprtssnast
321 isgrlS³²⁶pimt eqddlgdgdv hslvyppsaa kmastlpsls
361 eisnpenmen lldnlnllss ptsltvstqs spgsnmqqtp cysfappnts
411 lnS⁴¹³pS⁴¹⁵pnysk ytygqssmsp lpqmpmqtlq dskssyggln
451 qyncapgllk ellltsdS⁴⁶⁷pph ndlmS⁴⁷⁵pvdpg vaqpnsrvlg
491 qnvnmngpnsv mpaygsqash nkmnmmpssht hpghaqqtas
531 vngrtlphvv ntmphtsann rlT⁵⁵³pvktplq vplshpmqms
571 algsyssvss cngygrmgvl hqeklpsdld gmfierldcd
611 mesiimdlm dgdtldfnfd nvlpnqsfph svkttthswv sg
```

(amino acids whose phospho sites were identified by MS/MS using stringent selection criteria are in bold font—see Fig. 6A)

• Lower phospho in KO: S295, 467, 475 (S246 showed lower trend in KO but spectral count not >10)

• Higher phospho in KO: S326

• Possible sites phosphorylated by p38 according to Asada et al., Cellular Signalling, 19:519 (2007): Ser284, 295, 467, and 475

• S-A residues in 7A-FoxO1: S246, 284, 295, 413, 415, 429, 475

• Additional S-A residues in 9A-FoxO1: S326, 467

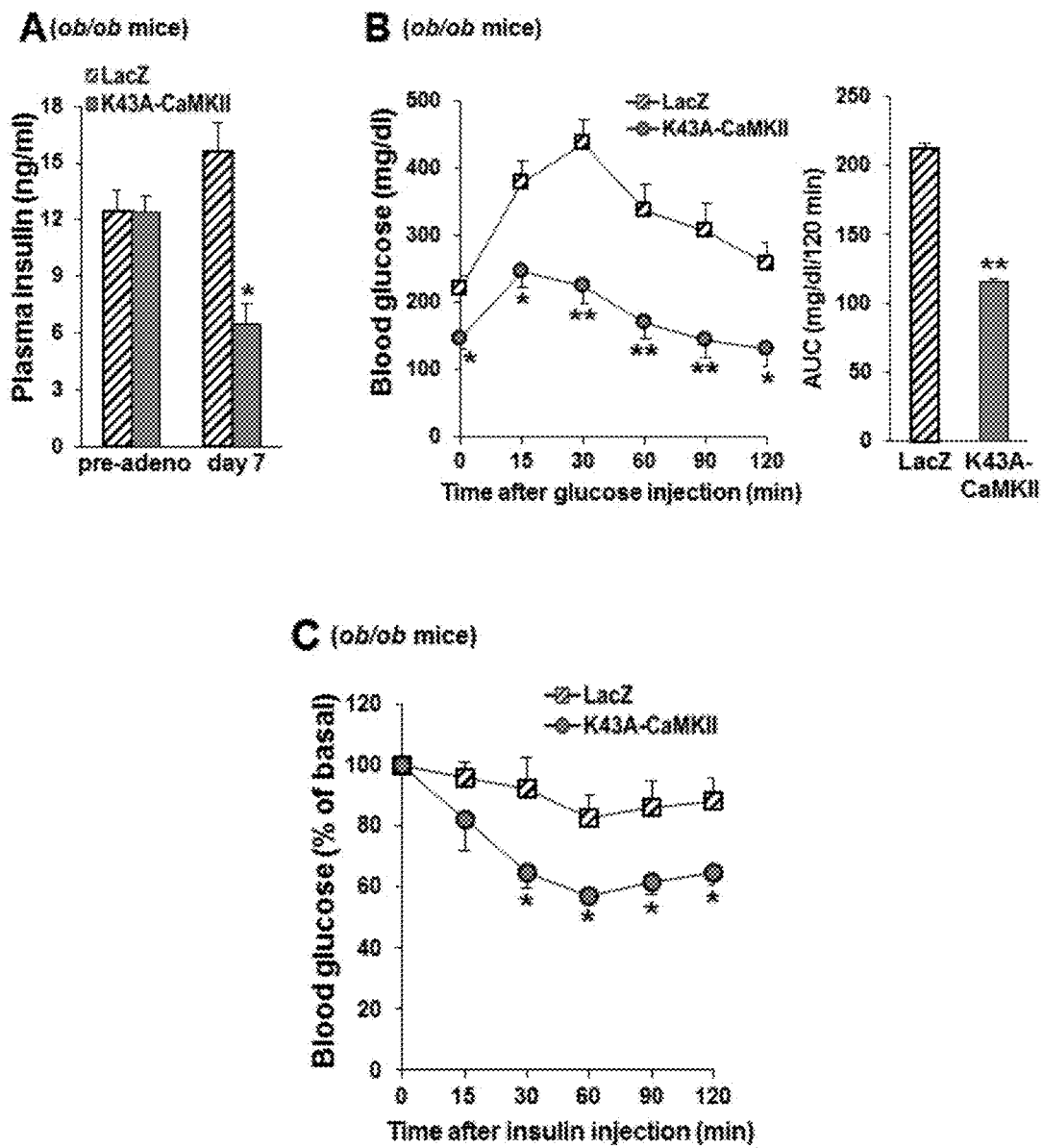
Figures 89A-C

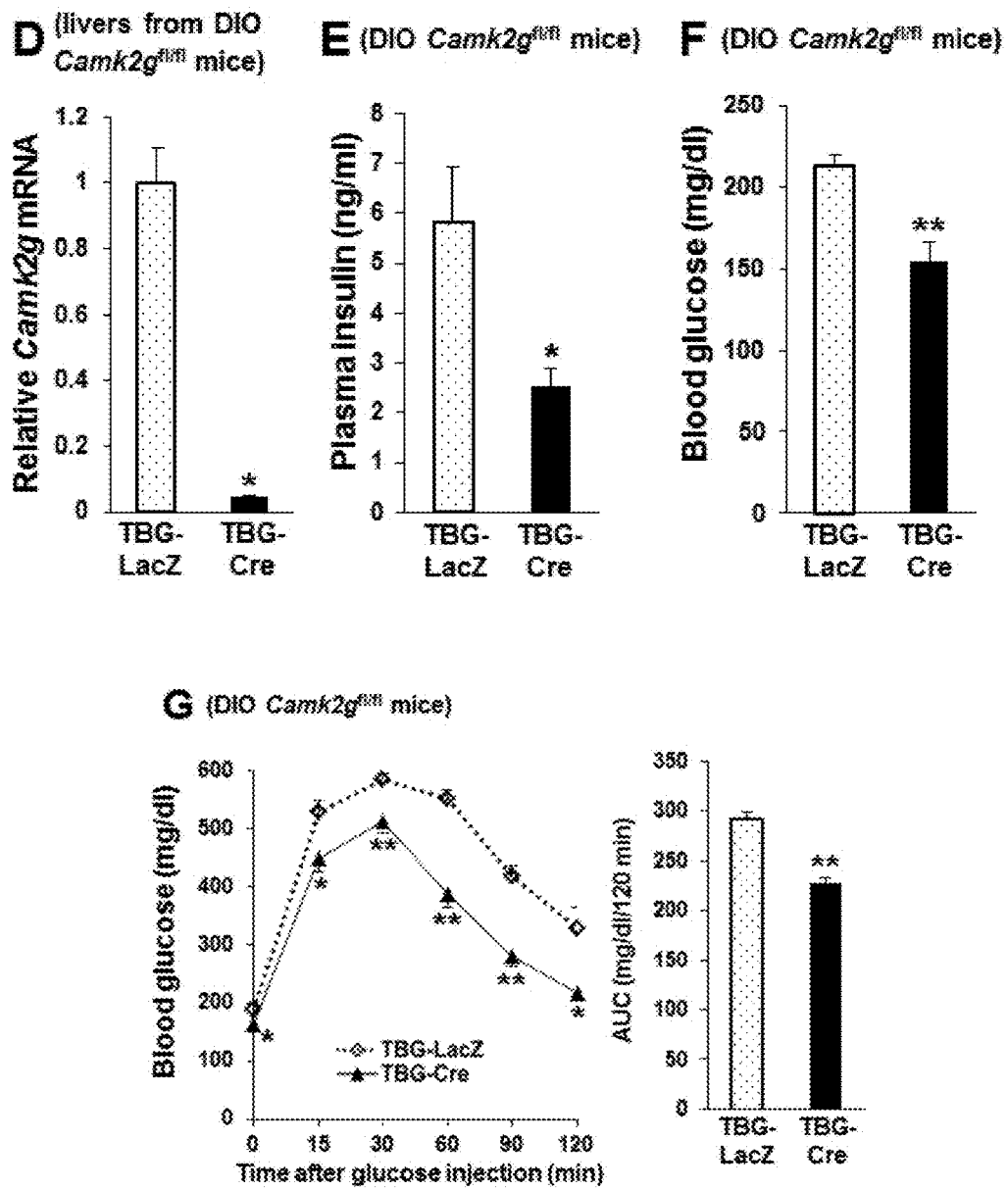
Figures 89D-G

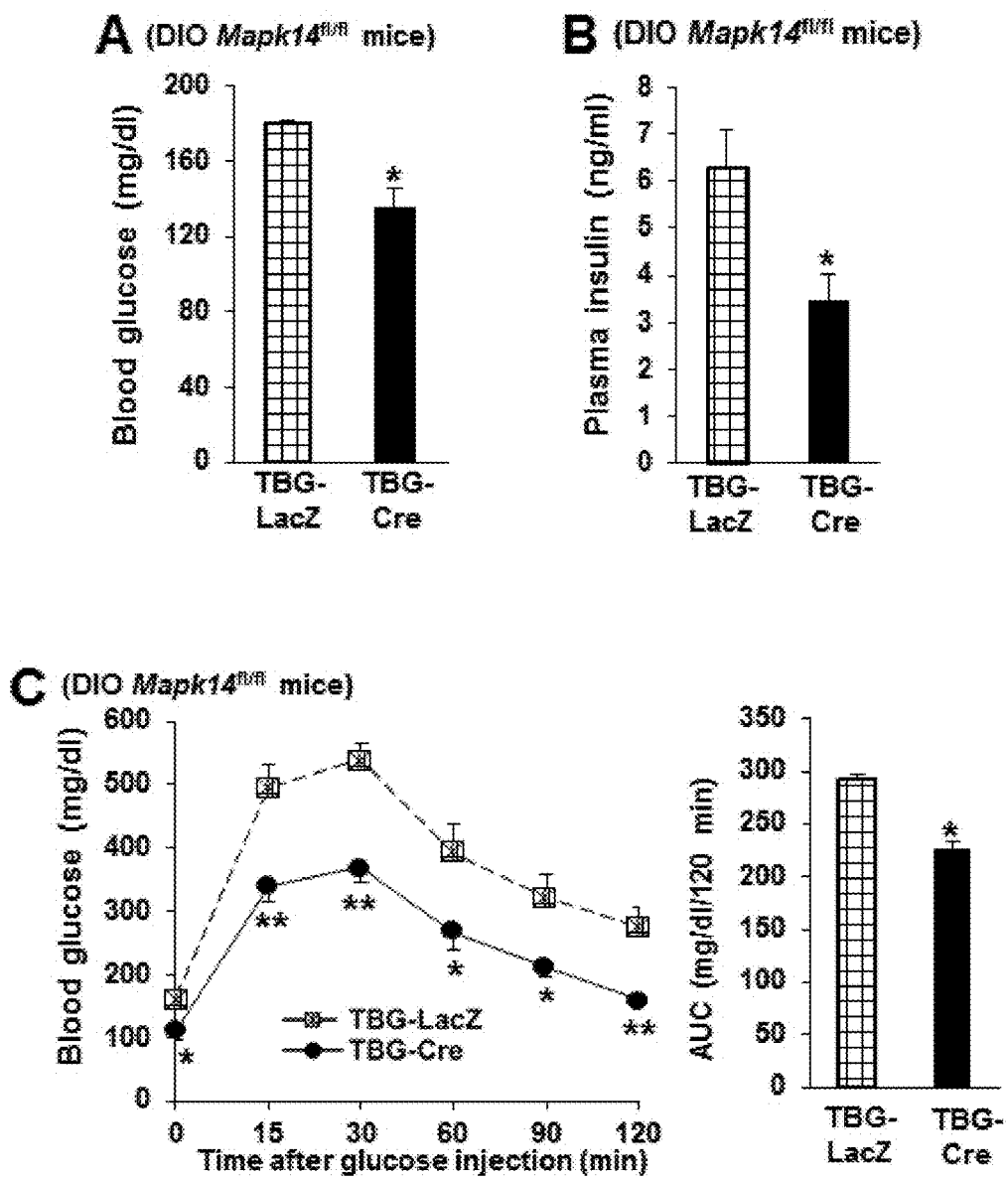
Figures 90A-C

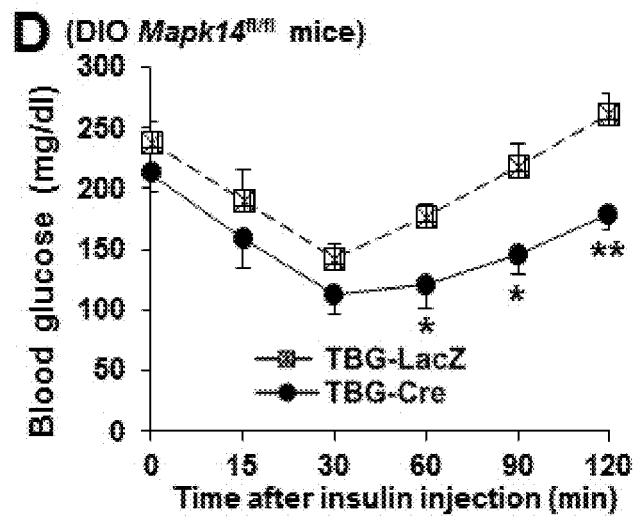
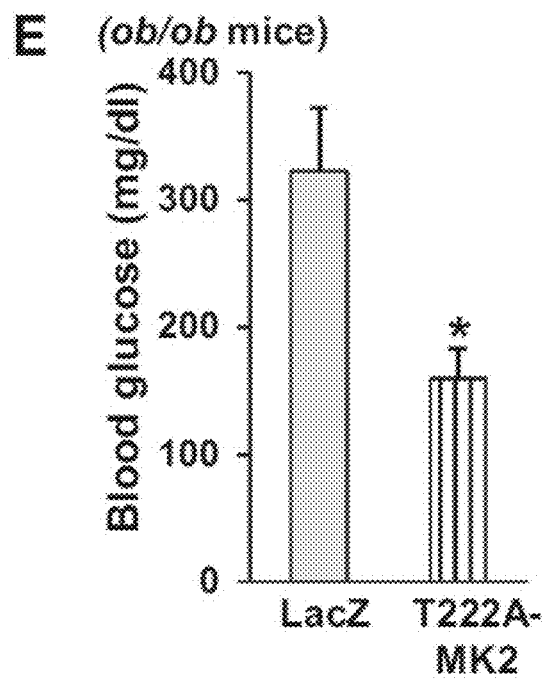
Figure 90D-E

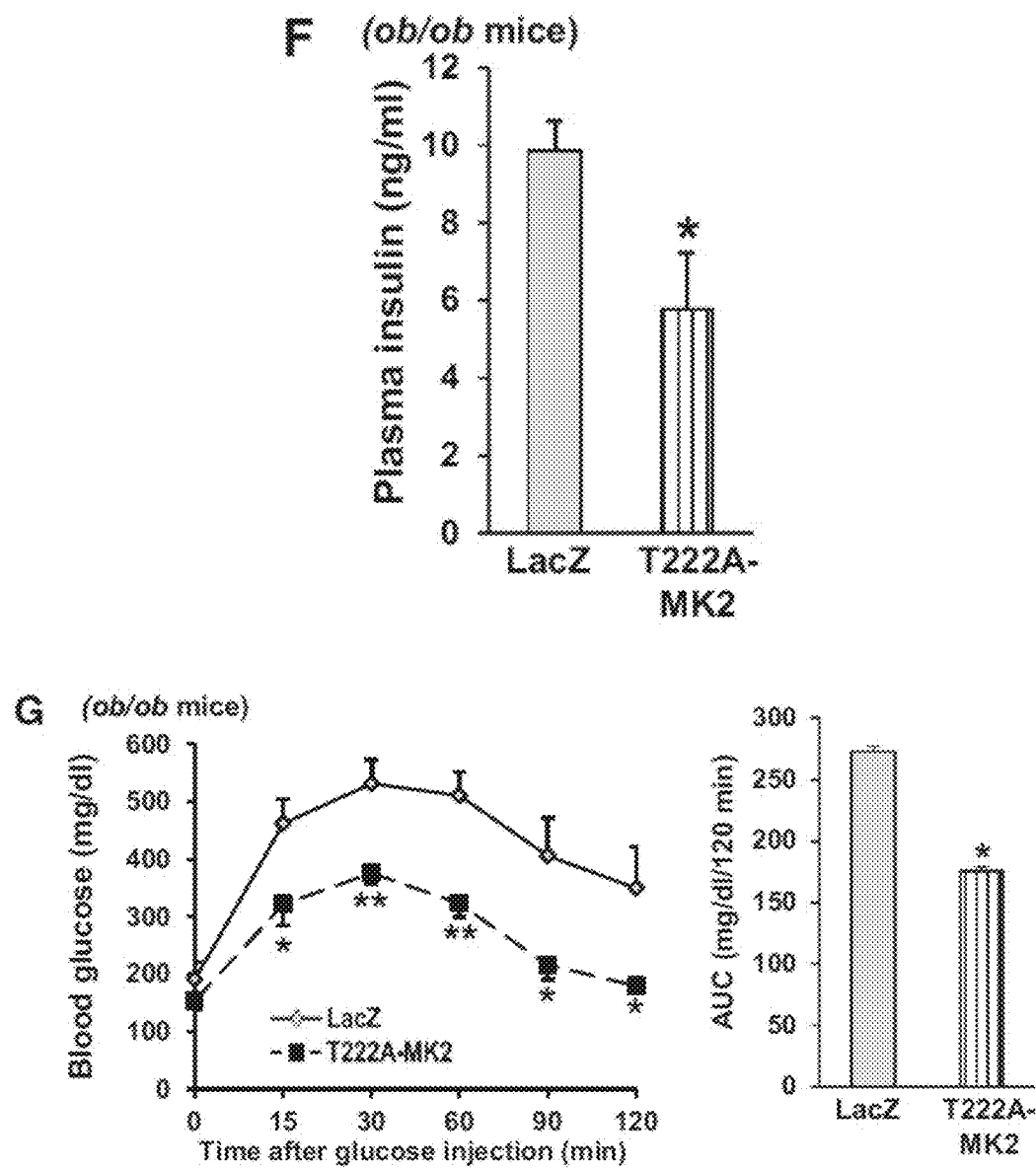
Figure 90F-G

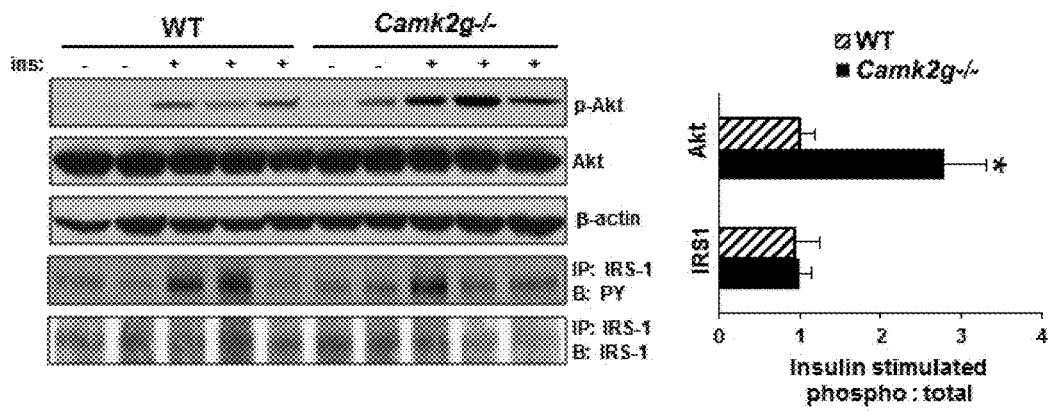
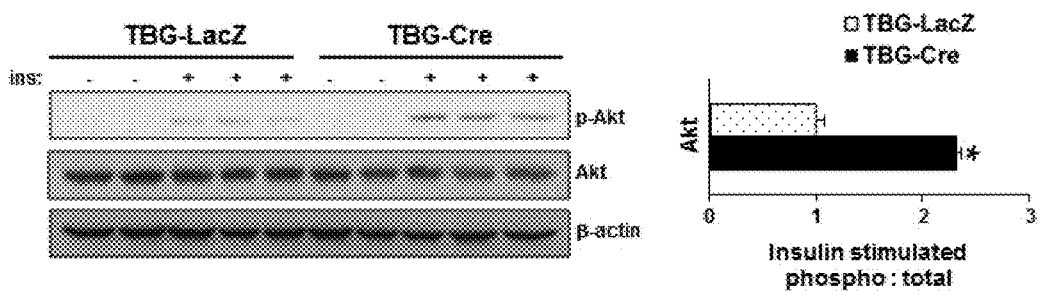
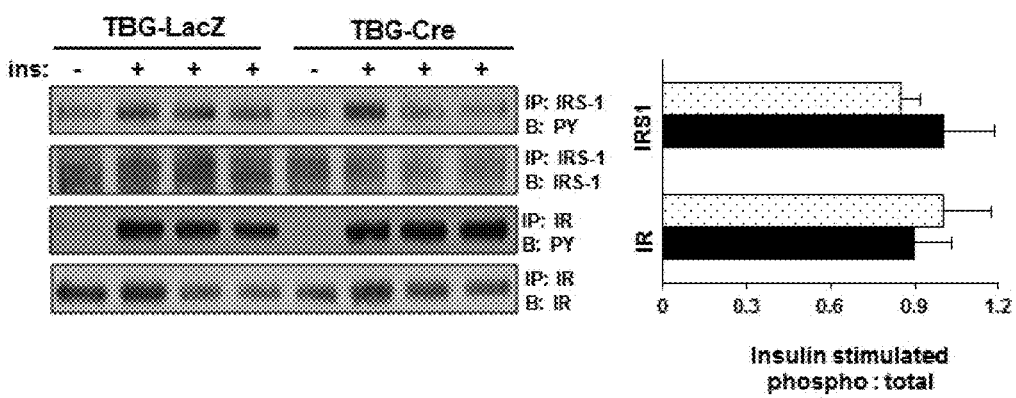
Figures 91A-B

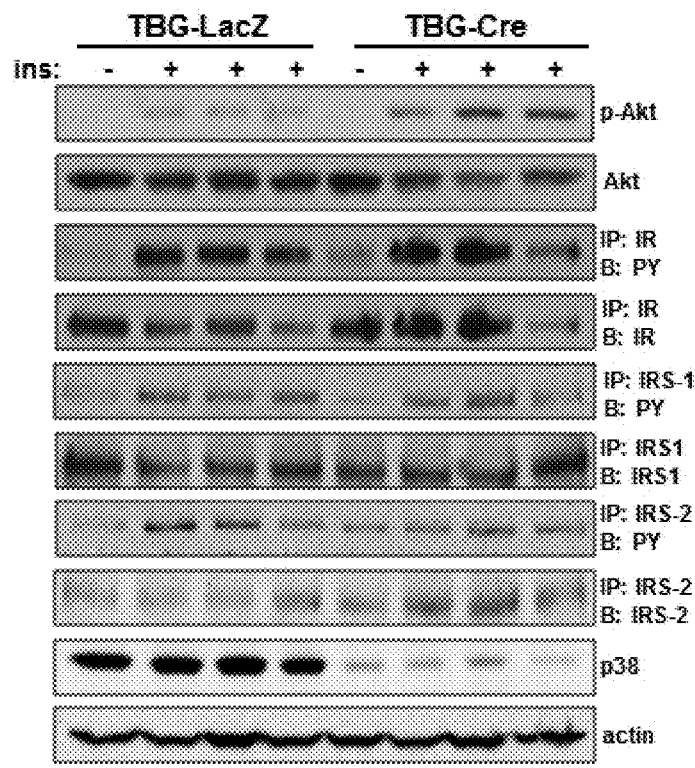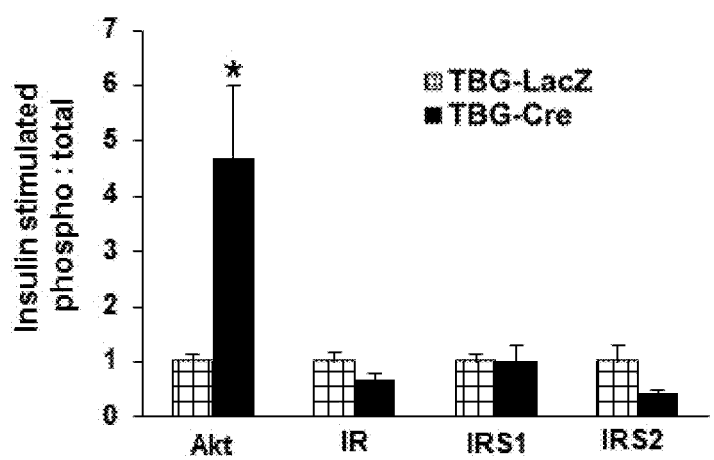
Figure 91C

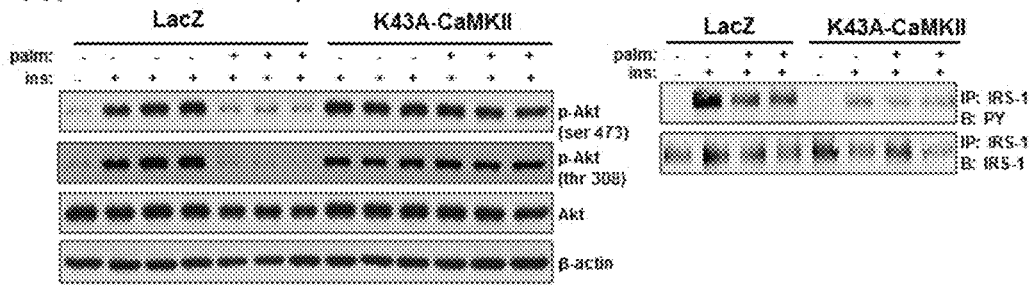
Figures 92A-B

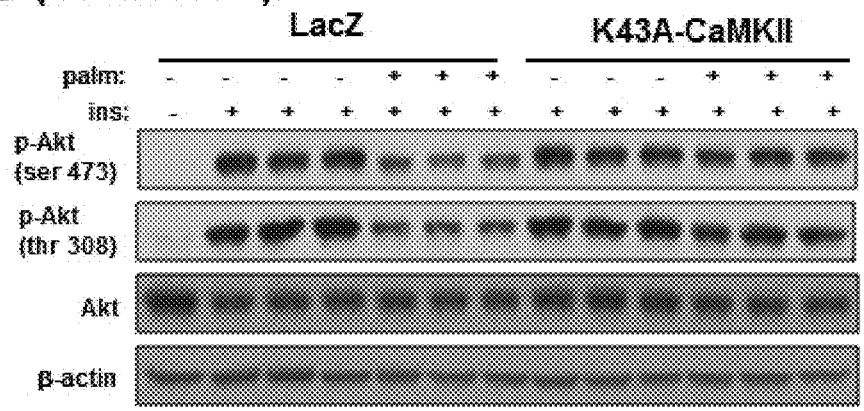
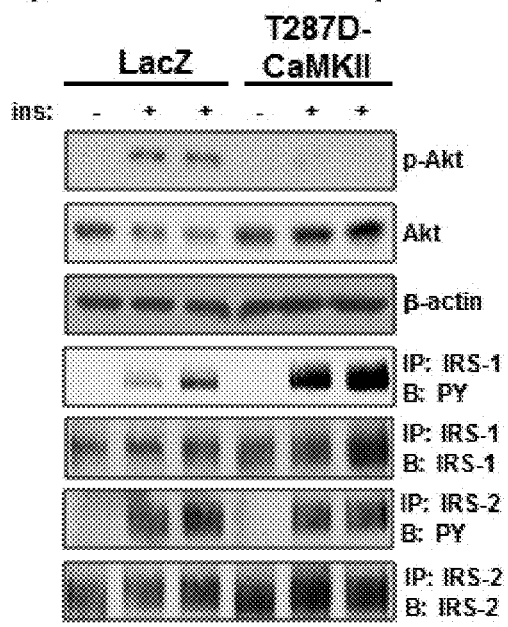
Figures 92C-D

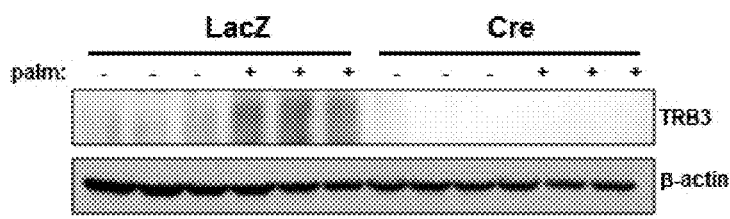
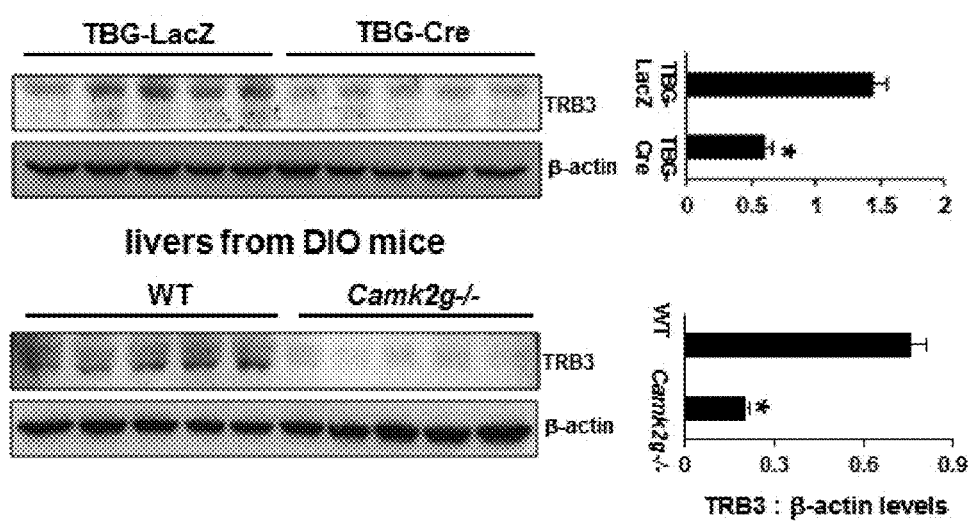
Figures 93A-B

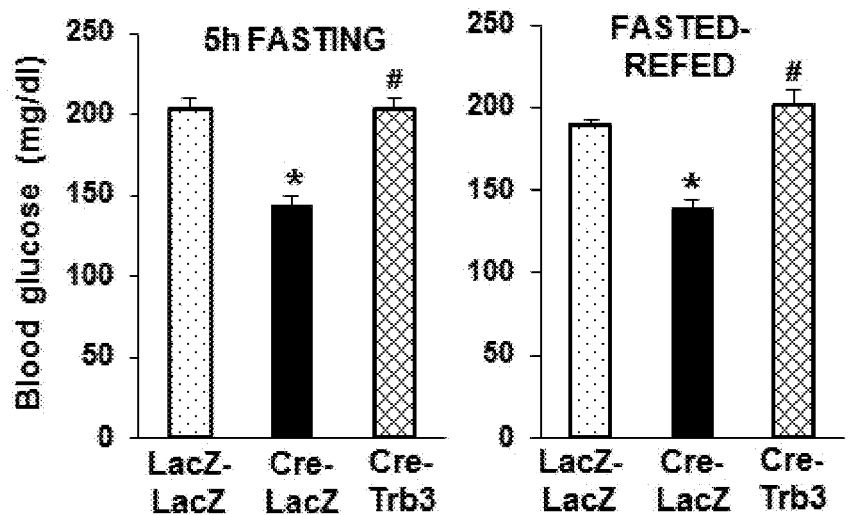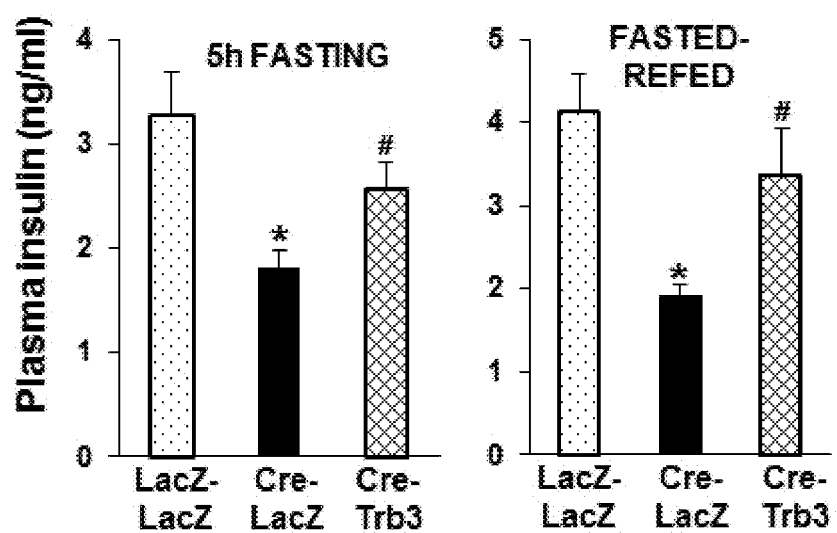
Figures 93C-D

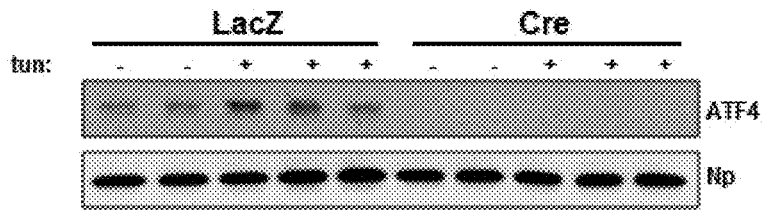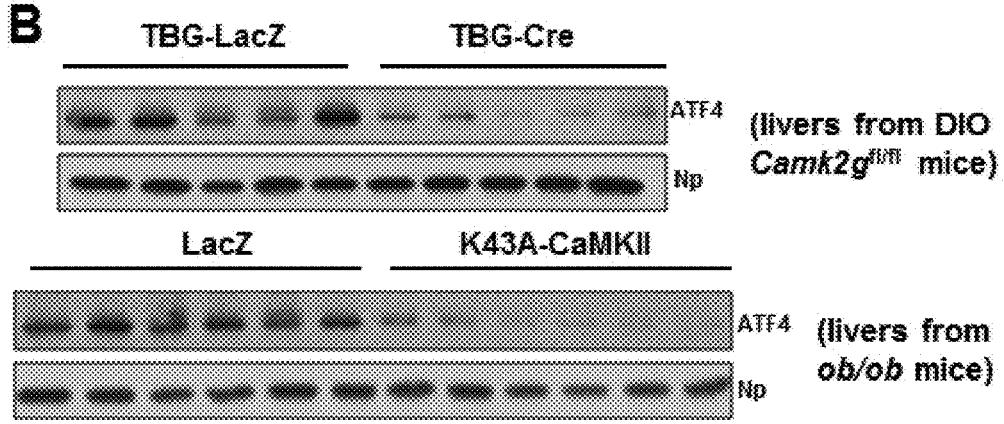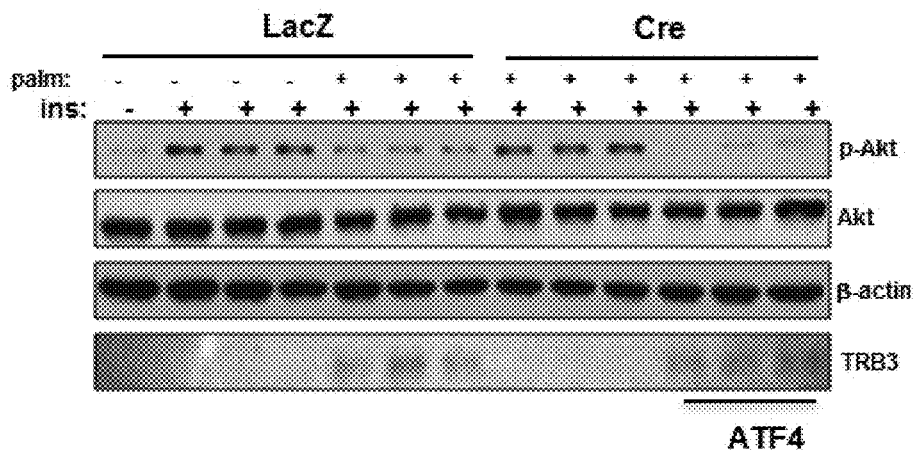
Figures 94A-C

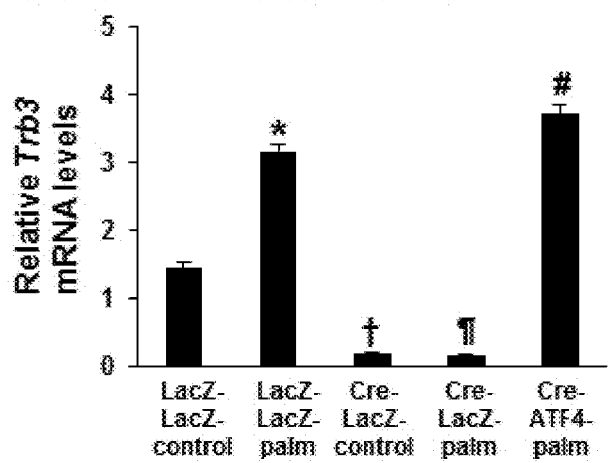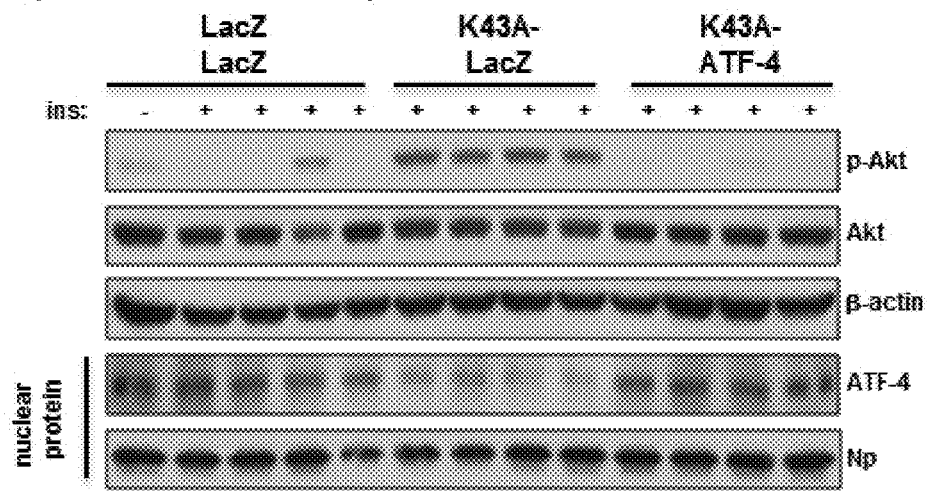
Figures 94D-E

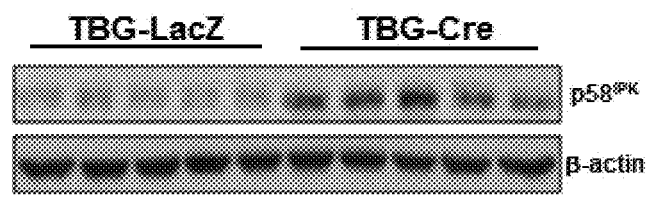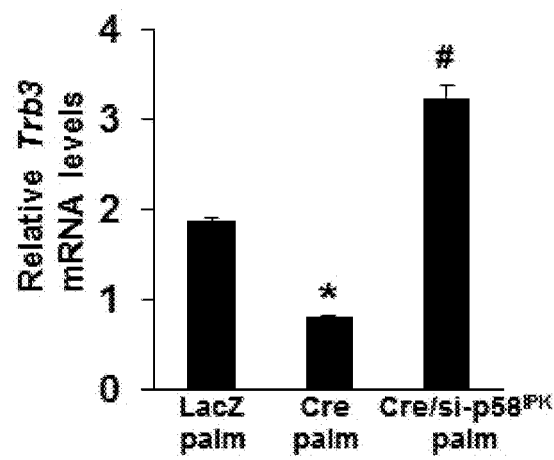
Figures 95A-B

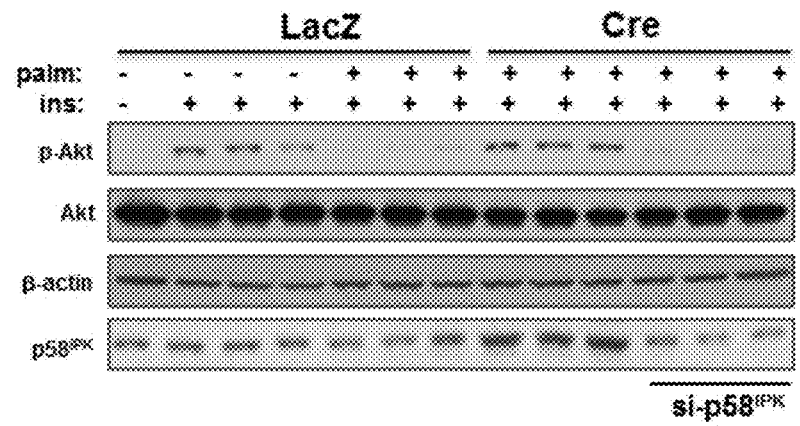
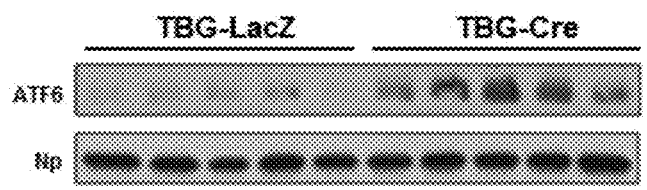
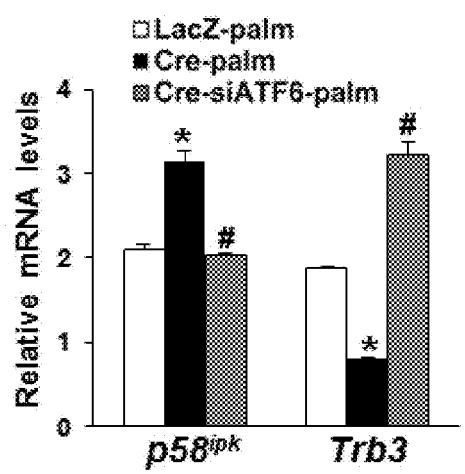
Figures 95C-E

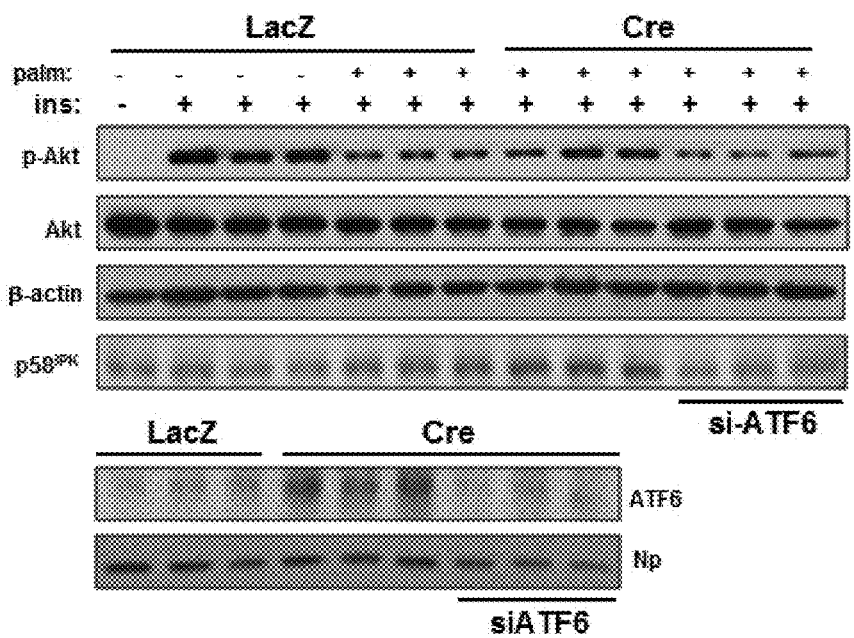
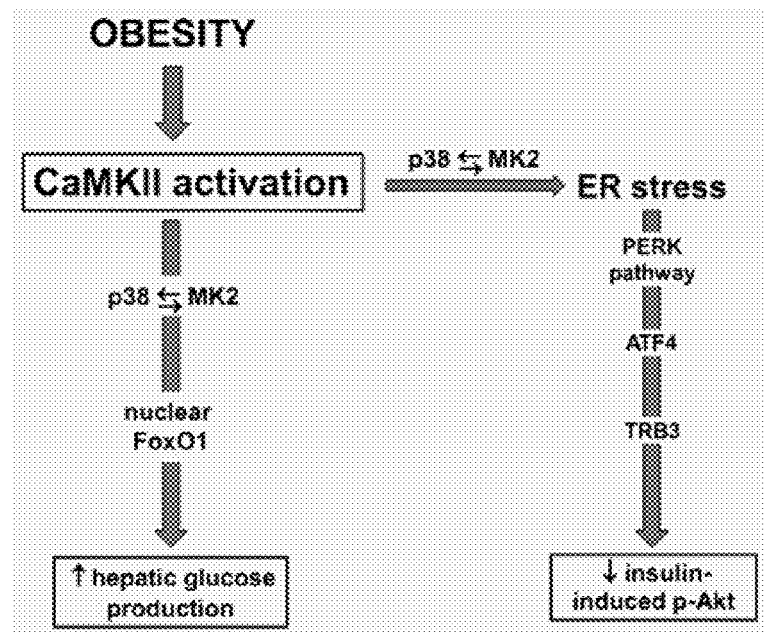
Figures 95F-G

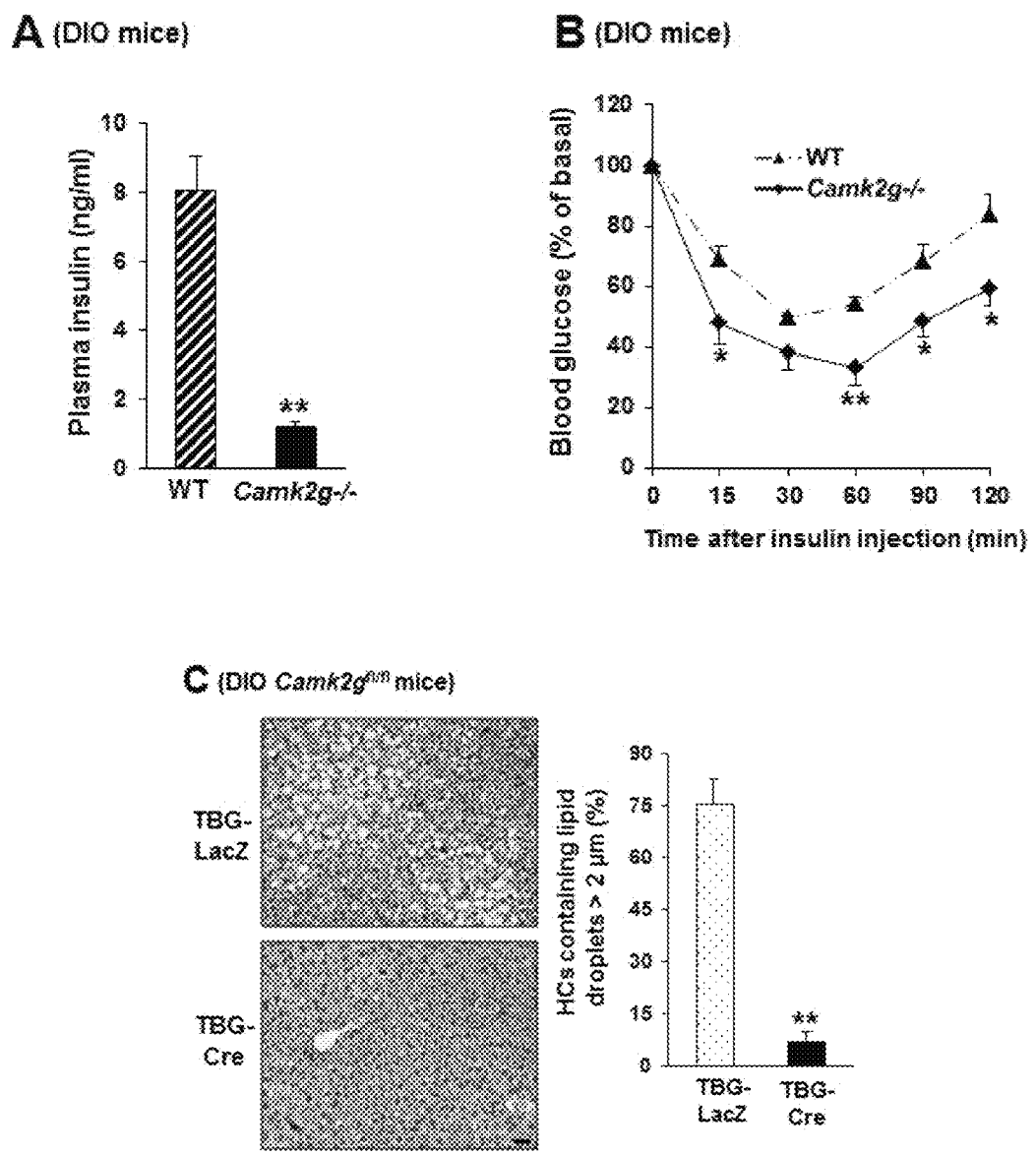
Figures 96A-C

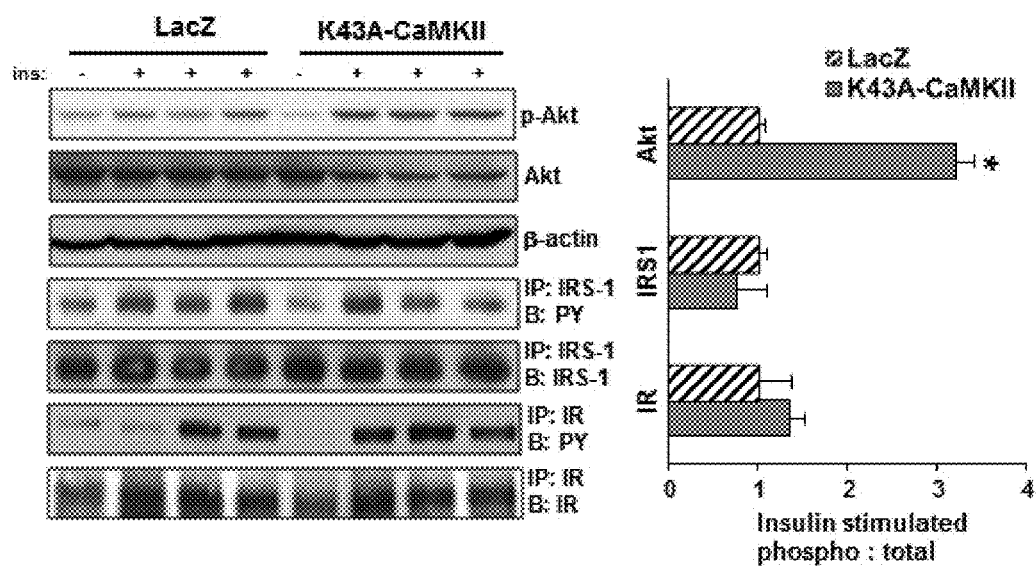
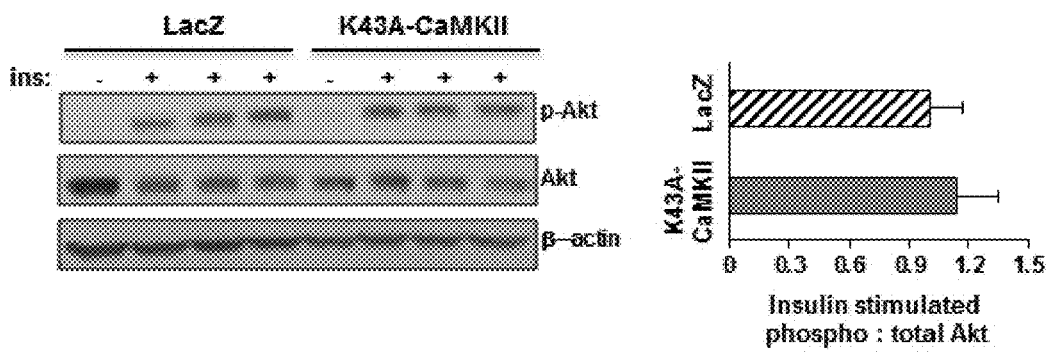
Figures 97A-B

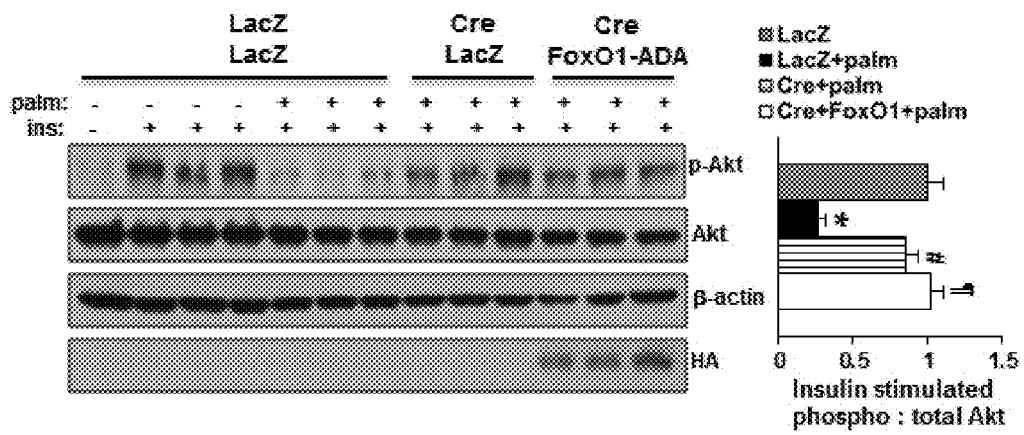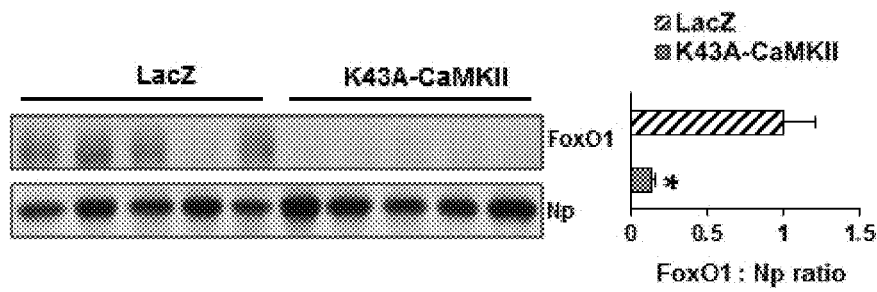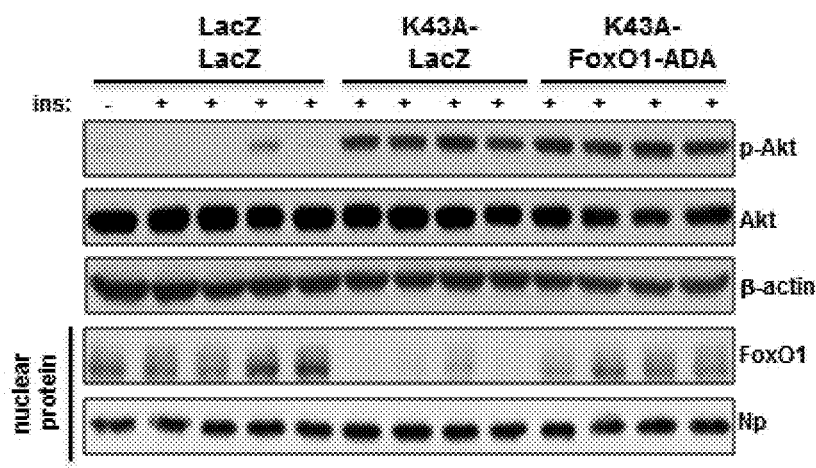
Figures 98B-D

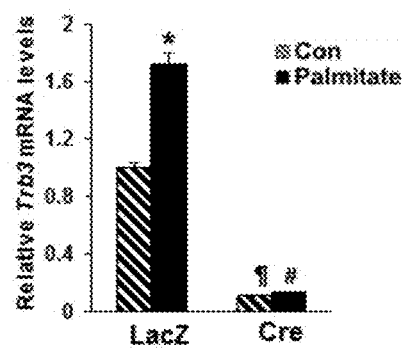
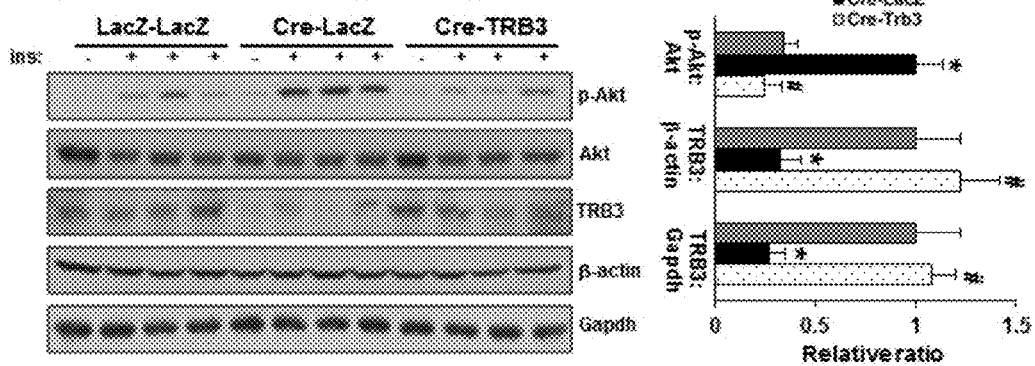
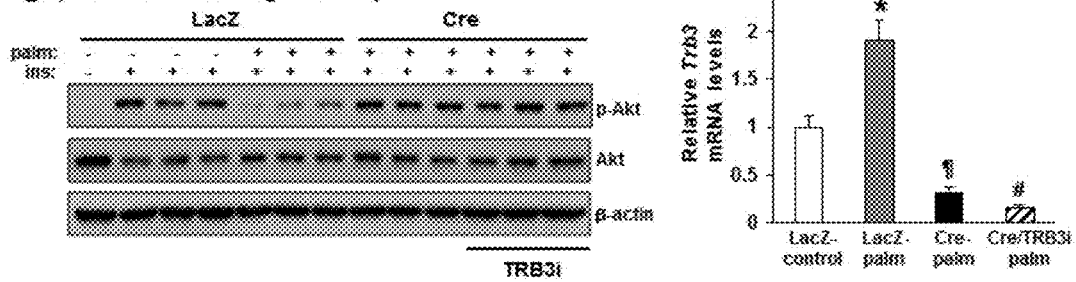
Figures 99A-C

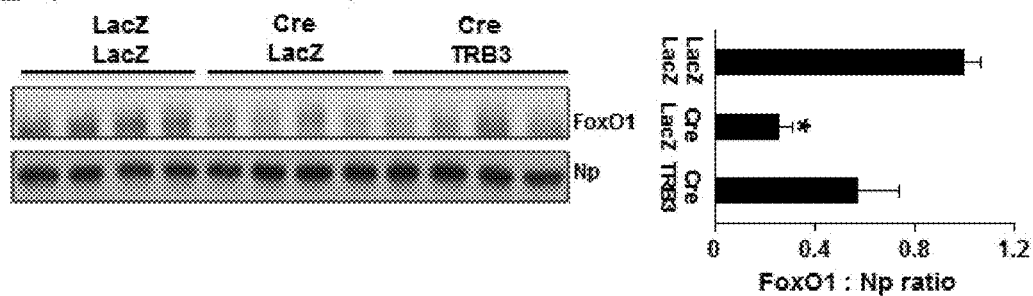
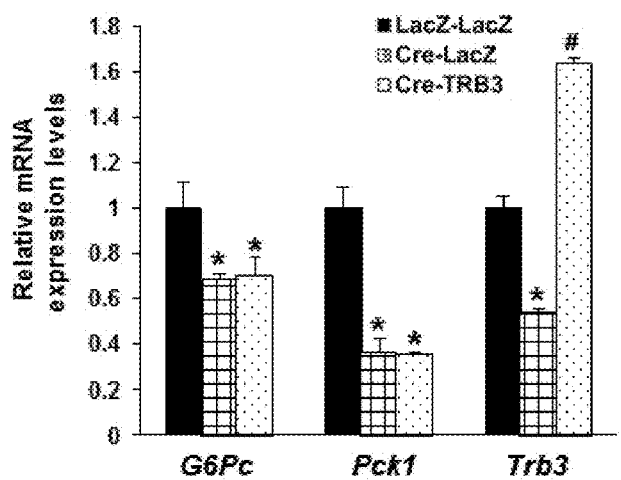
Figures 99D-E

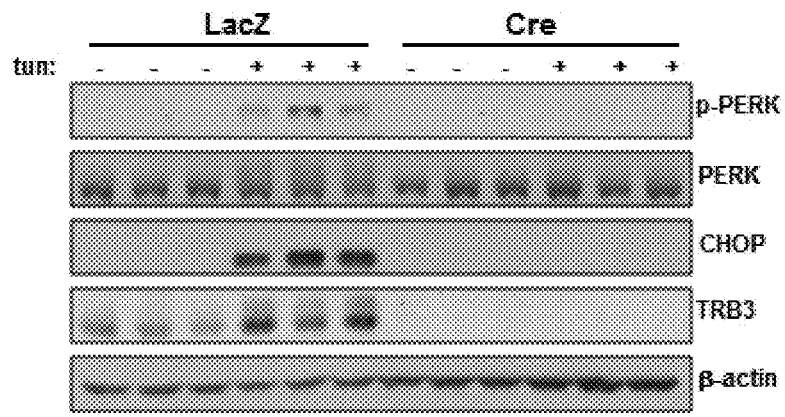
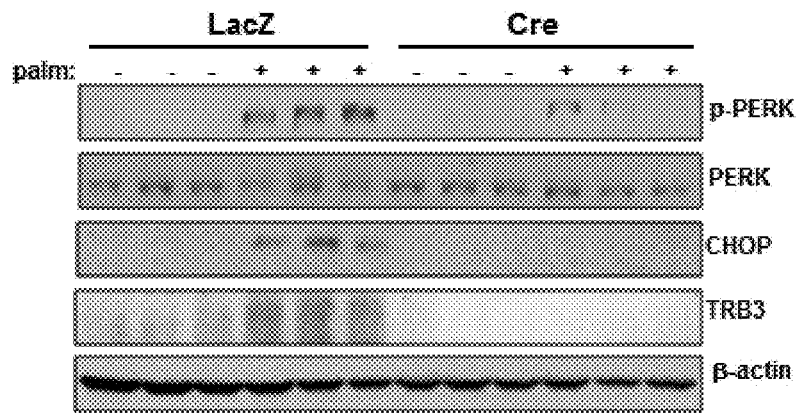
Figures 100A-B

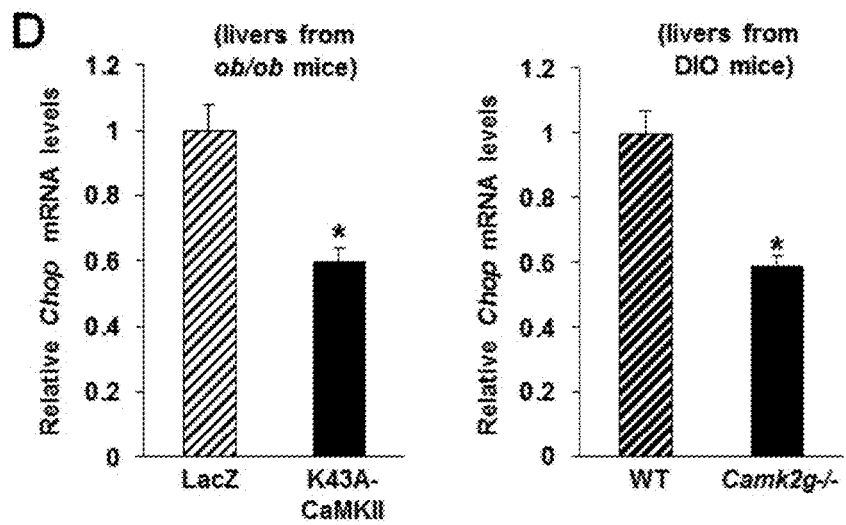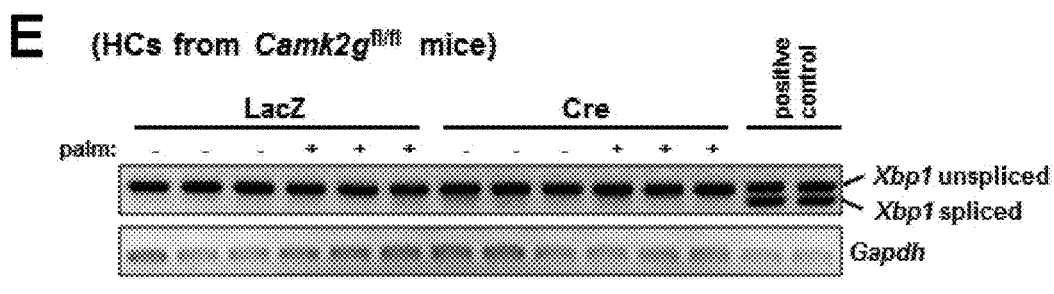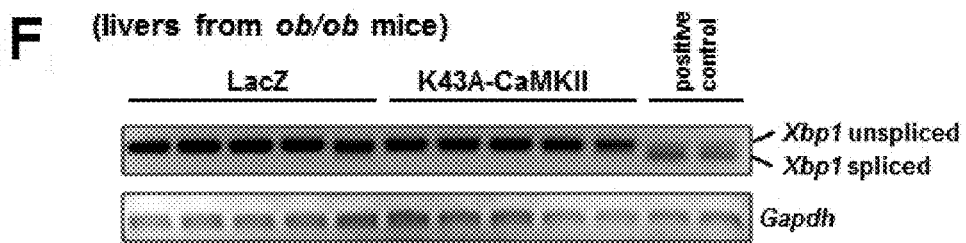
Figures 100D-F

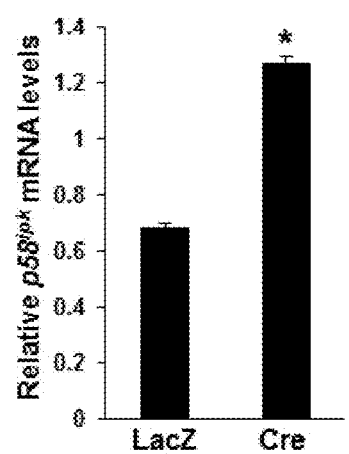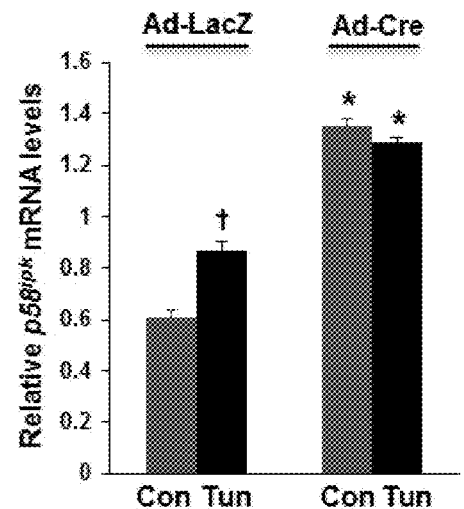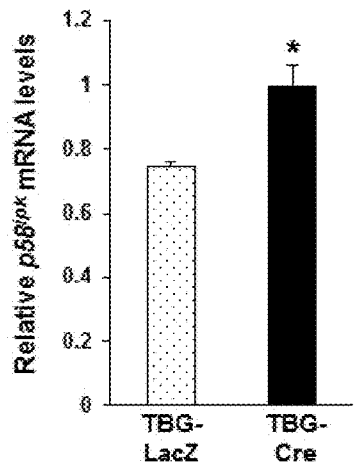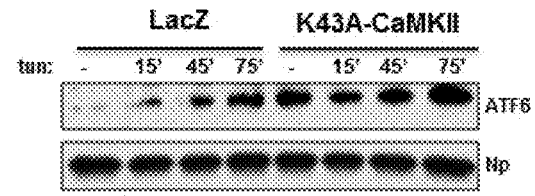
Figures 101A-D

Figures 111A-C

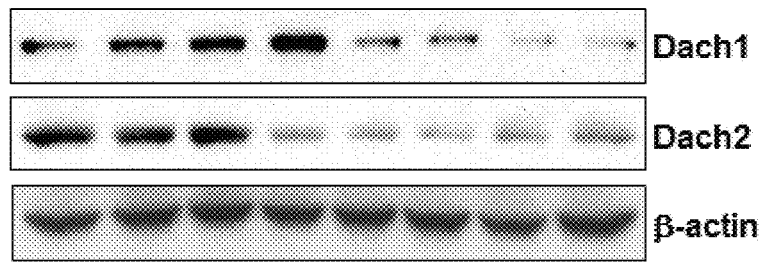
DIO *Camk2g*$^{fl/fl}$
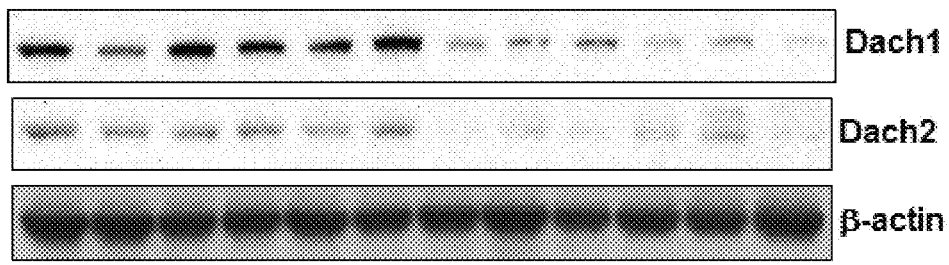
*ob/ob*
Figure 114

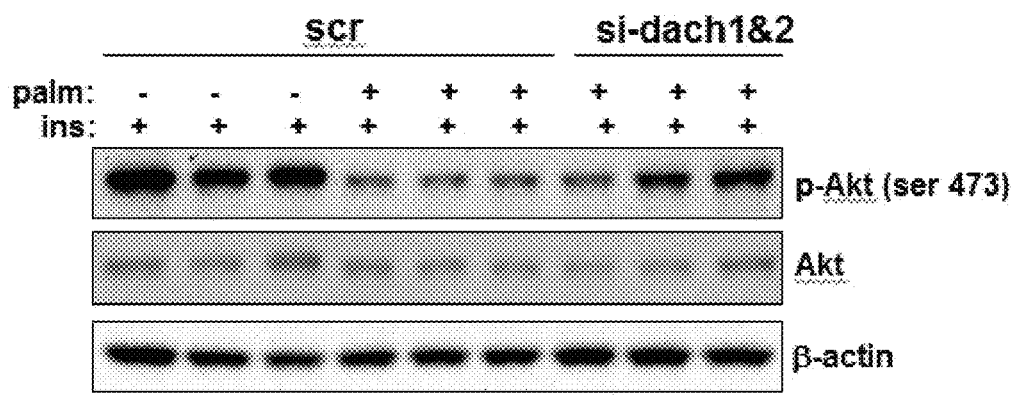
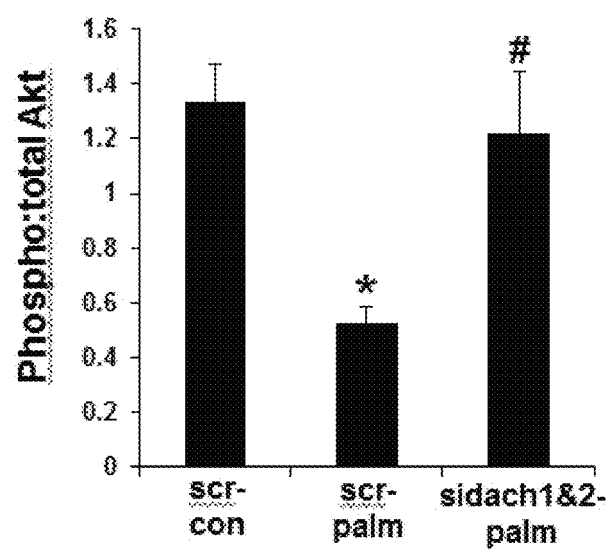
WT primary hepatocytes
Figure 120

SEQUENCE LISTING

```
<160> NUMBER OF SEQ ID NOS: 34

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Met Gly Ser Ser Lys Ser Lys Pro Lys Asp Pro Ser Gln Arg
1               5                   10

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gggtaccgca tgtacaggaa aa                                              22

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gggtactgga atagcctctt cc                                              22

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gggtaacaag caccaccatc cc                                              22

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gggcaagctg caggtgttcc tg                                              22
```

```
<210> SEQ ID NO 6
<211> LENGTH: 25
<212> TYPE: PRT
<213> ORGANISM: Mus sp.
<220> FEATURE:
<221> NAME/KEY: MOD_RES
<222> LOCATION: (9)..(9)
<223> OTHER INFORMATION: Phospho-Ser
<220> FEATURE:
<221> NAME/KEY: MOD_RES
<222> LOCATION: (20)..(20)
<223> OTHER INFORMATION: Phospho-Ser

<400> SEQUENCE: 6

Ser Gly Gln Glu Gly Pro Gly Asp Ser Pro Gly Ser Gln Phe Ser Lys
1               5                   10                  15

Trp Pro Ala Ser Pro Gly Ser His Ser
            20                  25

<210> SEQ ID NO 7
<211> LENGTH: 39
<212> TYPE: PRT
<213> ORGANISM: Mus sp.

<400> SEQUENCE: 7

His Arg Ser Thr Val Ala Ser Met Met His Arg Gln Glu Thr Val Asp
1               5                   10                  15

Cys Leu Lys Lys Phe Asn Ala Arg Arg Lys Leu Lys Gly Ala Ile Leu
            20                  25                  30

Thr Thr Met Leu Ala Thr Arg
        35

<210> SEQ ID NO 8
<211> LENGTH: 23
<212> TYPE: PRT
<213> ORGANISM: Mus sp.
<220> FEATURE:
<221> NAME/KEY: MOD_RES
<222> LOCATION: (15)..(15)
<223> OTHER INFORMATION: Phospho-Ser

<400> SEQUENCE: 8

Lys Lys Ala Ser Leu Gln Ser Gly Gln Glu Gly Pro Gly Asp Ser Pro
1               5                   10                  15

Gly Ser Gln Phe Ser Lys Trp
            20

<210> SEQ ID NO 9
<211> LENGTH: 24
<212> TYPE: PRT
<213> ORGANISM: Mus sp.
<220> FEATURE:
<221> NAME/KEY: MOD_RES
<222> LOCATION: (5)..(5)
<223> OTHER INFORMATION: Phospho-Ser

<400> SEQUENCE: 9

Lys Trp Pro Ala Ser Pro Gly Ser His Ser Asn Asp Asp Phe Asp Asn
1               5                   10                  15

Trp Ser Thr Phe Arg Pro Arg Thr
            20

<210> SEQ ID NO 10
<211> LENGTH: 40
<212> TYPE: PRT
```

```
<213> ORGANISM: Mus sp.
<220> FEATURE:
<221> NAME/KEY: MOD_RES
<222> LOCATION: (14)..(14)
<223> OTHER INFORMATION: Phospho-Ser

<400> SEQUENCE: 10

Arg Thr Ser Ser Asn Ala Ser Thr Ile Ser Gly Arg Leu Ser Pro Ile
1               5                   10                  15
Met Thr Glu Gln Asp Asp Leu Gly Asp Gly Asp Val His Ser Leu Val
            20                  25                  30
Tyr Pro Pro Ser Ala Ala Lys Met
        35                  40

<210> SEQ ID NO 11
<211> LENGTH: 29
<212> TYPE: PRT
<213> ORGANISM: Mus sp.
<220> FEATURE:
<221> NAME/KEY: MOD_RES
<222> LOCATION: (8)..(8)
<223> OTHER INFORMATION: Phospho-Ser

<400> SEQUENCE: 11

Lys Glu Leu Leu Thr Ser Asp Ser Pro Pro His Asn Asp Ile Met Ser
1               5                   10                  15
Pro Val Asp Pro Gly Val Ala Gln Pro Asn Ser Arg Val
            20                  25

<210> SEQ ID NO 12
<211> LENGTH: 29
<212> TYPE: PRT
<213> ORGANISM: Mus sp.
<220> FEATURE:
<221> NAME/KEY: MOD_RES
<222> LOCATION: (16)..(16)
<223> OTHER INFORMATION: Phospho-Ser

<400> SEQUENCE: 12

Lys Glu Leu Leu Thr Ser Asp Ser Pro Pro His Asn Asp Ile Met Ser
1               5                   10                  15
Pro Val Asp Pro Gly Val Ala Gln Pro Asn Ser Arg Val
            20                  25

<210> SEQ ID NO 13
<211> LENGTH: 10
<212> TYPE: PRT
<213> ORGANISM: Mus sp.
<220> FEATURE:
<221> NAME/KEY: MOD_RES
<222> LOCATION: (4)..(4)
<223> OTHER INFORMATION: Phospho-Thr

<400> SEQUENCE: 13

Arg Ser Cys Thr Trp Pro Leu Pro Arg Pro
1               5                   10

<210> SEQ ID NO 14
<211> LENGTH: 20
<212> TYPE: PRT
<213> ORGANISM: Mus sp.
<220> FEATURE:
<221> NAME/KEY: MOD_RES
<222> LOCATION: (17)..(17)
<223> OTHER INFORMATION: Phospho-Ser

<400> SEQUENCE: 14
```

-continued

Lys Ser Ser Trp Trp Met Leu Asn Pro Glu Gly Gly Lys Ser Gly Lys
1               5                   10                  15

Ser Pro Arg Arg
            20

<210> SEQ ID NO 15
<211> LENGTH: 16
<212> TYPE: PRT
<213> ORGANISM: Mus sp.
<220> FEATURE:
<221> NAME/KEY: MOD_RES
<222> LOCATION: (4)..(4)
<223> OTHER INFORMATION: Phospho-Ser

<400> SEQUENCE: 15

Arg Ala Ala Ser Met Asp Asn Asn Ser Lys Phe Ala Lys Ser Arg Gly
1               5                   10                  15

<210> SEQ ID NO 16
<211> LENGTH: 21
<212> TYPE: PRT
<213> ORGANISM: Mus sp.
<220> FEATURE:
<221> NAME/KEY: MOD_RES
<222> LOCATION: (13)..(13)
<223> OTHER INFORMATION: Phospho-Ser

<400> SEQUENCE: 16

Cys Tyr Ser Phe Ala Pro Pro Asn Thr Ser Leu Asn Ser Pro Ser Pro
1               5                   10                  15

Asn Tyr Ser Lys Tyr
            20

<210> SEQ ID NO 17
<211> LENGTH: 21
<212> TYPE: PRT
<213> ORGANISM: Mus sp.
<220> FEATURE:
<221> NAME/KEY: MOD_RES
<222> LOCATION: (15)..(15)
<223> OTHER INFORMATION: Phospho-Ser

<400> SEQUENCE: 17

Cys Tyr Ser Phe Ala Pro Pro Asn Thr Ser Leu Asn Ser Pro Ser Pro
1               5                   10                  15

Asn Tyr Ser Lys Tyr
            20

<210> SEQ ID NO 18
<211> LENGTH: 24
<212> TYPE: PRT
<213> ORGANISM: Mus sp.
<220> FEATURE:
<221> NAME/KEY: MOD_RES
<222> LOCATION: (20)..(20)
<223> OTHER INFORMATION: Phospho-Thr

<400> SEQUENCE: 18

Arg Thr Leu Pro His Val Val Asn Thr Met Pro His Thr Ser Ala Met
1               5                   10                  15

Asn Arg Leu Thr Pro Val Lys Thr
            20

<210> SEQ ID NO 19
<211> LENGTH: 652

```
<212> TYPE: PRT
<213> ORGANISM: Mus sp.
<220> FEATURE:
<221> NAME/KEY: MOD_RES
<222> LOCATION: (24)..(24)
<223> OTHER INFORMATION: Phospho-Thr
<220> FEATURE:
<221> NAME/KEY: MOD_RES
<222> LOCATION: (246)..(246)
<223> OTHER INFORMATION: Phospho-Ser
<220> FEATURE:
<221> NAME/KEY: MOD_RES
<222> LOCATION: (253)..(253)
<223> OTHER INFORMATION: Phospho-Ser
<220> FEATURE:
<221> NAME/KEY: MOD_RES
<222> LOCATION: (284)..(284)
<223> OTHER INFORMATION: Phospho-Ser
<220> FEATURE:
<221> NAME/KEY: MOD_RES
<222> LOCATION: (295)..(295)
<223> OTHER INFORMATION: Phospho-Ser
<220> FEATURE:
<221> NAME/KEY: MOD_RES
<222> LOCATION: (326)..(326)
<223> OTHER INFORMATION: Phospho-Ser
<220> FEATURE:
<221> NAME/KEY: MOD_RES
<222> LOCATION: (413)..(413)
<223> OTHER INFORMATION: Phospho-Ser
<220> FEATURE:
<221> NAME/KEY: MOD_RES
<222> LOCATION: (415)..(415)
<223> OTHER INFORMATION: Phospho-Ser
<220> FEATURE:
<221> NAME/KEY: MOD_RES
<222> LOCATION: (467)..(467)
<223> OTHER INFORMATION: Phospho-Ser
<220> FEATURE:
<221> NAME/KEY: MOD_RES
<222> LOCATION: (475)..(475)
<223> OTHER INFORMATION: Phospho-Ser
<220> FEATURE:
<221> NAME/KEY: MOD_RES
<222> LOCATION: (553)..(553)
<223> OTHER INFORMATION: Phospho-Thr

<400> SEQUENCE: 19

Met Ala Glu Ala Pro Gln Val Val Glu Thr Asp Pro Asp Phe Glu Pro
1               5                   10                  15

Leu Pro Arg Gln Arg Ser Cys Thr Trp Pro Leu Pro Arg Pro Glu Phe
            20                  25                  30

Asn Gln Ser Asn Ser Thr Thr Ser Ser Pro Ala Pro Ser Gly Gly Ala
        35                  40                  45

Ala Ala Asn Pro Asp Ala Ala Ala Ser Leu Ala Ser Ala Ser Ala Val
    50                  55                  60

Ser Thr Asp Phe Met Ser Asn Leu Ser Leu Leu Glu Glu Ser Glu Asp
65                  70                  75                  80

Phe Ala Arg Ala Pro Gly Cys Val Ala Val Ala Ala Ala Ala Ala Ala
            85                  90                  95

Ser Arg Gly Leu Cys Gly Asp Phe Gln Gly Pro Glu Ala Gly Cys Val
            100                 105                 110

His Pro Ala Pro Pro Gln Pro Pro Thr Gly Pro Leu Ser Gln Pro
        115                 120                 125

Pro Pro Val Pro Pro Ser Ala Ala Ala Ala Gly Pro Leu Ala Gly
    130                 135                 140

Gln Pro Arg Lys Thr Ser Ser Ser Arg Arg Asn Ala Trp Gly Asn Leu
145                 150                 155                 160
```

-continued

```
Ser Tyr Ala Asp Leu Ile Thr Lys Ala Ile Glu Ser Ala Glu Lys
            165                 170                 175

Arg Leu Thr Leu Ser Gln Ile Tyr Glu Trp Met Val Lys Ser Val Pro
        180                 185                 190

Tyr Phe Lys Asp Lys Gly Asp Ser Asn Ser Ser Ala Gly Trp Lys Asn
        195                 200                 205

Ser Ile Arg His Asn Leu Ser Leu His Ser Lys Phe Ile Arg Val Gln
    210                 215                 220

Asn Glu Gly Thr Gly Lys Ser Ser Trp Trp Met Leu Asn Pro Glu Gly
225                 230                 235                 240

Gly Lys Ser Gly Lys Ser Pro Arg Arg Ala Ala Ser Met Asp Asn
                245                 250                 255

Asn Ser Lys Phe Ala Lys Ser Arg Gly Arg Ala Ala Lys Lys Lys Ala
                260                 265                 270

Ser Leu Gln Ser Gly Gln Glu Gly Pro Gly Asp Ser Pro Gly Ser Gln
            275                 280                 285

Phe Ser Lys Trp Pro Ala Ser Pro Gly Ser His Ser Asn Asp Asp Phe
    290                 295                 300

Asp Asn Trp Ser Thr Phe Arg Pro Arg Thr Ser Ser Asn Ala Ser Thr
305                 310                 315                 320

Ile Ser Gly Arg Leu Ser Pro Ile Met Thr Glu Gln Asp Asp Leu Gly
                325                 330                 335

Asp Gly Asp Val His Ser Leu Val Tyr Pro Pro Ser Ala Ala Lys Met
                340                 345                 350

Ala Ser Thr Leu Pro Ser Leu Ser Glu Ile Ser Asn Pro Glu Asn Met
            355                 360                 365

Glu Asn Leu Leu Asp Asn Leu Asn Leu Leu Ser Ser Pro Thr Ser Leu
    370                 375                 380

Thr Val Ser Thr Gln Ser Ser Pro Gly Ser Met Met Gln Gln Thr Pro
385                 390                 395                 400

Cys Tyr Ser Phe Ala Pro Pro Asn Thr Ser Leu Asn Ser Pro Ser Pro
                405                 410                 415

Asn Tyr Ser Lys Tyr Thr Tyr Gly Gln Ser Ser Met Ser Pro Leu Pro
            420                 425                 430

Gln Met Pro Met Gln Thr Leu Gln Asp Ser Lys Ser Ser Tyr Gly Gly
        435                 440                 445

Leu Asn Gln Tyr Asn Cys Ala Pro Gly Leu Leu Lys Glu Leu Leu Thr
    450                 455                 460

Ser Asp Ser Pro Pro His Asn Asp Ile Met Ser Pro Val Asp Pro Gly
465                 470                 475                 480

Val Ala Gln Pro Asn Ser Arg Val Leu Gly Gln Asn Val Met Met Gly
                485                 490                 495

Pro Asn Ser Val Met Pro Ala Tyr Gly Ser Gln Ala Ser His Asn Lys
            500                 505                 510

Met Met Asn Pro Ser Ser His Thr His Pro Gly His Ala Gln Gln Thr
        515                 520                 525

Ala Ser Val Asn Gly Arg Thr Leu Pro His Val Val Asn Thr Met Pro
    530                 535                 540

His Thr Ser Ala Met Asn Arg Leu Thr Pro Val Lys Thr Pro Leu Gln
545                 550                 555                 560

Val Pro Leu Ser His Pro Met Gln Met Ser Ala Leu Gly Ser Tyr Ser
                565                 570                 575

Ser Val Ser Ser Cys Asn Gly Tyr Gly Arg Met Gly Val Leu His Gln
```

```
                        580                 585                 590
Glu Lys Leu Pro Ser Asp Leu Asp Gly Met Phe Ile Glu Arg Leu Asp
            595                 600                 605

Cys Asp Met Glu Ser Ile Ile Arg Asn Asp Leu Met Asp Gly Asp Thr
        610                 615                 620

Leu Asp Phe Asn Phe Asp Asn Val Leu Pro Asn Gln Ser Phe Pro His
625                 630                 635                 640

Ser Val Lys Thr Thr Thr His Ser Trp Val Ser Gly
                645                 650

<210> SEQ ID NO 20
<211> LENGTH: 27
<212> TYPE: PRT
<213> ORGANISM: Mus sp.
<220> FEATURE:
<221> NAME/KEY: MOD_RES
<222> LOCATION: (7)..(7)
<223> OTHER INFORMATION: Phospho-Ser

<400> SEQUENCE: 20

Glu Leu Leu Thr Ser Asp Ser Pro Pro His Asn Asp Ile Met Ser Pro
1               5                   10                  15

Val Asp Pro Gly Val Ala Gln Pro Asn Ser Arg
            20                  25

<210> SEQ ID NO 21
<211> LENGTH: 27
<212> TYPE: PRT
<213> ORGANISM: Mus sp.
<220> FEATURE:
<221> NAME/KEY: MOD_RES
<222> LOCATION: (15)..(15)
<223> OTHER INFORMATION: Phospho-Ser

<400> SEQUENCE: 21

Glu Leu Leu Thr Ser Asp Ser Pro Pro His Asn Asp Ile Met Ser Pro
1               5                   10                  15

Val Asp Pro Gly Val Ala Gln Pro Asn Ser Arg
            20                  25

<210> SEQ ID NO 22
<211> LENGTH: 6
<212> TYPE: PRT
<213> ORGANISM: Mus sp.

<400> SEQUENCE: 22

Pro Asn Ile Ile Leu Thr
1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Asn Ala Ile Ala Ala
1               5

<210> SEQ ID NO 24
<211> LENGTH: 10
<212> TYPE: PRT
```

```
<213> ORGANISM: Mus sp.

<400> SEQUENCE: 24

Pro Gly Ile Asn Ile Phe Pro Ser Pro Asp
1               5                   10

<210> SEQ ID NO 25
<211> LENGTH: 9
<212> TYPE: PRT
<213> ORGANISM: Mus sp.

<400> SEQUENCE: 25

Arg Leu Pro Ala Leu Leu Glu Lys Asn
1               5

<210> SEQ ID NO 26
<211> LENGTH: 12
<212> TYPE: PRT
<213> ORGANISM: Mus sp.

<400> SEQUENCE: 26

Arg Ser Gly Gly Gly Val Gly Asp Val Leu Arg Lys
1               5                   10

<210> SEQ ID NO 27
<211> LENGTH: 23
<212> TYPE: PRT
<213> ORGANISM: Mus sp.

<400> SEQUENCE: 27

Arg Asp Leu Asp Phe Ala Asn Asp Ala Ser Lys Val Leu Gly Ser Ile
1               5                   10                  15

Ala Gly Lys Leu Glu Lys Gly
            20

<210> SEQ ID NO 28
<211> LENGTH: 8
<212> TYPE: PRT
<213> ORGANISM: Mus sp.

<400> SEQUENCE: 28

Arg Asp Ala Pro Ser Arg Lys Lys
1               5

<210> SEQ ID NO 29
<211> LENGTH: 10
<212> TYPE: PRT
<213> ORGANISM: Mus sp.

<400> SEQUENCE: 29

Lys Met Ala Lys Gly Glu Glu Asn Lys Gly
1               5                   10

<210> SEQ ID NO 30
<211> LENGTH: 13
<212> TYPE: PRT
<213> ORGANISM: Mus sp.

<400> SEQUENCE: 30

Lys Asp Asp Ile Leu Lys Gly Gly Asp Val Val Arg Leu
1               5                   10

<210> SEQ ID NO 31
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
aactccagct agaaaatcag c                                              21

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
accaccatgg agaaggctgg                                                20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ccatgggaag atgttctggg                                                20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ctcagtgtag cccaggatgc                                                20
```

METHOD OF TREATING A METABOLIC DISORDER INDUCED BY OBESITY IN A SUBJECT IN NEED THEREOF BY ADMINISTERING MK2/3 INHIBITORS

This application is a continuation-in-part of International Application No. PCT/US2012/053552, filed Aug. 31, 2012, which claims the benefit of U.S. Provisional Application No. 61/530,851, filed Sep. 2, 2011, U.S. Provisional Application No. 61/618,551, filed Mar. 30, 2012, U.S. Provisional Application No. 61/621,407, filed Apr. 6, 2012, U.S. Provisional Application No. 61/676,091, filed Jul. 26, 2012, and U.S. Provisional Application No. 61/676,152, filed Jul. 26, 2012, all of which are herein incorporated by reference in their entireties.

GOVERNMENT SUPPORT

This invention was made with government support under Grant No. P01 HL087123 awarded by the National Institute of Health and the National Heart, Lung and Blood Institute, and Grant Nos. R01-DK049777, R01-DK083834 and R01-DK091618 awarded by the National Institute of Health and the National Institute of Diabetes and Digestive and Kidney Diseases. Thus, the United States Government has certain rights in the present invention.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described herein.

SEQUENCE LISTING

The instant application contains a Sequence Listing which has been submitted electronically in ASCII format and is hereby incorporated by reference in its entirety. Said ASCII copy, created on May 22, 2014, is named 19240.956US6_SL.txt and is 15,494 bytes in size.

BACKGROUND OF THE INVENTION

Obesity-induced insulin resistance and disturbances in liver glucose and fat metabolism increase the risk for heart disease, cancer, and other widespread and devastating diseases. Current treatments options are severely limited, leading to a critical unmet clinical need affecting hundreds of millions of overweight people in the current obesity epidemic. There is a need for methods to treat and diagnose obesity-induced insulin resistance and disturbances in liver glucose and fat metabolism. This invention addresses these needs.

SUMMARY OF THE INVENTION

The present disclosure provides methods for the treatment and/or prevention of a metabolic disorder. The present disclosure also provides methods for identifying a compound or a combination of compounds for the treatment and/or prevention of a metabolic disorder in a subject.

The present disclosure provides methods for the treatment and/or prevention of a metabolic disorder. In one aspect, the present disclosure provides a method of treating or preventing a metabolic disorder in a subject, wherein the disorder is induced by obesity, the method comprising reducing the activity of CaMKII, thereby treating or preventing the disorder. In one embodiment, the disorder is selected from the group consisting of Type 1 diabetes, Type 2 diabetes, insulin resistance and metabolic syndrome. In another embodiment, the treating or preventing affects glycogenolysis or gluconeogenesis in the subject. In one embodiment, the treating or preventing reduces hepatic glucose production, hyperglycemia, fatty liver, insulin resistance, insulin resistance-associated inflammation, insulin resistance-associated dyslipidemia, or any combination thereof, in the subject. In another embodiment, the treating or preventing reduces phosphorylation and/or activation of CaMKII. In one embodiment, the activity of CaMKII is a glucagon-induced activity. In one embodiment, the treating or preventing reduces expression of G6pc and/or Pck1 in a cell of the subject. In another embodiment, the treating or preventing reduces the amount of FoxO1 protein level in the nucleus of a cell of the subject. In another embodiment, the treating or preventing reduces phosphorylation of amino acid S284, S295, S326, S467, S475, S246, S253, S413, or S415, or any combination thereof, of the FoxO1 protein.

In another aspect, the present disclosure provides a method of treating or preventing coronary artery disease in a subject with a metabolic disorder, the method comprising reducing the activity of CaMKII in the subject, thereby treating or preventing the coronary artery disease. In one embodiment, the disorder is selected from the group consisting of Type 1 diabetes, Type 2 diabetes, insulin resistance and metabolic syndrome. In another embodiment, the treating or preventing affects glycogenolysis or gluconeogenesis in the subject. In one embodiment, the treating or preventing reduces hepatic glucose production, hyperglycemia, fatty liver, insulin resistance, insulin resistance-associated inflammation, insulin resistance-associated dyslipidemia, or any combination thereof, in the subject. In another embodiment, the treating or preventing reduces phosphorylation and/or activation of CaMKII. In one embodiment, the activity of CaMKII is a glucagon-induced activity. In one embodiment, the treating or preventing reduces expression of G6pc and/or Pck1 in a cell of the subject. In another embodiment, the treating or preventing reduces the amount of FoxO1 protein level in the nucleus of a cell of the subject. In another embodiment, the treating or preventing reduces phosphorylation of amino acid S284, S295, S326, S467, S475, S246, S253, S413, or S415, or any combination thereof, of the FoxO1 protein. In one embodiment, the treating or preventing comprises reducing CaMKII activity in a macrophage of the subject.

In one embodiment, the coronary artery disease is associated with atherogenesis and/or atherosclerosis. In another embodiment, the method further comprises treating or preventing heart failure, hypertension and/or renal disease. In another embodiment, the disorder is associated with advanced lesional macrophage apoptosis. In another embodiment, the disorder is associated with plaque necrosis. In another embodiment, the treating or preventing coronary artery disease in a subject with a metabolic disorder results in lowering hyperinsulinemia and/or dyslipidemia. In another embodiment, the treating or preventing coronary artery disease in a subject with a metabolic disorder results in lowering atherogenesis and/or atherosclerosis.

In one embodiment, the treating or preventing comprises a step of administering to the subject an antisense RNA that reduces expression of the gene encoding the CaMKII protein. In another embodiment, the treating or preventing comprises a step of administering to the subject a peptide or a polypeptide that specifically binds to the CaMKII protein. In another embodiment, the treating or preventing comprises a step of administering to the subject a small molecule. In one embodiment, the small molecule is a CaMKII inhibitor selected from the group consisting of KN-93, lavendustin C, CK59, Ant-CaMKIINtide, KN62, DY9760e, K-252a *Nocardiopsis* sp., H89 dihydrochloride, PP1 Analog II, 1NM-PP1, eEF-2 kinase inhibitor NH125, and STO-609.

In another aspect, the present disclosure provides a method of reducing hepatic glucose production in a subject, the method comprising reducing the activity of CaMKII, thereby resulting in the reduction of hepatic glucose in the subject. In one embodiment, the reducing hepatic glucose production reduces phosphorylation and/or activation of CaMKII. In another embodiment, the activity of CaMKII is a glucagon-induced activity. In another embodiment, the reducing hepatic glucose production reduces expression of G6pc and/or Pck1 in a cell of the subject. In one embodiment, the reducing hepatic glucose production reduces hyperglycemia, fatty liver, insulin resistance, insulin resistance-associated inflammation, insulin resistance-associated dyslipidemia, or any combination thereof, in the subject. In another embodiment, the reducing hepatic glucose production reduces the amount of FoxO1 protein level in the nucleus of a cell of the subject. In another embodiment, the reducing hepatic glucose production reduces phosphorylation of amino acid S284, S295, S326, S467, S475, S246, S253, S413, or S415, or any combination thereof, of the FoxO1 protein.

In one embodiment, the reducing hepatic glucose production comprises a step of administering to the subject an antisense RNA that reduces expression of the gene encoding the CaMKII protein. In another embodiment, the reducing hepatic glucose production comprises a step of administering to the subject a peptide or a polypeptide that specifically binds to the CaMKII protein. In another embodiment, the reducing hepatic glucose production comprises a step of administering to the subject a small molecule. In one embodiment, the small molecule is a CaMKII inhibitor selected from the group consisting of KN-93, lavendustin C, CK59, Ant-CaMKIINtide, KN62, DY9760e, K-252a *Nocardiopsis* sp., H89 dihydrochloride, PP1 Analog II, 1NM-PP1, eEF-2 kinase inhibitor NH125, and STO-609.

In another aspect, the present disclosure provides a method for identifying a compound that inhibits the activity of CaMKII, the method comprising a) contacting a cell with a CaMKII fusion protein, wherein the CaMKII fusion protein comprises an acceptor fluorophore protein at one terminus, and a donor fluorophore protein at the other terminus; and b) measuring FRET efficiency in the absence and in the presence of a test compound, wherein a greater FRET efficiency in the presence of the test compound compared to the FRET efficiency in the absence of the test compound indicates that the test compound inhibits the activity of CaMKII.

In one embodiment the acceptor fluorophore protein is selected from the group consisting of mOrange, mStrawberry, Venus, yellow fluorescent protein, cyan fluorescent protein, red fluorescent protein and green fluorescent protein.

In another embodiment, the cell is a HEK293T cell, a hepatocyte, a U2OS cell, a HeLa cell, a murine embryonic fibroblast (MEF) or a macrophage. In another embodiment, the cell is from a Insr−/− mouse, a Camk2g−/− mouse, a Foxo1−/− mouse, a db/db mouse, a ob/ob mouse, a p38−/− mouse, a Non Obese Diabetes (NOD) mouse, a mouse fed a high fat diet, or a streptozotocin-treated mouse. In another embodiment, the cell is from a mouse expressing a mutant FoxO1 protein. In one embodiment, the mutant FoxO1 protein comprises alanine substitutions at S284, S295, S326, S467, S475, S246, S253, S413, or S415, or aspartic acid substitutions at S284, S295, S326, S467, S475, S246, S253, S413, or S415, or any combination thereof.

In one embodiment, the cell is subjected to ER stress. In another embodiment, the cell is treated with glucagon, 8-bromo cAMP, H89 dihydrochloride, Xestospongin C, forskolin, saturated fatty acids, or any combination thereof.

In one aspect, the present disclosure provides a method of treating or preventing a metabolic disorder in a subject, wherein the disorder is induced by obesity, the method comprising reducing the activity of IP3R1, IP3R2 or IP3R3, thereby treating or preventing the disorder. In another aspect, the present disclosure provides a method of treating or preventing a metabolic disorder in a subject, wherein the disorder is induced by obesity, the method comprising reducing the activity of calcineurin, thereby treating or preventing the disorder.

In one embodiment, the disorder is selected from the group consisting of Type 1 diabetes, Type 2 diabetes, insulin resistance, obesity, and metabolic syndrome.

In another embodiment, the treating or preventing affects glycogenolysis or gluconeogenesis in the subject.

In one embodiment, the treating or preventing reduces hepatic glucose production, hyperglycemia, fatty liver, insulin resistance, insulin resistance-associated inflammation, insulin resistance-associated dyslipidemia, or any combination thereof, in the subject.

In one embodiment, the treating or preventing comprises a step of administering to the subject an antisense RNA that reduces expression of the gene encoding the IP3R1 protein, IP3R2 protein or IP3R3 protein. In another embodiment, the treating or preventing comprises a step of administering to the subject a peptide or a polypeptide that specifically binds to the IP3R1 protein, IP3R2 protein or IP3R3 protein.

In one embodiment, the treating or preventing comprises a step of administering to the subject a small molecule. In one embodiment, the small molecule is a IP3R1 protein inhibitor, IP3R2 protein inhibitor or IP3R3 protein inhibitor.

In one embodiment, the treating or preventing comprises a step of administering to the subject an antisense RNA that reduces expression of the gene encoding the calcineurin protein. In another embodiment, the treating or preventing comprises a step of administering to the subject a peptide or a polypeptide that specifically binds to the calcineurin protein.

In one embodiment, the treating or preventing comprises a step of administering to the subject a small molecule. In another embodiment, the small molecule is a calcineurin inhibitor.

In another aspect, the present disclosure provides a method for identifying a compound that inhibits the activity of IP3R1, IP3R2 or IP3R3, the method comprising a) contacting a cell with a test compound; and b) measuring IP3R1, IP3R2 or IP3R3 activity, wherein a reduction of the activity of IP3R1, IP3R2 or IP3R3 in the presence of the compound compared to the activity of IP3R1, IP3R2 or IP3R3 in the absence of the compound indicates that the compound is an inhibitor of IP3R1, IP3R2 or IP3R3, respectively.

In one embodiment, the activity is measured by calcium release into the cytosol of the cell after stimulation with an inducer of IP3. In one embodiment, calcium release is measured by an increase in the fluorescence of a cytosolic calcium dye. In one embodiment, the cytosolic calcium dye is Fluo-3.

In another aspect, the present disclosure provides a method for identifying a compound that inhibits the activity of calcineurin, the method comprising a) contacting a cell with a test compound; and b) measuring calcineurin activity, wherein a reduction of the activity of calcineurin in the presence of the compound compared to the activity of calcineurin in the absence of the compound indicates that the compound is an inhibitor of calcineurin.

In one embodiment, the activity of calcineurin is measured through detection of phosphatase activity using a calcineurin substrate peptide. In one embodiment, the cell is a HEK293T cell, a hepatocyte, a U2OS cell, a HeLa cell, or a murine embryonic fibroblast (MEF). In another embodiment, the cell is from a db/db mouse, a ob/ob mouse, a Non Obese Diabetes (NOD) mouse, a mouse fed a high fat diet, or a streptozotocin-treated mouse.

In one embodiment, the cell is treated with glucagon, H89 dihydrochloride, insulin, forskolin, an inducer of ER stress, tunicamycin, saturated fatty acids, or any combination thereof.

In another aspect, the present disclosure provides a method of treating or preventing a metabolic disorder in a subject, wherein the disorder is induced by obesity, the method comprising reducing the activity of p38, thereby treating or preventing the disorder. In another aspect, the present disclosure provides a method of treating or preventing a metabolic disorder in a subject, wherein the disorder is induced by obesity, the method comprising reducing the activity of MK2/3, thereby treating or preventing the disorder.

In one embodiment, the disorder is selected from the group consisting of Type 1 diabetes, Type 2 diabetes, insulin resistance, obesity and metabolic syndrome.

In one embodiment, the treating or preventing affects glycogenolysis or gluconeogenesis in the subject. In another embodiment, the treating or preventing reduces hepatic glucose production, hyperglycemia, fatty liver, insulin resistance, insulin resistance-associated inflammation, insulin resistance-associated dyslipidemia, or any combination thereof, in the subject.

In one embodiment, the treating or preventing comprises a step of administering to the subject an antisense RNA that reduces expression of the gene encoding the p38 protein. In another embodiment, the treating or preventing comprises a step of administering to the subject a peptide or a polypeptide that specifically binds to the p38 protein. In another embodiment, the treating or preventing comprises a step of administering to the subject a small molecule. In one embodiment, the small molecule is a p38 inhibitor.

In one embodiment, the treating or preventing comprises a step of administering to the subject an antisense RNA that reduces expression of the gene encoding the MK2/3 protein. In another embodiment, the treating or preventing comprises a step of administering to the subject a peptide or a polypeptide that specifically binds to the MK2/3 protein. In one embodiment, the treating or preventing comprises a step of administering to the subject a small molecule. In one embodiment, the small molecule is a MK2/3 inhibitor.

In another aspect, the present disclosure provides a method for identifying a compound that inhibits the activity of p38, the method comprising a) contacting a cell with a test compound; and b) measuring p38 kinase activity, wherein a reduction of the kinase activity of p38 in the presence of the compound compared to the kinase activity of p38 in the absence of the compound indicates that the compound is an inhibitor of p38. In another aspect, the present disclosure provides a method for identifying a compound that inhibits the activity of MK2/3, the method comprising a) contacting a cell with a test compound; and b) measuring MK2/3 kinase activity, wherein a reduction of the kinase activity of MK2/3 in the presence of the compound compared to the kinase activity of MK2/3 in the absence of the compound indicates that the compound is an inhibitor of MK2/3.

In one embodiment, p38 kinase activity is measured using a p38-specific peptide. In one embodiment, MK2/3 kinase activity is measured using a MK2/3-specific peptide.

In one embodiment, the cell is a HEK293T cell, a hepatocyte, a U2OS cell, a HeLa cell, a macrophage or a murine embryonic fibroblast (MEF). In another embodiment, the cell is from a Insr−/− mouse, a db/db mouse, a ob/ob mouse, a Non Obese Diabetes (NOD) mouse, a mouse fed a high fat diet, or a streptozotocin-treated mouse. In another embodiment, the cell is treated with glucagon, 8-bromo cAMP, H89 dihydrochloride, forskolin, saturated fatty acids, or any combination thereof.

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE FIGURES

The patent or application file contains at least one drawing executed in color. Copies of this patent or patent application publication with color drawing(s) will be provided by the United States Patent and Trademark Office upon request and payment of the necessary fee.

FIG. 1A. CaMKII enzyme activity was assayed in triplicate wells of primary mouse HCs stimulated with 100 nM glucagon (Gluc) or vehicle control (Veh) for the indicated times (*$P<0.05$ and **$P<0.01$ vs. Veh; mean±S.E.M.). FIGS. 1B-1J. Extracts of HCs or liver were probed for phospho-CaMKII, total CaMKII, and β-actin by immunoblot assay. FIG. 1B. HCs were incubated with 00 nM glucagon for the indicated times; FIG. 1C. Glucagon was added to HCs that were pre-treated for 1 h with vehicle control (Veh) or 5 μM BAPTA-AM; FIG. 1D. Glucagon was added to HCs that were pre-treated with 0.5 μM xestospongin (XesC) or to HCs from Ip3r1fl/fl mice transduced with adeno-LacZ control or adeno-Cre (bar graph=Ip3r1 mRNA levels); FIG. 1E. Glucagon was added to HCs that were pre-treated for 1 h with vehicle control (Veh) or 10 μM H89. FIG. 1F. HCs were incubated with 100 μM 8-bromo-cAMP for the indicated times. FIGS. 1G-1J. In vivo experiments. In FIG. 1G, mice were treated for 30 min with 200 μg kg−1 body weight of glucagon i.p., and in FIG. 1H, mice were pre-treated with 10 pmol g–1 xestospongin C or vehicle control i.p. 4 days prior to glucagon treatment. In FIGS. 1I-1J, mice were fed ad libitum or fasted for 12 h, or fasted for 12 h and then re-fed for 4 h.

FIG. 2A Primary mouse hepatocytes were transduced with adenoviral vectors expressing LacZ, CA-CaMKII, or K43A-CaMKII at an MOI of 20. Cells were serum depleted overnight and then incubated with forskolin (10 μm) for 14 h in serum- and glucose-free media. Glucose content was measured as described. FIG. 2B As in FIG. 2A except that WT and Camk2g–/– hepatocytes were used. FIG. 2C Primary mouse hepatocytes were infected with adenoviral vectors expressing LacZ, CA-CaMKII, or K43A-CaMKII at an MOI of 20. Cells were serum depleted overnight and were then incubated with forskolin (10 μm) for 5 h in serum-free media. RNA was isolated and gene expression was analyzed by real-time Q-PCR. (*, $P<0.05$; , $P<0.01$) FIG. 2D Primary hepatocytes from WT and Camk2g–/– mice were serum depleted overnight and then incubated with forskolin (10 μm) for 5 h in serum-free media. RNA was assayed for G6pc and Pck1 mRNA by real-time Q-PCR. (, $P<0.01$; ****, $P<0.0005$). FIG. 2E. As in FIG. 2D, except that glucagon (100 nm) was used to stimulate gluconeogenesis. (*, $P<0.05$; **, $P<0.01$)

FIG. 3A Primary hepatocytes from WT and Camk2g–/– mice were transduced with an adenovirus expressing murine GFP-FoxO1 at an MOI of 2. Cells were serum depleted overnight and then incubated for 5 h in serum-free media. FoxO1 subcellular localization was assessed by indirect immunofluorescence. Bar, 10 μm. Data are quantified in the right panel. (**, $P<0.0005$). FIG. 3B Primary mouse hepatocytes were transduced with adenoviral vectors expressing LacZ, CA-CaMKII, or K43A-CaMKII at an MOI of 20. 4 h later cells were infected with murine GFP-FoxO1 adenovirus at an MOI of 5. Cells were serum depleted overnight and then incubated for 5 h in serum-free media. FoxO1 subcellular localization was subsequently assessed by indirect immunofluorescence. Bar, 5 μm. Data are quantified in the lower panel. (**, $P<0.0005$; ####  $P<0.0005$). FIG. 3C Primary mouse hepatocytes were infected with adenoviral vectors expressing LacZ or CA-CaMKII. Nuclear extracts were assayed by immunoblot for FoxO1 and nucleophosmin (nuclear loading control).

FIG. 4A Blood glucose concentrations in 8 week-old WT and Camk2g–/– mice fasted for 12 h. (*, $P<0.05$) FIG. 4B 8-10 week-old WT and Camk2g–/– mice were fasted for 18 h and then challenged with pyruvate (2 mg kg-1). (*, $P<0.05$; , $P<0.01$; *, $P<0.005$) FIG. 4C Liver G6pc and Pck1 gene expression levels in WT and Camk2g–/– mice fasted for 12 h. (, $P<0.01$; *, $P<0.001$) FIG. 4D As in FIG. 4C, except that liver nuclear extracts were assayed for FoxO1 and nucleophosmin by immunoblot. Densitometric quantification of these data are shown in the lower panel. (***, $P<0.001$)

FIG. 5A Blood glucose levels at day 5 after a 12-h fast. (*, $P<0.001$) FIG. 5B Liver gluconeogenic gene expression in mice fasted for 12 h. (, $P<0.01$; ***, $P<0.001$). FIG. 5C. As in FIG. 5B, except that liver nuclear extracts were assayed for FoxO1 and nucleophosmin by immunoblot. FIG. 5D Liver glycogen content. FIG. 5E-5F LacZ or K43A-CaMKII treated mice were injected with 200 μg kg-1 body weight of glucagon intraperitoneally and sacrificed 30 min later. Liver G6pc mRNA was assayed, and liver sections were examined for glycogen content by PAS staining, which was quantified as percent of PAS-positive hepatocytes (n=4 mice). Bar, 20 μm.

FIG. 6A Blood glucose was assayed at day 6 after a 12-h fast. (*, $P<0.05$) FIG. 6B Pyruvate challenge test was conducted in mice fasted for 17 h. (*, $P<0.05$; , $P<0.01$; *, $P<0.005$) FIG. 6C G6pc and Pck1 mRNA levels were assayed in mice fasted for 12 h. (*, $P<0.05$) or fed ad libitum (*, $P<0.05$; ***, $P<0.005$). FIG. 6D Liver nuclear extracts were assayed for FoxO1 and nucleophosmin by immunoblot in fed mice injected with either control LacZ (n=5) or CA-CaMKII (n=5).

FIG. 7A Primary hepatocytes from WT and Camk2g–/– mice were transduced with an adenovirus expressing FoxO1-ADA at an MOI of 0.2. Cells were serum depleted overnight and then incubated with forskolin (10 μm) for 5 h in serum-free media. RNA was isolated and gene expression was analyzed by real-time Q-PCR. (**, $P<0.01$; #, $P<0.05$; ##, $P<0.01$) FIG. 7B 8 wk-old WT mice were injected with $1.5\times10^9$ pfu of adenovirus containing either control LacZ (n=5) or K43A-CaMKII (n=10). One day later, half of the adeno-K43A-CaMKII injected mice received $0.1\times10^9$ pfu of adenovirus containing FoxO1-ADA, while rest of the mice received the LacZ control. Blood glucose levels were assayed at day 5 after a 12-h fast. (*, $P<0.05$; #, $P<0.05$) FIG. 7C Liver nuclear extracts were assayed for FoxO1 and nucleophosmin by immunoblot FIG. 7D G6pc, Pck1 and Igfbp1 mRNA levels were assayed from livers of mice fasted for 12 h. (*, $P<0.05$; **, $P<0.01$; #, $P<0.05$)

FIG. 8B lean or morbidly obese humans. Densitometry quantification is shown for the mouse data in FIG. 8A; $P<0.001$.

FIG. 9A-9B, Plasma insulin in fed and fasted WT (n=10) and Camk2g–/– (n=7) DIO-obese male mice. FIG. 9C, Insulin tolerance test (ITT) in WT and Camk2g–/– mice (n=5). FIG. 9D, Body weight. FIGS. 9E-G, Plasma insulin, glucose tolerance test (GTT), and liver mRNAs for FoxO1 targets in DIO mice before or after treatment with adeno-LacZ control or adeno-K43ACaMKII (dominant-negative) (n=6). In FIG. 9E, *, $P<0.01$ vs. pre-adeno and <0.005 vs. day 7 LacZ. In FIG. 9G, *, $P<0.01$. FIG. 9H-I, ob/ob obese mice were treated with the CaMKII inhibitor KN93 or its inactive homologue KN92. Blood glucose and expression of G6pc and Pck1 in the liver were then assayed (duplicate values that varied by 10%).

FIGS. 10A-B, 10D, Liver TG content, plasma lipids, and liver Tnfam-RNA were assayed in WT (n=10) and Camk2g–/– (n=7)

mice after DIO diet for 20 wks (G, *, P<0.005; H, *, P<0.05 **, P<0.01; I, *, P<0.05). FIG. 10C, Immunoblots of p- and total S6K and Sortilin-1 in livers from DIO mice before or after treatment with adeno-LacZ control or adeno-K43ACaMKII (dominant-negative).

FIG. 18. Hepatocyte CaMKII γ deficiency lessens hyperinsulinemia and subsequent dyslipidemia by decreasing gluconeogenesis (GNG) and hepatic glucose production (HGP) via a mechanism involving nuclear exclusion of FoxO1.

FIG. 19A, WT mice were fed ad libitum or fasted for 12 h (upper); or fasted for 12 h and then re-fed for 4 h (lower). Liver extracts were immunoblotted for p-CaMKII, total CaMKII, and β-actin. FIG. 19B, Blood glucose in 12-h-fasted WT and Camk2g−/− mice, or in WT mice treated with adeno-LacZ or adeno-K43A-CaMKII (*, P<0.001). FIG. 19C, Blood glucose in 18-h-fasted WT and Camk2g−/− mice challenged with 2 mg/kg pyruvate. FIG. 19D, Hepatic G6pc and Pck1 mRNA in mice treated with adeno-LacZ or adeno-K43A-CaMKII (*, P<0.01). FIG. 19E, Nuclear extracts from the livers from the experiment in B (left) were immunoblotted for FoxO1 and nucleophosmin (Np; nuclear loading control) and quantified by densitometry (*, P<0.001). FIG. 19F, Primary HCs from WT or Camk2g−/− mice (left)—or WT HCs transduced with adeno-LacZ, constitutive-active CaMKII (T287D), or K43A-CaMKII (right)—were (co)-transduced with adeno-GFP-FoxO1. FoxO1 subcellular localization in serum-starved cells was quantified by image analysis of immunofluorescence confocal microscopy data (*, #, P<0.005). FIG. 19G, HCs from WT or Camk2g−/− mice were transduced with adeno-LacZ or FoxO1-ADA, then serum-starved, treated with forskolin, and assayed for G6pc mRNA (*, P<0.01). FIG. 19H, Ser residues that were phosphorylated in serum starved WT HCs but not in CaMKII-deficient HCs; DBD=DNA-binding domain. FIG. 19H discloses SEQ ID NO: 6.

FIG. 21A shows direct signaling and transcriptional regulation of glycogenolysis and gluconeogenesis during hepatic glucose production. FIG. 21D is a diagram showing macrophage death in advanced atherosclerosis. FIG. 21E is a diagram that shows the calcium-sensing signaling molecule calcium/calmodulin-dependent protein kinase II (CaMKII). FIG. 21E(A) discloses SEQ ID NO: 7. FIG. 21F is a diagram showing a mechanism of macrophage death in atherosclerosis. FIGS. 21H-L show that glucagon activates CaMKII in cultured primary murine hepatocytes. FIG. 21H shows that glucagon activates CaMKII in primary murine hepatocytes. FIG. 21I shows the link between glucagon and activation of CaMKII. FIG. 21J shows the link between glucagon and an increase in calcium. FIG. 21K shows that glucagon, via IP3R, activates hepatic CaMKII in vivo. FIG. 21L shows that fasting activates and re-feeding suppresses hepatic CaMKII in vivo. FIG. 21AA presents in vivo evidence in fasting adeno-K43A CaMKII-transduced WT mice of hepatic Gcpc/Pck1 mRNA and nuclear FoxO1. FIG. 21AB presents in vivo evidence in glucagon-treated adeno-K43A CaMKII-transduced WT mice of hepatic Gcpc mRNA and glycogen stores. FIG. 21AC presents in vivo evidence in fasting adeno-CA CaMKII transduced WT mice of a blood glucose and pyruvate challenge test. FIG. 21AD presents in vivo evidence in fasting and fed adeno-CA CaMKII transduced WT mice of hepatic Gcpc/Pck1 mRNA.

FIG. 21AE presents in vivo evidence in fasting and fed adeno-CA CaMKII transduced WT mice of nuclear FoxO1. FIGS. 21AF-AH show causative evidence that the suppressive effects of CaMKII deficiency on HGP are mediated through nuclear exclusion of FoxO1. FIG. 21AF is a diagram that indicates that, without being bound by theory, the effects of CaMKII deficiency can be prevented by transduction with constitutively nuclear FoxO-ADA. FIG. 21AG shows G6pc/Pck1 in forskolin-treated primary hepatocytes. FIG. 21AH shows blood glucose levels and relative mRNA levels in blood glucose and FoxO1 genes in fasting adeno-K43A CaMKII-transduced mice. FIG. 21AI is a diagram that shows the relevance of CaMKII-mediated regulation of glucose production through FoxO1, to obesity and insulin resistance. FIG. 21AJ shows that CaMKIIγ is activated in the liver of obese mice. FIG. 21AK shows that CaMKIIγ is activated in the liver of obese humans. FIG. 21AL shows that CaMKIIγ deficiency reduces plasma insulin and improves insulin sensitivity in obese mice. FIG. 21AM shows that CaMKIIγ deficiency improves hepatic response to acute insulin in obese mice. FIGS. 21AN-AO show that acute adenovirus-mediated inhibition of CaMKIIγ improves metabolic parameters in ob/ob mice. FIG. 21AP shows that acute adenovirus-mediated inhibition of CaMKIIγ decreases expression of G6pc and Pck1 in livers of ob/ob mice. FIG. 21AQ shows that acute adenovirus-mediated inhibition of CaMKIIγ decreases nuclear FoxO1 in livers of ob/ob mice. FIG. 21AR shows that CaMKIIγ deficiency reduces fatty liver in obese mice. FIG. 21AS shows that CaMKII inhibition decreases hepatic lipogenic gene expression in ob/ob mice. FIG. 21AT shows that CaMKIIγ deficiency partially reduces plasma cholesterol and triglycerides in obese mice. FIG. 21AU shows that CaMKIIγ deficiency reduces heatic TNFα in obese mice. FIG. 21AV shows a working model of the regulation of glucagon-induced glucose production. Future studies include, but are not limited to, a direct assay of HGP and glucose utilization (clamp study), the mechanism of CaMKII regulation of nuclear FoxO1, how CaMKII deficiency can affect hepatic ER stress and vice-versa, what effect does CaMKII deficiency have on insulin sensitivity, whether CaMKII in liver macrophages plays a role in obesity, the effect of CaMKII on atherosclerosis and the therapeutic potential of CaMKII.

FIG. 22A RNA from HCs from 3 WT and 3 Camk2g$^{-/-}$ mice and mouse brain from a WT mouse were probed for the indicated Camk2 isoform mRNAs by RT-PCR. FIG. 22B HCs from WT and Camk2g$^{-/-}$ mice were serum-depleted overnight and then incubated with forskolin (10 μm) for 14 h in serum- and glucose-free media, and then glucose in the medium was assayed (**P<0.01 vs. WT in each group; mean±S.E.M.). FIG. 22C HCs from WT mice were transduced with adenoviral vectors expressing LacZ, CA-CaMKII, or KD-CaMKII at an MOI of 20 and then assayed for glucose production as in FIG. 22B (*P<0.05 and ** P<0.01 vs. LacZ in each group; mean±S.E.M.). FIG. 22D-22E HCs similar to those in FIG. 22B and FIG. 22C were serum-depleted overnight and then incubated for 5 h with 10 μM forskolin or 100 nM glucagon in serum-free media, as indicated. RNA was assayed for G6pc and Pck1 mRNA by RT-qPCR (*P<0.05 and **P<0.01 vs. LacZ or WT in each group; mean±S.E.M.).

FIG. 23A Blood glucose of 12-h-fasted 8-wk/o WT and Camk2g$^{-/-}$ mice (*P<0.05). FIG. 23B As in FIG. 23A, but the mice were fasted for 18 h and then challenged with 2 mg kg$^{-1}$ pyruvate (FIG. 23B). (*P<0.05; P<0.01; *P<0.005; mean±S.E.M.). FIG. 23C Liver G6pc and Pck1 mRNA in 12-h-fasted WT and Camk2g$^{-/-}$ mice (P<0.01; *P<0.001; mean±S.E.M.). FIG. 23D WT and Camk2g$^{-/-}$ mice were injected i.p. with glucagon (200 μg kg$^{-1}$) and sacrificed 30 min later. Liver G6pc mRNA was assayed (*P<0.05; mean±S.E.M.). FIGS. 23E-G 9-wk/o WT mice were administered 1.5×10$^9$ pfu of adeno-LacZ or KD-CaMKII, and 5 days later the following parameters were assayed in 12-h-fasted mice: FIG. 23E, blood glucose (*P<0.001; mean±S.E.M.); FIG. 23F, liver G6pc and Pck1 mRNA (P<0.01; *P<0.001; mean±S.E.M.); and FIG. 23G, liver glycogen content and PAS-positive cells (P<0.01; mean±S.E.M.). Panel G also shows liver glycogen content in fasted WT and Camk2g$^{-/-}$ mice (*P<0.05; mean±S.E.M.). For all panels, n=5/group except panel D, where n=4/group.

FIG. 24A HCs from WT and Camk2g$^{-/-}$ mice were transduced with an adenovirus expressing murine GFP-FoxO1 at an MOI of 2. Cells were serum-depleted overnight and then incubated for 5 h in serum-free media. FoxO1 subcellular localization was assessed by indirect immunofluorescence. Bar, 10 μm. Data are quantified in the right panel. (#P<0.0005; mean±S.E.M.). FIG. 24B HCs were transduced with adenoviral vectors expressing LacZ, CA-CaMKII, or KD-CaMKII at an MOI of 20 and then transduced 4 h later with adeno-GFP-FoxO1, followed by fluorescence microscopy and quantification as in FIG. 24A (#P<0.005 vs. LacZ; mean±S.E.M.). Bar, 5 μm. FIG. 24C HCs were transduced with adeno-LacZ or CA-CaMKII and then adeno-GFP-FoxO1 as in FIG. 24B. After incubation in serum-depleted medium o.n. and then serum-free medium for 5 h, the cells were treated with 100 nM insulin for the indicated times. FoxO1 subcellular localization was quantified as in FIG. 24B (*P<0.005 vs. LacZ in each group; mean±S.E.M.). FIG. 24D Nuclear FoxO1 and nucleophosmin were probed by immunoblot in livers from fasted WT mice, Camk2g$^{-/-}$ mice, or WT mice treated with adeno-LacZ or KD-CaMKII; from fed WT mice treated with adeno-LacZ or CA-CaMKII; or from fed WT mice treated for 30 min with 200 μg kg−1 body weight of glucagon i.p. For the glucagon experiment, the average FoxO:Np densitometric ratio values are in the graph (*P=0.029; blemishes in lanes 6 and 8 were excluded from the densitometry analysis).

FIG. 25A HCs from wild-type or L-FoxO1 knockout mice were transduced with adeno-LacZ or CA-CaMKII. The cells were serum-depleted overnight and then incubated for 5 h in the absence or presence of forskolin (10 μm) in serum-free media. RNA was assayed for G6pc mRNA (*P<0.001; mean±S.E.M.). FIG. 25B HCs from WT and Camk2g$^{-/-}$ mice were administered adeno-LacZ or FoxO1-ADA at an MOI of 0.2. Cells were serum-depleted overnight and then incubated for 5 h with 10 μM forskolin in serum-free media. RNA was assayed for G6pc and Pck1 mRNA (**P<0.01 vs. WT groups; #P<0.05 and ##P<0.01 vs. Camk2g$^{-/-}$/LacZ group; mean±S.E.M.). Inset, the nuclei from a parallel set of cells were probed for FoxO1 and nucleophosmin by immunoblot; the average densitometric ratio appears below each pair of lanes. FIG. 25C-E 8-wk/o WT mice were administered adeno-LacZ or KD-CaMKII, and then one day later, half of the adeno-KD-CaMKII mice received adeno-FoxO1-ADA, while the other half received adeno-LacZ control. Blood glucose levels were assayed at day 5 after a 12-h fast (*P<0.05 vs.

LacZ/LacZ; #P<0.05 vs. KD/LacZ; n=5/group; mean±S.E.M.), and liver was assayed for nuclear FoxO1 protein (**P<0.01 vs. KD/LacZ; mean±S.E.M.); G6pc, Pck1 and Igfbp1 mRNA (*P<0.05 and **P<0.01 vs. LacZ/LacZ; #P<0.05 vs. KD/LacZ; n=3/group; mean±S.E.M.). The inset to panel E shows the level of hemagglutinin (HA)-tagged KD-CaMKII protein (anti-HA immunoblot).

Figures 26B, 26C:
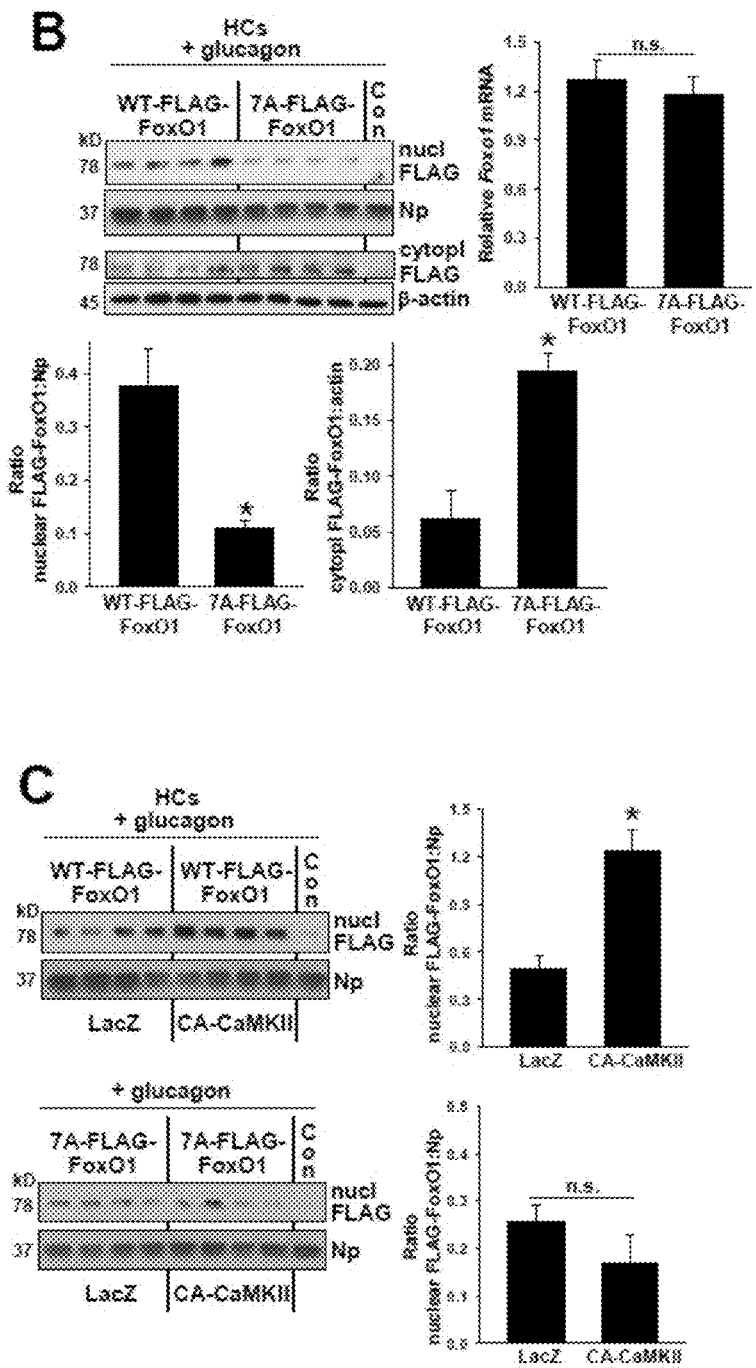

FIGS. 26A-C. The role of non-AKT-phospho-sites of FoxO1 in CaMKII-mediated FoxO1 nuclear localization. FIG. 26A HCs from WT and Camk2g$^{-/-}$ mice were transduced with adeno-FLAG-FoxO1 at an MOI of 2. Cells were serum-depleted overnight and then incubated for 5 h in serum-free media. FoxO1 was immunopurified using anti-FLAG, followed by reduction, alkylation, and proteolytic digestion. Phosphorylated peptides were enriched by TiO$_2$ chromatography and then analyzed by LC-MS/MS as described in Experimental Procedures. The table shows spectral count number, Debunker score, and Ascore of phosphorylated peptides (SEQ ID NOS 8-18, respectively, in order of appearance) in KO and WT samples; Δ in the peptide sequence indicates the phosphorylation site. The cut-off values for spectral count #, Debunker score, and Ascore are set at 5, 0.5 and 12 respectively. The spectra of peptides with scores that are below these values (italics) were checked manually to eliminate uncertain phosphorylation sites (FIGS. 31A-B for WT peptides 4 and 5; and http://fields.scripps.edu/published/foxo1_Tabas_2012/, incorporated by reference in their entireties, for KO peptides 7, 10, and 11). The KO/WT ratio of spectral counts was calculated only for peptides with a combined spectral count in KO and WT>10. FIG. 26B HCs from L-FoxO1 mice were transfected with expression plasmids encoding murine Flag-FoxO1 or Flag-7A-FoxO1 mutant. After 48 h, the cells were serum-depleted overnight and then incubated with glucagon (100 nm) for 4 h in serum-free media. Nuclear extracts were assayed by immunoblot for Flag and nucleophosmin (nuclear loading control), and RNA from a parallel set of cells was probed for Foxo1 mRNA by RT-qPCR. Densitometric quantification of the mRNA and immunoblot data is shown in the graph (*P<0.005; mean±S.E.M.) FIG. 26C Similar to FIG. 26B, except the HCs were transduced with adeno-LacZ or CA-CaMKII one day after the transfection with the WT or mutant FoxO1 plasmids (*P=0.003; mean±S.E.M.).

Figures 27A, 27B:
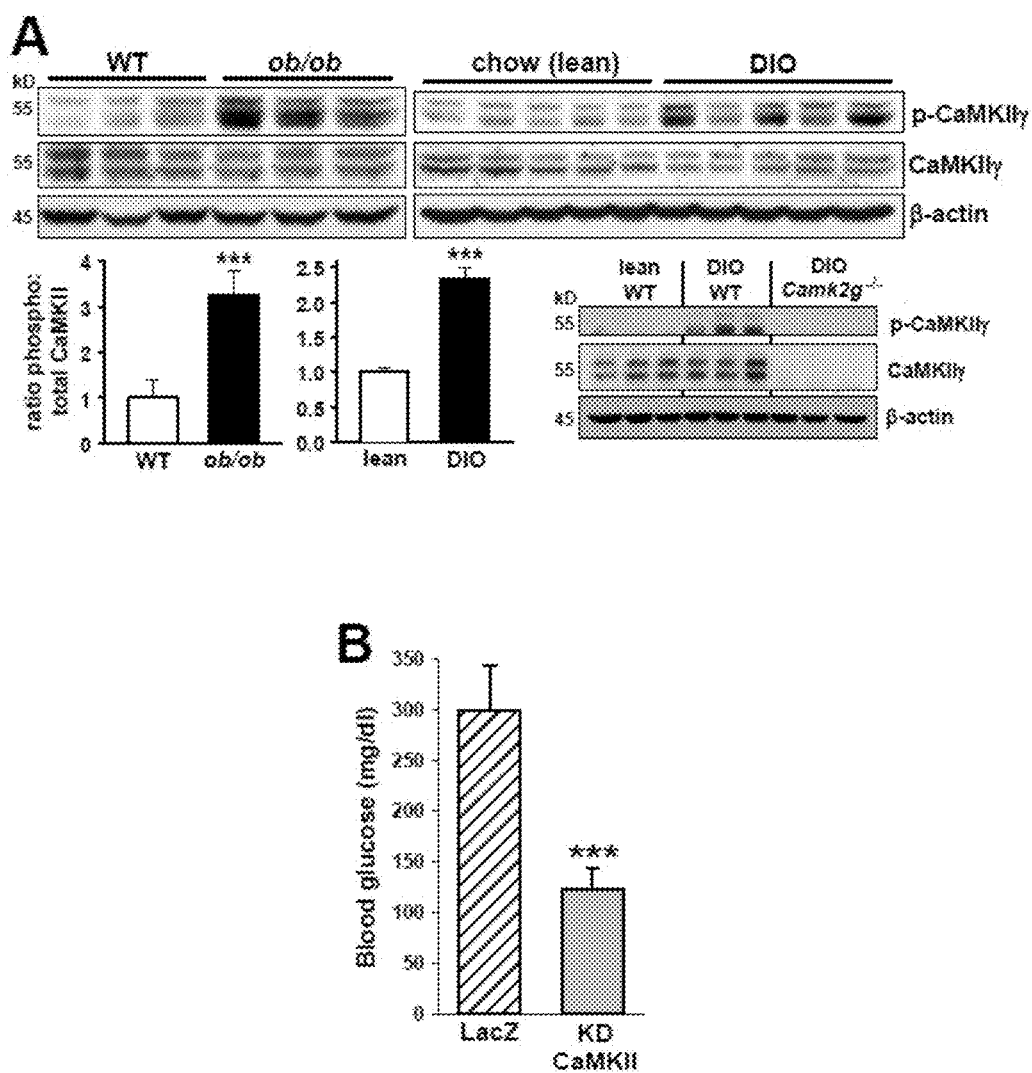
Figure 27C:
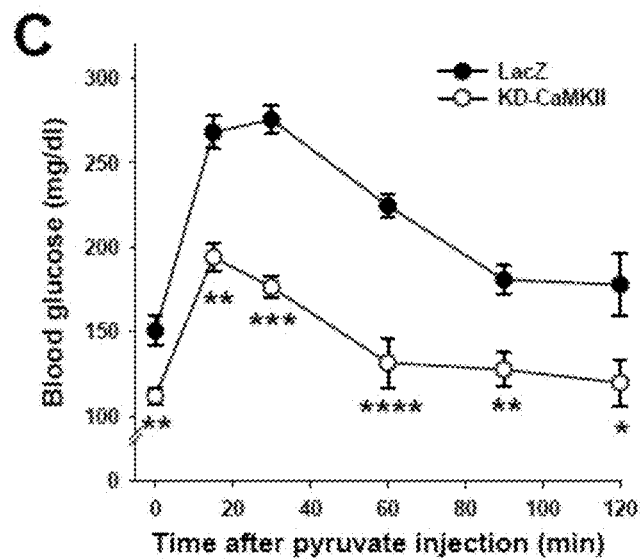
Figure 27D:
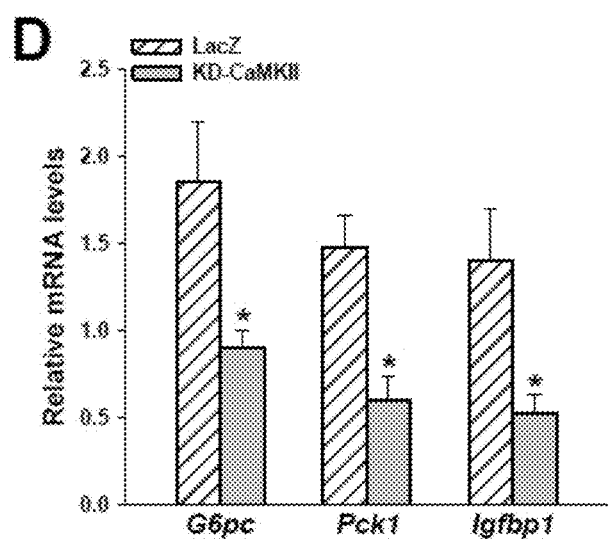

FIGS. 27A-D. The role of CaMKII in hepatic glucose metabolism in obesity FIG. 27A Liver extracts from 10-wk/o WT or ob/ob mice, or WT mice fed a chow or high-calorie diet for 20 wks (diet-induced obesity; DIO), were probed for p- and total CaMKIIγ and β-actin by immunoblot. Densitometric quantification is shown in the bar graph (***P<0.001; mean±S.E.M.). Antibody specificity is shown by the absence of p- and total CaMKIIγ bands in liver extracts from DIO Camk2g$^{-/-}$ mice. FIGS. 27B-D Fasting blood glucose, blood glucose after pyruvate challenge, and liver G6pc, Pck1 and Igfbp1 mRNA in ob/ob mice before or after treatment with adeno-LacZ or KD-CaMKII (n=5/group; *P<0.05, P<0.01, *P<0.005, and ****P<0.001 vs. LacZ; mean±S.E.M.).

Figure 28A:
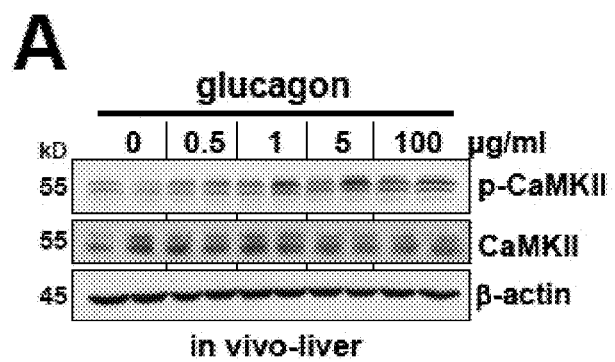
Figure 28B:
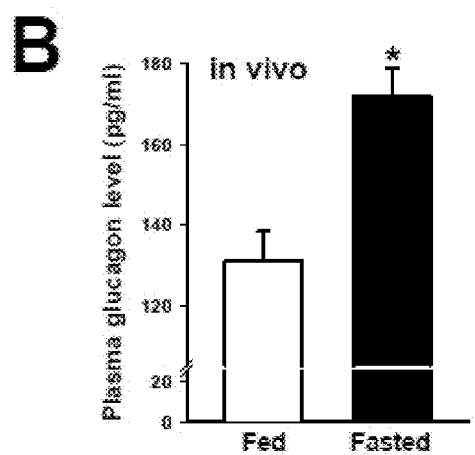
Figure 28C:
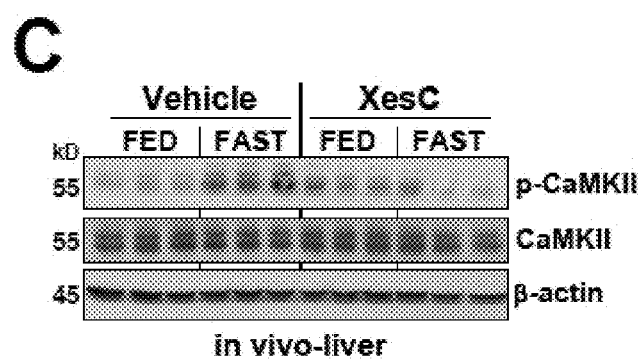
Figure 28D:
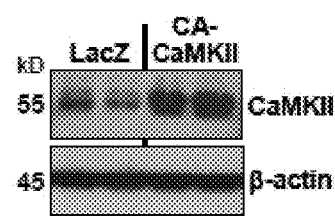
Figure 28E:
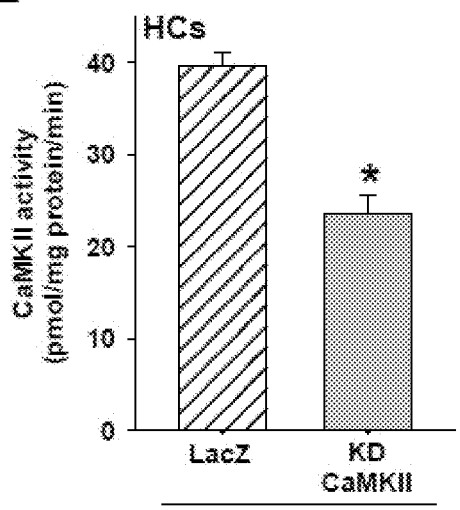
Figures 28F, 28G:
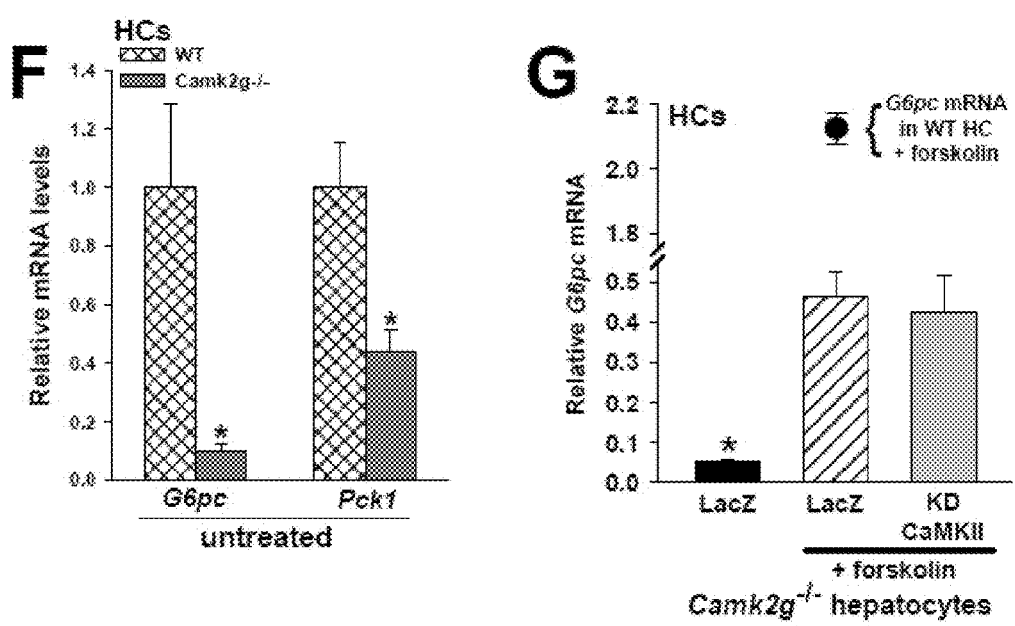

FIGS. 28A-G. (Related to FIGS. 1 and 22). FIG. 28A Mice were injected i.p. with the indicated doses of glucagon and sacrificed 15 min later. The livers were probed for phospho- and total CaMKII and β-actin by immunoblot. FIG. 28B Mice (n=5/group) were fed ad libitum or fasted for 12 h and then plasma was assayed for glucagon (*P=0.007; mean±S.E.M.). FIG. 28C Mice were injected i.p. with 10 pmol g$^{-1}$ xestospongin C (XesC) or vehicle control each day for 4 days and then fed ad libitum or fasted for 12 h. Liver phospho-CaMKII, total CaMKII, and β-actin levels were assayed by immunoblot. FIG. 28D Immunoblot of CaMKII in HCs transduced with adeno-LacZ vs. CA-CaMKII. FIG. 28E HCs were transduced with adeno-LacZ or KD-CaMKII. Cells were serum-depleted overnight and then assayed for CaMKII activity (*P<0.005; mean±S.E.M.). FIG. 28F G6pc and Pck1 mRNA levels in untreated HCs from WT vs. Camk2g$^{-/-}$ mice (*P 0.05). In comparison to the mRNA levels in forskolin-treated WT HCs in FIG. 22D, the levels of G6pc and Pck1 in untreated WT HCs was ~165-fold and ~2500-fold lower, respectively. FIG. 28G HCs from Camk2g$^{-/-}$ mice were transduced with adeno-LacZ or KD-CaMKII as in FIG. 28D, incubated for 14 h in media ±forskolin, and then assayed for G6pc mRNA (*P<0.05 vs. the other 2 groups; mean±S.E.M.). The black circle represents the G6pc mRNA value for forskolin-treated, adeno-LacZ WT HCs (1.99±0.3; *P<0.001 vs. Camk2g$^{-/-}$ value; mean±S.E.M.).

Figure 29A:
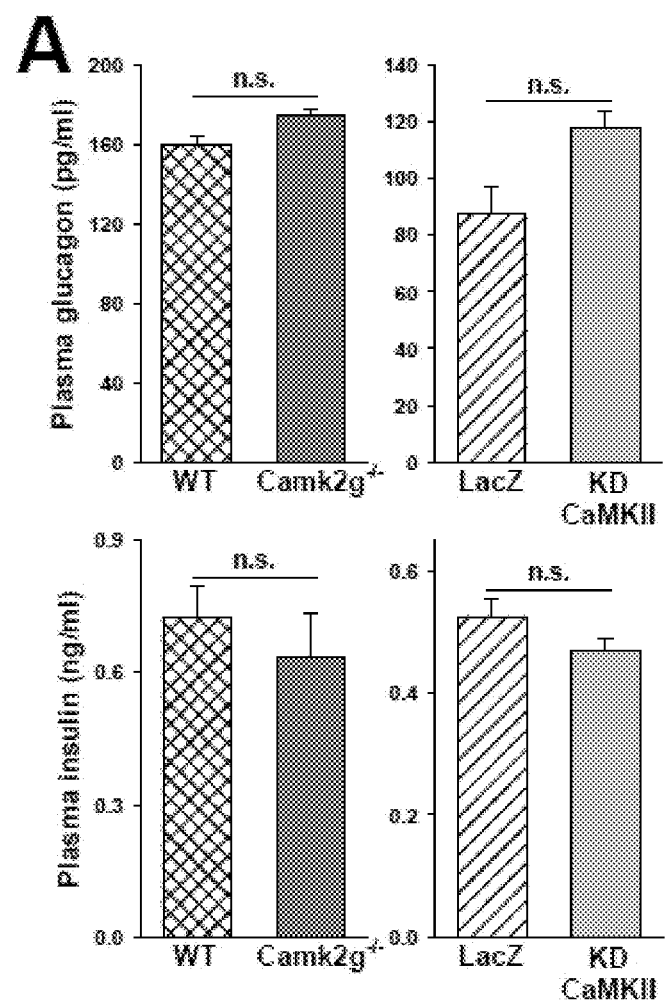
Figures 29B, 29C:
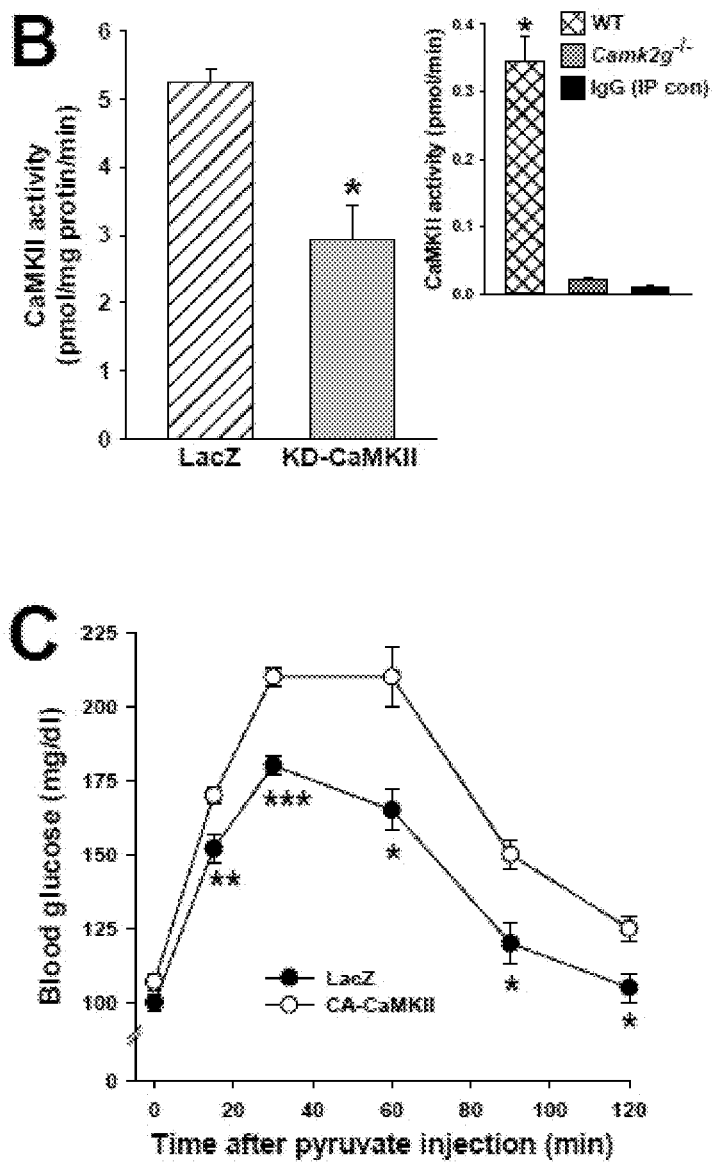
Figures 29D, 29E:
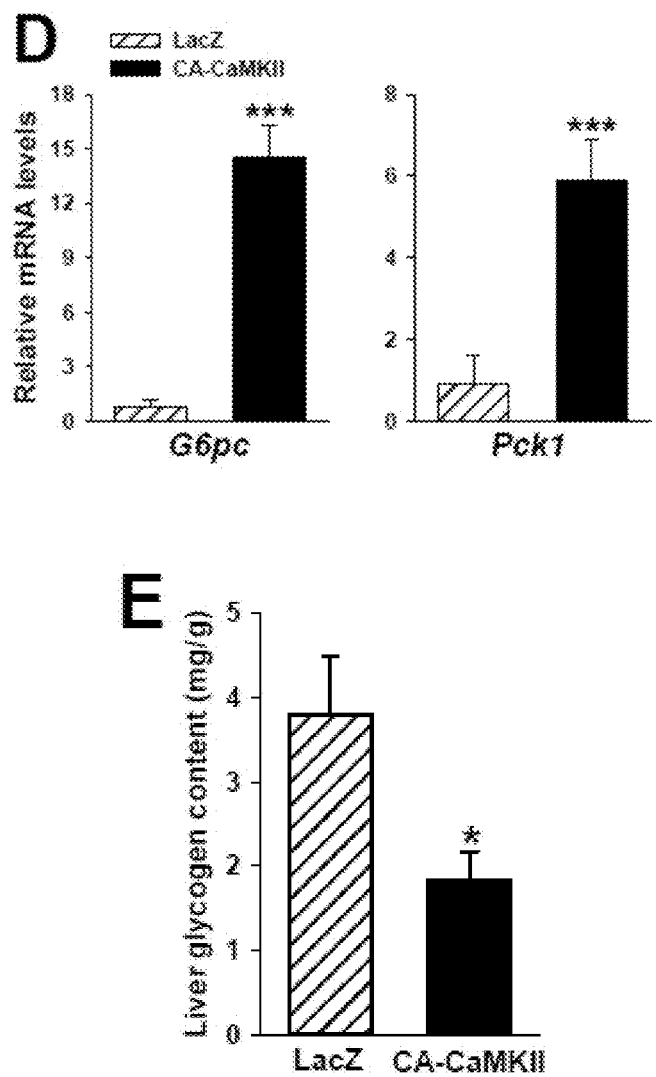

FIGS. 29A-E. Related to FIG. 23. FIG. 29A Fasting glucagon and insulin levels were assayed in the plasma of WT and Camk2g$^{-/-}$ mice and in WT mice treated with adeno-LacZ or KD-CaMKII (n=5/group); n.s., non-significant. FIG. 29B CaMKII was immunoprecipitated (IP) from the livers of mice treated with adeno-LacZ or KD-CaMKII and then assayed for CaMKII activity. The data in the inset validates the CaMKII assay by showing that kinase activity was negligible in the livers of Camk2g$^{-/-}$ mice and when non-immune IgG was used in the CaMKII IP part of the protocol (*P<0.006; mean±S.E.M.). FIG. 29C-D WT mice were treated with adeno-LacZ or CA-CaMKII (n=5/group). After 5 days, the mice were assayed for blood glucose before or after pyruvate challenge, and then, after a period of ad libitum feeding, the mice were sacrificed, and the livers were assayed for G6pc and Pck1 mRNA (*P<0.05;  P<0.01; *, P<0.005; mean±S.E.M.). FIG. 29E Mice were treated with adeno-LacZ or CA-CaMKII (n=5/group). After 5 days, the mice were fasted overnight and then the livers were assayed for glycogen content (*P<0.05; mean±S.E.M.).

Figures 30A, 30B:
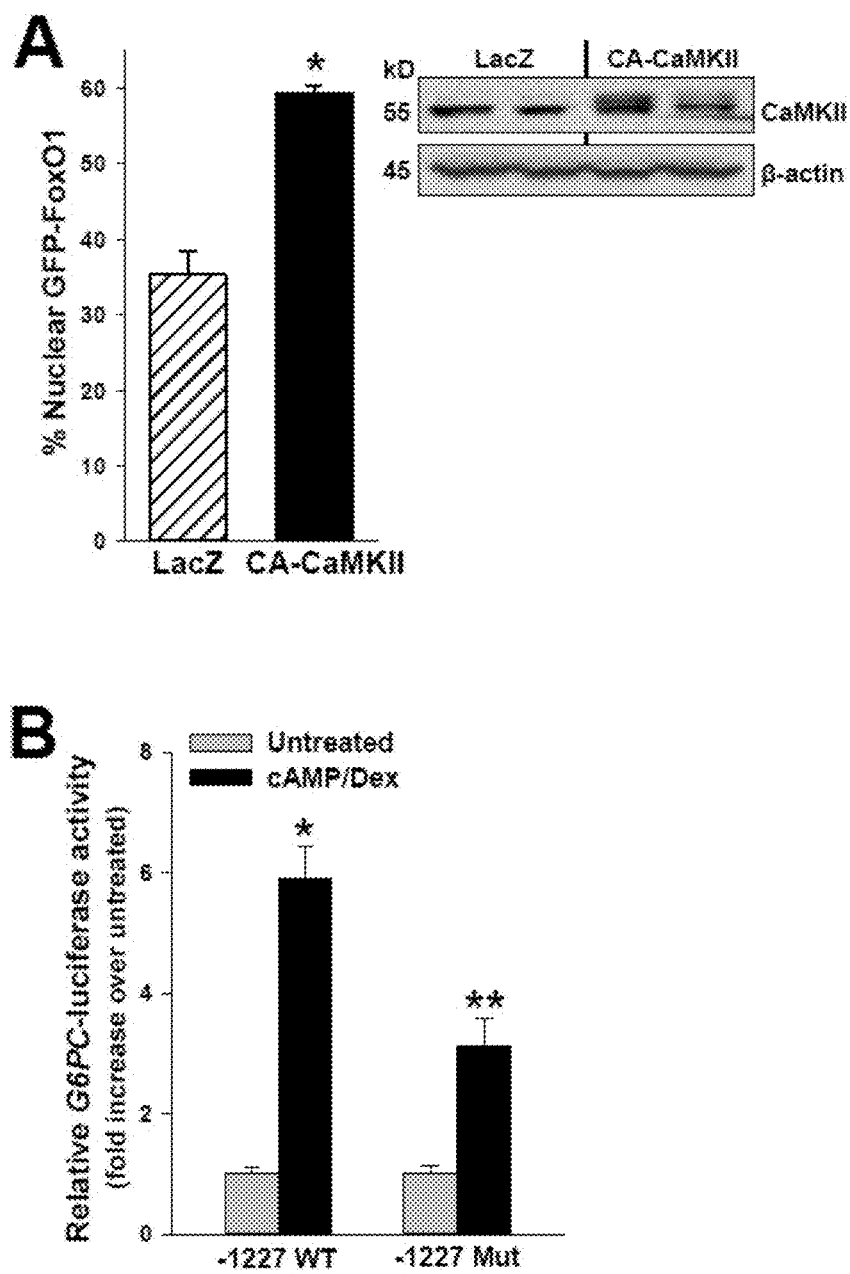
Figures 30C, 30D:
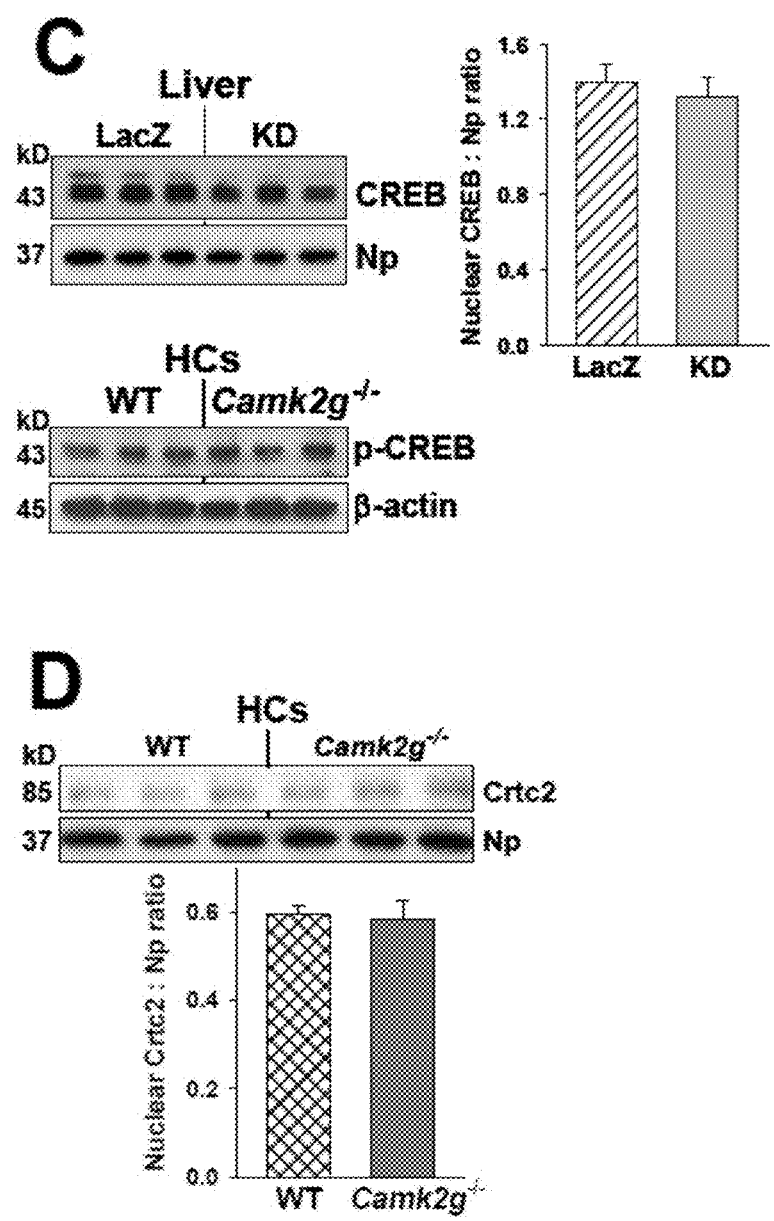

FIGS. 30A-D. Related to FIGS. 24-25. FIG. 30A HCs were transduced with adeno-LacZ or CA-CaMKII at an MOI of 1 and transduced 4 h later with adeno-GFP-FoxO1. After incubation in serum-depleted medium o.n. and then serum-free medium for 5 h, the cells were treated with 100 nM insulin for 15 min. FoxO1 subcellular localization was quantified. (*P<0.005; mean±S.E.M.). Inset, the lysate from a parallel set of cells were probed for CaMKII and β-actin by immunoblot. FIG. 30B FAO hepatocytes were transfected with luciferase fusion constructs encoding nucleotides −1227 to +57 of the G6PC promoter containing either intact (−1227 WT) or mutated FoxO binding sites (−1227 Mut). Relative luciferase activity was measured following a 16-h incubation in the absence or presence of 0.1 mM cAMP and 1 μM dexamethasone. *P<0.001 vs. all other groups; **P=0.009 vs. untreated Mut (mean±S.E.M.). FIG. 30C Nuclei from the livers of the adeno-LacZ and KD-CaMKII-treated mice were probed by immunoblot for CREB or Crtc2 and nucleophosmin (Np), and cell extracts of glucagon-treated HCs from WT or Camk2g$^{-/-}$ mice were probed for p-CREB and β-actin. FIG. 30D Nuclei from glucagon-treated HCs from WT or Camk2g$^{-/-}$ mice were probed for Crtc2 and nucleophosmin (Np).

Figures 31A, 31B:
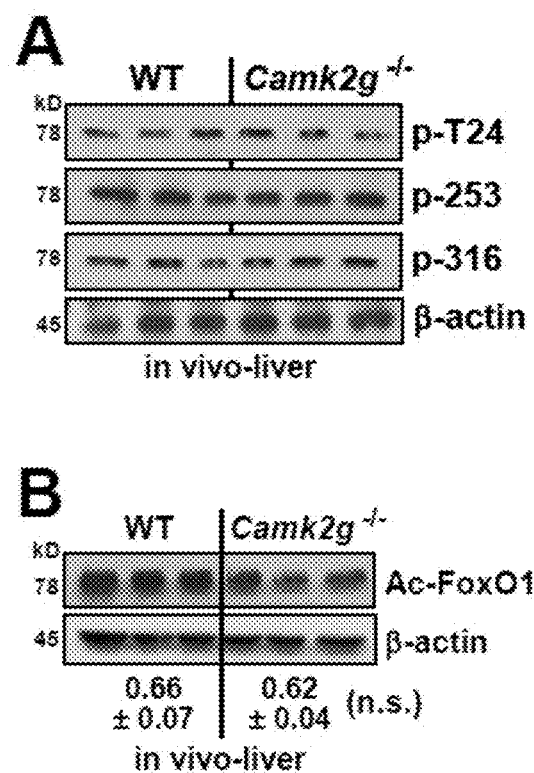
Figure 31D:
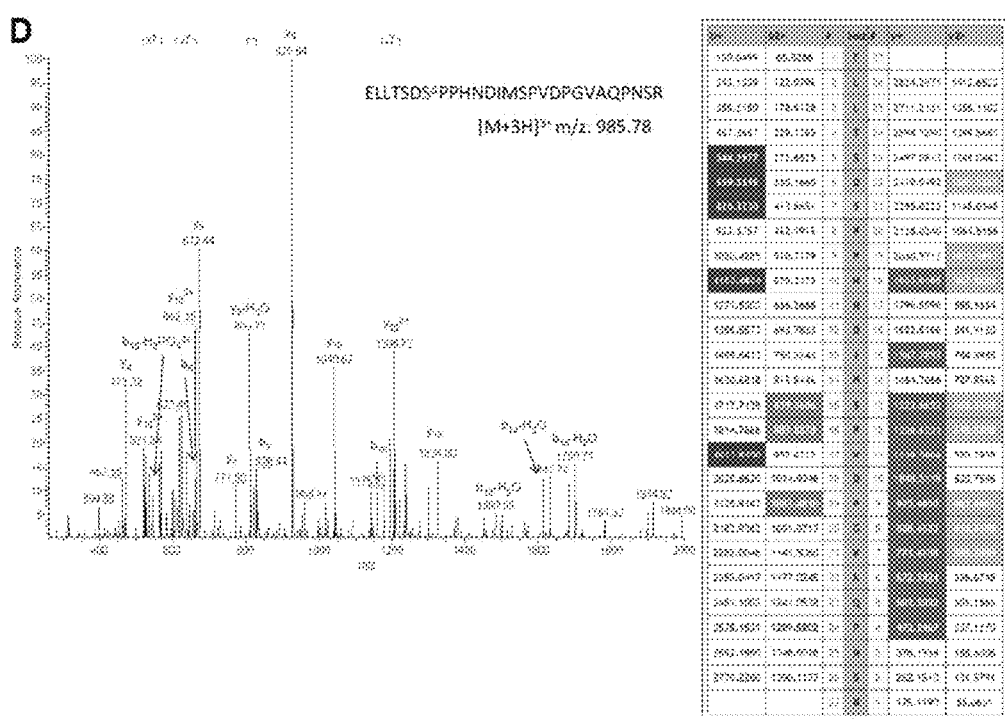
Figure 31E:
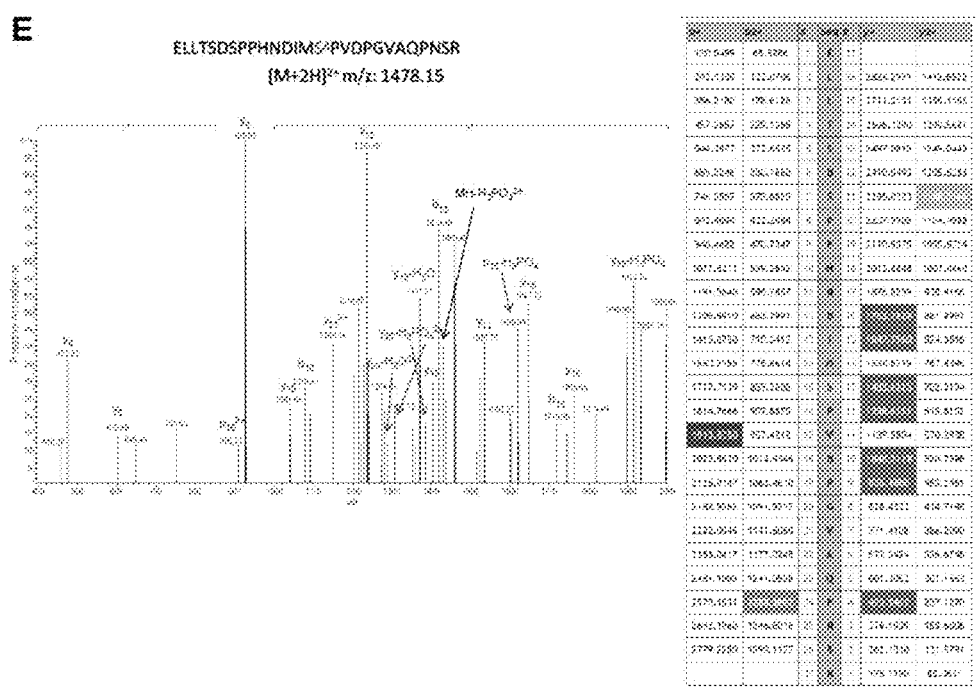
Figure 31F:
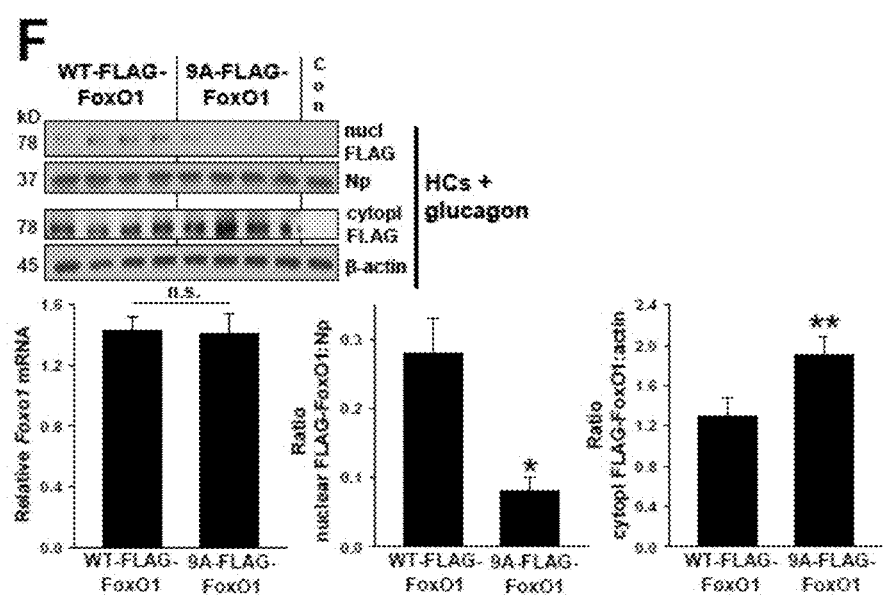

FIGS. 31A-F. Related to FIG. 26—FoxO1 phosphorylation. FIG. 31A Extracts of liver from fasted WT and Camk2g$^{-/-}$ mice were immunoblotted for phospho-T24-, 253-, and 316-FoxO1 and β-actin. FIG. 31B Extracts of liver from fasted adeno-FoxO1-treated WT and Camk2g$^{-/-}$ mice immunoblotted for acetylated FoxO1 (Ac-FoxO1) and β-actin. Average Ac-FoxO:β-actin densitometric ratio values appear below the blot; n.s., non-significant. FIG. 31C Murine FoxO1 sequence (SEQ ID NO: 19), with identified phospho-sites in bold font; summary of data for key residues relevant to FIGS. 26, 31F, and 32 are shown below in the bullet list below the sequence. FIG. 31D MS/MS spectra and b, y ion table of phosphorylated peptide #4 (SEQ ID NO: 20) from Camk2g$^{-/-}$ HCs. FIG. 31E MS/MS spectra and b, y ion table of phosphorylated peptide #5 (SEQ ID NO: 21) from Camk2g$^{-/-}$ HCs. FIG. 31F Similar to the experiment in FIG. 26B, except the L-Foxo1 HCs were transfected with FLAG-9A-FoxO1 mutant instead of FLAG-7A-Foxo1 (*P=0.006; **P=0.02; mean±S.E.M.).

Figure 32A:
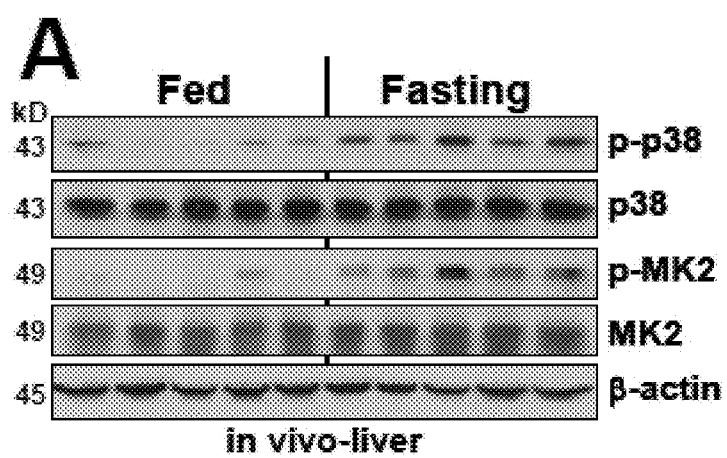
Figure 32B:
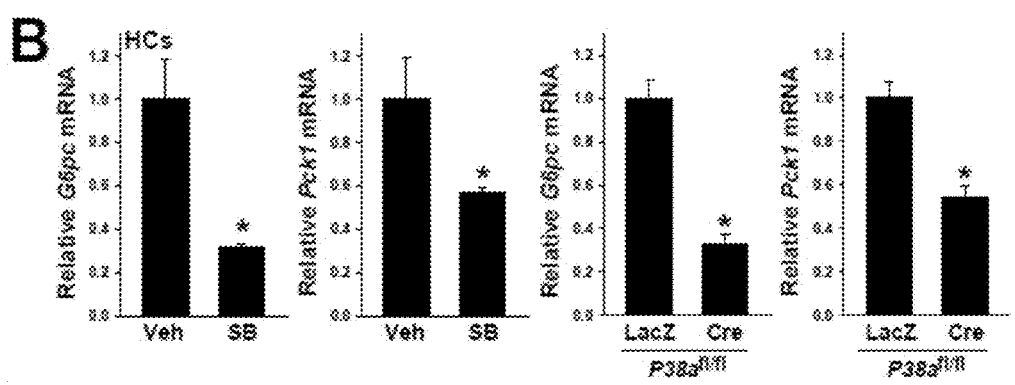
Figure 32C:
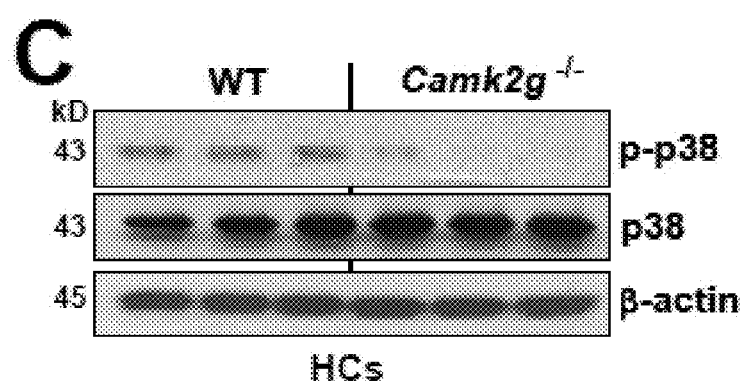
Figure 32D:
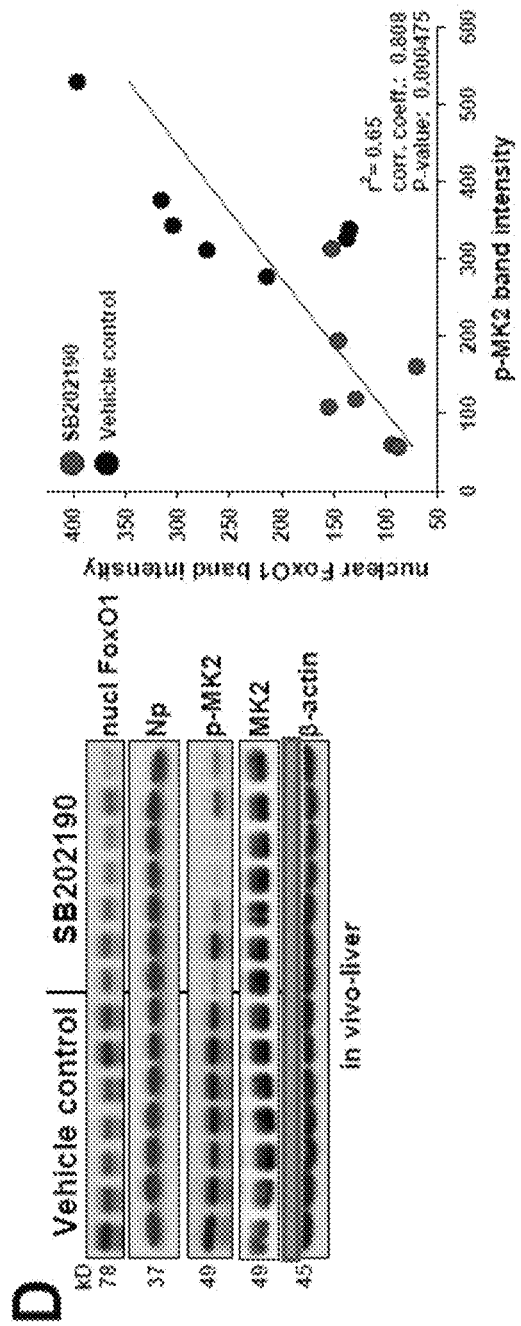
Figure 32E:
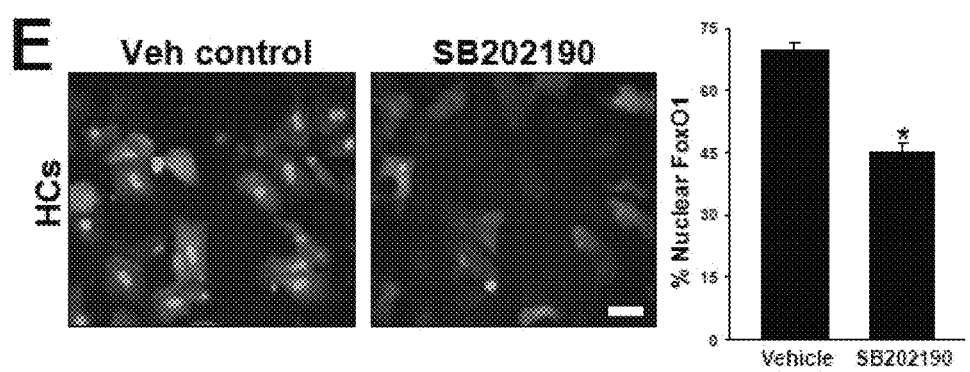

FIG. 32A-E. Related to FIG. 26—p38. FIG. 32A Mice were fed ad libitum or fasted for 12 h. Liver phospho-p38, total p38, p-MK2, total MK-2, and β-actin were assayed by immunoblot. FIG. 32B WT HCs were serum-depleted overnight and then incubated for 5 h with 100 nm glucagon in serum-free media with or without SB202190; or glucagon was added to HCs from P38a$^{fl/fl}$ mice treated with adeno-LacZ (control) or adeno-Cre. RNA was assayed for G6pc and Pck1 mRNA (*P<0.05; mean±S.E.M.). FIG. 32C HCs from fasting WT and Camk2g$^{-/-}$ mice were assayed for p-p38, total p38, and β-actin. FIG. 32D WT mice were injected i.p. with 12.5 mg kg$^{-1}$ body weight of p38 inhibitor (SB202190) or vehicle control. 12 h later, the mice were injected with an additional dose of SB202190 and fasted overnight. The livers were assayed for nuclear FoxO1, nucleophosmin, p-MK2, total MK-2, and β-actin. The correlation between nuclear FoxO1 and p-MK2 band intensities is shown in the graph. FIG. 32E Adeno-GFP-FoxO1-transduced HCs were serum-depleted overnight, and then incubated for 5 h in serum-free media with SB202190 or vehicle (Veh) control. FoxO1 localization was assessed by indirect immunofluorescence (Bar, 10 µm; *P<0.05; mean±S.E.M.).

Figures 33A, 33B, 33C, 33D:
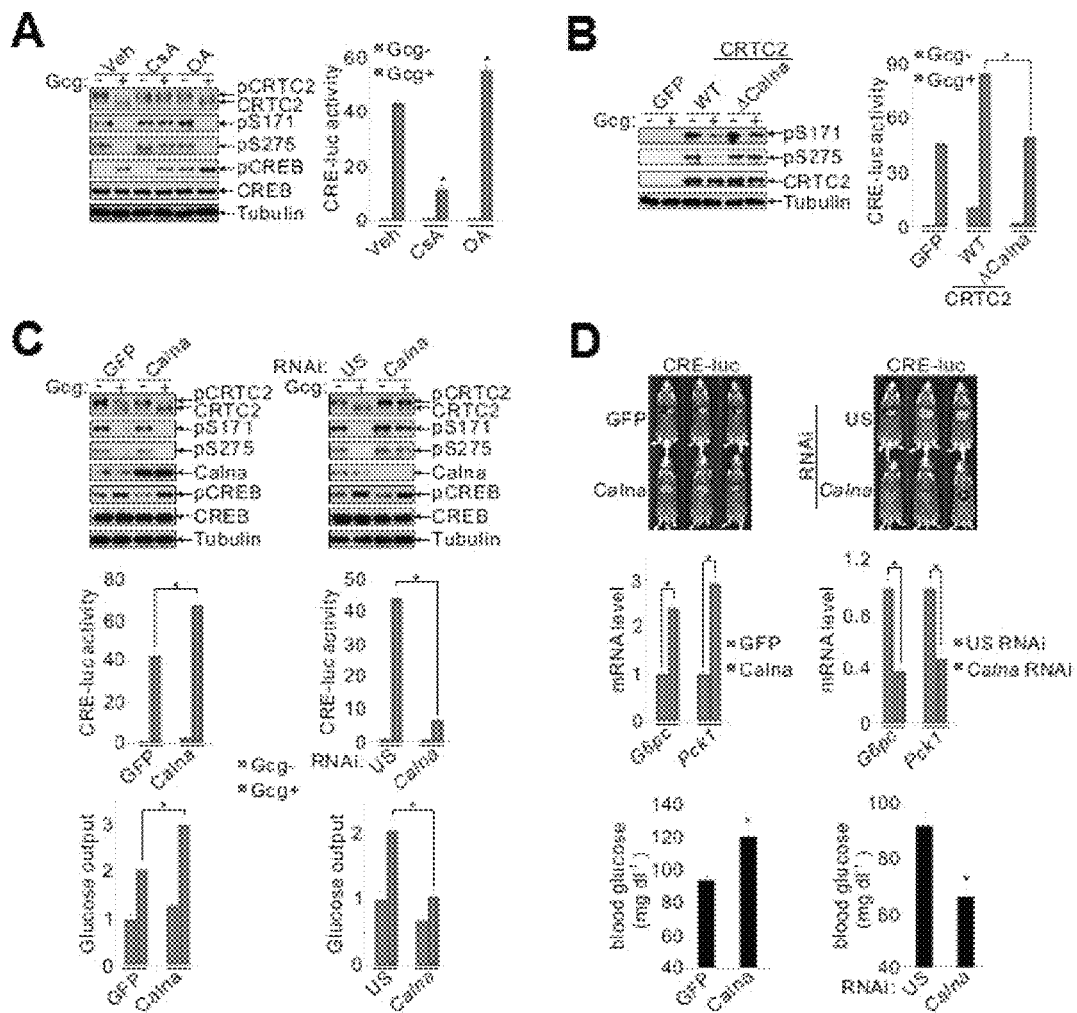

FIGS. 33A-D. Calcineurin promotes CRTC2 activation during fasting. FIG. 33A. Effect of Ser/Thr phosphatase inhibitors (okadaic acid (OA), cyclosporin A (CsA)) on CRTC2 dephosphorylation and CRE-luciferase (luc) reporter activation (*P<0.001; n=3). FIG. 33B. Effect of glucagon (Gcg) on dephosphorylation (left) and activity (right) of wild-type (WT) and calcineurin-defective (ΔCalna) CRTC2 in hepatocytes (*P<0.001; n=3). FIG. 33C. Effect of calcineurin A over-expression (left) or knockdown (right) on CRTC2 dephosphorylation (top), CRE-luc reporter activity (middle, *P<0.001; n=3), and glucose output (bottom, *P<0.001; n=3) from hepatocytes. FIG. 33D. Effect of hepatic calcineurin over-expression (left) or knockdown (right) on CRE-luc activity, gluconeogenic gene (Pck1, G6pc) expression, and blood glucose concentrations in 6-8 hour fasted mice (*P<0.01; n=5). For this and other figures, data are shown as mean±s.e.m.

Figures 34A, 34B, 34C, 34D:
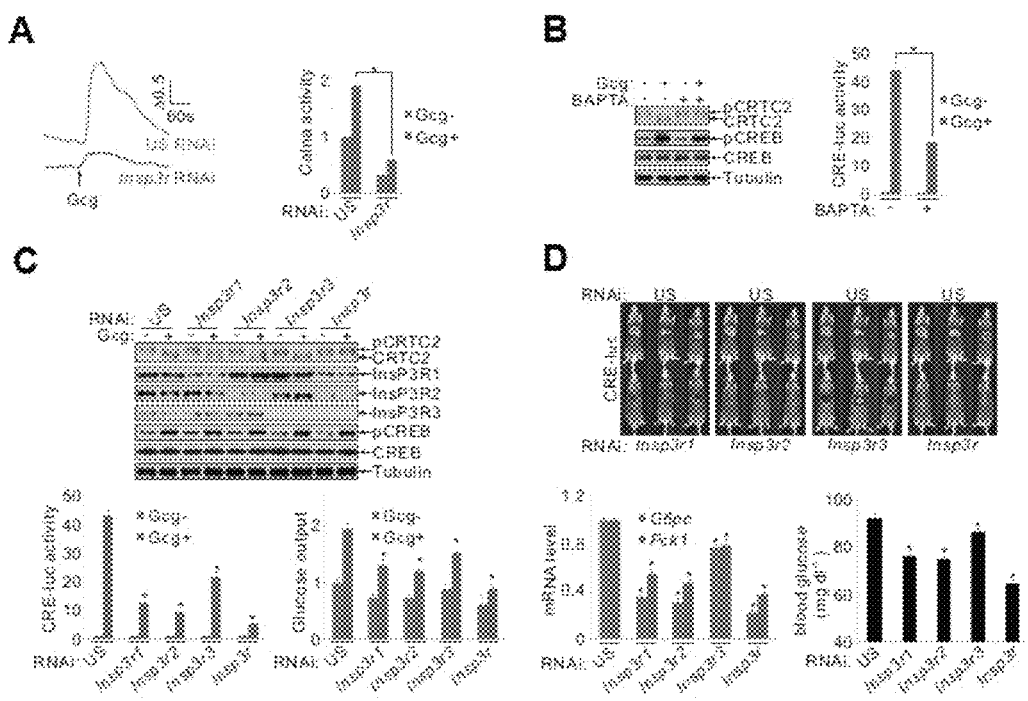

FIGS. 34A-D. Glucagon stimulates CRTC2 dephosphorylation via activation of InsP3 receptors. FIG. 34A. Effect of glucagon (Gcg) on calcium mobilization in hepatocytes by fluorescence imaging. Calcium mobilization and calcineurin activation following knockdown of all three InsP3R family members shown (*P<0.001; n=3). FIG. 34B. Effect of calcium chelator (BAPTA) on CRTC2 dephosphorylation and CRE-luc activation (*P<0.001; n=3). FIG. 34C. Effect of InsP3R depletion on CRTC2 dephosphorylation, CRE-luc activity, and glucose output from hepatocytes (*P<0.001; n=3). FIG. 34D. Effect of hepatic InsP3R knockdown on CRE-luc activity, blood glucose, and gluconeogenic gene expression (*P<0.01; n=5).

Figures 35A, 35B, 35C, 35D, 35E, 35F:
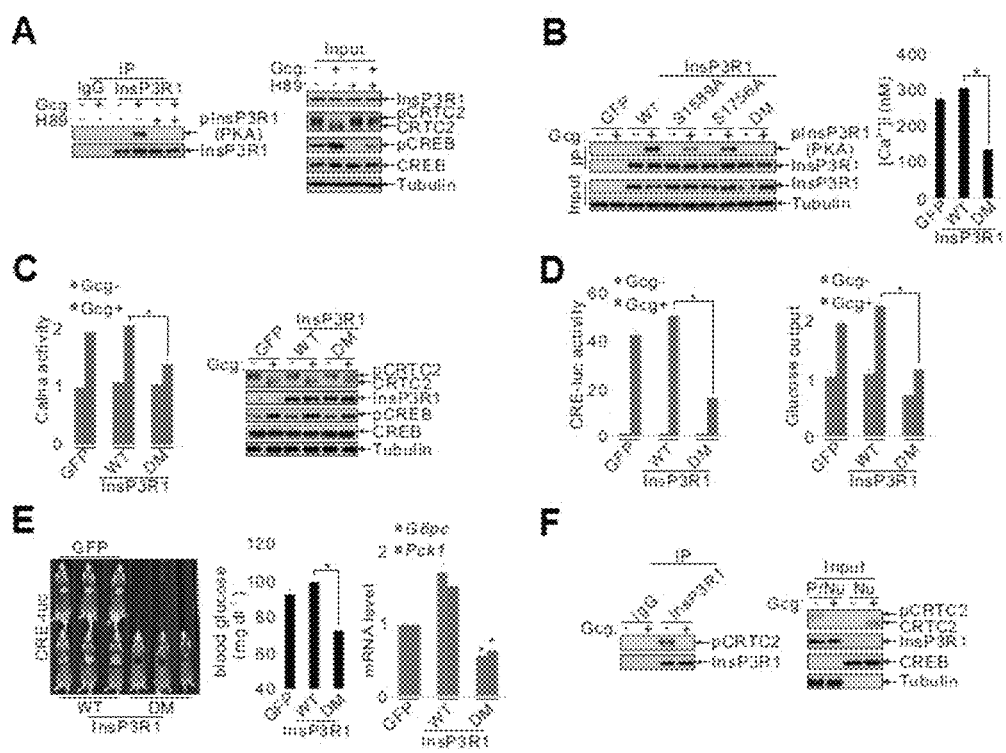

FIGS. 35A-F. Glucagon stimulates CRTC2 activity via PKA-dependent phosphorylation of InsP3Rs. FIGS. 35A. and B Immunoblots of InsP3R1 immunoprecipitates using phospho-PKA substrate antiserum to show effect of H89 (A) and Ala mutations (B) at one or both (DM) PKA consensus sites (Ser1589, Ser1756) on InsP3R1 phosphorylation in hepatocytes exposed to glucagon (Gcg). Effect of wild-type and PKA-mutant InsP3R1 on calcium mobilization in response to Gcg (B) shown (*P<0.001; n=3). FIGS. 35C. and D. Effect of wild-type or PKA-defective InsP3R1 (DM) on calcineurin (Calna) activation (C) and CRTC2 dephosphorylation (C), as well as CRE-luc activation (D) and glucose output (D) from hepatocytes (*P<0.001; n=3). FIG. 35E. Effect of wild-type and PKA-defective InsP3R1 on hepatic CRE-luc activity, fasting blood glucose, and gluconeogenic gene expression (G6pc, Pck1) (*P<0.01 versus wild-type; n=5). FIG. 35F. Co-immunoprecipitation of CRTC2 with InsP3R1 in primary hepatocytes. Exposure to glucagon (100 nM; 15 minutes) indicated. Input levels of CRTC2 and InsP3R1 in nuclear (Nu) and post-nuclear (p/Nu) supernatant fractions shown.

Figures 36A, 36B:
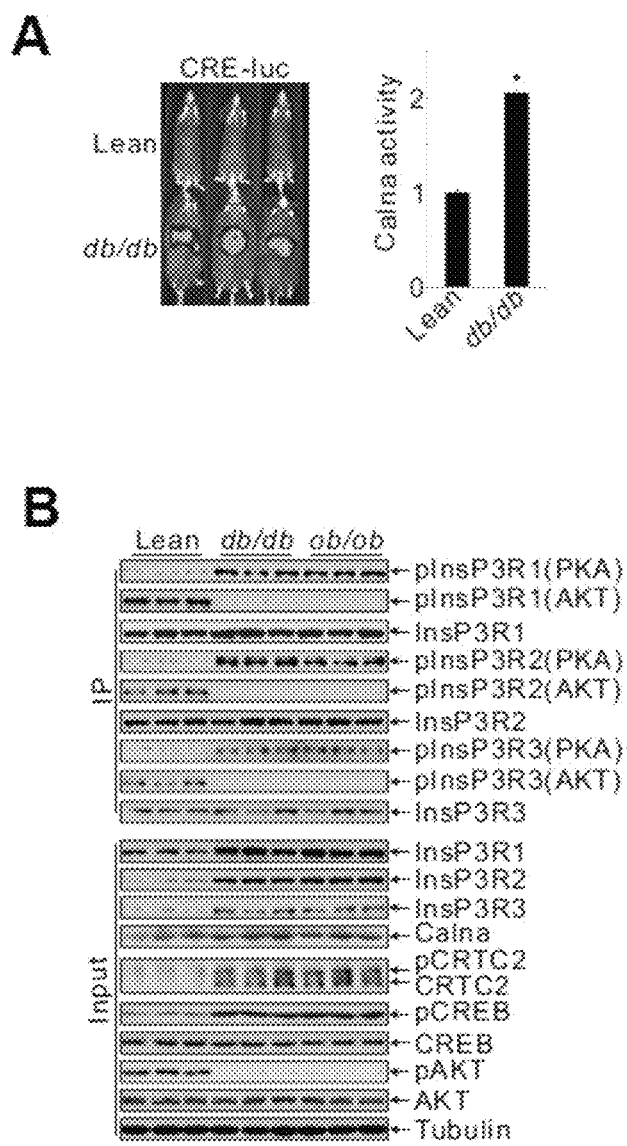
Figure 36C:
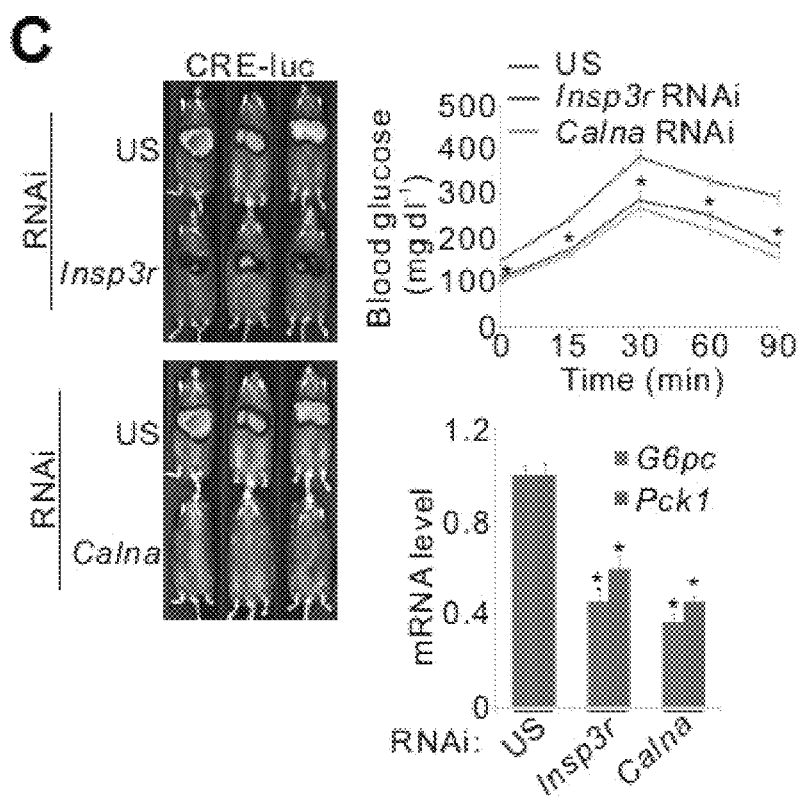

FIGS. 36A-C. InsP3R activity is upregulated in diabetes. FIG. 36A. Hepatic CRE-luc and calcineurin activity in lean and db/db mice (*P<0.001; n=5). FIG. 36B Immunoblots showing relative amounts and phosphorylation of InsP3R family members in livers of ad libitum fed lean, db/db, or ob/ob mice. InsP3R phosphorylation at PKA or AKT sites indicated. FIG. 36C. Effect of RNAi-mediated depletion of InsP3Rs or calcineurin A on CRE-luc activity, gluconeogenic gene expression, and hepatic glucose production in db/db mice, determined by pyruvate tolerance testing (*P<0.01; n=5).

Figures 37A, 37B, 37C, 37D, 37E:
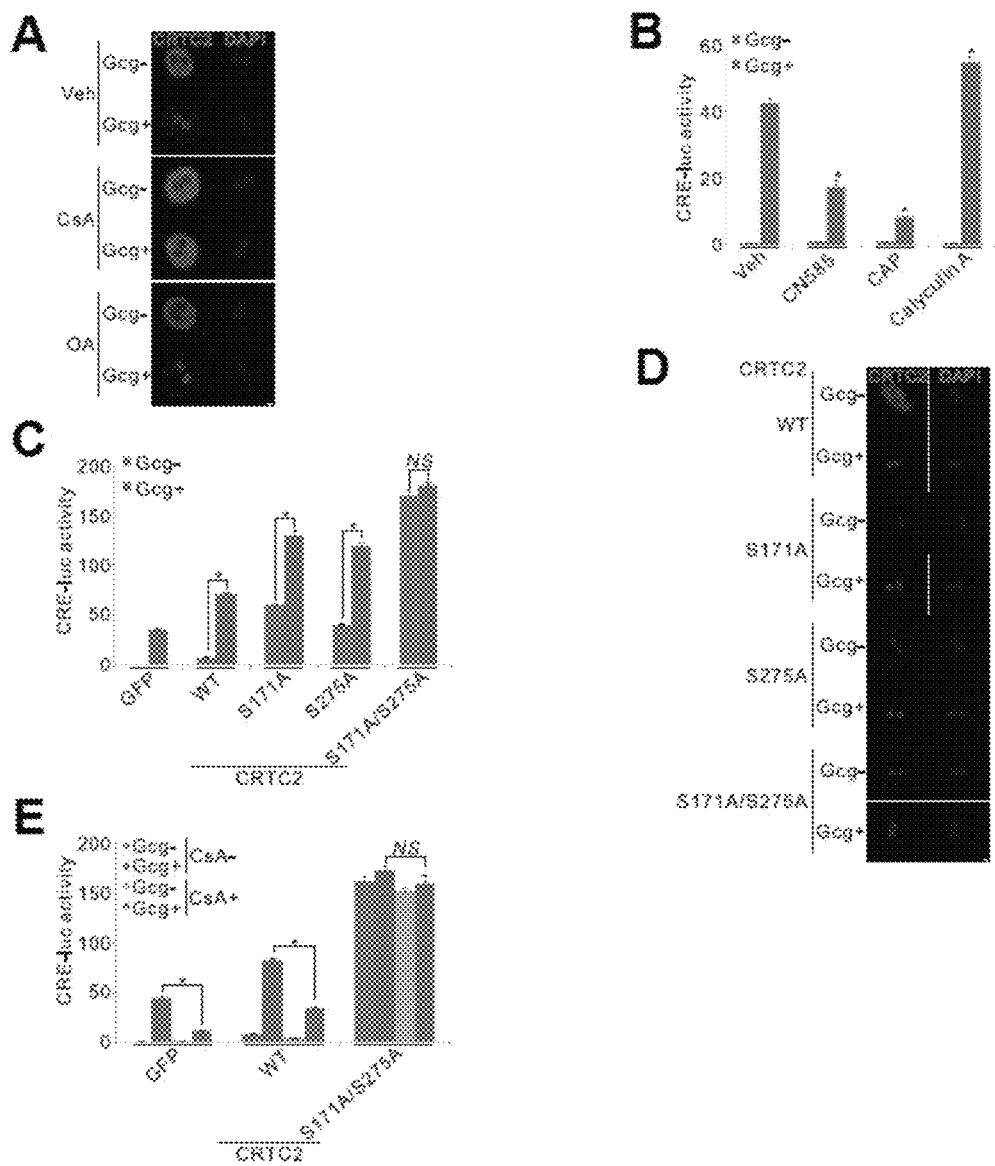

FIGS. 37A-E. Glucagon stimulates CRTC2 activity in hepatocytes via a calcineurin-dependent mechanism. FIG. 37A. Effect of Ser/Thr phosphatase inhibitors (okadaic acid (OA), cyclosporin A (CsA)) on CRTC2 localization in primary mouse hepatocytes exposed to glucagon (Gcg). Scale bar, 5 µm. FIG. 37B. Effect of calcineurin inhibitors (calcineurin autoinhibitory peptide (CAP), CN585) and PP1/PP2A inhibitor (calyculin A) on CRE-luciferase reporter activity in primary hepatocytes (*P<0.001; n=3). FIGS. 37C. and D. Effect of wild-type and phosphorylation-defective (S171A, S275A) active CRTC2 mutants on CRE-luc activity (C) (*P<0.001; n=3) and CRTC2 cellular localization FIG. 37D. Glucagon treatment indicated. Scale bar, 5 µm. FIG. 37E. Effect of CsA on CRE-luc activity in cells expressing wild-type or constitutively active (S171A/S275A) mutant CRTC2 (*P<0.001; n=3). NS, no statistical difference.

Figures 38A, 38B, 38C, 38D:
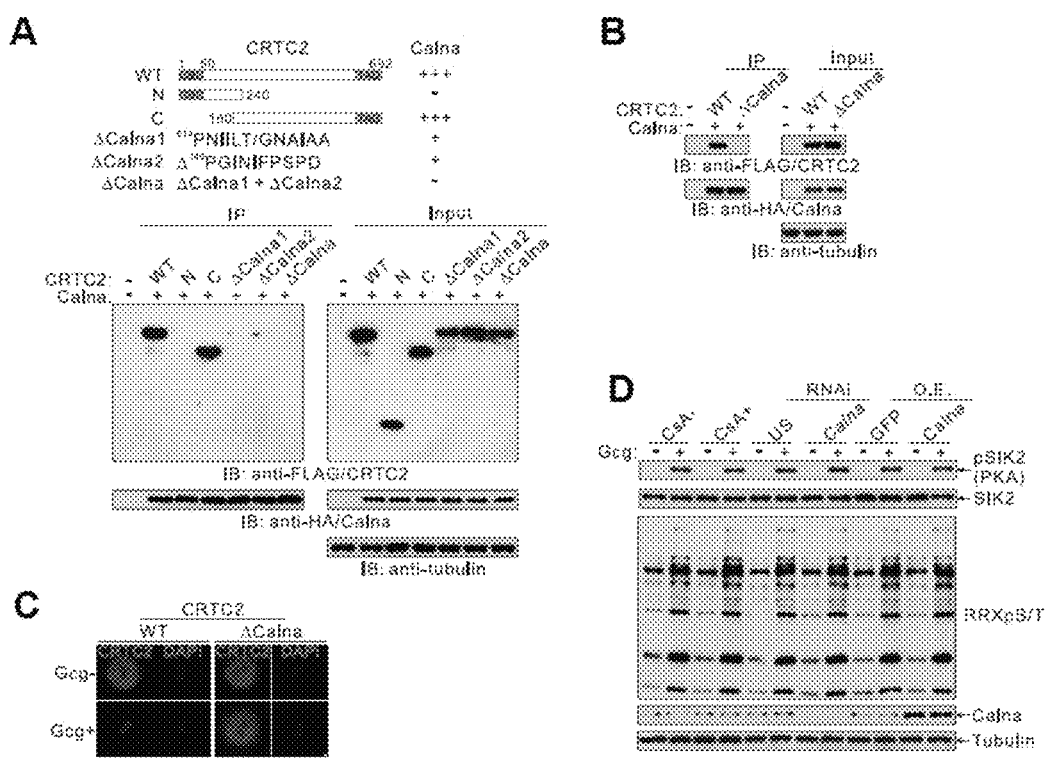

FIGS. 38A-D. Calcineurin modulates CRTC2 activity in hepatocytes. FIG. 38A. Analysis of calcineurin binding sites in CRTC2. Different CRTC2 polypeptides and amino acid substitutions/deletions indicated in schematic Immunoblot of flag-tagged CRTC2 recovered from IPs of HA-tagged calcineurin (Calna) in HEK293T cells shown. FIG. 38A discloses SEQ ID NOS 22-24, respectively, in order of appearance. FIG. 38B. Co-immunoprecipitation assay showing relative binding of wild-type and mutant CRTC2 polypeptides to calcineurin in cultures of primary hepatocytes. Cells infected with adenovirus encoding wild-type or calcineurin-defective (ΔCalna) Flag-tagged CRTC2 plus HA-tagged calcineurin A (Calna) indicated. Recovery of CRTC2 polypeptides from HA-Calcineurin IPs shown. FIG. 38C. Nuclear shuttling of wild-type (WT) and calcineurin-defective (ΔCalna) CRTC2 in hepatocytes exposed to glucagon. Scale bar, 5 µm. FIG. 38D. Effect of Calna over-expression (O.E.) or depletion by RNAi-mediated knockdown on downstream PKA signaling in hepatocytes using phospho-PKA substrate antibody (anti-RRXpS/T).

Figures 39A, 39B:
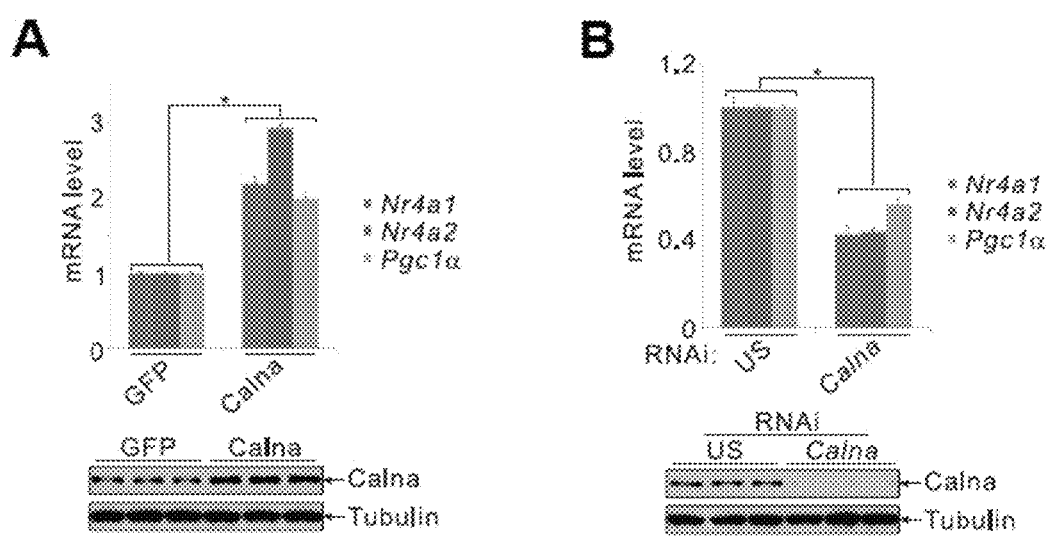

FIGS. 39A-B. Calcineurin regulates CRTC2 activity in liver. Effect of calcineurin (Calna) over-expression (A) or RNAi-mediated depletion (B) on mRNA amounts for fasting-inducible CREB target genes (Nr4a1, Nr4a2, Pgc1α) in livers of fasted mice (*P<0.01; n=5). Immunoblot showing relative calcineurin protein amounts in livers from calcineurin overexpressing or knockdown mice compared to controls.

Figures 40A, 40B, 40C:
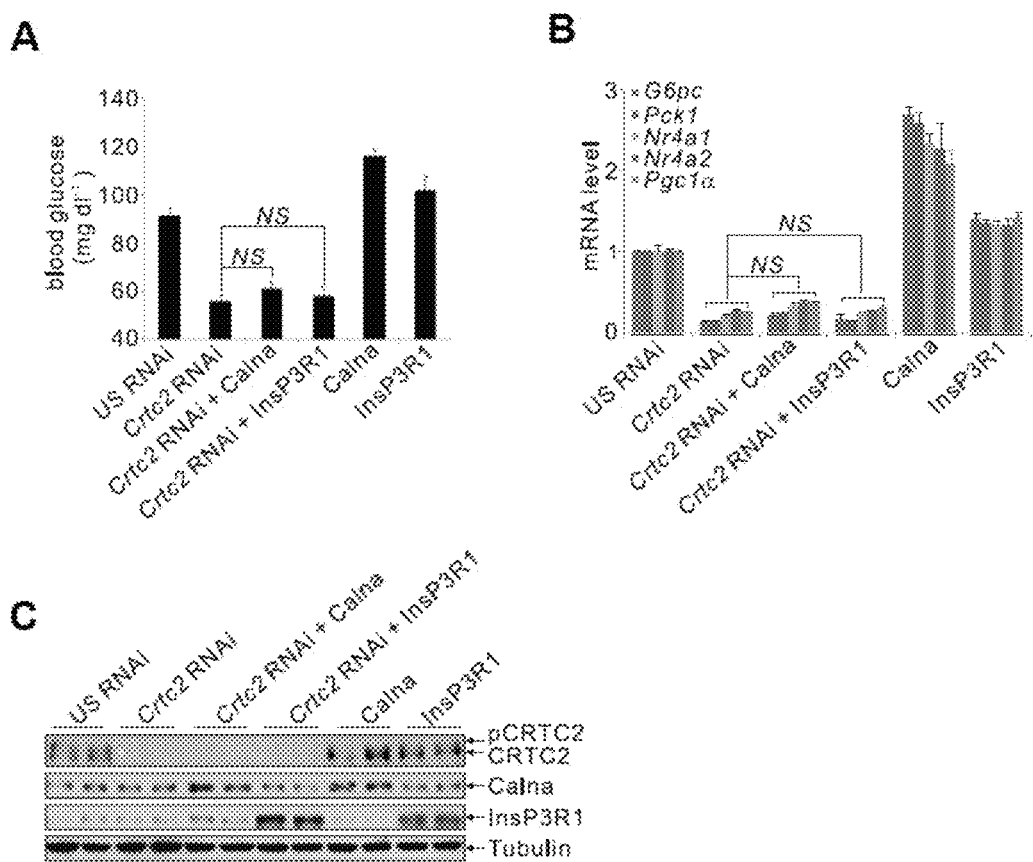

FIGS. 40A-C. Calcineurin and InsP3Rs regulate gluconeogenesis by modulating CRTC2 activity. FIGS. 40A-B. Effect of adenovirally encoded Crtc2 RNAi on blood glucose concentrations (A) and hepatic gene expression (B), in fasted mice expressing adenovirally encoded calcineurin or InsP3R1, as indicated. n=4. NS, no statistical difference. FIG. 40C. Immunoblot showing hepatic protein amounts for CRTC2, Calcineurin (Calna), and InsP3R1 in mice characterized in panels A and B.

Figures 41A, 41B, 41C:
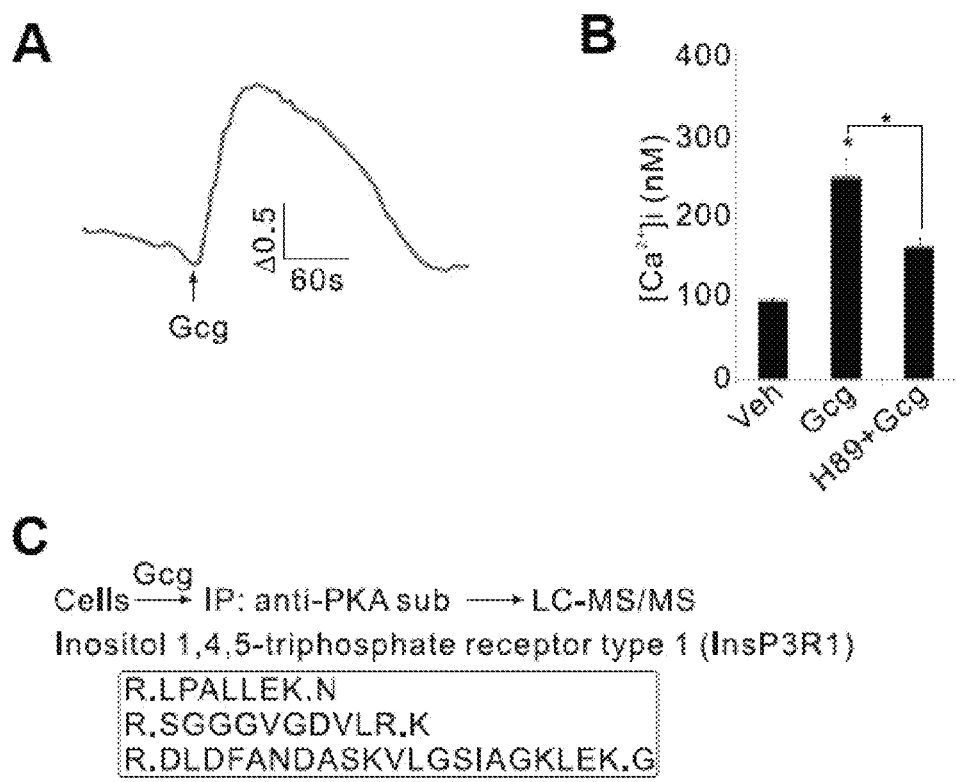

FIGS. 41A-C. Glucagon stimulates calcium mobilization in hepatocytes. FIGS. 41A. and B. Effect of glucagon (Gcg) and PKA inhibitor H89 on calcium mobilization in primary hepatocytes by fluorescence imaging (*P<0.001; n=3). FIG. 41C. InsP3R1 peptides (SEQ ID NOS 25-27, respectively, in order of appearance) identified by MS analysis of immunoprecipitates prepared with phospho-PKA substrate antiserum on lysates from primary hepatocytes exposed to glucagon (Gcg).

Figures 42A, 42B, 42C, 42D, 42E:
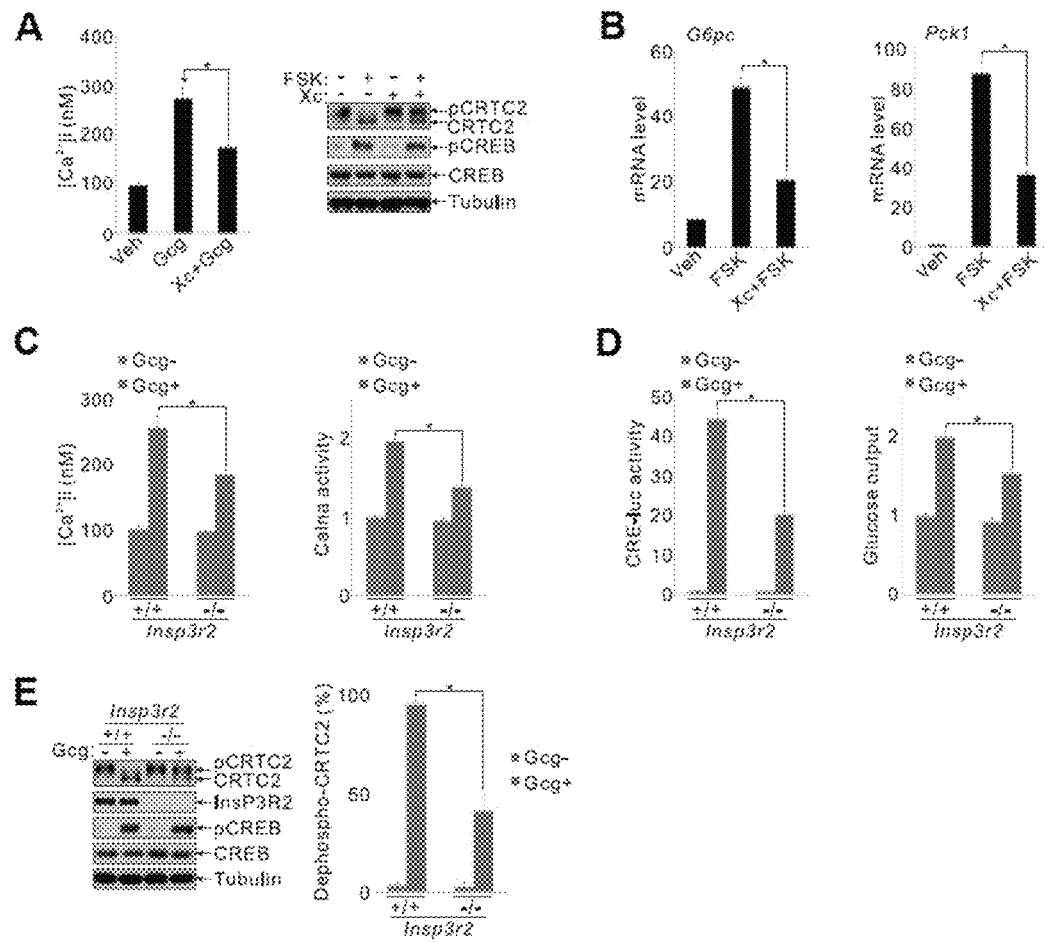

FIGS. 42A-E. InsP3 Receptors are required for CRTC2 activation in response to cAMP agonists. FIG. 42A, B. Effect of Xestospongin C (Xc) on calcium mobilization and CRTC2 dephosphorylation (A) and on mRNA amounts for glucose-6-phosphatase (G6pc) and PEPCK (Pck1) (B) in primary hepatocytes exposed to Forskolin (FSK) (*P<0.001; n=3). FIG. 42C-E. Effects of glucagon on calcium mobilization and calcineurin activation (C) (*P<0.001; n=4) as well as CRE-luc reporter activation and glucose secretion (D) (*P<0.001; n=4) and CRTC2 dephosphorylation (E) in primary hepatocytes from InsP3R2 knockout mice and control littermates. FIG. 42E. Bar graph on right shows relative dephosphorylation of CRTC2 in wild-type and InsP3R2 knockout hepatocytes exposed to glucagon, determined by densitometry (*P<0.01; n=3).

Figures 43A, 43B, 43C, 43D, 43E:
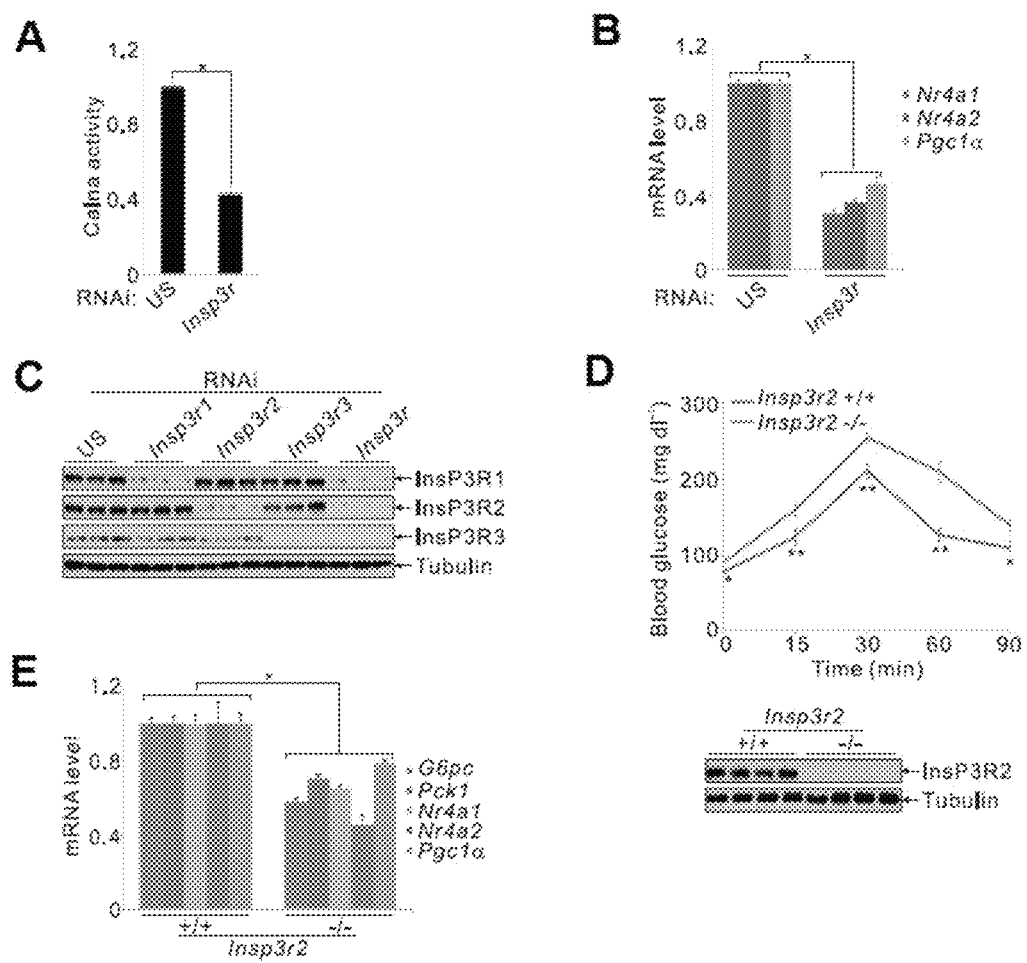

FIGS. 43A-E. InsP3Rs modulate hepatic gluconeogenesis. FIG. 43A. Effect of RNAi-mediated depletion of all three InsP3R family members on calcineurin activation in fasted livers (*P<0.001; n=5). FIGS. 43B and C. Effect of hepatic InsP3R knockdown on mRNA amounts for fasting inducible CREB target genes (B) and on InsP3R protein amounts (C) in livers of mice (*P<0.01; n=5). FIGS. 43D. and E. Hepatic gluconeogenesis, measured by pyruvate tolerance testing (D) (*P<0.02; **P<0.01; n=4) and gluconeogenic gene expression (E) (*P<0.01; n=4) in wild-type and InsP3R2 knockout mice Immunoblot shows InsP3R2 protein amounts in hepatic extracts from control and InsP3R2 knockout mice.

Figure 44A:
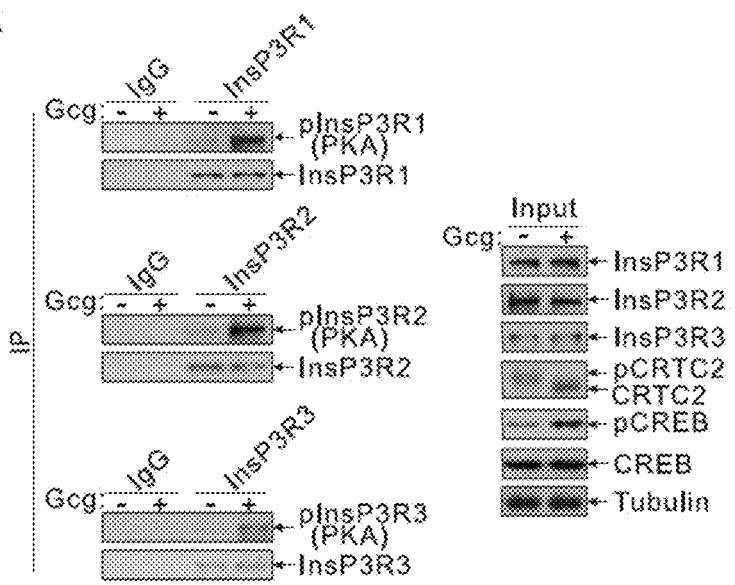
Figure 44B:
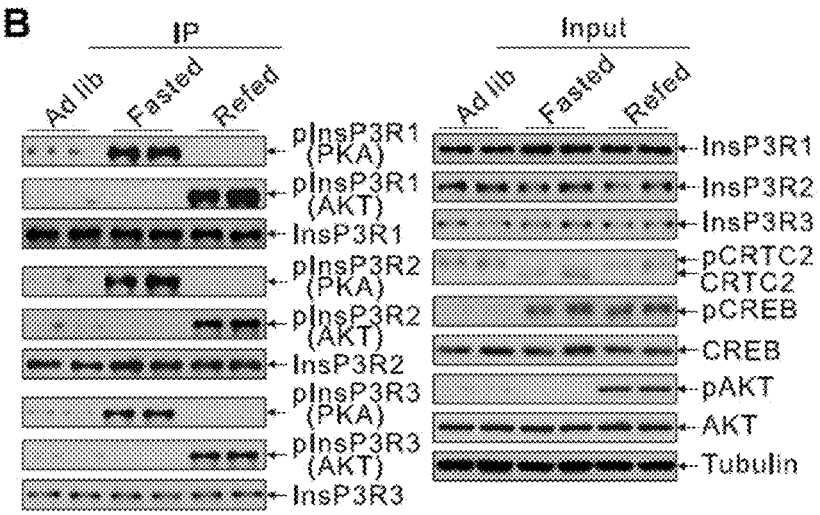
Figure 44C:
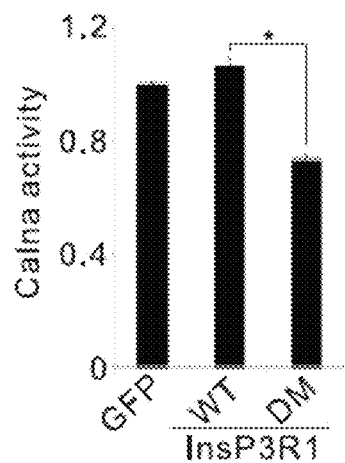
Figure 44D:
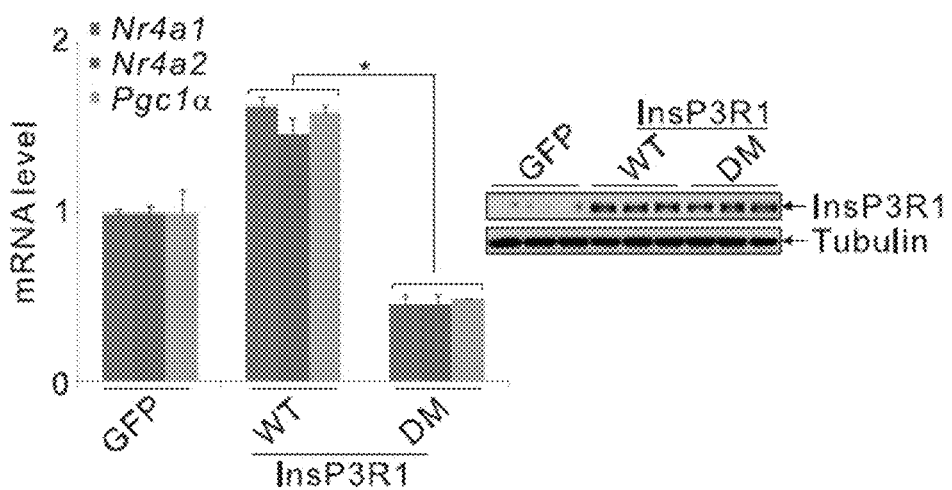

FIGS. 44A-D. Glucagon modulates InsP3R activity via PKA-mediated phosphorylation. FIG. 44A Immunoblots showing effect of glucagon (Gcg) on InsP3R phosphorylation, using phospho-PKA substrate antiserum on immunoprecipitates of InsP3Rs prepared from primary hepatocytes. FIG. 44B Immunoblots showing phosphorylation of InsP3R at PKA or AKT sites in livers of 6-8 hour fasted or 2 hour-refed mouse livers. FIGS. 44C. and D. Effect of wild-type and PKA-defective (DM) InsP3R1 on calcineurin (Calna) activation (C, * P<0.001, n=5) and CREB target genes (D, *P<0.01, n=5) in fasted livers. Right, immunoblot showing relative InsP3R protein amounts in livers of mice injected with adenovirus encoding wild-type or PKA-defective (DM) InsP3R1.

Figures 45A, 45B, 45C, 45D:
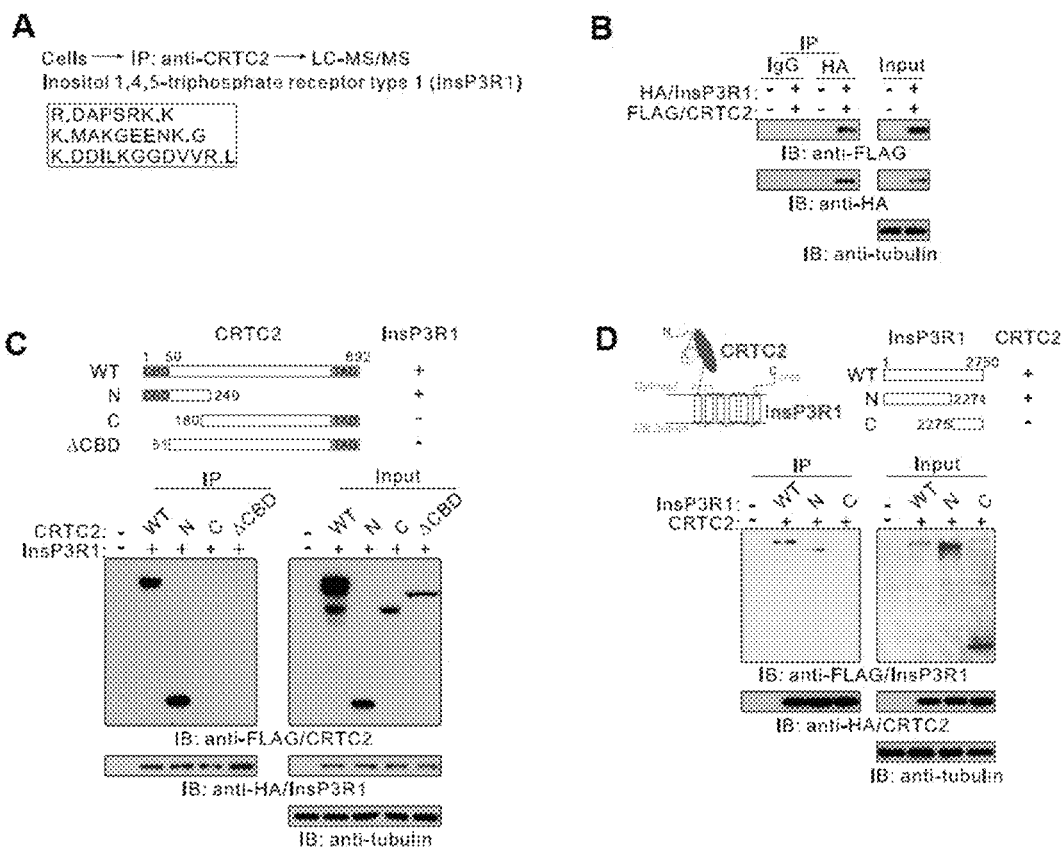
Figures 45E, 45F, 45G, 45H, 45I:
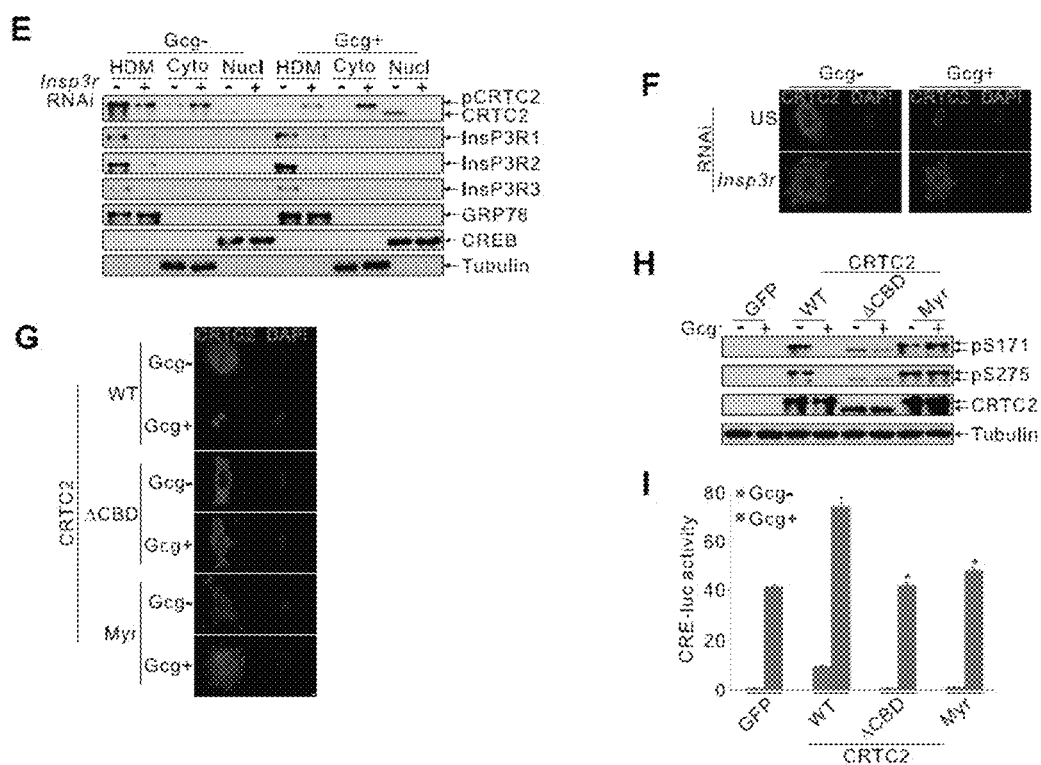

FIGS. 45A-I. Association of InsP3Rs with CRTC2 in hepatocytes. FIG. 45A. InsP3R1 peptides (SEQ ID NOS 28-30, respectively, in order of appearance) recovered from anti-CRTC2 immunoprecipitates by MS analysis. FIG. 45B. Co-immunoprecipitation assay showing amounts of Flag-tagged CRTC2 recovered from IPs of HA-tagged InsP3R1 in HEK293T cells. FIGS. 45C. and D. Deletion analysis of regions in CRTC2 (C) and InsP3R1 (D) required for the CRTC2:InsP3R1 interaction. Interaction competent CRTC2 and InsP3R1 polypeptides indicated in each schematic (+). FIG. 45E. Effect of InsP3R depletion on CRTC2 protein amounts associated with ER enriched high density microsomes (HDM) as well as cytosolic (Cyto), and nuclear (Nucl) fractions in hepatocytes exposed to glucagon (Gcg). Relative amounts of ER-localized (GRP78), cytosolic (Tubulin), and nuclear (CREB) proteins in each fraction indicated. FIG. 45F. Effect of InsP3R depletion on CRTC2 localization in hepatocytes. Scale bar, 5 μm.

FIGS. 45G.-I. Cellular localization (G), phosphorylation state (H) and activity (I) of wild-type, InsP3R-defective (ΔCBD, 51-692 aa), and myristoylated CRTC2 mutant polypeptides (*P<0.001; n=3). Scale bar, 5 μm.

Figures 46A, 46B, 46C, 46D:
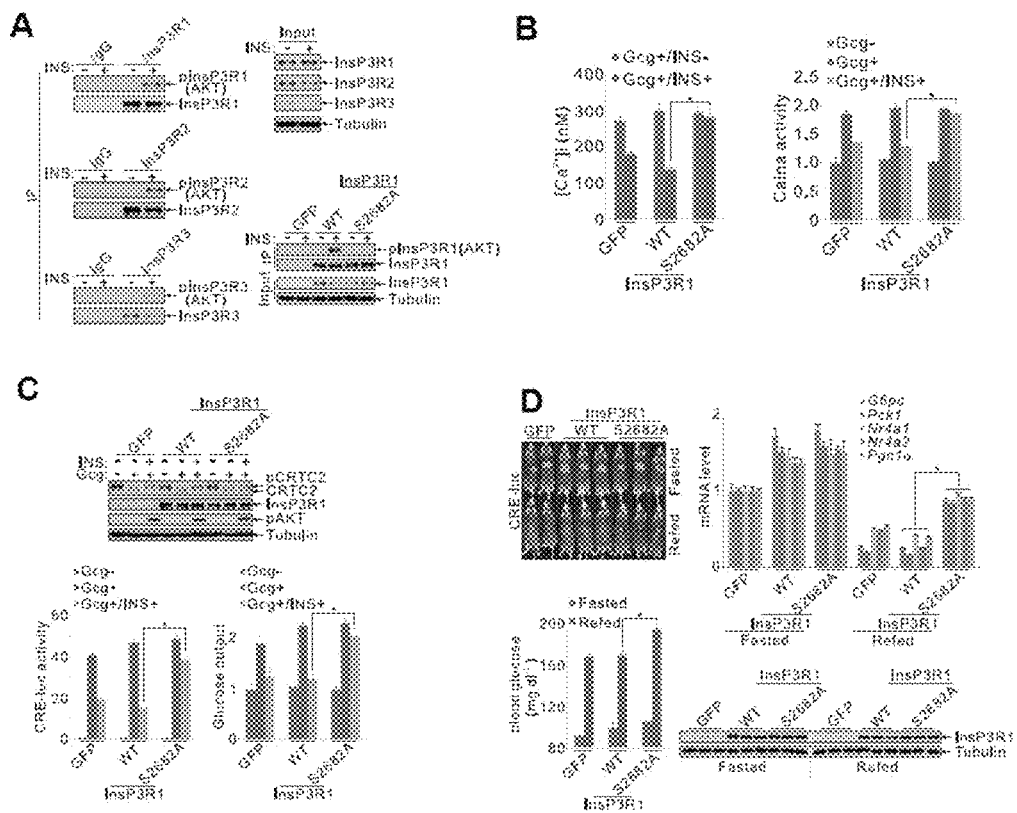

FIGS. 46A-D. Insulin down-regulates CRTC2 activity via the AKT-mediated phosphorylation of InsP3Rs. FIG. 46A. Left, immunoblots showing effect of insulin (INS) on InsP3R phosphorylation, using phospho-AKT substrate antiserum on immunoprecipitates of InsP3Rs prepared from primary hepatocytes. Bottom right, effect of insulin (INS) on phosphorylation of wild-type and mutant InsP3R1 containing an alanine substitution at the consensus AKT phosphorylation site (Ser2682). FIG. 46B. Effect of insulin on glucagon (Gcg)-induced calcium mobilization and calcineurin (Calna) activation in primary hepatocytes expressing wild-type or AKT-defective (S2682A) InsP3R1 (*P<0.001; n=3). FIG. 46C. Effect of wild-type and AKT-defective (S2862A) InsP3R1 on CRTC2 dephosphorylation (top), CRE-luc reporter activation (bottom left), and glucose output (bottom right) from hepatocytes (*P<0.001; n=3). FIG. 46D. Effect of wildtype and AKT-defective (S2682A) InsP3R1 on CRE-luc activity, blood glucose, and CREB target gene expression (G6pc, Pck1, Nr4a1, Nr4a2, Pgc1α) in fasting or refed mice (*P<0.01; n=5). Bottom right, immunoblot showing relative InsP3R protein amounts in livers of mice injected with adenovirus encoding wild-type or AKT defective (S2682A) InsP3R1 (*P<0.01; n=5).

Figures 47A, 47B, 47C:
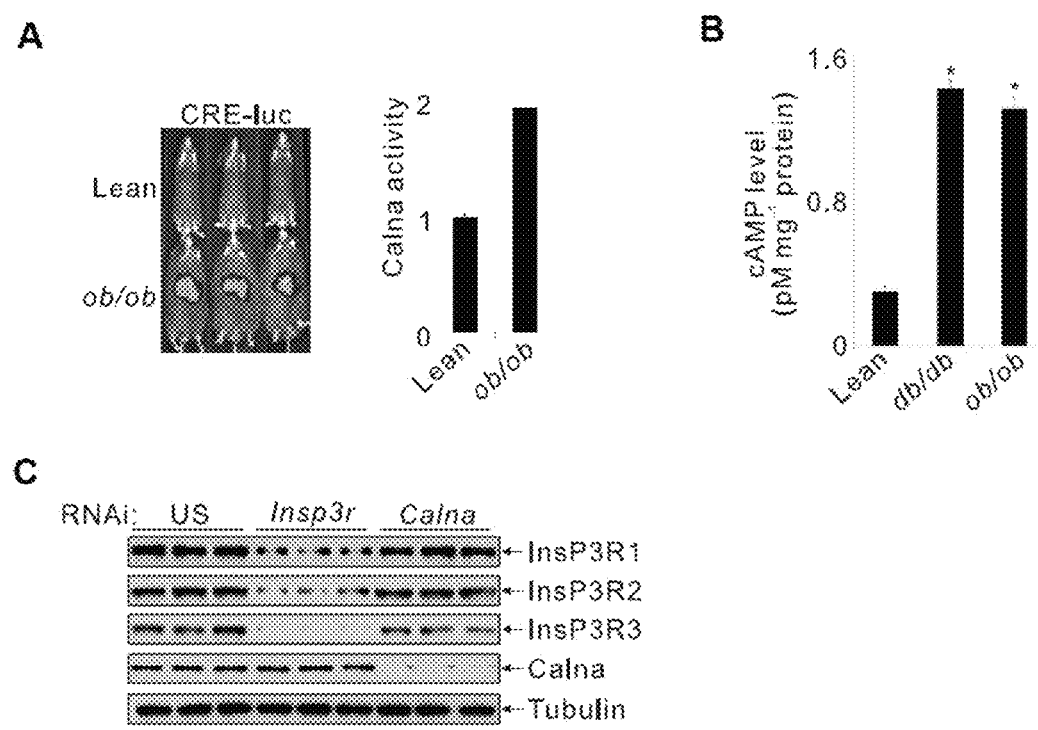

FIGS. 47A-C. Hepatic cAMP signaling and calcineurin activity are increased in obesity. FIGS. 47A. and B. Hepatic CRE-luc reporter activity and calcineurin activity (A) as well as cAMP content (B) in lean, db/db, and ob/ob mice (*P<0.001; n=5). FIG. 47C Immunoblot of InsP3R and calcineurin (Calna) proteins amounts in livers of mice injected with Insp3r or Calna RNAi adenovirus.

Figure 48:
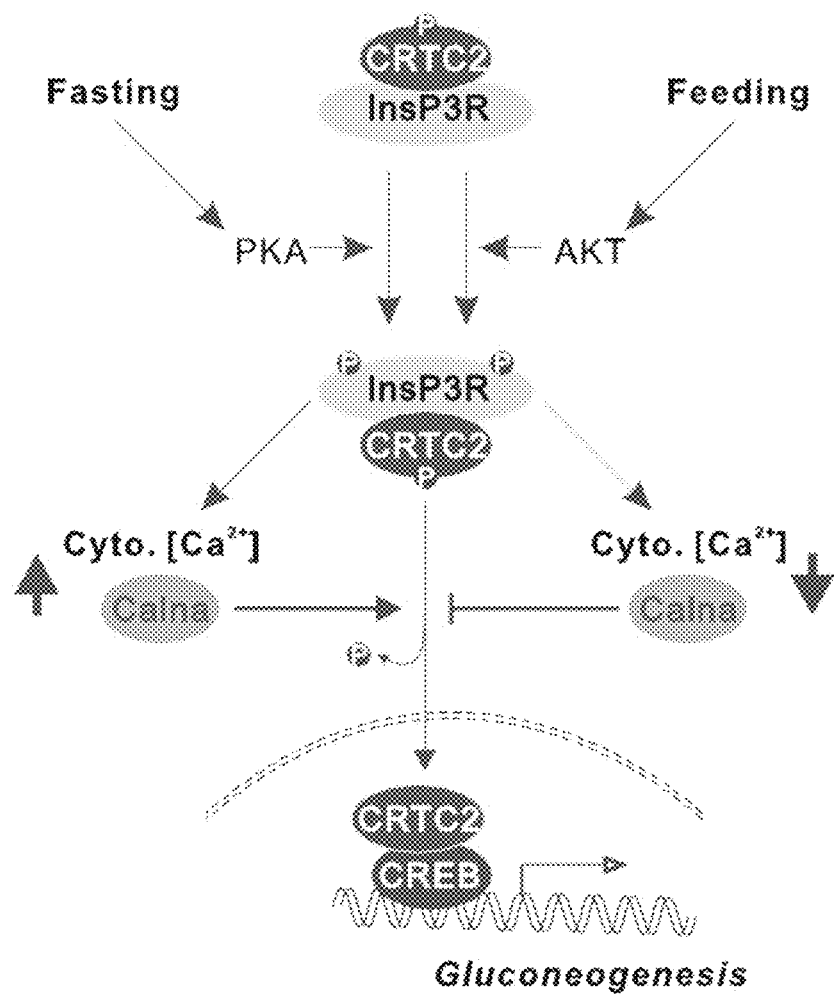

FIG. 48. Fasting and feeding pathways regulate CRTC2-dependent gluconeogenesis through antagonistic effects on InsP3R activity. Fasting signaling activates InsP3Rs via PKA-dependent phosphorylation, leading to increases in calcineurin (Calna) activity and in the subsequent dephosphorylation of CRTC2. By contrast, feeding inhibits InsP3R activity via AKT-dependent phosphorylation, thereby blocking the calcineurin-dependent dephosphorylation of CRTC2.

Figures 49A, 49B:
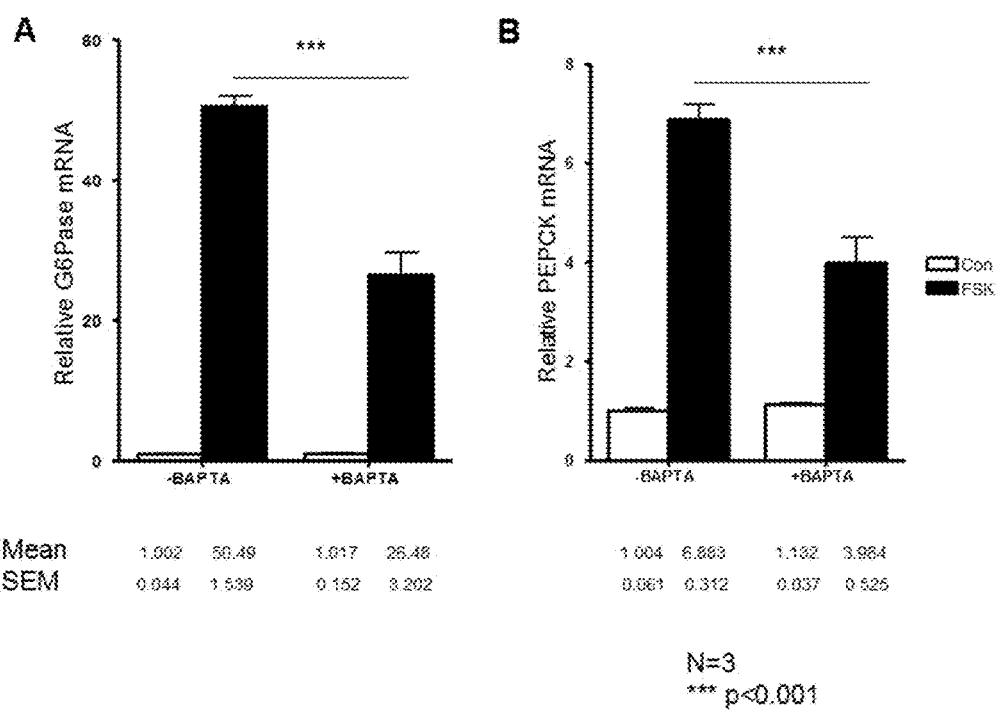
Figures 49C, 49D:
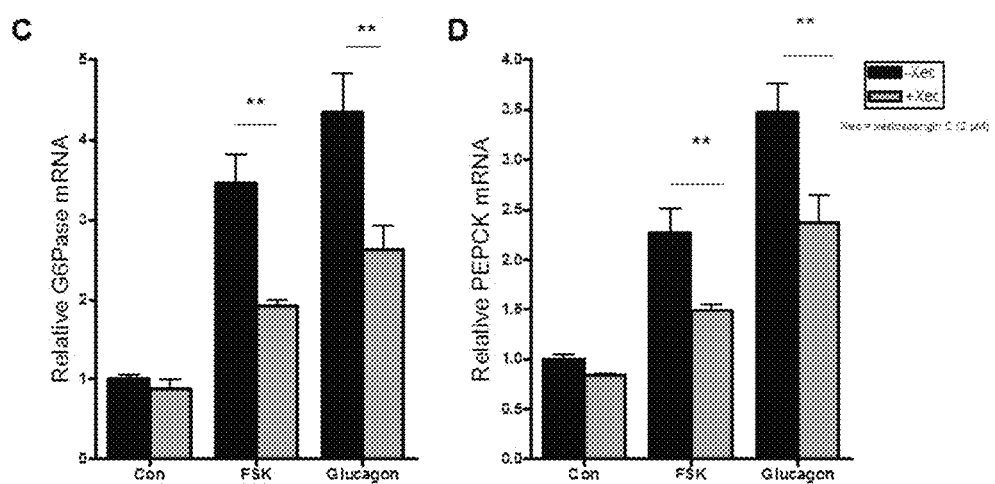
Figures 49E, 49F:
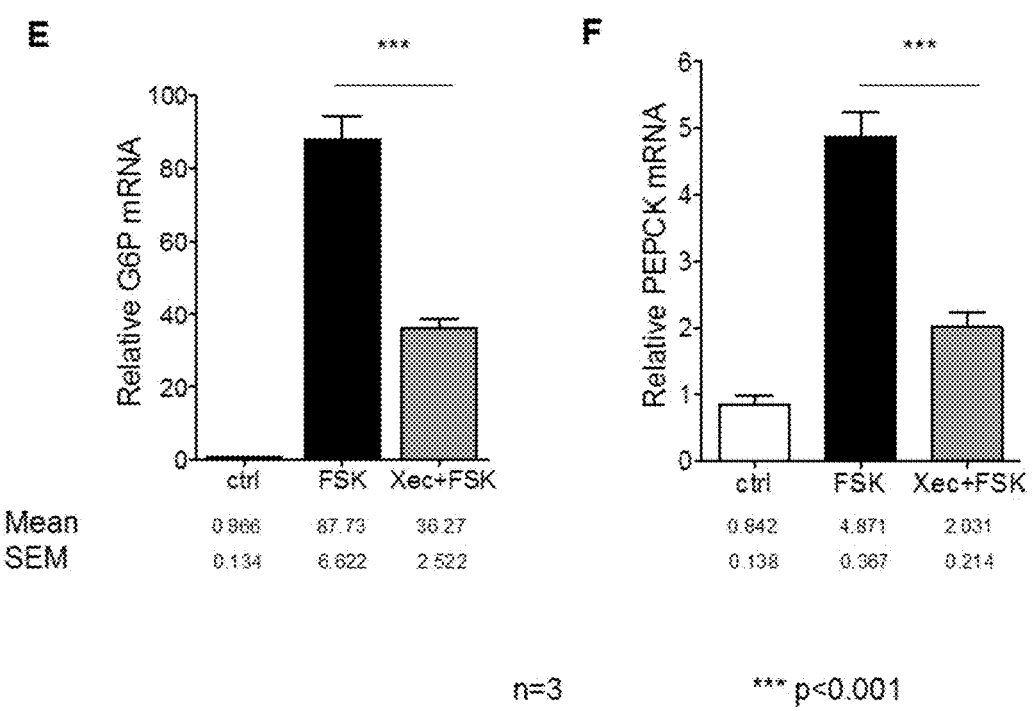
Figures 49G, 49H:
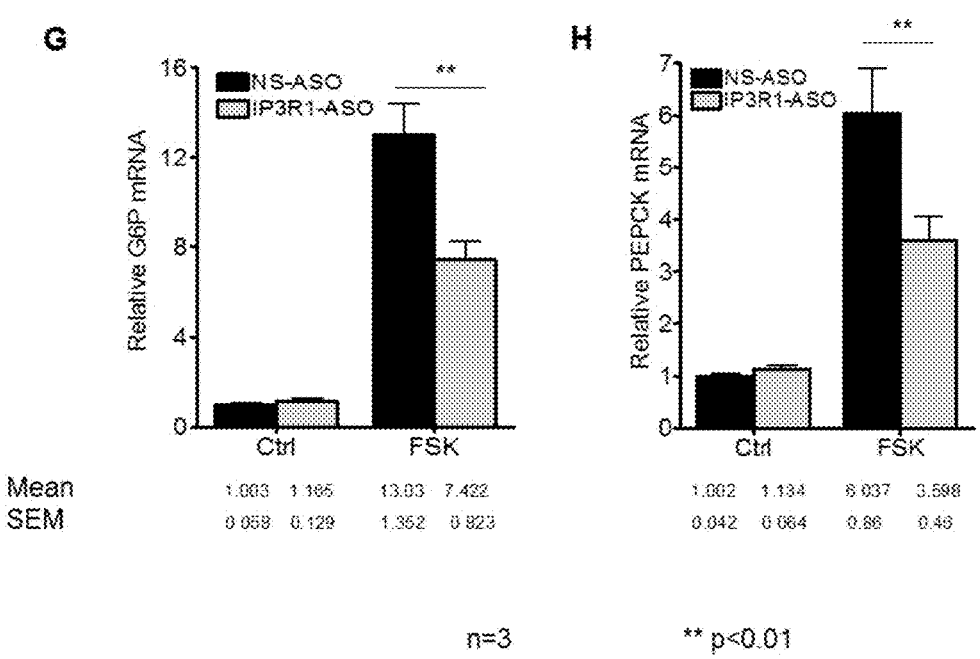
Figure 49I:
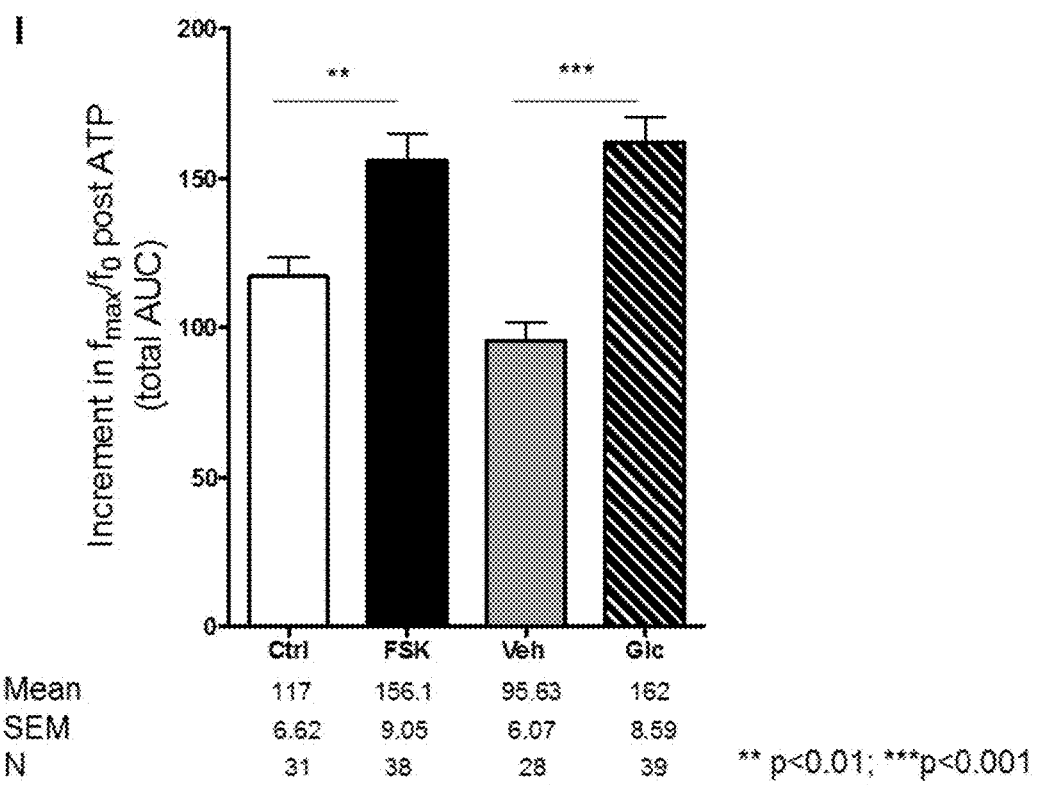
Figure 49J:
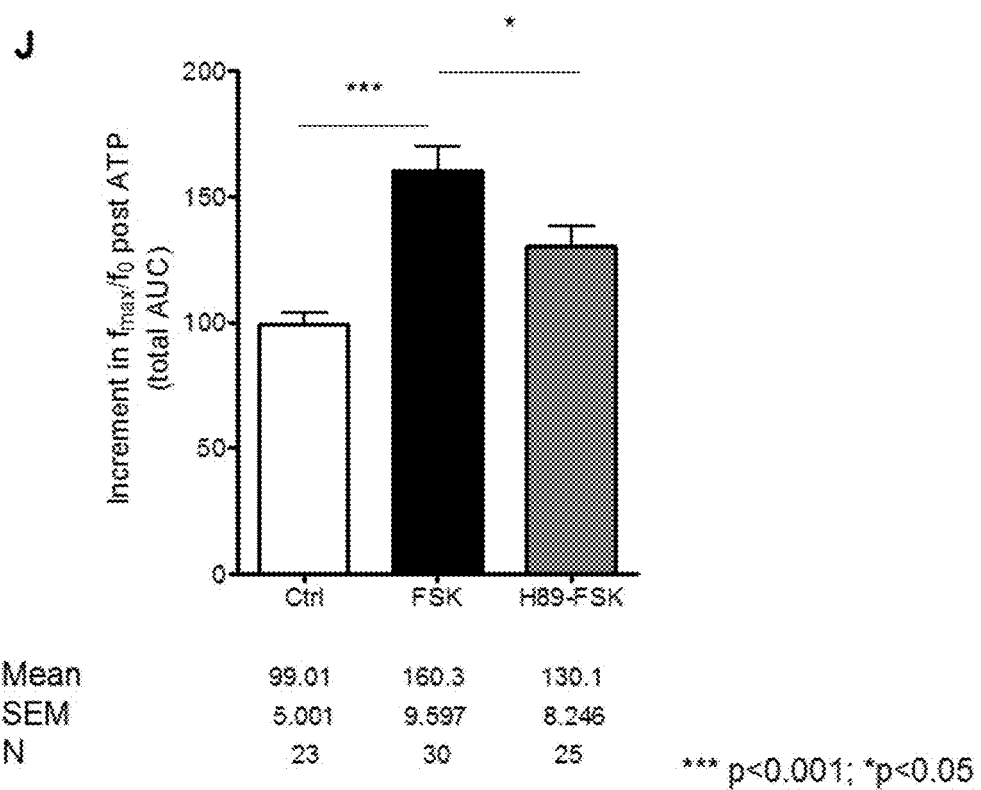
Figures 49K, 49L:
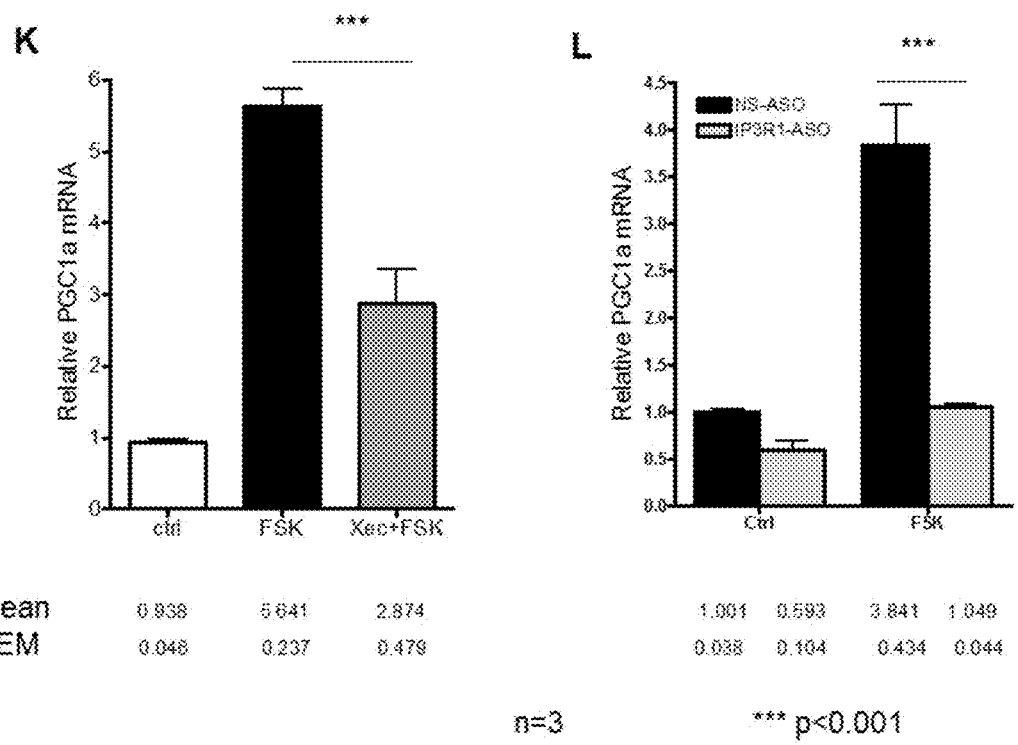
Figures 49M, 49N:
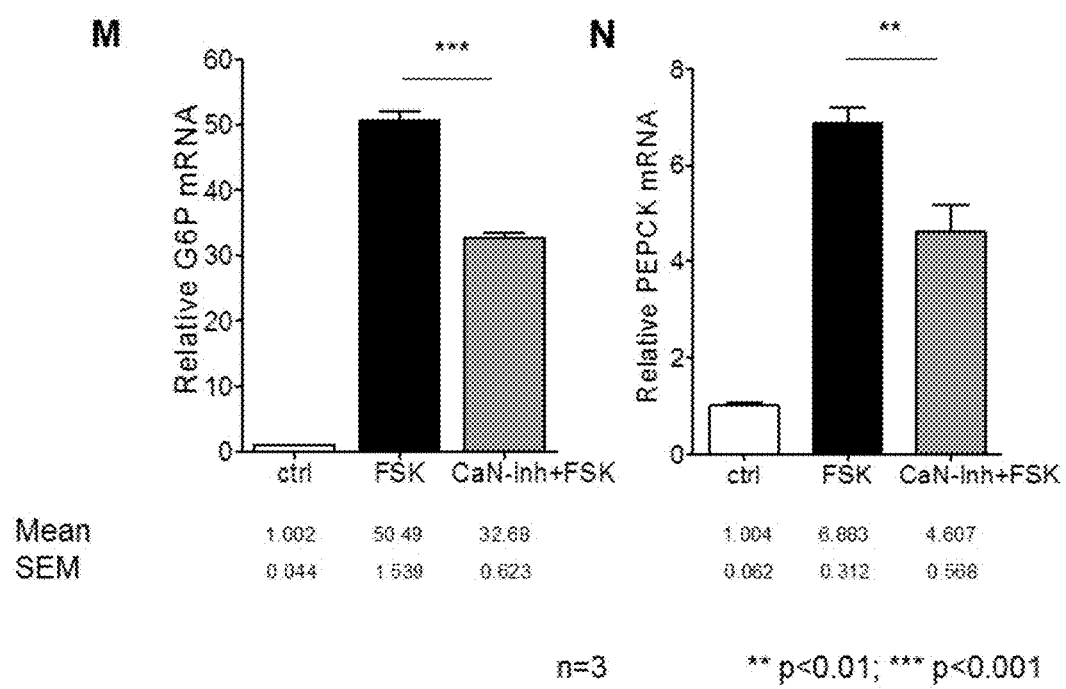
Figure 49O:
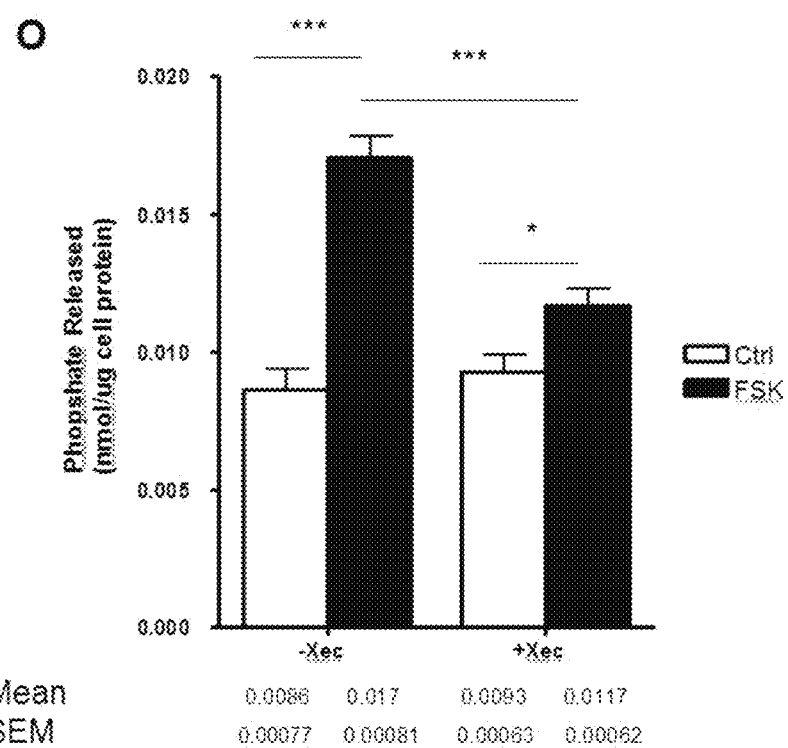
Figures 49P, 49Q:
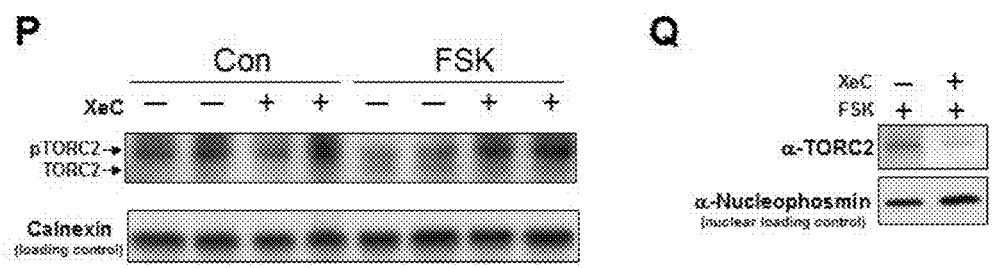
Figure 49R:
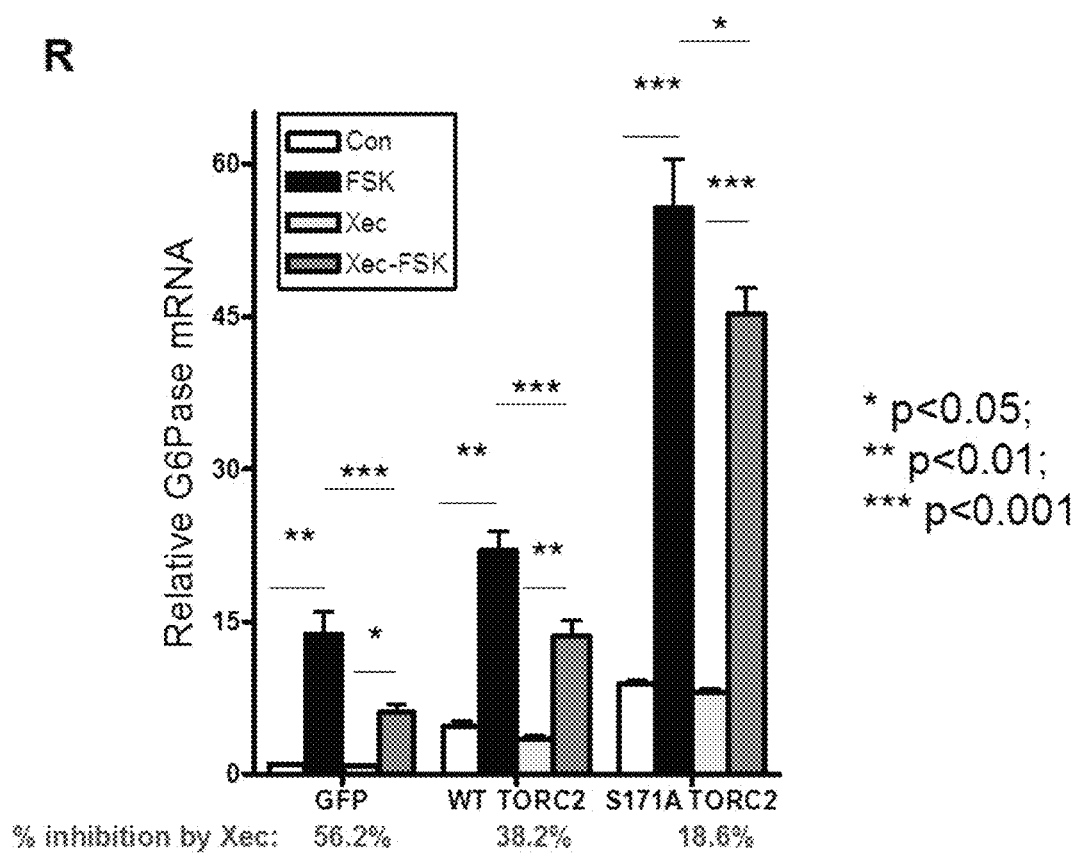
Figure 49S:
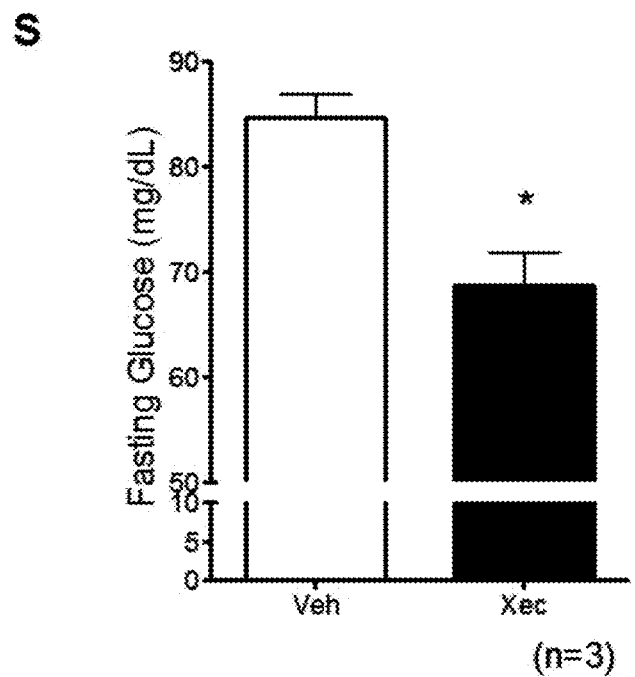

FIGS. 49A-S. The role of IP3R in forskolin/glucagon-induced G6Pase/PEPCK in cultured hepatocytes and in fasting blood glucose in vivo. FIG. 49 A,B. FSK-Induced G6Pase and PEPCK is Calcium-Dependent. FIG. 49C-D.

IP3R Activity is Required for Forskolin- and Glucagon-Induced G6Pase and PEPCK (FAO rat hepatocyte cell line). FIG. 49E-F. IP3R Activity is Required for Forskolin-Induced G6Pase and PEPCK (primary murine hepatocytes). FIG. 49G-H. IP3R1 Anti-Sense Oligonucleotide Suppresses Forskolin-Induced G6Pase and PEPCK (primary murine hepatocytes). FIG. 49I. Forskolin Activates IP3R Activity in FAO Hepatocytes (Inositol/ATP-Induced Calcium Release Assay). FIG. 49J. The PKA Inhibitor H89 Suppresses Forskolin-Induced IP3R Activation. FIG. 49K-L. IP3R Activity is Required for Forskolin-Induced PGC1a. FIG. 49M-N. Calcineurin Inhibitory Peptide Suppresses Forskolin-Induced G6Pase and PEPCK. FIG. 49O. IP3R Activity is Required for Forskolin-Induced Calcineurin Activation. FIG. 49P-Q. IP3R Activity is Required for Forskolin-Induced TORC2 Dephosphorylation and Nuclear Localization. FIG. 49R. TORC2 Transduction Partially Restores Forskolin-Induced G6Pase in IP3R-Inhibited Hepatocytes. FIG. 49S. Xestospongin C Treatment Reduces Fasting Glucose Levels in C57BL/6J Mice.

Figure 50A:
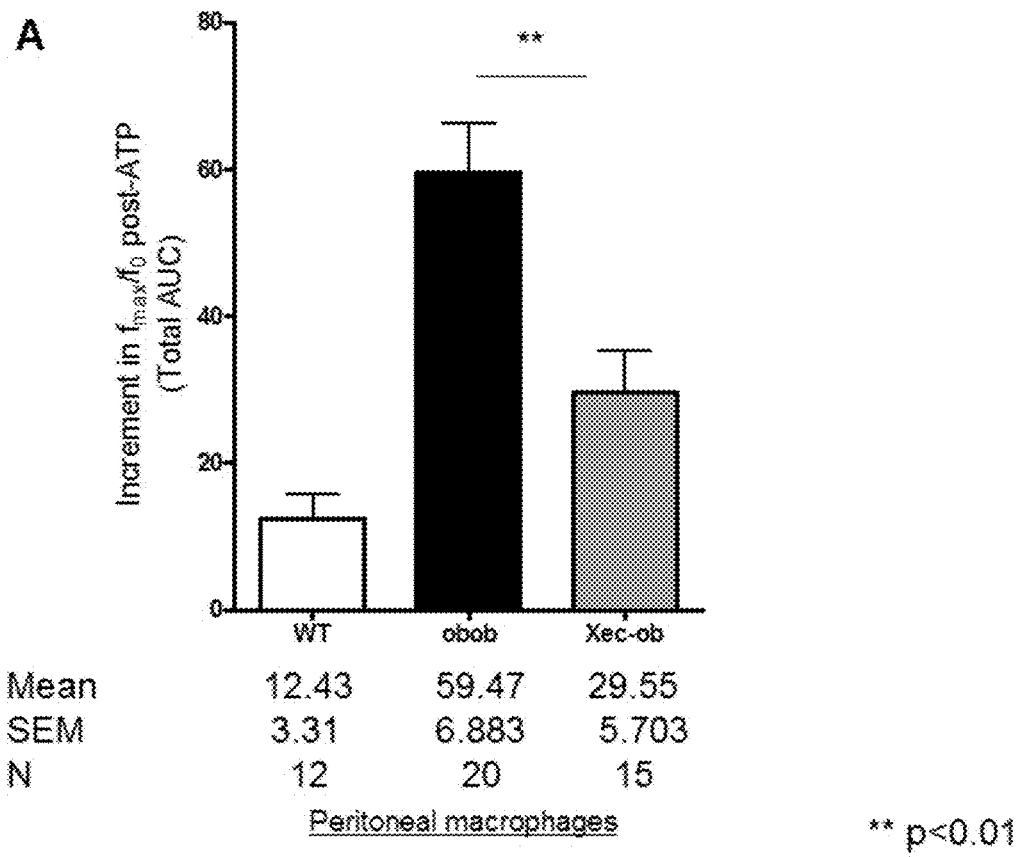
Figure 50B:
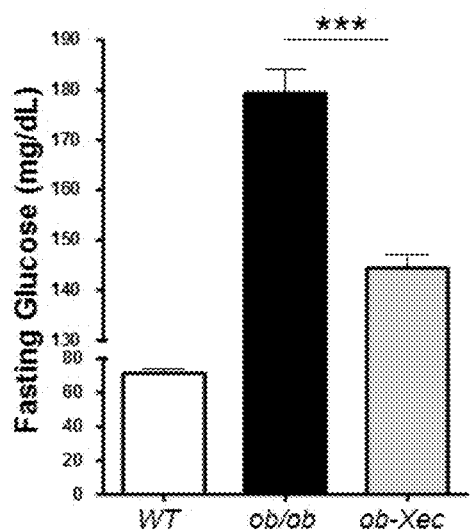
Figure 50C:
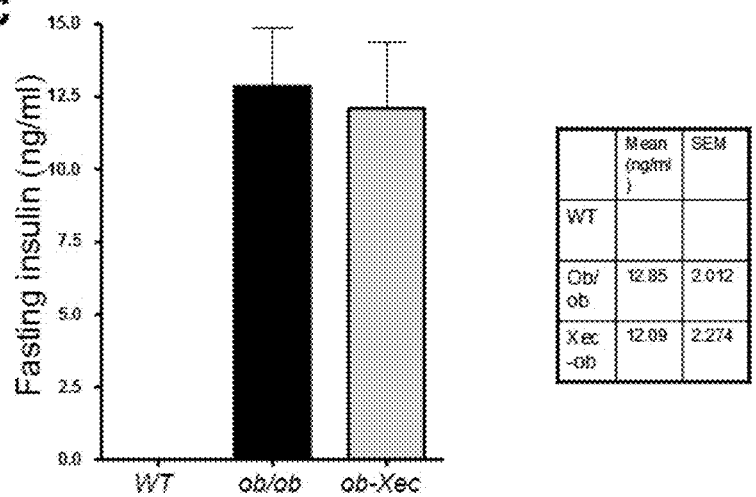
Figure 50D:
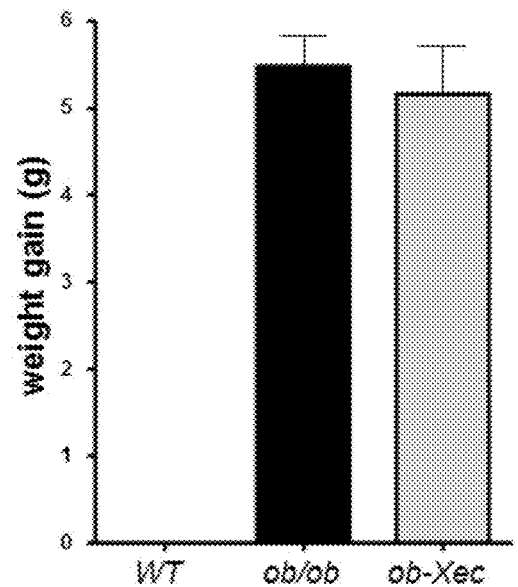
Figure 50E:
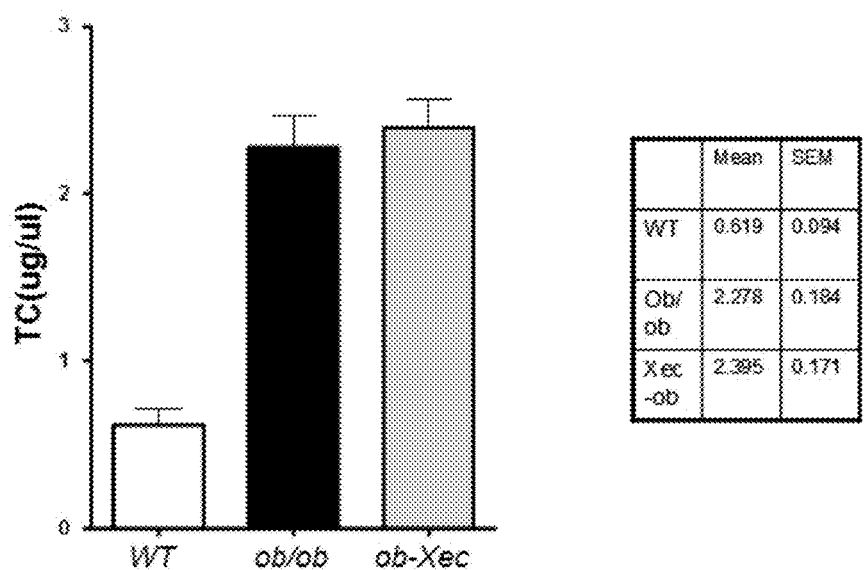
Figure 50F:
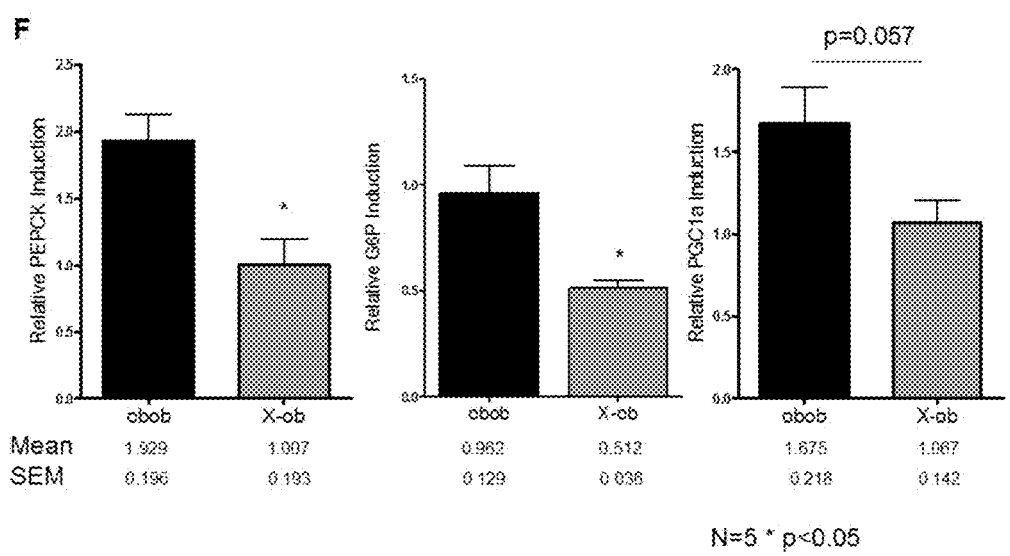
Figure 50G:
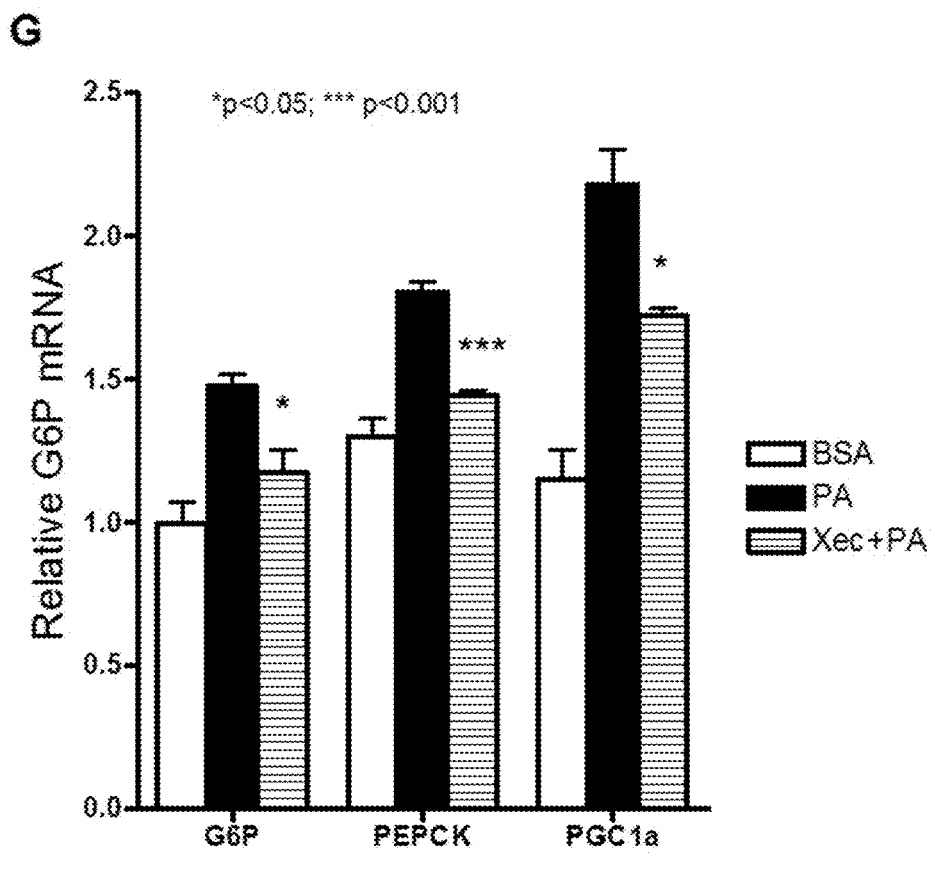
Figure 50H:
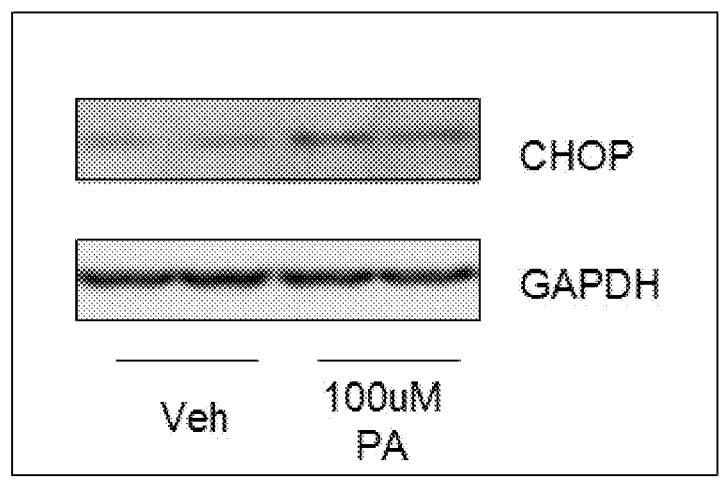
Figure 50I:
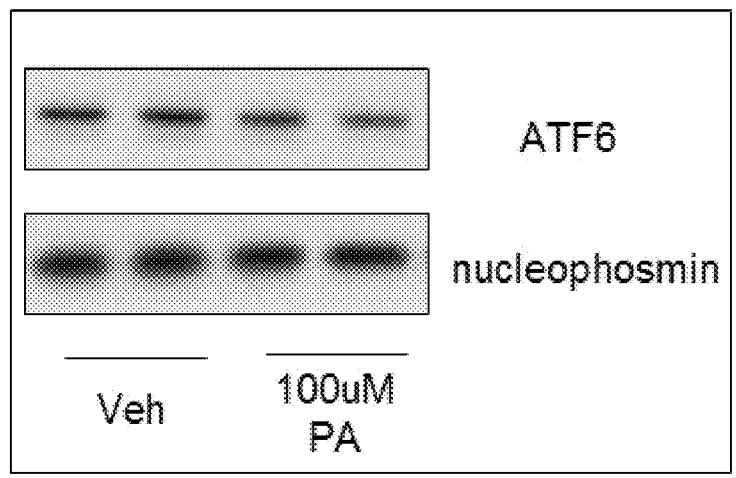
Figures 50J, 50K:
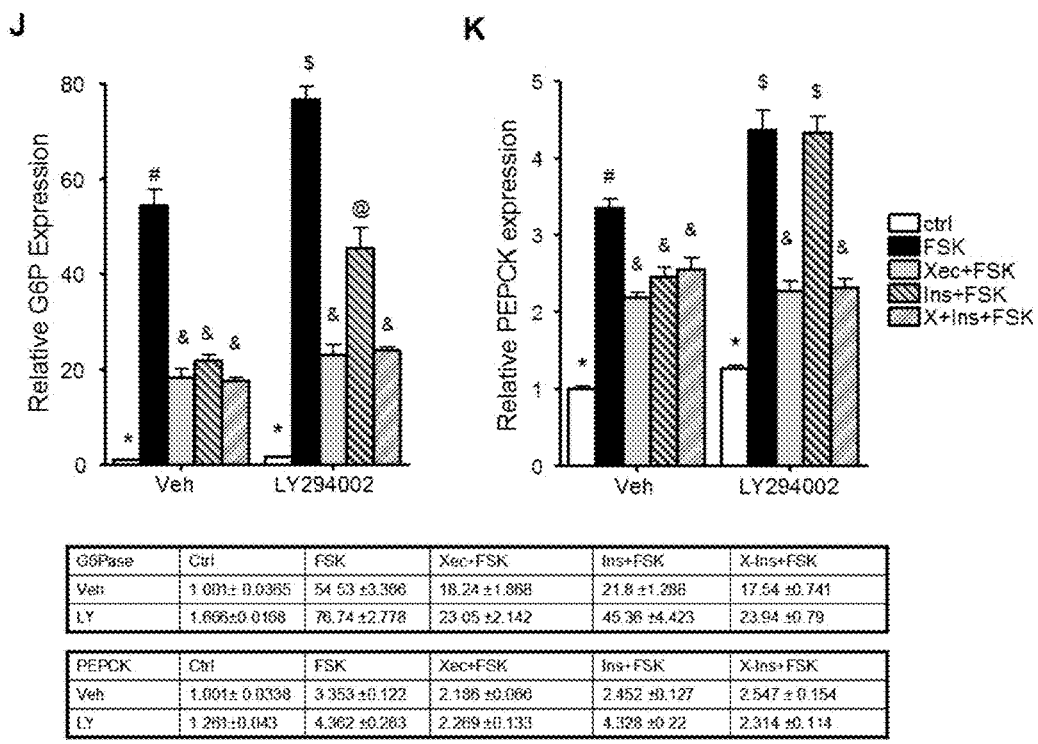
Figure 50L:
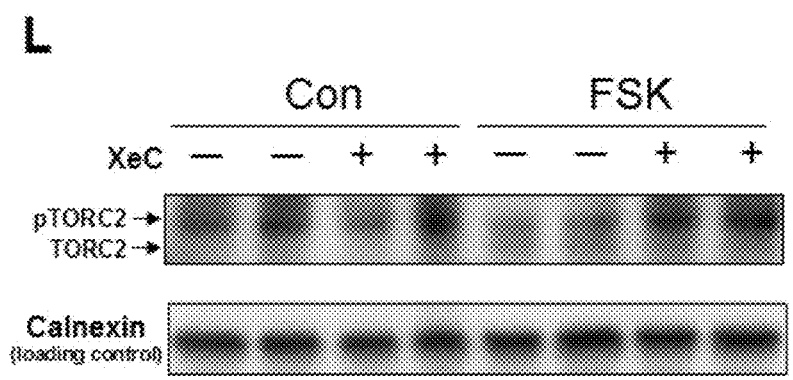
Figure 50M:
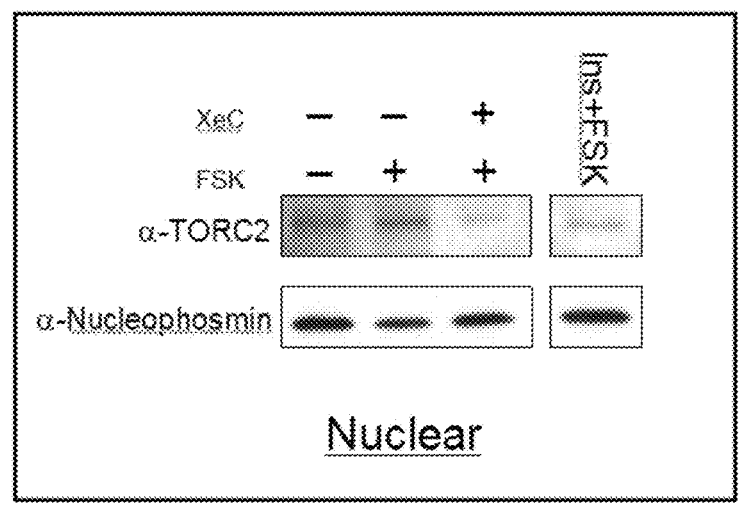

FIGS. 50A-M. The role of IP3R in obesity/insulin resistance induced hyperglycemia and gluconeogenesis. FIG. 50A. Evidence that Xestospongin C Treatment of ob/ob Mice Inhibits IP3R Assay of IICR in Freshly Isolated Peritoneal Cavity Macrophages. FIG. 50B-E. Inhibition of IP3R Reduces Fasting Blood Glucose Levels in ob/ob Mice. FIG. 50F. Inhibition of IP3R Reduces Hepatic Expression of PEPCK, G6Pase, and PGC1α in ob/ob. FIG. 50G-I. Inhibition of IP3R Reduces Expression of PEPCK, G6Pase, and PGC1α in Palmitate-Treated Hepatocytes as a Model of ER Stress and Insulin Resistance. FIG. 50J-K. Inhibition of IP3R Reduces Expression of G6Pase and PEPCK in Akt-Inhibited Hepatocytes as a Model of Insulin Resistance. FIG. 50L. IP3R Activity is Required for Forskolin-Induced TORC2 Dephosphorylation. FIG. 50M. IP3R Activation is Required for TORC2 Nuclear Retention.

Figure 51:
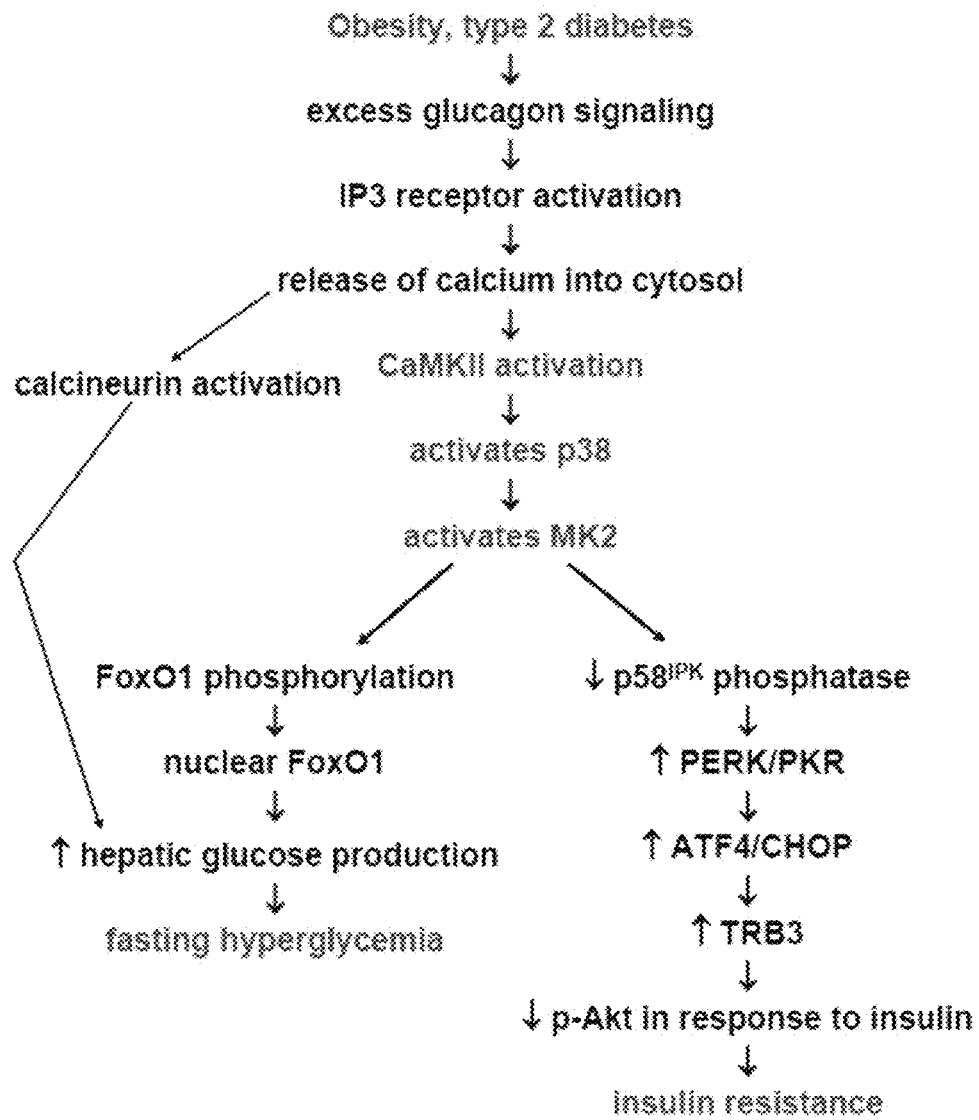

FIG. 51. Diagram showing the IP3R pathway.

Figure 52:
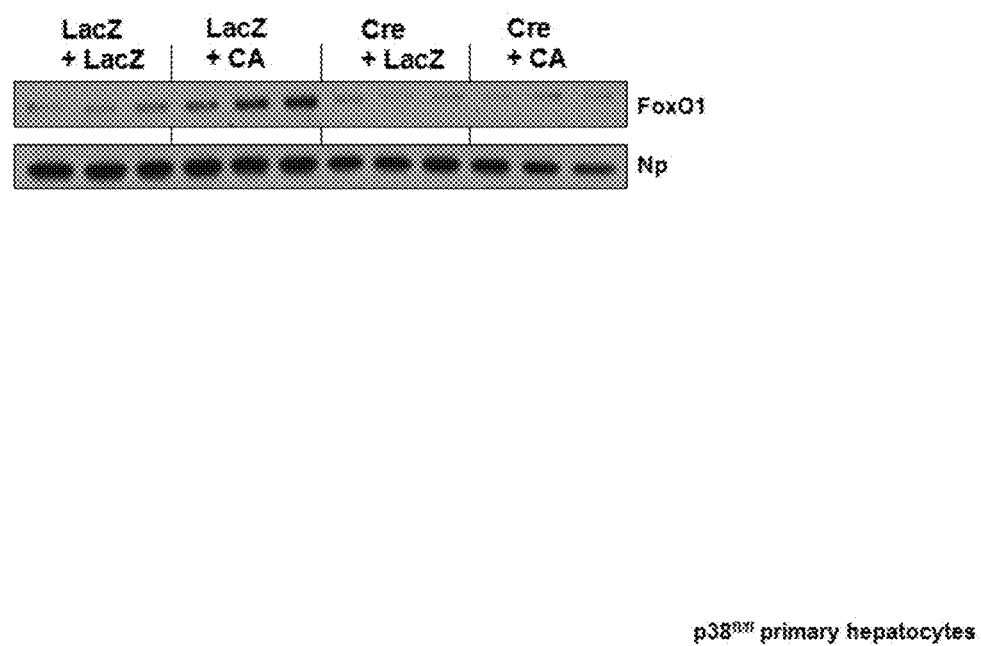

FIG. 52. CA-CaMKII does not increase nuclear FoxO1 in p38 deficient hepatocytes. Primary hepatocytes (HCs) from p38$^{fl/fl}$ mice were transduced with adeno-LacZ or adeno-Cre. After 12 h, half of the cells were transduced with adeno-CA-CaMKII while the other half was transduced with adeno-LacZ. Cells were incubated in serum-depleted medium o.n. and then serum-free medium for 5 h. Nuclear extracts were assayed by immunoblot for FoxO1 and nucleophosmin (Np).

Figures 53A, 53B:
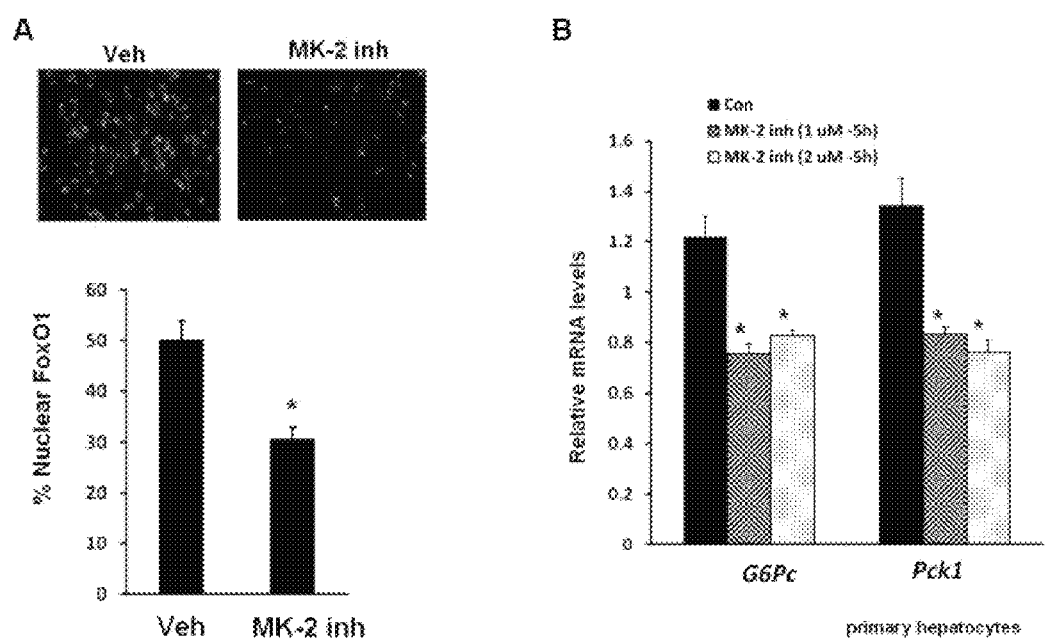

FIGS. 53A-B. MK-2 regulates hepatic FoxO1 subcellular localization and hepatic G6Pc and Pck1. FIG. 53A. Adeno-GFP-FoxO1-transduced HCs were serum-depleted overnight, and then incubated for 30 min in serum-free media with 2 uM MK-2 inhibitor or vehicle (Veh) control. FoxO1 localization was assessed by indirect immunofluorescence (Bar, 10 nm; *P<0.005; mean±S.E.M.). FIG. 53B WT HCs were serum-depleted overnight and then incubated for 5 h with 100 nm glucagon in serum-free media with or without MK-2 inhibitor. RNA was assayed for G6pc and Pck1 mRNA (*P<0.005; mean±S.E.M.). MK-2 Inhibitor is from Calbiochem (cat#475864): 2-(2-Quinolin-3-ylpyridin-4-yl)-1,5,6,7-tetrahydro-4H-pyrrolo-[3,2-c]pyridin-4-one.

Figure 54:
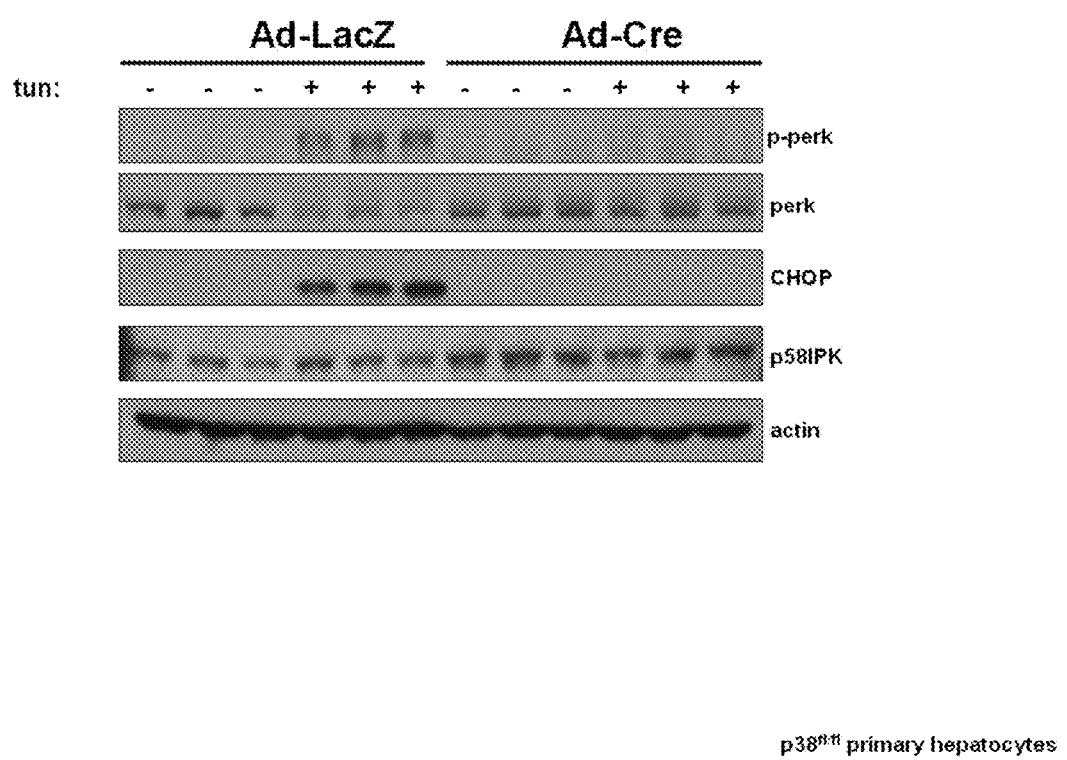

FIG. 54. p38 deficiency suppresses tunicamycin induced UPR activation. Tunicamycin was added to HCs from p38$^{fl/fl}$ mice transduced with adeno-LacZ control or adeno-Cre. Lysates were immunoblotted for p-PERK, PERK, CHOP, p58IPK and actin.

Figure 55:
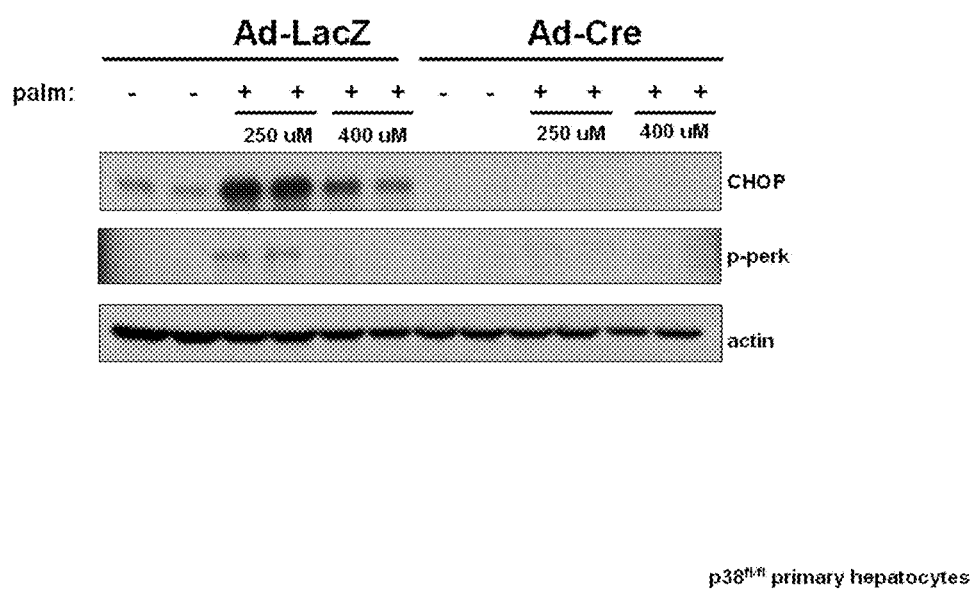

FIG. 55. p38 deficiency suppresses palmitate induced UPR activation. Palmitate was added to HCs from p38$^{fl/fl}$ mice transduced with adeno-LacZ control or adeno-Cre. Lysates were immunoblotted for p-PERK, CHOP and actin.

Figure 56:
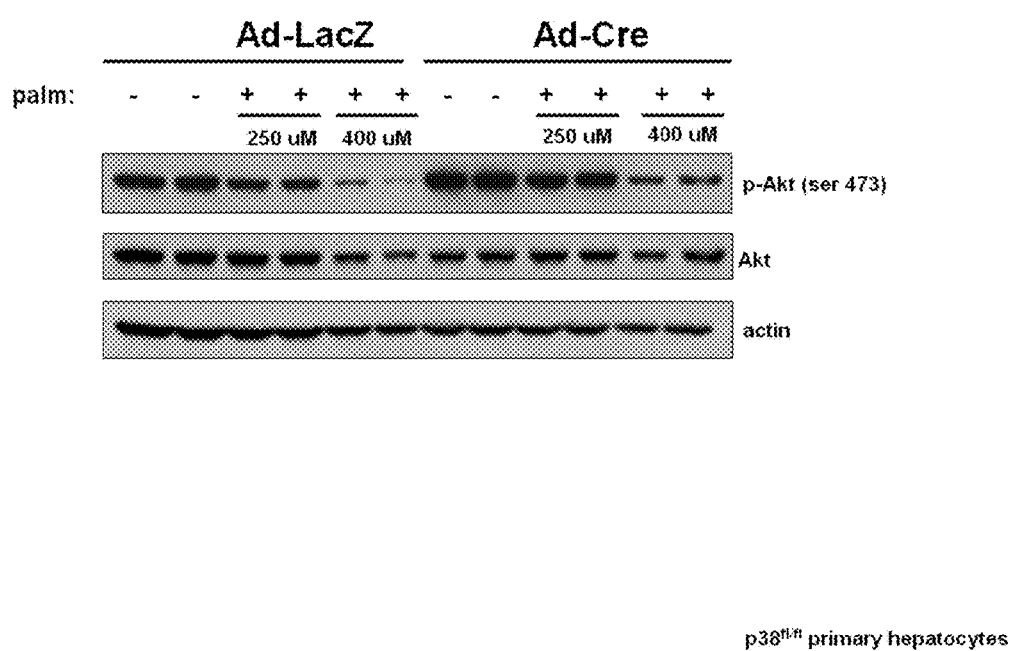

FIG. 56. Acute insulin-induced p-AKT in HCs is enhanced by p38 deficiency. As in FIG. 55, except the HCs were treated with 100 nM insulin for 5 min. Lysates were immunoblotted for p-Akt, Akt and actin.

Figure 57A:
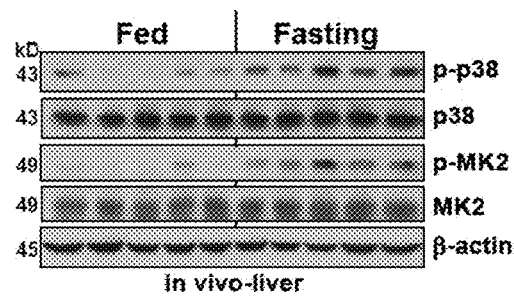
Figure 57B:
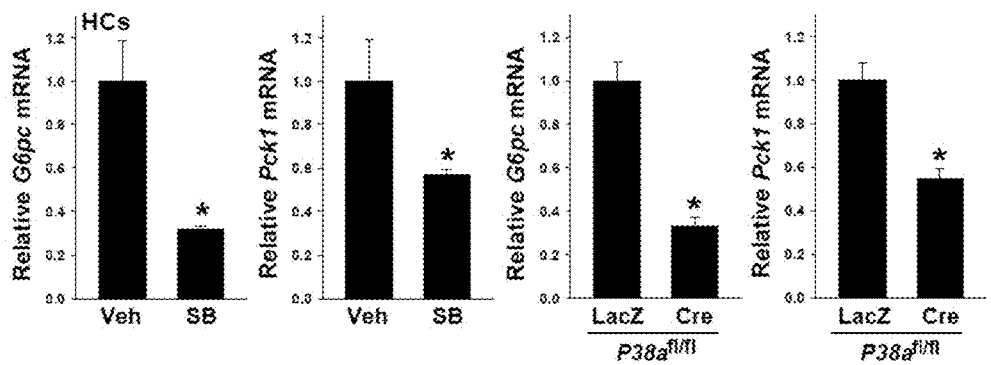
Figure 57C:
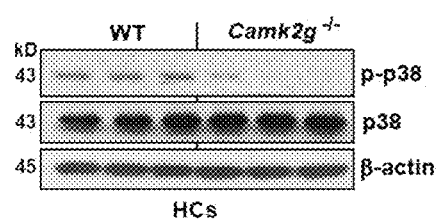
Figure 57D:
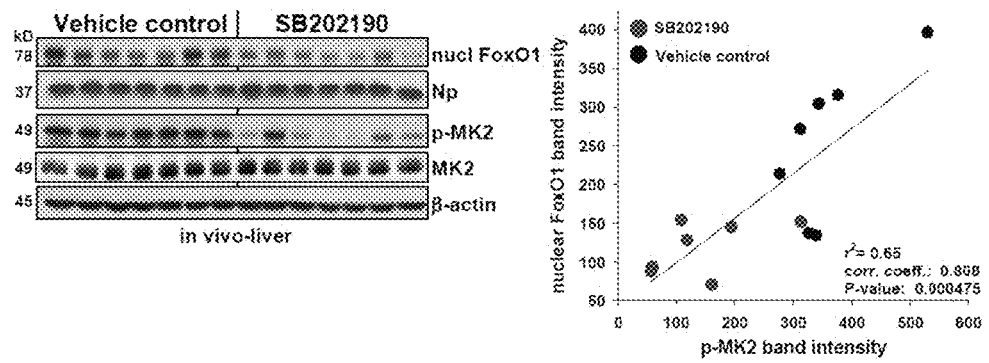
Figure 57E:
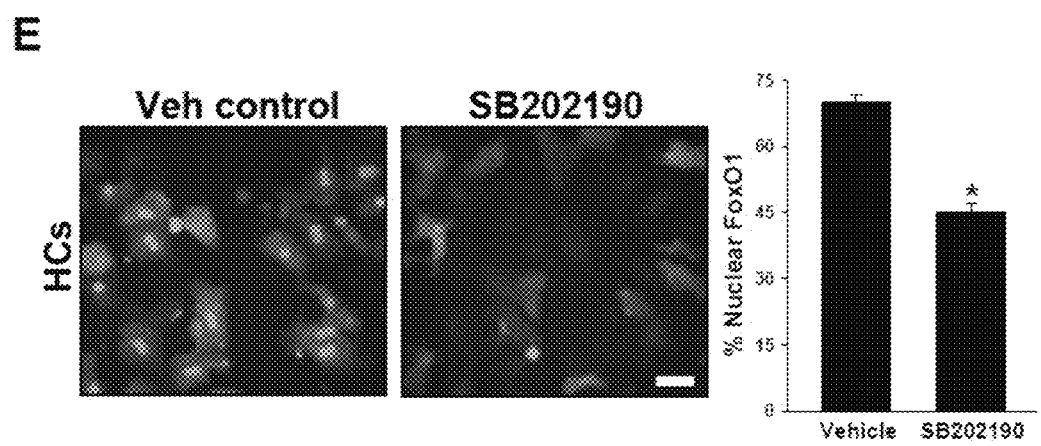

FIGS. 57A-E. FIG. 57A. Mice were fed ad libitum or fasted for 12 h. Liver phospho-p38, total p38, p-MK2, total MK-2, and β-actin were assayed by immunoblot. FIG. 57B WT HCs were serum-depleted overnight and then incubated for 5 h with 100 nm glucagon in serum-free media with or without SB202190; or glucagon was added to HCs from P38afl/fl mice treated with adeno-LacZ (control) or adeno-Cre. RNA was assayed for G6pc and Pck1 mRNA (*P<0.05; mean±S.E.M.). FIG. 57C. HCs from fasting WT and Camk2g-/- mice were assayed for p-p38, total p38, and β-actin. FIG. 57D. WT mice were injected i.p. with 12.5 mg kg-1 body weight of p38 inhibitor (SB202190) or vehicle control. 12 h later, the mice were injected with an additional dose of SB202190 and fasted overnight. The livers were assayed for nuclear FoxO1, nucleophosmin, p-MK2, total MK-2, and β-actin. The correlation between nuclear FoxO1 and p-MK2 band intensities is shown in the graph. FIG. 57E. Adeno-GFP-FoxO1-transduced HCs were serum-depleted overnight, and then incubated for 5 h in serum-free media with SB202190 or vehicle (Veh) control. FoxO1 localization was assessed by indirect immunofluorescence (Bar, 10 μm; *P<0.05; mean±S.E.M.).

Figure 58:
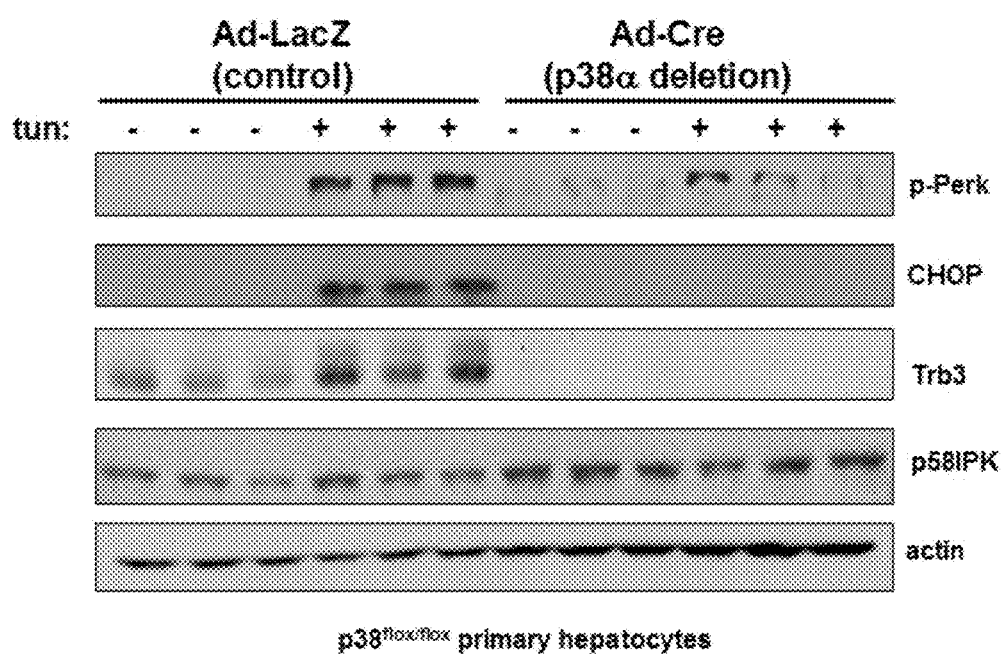

FIG. 58. p38 deficiency decreases tunicamycin-induced UPR activation. Primary hepatocytes from p38α$^{flox/flox}$ mice were transduced at an MOI of 5 with control adeno-LacZ (Ad-LacZ) or adeno-Cre (Ad-Cre) to delete p38. 36 h later, the cells were treated with 0.5 ug/ml tunicamycin for 4 hours. Lysates were then immunoblotted for p-Perk, CHOP, Trb3, p58IPK and actin.

Figure 59:
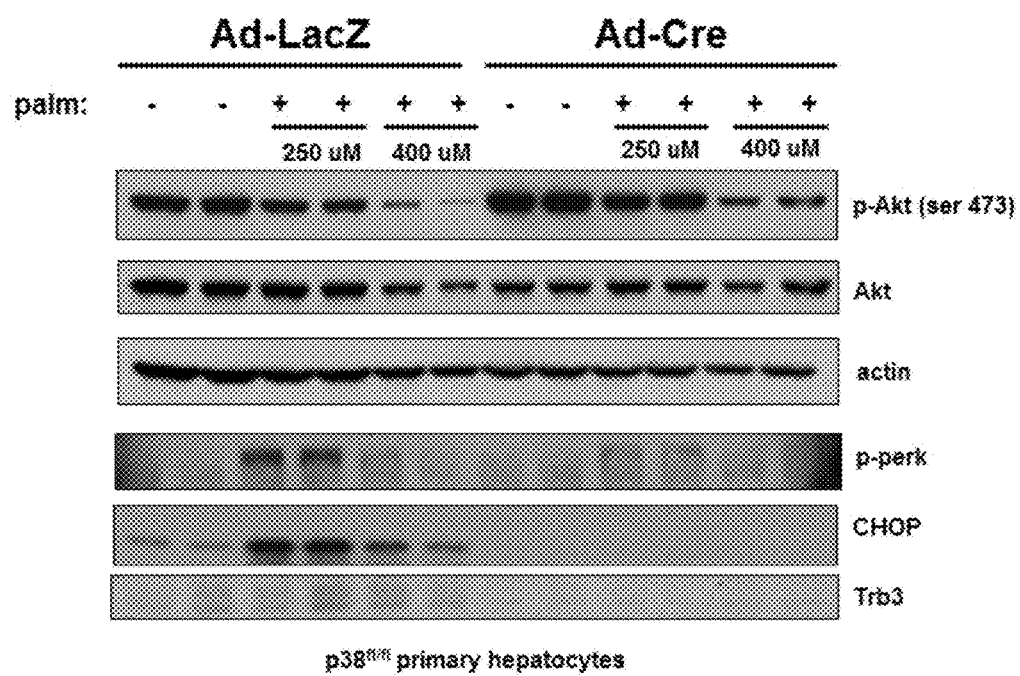

FIG. 59. p38 deficiency blunts palmitate-induced insulin resistance. Primary hepatocytes from p38$^{fl/fl}$ mice were transduced with adeno-LacZ (Ad-LacZ) or adeno-Cre (Ad-Cre) at an MOI of 5. 24 h later, cells were treated o/n with palmitate. After incubation in serum-free medium for 5 h with palmitate, the cells were treated with 100 nM insulin for 5 min. Lysates were then immunoblotted for p-Akt, Akt, actin, p-perk, CHOP and Trb3.

Figure 60:
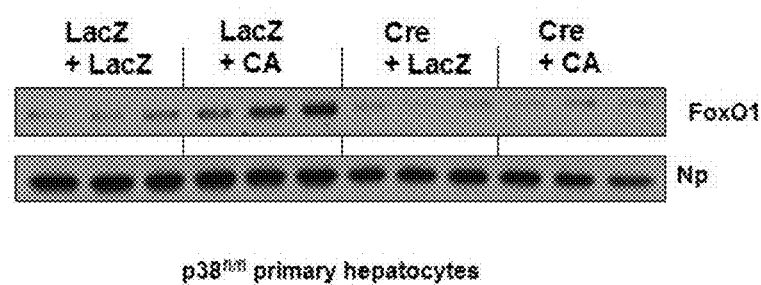

FIG. 60. CA-CaMKII does not increase nuclear FoxO1 in p38-deficient hepatocytes: Evidence that CaMKII and p38 are in the same signaling pathway. Primary hepatocytes from p38$^{fl/fl}$ mice were transduced o/n with adeno-LacZ (Ad-LacZ) or adeno-Cre (Ad-Cre) at an MOI of 5, followed by transduction with adeno-LacZ or adeno-CA-CaMKII (CA) at an MOI of 1. After 12 h, the cells were serum-depleted overnight and then incubated for 4 h in serum-free media. Nuclear extracts were assayed by immunoblot for FoxO1 and nucleophosmin (nuclear loading control).

Figure 61:
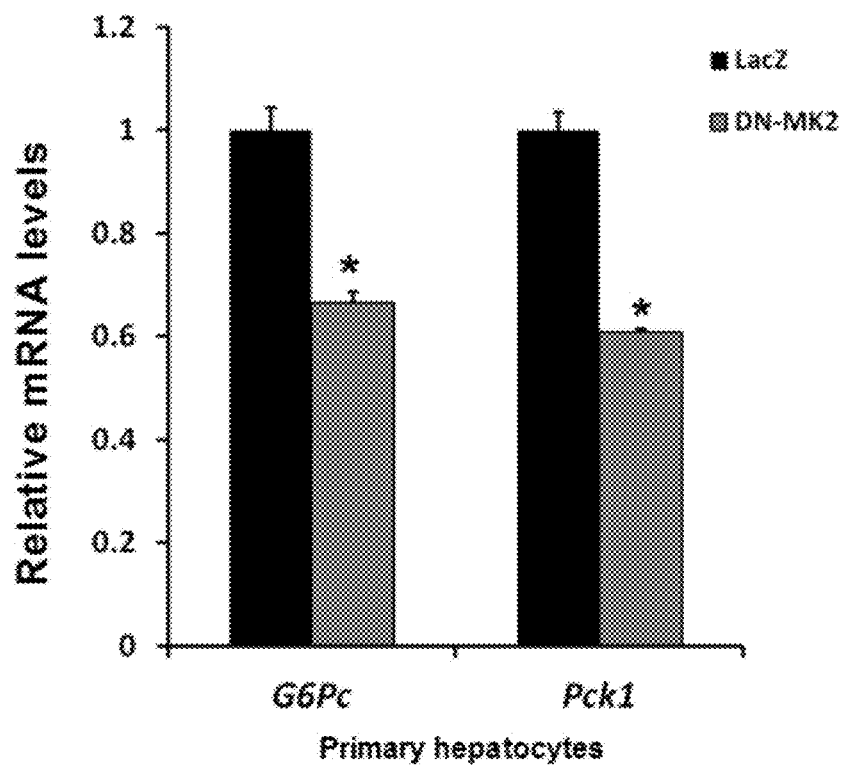

FIG. 61. Dominant negative (DN)-MK2 suppresses forskolin-induced Pck1 and G6Pc induction. Primary hepatocytes from WT mice were transduced with adenoviral vectors expressing either LacZ or DN-MK2. Cells were then serum-depleted overnight and then incubated for 5 h with 2 μM forskolin in serum-free media. RNA was assayed for G6pc and Pck1 mRNA by RT-qPCR. *, P<0.0001

Figure 62:
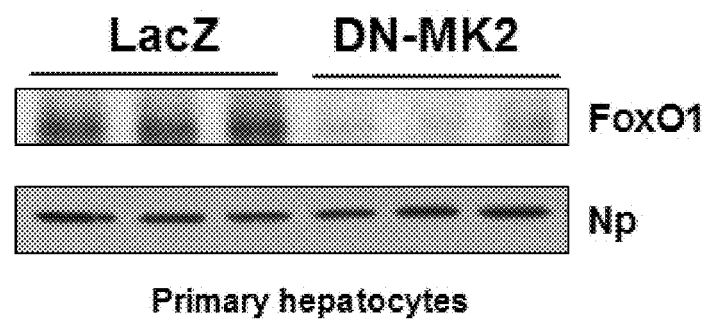

FIG. 62. DN-MK2 decreases nuclear FoxO1 levels. Primary hepatocytes from WT mice were transduced with adeno-LacZ (LacZ) or adeno-DN-MK2 (DN-MK2) at an MOI of 1. After 24 h, the cells were serum-depleted overnight and then incubated for 4 h in serum-free media. Nuclear extracts were assayed by immunoblot for FoxO1 and nucleophosmin (nuclear loading control).

Figure 63:
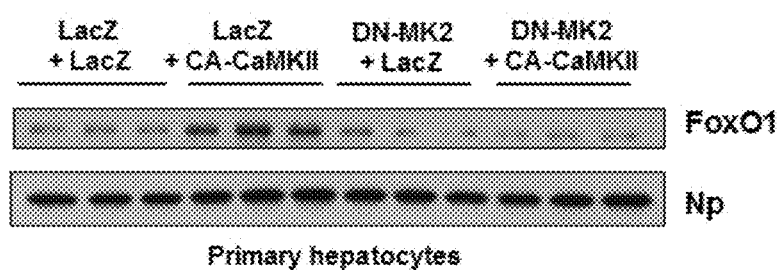

FIG. 63. Constitutively active (CA)-CaMKII does not increase nuclear FoxO1 in MK-2 inhibited hepatocytes: Evidence that CaMKII and MK2 are in the same signaling pathway. Primary hepatocytes from WT mice were transduced o/n with adeno-LacZ (LacZ) or adeno-DN-MK2 (DN-MK2) at an MOI of 1, followed by transduction with adeno-LacZ or adeno-CA-CaMKII (CA-CaMKII) at an MOI of 1. After 12 h, the cells were serum-depleted overnight and then incubated for 4 h in serum-free media. Nuclear extracts were assayed by immunoblot for FoxO1 and nucleophosmin (nuclear loading control).

Figure 64:
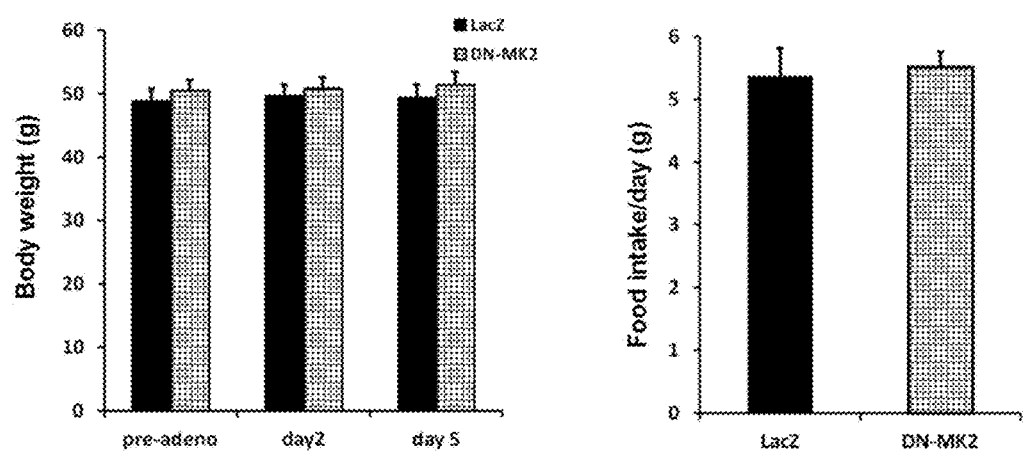

FIG. 64. Hepatic MK-2 inhibition does not change body weight or food intake. 10 week-old ob/ob mice were injected with $1 \times 10^9$ pfu of adenovirus containing either control LacZ (n=5) or DN-MK-2 (n=5)

Figure 65:
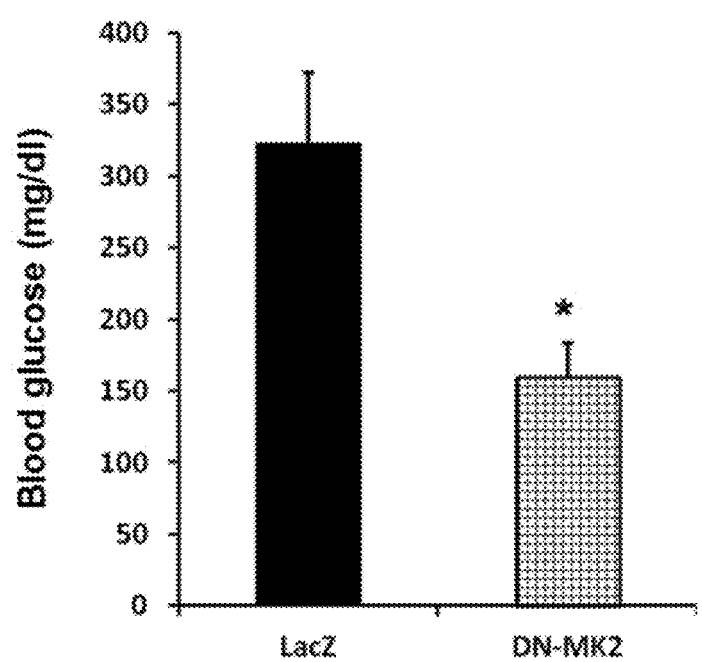

FIG. 65. Hepatic MK-2 inhibition improves hyperglycemia in obese mice. 10 week-old ob/ob mice were injected with $1 \times 10^9$ pfu of adenovirus containing either control LacZ (n=5) or DN-MK-2 (n=5). Blood glucose levels on day 3 after 6 h fasting; **=p<0.05

Figure 66:
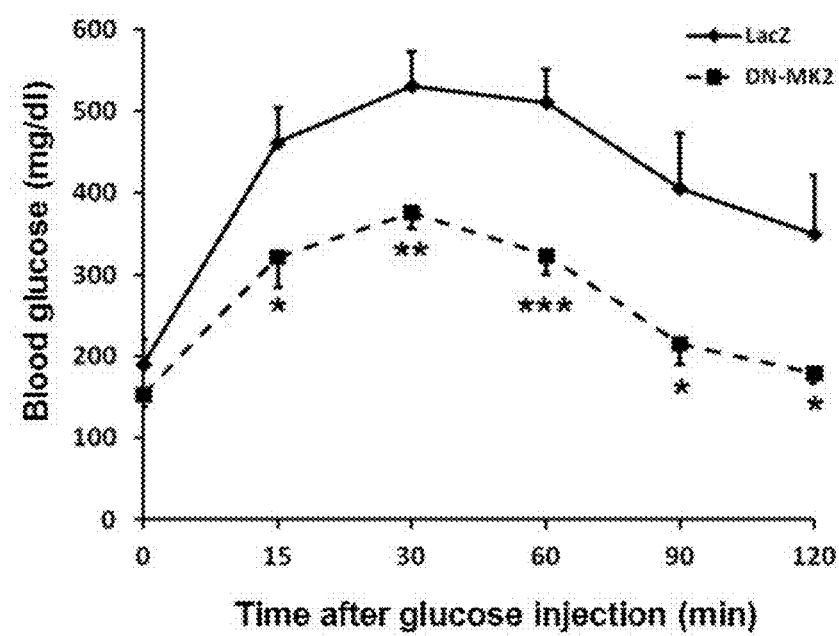

FIG. 66. Hepatic MK-2 inhibition improves hyperglycemia in obese mice (absolute values). Glucose tolerance test (0.5 g/kg i.p.) was performed on day 5 (n=5 for each group) *=p<0.05, =p<0.01, *=p<0.005

Figure 67:
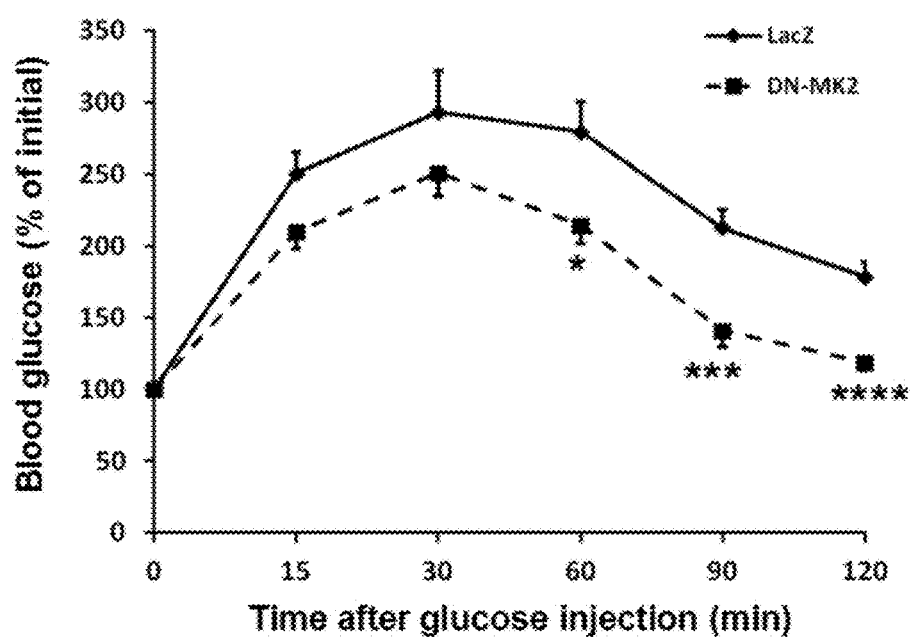

FIG. 67. Hepatic MK-2 inhibition improves hyperglycemia in obese mice (relative to time=0). Glucose tolerance test (0.5 g/kg i.p.) was performed on day 5 (n=5 for each group) *=p<0.05, =p<0.01, *=p<0.005

Figure 68:
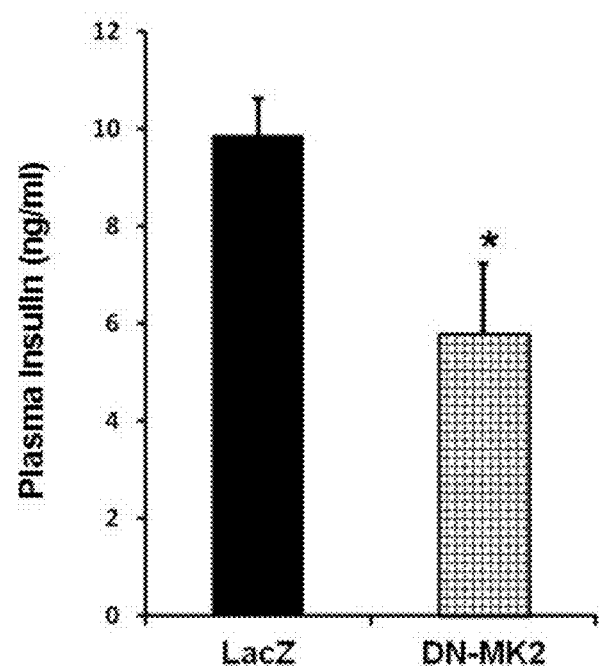

FIG. 68. Hepatic MK-2 inhibition improves hyperinsulinemia in obese mice. 10 week-old ob/ob mice were injected with $1 \times 10^9$ pfu of adenovirus containing either control LacZ (n=5) or DN-MK-2 (n=5). Serum insulin levels on day 8 after 6 h fasting; **=p<0.05

Figure 69:
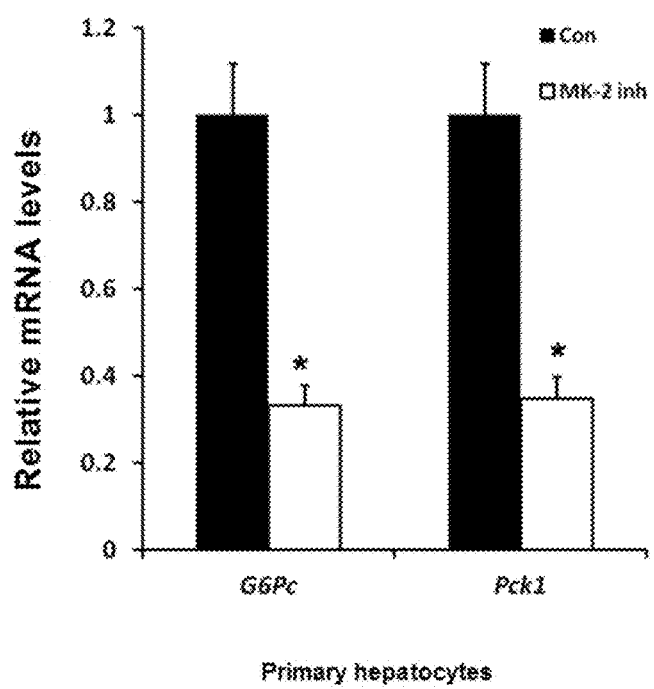

FIG. 69. MK-2 inhibitor suppresses forskolin-induced Pck1 and G6Pc induction in primary hepatocytes. Primary hepatocytes from WT mice were serum-depleted overnight and then pre-treated with 300 nM MK-2 inhibitor (compound 28) or vehicle for 1 h. Cells were then treated with 2 μM forskolin in serum-free media with or without the inhibitor for 4 h. RNA was assayed for G6pc and Pck1 mRNA by RT-qPCR. *, P<0.0001.

FIGS. 70-76 show MK-2 inhibitor studies in obese mice (Compound 28 from Huang et al.*). —MK-2 inhibitor (10 μg/mouse; 0.2 mg/kg) or vehicle control was administered to ob/ob mice once daily by intraperitoneal injections (in 150 ul total volume). See Huang X, Zhu X, Chen X, Zhou W, Xiao D, Degrado S, Aslanian R, Fossetta J, Lundell D, Tian F, Trivedi P, Palani A. *Bioorg Med Chem Lett.* 2012 Jan. 1; 22(1):65-70, "A three-step protocol for lead optimization: quick identification of key conformational features and functional groups in the SAR studies of non-ATP competitive MK2 (MAPKAPK2) inhibitors". Department of Medicinal Chemistry, Merck Research Laboratories, 2015 Galloping Hill Road, Kenilworth, N.J. 07033, USA.

Figure 70:
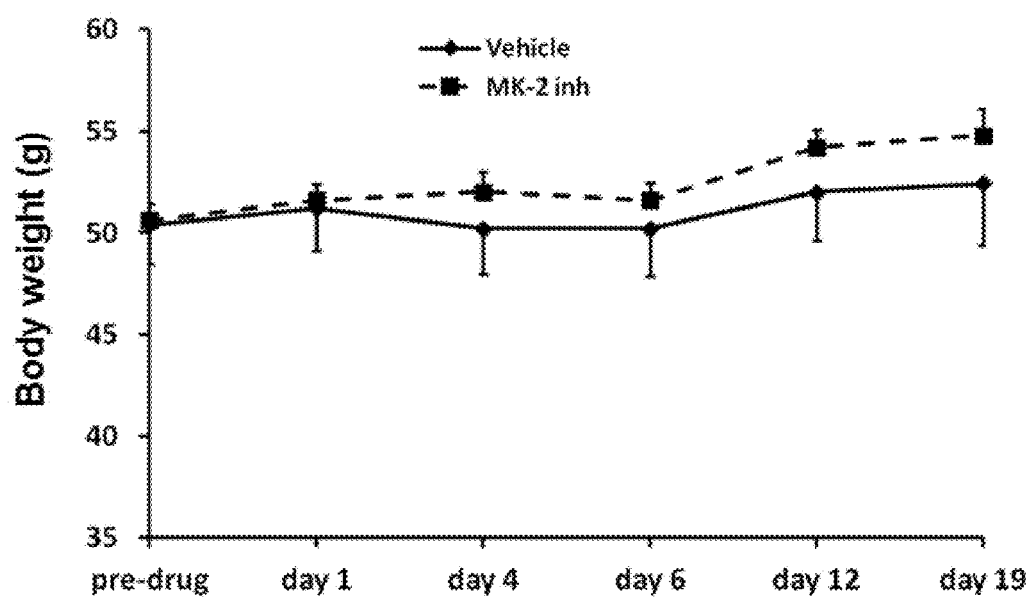

FIG. 70 shows that MK-2 inhibitor does not change body weight. 10 week-old ob/ob mice were administered with MK-2 inhibitor once daily by intraperitoneal injections (150 ul total volume).

Figure 71:
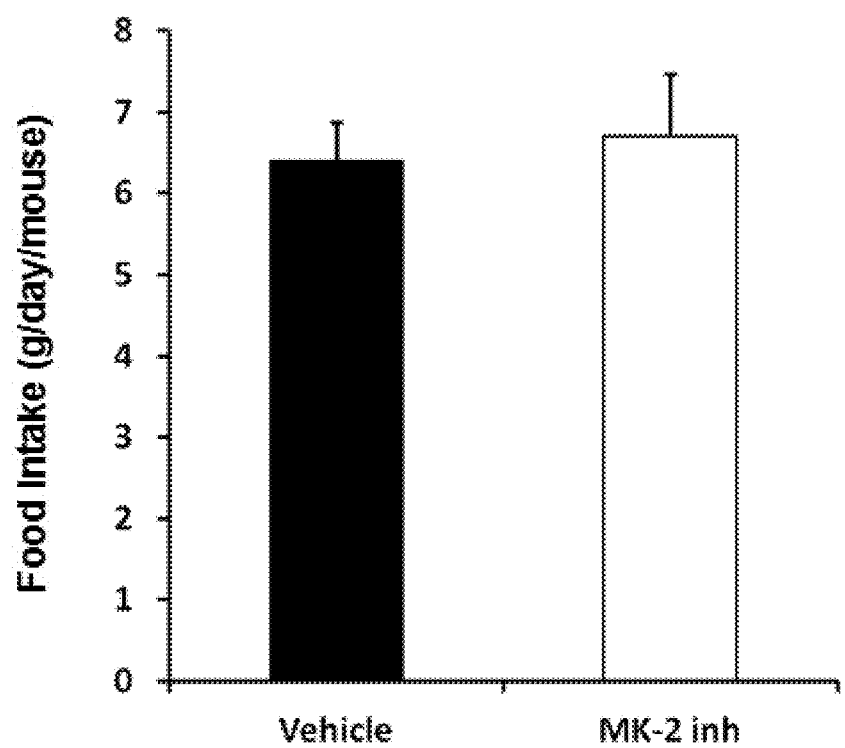

FIG. 71 shows that MK-2 inhibitor does not change food intake. 10 week-old ob/ob mice were administered with MK-2 inhibitor once daily by intraperitoneal injections (150 ul total volume).

Figure 72:
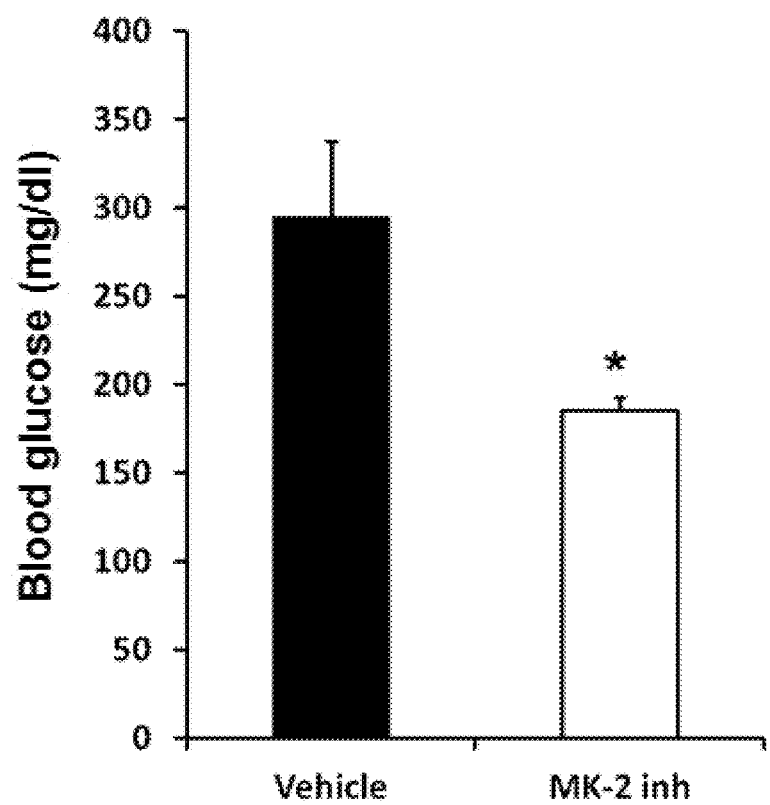

FIG. 72 shows that MK-2 inhibitor decreases fasting blood glucose. 10 week-old ob/ob mice were administered with MK-2 inhibitor once daily by intraperitoneal injections (150 ul total volume). 6 h fasting blood glucose levels on day 5. *, p<0.05

Figure 73:
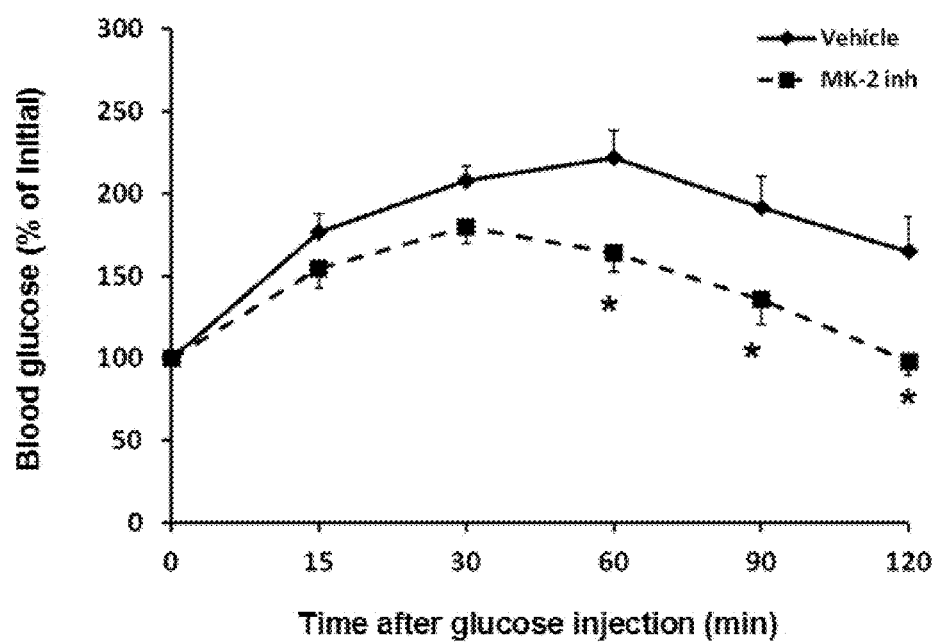

FIG. 73 shows that MK-2 inhibitor improves hyperglycemia in obese mice. 10 week-old ob/ob mice were administered with MK-2 inhibitor once daily by intraperitoneal injections (150 ul total volume). Glucose tolerance test (0.5 g/kg i.p.) was performed on day 7. *, p<0.05

Figure 74:
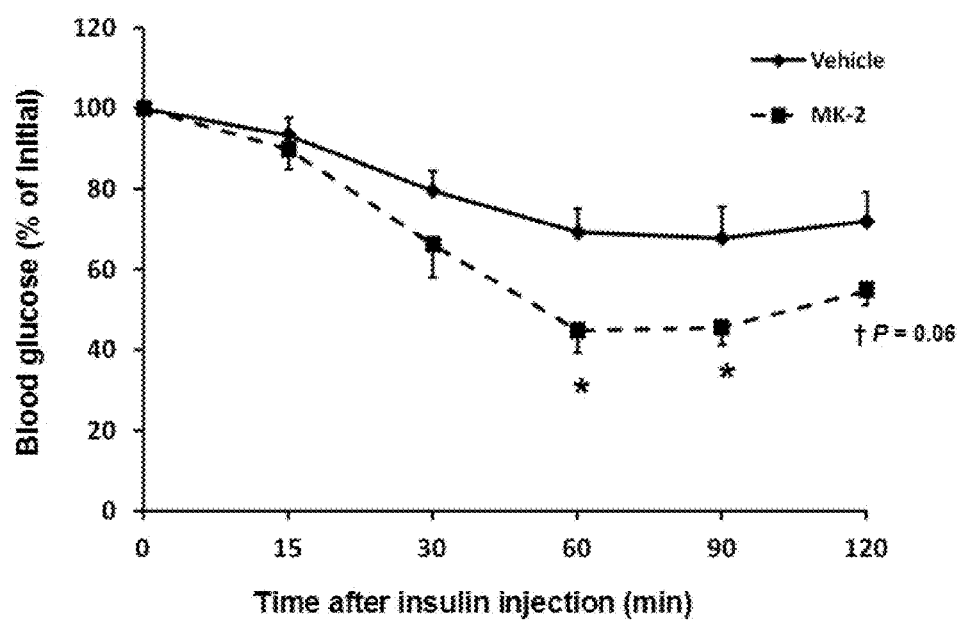

FIG. 74 shows that MK-2 inhibitor improves insulin resistance in obese mice. 10 week-old ob/ob mice were administered with MK-2 inhibitor once daily by intraperitoneal injections (150 ul total volume). Insulin tolerance test (1.5 IU/kg) was performed on day 12. *, p<0.05

Figure 75:
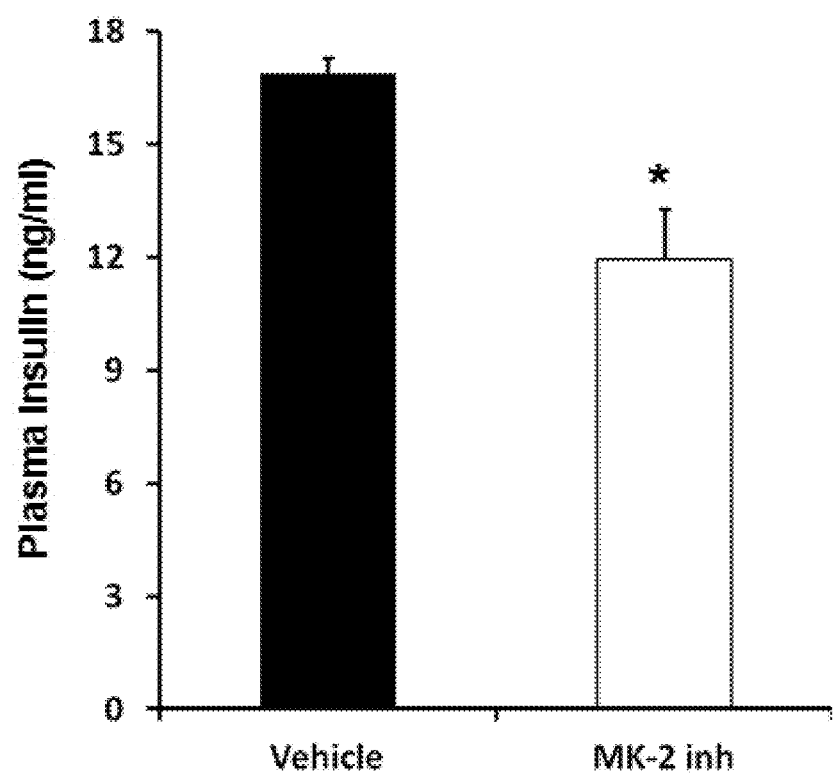

FIG. 75 shows that MK-2 inhibitor decreases fasting insulin levels. 10 week-old ob/ob mice were administered with MK-2 inhibitor once daily by intraperitoneal injections (150 ul total volume). 6 h fasting insulin levels on day 10. *, p<0.05

Figure 76:
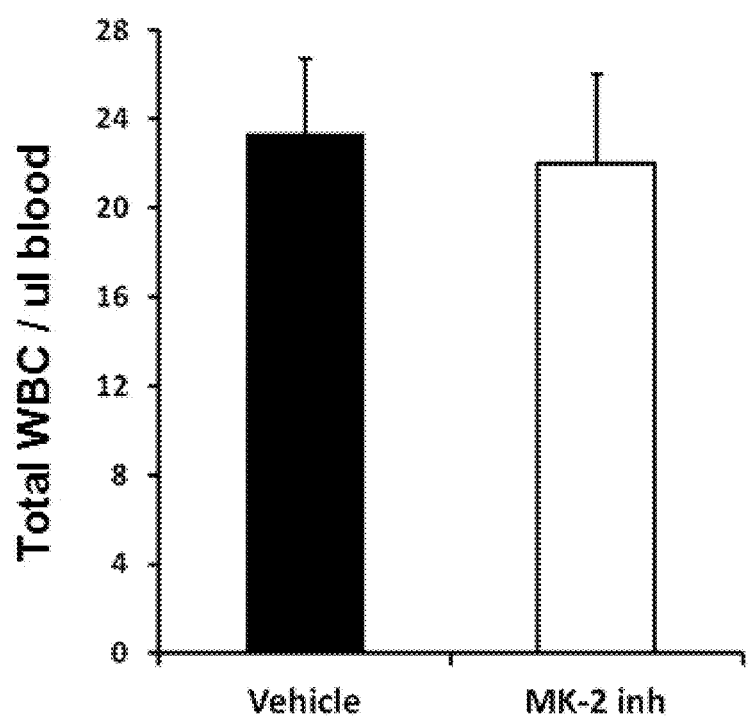

FIG. 76 shows that MK-2 inhibitor does not change total WBC. 10 week-old ob/ob mice were administered with MK-2 inhibitor once daily by intraperitoneal injections (150 ul total volume). Total WBC count levels on day 18.

Figure 77:
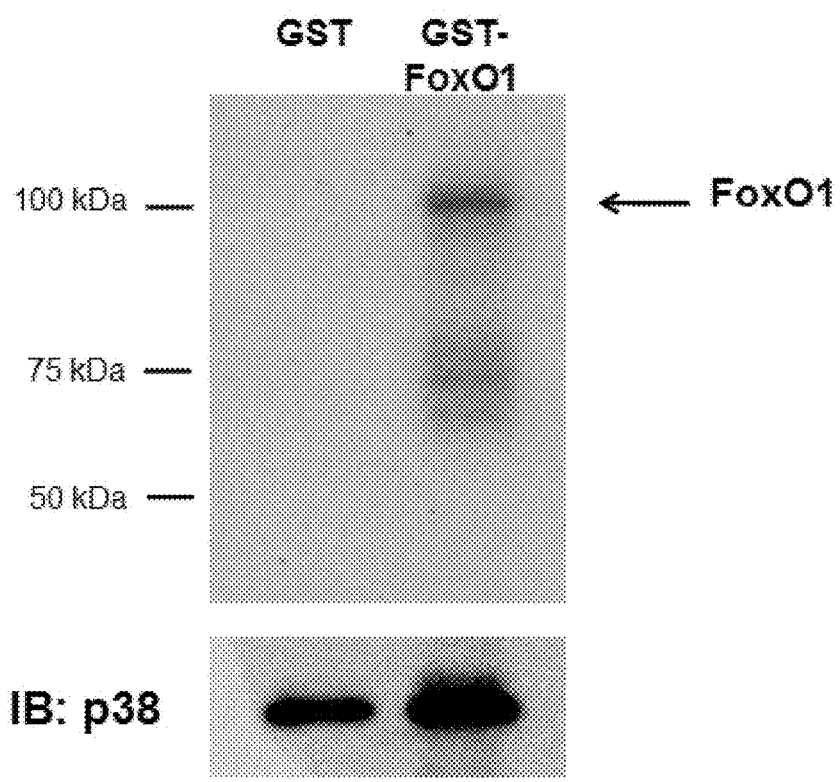

FIG. 77. In vitro phosphorylation of FoxO1 by p38. 1 ug WT GST-FoxO1 or GST control were incubated with 25 ug activated p38 (Upstate Biotechnology) at 30° C. for 30 minutes in 15 ul kinase buffer containing 25 mM Tris-HCl (pH 7.5), 5 mM beta-glycerophosphate, 2 mM dithiothreitol (DTT), 0.1 mM Na3VO4, 10 mM MgCl2 and 2.5 μCi [γ-32P] ATP. Samples were separated by SDS-PAGE and visualized by autoradiography followed by immunoblot analysis.

Figure 78:
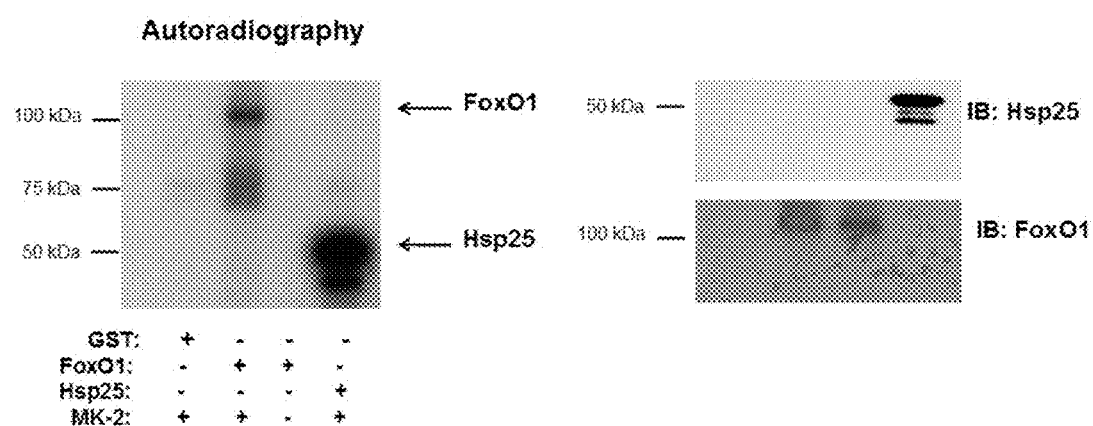

FIG. 78. In vitro phosphorylation of FoxO1 by MK-2. 1 ug WT GST-Foxo1, GST (control) or GST-Hsp25 were incubated with or without 25 ug activated MK-2 (Upstate Biotechnology) at 30° C. for 30 minutes in 15 ul kinase buffer containing 25 mM Tris-HCl (pH 7.5), 5 mM beta-glycerophosphate, 2 mM dithiothreitol (DTT), 0.1 mM Na3VO4, 10 mM MgCl2 and 2.5 μCi [γ-32P] ATP. Samples were separated by SDS-PAGE and visualized by autoradiography followed by immunoblot analysis.

Figure 79:
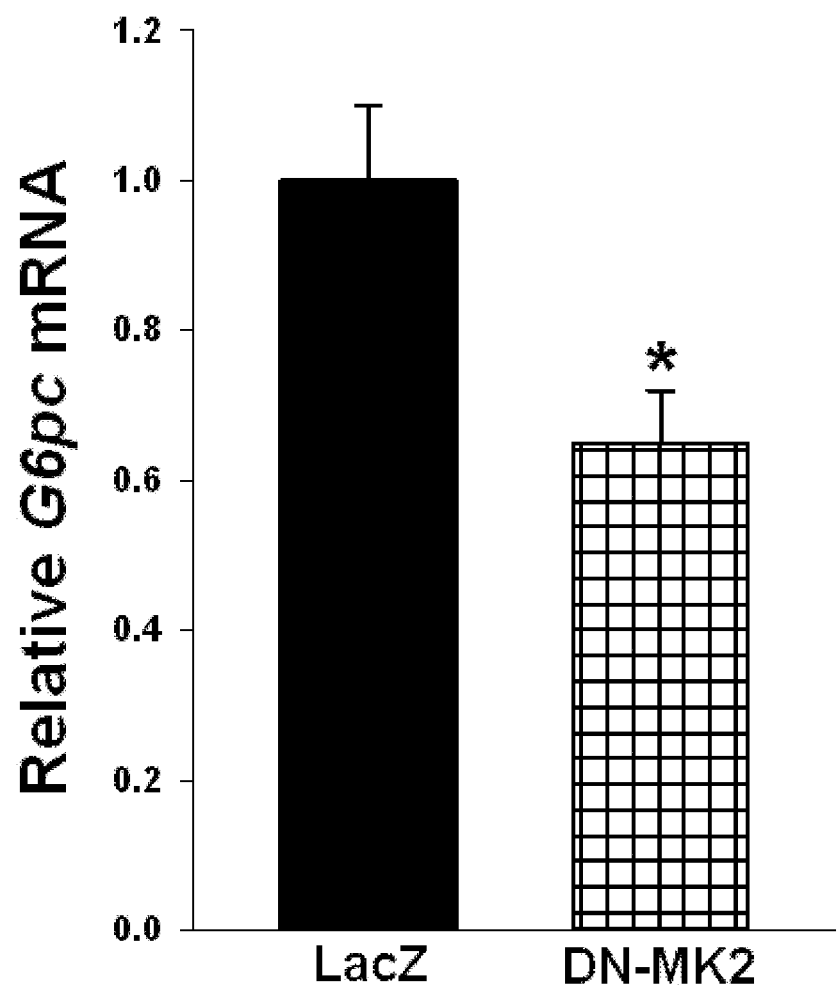

FIG. 79. Dominant-Negative MK2 Lowers Hepatic G6pc in ob/ob Mice. 9 week-old ob/ob mice were injected with $1 \times 10^9$ pfu of adenoviruses containing either control LacZ (n=5) or DN-MK2 (n=5). Liver G6pc mRNA was analyzed 8 days after the injection. (*p<0.05).

Figure 80:
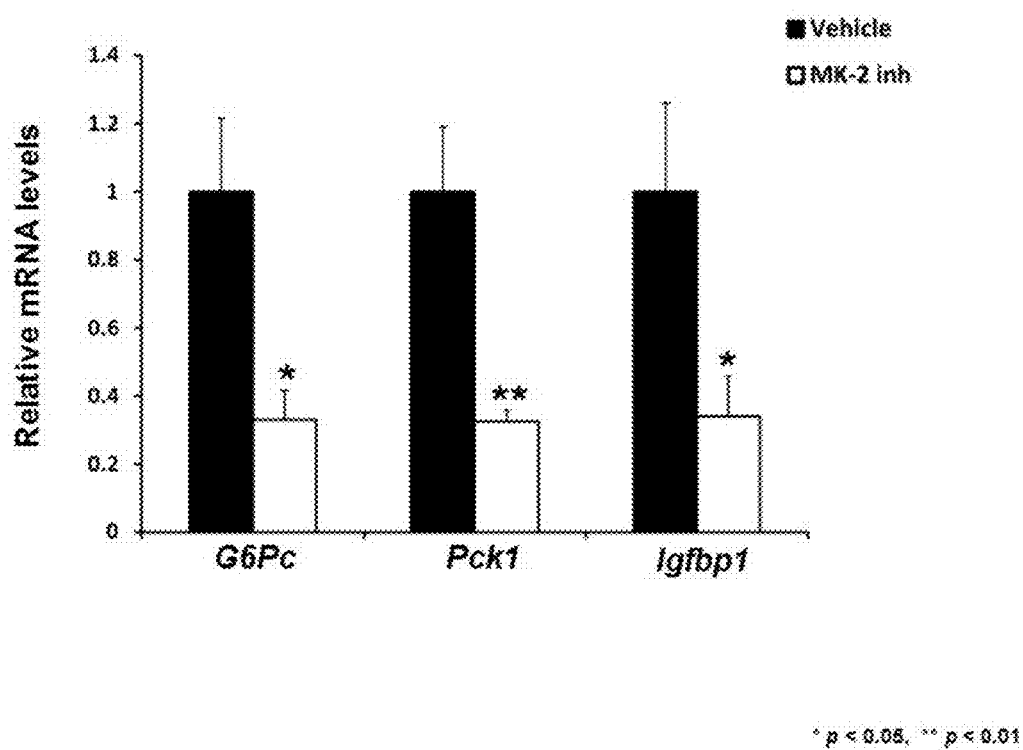

FIG. 80. MK-2 Inhibitor Lowers FoxO1 Target Genes in the Livers of ob/ob Mice. 10 week-old ob/ob mice were treated with MK-2 inhibitor (0.2 mg/kg) or vehicle control once daily by intraperitoneal injections for 20 days. Liver G6pc, Pck1 and Igfbp-1 mRNAs were analyzed by qRT-PCR. (*p<0.05, ** p<0.05). The MK-2 inhibitor used in FIGS. 80-85 is Compound 28 described in Huang X, Zhu X, Chen X, Zhou W, Xiao D, Degrado S, Aslanian R, Fossetta J, Lundell D, Tian F, Trivedi P, Palani A. *Bioorg Med Chem Lett.* 2012 Jan. 1; 22(1):65-70, "A three-step protocol for lead optimization: quick identification of key conformational features and functional groups in the SAR studies of non-ATP competitive MK2 (MAPKAPK2) inhibitors". Department of Medicinal Chemistry, Merck Research Laboratories, 2015 Galloping Hill Road, Kenilworth, N.J. 07033, USA.

Figure 81:
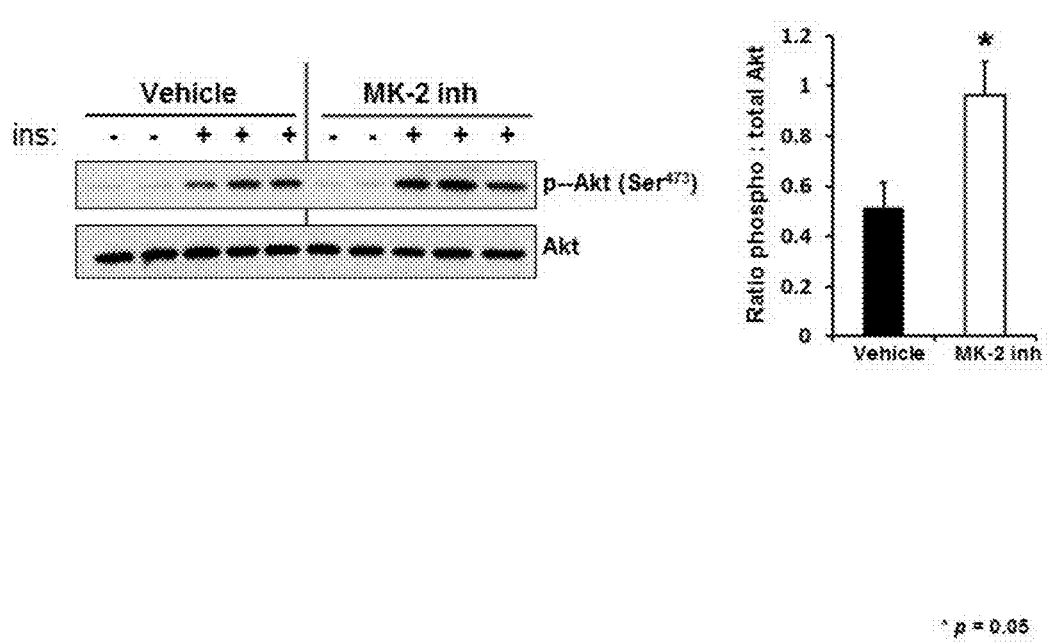

FIG. 81: MK-2 Inhibitor Improves Hepatic Insulin Signaling in ob/ob Mice. 10 week-old ob/ob mice were treated with MK-2 inhibitor (0.2 mg/kg) or vehicle control once daily by intraperitoneal injections for 20 days. Following 6 hours of fasting, insulin (2 IU/kg) was injected into the mice through portal vein for 3 minutes. Liver phospho-Akt (serine 473) and total Akt levels were analyzed via western blotting. Densitometric quantification of the immunoblot data is shown in the graph. (*p<0.05).

Figure 82:
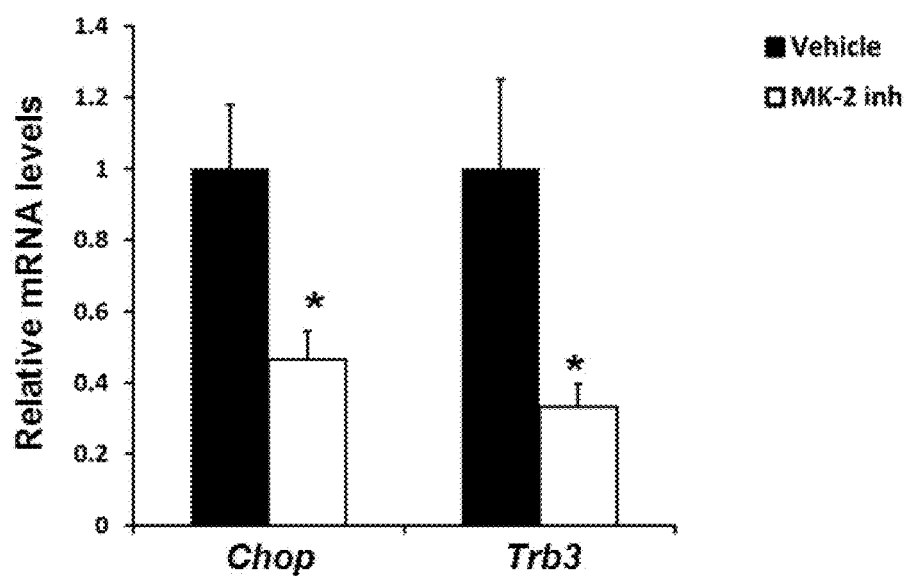

FIG. 82. MK-2 Inhibitor Lowers Chop and Trib3 mRNAs in the Livers of ob/ob Mice. As in FIG. 80, except that liver Chop and Trb3 mRNA levels were analyzed. (*p<0.05).

Figure 83:
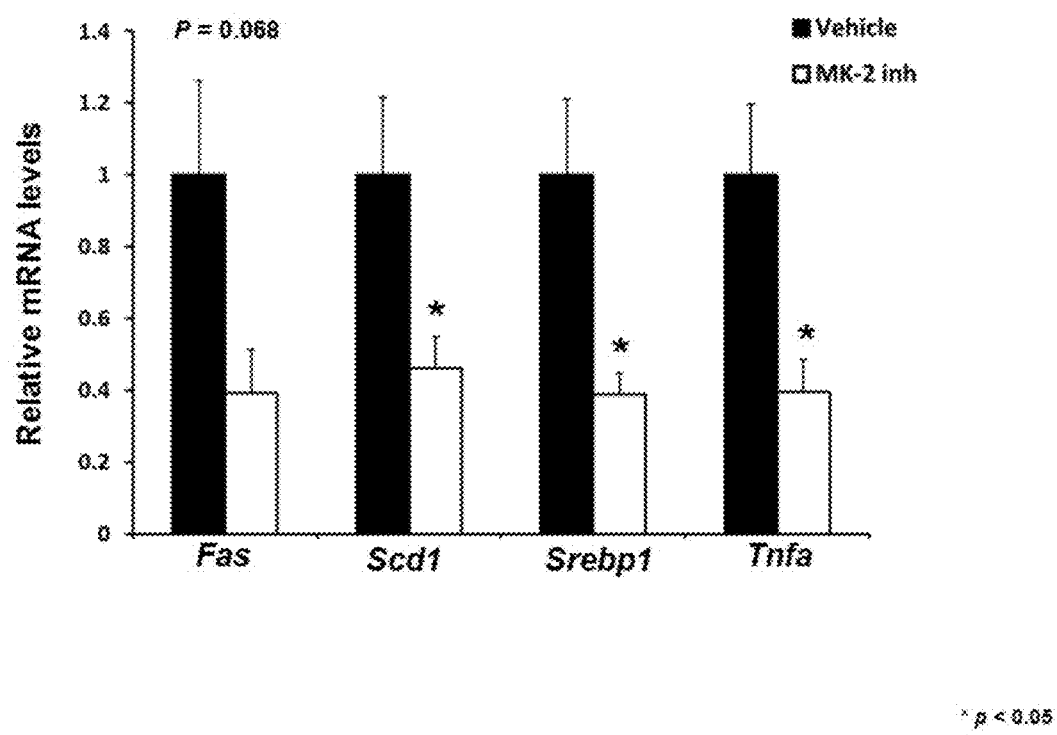

FIG. 83. MK-2 Inhibitor Lowers FA Synthesis mRNAs and Tnfa mRNA in the Livers of ob/ob Mice. As in FIG. 80, except that liver Fas, Scd1, Srebp1, Tnfa mRNA levels were analyzed. (*p<0.05).

Figure 84:
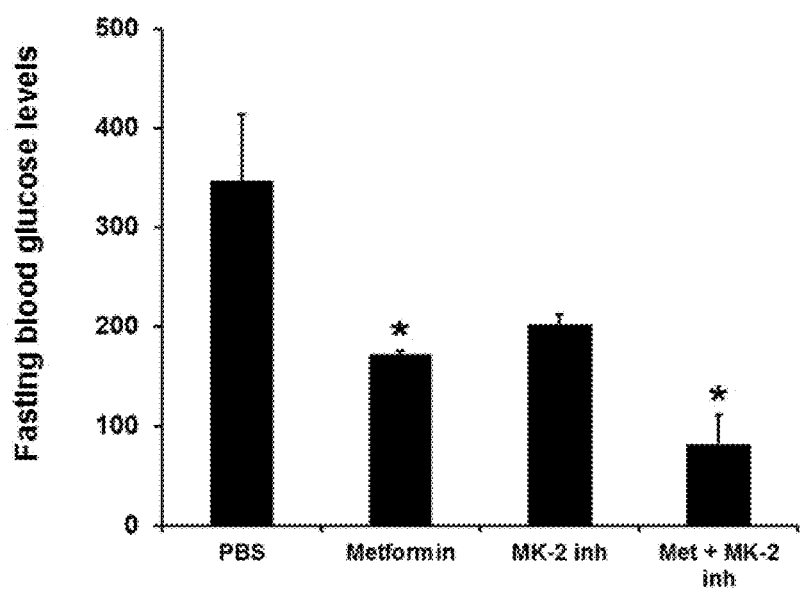

FIG. 84. MK-2 Inhibitor-Mediated Decrease in FBG is Additive with Metformin. 10 week-old ob/ob mice were treated with once daily injections of vehicle control, MK-2 inhibitor (0.2 mg/kg) alone, metformin (250 mg/kg) alone or MK-2 inhibitor and metformin together for 5 days. 6-hour fasting blood glucose levels are shown. (*p<0.05).

Figure 85:
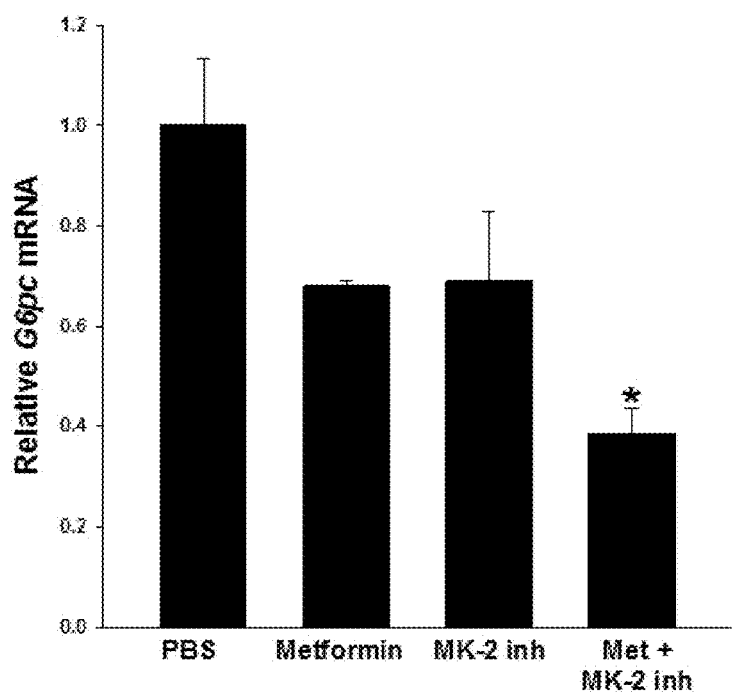

FIG. 85. MK-2 Inhibitor-Mediated Decrease in Hepatic G6pc is Additive with Metformin. As in FIG. 84, except that liver G6Pc mRNA was analyzed by qRT-PCR. (*p<0.05).

Figure 86:
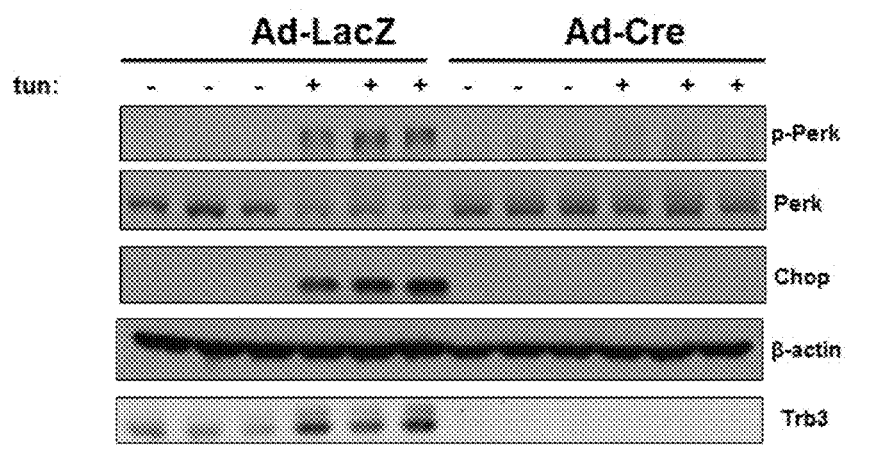

FIG. 86. p38 deficiency suppresses tunicamycin induced UPR activation and Trb3 upregulation. Primary mouse hepatocytes from p38 floxed mice were transduced with adenoviral vectors expressing LacZ or Cre at an MOI of 10. 36 hours after transfection, cells were treated with tunicamycin (1 µg/ml) for 4 hours. Cell lysates were assayed by immunoblot for phospho-Perk, Perk, Chop, β-actin and Trb3.

Figure 87:
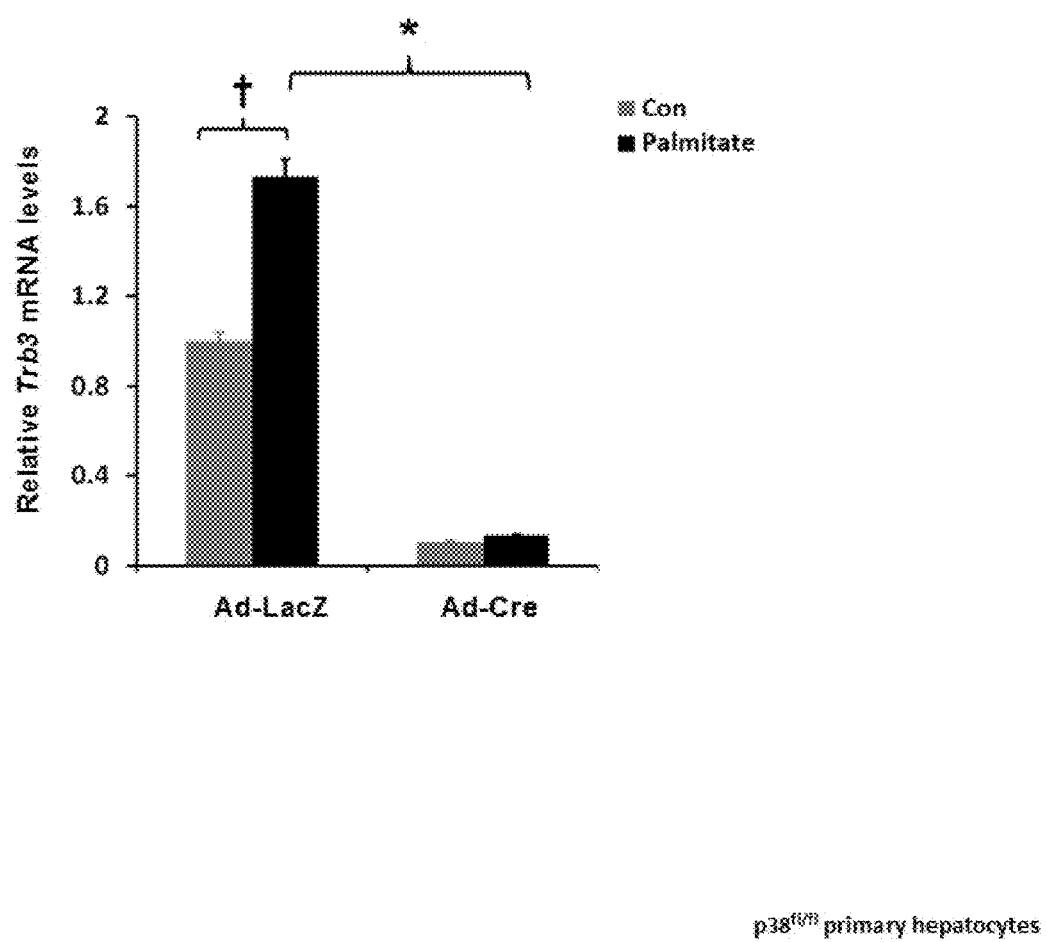

FIG. 87. p38 deficiency suppresses Trb3 mRNA levels. Primary mouse hepatocytes from p38 floxed mice were transduced with adenoviral vectors expressing LacZ or Cre at an MOI of 10. 24 hours after transfection, cells were treated with palmitate (300 µm) for 18 hours. Trb3 mRNA was assayed by qRT-PCR. (†, P<0.0005; *, P<0.0001).

Figure 88:
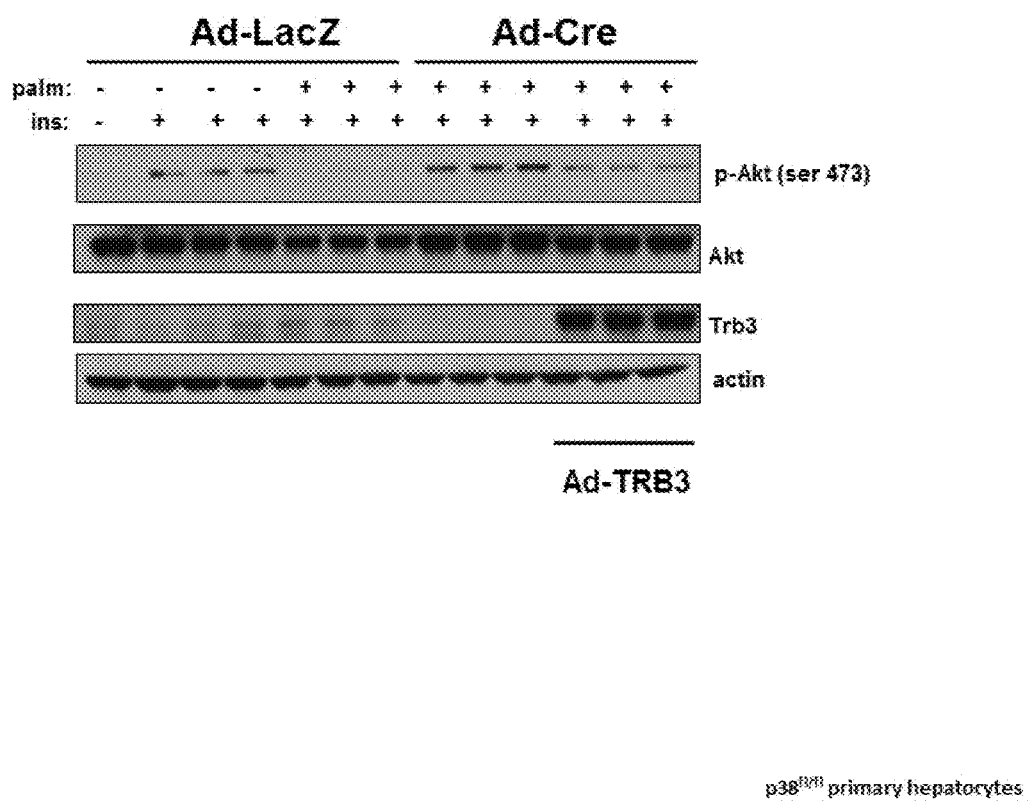

FIG. 88. Acute insulin-induced p-AKT enhancement in p38−/− hepatocytes is rescued by transduction with Ad-Trb3. Primary mouse hepatocytes from p38 floxed mice were transduced with adenoviral vectors expressing LacZ or Cre at an MOI of 10. After overnight incubation, half of the adeno-Cre treated cells were transduced with adeno-Trb3 while rest of the cells received adeno-LacZ. After 12 hours, cells were treated with palmitate (300 nm) for 14 hours, followed by treatment in serum-free media for 5 hours. After 5-hour incubation in serum-free media, cells were stimulated with insulin (100 nm) for 5 minutes. Cell lysates were then assayed by immunoblot for phospho-Akt (serine 473), Akt, Trb3 and β-actin.

FIGS. 89A-G. Inhibition or Deletion of Liver CaMKIIγ Lowers Plasma Insulin and Improves Response to Glucose and Insulin Challenge in Obese Mice. FIG. 89A. 9-wk-old ob/ob mice were fasted for 6 h, assayed for plasma insulin ("pre-adeno"), and then injected with adeno-LacZ (n=6) or -K43A-CaMKII (n=6). Seven days later, after a 6 h fast, the mice were assayed again for plasma insulin ("day 7") (*p<0.05, **p<0.01; mean±S.E.M.). FIG. 89B. Glucose tolerance tests were performed after overnight fasting (*p<0.05, p<0.01; mean±S.E.M.). Area under the curve (AUC) is quantified in the right panel (p<0.01; mean±S.E.M.). FIG. 89C. Insulin tolerance tests were performed after 6 h fasting (*p<0.05; mean±S.E.M.). FIGS. 89D-G. Liver CaMKIIγ mRNA, fasting plasma insulin, fasting blood glucose and blood glucose after glucose challenge in DIO Camk2g$^{fl/fl}$ mice after treatment with adeno-associated virus (AAV) containing either hepatocyte-specific TBG-Cre recombinase (TBG-Cre) (n=5) or the control vector (TBG-LacZ) (n=5) (*p<0.05, p<0.01; mean±S.E.M.). Area under the curve (AUC) for the glucose tolerance test is quantified in the right panel (p<0.01; mean±S.E.M.). See also FIG. 96.

FIGS. 90A-G. Inhibition or Deletion of p38α or MAP-KAPK2 (MK2) Lowers Plasma Glucose and Insulin and Improves Response to Glucose and Insulin Challenge in Obese mice. FIGS. 90A-D. Fasting blood glucose, plasma insulin, glucose and insulin tolerance tests in DIO Mapk14$^{fl/fl}$ mice after treatment with AAV-TBG-LacZ (n=5) or AAV-TBG-Cre (n=5) (*p<0.05; mean±S.E.M.). Area under the curve (AUC) for the glucose tolerance test is quantified in the right panel (*p<0.05; mean±S.E.M.). FIGS. 90E-G. Fasting blood glucose and plasma insulin; and blood glucose after glucose challenge in ob/ob mice administered 1×10⁹ pfu of adeno-LacZ (n=5) or adeno-T222A-MK2 (n=5) (*p<0.05, **p<0.01; mean±S.E.M.). Area under the curve (AUC) for the glucose tolerance test is quantified in the right panel (*p<0.05; mean±S.E.M.).

FIGS. 91A-C. Deletion of CaMKII or p38α Improves Insulin-induced Akt Phosphorylation in Obese Mice. FIG. 91A. DIO Camk2g$^{−/−}$ or WT mice were fasted for 6 h and then injected with 1.5 IU/kg insulin through the portal vein. Total liver extracts were then assayed for p-Akt, total Akt, and β-actin by immunoblot or immunoprecipitated (IP) for IRS-1 and then assayed by immunoblot (FIG. 91B) for IRS-1 or for phospho-Tyr (PY). Densitometric quantification of the immunoblot data is shown in the graph (*p<0.05; mean±S.E.M.). FIG. 91B. As in FIG. 91A, except that DIO Camk2g$^{fl/fl}$ mice treated with AAV-TBG-LacZ or AAV-TBG-Cre were used and p-IR was also assayed by IP/B (*p<0.05; mean±S.E.M.). FIG. 91C. As in FIG. 91B, except that DIO Mapk14$^{fl/fl}$ mice were used, and p-IRS-2 was also assayed by IP/B (*p<0.05; mean±S.E.M.). See also FIG. 97-98.

FIGS. 92A-D. Inhibition of CaMKII or p38α Improves Insulin-induced Akt Phosphorylation in Palmitate-treated Primary Hepatocytes. FIG. 92A. Primary HCs from WT mice were transduced with adeno-LacZ or -K43A-CaMKII at an MOI of 10 and then 24 h later incubated with either BSA control or 0.2 mM palmitate for 19 h, with the last 5 h in serum-free media. The cells were then treated with 100 nM insulin or vehicle control for 5 min, and lysates were probed for p-Akt, total Akt, and β-actin by immunoblot (left panel) or immunoprecipitated for IRS-1 and then assayed by immunoblot for the total level of IRS-1 or for phospho-Tyr (PY) (right panel). FIG. 92B. HCs from Mapk14$^{fl/fl}$ mice were transduced with adeno-LacZ or -Cre and 24 h later incubated with palmitate and then insulin as in FIG. 92A. Lysates were probed for p-Akt, total Akt, β-actin (upper panel), p-GSK3β, total GSK3β, p-FoxO1 and total FoxO1 by immunoblot or immunoprecipitated for IR and IRS-1 and then assayed by immunoblot for the total level of the respective proteins or for phospho-Tyr (lower panel). FIG. 92C. Primary human HCs (metabolism-controlled) were transduced with adeno-LacZ or -K43A-CaMKII at an MOI of 30 and then 36 h later incubated with either BSA control or 0.2 mM palmitate for 10 h, with the last 5 h in serum-free media. The cells were then treated with 100 nM insulin or vehicle control for 5 min, and lysates were probed for p-Aid, total Aid, and β-actin by immunoblot. FIG. 92D. As in FIG. 92A, except adeno-T287D-CaMKII was used, and IRS-2 was also assayed. See also FIG. 98.

Figure 93E:
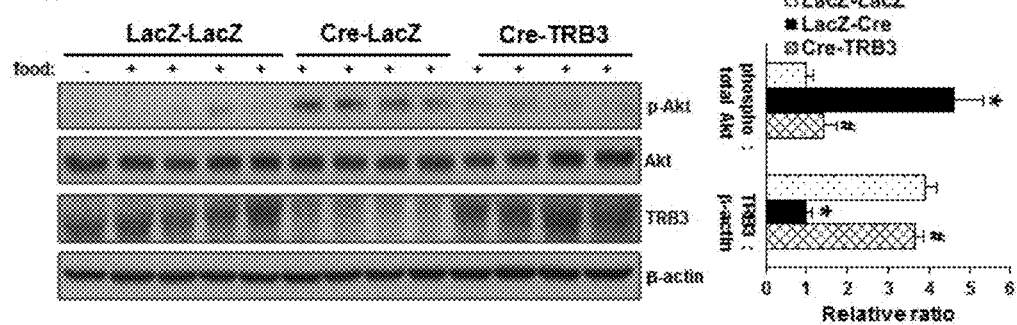

FIGS. 93A-E: Improvement in Insulin-induced Akt Phosphorylation and Glucose Homeostasis by CaMKII Deficiency are Abrogated by Restoring TRB3. FIG. 93A. HCs from Camk2g$^{fl/fl}$ mice were transduced with adeno-LacZ or -Cre and then 24 h later incubated with BSA or palmitate (0.2 mM) for 19 h. Lysates were immunoblotted for TRB3 and β-actin. FIG. 93B. TRB3 and β-actin were probed in livers from DIO WT mice, Camk2g$^{−/−}$ mice, or Camk2g$^{fl/fl}$ mice treated with TBG-LacZ or TBG-Cre. Densitometric quantification of the immunoblot data is shown in the graph (*p<0.05; mean±S.E.M.). FIGS. 93C-E. DIO Camk2g$^{fl/fl}$ mice were treated with TBG-Cre or TBG-LacZ, and five days later, half of the TBG-LacZ mice received adeno-TRB3, while the other half received adeno-LacZ control. Livers were assayed for p-Akt, total Aid, TRB3 and β-actin by immunoblotting after fasting the mice for 16 h and then re-feeding them for 4 h. 5 h fasting and fasted-refed blood glucose and plasma insulin were assayed after 4 weeks of treatment (Differing symbols indicate p<0.05; mean±S.E.M.). See also FIG. 99.

Figure 94F:
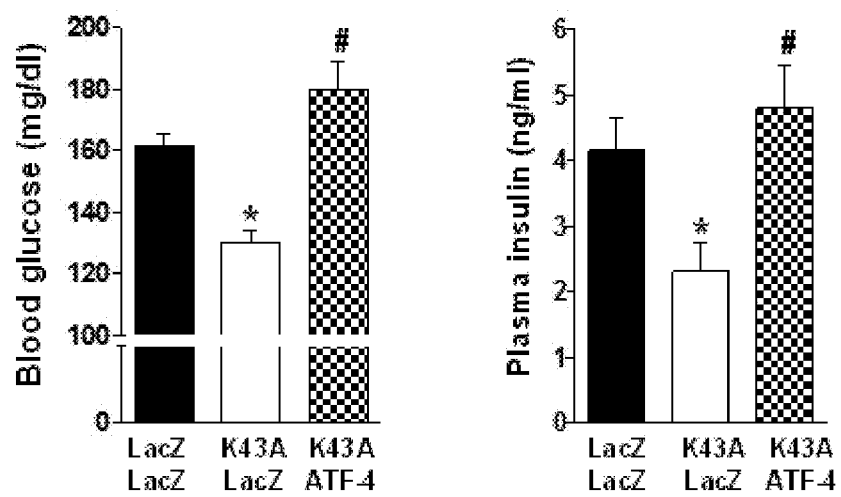

FIGS. 94A-F: Improvement in Insulin-induced Akt Phosphorylation and Glucose Homeostasis by CaMKII Deficiency are Abrogated by Restoring ATF4. FIG. 94A. HCs from Camk2g$^{fl/fl}$ mice were transduced with adeno-LacZ or -Cre. 24 h later, cells were incubated with tunicamycin (0.5 µg/ml) or vehicle control for 4 h. Nuclear lysates were immunoblotted for ATF4 and nucleophosmin (Np) as a loading control. FIG. 94B. Nuclear ATF4 and nucleophosmin (Np) were probed in livers from DIO Camk2g$^{fl/fl}$ mice treated with TBG-Cre or TBG-LacZ or ob/ob mice treated with adeno-LacZ or -K43A-CaMKII. FIG. 94C. HCs from Camk2e mice were transduced with adeno-LacZ or -Cre and then 4 h later, half of the adeno-Cre transduced cells received adeno-ATF4, while the other half received adeno-LacZ control. After 24 h, the cells were incubated with palmitate and then insulin-induced p-Akt was assayed as in FIG. 92. FIG. 94D. As in FIG. 94C, except that Trb3 mRNA was assayed by RT-qPCR (Bars with different symbols are different from each other and control, p<0.01; mean±S.E.M.). FIGS. 94E-F. Sixteen-week-old DIO mice were administered adeno-LacZ or -K43A-CaMKII, and then, two days later, half of the adeno-K43A-CaMKII mice received adeno-ATF4 while the other half received adeno-LacZ control. Livers were assayed for p-Akt, total Aid, β-actin and nuclear ATF4 and nucleophosmin (Np) by immunoblotting after insulin injection through portal vein. 5 h fasting blood glucose and plasma insulin were assayed after three weeks of treatment (Differing symbols indicate p<0.05; mean±S.E.M.). See also FIG. 100.

FIGS. 95A-G: Acute Insulin-induced p-Akt Enhancement in Camk2g$^{-/-}$ Hepatocytes is Partially Abrogated by ATF6 Inhibition. FIG. 95A. p58$^{IPK}$ and β-actin were probed by immunoblot in livers from DIO Camk2g$^{fl/fl}$ mice treated with AAV-TBG-Cre or AAV-TBG-LacZ. FIG. 95B. HCs from Camk2g$^{fl/fl}$ mice were pretreated with either scrambled RNA (first 2 bars) or siRNA targeting p58$^{ipk}$ (si-p58). After 12 h, the cells were transduced with adeno-LacZ or -Cre. After an additional 24 h, the cells were incubated with BSA control or palmitate (0.2 mM) for 19 h, with the last 5 h in serum-free media. The cells were then assayed for Trb3 mRNA by RT-qPCR (Bars with different symbols are different from each other and control, p<0.05; mean±S.E.M.). FIG. 95C. As in FIG. 95B, except the cells were then treated with ±100 nM insulin for 5 min, and lysates were immunoblotted for p-Akt, total Aid, β-actin, and p58$^{IPK}$ by immunoblot. FIG. 95D. Nuclear ATF6 and nucleophosmin (Np) were probed by immunoblot in livers from DIO Camk2g$^{fl/fl}$ mice treated with AAV-TBG-Cre or AAV-TBG-LacZ. FIG. 95E. As in FIG. 95B, except siRNA targeting Atf6 (siATF6) was used, and p58$^{ipk}$ mRNA was also assayed; first 2 bars in each group received scrambled RNA (Bars with different symbols are different from each other and control, p<0.05; mean±S.E.M.). FIG. 95F. HCs were prepared as in FIG. 95C, except siRNA targeting Atf6 (siATF6) was used. Lysates were immunoblotted for p-Akt, total Akt, β-actin and p58$^{IPK}$ by immunoblot. In the lower blot, nuclei from a parallel set of cells treated with palmitate were probed for ATF6 and nucleophosmin (Np) by immunoblot. FIG. 95G. The data here and previously (Ozcan et al., 2012) support an integrated scheme in which CaMKII mediates two key pathways, one contributing to defective insulin signaling and the other to excessive HGP. Thus, inhibition of liver CaMKII or its downstream agent p38 improves the two cardinal features of T2D. See also FIG. 101.

FIGS. 96A-C: Related to FIG. 89. FIGS. 96A-B. Fasting plasma insulin levels and insulin tolerance tests in DIO Camk2g$^{-/-}$ (n=7) or WT (n=10) mice (mean±SEM;  p<0.01). FIG. 96C. Representative images of H&E staining of liver sections from the two groups of mice. Scale bar, 20 µm. For quantification, 2 separate liver sections from 5 mice in each group were analyzed for the percentage of HCs containing lipid droplets greater than 2 µm in diameter (mean±SEM;  p<0.01).

Figure 97C:
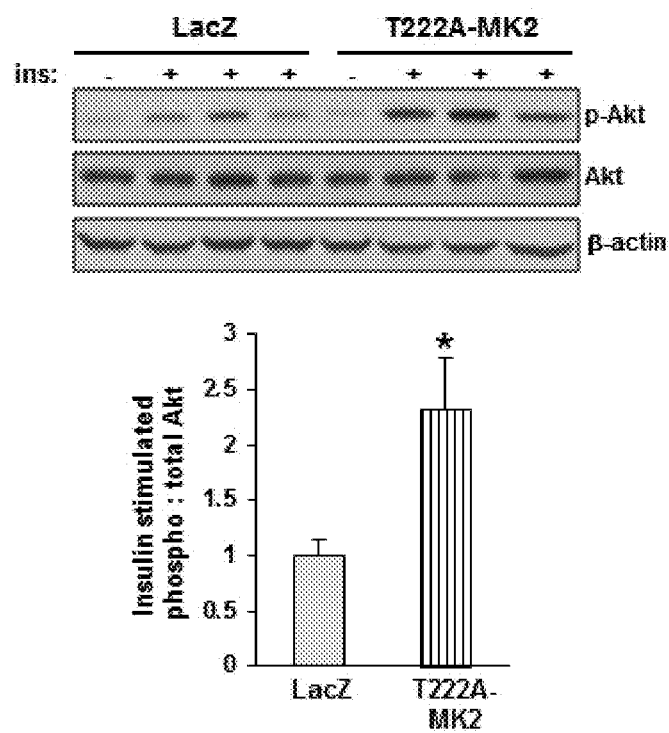

FIGS. 97A-C. Related to FIG. 91. FIG. 97A. Ob/ob mice administered adeno-LacZ or -K43A-CaMKII were fasted for 6 h and then injected with 2 IU/kg insulin through the portal vein. Liver extracts were assayed for p-Aid, total Aid, and β-actin by immunoblot or immunoprecipitated for IRS-1 or IR and then assayed by immunoblot for IRS-1, IR, or phospho-Tyr (PY). Densitometric quantification of the immunoblot data is shown in the graph (mean±SEM; *p<0.05). FIG. 97B. As in FIG. 97A, except WT lean mice were used. FIG. 97C. As in (A), except adeno-T222A-MK2 was used (mean±SEM; *p<0.05).

Figure 98A:
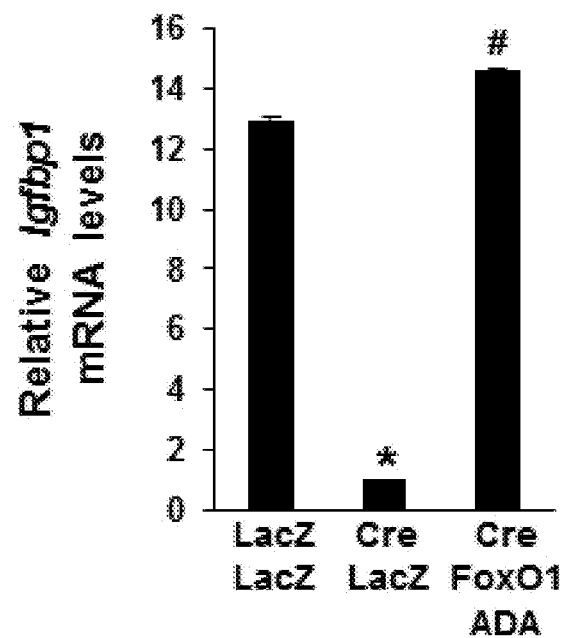

FIGS. 98A-D. Related to FIGS. 91-92. Improvement in Insulin-induced Akt Phosphorylation in Camk2g$^{-/-}$ Hepatocytes is not Abrogated by Restoring Nuclear FoxO1. FIGS. 98A-B. HCs from Camk2e mice were transduced with adeno-LacZ or -Cre, and then 4 h later half of the adeno-Cre-transduced cells received HA-tagged adeno-FoxO1-ADA while the other half received adeno-LacZ control. After an additional 24 h of incubation, the cells were incubated with palmitate and then insulin as in FIG. 92. One set of cells were harvested and assayed for Igfbp1 mRNA levels by RT-qPCR and another set was assayed for p-Akt, total Akt, β-actin by immunoblotting (mean±SEM; bars with different symbols are different from each other and control, p<0.005). Densitometric quantification of the immunoblot data is shown in the graph (mean±SEM; differing symbols indicate p<0.05). FIG. 98C. Nuclear FoxO1 and nucleophosmin (Np) were probed by immunoblot in livers from ob/ob mice treated with adeno-LacZ or -K43A-CaMKII. Densitometric quantification of the immunoblot data is shown in the graph (mean±SEM; *p<0.05). FIG. 98D. Sixteen-week-old DIO mice were administered adeno-LacZ or K43A-CaMKII, and then, two days later, half of the adeno-K43A-CaMKII mice received adeno-FoxO1-ADA, while the other half received adeno-LacZ control. Three weeks later, mice were fasted for 6 h and then injected with 1.5 IU/kg insulin through the portal vein. Liver extracts were assayed for p-Akt, total Akt, β-actin or nuclear FoxO1 and nucleophosmin (Np) by immunoblot.

FIGS. 99A-E. Related to FIG. 93. FIG. 99A. HCs from Camk2g$^{fl/fl}$ mice were transduced with adeno-LacZ or -Cre and then 24 h later incubated with BSA or palmitate (0.2 mM) for 19 h. Trb3 mRNA levels were analyzed by RT-qPCR (mean±SEM; different symbols indicate p<0.05). FIG. 99B. DIO Camk2g$^{fl/fl}$ mice were treated with TBG-Cre or TBG-LacZ, and one week later half of the TBG-LacZ mice received adeno-TRB3, while the other half received adeno-LacZ control. Eight days later, after 6 h fasting, the mice were injected with 1.5 IU/kg insulin through the portal vein. Total liver extracts were assayed for p-Akt, total Akt, TRB3, and β-actin by immunoblot. Densitometric quantification of the immunoblot data are shown in the graph (mean±SEM; bars with different symbols are different from each other and control, p<0.05). FIG. 99C. HCs from Camk2g$^{fl/fl}$ mice were transduced with adeno-LacZ or -Cre and five hours later, half of the adeno-LacZ treated cells received adeno-shTRB3, while the other half received adeno-LacZ control. 24 h later, the cells were incubated with either BSA control or palmitate (0.2 mM) for 19 h, with the last 5 h in serum-free media followed by ±100 nM insulin stimulation for 5 min. One set of cells were harvested and assayed for p-Aid, total Akt, β-actin by immunoblotting and another set was assayed for Trb3 mRNA levels by RT-qPCR (mean±SEM; bars with different symbols are different from each other and control, p<0.05). FIG. 99D. As in FIG. 99B, except nuclear FoxO1 and nucleophosmin (Np) were probed by immunoblot in livers from DIO mice treated with LacZ or K43A-CaMKII. Densitometric quantification of the immunoblot data is shown in the graph (mean±SEM; *p<0.05). FIG. 99E. HCs from Camk2g$^{fl/fl}$ mice were transduced with adenoviral vectors expressing LacZ or Cre and 4 h later, half of the adeno-Cre treated cells received TRB3 whereas the rest received LacZ. 24 h later, cells were serum-depleted overnight and then incubated for 5 h with forskolin (10 µm) in serum-free media. RNA was assayed for G6Pc, Pck1 and Trb3 mRNA (mean±SEM; *p<0.05).

Figure 100C:
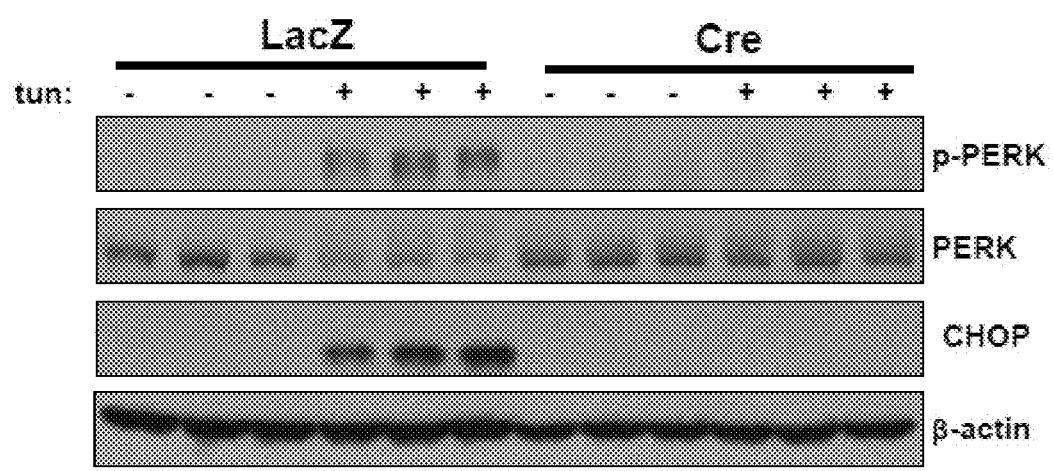

FIGS. 100A-F: Related to FIG. 94. Deficiency of p38α or CaMKII Suppresses the PERK Branch of the UPR. FIGS. 100A-B. HCs from Camk2g$^{fl/fl}$ mice were transduced with adenoviral vectors expressing LacZ or Cre at an MOI of 10. After 24 h, cells were incubated with tunicamycin (0.5 µg/ml) for 4 h or with palmitate (0.2 mm) for 19 h. Lysates were immunoblotted for p-PERK, PERK, CHOP and β-actin by immunoblot. FIG. 100C. As in FIG. 100A, except that Mapk14$^{fl/fl}$ HCs were used. FIG. 100D. Chop mRNA levels were assayed by RT-qPCR in the livers of ob/ob mice treated with adeno-LacZ or -K43-CaMKII or in the livers of DIO WT or Camk2g$^{-/-}$ mice (mean±SEM; *p<0.05). FIG. 100E. HCs from Camk2g$^{fl/fl}$ mice were treated as in FIG. 100B. RNA was extracted and assayed for spliced and unspliced Xbp1 and Gapdh loading control by RT-PCR. Tunicamycin (0.5 µg/ml) treated HCs were used as a positive control. FIG. 100F. Livers from ob/ob mice treated with adeno-LacZ or -K43A-CaMKII were assayed for spliced and unspliced Xbp1 and Gapdh loading control by RT-PCR. Tunicamycin (0.5 µg/ml) treated HCs were used as a positive control.

FIGS. 101A-D. Related to FIG. 95. Deficiency of CaM-KII or P38α Increases p58$^{ipk}$ and Nuclear ATF6. FIG. 101A. HCs from Camk2g$^{fl/fl}$ mice were transduced with adeno-LacZ or -Cre. After 24 h, p58$^{ipk}$ mRNA levels were assayed by RT-qPCR (mean±SEM; * p<0.05). FIG. 101B. HCs from Mapk14$^{fl/fl}$ mice were transduced with adenoviral vectors expressing LacZ or Cre at an MOI of 10. After 24 h, the cells were incubated with tunicamycin (0.5 µg/ml) for 5 h and p58$^{ipk}$ mRNA levels were assayed (mean±SEM; bars with different symbols are different from each other and control, p<0.05). FIG. 101C. p58$^{ipk}$ mRNA levels were assayed in livers of DIO Camk2g$^{fl/fl}$ mice treated with AAV-TBG-Cre or AAV-TBG-LacZ (mean±SEM; *p<0.05). FIG. 101D. HCs from WT mice were transduced with adeno-LacZ or -K43A-CaMKII. After 24 h, the cells were treated with tunicamycin for the indicated times. Nuclear extracts were immunoblotted for ATF6 and nucleophosmin (Np) as a loading control.

Figure 102:
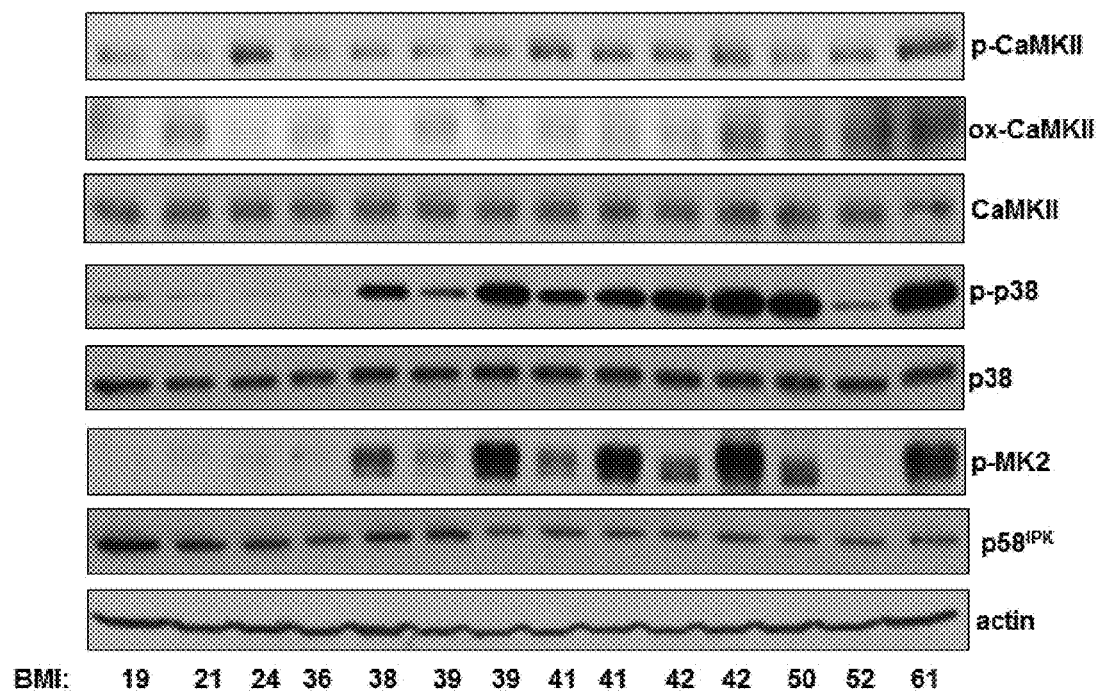

FIG. 102. CaMKII-p38-MK2 pathway is induced in obese human liver. Frozen liver biopsy samples from human subjects with different BMIs were lysed and total liver extracts were then assayed for p-CaMKII, ox-CaMKII, CaMKII, p-38, p38, p-MK2, p58$^{IPK}$ and β-actin by immunoblot.

Figure 103:
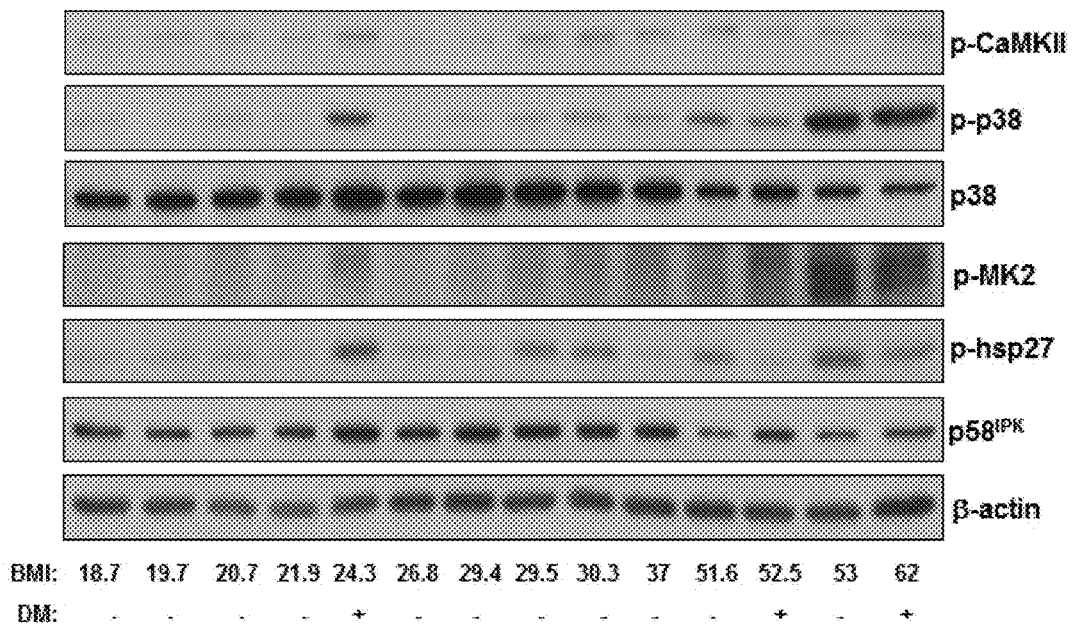

FIG. 103. CaMKII-p38-MK2 pathway is induced in another cohort of obese human liver samples. Frozen liver biopsy samples from human subjects with different BMIs were lysed and total liver extracts were then assayed for p-CaMKII, p-38, p38, p-MK2, p-hsp27, p58$^{fl/fl}$ and β-actin by immunoblot.

Figure 104:
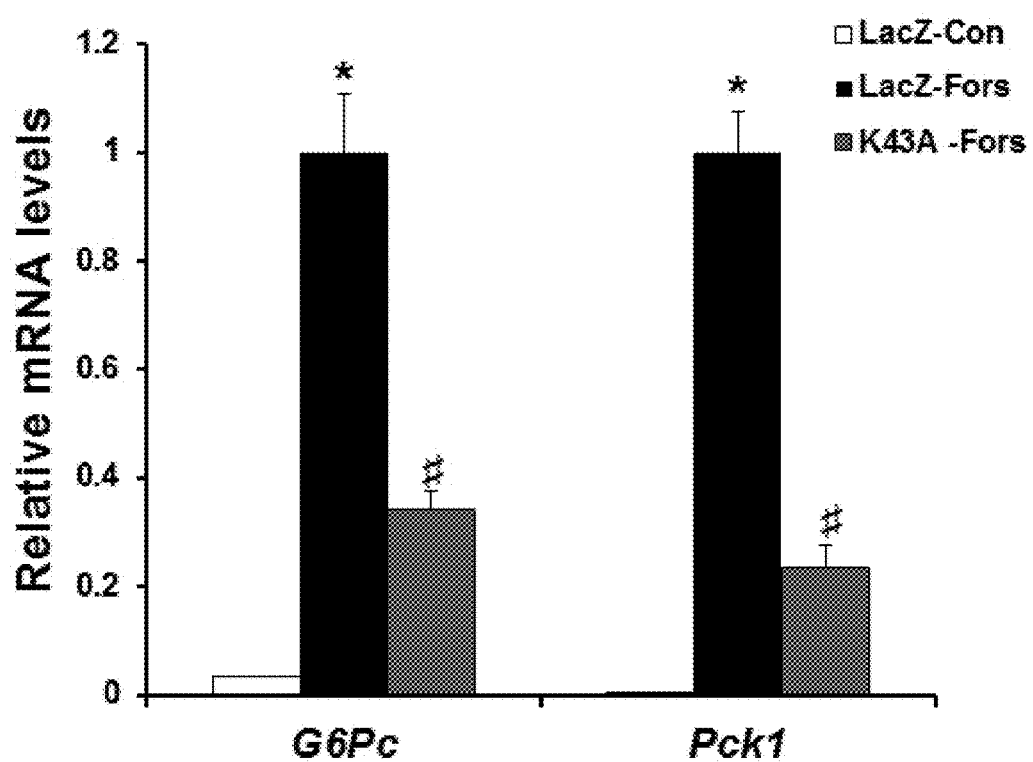

FIG. 104. CaMKII regulates G6Pc and Pck1 expression in primary human hepatocytes (HCs). Primary human HCs (metabolism-qualified) were transduced with adeno-LacZ or -K43A-CaMKII at an MOI of 30. 24 h later cells were serum-depleted overnight and then incubated for 5 h with 10 µM forskolin. RNA was assayed for G6pc and Pck1 mRNA by RT-qPCR (Differing symbols indicate p<0.05; mean±S.E.M.).

Figure 105:
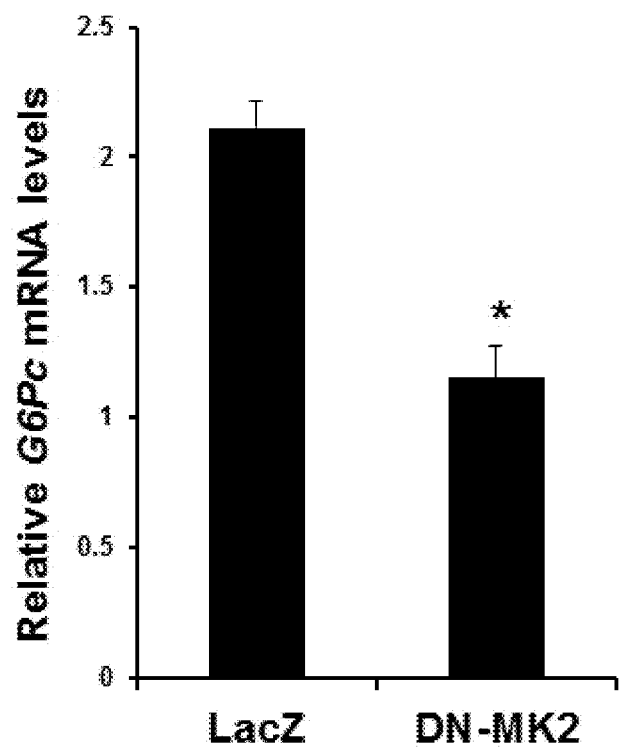

FIG. 105. MK2 regulates G6Pc expression in primary human hepatocytes (HCs). Primary human HCs (metabolism-qualified) were transduced with adeno-LacZ or -DN-MK2 at an MOI of 20. 24 h later cells were serum-depleted overnight and then incubated for 5 h with 10 µM forskolin. RNA was assayed for G6pc mRNA by RT-qPCR (**P<0.05; mean±S.E.M.).

Figure 106:
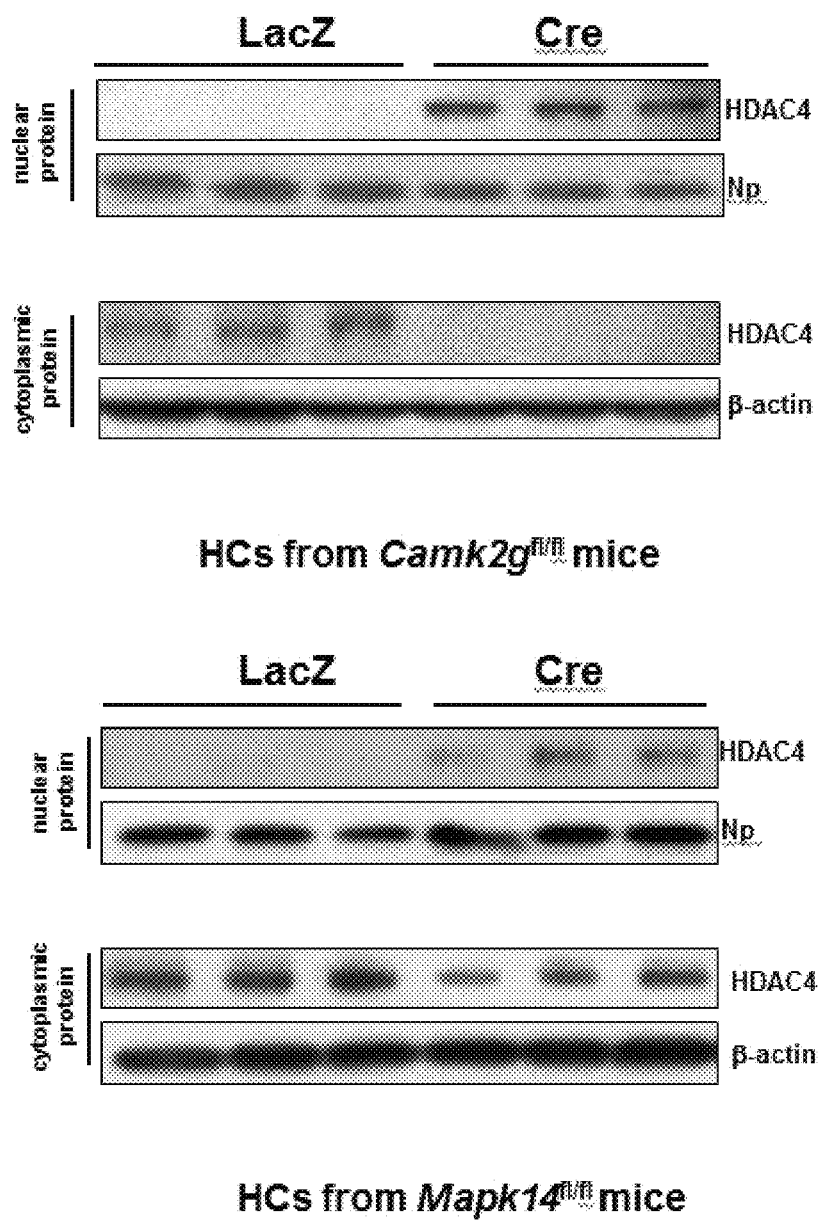

FIG. 106. CaMKII or p38 deficiency increases nuclear HDAC4. Primary HCs from Camk2g$^{fl/fl}$ or Mapk14$^{fl/fl}$ mice were transduced with adeno-LacZ or -Cre at an MOI of 10. 36 h later nuclear and cytoplasmic proteins were isolated and HDAC4, β-actin and nucleophosmin (Np) levels were assayed by immunoblotting.

Figure 107:
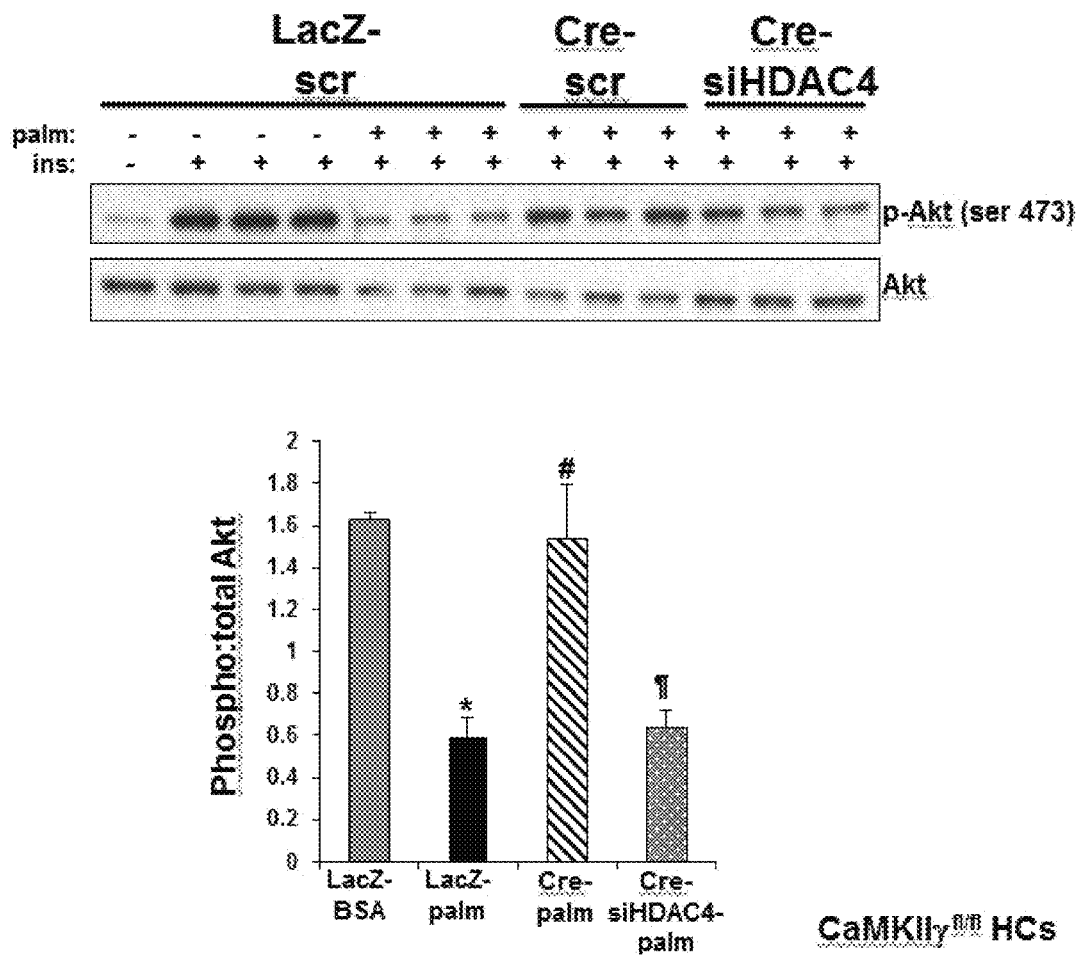

FIG. 107. Improvement in insulin-mediated Akt phosphorylation by CaMKII deficiency is partially abrogated by HDAC4 inhibition. HCs from Camk2g$^{fl/fl}$ mice were pretreated with either scrambled RNA (scr) or siRNA targeting HDAC4 (si-HDAC4). After 12 h, the cells were transduced with adeno-LacZ or -Cre. After an additional 24 h, the cells were incubated with BSA control or palmitate (0.2 mM) for 19 h, with the last 5 h in serum-free media and subsequently treated with ±100 nM insulin for 5 min. Lysates were immunoblotted for p-Akt and Akt by immunoblot. Densitometric quantification of the immunoblot data is shown in the graph (Bars with different symbols are different from each other and control, p<0.05; mean S.E.M.).

Figure 108:
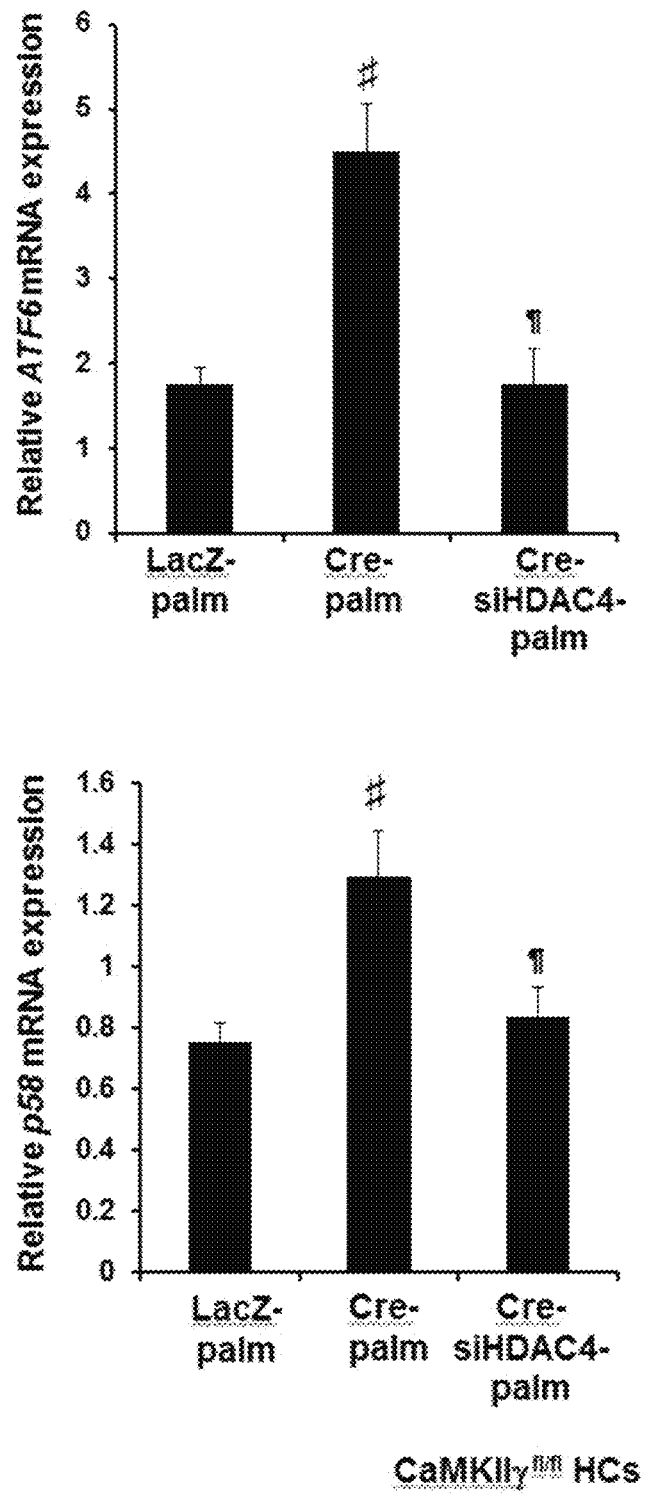

FIG. 108. Increased ATF6 and p58 levels in CaMKII deficient HCs are partially abrogated by HDAC4 inhibition. HCs from Camk2g$^{fl/fl}$ mice were pretreated with either scrambled RNA or siRNA targeting HDAC4 (si-HDAC4). After 12 h, the cells were transduced with adeno-LacZ or -Cre. After an additional 24 h, the cells were incubated with BSA control or palmitate (0.2 mM) for 14 h. RNA was assayed for Atf6 and p58$^{ipk}$ mRNA by RT-qPCR (Bars with different symbols are different from each other and control, p<0.05; mean±S.E.M.).

Figure 109:
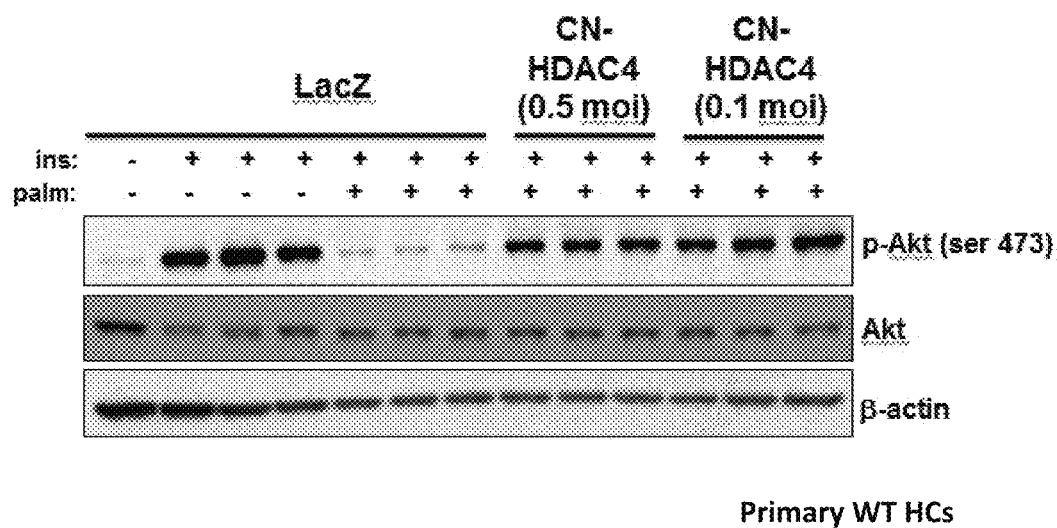

FIG. 109. Constitutively nuclear (CN) HDAC4 improves insulin-induced Akt phosphorylation in palmitate-treated primary hepatocytes. Primary HCs from WT mice were transduced with adeno-LacZ or -CN-HDAC4 at different MOI's as indicated. 24 h later cells were incubated with either BSA control or 0.2 mM palmitate for 19 h, with the last 5 h in serum-free media and subsequently treated with ±100 nM insulin for 5 min. Lysates were immunoblotted for p-Akt, Akt and β-actin by immunoblot.

Figure 110:
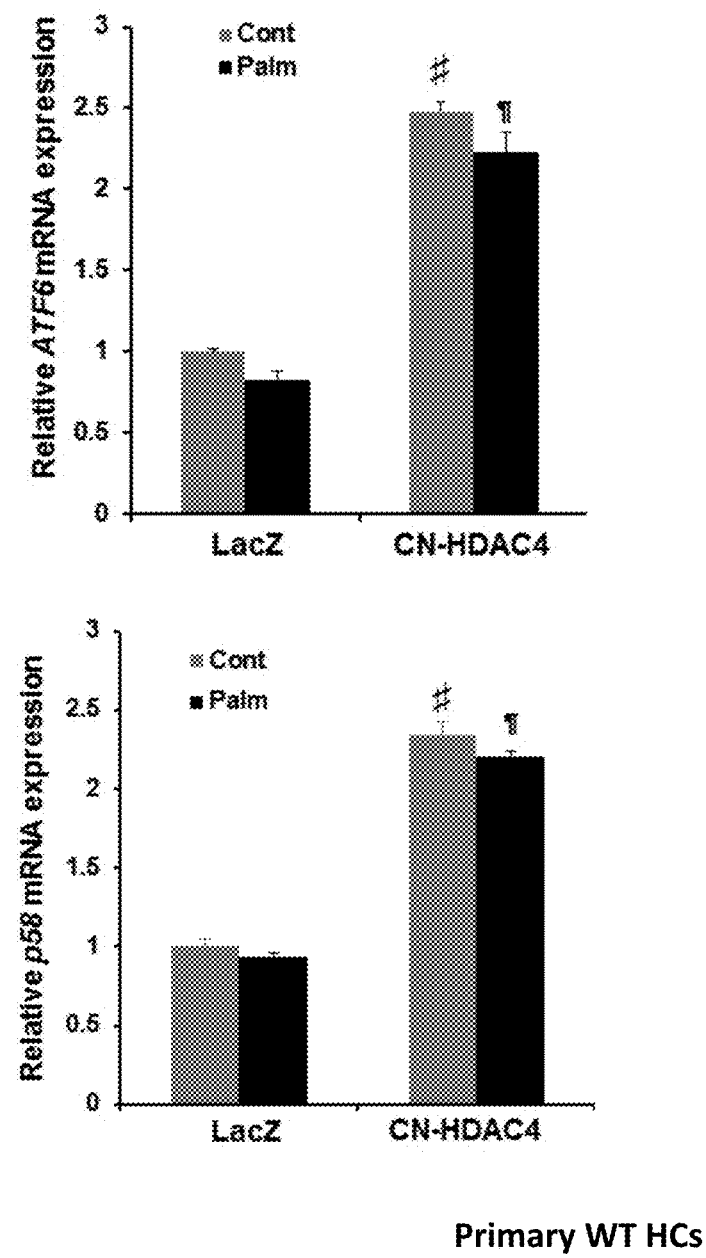

FIG. 110. CN-HDAC4 increases Atf6 and p58 mRNA levels. Primary HCs from WT mice were transduced with adeno-LacZ or -CN-HDAC4 at an MOI of 0.1. 24 h later cells were incubated with either BSA control or 0.2 mM palmitate for 14 h. RNA was assayed for Atf6 and p58$^{ipk}$ mRNA by RT-qPCR (Bars with different symbols are different from each other and control, p<0.05; mean±S.E.M.).

Figure 111:
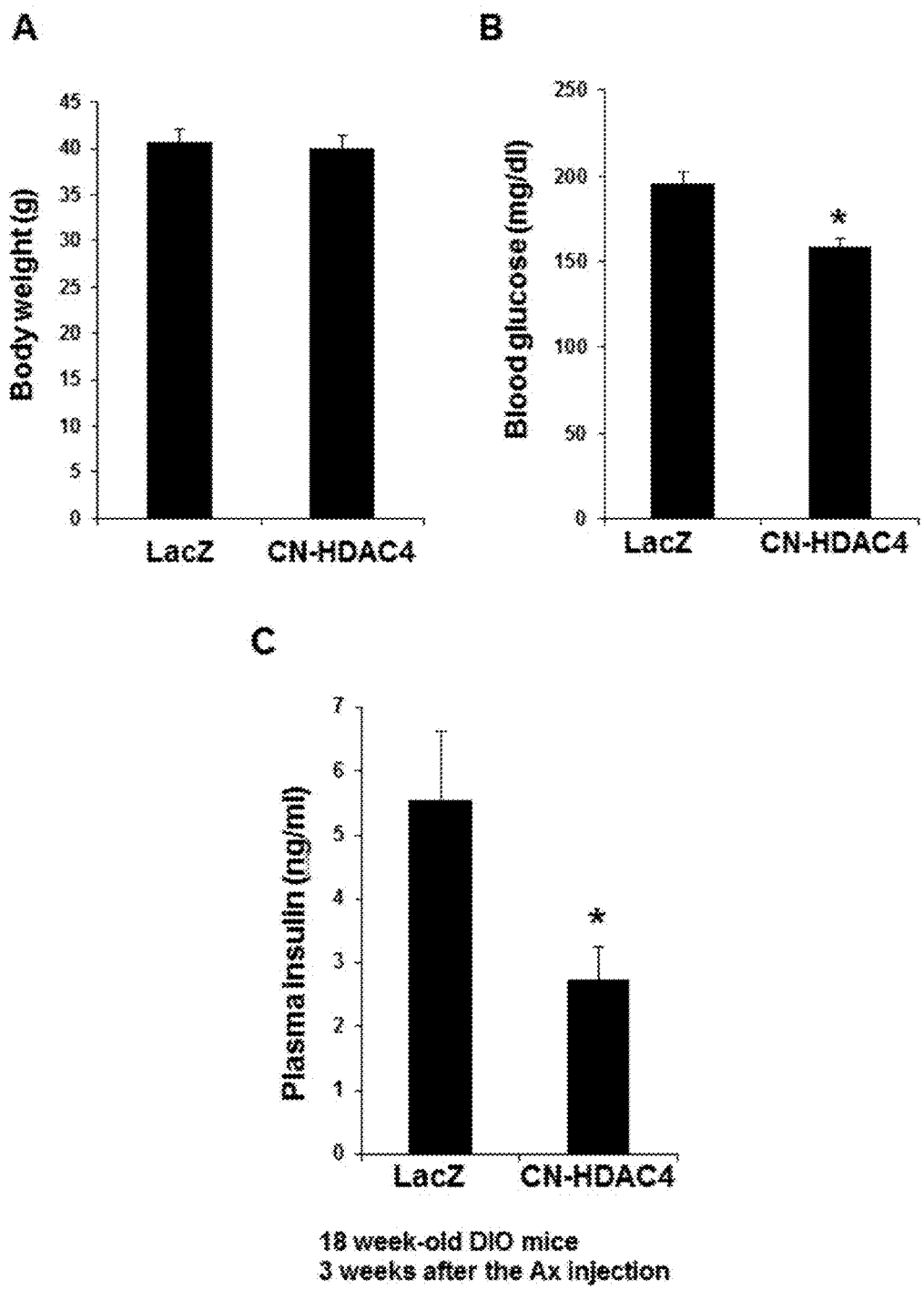

FIGS. 111A-C. CN-HDAC4 improves hyperglycemia in diet-induced obese (DIO) mice. 18 wk-old DIO mice were injected with adeno-LacZ (n=6) or -CN-HDAC4 (n=6). FIGS. 111A-C. Body weight, fasting blood glucose and plasma insulin levels of DIO mice 2 weeks after treatment (*p<0.05; mean±S.E.M.) are shown.

Figure 112:
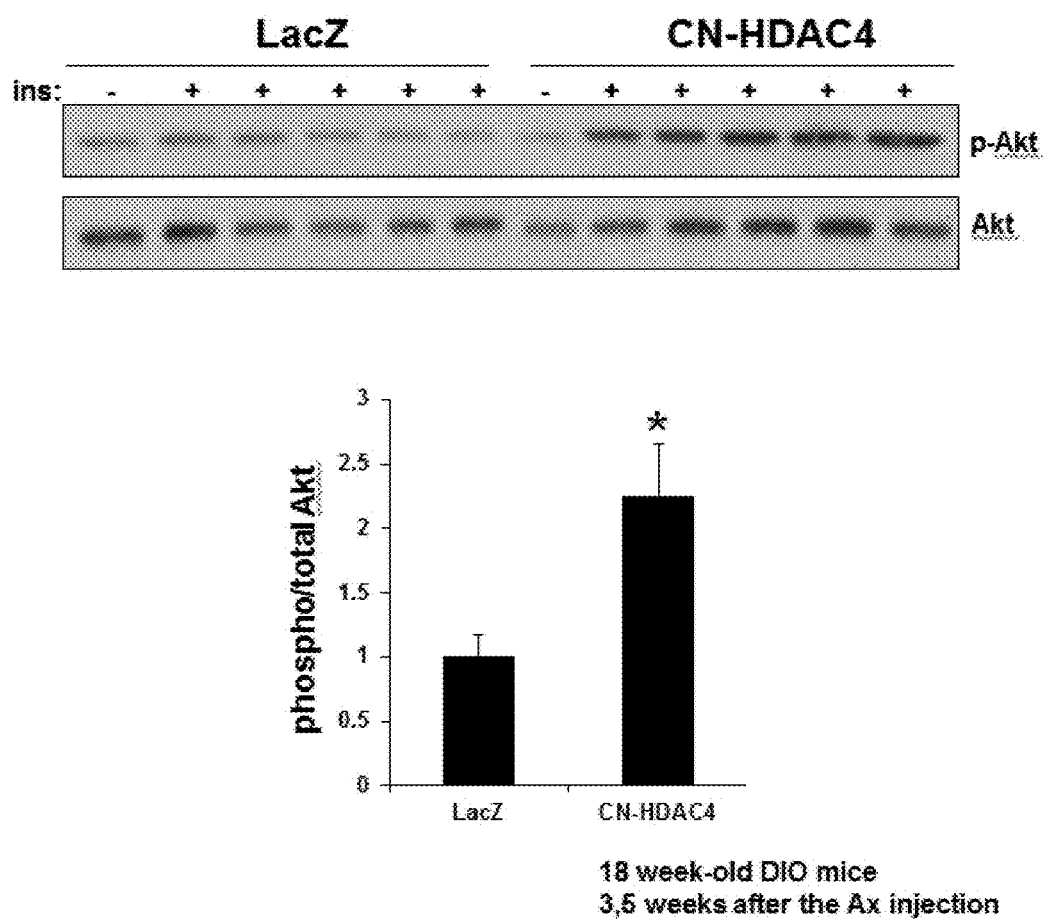

FIG. 112. CN-HDAC4 overexpression improves insulin-induced Akt phosphorylation in obese mice liver. 18 wk-old DIO mice injected with adeno-LacZ or -CN-HDAC4. 3 weeks after the treatment, mice were fasted for 5 h and then injected with 1.5 IU/kg insulin through the portal vein. Total liver extracts were then assayed for p-Akt and Akt by immunoblot. Densitometric quantification of the immunoblot data is shown in the graph (*p<0.05; mean±S.E.M.).

Figure 113:
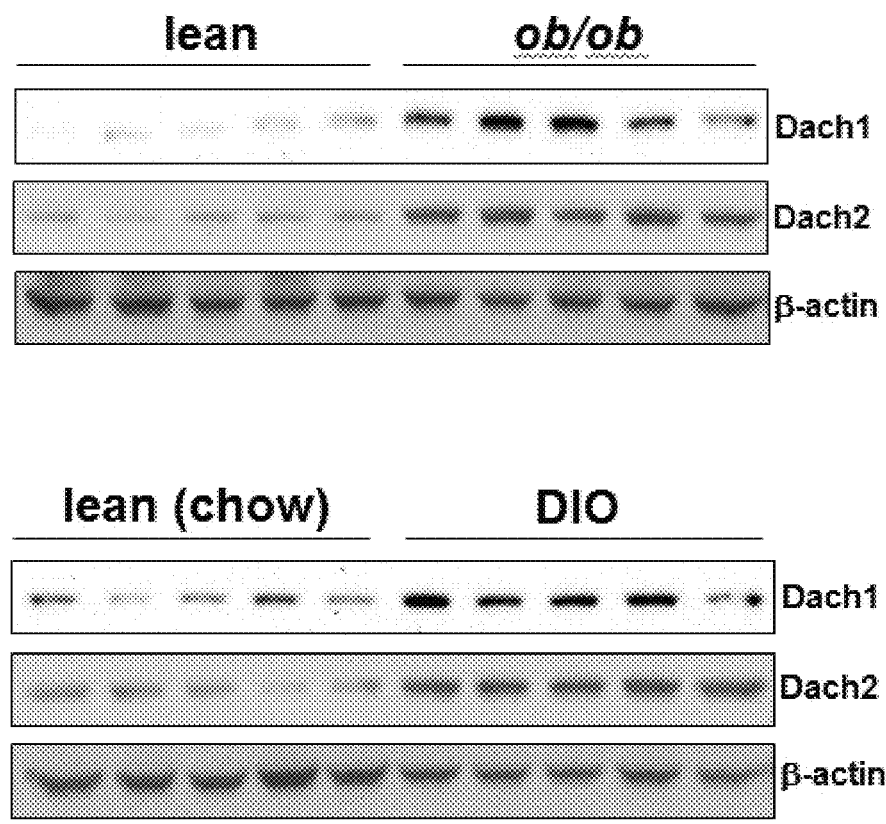

FIG. 113. Hepatic dach1 and dach2 levels are increased in obesity. Liver extracts from 10-week-old WT or ob/ob mice, or WT mice fed a chow or high fat-high calorie diet for 15 wks (DIO), were probed for dach1, dach2 and β-actin by immunoblot.

FIG. 114. CaMKII deficiency decreases hepatic dach1 and dach2 levels. Dach1, dach2 and β-actin were probed in livers from DIO Camk2g$^{fl/fl}$ mice treated with TBG-LacZ or TBG-Cre or ob/ob mice treated with adeno-LacZ or adeno-K43A-CaMKII.

Figure 115:
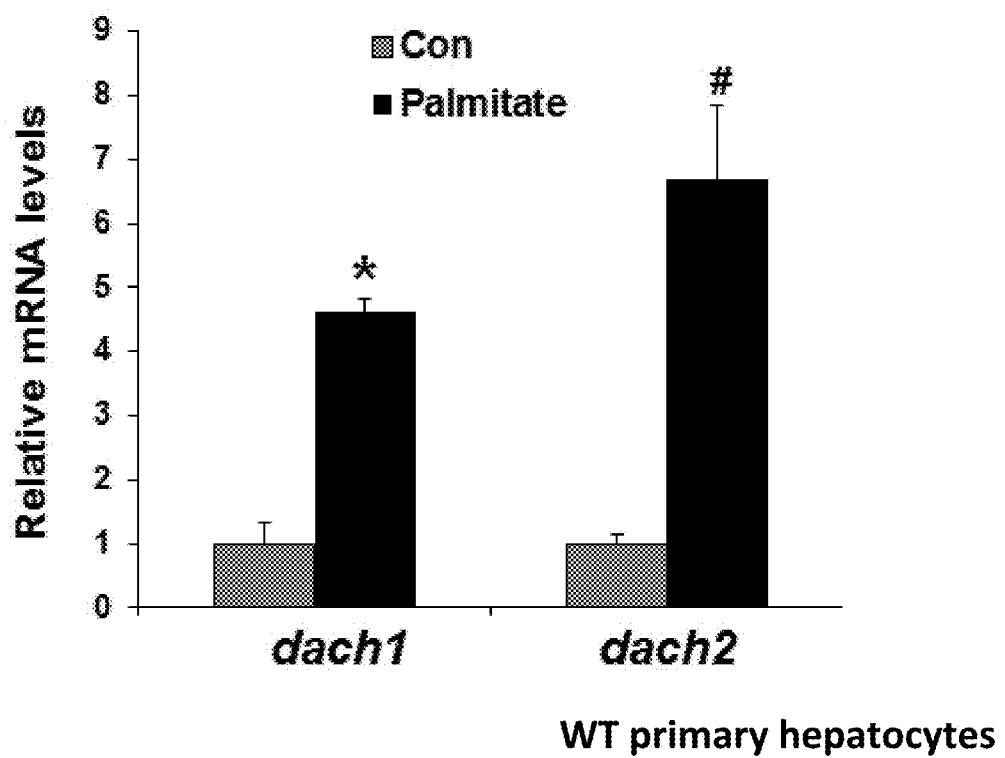

FIG. 115. Palmitate induces dach1 and dach2 mRNA levels. Primary HCs from WT mice were treated with 0.5 mM palmitate for 6 h. RNA was assayed for dach1 and dach2 mRNA by RT-qPCR (*p<0.05; mean±S.E.M.).

Figure 116:
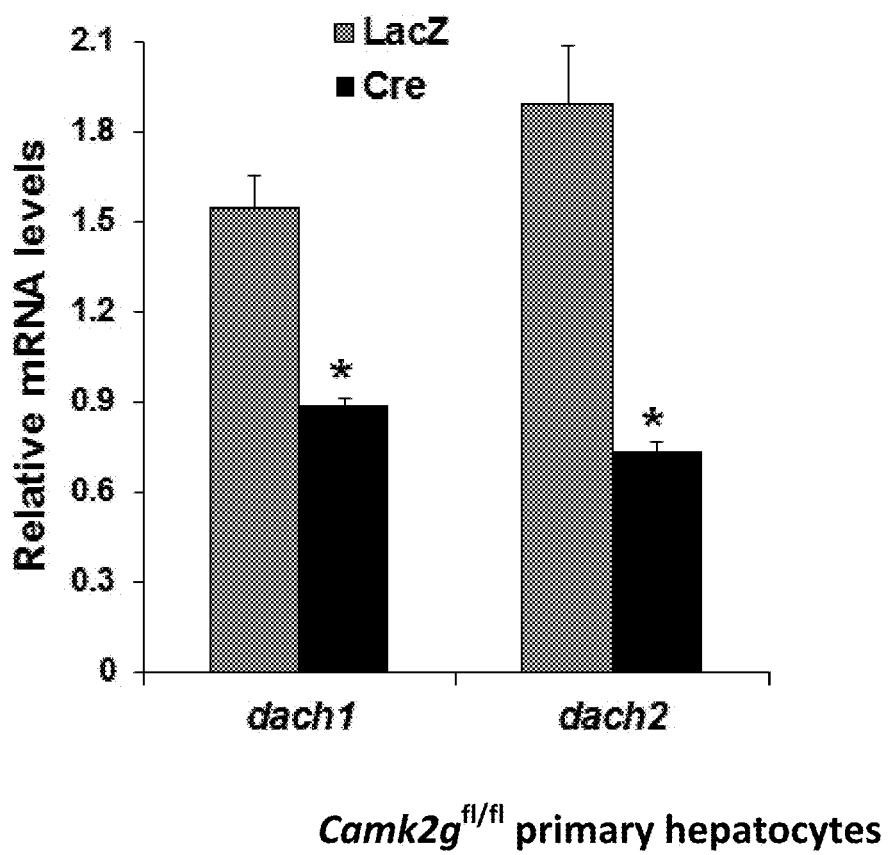

FIG. 116. CaMKII inhibition decreases palmitate-induced dach1 and dach2 levels. HCs from Camk2g$^{fl/fl}$ mice were treated with adeno-LacZ or adeno-Cre. 36 h later, cell were treated with 0.5 mM palmitate for 6 h. RNA was assayed for dach1 and dach2 mRNA by RT-qPCR (*p<0.05; mean±S.E.M.).

Figure 117:
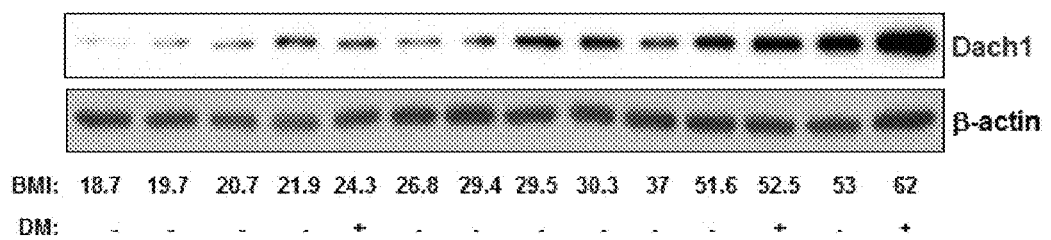

FIG. 117. Dach1 is induced in obese human liver. Frozen liver biopsy samples from human subjects with different BMIs were lysed and total liver extracts were then assayed for dach1 and β-actin by immunoblot.

Figure 118:
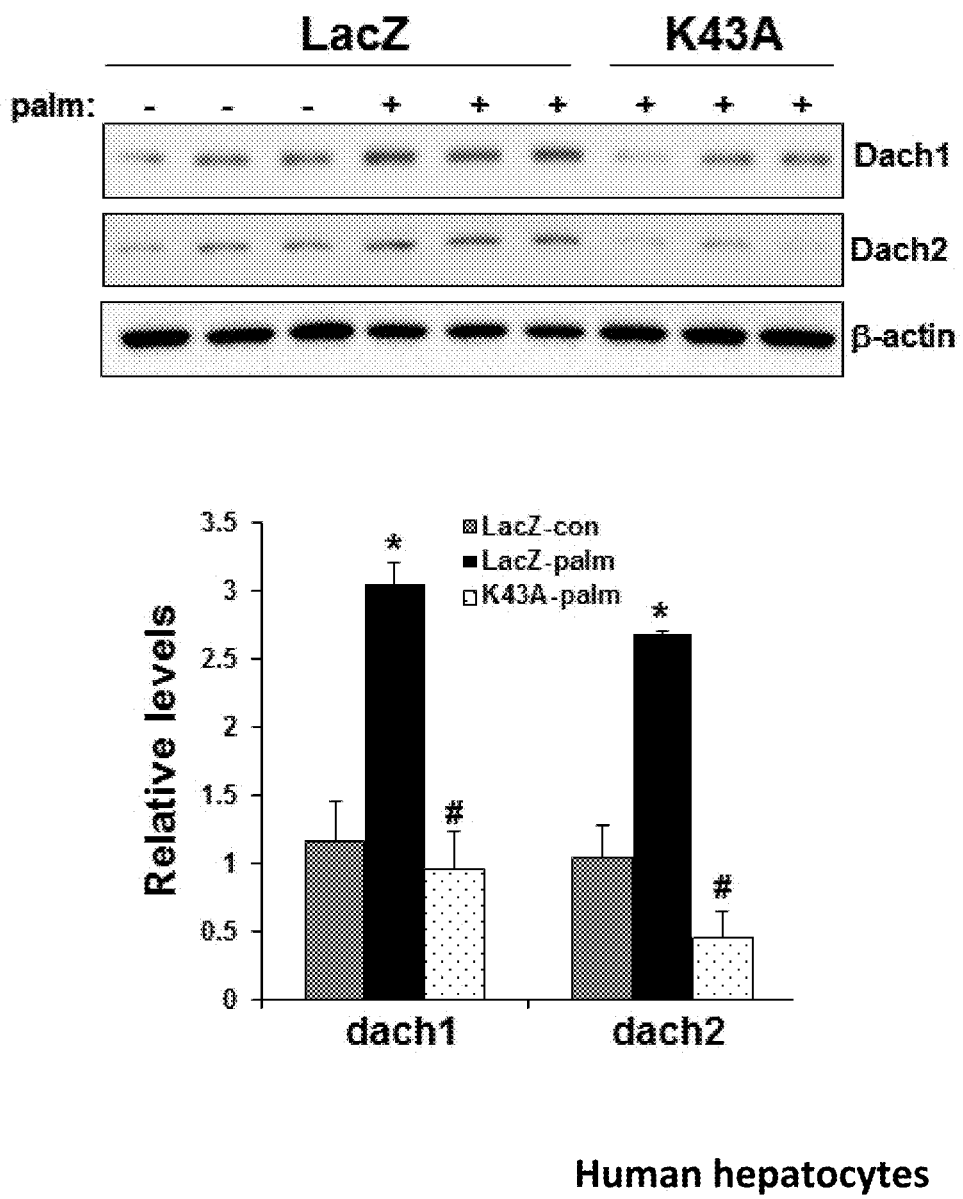

FIG. 118. CaMKII inhibition decreases palmitate-induced dach1 and dach2 levels in human hepatocytes. Primary human HCs (metabolism-qualified) were transduced with adeno-LacZ or -K43A-CaMKII at an MOI of 30. 24 h later cells were treated with 0.3 mM palmitate for 14 h. Lysates were probed for dach1, dach2 and β-actin by immunoblot. Densitometric quantification of the immunoblot data is shown in the graph (Bars with different symbols are different from each other and control, p<0.05; mean±S.E.M.).

Figure 119:
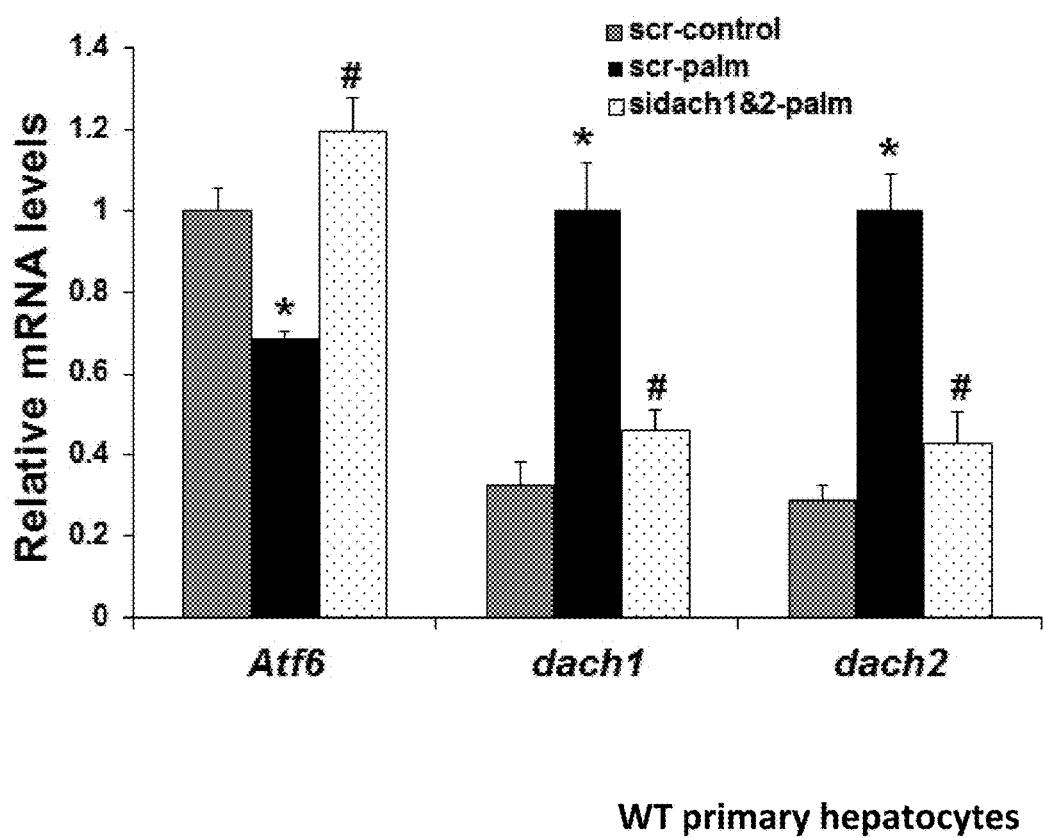

FIG. 119. Dach1&2 inhibition increases ATF6 levels. Primary HCs from WT mice were treated with either scrambled RNA (scr) or siRNAs targeting both dach1 and dach2 (si-dach1&2). 60 h later, cells were treated with 0.5 mM palmitate for 5 and RNA was assayed for Atf6, dach1 and dach2 mRNA by RT-qPCR (Bars with different symbols are different from each other and control, p<0.05; mean±S.E.M.).

FIG. 120. Dach1&2 silencing improves insulin-induced Akt phosphorylation in palmitate-treated primary hepatocytes. Primary HCs from WT mice were treated with either scrambled RNA (scr) or siRNAs targeting both dach1 and dach2 (si-dach1&2). 48 h later, cells were treated with 0.3 mM palmitate for 19 h, with the last 5 h in serum-free media and subsequently treated with ±100 nM insulin for 5 min. Lysates were immunoblotted for p-Akt, Akt and β-actin by immunoblot. Densitometric quantification of the immunoblot data is shown in the graph (Bars with different symbols are different from each other and control, p<0.05; mean±S.E.M.).

Figure 121:
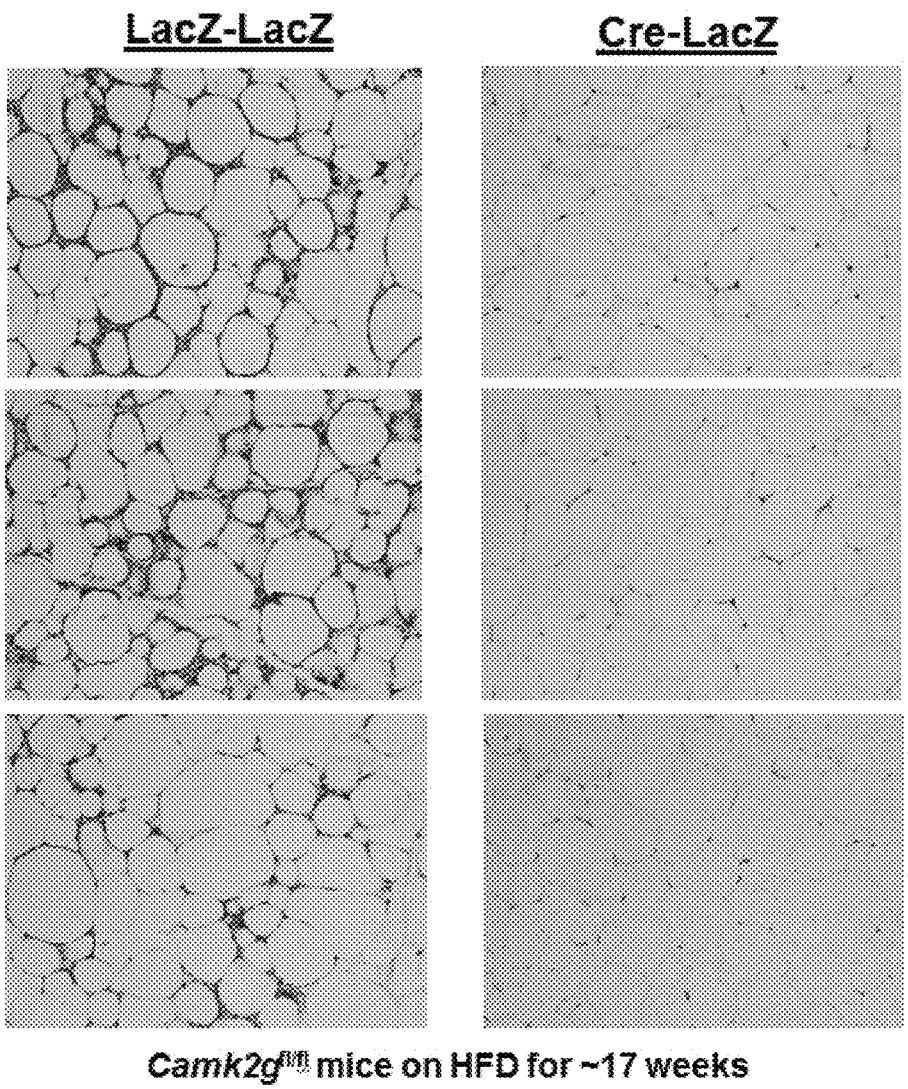

FIG. 121. Hepatic CaMKIIγ deletion suppresses visceral adipose tissue (VAT) inflammation. 15 wk-old DIO Camk2g$^{fl/fl}$ mice were injected with AAV-TBG-LacZ or -TBG-Cre. 4 weeks after the treatment, VAT was assayed for inflammatory cell infiltration via H&E staining.

Figure 122:
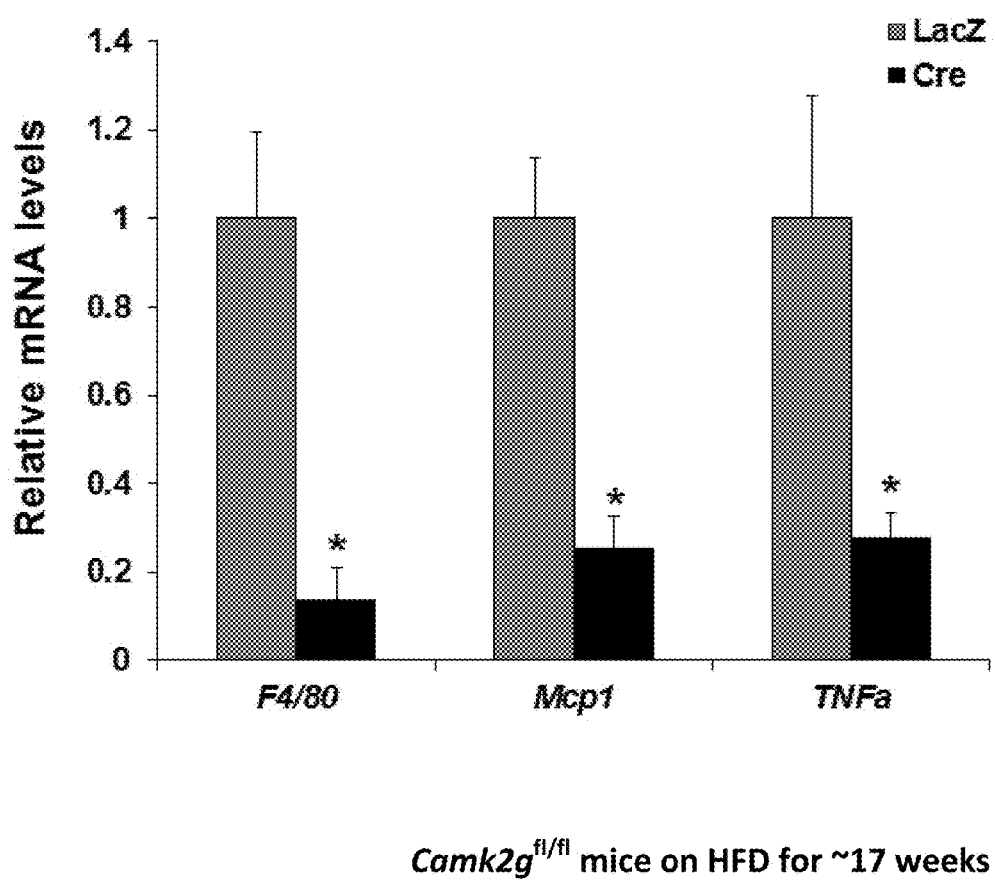

FIG. 122. Hepatic CaMKIIγ deletion suppresses expression of inflammatory genes in VAT. 15 wk-old DIO Camk2g$^{fl/fl}$ mice were injected with AAV-TBG-LacZ or -TBG-Cre. 4 weeks after the treatment, RNA from VAT was assayed for F4/80, Mcp1 and Tnfα mRNA by RT-qPCR (*p<0.05; mean±S.E.M.). The figure shows the relative mRNA levels in Camk2g$^{fl/fl}$ mice on HFD for about 17 weeks.

Figure 123:
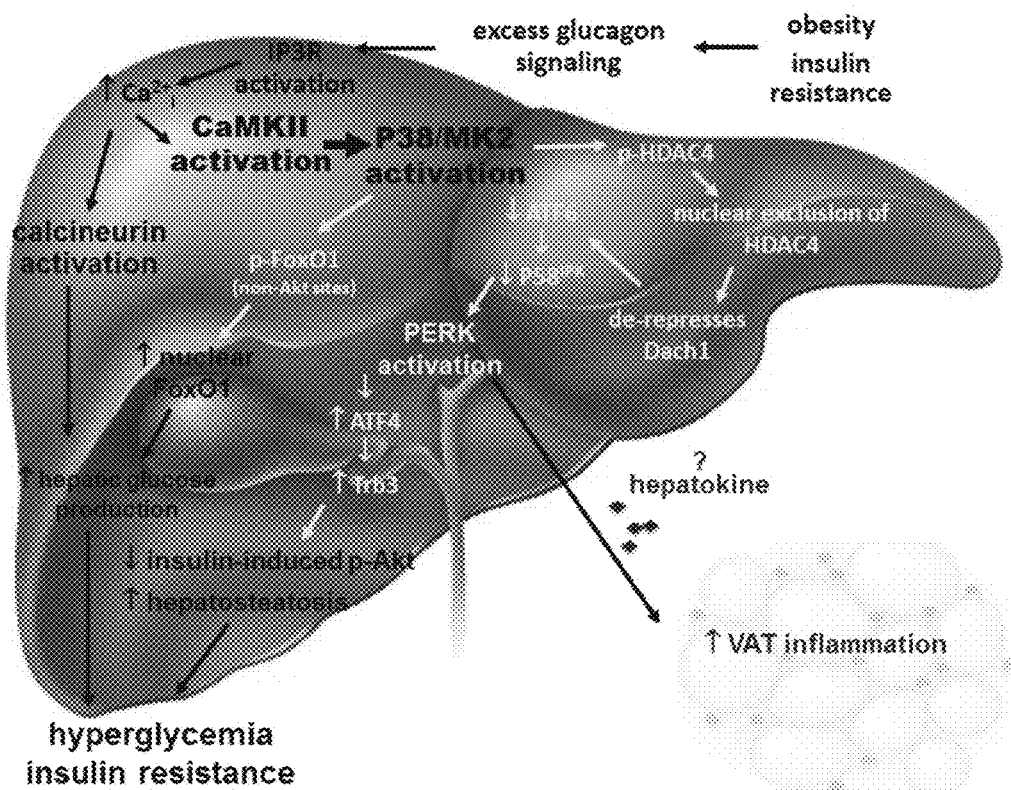

FIG. 123. Diagram showing the CaMKII-p38-MK2 pathway.

DETAILED DESCRIPTION OF THE INVENTION

The patent and scientific literature referred to herein establishes knowledge that is available to those skilled in the art. The issued patents, applications, and other publications that are cited herein are hereby incorporated by reference to the same extent as if each was specifically and individually indicated to be incorporated by reference.

As would be apparent to one of ordinary skill in the art, any method or composition described herein can be implemented with respect to any other method or composition described herein.

DEFINITIONS AND ABBREVIATIONS

The singular forms "a," "an," and "the" include plural reference unless the context clearly dictates otherwise.

The use of the word "a" or "an" when used in conjunction with the term "comprising" in the claims and/or the specification may mean "one," but it is also consistent with the meaning of "one or more," "at least one," and "one or more than one."

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the abbreviation "CaMKII" refers to the enzyme calcium calmodulin-dependent kinase II, including any of its isoforms and their splice variants. The nucleic acid sequences of the genes encoding the different isoforms of CaMKII, including, but not limited to, the nucleic acid sequences of the open reading frames of the genes, are known in the art. The nucleic acid sequences of the genes encoding the different isoforms of human CaMKII, including, but not limited to, the nucleic acid sequences of the open reading frames of the genes, are known in the art. The amino acid sequences of the CaMKII polypeptides and proteins, including, but not limited to, the amino acid sequences of the human CaMKII polypeptides and proteins, are known in the art. Sequences of transcript variants and splice variants are also known in the art (see e.g. Couchonnal and Anderson, 2008, which is incorporated by reference in its entirety). The accession number of the nucleic acid sequence of *mus musculus* CaMKII-γ is NM_178597 and the accession number of the nucleic acid sequence of human CaMKII-γ is NM_172171.2. The accession number of the amino acid sequence of *mus musculus* CaMKII-γ is NP_848712.2 and the accession number of the amino acid sequence of human CaMKII-γ is NP_751911.1.

As used herein, the abbreviation "IP3R" refers to the inositol 1,4,5-triphosphate receptor, including any of its isoforms and their splice variants. Within the IP3R family, several isoforms have been identified and characterized. The abbreviation "IP3R1" refers to isoform IP3R type I, the abbreviation "IP3R2" refers to isoform IP3R type II, and the abbreviation "IP3R3" refers to isoform IP3R type III. The nucleic acid sequences of the genes encoding the different isoforms of IP3R, including, but not limited to, the nucleic acid sequences of the open reading frames of the genes, are known in the art. The nucleic acid sequences of the genes encoding the different isoforms of human IP3R, including, but not limited to, the nucleic acid sequences of the open reading frames of the genes, are known in the art. The amino acid sequences of the IP3R polypeptides and proteins, including, but not limited to, the amino acid sequences of the human IP3R polypeptides and proteins of the different IP3R isoforms, are known in the art. The accession number of the nucleic acid sequence of *mus musculus* IP3R1 is NM_010585.5 and the accession number of the nucleic acid sequence of human IP3R1 is NM_001099952.2. The accession number of the amino acid sequence of *mus musculus* IP3R1 is NP_034715.3 and the accession number of the amino acid sequence of human IP3R1 is NP_001093422.2. For additional information on IP3R, see Wehrens et al., 2005, Annu Rev Physiol., 67:69-98. "Intracellular calcium release and cardiac disease"; see also Patterson et al., 2004, Annu Rev Biochem. 73:437-65. "Inositol 1,4,5-trisphosphate receptors as signal integrators." and Volpe et al., 1990, Am J Physiol.; 258(6 Pt 1):C1086-91. "Regulation of inositol 1,4,5-triphosphate-induced Ca2+ release. II. Effect of cAMP-dependent protein kinase.", all of which are incorporated by reference herein.

As used herein, the abbreviation "p38" refers to any of the p38 mitogen-activated protein (MAP) kinases. Several p38 MAP kinases have been identified, including p38-α (also known as MAPK14), p38-β (also known as MAPK11), p38-γ (also known as MAPK12/ERK6) and p38-δ (also known as MAPK13/SAPK4). The nucleic acid sequences of the genes encoding p38, including, but not limited to, the nucleic acid sequences of the open reading frames of the genes, are known in the art. The nucleic acid sequences of the genes encoding the human p38, including, but not limited to, the nucleic acid sequences of the open reading frames of the genes, are known in the art. The amino acid sequences of p38 polypeptides and proteins, including, but not limited to, the amino acid sequences of the human p38 polypeptides and proteins, are known in the art. The accession number of the nucleic acid sequence of *mus musculus* p38-α (MAPK14) is NM_011951.3 and the accession number of the nucleic acid sequence of human p38-α (MAPK14) is NM_001315.2. The accession number of the amino acid sequence of *mus musculus* p38-α (MAPK14) is NP_036081.1 and the accession number of the amino acid sequence of human p38-α (MAPK14) is NP_001306.1. For additional information on p38, see Marber et al., 2011, *J Mol Cell Cardiol.*; 51(4):485-90 "The p38 mitogen-activated protein kinase pathway—a potential target for intervention in infarction, hypertrophy, and heart failure."; see also Kostenko et al., 2011, *World J Biol Chem.* 26; 2(5):73-89. "Physiological roles of mitogen-activated-protein-kinase-activated p38-regulated/activated protein kinase." and Cuadrado et al., 2010, *Biochem J.*; 429(3):403-17. "Mechanisms and functions of p38 MAPK signalling.", all of which are incorporated by reference herein.

As used herein, the abbreviation "MK2" refers to the p38-activated kinase MK2, also known as MAP kinase activated protein kinase 2 (or MAPKAPK2). The nucleic acid sequence of the gene encoding MK2, including, but not limited to, the nucleic acid sequence of the open reading frame of the gene, is known in the art. The nucleic acid sequence of the gene encoding the human MK2, including, but not limited to, the nucleic acid sequence of the open reading frame of the gene, is known in the art. The amino acid sequence of MK2 polypeptides and proteins, including, but not limited to, the amino acid sequences of the human MK2 polypeptides and proteins, are known in the art. The accession number of the nucleic acid sequence of *mus musculus* MK2 is NM_008551 and the accession number of the nucleic acid sequence of human MK2 is NM_004759.4. The accession number of the amino acid sequence of *mus musculus* MK2 is NP_032577.1 and the accession number of the amino acid sequence of human MK2 is NP_004750.1.

As used herein, the abbreviation "MK3" refers to the p38-activated kinase MK3, also known as MAP kinase activated protein kinase 3 (or MAPKAPK3). The nucleic acid sequence of the gene encoding MK3, including, but not limited to, the nucleic acid sequence of the open reading frame of the gene, is known in the art. The nucleic acid sequence of the gene encoding the human MK3, including, but not limited to, the nucleic acid sequence of the open reading frame of the gene, is known in the art. The amino acid sequence of MK3 polypeptides and proteins, including, but not limited to, the amino acid sequences of the human MK3 polypeptides and proteins, are known in the art. The abbreviation "MK2/3" refers to either MK2, or MK3 or both MK2 and MK3. The accession number of the nucleic acid sequence of *mus musculus* MK3 is NM_178907.3 and the accession number of the nucleic acid sequence of human MK3 is NM_001243926.1. The accession number of the amino acid sequence of *mus musculus* MK3 is NP_849238 and the accession number of the amino acid sequence of human MK3 is NP_004626.1. For additional information on MK2 and MK3, see Gaestel et al., 2006, *Nat Rev Mol Cell Biol.* 7(2):120-30. "MAPKAP kinases—MKs—two's company, three's a crowd."; see also Shiryaev et al., 2010, *Cell Signal.*; 22(8):1185-92. "Mitogen-activated protein kinase p38 and MK2, MK3 and MK5: ménage à trois or ménage à quatre?" and Kotlyarov et al., 2002, *Biochem Soc Trans.*; 30(Pt 6):959-63. "Is MK2 (mitogen-activated protein kinase-activated protein kinase 2) the key for understanding post-transcriptional regulation of gene expression?", all of which are incorporated by reference herein.

As used herein, the term "calcineurin" refers to either the catalytic subunit of the protein phosphatase calcineurin, or the regulatory subunit of the protein phosphatase calcineurin, or both, including any of their isoforms and their splice variants. The nucleic acid sequences of the genes encoding the different isoforms of the subunits of calcineurin, including, but not limited to, the nucleic acid sequences of the open reading frames of the genes, are known in the art. The nucleic acid sequences of the genes encoding the different isoforms of the subunits of human calcineurin, including, but not limited to, the nucleic acid sequences of the open reading frames of the genes, are known in the art. The amino acid sequences of the calcineurin polypeptides and proteins, including, but not limited to, the amino acid sequences of the human calcineurin polypeptides and proteins, are known in the art. The accession number of the nucleic acid sequence of *mus musculus* calcineurin subunit B is NM_024459.2 and the accession number of the nucleic acid sequence of human calcineurin catalytic subunit is NM_000944.4. The accession number of the amino acid sequence of *mus musculus* calcineurin subunit B is NP_077779.2 and the accession number of the amino acid sequence of human calcineurin catalytic subunit is NP_000935.1. For additional information on calcineurin, see Wilkins et al., 2004, *Biochem Biophys Res Commun.* 1; 322(4):1178-91. "Calcium-calcineurin signaling in the regulation of cardiac hypertrophy."; see also Periasamy, 2002, *J Mol Cell Cardiol.* 34(3):259-62. "Calcineurin and the heartbeat, an evolving story." and Buchholz et al., 2007, *Cell Cycle.* 6(1):16-9. "An emerging role for Ca2+/calcineurin/NFAT signaling in cancerogenesis.", all of which are incorporated by reference herein.

As used herein, the abbreviation "HDAC4" refers to Histone Deacetylase 4. The nucleic acid sequence of the gene encoding HDAC4, including, but not limited to, the nucleic acid sequence of the open reading frame of the gene, is known in the art. The nucleic acid sequence of the gene encoding the human HDAC4, including, but not limited to, the nucleic acid sequence of the open reading frame of the gene, is known in the art. The amino acid sequence of HDAC4 polypeptides and proteins, including, but not limited to, the amino acid sequences of the human HDAC4 polypeptides and proteins, are known in the art. The accession number of the nucleic acid sequence of *mus musculus* HDAC4 is NM_207225 and the accession number of the nucleic acid sequence of human HDAC4 is NM_006037. The accession number of the amino acid sequence of *mus musculus* HDAC4 is NP_997108 and the accession number of the amino acid sequence of human HDAC4 is NP_006028.2. For additional information on HDAC4, see e.g., Abu-Farha et al., 2013, Proteomics analysis of human obesity reveals the epigenetic factor HDAC4 as a potential target for obesity, PLoS One. 2013 Sep. 24; 8(9):e75342. doi: 10.1371/journal.pone.0075342. eCollection 2013; Zhang et al., 2007, CaMKIIdelta isoforms differentially affect calcium handling but similarly regulate HDAC/MEF2 transcriptional responses, J Biol Chem., 282(48):35078-87; Backs et al., 2009, The delta isoform of CaM kinase II is required for pathological cardiac hypertrophy and remodeling after pressure overload, Proc Natl Acad Sci USA, 106(7):2342-7; Backs et al., 2006, CaM kinase II selectively signals to histone deacetylase 4 during cardiomyocyte hypertrophy, J Clin Invest., 116(7):1853-64, all of which are incorporated by reference herein.

As used herein, the abbreviation "Dach1" refers to Dachshund Homolog 1. The nucleic acid sequence of the gene encoding Dach1, including, but not limited to, the nucleic acid sequence of the open reading frame of the gene, is known in the art. The nucleic acid sequence of the gene encoding the human Dach1, including, but not limited to, the nucleic acid sequence of the open reading frame of the gene, is known in the art. The amino acid sequence of Dach1 polypeptides and proteins, including, but not limited to, the amino acid sequences of the human Dach1 polypeptides and proteins, are known in the art. The accession number of the nucleic acid sequence of *mus musculus* Dach1 is NM_007826.3 and the accession number of the nucleic acid sequence of human Dach1 is NM_080759.4. The accession number of the amino acid sequence of *mus musculus* Dach1 is NP_031852 and the accession number of the amino acid sequence of human Dach1 is NP_542937.2. For additional information on Dach1, see Liang et al., 2012, Increased expression of dachshund homolog 1 in ovarian cancer as a predictor for poor outcome, Int J Gynecol Cancer, 22(3): 386-93; Wu et al., 2003, DACH1 inhibits transforming growth factor-beta signaling through binding Smad4, J Biol Chem., 278(51):51673-84; Sundaram et al., 2008, DACH1 negatively regulates the human RANK ligand gene expression in stromal/preosteoblast cells, J Cell Biochem; 103(6): 1747-59; Davis et al., 2001, Dach1 mutant mice bear no gross abnormalities in eye, limb, and brain development and exhibit postnatal lethality, Mol Cell Biol., 21(5):1484-90, all of which are incorporated by reference herein.

As used herein, the abbreviation "Dach2" refers to Dachshund Homolog 2. The nucleic acid sequence of the gene encoding Dach2, including, but not limited to, the nucleic acid sequence of the open reading frame of the gene, is known in the art. The nucleic acid sequence of the gene encoding the human Dach2, including, but not limited to, the nucleic acid sequence of the open reading frame of the gene, is known in the art. The amino acid sequence of Dach2 polypeptides and proteins, including, but not limited to, the amino acid sequences of the human Dach2 polypeptides and proteins, are known in the art. The accession number of the nucleic acid sequence of *mus musculus* Dach2 is NM_001142570.1 and the accession number of the nucleic acid sequence of human Dach2 is NM_080760.4. The accession number of the amino acid sequence of *mus musculus* Dach2 is NP_291083.1 and the accession number of the amino acid sequence of human Dach2 is NP_444511.1. For additional information on Dach2, see Nodin et al., 2012, Discovery of dachshund 2 protein as a novel biomarker of poor prognosis in epithelial ovarian cancer, J Ovarian Res., 5(1):6; Tang et al., 2009, A histone deacetylase 4/myogenin positive feedback loop coordinates denervation-dependent gene induction and suppression, Mol Biol Cell., 20(4):1120-31; Tang et al., 2006, Activity-dependent gene regulation in skeletal muscle is mediated by a histone deacetylase (HDAC)-Dach2-myogenin signal transduction cascade, Proc Natl Acad Sci USA., 103(45):16977-82; Davis et al., 2006, Mouse Dach2 mutants do not exhibit gross defects in eye development or brain function, Genesis, 44(2):84-92, all of which are incorporated by reference herein.

As used herein, the term "metabolic syndrome" is used to describe a combination of medical disorders that, when occurring together, increase the risk for cardiovascular disease, stroke and type 2 diabetes. These disorders include, but are not limited to, central obesity (extra weight around the middle and upper parts of the body); insulin resistance; aging; stress; hormonal changes; excess blood clotting; dyslipidemia, which includes low HDL; a type of LDL that promotes heart disease; and elevated apolipoprotein B100.

Methods for Treatment and Prevention

The present invention relates to the discovery that a calcium-sensing enzyme, CaMKII, is activated in a calcium- and IP3R-dependent manner by cAMP and glucagon in primary HCs and by glucagon and fasting in vivo. Genetic deficiency or inhibition of CaMKII blocks nuclear translocation of FoxO1 by affecting its phosphorylation, impairs fasting- and glucagon/cAMP-induced glycogenolysis and gluconeogenesis, and lowers blood glucose levels, while constitutively active CaMKII has the opposite effects. The suppressive effect of CaMKII deficiency on glucose metabolism is abrogated by transduction with constitutively nuclear FoxO1, indicating that the effect of CaMKII deficiency requires nuclear exclusion of FoxO1. This same pathway is also involved in excessive HGP in the setting of obesity. These results reveal a calcium-mediated signaling pathway involved in FoxO1 nuclear localization and hepatic glucose homeostasis.

The present invention also relates to discoveries, including validation in models of obesity, that indicate that inhibitors of two drug targets—a liver calcium transporter called IP3 receptor and a liver phosphatase enzyme called calcineurin—can be invaluable in this niche. A new role for IP3 receptors and calcineurin in hepatic glucose production (HGP), which is excessively activated in obesity and type 2 diabetes, was recently discovered. Glucagon in fasting or obesity activates IP3 receptors and IP3R-induced calcium release from the endoplasmic reticulum to the cytosol. The released calcium then activates 2 calcium-sensitive enzymes. One of the enzymes is CaMKII. Activation of CaMKII is essential, because it facilitates the entry of FoxO1 into the nucleus, which then induces genes for HGP and is partially responsible for fasting hyperglycemia and metabolic disturbances in a mouse model of obesity. Calcineurin is the other enzyme that is activated by the released calcium. Calcineurin is a phosphatase that dephosphorylates another transcription factor called Crtc2, thus facilitating its entry into the nucleus. Crtc2 works together with FoxO1 to induce genes for HGP in obesity. Thus inhibition of Crtc2, like that of CaMKII, suppresses fasting hyperglycemia in a mouse model of obesity. Thus, this invention provides for the development and testing of IP3 receptor and calcineurin inhibitors in a pre-clinical model of obesity and insulin resistance.

Finally, this invention relates to the discovery that p38, MK2/3, HDAC4, Dach1, and Dach2 inhibitors and activators can also be invaluable in this niche.

The invention provides for methods of treating or preventing a metabolic disorder in a subject, methods of treating or preventing coronary artery disease in a subject with a metabolic disorder, as well as methods of reducing hepatic glucose production in a subject. The invention provides for the treatment and/or prevention of a metabolic disorder in a subject, the treatment and/or prevention of a coronary artery disease in a subject with a metabolic disorder, as well as methods of reducing hepatic glucose production in a subject, by administering to the subject compound(s) that inhibit or reduce the activity of CaMKII, IP3R, including, but not limited to, IP3R1, IP3R2, and IP3R3, calcineurin, p38, MK2/3, HDAC4, Dach1 and/or Dach2, or any combination thereof, or compounds that increase the activity of CaMKII, IP3R, including, but not limited to, IP3R1, IP3R2, and IP3R3, calcineurin, p38, MK2/3, HDAC4, Dach1 and/or Dach2, or any combination thereof.

The invention also provides methods of identifying a compound that inhibits the activity of CaMKII or reduces the activity and/or activation of CaMKII. The present invention thus also provides for the screening, development, and testing of inhibitors of CaMKII to prevent the metabolic disturbances of obesity, type 1 diabetes and type 2 diabetes. The invention further provides for the screening, development, and testing of inhibitors of CaMKII to prevent the metabolic disturbances of obesity, type 1 diabetes and type 2 diabetes in combination with other inhibitors or activators, such as, but not limited to, inhibitors or activators of IP3R, including, but not limited to, IP3R1, IP3R2, and IP3R3, calcineurin, p38, MK2/3, HDAC4, Dach1 and/or Dach2.

The present invention also provides for the screening, development, and testing of inhibitors of IP3R, including, but not limited to, IP3R1, IP3R2, and IP3R3, and inhibitors of calcineurin, to prevent the metabolic disturbances of obesity, type 1 diabetes and type 2 diabetes. The invention further provides for the screening, development, and testing of inhibitors of IP3R, including, but not limited to, IP3R1, IP3R2, and IP3R3 and/or inhibitors of calcineurin, to prevent the metabolic disturbances of obesity, type 1 diabetes and type 2 diabetes in combination with other inhibitors or activators, such as, but not limited to, inhibitors or activators of CaMKII, calcineurin, p38, MK2/3, HDAC4, Dach1 and/or Dach2.

The present invention also provides for the screening, development, and testing of inhibitors of p38 and MK2/3 to prevent the metabolic disturbances of obesity, type 1 diabetes and type 2 diabetes. The invention further provides for the screening, development, and testing of inhibitors of p38 and MK2/3 to prevent the metabolic disturbances of obesity type 1 diabetes, and type 2 diabetes in combination with other inhibitors or activators, such as, but not limited to, inhibitors or activators of CaMKII, IP3R, including, but not limited to, IP3R1, IP3R2, and IP3R3, calcineurin, HDAC4, Dach1 and/or Dach2.

The present invention also provides for the screening, development, and testing of inhibitors, or activators, of HDAC4, Dach1 and/or Dach2, to prevent the metabolic disturbances of obesity, type 1 diabetes and type 2 diabetes. The invention further provides for the screening, development, and testing of inhibitors, or activators, of HDAC4, Dach1 and/or Dach2 to prevent the metabolic disturbances of obesity type 1 diabetes, and type 2 diabetes in combination with other inhibitors, such as, but not limited to, inhibitors of CaMKII, IP3R, including, but not limited to, IP3R1, IP3R2, and IP3R3, calcineurin, p38 and MK2/3.

In certain aspects, the invention described herein is based on the finding that inhibitors of CaMKII can treat obesity-induced insulin resistance and disturbances in liver glucose and fat metabolism.

In certain aspects, the invention described herein provides CaMKII inhibitors for the purpose of drug development to improve the metabolic disturbances and their consequences in obesity, metabolic syndrome, type 1 diabetes and type 2 diabetes.

In certain aspects, the invention described herein provides methods for treating and diagnosing metabolic disturbances including heart disease, of insulin resistant states such as obesity, metabolic syndrome, and type 2 diabetes.

In certain aspects, the invention relates to findings related to the role of hepatic CaMKII in glucagon-mediated hepatic glucose production (HGP).

As described herein, CaMKII is activated by glucagon in primary hepatocytes and by glucagon and fasting in vivo. Genetic deficiency or inhibition of hepatic CaMKII lowered blood glucose levels, suppresses the HGP genes G6pc and Pck1, decreases glycogen depletion, and blocks nuclear translocation of the HGP transcription factor FoxO1. Conversely, constitutively active CaMKII induces G6pc and Pck1, stimulates glucose production, and raises blood glucose levels. The suppressive effect of CaMKII deficiency on glucose metabolism is abrogated by constitutively nuclear FoxO1, indicating that the effect of CaMKII deficiency can require nuclear exclusion of FoxO1.

The results described herein identify a molecular pathway regulated by CaMKII in the control of HGP.

In certain aspects, the invention is related to the finding that fasting and glucagon activate hepatic CaMKII. In certain aspects, the invention is related to the finding that CaMKII stimulates hepatic glucose production. In certain aspects, the invention is related to the finding that CaMKII promotes nuclear localization and activation of FoxO1. In certain aspects, the invention is related to the finding that impaired glucose production in CaMKII deficiency requires nuclear exclusion of FoxO1. In certain aspects, the methods described herein are useful for treating and diagnosing heart failure since overactive CaMKII has been implicated in heart failure.

The present disclosure provides methods for the treatment and/or prevention of a metabolic disorder. In one aspect, the present disclosure provides a method of treating or preventing a metabolic disorder in a subject in need thereof, the method comprising administering to the subject a therapeutically effective amount of an inhibitor of CaMKII, thereby treating or preventing the disorder. In another aspect, the present disclosure provides a method of treating or preventing a metabolic disorder in a subject in need thereof, the method comprising administering to the subject a therapeutically effective amount of an inhibitor of IP3R1, IP3R2, and/or IP3R3, thereby treating or preventing the disorder. In another aspect, the present disclosure provides a method of treating or preventing a metabolic disorder in a subject in need thereof, the method comprising administering to the subject a therapeutically effective amount of an inhibitor of calcineurin, thereby treating or preventing the disorder. In another aspect, the present disclosure provides a method of treating or preventing a metabolic disorder in a subject in need thereof, the method comprising administering to the subject a therapeutically effective amount of an inhibitor of p38, thereby treating or preventing the disorder. In another aspect, the present disclosure provides a method of treating or preventing a metabolic disorder in a subject in need thereof, the method comprising administering to the subject a therapeutically effective amount of an inhibitor of MK2/3, thereby treating or preventing the disorder.

In another aspect, the present disclosure provides a method of treating or preventing a metabolic disorder in a subject in need thereof, the method comprising administering to the subject a therapeutically effective amount of an inhibitor or an activator of HDAC4, thereby treating or preventing the disorder. In another aspect, the present disclosure provides a method of treating or preventing a metabolic disorder in a subject in need thereof, the method comprising administering to the subject a therapeutically effective amount of an inhibitor or an activator of Dach1, thereby treating or preventing the disorder. In another aspect, the present disclosure provides a method of treating or preventing a metabolic disorder in a subject in need thereof, the method comprising administering to the subject a therapeutically effective amount of an inhibitor or an activator of Dach2, thereby treating or preventing the disorder.

In another aspect, the present disclosure provides a method of treating or preventing a metabolic disorder in a subject in need thereof, the method comprising administering to the subject a therapeutically effective amount of an inhibitor or an activator of CaMKII, IP3R1, IP3R2, IP3R3, calcineurin, p38, MK2/3, HDAC4, Dach1, Dach2, or any combination thereof, thereby treating or preventing the disorder.

In one aspect, the present disclosure provides a method of treating or preventing a metabolic disorder in a subject, the method comprising reducing the activity of CaMKII, thereby treating or preventing the disorder. In one aspect, the present disclosure provides a method of treating or preventing a metabolic disorder in a subject, wherein the disorder is induced by obesity, the method comprising reducing the activity of CaMKII, thereby treating or preventing the disorder. In one aspect, the present disclosure provides a method of treating or preventing a metabolic disorder in a subject, wherein the disorder is not induced by obesity, the method comprising reducing the activity of CaMKII, thereby treating or preventing the disorder.

In one embodiment, the disorder is selected from the group consisting of Type 1 diabetes, Type 2 diabetes, insulin resistance and metabolic syndrome.

In one embodiment, the treating or preventing affects glycogenolysis or gluconeogenesis in the subject. In another embodiment, the treating or preventing does not affect glycogenolysis or gluconeogenesis in the subject.

In one embodiment, the treating or preventing reduces hepatic glucose production, hyperglycemia, fatty liver, insulin resistance, insulin resistance-associated inflammation, insulin resistance-associated dyslipidemia, or any combination thereof, in the subject. In another embodiment, the treating or preventing increases hepatic glucose production, hyperglycemia, fatty liver, insulin resistance, insulin resistance-associated inflammation, insulin resistance-associated dyslipidemia, or any combination thereof, in the subject. In another embodiment, the treating or preventing has no effect on hepatic glucose production, hyperglycemia, fatty liver, insulin resistance, insulin resistance-associated inflammation, insulin resistance-associated dyslipidemia, or any combination thereof, in the subject.

In one embodiment, the treating or preventing reduces phosphorylation and/or activation of CaMKII. In another embodiment, the treating or preventing inhibits phosphorylation of CaMKII. In another embodiment, the treating or preventing inhibits the activity and/or activation of CaMKII. In one embodiment, the treating or preventing increases phosphorylation and/or activation of CaMKII. In another embodiment, the treating or preventing increases the activity and/or activation of CaMKII.

In one embodiment, the activity of CaMKII is a glucagon-induced activity.

In one embodiment, the treating or preventing reduces or inhibits expression of G6pc and/or Pck1 in a cell of the subject. In one embodiment, the treating or preventing increases expression of G6pc and/or Pck1 in a cell of the subject In another embodiment, the treating or preventing reduces the amount of FoxO1 protein level in the nucleus of a cell of the subject. In another embodiment, the treating or preventing increases the amount of FoxO1 protein level in the nucleus of a cell of the subject.

In another embodiment, the treating or preventing reduces or inhibits phosphorylation of amino acid S284, S295, S326, S467, S475, S246, S253, S413, or S415, or any combination thereof, of the FoxO1 protein. In another embodiment, the treating or preventing increases phosphorylation of amino acid S284, S295, S326, S467, S475, S246, S253, S413, or S415, or any combination thereof, of the FoxO1 protein.

In another aspect, the present disclosure provides a method of treating or preventing coronary artery disease in a subject, the method comprising reducing the activity of CaMKII in the subject, thereby treating or preventing the coronary artery disease. The present disclosure provides a method of treating or preventing coronary artery disease in a subject with a metabolic disorder, the method comprising increasing the activity of CaMKII in the subject, thereby treating or preventing the coronary artery disease.

In one embodiment, the disorder is selected from the group consisting of Type 1 diabetes, Type 2 diabetes, insulin resistance and metabolic syndrome.

In another embodiment, the treating or preventing affects glycogenolysis or gluconeogenesis in the subject. In another embodiment, the treating or preventing does not affect glycogenolysis or gluconeogenesis in the subject.

In one embodiment, the treating or preventing reduces hepatic glucose production, hyperglycemia, fatty liver, insulin resistance, insulin resistance-associated inflammation, insulin resistance-associated dyslipidemia, or any combination thereof, in the subject. In another embodiment, the treating or preventing increases hepatic glucose production, hyperglycemia, fatty liver, insulin resistance, insulin resistance-associated inflammation, insulin resistance-associated dyslipidemia, or any combination thereof, in the subject.

In one embodiment, the treating or preventing reduces phosphorylation and/or activation of CaMKII. In another embodiment, the treating or preventing increases phosphorylation and/or activation of CaMKII.

In one embodiment, the activity of CaMKII is a glucagon-induced activity. In another embodiment, the activity of CaMKII is not a glucagon-induced activity.

In one embodiment, the treating or preventing reduces expression of G6pc and/or Pck1 in a cell of the subject. In another embodiment, the treating or preventing increases expression of G6pc and/or Pck1 in a cell of the subject.

In one embodiment, the treating or preventing reduces the amount of FoxO1 protein level in the nucleus of a cell of the subject. In another embodiment, the treating or preventing increases the amount of FoxO1 protein level in the nucleus of a cell of the subject.

In another embodiment, the treating or preventing reduces phosphorylation of amino acid S284, S295, S326, S467, S475, S246, S253, S413, or S415, or any combination thereof, of the FoxO1 protein. In another embodiment, the treating or preventing increases phosphorylation of amino acid S284, S295, S326, S467, S475, S246, S253, S413, or S415, or any combination thereof, of the FoxO1 protein.

In one embodiment, the treating or preventing comprises reducing CaMKII activity in a macrophage of the subject. In another embodiment, the treating or preventing comprises increasing CaMKII activity in a macrophage of the subject.

In one embodiment, the coronary artery disease is associated with atherogenesis and/or atherosclerosis. In another embodiment, the method further comprises treating or preventing heart failure, hypertension and/or renal disease. In another embodiment, the disorder is associated with advanced lesional macrophage apoptosis. In another embodiment, the disorder is associated with plaque necrosis.

In one embodiment, the treating or preventing coronary artery disease in a subject with a metabolic disorder results in lowering hyperinsulinemia and/or dyslipidemia. In another embodiment, the treating or preventing coronary artery disease in a subject with a metabolic disorder results in increasing hyperinsulinemia and/or dyslipidemia.

In one embodiment, the treating or preventing coronary artery disease in a subject with a metabolic disorder results in lowering atherogenesis and/or atherosclerosis. In another embodiment, the treating or preventing coronary artery disease in a subject with a metabolic disorder results in increasing atherogenesis and/or atherosclerosis.

In one embodiment, the treating or preventing comprises a step of administering to the subject an inhibitor of the CaMKII protein. In one embodiment, the treating or preventing comprises a step of administering to the subject an antisense RNA, or a siRNA, that reduces expression of the gene encoding the CaMKII protein. In another embodiment, the treating or preventing comprises a step of administering to the subject a peptide or a polypeptide that specifically binds to the CaMKII protein. In another embodiment, the treating or preventing comprises a step of administering to the subject a small molecule. In one embodiment, the small molecule is a CaMKII inhibitor selected from the group consisting of KN-93, lavendustin C, CK59, Ant-CaMKIINtide, KN62, DY9760e, K-252a *Nocardiopsis* sp., H89 dihydrochloride, PP1 Analog II, 1NM-PP1, eEF-2 kinase inhibitor NH125, and STO-609.

In another aspect, the present disclosure provides a method of reducing hepatic glucose production in a subject, the method comprising reducing the activity of CaMKII, thereby resulting in the reduction of hepatic glucose in the subject. In another aspect, the present disclosure provides a method of reducing hepatic glucose production in a subject, the method comprising increasing the activity of CaMKII, thereby resulting in the reduction of hepatic glucose in the subject.

In another aspect, the present disclosure provides a method of increasing hepatic glucose production in a subject, the method comprising increasing the activity of CaMKII, thereby resulting in the increase of hepatic glucose in the subject. In another aspect, the present disclosure provides a method of increasing hepatic glucose production in a subject, the method comprising reducing the activity of CaMKII, thereby resulting in the increase of hepatic glucose in the subject.

In one embodiment, the reducing hepatic glucose production reduces phosphorylation and/or activation of CaMKII. In another embodiment, the reducing hepatic glucose production increases phosphorylation and/or activation of CaMKII.

In one embodiment, the increasing hepatic glucose production reduces phosphorylation and/or activation of CaMKII. In another embodiment, the increasing hepatic glucose production increases phosphorylation and/or activation of CaMKII.

In one embodiment, the activity of CaMKII is a glucagon-induced activity.

In one embodiment, the reducing hepatic glucose production reduces expression of G6pc and/or Pck1 in a cell of the subject. In another embodiment, the reducing hepatic glucose production increases expression of G6pc and/or Pck1 in a cell of the subject. In one embodiment, the increasing hepatic glucose production reduces expression of G6pc and/or Pck1 in a cell of the subject. In another embodiment, the increasing hepatic glucose production increases expression of G6pc and/or Pck1 in a cell of the subject.

In one embodiment, the reducing hepatic glucose production reduces hyperglycemia, fatty liver, insulin resistance, insulin resistance-associated inflammation, insulin resistance-associated dyslipidemia, or any combination thereof, in the subject. In another embodiment, the reducing hepatic glucose production increases hyperglycemia, fatty liver, insulin resistance, insulin resistance-associated inflammation, insulin resistance-associated dyslipidemia, or any combination thereof, in the subject. In one embodiment, the increasing hepatic glucose production reduces hyperglycemia, fatty liver, insulin resistance, insulin resistance-associated inflammation, insulin resistance-associated dyslipidemia, or any combination thereof, in the subject. In another embodiment, the increasing hepatic glucose production increases hyperglycemia, fatty liver, insulin resistance, insulin resistance-associated inflammation, insulin resistance-associated dyslipidemia, or any combination thereof, in the subject.

In another embodiment, the reducing hepatic glucose production reduces the amount of FoxO1 protein level in the nucleus of a cell of the subject. In another embodiment, the reducing hepatic glucose production reduces phosphorylation of amino acid S284, S295, S326, S467, S475, S246, S253, S413, or S415, or any combination thereof, of the FoxO1 protein. In another embodiment, the reducing hepatic glucose production increases the amount of FoxO1 protein level in the nucleus of a cell of the subject. In another embodiment, the reducing hepatic glucose production increases phosphorylation of amino acid S284, S295, S326, S467, S475, S246, S253, S413, or S415, or any combination thereof, of the FoxO1 protein.

In another embodiment, the increasing hepatic glucose production reduces the amount of FoxO1 protein level in the nucleus of a cell of the subject. In another embodiment, the increasing hepatic glucose production reduces phosphorylation of amino acid S284, S295, S326, S467, S475, S246, S253, S413, or S415, or any combination thereof, of the FoxO1 protein. In another embodiment, the increasing hepatic glucose production increases the amount of FoxO1 protein level in the nucleus of a cell of the subject. In another embodiment, the increasing hepatic glucose production increases phosphorylation of amino acid S284, S295, S326, S467, S475, S246, S253, S413, or S415, or any combination thereof, of the FoxO1 protein.

In one embodiment, the reducing hepatic glucose production comprises a step of administering to the subject an antisense RNA that reduces expression of the gene encoding the CaMKII protein. In one embodiment, the increasing hepatic glucose production comprises a step of administering to the subject an antisense RNA that reduces expression of the gene encoding the CaMKII protein.

In another embodiment, the reducing hepatic glucose production comprises a step of administering to the subject a peptide or a polypeptide that specifically binds to the CaMKII protein. In another embodiment, the increasing hepatic glucose production comprises a step of administering to the subject a peptide or a polypeptide that specifically binds to the CaMKII protein.

In another embodiment, the reducing hepatic glucose production comprises a step of administering to the subject a small molecule. In another embodiment, the increasing hepatic glucose production comprises a step of administering to the subject a small molecule.

In one embodiment, the small molecule is a CaMKII inhibitor selected from the group consisting of KN-93, lavendustin C, CK59, Ant-CaMKIINtide, KN62, DY9760e, K-252a *Nocardiopsis* sp., H89 dihydrochloride, PP1 Analog II, 1NM-PP1, eEF-2 kinase inhibitor NH125, and STO-609.

In one aspect, the present disclosure provides a method of treating or preventing a metabolic disorder in a subject, the method comprising reducing the activity of IP3R1, IP3R2 or IP3R3, thereby treating or preventing the disorder. The present disclosure provides a method of treating or preventing a metabolic disorder in a subject, wherein the disorder is induced by obesity, the method comprising reducing the activity of IP3R1, IP3R2 or IP3R3, thereby treating or preventing the disorder. The present disclosure provides a method of treating or preventing a metabolic disorder in a subject, wherein the disorder is not induced by obesity, the method comprising reducing the activity of IP3R1, IP3R2 or IP3R3, thereby treating or preventing the disorder.

In another aspect, the present disclosure provides a method of treating or preventing coronary artery disease in a subject, the method comprising reducing the activity of IP3R1, IP3R2 or IP3R3 in the subject, thereby treating or preventing the coronary artery disease. The present disclosure provides a method of treating or preventing coronary artery disease in a subject with a metabolic disorder, the method comprising reducing the activity of IP3R1, IP3R2 or IP3R3 in the subject, thereby treating or preventing the coronary artery disease. The present disclosure provides a method of treating or preventing coronary artery disease in a subject with a metabolic disorder, the method comprising increasing the activity of IP3R1, IP3R2 or IP3R3 in the subject, thereby treating or preventing the coronary artery disease.

In another aspect, the present disclosure provides a method of treating or preventing a metabolic disorder in a subject, the method comprising reducing the activity of calcineurin, thereby treating or preventing the disorder. In another aspect, the present disclosure provides a method of treating or preventing a metabolic disorder in a subject, wherein the disorder is induced by obesity, the method comprising reducing the activity of calcineurin, thereby treating or preventing the disorder. In another aspect, the present disclosure provides a method of treating or preventing a metabolic disorder in a subject, wherein the disorder is not induced by obesity, the method comprising reducing the activity of calcineurin, thereby treating or preventing the disorder.

In another aspect, the present disclosure provides a method of treating or preventing coronary artery disease in a subject, the method comprising reducing the activity of calcineurin in the subject, thereby treating or preventing the coronary artery disease. The present disclosure provides a method of treating or preventing coronary artery disease in a subject with a metabolic disorder, the method comprising reducing the activity of calcineurin in the subject, thereby treating or preventing the coronary artery disease. The present disclosure provides a method of treating or preventing coronary artery disease in a subject with a metabolic disorder, the method comprising increasing the activity of calcineurin in the subject, thereby treating or preventing the coronary artery disease.

In one embodiment, the disorder is selected from the group consisting of Type 1 diabetes, Type 2 diabetes, insulin resistance, obesity, and metabolic syndrome.

In one embodiment, the treating or preventing affects glycogenolysis or gluconeogenesis in the subject. In another embodiment, the treating or preventing does not affect glycogenolysis or gluconeogenesis in the subject.

In one embodiment, the treating or preventing reduces hepatic glucose production, hyperglycemia, fatty liver, insulin resistance, insulin resistance-associated inflammation, insulin resistance-associated dyslipidemia, or any combination thereof, in the subject. In another embodiment, the treating or preventing increases hepatic glucose production, hyperglycemia, fatty liver, insulin resistance, insulin resistance-associated inflammation, insulin resistance-associated dyslipidemia, or any combination thereof, in the subject.

In one embodiment, the treating or preventing comprises a step of administering to the subject an inhibitor of the IP3R1 protein, IP3R2 protein, IP3R3 protein, or any combination thereof. In one embodiment, the inhibitor is Xestospongin C. In another embodiment, the inhibitor is 2-APB. In another embodiment, the inhibitor is caffeine.

In one embodiment, the treating or preventing comprises a step of administering to the subject an antisense RNA, or a siRNA, that reduces expression of the gene encoding the IP3R1 protein, IP3R2 protein or IP3R3 protein, or any combination thereof. In another embodiment, the treating or preventing comprises a step of administering to the subject a peptide or a polypeptide that specifically binds to the IP3R1 protein, IP3R2 protein or IP3R3 protein, or any combination thereof.

In one embodiment, the treating or preventing comprises a step of administering to the subject a small molecule. In one embodiment, the small molecule is a IP3R1 protein inhibitor, IP3R2 protein inhibitor or IP3R3 protein inhibitor. In one embodiment, the small molecule is Xestospongin C. In another embodiment, the small molecule is 2-APB. In another embodiment, the small molecule is caffeine.

In one embodiment, the treating or preventing comprises a step of administering to the subject an inhibitor of calcineurin. In one embodiment, the inhibitor of calcineurin is cyclosporin A. In another embodiment, the inhibitor of calcineurin is pimecrolimus. In another embodiment, the inhibitor of calcineurin is tacrolimus.

In one embodiment, the treating or preventing comprises a step of administering to the subject an antisense RNA, or a siRNA, that reduces expression of the gene encoding the calcineurin protein. In another embodiment, the treating or preventing comprises a step of administering to the subject a peptide or a oligopeptide or a polypeptide that specifically binds to the calcineurin protein. In one embodiment, the oligopeptide is cyclosporin A.

In one embodiment, the treating or preventing comprises a step of administering to the subject a small molecule. In another embodiment, the small molecule is a calcineurin inhibitor. In one embodiment, the small molecule is pimecrolimus. In another embodiment, the small molecule is tacrolimus.

In another aspect, the present disclosure provides a method of treating or preventing a metabolic disorder in a subject, the method comprising reducing the activity of p38, thereby treating or preventing the disorder. In another aspect, the present disclosure provides a method of treating or preventing a metabolic disorder in a subject, wherein the disorder is induced by obesity, the method comprising reducing the activity of p38, thereby treating or preventing the disorder. In another aspect, the present disclosure provides a method of treating or preventing a metabolic disorder in a subject, wherein the disorder is not induced by obesity, the method comprising reducing the activity of p38, thereby treating or preventing the disorder.

In another aspect, the present disclosure provides a method of treating or preventing coronary artery disease in a subject, the method comprising reducing the activity of p38 in the subject, thereby treating or preventing the coronary artery disease. The present disclosure provides a method of treating or preventing coronary artery disease in a subject with a metabolic disorder, the method comprising reducing the activity of p38 in the subject, thereby treating or preventing the coronary artery disease. The present disclosure provides a method of treating or preventing coronary artery disease in a subject with a metabolic disorder, the method comprising increasing the activity of p38 in the subject, thereby treating or preventing the coronary artery disease.

In another aspect, the present disclosure provides a method of treating or preventing a metabolic disorder in a subject, the method comprising reducing the activity of MK2/3, thereby treating or preventing the disorder. In another aspect, the present disclosure provides a method of treating or preventing a metabolic disorder in a subject, wherein the disorder is induced by obesity, the method comprising reducing the activity of MK2/3, thereby treating or preventing the disorder. In another aspect, the present disclosure provides a method of treating or preventing a metabolic disorder in a subject, wherein the disorder is not induced by obesity, the method comprising reducing the activity of MK2/3, thereby treating or preventing the disorder.

In another aspect, the present disclosure provides a method of treating or preventing coronary artery disease in a subject, the method comprising reducing the activity of MK2/3 in the subject, thereby treating or preventing the coronary artery disease. The present disclosure provides a method of treating or preventing coronary artery disease in a subject with a metabolic disorder, the method comprising reducing the activity of MK2/3 in the subject, thereby treating or preventing the coronary artery disease. The present disclosure provides a method of treating or preventing coronary artery disease in a subject with a metabolic disorder, the method comprising increasing the activity of MK2/3 in the subject, thereby treating or preventing the coronary artery disease.

In one embodiment, the disorder is selected from the group consisting of Type 1 diabetes, Type 2 diabetes, insulin resistance, obesity and metabolic syndrome.

In one embodiment, the treating or preventing affects glycogenolysis or gluconeogenesis in the subject. In another embodiment, the treating or preventing does not affect glycogenolysis or gluconeogenesis in the subject.

In one embodiment, the treating or preventing reduces hepatic glucose production, hyperglycemia, fatty liver, insulin resistance, insulin resistance-associated inflammation, insulin resistance-associated dyslipidemia, or any combination thereof, in the subject. In another embodiment, the treating or preventing increases hepatic glucose production, hyperglycemia, fatty liver, insulin resistance, insulin resistance-associated inflammation, insulin resistance-associated dyslipidemia, or any combination thereof, in the subject.

In one embodiment, the treating or preventing comprises a step of administering to the subject an inhibitor of p38. In one embodiment, the inhibitor of p38 is SB203580. In another embodiment, the inhibitor of p38 is SB 202190. In another embodiment, the inhibitor of p38 is SB 239063.

In one embodiment, the treating or preventing comprises a step of administering to the subject an antisense RNA, or a siRNA, that reduces expression of the gene encoding the p38 protein. In another embodiment, the treating or preventing comprises a step of administering to the subject a peptide or a polypeptide that specifically binds to the p38 protein. In another embodiment, the treating or preventing comprises a step of administering to the subject a small molecule. In one embodiment, the small molecule is a p38 inhibitor. In one embodiment, the small molecule is SB203580. In another embodiment, the small molecule is SB 202190. In another embodiment, the small molecule is SB 239063.

In one embodiment, the treating or preventing comprises a step of administering to the subject an inhibitor of MK2/3. In one embodiment, the inhibitor of MK2/3 is Hsp25 kinase inhibitor.

In one embodiment, the treating or preventing comprises a step of administering to the subject an antisense RNA, or siRNA, that reduces expression of the gene encoding the MK2/3 protein. In another embodiment, the treating or preventing comprises a step of administering to the subject a peptide or a polypeptide that specifically binds to the MK2/3 protein. In one embodiment, the peptide is Hsp25 Kinase Inhibitor. In one embodiment, the treating or preventing comprises a step of administering to the subject a small molecule. In one embodiment, the small molecule is a MK2/3 inhibitor.

In one aspect, the present disclosure provides a method of treating or preventing a metabolic disorder in a subject, the method comprising reducing the activity of HDAC4, thereby treating or preventing the disorder. In another aspect, the present disclosure provides a method of treating or preventing a metabolic disorder in a subject, the method comprising increasing the activity of HDAC4, thereby treating or preventing the disorder.

In one aspect, the present disclosure provides a method of treating or preventing a metabolic disorder in a subject, wherein the disorder is induced by obesity, the method comprising reducing the activity of HDAC4, thereby treating or preventing the disorder. In another aspect, the present disclosure provides a method of treating or preventing a metabolic disorder in a subject, wherein the disorder is induced by obesity, the method comprising increasing the activity of HDAC4, thereby treating or preventing the disorder.

In one aspect, the present disclosure provides a method of treating or preventing a metabolic disorder in a subject, wherein the disorder is not induced by obesity, the method comprising reducing the activity of HDAC4, thereby treating or preventing the disorder. In another aspect, the present disclosure provides a method of treating or preventing a metabolic disorder in a subject, wherein the disorder is not induced by obesity, the method comprising increasing the activity of HDAC4, thereby treating or preventing the disorder.

In another aspect, the present disclosure provides a method of treating or preventing coronary artery disease in a subject, the method comprising increasing the activity of HDAC4 in the subject, thereby treating or preventing the coronary artery disease. The present disclosure also provides a method of treating or preventing coronary artery disease in a subject, the method comprising reducing the activity of HDAC4 in the subject, thereby treating or preventing the coronary artery disease. The present disclosure provides a method of treating or preventing coronary artery disease in a subject with a metabolic disorder, the method comprising reducing the activity of HDAC4 in the subject, thereby treating or preventing the coronary artery disease. The present disclosure provides a method of treating or preventing coronary artery disease in a subject with a metabolic disorder, the method comprising increasing the activity of HDAC4 in the subject, thereby treating or preventing the coronary artery disease.

In one aspect, the present disclosure provides a method of treating or preventing a metabolic disorder in a subject, the method comprising reducing the activity of Dach1, thereby treating or preventing the disorder. In another aspect, the present disclosure provides a method of treating or preventing a metabolic disorder in a subject, the method comprising increasing the activity of Dach1, thereby treating or preventing the disorder.

In another aspect, the present disclosure provides a method of treating or preventing a metabolic disorder in a subject, wherein the disorder is induced by obesity, the method comprising reducing the activity of Dach1, thereby treating or preventing the disorder. In another aspect, the present disclosure provides a method of treating or preventing a metabolic disorder in a subject, wherein the disorder is induced by obesity, the method comprising increasing the activity of Dach1, thereby treating or preventing the disorder.

In another aspect, the present disclosure provides a method of treating or preventing a metabolic disorder in a subject, wherein the disorder is not induced by obesity, the method comprising reducing the activity of Dach1, thereby treating or preventing the disorder. In another aspect, the present disclosure provides a method of treating or preventing a metabolic disorder in a subject, wherein the disorder is not induced by obesity, the method comprising increasing the activity of Dach1, thereby treating or preventing the disorder.

In another aspect, the present disclosure provides a method of treating or preventing coronary artery disease in a subject, the method comprising increasing the activity of Dach1 in the subject, thereby treating or preventing the coronary artery disease. The present disclosure also provides a method of treating or preventing coronary artery disease in a subject, the method comprising reducing the activity of Dach1 in the subject, thereby treating or preventing the coronary artery disease. The present disclosure provides a method of treating or preventing coronary artery disease in a subject with a metabolic disorder, the method comprising reducing the activity of Dach1 in the subject, thereby treating or preventing the coronary artery disease. The present disclosure provides a method of treating or preventing coronary artery disease in a subject with a metabolic disorder, the method comprising increasing the activity of Dach1 in the subject, thereby treating or preventing the coronary artery disease.

In one aspect, the present disclosure provides a method of treating or preventing a metabolic disorder in a subject, the method comprising reducing the activity of Dach2, thereby treating or preventing the disorder. In another aspect, the present disclosure provides a method of treating or preventing a metabolic disorder in a subject, the method comprising increasing the activity of Dach2, thereby treating or preventing the disorder.

In another aspect, the present disclosure provides a method of treating or preventing a metabolic disorder in a subject, wherein the disorder is induced by obesity, the method comprising reducing the activity of Dach2, thereby treating or preventing the disorder. In another aspect, the present disclosure provides a method of treating or preventing a metabolic disorder in a subject, wherein the disorder is induced by obesity, the method comprising increasing the activity of Dach2, thereby treating or preventing the disorder.

In another aspect, the present disclosure provides a method of treating or preventing a metabolic disorder in a subject, wherein the disorder is not induced by obesity, the method comprising reducing the activity of Dach2, thereby treating or preventing the disorder. In another aspect, the present disclosure provides a method of treating or preventing a metabolic disorder in a subject, wherein the disorder is not induced by obesity, the method comprising increasing the activity of Dach2, thereby treating or preventing the disorder.

In another aspect, the present disclosure provides a method of treating or preventing coronary artery disease in a subject, the method comprising increasing the activity of Dach2 in the subject, thereby treating or preventing the coronary artery disease. The present disclosure also provides a method of treating or preventing coronary artery disease in a subject, the method comprising reducing the activity of Dach2 in the subject, thereby treating or preventing the coronary artery disease. The present disclosure provides a method of treating or preventing coronary artery disease in a subject with a metabolic disorder, the method comprising reducing the activity of Dach2 in the subject, thereby treating or preventing the coronary artery disease. The present disclosure provides a method of treating or preventing coronary artery disease in a subject with a metabolic disorder, the method comprising increasing the activity of Dach2 in the subject, thereby treating or preventing the coronary artery disease.

In one embodiment, the disorder is selected from the group consisting of Type 1 diabetes, Type 2 diabetes, insulin resistance, obesity and metabolic syndrome.

In one embodiment, the treating or preventing affects glycogenolysis or gluconeogenesis in the subject. In another embodiment, the treating or preventing does not affect glycogenolysis or gluconeogenesis in the subject.

In one embodiment, the treating or preventing reduces hepatic glucose production, hyperglycemia, fatty liver, insulin resistance, insulin resistance-associated inflammation, insulin resistance-associated dyslipidemia, or any combination thereof, in the subject. In another embodiment, the treating or preventing increases hepatic glucose production, hyperglycemia, fatty liver, insulin resistance, insulin resistance-associated inflammation, insulin resistance-associated dyslipidemia, or any combination thereof, in the subject.

In one embodiment, the treating or preventing comprises a step of administering to the subject an inhibitor of HDAC4. In another embodiment, the treating or preventing comprises a step of administering to the subject an activator of HDAC4.

In one embodiment, the treating or preventing comprises a step of administering to the subject an inhibitor of Dach1. In another embodiment, the treating or preventing comprises a step of administering to the subject an activator of Dach1.

In one embodiment, the treating or preventing comprises a step of administering to the subject an inhibitor of Dach2. In another embodiment, the treating or preventing comprises a step of administering to the subject an activator of Dach2.

In one embodiment, the treating or preventing comprises a step of administering to the subject an antisense RNA, or a siRNA, that reduces expression of the gene encoding the HDAC4 protein.

In another embodiment, the treating or preventing comprises a step of administering to the subject a peptide or a polypeptide that specifically binds to the HDAC4 protein. In one embodiment, the peptide or polypeptide reduces the activity of the HDAC4 protein. In another embodiment, the peptide or polypeptide increases the activity of the HDAC4 protein.

In one embodiment, the treating or preventing comprises a step of administering to the subject a small molecule. In one embodiment, the small molecule binds to the HDAC4 protein. In one embodiment, the small molecule reduces the activity of the HDAC4 protein. In another embodiment, the small molecule increases the activity of the HDAC4 protein.

In one embodiment, the treating or preventing comprises a step of increasing the phosphorylation of HDAC4. In another step, the treating or preventing comprises a step of decreasing the phosphorylation of HDAC4. In one embodiment, the treating or preventing comprises a step of increasing nuclear HDAC4. In another step, the treating or preventing comprises a step of decreasing nuclear HDAC4.

In one embodiment, the treating or preventing comprises a step of increasing the expression of the Atf6 gene and/or the p58 gene. In another embodiment, the treating or preventing comprises a step of decreasing the expression of the Atf6 gene and/or the p58 gene. In one embodiment, the treating or preventing comprises a step of increasing the levels of Atf6 protein and/or p58 protein. In another embodiment, the treating or preventing comprises a step of decreasing the levels of Atf6 protein and/or p58 protein. In one embodiment, the treating or preventing comprises a step of increasing the activity of Atf6 and/or p58. In another embodiment, the treating or preventing comprises a step of decreasing the activity of Atf6 and/or p58.

In another embodiment, the treating or preventing comprises a step of increasing Akt phosphorylation. In yet another embodiment, the treating or preventing comprises a step of decreasing Akt phosphorylation.

In one embodiment, the treating or preventing comprises a step of administering to the subject an antisense RNA, or a siRNA, that reduces expression of the gene encoding the Dach1 protein.

In another embodiment, the treating or preventing comprises a step of administering to the subject a peptide or a polypeptide that specifically binds to the Dach1 protein. In one embodiment, the peptide or polypeptide reduces the activity of the Dach1 protein. In another embodiment, the peptide or polypeptide increases the activity of the Dach1 protein.

In one embodiment, the treating or preventing comprises a step of administering to the subject a small molecule. In one embodiment, the small molecule binds to the Dach1 protein. In one embodiment, the small molecule reduces the activity of the Dach1 protein. In another embodiment, the small molecule increases the activity of the Dach1 protein.

In one embodiment, the treating or preventing comprises a step of increasing the phosphorylation of Dach1. In another step, the treating or preventing comprises a step of decreasing the phosphorylation of Dach1. In one embodiment, the treating or preventing comprises a step of repressing Dach1. In another step, the treating or preventing comprises a step of de-repressing Dach1.

In one embodiment, the treating or preventing comprises a step of administering to the subject an antisense RNA, or a siRNA, that reduces expression of the gene encoding the Dach2 protein.

In another embodiment, the treating or preventing comprises a step of administering to the subject a peptide or a polypeptide that specifically binds to the Dach2 protein. In one embodiment, the peptide or polypeptide reduces the activity of the Dach2 protein. In another embodiment, the peptide or polypeptide increases the activity of the Dach2 protein.

In one embodiment, the treating or preventing comprises a step of administering to the subject a small molecule. In one embodiment, the small molecule binds to the Dach2 protein. In one embodiment, the small molecule reduces the activity of the Dach2 protein. In another embodiment, the small molecule increases the activity of the Dach2 protein.

In one embodiment, the treating or preventing comprises a step of increasing the phosphorylation of Dach2. In another step, the treating or preventing comprises a step of decreasing the phosphorylation of Dach2. In one embodiment, the treating or preventing comprises a step of repressing Dach2. In another step, the treating or preventing comprises a step of de-repressing Dach2.

In other aspects, the methods above are used to reduce hepatic glucose production in a subject by reducing the activity of IP3R, calcineurin, p38, MK2/3, HDAC4, Dach1 and/or Dach2. In yet other aspects, the methods above are used to reduce hepatic glucose production in a subject by increasing the activity of IP3R, calcineurin, p38, MK2/3, HDAC4, Dach1 and/or Dach2.

In other aspects, the methods above are used to increase hepatic glucose production in a subject by reducing the activity of IP3R, calcineurin, p38, MK2/3, HDAC4, Dach1 and/or Dach2. In yet other aspects, the methods above are used to increase hepatic glucose production in a subject by increasing the activity of IP3R, calcineurin, p38, MK2/3, HDAC4, Dach1 and/or Dach2.

Methods for Screening

The disclosure provides methods for identifying a compound or combination of compounds that treat or prevent a metabolic disorder in a subject. The disclosure also provides methods for identifying a compound or combination of compounds that treat or prevent coronary artery disease in a subject with a metabolic disorder. In one embodiment, the disorder is induced by obesity. In another embodiment, the disorder is not induced by obesity. The disclosure also provides methods for identifying a compound or combination of compounds that reduce hepatic glucose production in a subject.

The disclosure also provides methods for the identification of a compound or a combination of compounds that inhibit, or reduce, the activity and/or activation of CaMKII. The disclosure also provides methods for the identification of a compound or a combination of compounds that inhibit, or reduce, the activity and/or activation of IP3R, including, but not limited to, IP3R1, IP3R2, and IP3R3. The disclosure also provides methods for the identification of a compound or a combination of compounds that inhibit, or reduce, the activity and/or activation of calcineurin. The disclosure also provides methods for the identification of a compound or a combination of compounds that inhibit, or reduce, the activity and/or activation of p38. The disclosure also provides methods for the identification of a compound or a combination of compounds that inhibit, or reduce, the activity and/or activation of MK2/3.

The disclosure also provides methods for the identification of a compound or a combination of compounds that inhibit, or reduce, the activity and/or activation of HDAC4. The disclosure also provides methods for the identification of a compound or a combination of compounds that activate, or increase the activity and/or activation of, HDAC4.

The disclosure also provides methods for the identification of a compound or a combination of compounds that inhibit, or reduce, the activity and/or activation of Dach1. The disclosure also provides methods for the identification of a compound or a combination of compounds that activate, or increase the activity and/or activation of, Dach1.

The disclosure also provides methods for the identification of a compound or a combination of compounds that inhibit, or reduce, the activity and/or activation of Dach2. The disclosure also provides methods for the identification of a compound or a combination of compounds that activate, or increase the activity and/or activation of, Dach2.

The disclosure also provides methods for the identification of a compound or a combination of compounds that inhibit the activity and/or activation of CaMKII, IP3R, including, but not limited to, IP3R1, IP3R2, and IP3R3, calcineurin, p38, MK2/3, HDAC4, Dach1, Dach2, or any combination thereof. The disclosure also provides methods for the identification of a compound or a combination of compounds that reduce the activity of CaMKII, IP3R, including, but not limited to, IP3R1, IP3R2, and IP3R3, calcineurin, p38, MK2/3, HDAC4, Dach1, Dach2, or any combination thereof.

The disclosure also provides methods for the identification of a compound or a combination of compounds that activate CaMKII, IP3R, including, but not limited to, IP3R1, IP3R2, and IP3R3, calcineurin, p38, MK2/3, HDAC4, Dach1, Dach2, or any combination thereof. The disclosure also provides methods for the identification of a compound or a combination of compounds that increase the activity of CaMKII, IP3R, including, but not limited to, IP3R1, IP3R2, and IP3R3, calcineurin, p38, MK2/3, HDAC4, Dach1, Dach2, or any combination thereof.

The present disclosure provides a method for identifying a compound that inhibits the activity of CaMKII, the method comprising a) contacting a cell with a CaMKII fusion protein, wherein the CaMKII fusion protein comprises an acceptor fluorophore protein at one terminus, and a donor fluorophore protein at the other terminus; and b) measuring FRET efficiency in the absence and in the presence of a test compound, wherein a greater FRET efficiency in the presence of the test compound compared to the FRET efficiency in the absence of the test compound indicates that the test compound inhibits the activity of CaMKII (see Takao et al., 2005; and Kwok et al., 2008, which are incorporated by reference in their entireties).

The present disclosure provides a method for identifying a compound that inhibits the activity of CaMKII, the method comprising a) contacting a cell with a CaMKII fusion protein, wherein the CaMKII fusion protein comprises an acceptor fluorophore protein at one terminus, and a donor fluorophore protein at the other terminus; and b) measuring the ratio of the donor protein to the acceptor protein in the absence and in the presence of a test compound, wherein a decrease of the ratio in the presence of the test compound compared to the ratio in the absence of the test compound indicates that the test compound inhibits the activity of CaMKII (see Takao et al., 2005; and Kwok et al., 2008, which are incorporated by reference in their entireties).

In one embodiment the acceptor fluorophore protein is selected from the group consisting of mOrange, mStrawberry, Venus, yellow fluorescent protein, cyan fluorescent protein, red fluorescent protein and green fluorescent protein. In another embodiment, the donor protein is selected from the group consisting of mOrange, mStrawberry, Venus, yellow fluorescent protein, cyan fluorescent protein, red fluorescent protein and green fluorescent protein (see Takao et al., 2005; and Kwok et al., 2008, which are incorporated by reference in their entireties).

In one embodiment, the cell is a HEK293T cell, a hepatocyte, a U2OS cell, a HeLa cell, a murine embryonic fibroblast (MEF) or a macrophage. In another embodiment, the cell is from a Insr−/− mouse, a Camk2g−/− mouse, a Foxo1−/− mouse, a db/db mouse, a ob/ob mouse, a p38−/− mouse, a Non Obese Diabetes (NOD) mouse, a mouse fed a high fat diet, or a streptozotocin-treated mouse. In another embodiment, the cell is from a mouse expressing a mutant FoxO1 protein. In one embodiment, the mutant FoxO1 protein comprises alanine substitutions at S284, S295, S326, S467, S475, S246, S253, S413, or S415, or aspartic acid substitutions at S284, S295, S326, S467, S475, S246, S253, S413, or S415, or any combination thereof.

In one embodiment, the cell is subjected to ER stress. In another embodiment, the cell is treated with glucagon, 8-bromo cAMP, H89 dihydrochloride, Xestospongin C, forskolin, saturated fatty acids, or any combination thereof.

In another aspect, the present disclosure provides a method for identifying a compound that inhibits the activity of IP3R1, IP3R2 or IP3R3, the method comprising a) contacting a cell with a test compound; and b) measuring IP3R1, IP3R2 or IP3R3 activity, wherein a reduction of the activity of IP3R1, IP3R2 or IP3R3 in the presence of the compound compared to the activity of IP3R1, IP3R2 or IP3R3 in the absence of the compound indicates that the compound is an inhibitor of IP3R1, IP3R2 or IP3R3, respectively.

In one embodiment, the activity is measured by calcium release into the cytosol of the cell after stimulation with an inducer of IP3. In one embodiment, calcium release is measured by an increase in the fluorescence of a cytosolic calcium dye. In one embodiment, the cytosolic calcium dye is Fluo-3.

In another aspect, the present disclosure provides a method for identifying a compound that inhibits the activity of calcineurin, the method comprising a) contacting a cell with a test compound; and b) measuring calcineurin activity, wherein a reduction of the activity of calcineurin in the presence of the compound compared to the activity of calcineurin in the absence of the compound indicates that the compound is an inhibitor of calcineurin.

In one embodiment, the activity of calcineurin is measured through detection of phosphatase activity using a calcineurin substrate peptide. In one embodiment, the cell is a HEK293T cell, a hepatocyte, a U2OS cell, a HeLa cell, or a murine embryonic fibroblast (MEF). In another embodiment, the cell is from a db/db mouse, a ob/ob mouse, a Non Obese Diabetes (NOD) mouse, a mouse fed a high fat diet, or a streptozotocin-treated mouse.

In one embodiment, the cell is treated with glucagon, H89 dihydrochloride, insulin, forskolin, an inducer of ER stress, tunicamycin, saturated fatty acids, or any combination thereof.

In another aspect, the present disclosure provides a method for identifying a compound that inhibits the activity of p38, the method comprising a) contacting a cell with a test compound; and b) measuring p38 kinase activity, wherein a reduction of the kinase activity of p38 in the presence of the compound compared to the kinase activity of p38 in the absence of the compound indicates that the compound is an inhibitor of p38. In another aspect, the present disclosure provides a method for identifying a compound that inhibits the activity of MK2/3, the method comprising a) contacting a cell with a test compound; and b) measuring MK2/3 kinase activity, wherein a reduction of the kinase activity of MK2/3 in the presence of the compound compared to the kinase activity of MK2/3 in the absence of the compound indicates that the compound is an inhibitor of MK2/3.

In one embodiment, p38 kinase activity is measured using a p38-specific peptide. In one embodiment, MK2/3 kinase activity is measured using a MK2/3-specific peptide.

In one embodiment, the cell is a HEK293T cell, a hepatocyte, a U2OS cell, a HeLa cell, a macrophage or a murine embryonic fibroblast (MEF). In another embodiment, the cell is from a Insr−/− mouse, a db/db mouse, a ob/ob mouse, a Non Obese Diabetes (NOD) mouse, a mouse fed a high fat diet, or a streptozotocin-treated mouse. In another embodiment, the cell is treated with glucagon, 8-bromo cAMP, H89 dihydrochloride, forskolin, saturated fatty acids, or any combination thereof.

In another aspect, the present disclosure provides a method for identifying a compound that inhibits the activity of HDAC4, the method comprising a) contacting a cell with a test compound; and b) measuring HDAC4 activity, wherein a reduction of the activity of HDAC4 in the presence of the compound compared to the activity of HDAC4 in the absence of the compound indicates that the compound is an inhibitor of HDAC4. In another aspect, the present disclosure provides a method for identifying a compound that inhibits the activity of Dach1, the method comprising a) contacting a cell with a test compound; and b) measuring Dach1 activity, wherein a reduction of the activity of Dach1 in the presence of the compound compared to the activity of Dach1 in the absence of the compound indicates that the compound is an inhibitor of Dach1. In another aspect, the present disclosure provides a method for identifying a compound that inhibits the activity of Dach2, the method comprising a) contacting a cell with a test compound; and b) measuring Dach2 activity, wherein a reduction of the activity of Dach2 in the presence of the compound compared to the activity of Dach2 in the absence of the compound indicates that the compound is an inhibitor of Dach2.

In another aspect, the present disclosure provides a method for identifying a compound that increases the activity of HDAC4, the method comprising a) contacting a cell with a test compound; and b) measuring HDAC4 activity, wherein an increase in the activity of HDAC4 in the presence of the compound compared to the activity of HDAC4 in the absence of the compound indicates that the compound is an activator of HDAC4. In another aspect, the present disclosure provides a method for identifying a compound that increases the activity of Dach1, the method comprising a) contacting a cell with a test compound; and b) measuring Dach1 activity, wherein an increase in the activity of Dach1 in the presence of the compound compared to the activity of Dach1 in the absence of the compound indicates that the compound is an activator of Dach1. In another aspect, the present disclosure provides a method for identifying a compound that increases the activity of Dach2, the method comprising a) contacting a cell with a test compound; and b) measuring Dach2 activity, wherein an increase in the activity of Dach2 in the presence of the compound compared to the activity of Dach2 in the absence of the compound indicates that the compound is an activator of Dach2.

In one embodiment, the HDAC4 activity is measured using a HDAC4-specific peptide. In one embodiment, the Dach1 activity is measured using a Dach1-specific peptide. In one embodiment, the Dach2 activity is measured using a Dach2-specific peptide.

In one embodiment, HDAC4 is constitutively in the nucleus. In another embodiment, HDAC4 is constitutively nuclear HDAC4 (CN-HDAC4).

In one embodiment, the cell is a HEK293T cell, a hepatocyte, a U2OS cell, a HeLa cell, a macrophage, a Camk2g$^{fl/fl}$ cell, Mapk14$^{fl/fl}$ cell, a palmitate-treated hepatocyte, or a murine embryonic fibroblast (MEF). In another embodiment, the cell is from a human, a wild-type mouse, a Insr−/− mouse, a db/db mouse, a ob/ob mouse, a Non Obese Diabetes (NOD) mouse, a diet-induced obese (DIO) mouse, a mouse fed a high fat diet, or a streptozotocin-treated mouse. In another embodiment, the cell is treated with glucagon, 8-bromo cAMP, H89 dihydrochloride, forskolin, saturated fatty acids, palmitate, or any combination thereof.

In one aspect, the method comprises administering a test compound or a combination of test compounds to an animal that is a model of a metabolic disorder, or cardiovascular disease, such as coronary artery disease, and determining whether the compound or combination of compounds improves metabolic function, and/or cardiovascular function in the animal, compared to an animal not so treated.

The invention provides methods for identifying compounds which can be used for treating or preventing a metabolic disorder in a subject, treating or preventing coronary artery disease in a subject with a metabolic disorder and/or reducing hepatic glucose production in a subject. The invention provides methods for identifying compounds that inhibit the activity of CaMKII or reduce the phosphorylation and/or activation of CaMKII. The invention provides methods for identifying compounds that inhibit the activity of IP3R, including, but not limited to, IP3R1, IP3R2, and IP3R3, or reduce the phosphorylation and/or activation of IP3R, including, but not limited to, IP3R1, IP3R2, and IP3R3. The invention provides methods for identifying compounds that inhibit the activity of calcineurin, or reduce the phosphorylation and/or activation of calcineurin. The invention provides methods for identifying compounds that inhibit the activity of p38, or reduce the phosphorylation and/or activation of p38. The invention provides methods for identifying compounds that inhibit the activity of HDAC4, or reduce the phosphorylation and/or activation of HDAC4. The invention provides methods for identifying compounds that inhibit the activity of Dach1, or reduce the phosphorylation and/or activation of Dach1. The invention provides methods for identifying compounds that inhibit the activity of Dach2, or reduce the phosphorylation and/or activation of Dach2.

The invention provides methods for identifying compounds that increase the activity of HDAC4, or increase the phosphorylation and/or activation of HDAC4. The invention provides methods for identifying compounds that increase the activity of Dach1, or increase the phosphorylation and/or activation of Dach1. The invention provides methods for identifying compounds that increase the activity of Dach2, or increase the phosphorylation and/or activation of Dach2.

The methods can comprise the identification of test compounds or agents (e.g., peptides (such as antibodies or fragments thereof), small molecules, or nucleic acids (such as siRNA or antisense RNA), or other agents).

In one embodiment, a compound can be a peptide fragment. Fragments include all possible amino acid lengths between and including about 8 and about 100 amino acids, for example, lengths between about 10 and about 100 amino acids, between about 15 and about 100 amino acids, between about 20 and about 100 amino acids, between about 35 and about 100 amino acids, between about 40 and about 100 amino acids, between about 50 and about 100 amino acids, between about 70 and about 100 amino acids, between about 75 and about 100 amino acids, or between about 80 and about 100 amino acids. These peptide fragments can be obtained commercially or synthesized via liquid phase or solid phase synthesis methods (Atherton et al., (1989) Solid Phase Peptide Synthesis: a Practical Approach. IRL Press, Oxford, England). The peptide fragments can be isolated from a natural source, genetically engineered, or chemically prepared. These methods are well known in the art.

A compound can be a protein, such as an antibody (monoclonal, polyclonal, humanized, chimeric, or fully human), or a binding fragment thereof. An antibody fragment can be a form of an antibody other than the full-length form and includes portions or components that exist within full-length antibodies, in addition to antibody fragments that have been engineered. Antibody fragments can include, but are not limited to, single chain Fv (scFv), diabodies, Fv, and (Fab)$_2$, triabodies, Fc, Fab, CDR1, CDR2, CDR3, combinations of CDR's, variable regions, tetrabodies, bifunctional hybrid antibodies, framework regions, constant regions, and the like (see, Maynard et al., (2000) Ann. Rev. Biomed. Eng. 2:339-76; Hudson (1998) Curr. Opin. Biotechnol. 9:395-402). Antibodies can be obtained commercially, custom generated, or synthesized against an antigen of interest according to methods established in the art (Janeway et al., (2001) Immunobiology, 5th ed., Garland Publishing).

A compound can be selected from the group comprising: siRNA; interfering RNA or RNAi; dsRNA; RNA Polymerase III transcribed DNAs; ribozymes; and antisense nucleic acids, which can be RNA, DNA, or an artificial nucleic acid. Antisense oligonucleotides, including antisense DNA, RNA, and DNA/RNA molecules, act to directly block the translation of mRNA by binding to targeted mRNA and preventing protein translation. Antisense oligonucleotides of at least about 15 bases can be synthesized, e.g., by conventional phosphodiester techniques (Dallas et al., (2006) Med. Sci. Monit. 12(4):RA67-74; Kalota et al., (2006) Handb. Exp. Pharmacol. 173:173-96; Lutzelburger et al., (2006) Handb. Exp. Pharmacol. 173:243-59). Antisense nucleotide sequences include, but are not limited to: morpholinos, 2'-O-methyl polynucleotides, DNA, RNA and the like.

siRNA comprises a double stranded structure containing from about 15 to about 50 base pairs, for example from about 21 to about 25 base pairs, and having a nucleotide sequence identical or nearly identical to an expressed target gene or RNA within the cell. The siRNA comprise a sense RNA strand and a complementary antisense RNA strand annealed together by standard Watson-Crick base-pairing interactions. The sense strand comprises a nucleic acid sequence which is substantially identical to a nucleic acid sequence contained within the target miRNA molecule. "Substantially identical" to a target sequence contained within the target mRNA refers to a nucleic acid sequence that differs from the target sequence by about 3% or less. The sense and antisense strands of the siRNA can comprise two complementary, single-stranded RNA molecules, or can comprise a single molecule in which two complementary portions are base-paired and are covalently linked by a single-stranded "hairpin" area. See also, McMnaus and Sharp (2002) Nat Rev Genetics, 3:737-47, and Sen and Blau (2006) FASEB J., 20:1293-99, the entire disclosures of which are herein incorporated by reference.

The siRNA can be altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, or modifications that make the siRNA resistant to nuclease digestion, or the substitution of one or more nucleotides in the siRNA with deoxyribonucleotides. One or both strands of the siRNA can also comprise a 3' overhang. As used herein, a 3' overhang refers to at least one unpaired nucleotide extending from the 3'-end of a duplexed RNA strand. For example, the siRNA can comprise at least one 3' overhang of from 1 to about 6 nucleotides (which includes ribonucleotides or deoxyribonucleotides) in length, or from 1 to about 5 nucleotides in length, or from 1 to about 4 nucleotides in length, or from about 2 to about 4 nucleotides in length. For example, each strand of the siRNA can comprise 3' overhangs of dithymidylic acid ("TT") or diuridylic acid ("uu").

siRNA can be produced chemically or biologically, or can be expressed from a recombinant plasmid or viral vector (for example, see U.S. Pat. No. 7,294,504 and U.S. Pat. No. 7,422,896, the entire disclosures of which are herein incorporated by reference). Exemplary methods for producing and testing dsRNA or siRNA molecules are described in U.S. Patent Application Publication No. 2002/0173478 to Gewirtz, U.S. Patent Application Publication No. 2007/0072204 to Hannon et al., and in U.S. Patent Application Publication No. 2004/0018176 to Reich et al., the entire disclosures of which are herein incorporated by reference.

RNA polymerase III transcribed DNAs contain promoters, such as the U6 promoter. These DNAs can be transcribed to produce small hairpin RNAs in the cell that can function as siRNA or linear RNAs that can function as antisense RNA. A compound can contain ribonucleotides, deoxyribonucleotides, synthetic nucleotides, or any suitable combination such that the target RNA and/or gene is inhibited. In addition, these forms of nucleic acid can be single, double, triple, or quadruple stranded. (see for example Bass (2001) *Nature,* 411, 428 429; Elbashir et al., (2001) *Nature,* 411, 494 498; and PCT Publication Nos. WO 00/44895, WO 01/36646, WO 99/32619, WO 00/01846, WO 01/29058, WO 99/07409, WO 00/44914).

A compound can be a small molecule that binds to a protein and disrupts its function, or conversely, enhances its function. Small molecules are a diverse group of synthetic and natural substances generally having low molecular weights. They can be isolated from natural sources (for example, plants, fungi, microbes and the like), are obtained commercially and/or available as libraries or collections, or synthesized. Candidate small molecules can be identified via in silico screening or high-through-put (HTP) screening of combinatorial libraries. Most conventional pharmaceuticals, such as aspirin, penicillin, and many chemotherapeutics, are small molecules, can be obtained commercially, can be chemically synthesized, or can be obtained from random or combinatorial libraries as described below (Werner et al., (2006) *Brief Funct. Genomic Proteomic* 5(1):32-6).

Knowledge of the primary sequence of a molecule of interest, and the similarity of that sequence with proteins of known function, can provide information as to the inhibitors or antagonists of the protein of interest in addition to agonists. Identification and screening of agonists and antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Test compounds can be screened from large libraries of synthetic or natural compounds (see Wang et al., (2007) *Curr Med Chem,* 14(2):133-55; Mannhold (2006) *Curr Top Med Chem,* 6 (10):1031-47; and Hensen (2006) *Curr Med Chem* 13(4):361-76). Numerous means are currently used for random and directed synthesis of saccharide, peptide, and nucleic acid based compounds. Synthetic compound libraries are commercially available from Maybridge Chemical Co. (Trevillet, Cornwall, UK), AMRI (Albany, N.Y.), ChemBridge (San Diego, Calif.), and MicroSource (Gaylordsville, Conn.). A rare chemical library is available from Aldrich (Milwaukee, Wis.). Alternatively, libraries of natural compounds in the form of bacterial, fungal, plant and animal extracts are available from e.g. Pan Laboratories (Bothell, Wash.) or MycoSearch (N.C.), or are readily producible. Additionally, natural and synthetically produced libraries and compounds are readily modified through conventional chemical, physical, and biochemical means (Blondelle et al., (1996) *Tib Tech* 14:60).

Methods for preparing libraries of molecules are well known in the art and many libraries are commercially available. Libraries of interest in the invention include peptide libraries, randomized oligonucleotide libraries, synthetic organic combinatorial libraries, and the like. Degenerate peptide libraries can be readily prepared in solution, in immobilized form as bacterial flagella peptide display libraries or as phage display libraries. Peptide ligands can be selected from combinatorial libraries of peptides containing at least one amino acid. Libraries can be synthesized of peptoids and non-peptide synthetic moieties. Such libraries can further be synthesized which contain non-peptide synthetic moieties, which are less subject to enzymatic degradation compared to their naturally-occurring counterparts. For example, libraries can also include, but are not limited to, peptide-on-plasmid libraries, synthetic small molecule libraries, aptamer libraries, in vitro translation-based libraries, polysome libraries, synthetic peptide libraries, neurotransmitter libraries, and chemical libraries.

Examples of chemically synthesized libraries are described in Fodor et al., (1991) *Science* 251:767-773; Houghten et al., (1991) *Nature* 354:84-86; Lam et al., (1991) *Nature* 354:82-84; Medynski, (1994) *BioTechnology* 12:709-710; Gallop et al., (1994) *J. Medicinal Chemistry* 37(9):1233-1251; Ohlmeyer et al., (1993) *Proc. Natl. Acad. Sci. USA* 90:10922-10926; Erb et al., (1994) *Proc. Natl. Acad. Sci. USA* 91:11422-11426; Houghten et al., (1992) *Biotechniques* 13:412; Jayawickreme et al., (1994) *Proc. Natl. Acad. Sci. USA* 91:1614-1618; Salmon et al., (1993) *Proc. Natl. Acad. Sci. USA* 90:11708-11712; PCT Publication No. WO 93/20242, dated Oct. 14, 1993; and Brenner et al., (1992) *Proc. Natl. Acad. Sci. USA* 89:5381-5383. Examples of phage display libraries are described in Scott et al., (1990) *Science* 249:386-390; Devlin et al., (1990) *Science,* 249:404-406; Christian, et al., (1992) *J. Mol. Biol.* 227:711-718; Lenstra, (1992) *J. Immunol. Meth.* 152:149-157; Kay et al., (1993) *Gene* 128:59-65; and PCT Publication No. WO 94/18318. In vitro translation-based libraries include but are not limited to those described in PCT Publication No. WO 91/05058; and Mattheakis et al., (1994) *Proc. Natl. Acad. Sci. USA* 91:9022-9026.

Screening the libraries can be accomplished by any variety of commonly known methods. See, for example, the following references, which disclose screening of peptide libraries: Parmley and Smith, (1989) *Adv. Exp. Med. Biol.* 251:215-218; Scott and Smith, (1990) *Science* 249:386-390; Fowlkes et al., (1992) *BioTechniques* 13:422-427; Oldenburg et al., (1992) *Proc. Natl. Acad. Sci. USA* 89:5393-5397; Yu et al., (1994) *Cell* 76:933-945; Staudt et al., (1988) *Science* 241:577-580; Bock et al., (1992) *Nature* 355:564-566; Tuerk et al., (1992) *Proc. Natl. Acad. Sci. USA* 89:6988-6992; Ellington et al., (1992) *Nature* 355:850-852; U.S. Pat. Nos. 5,096,815; 5,223,409; and 5,198,346, all to Ladner et al.; Rebar et al., (1993) *Science* 263:671-673; and PCT Pub. WO 94/18318.

Small molecule combinatorial libraries can also be generated and screened. A combinatorial library of small organic compounds is a collection of closely related analogs that differ from each other in one or more points of diversity and are synthesized by organic techniques using multi-step processes. Combinatorial libraries include a vast number of small organic compounds. One type of combinatorial library is prepared by means of parallel synthesis methods to produce a compound array. A compound array can be a collection of compounds identifiable by their spatial addresses in Cartesian coordinates and arranged such that each compound has a common molecular core and one or more variable structural diversity elements. The compounds in such a compound array are produced in parallel in separate reaction vessels, with each compound identified and tracked by its spatial address. Examples of parallel synthesis mixtures and parallel synthesis methods are provided in U.S. Ser. No. 08/177,497, filed Jan. 5, 1994 and its corresponding PCT published patent application WO95/18972, published Jul. 13, 1995 and U.S. Pat. No. 5,712,171 granted Jan. 27, 1998 and its corresponding PCT published patent application WO96/22529, which are hereby incorporated by reference.

In one non-limiting example, non-peptide libraries, such as a benzodiazepine library (see e.g., Bunin et al., (1994) *Proc. Natl. Acad. Sci. USA* 91:4708-4712), can be screened. Peptoid libraries, such as that described by Simon et al., (1992) *Proc. Natl. Acad. Sci. USA* 89:9367-9371, can also be used. Another example of a library that can be used, in which the amide functionalities in peptides have been permethylated to generate a chemically transformed combinatorial library, is described by Ostresh et al. (1994), *Proc. Natl. Acad. Sci. USA* 91:11138-11142.

Computer modeling and searching technologies permit the identification of compounds, or the improvement of already identified compounds, that can treat or prevent a metabolic disorder in a subject, treat or prevent coronary artery disease in a subject with a metabolic disorder, reduce hepatic glucose production in a subject, and/or inhibit or reduce the activity and/or activation, and/or increase the activity, of CaMKII, IP3R, including but not limited to, IP3R1, IP3R2, IP3R3, calcineurin, p38, MK2/3, HDAC4, Dach1, Dach2, or any combination thereof. Other methods for preparing or identifying peptides that bind to a target are known in the art. Molecular imprinting, for instance, can be used for the de novo construction of macromolecular structures such as peptides that bind to a molecule. See, for example, Kenneth J. Shea, *Molecular Imprinting of Synthetic Network Polymers: The De Novo synthesis of Macromolecular Binding and Catalytic Sites*, TRIP Vol. 2, No. 5, May 1994; Mosbach, (1994) *Trends in Biochem. Sci.*, 19(9); and Wulff, G., in *Polymeric Reagents and Catalysts* (Ford, W. T., Ed.) ACS Symposium Series No. 308, pp 186-230, American Chemical Society (1986). One method for preparing such structures involves the steps of: (i) polymerization of functional monomers around a known substrate (the template) that exhibits a desired activity; (ii) removal of the template molecule; and then (iii) polymerization of a second class of monomers in, the void left by the template, to provide a new molecule which exhibits one or more desired properties which are similar to that of the template. In addition to preparing peptides in this manner other binding molecules such as polysaccharides, nucleosides, drugs, nucleoproteins, lipoproteins, carbohydrates, glycoproteins, steroids, lipids, and other biologically active materials can also be prepared. This method is useful for designing a wide variety of biological mimics that are more stable than their natural counterparts, because they are prepared by the free radical polymerization of functional monomers, resulting in a compound with a nonbiodegradable backbone. Other methods for designing such molecules include for example drug design based on structure activity relationships, which require the synthesis and evaluation of a number of compounds and molecular modeling.

Screening Assays.

Test compounds or agents can be identified by two types of assays: (a) cell-based assays; or (b) cell-free assays. The assay can be a binding assay comprising direct or indirect measurement of the binding of a test compound. The assay can also be an activity assay comprising direct or indirect measurement of the activity of a compound. The assay can also be an expression assay comprising direct or indirect measurement of the expression of mRNA nucleic acid sequences or a protein encoded by a gene of interest. The various screening assays can be combined with an in vivo assay comprising measuring the effect of the test compound on the symptoms of a metabolic disorder or coronary artery disease or elevated hepatic glucose. An in vivo assay can also comprise assessing the effect of a test compound on a metabolic disorder or coronary artery disease or elevated hepatic glucose in known mammalian models.

Assays for screening test compounds that bind to or modulate the activity of a protein of interest can also be carried out. The test compound can be obtained by any suitable means, such as from conventional compound libraries. Determining the ability of the test compound to bind to a membrane-bound form of the protein can be accomplished via coupling the test compound with a radioisotope or enzymatic label such that binding of the test compound to the cell expressing a protein of interest can be measured by detecting the labeled compound in a complex. For example, the test compound can be labeled with $^{3}H$, $^{14}C$, $^{35}S$, or $^{125}I$, either directly or indirectly, and the radioisotope can be subsequently detected by direct counting of radioemmission or by scintillation counting. Alternatively, the test compound can be enzymatically labeled with, for example, horseradish peroxidase, alkaline phosphatase, or luciferase, and the enzymatic label detected by determination of conversion of an appropriate substrate to product.

A protein of interest or the target of a protein of interest can be immobilized to facilitate the separation of complexed from uncomplexed forms of one or both of the proteins. Binding of a test compound to a protein of interest, such as CaMKII, IP3R, including but not limited to, IP3R1, IP3R2, IP3R3, calcineurin, p38, MK2/3, HDAC4, Dach1, or Dach2, or a variant thereof, or interaction of a protein of interest with a target molecule in the presence and absence of a test compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix (for example, glutathione-S-transferase (GST) fusion proteins or glutathione-S-transferase fusion proteins can be adsorbed onto glutathione sepharose beads (Sigma Chemical; St. Louis, Mo.) or glutathione derivatized microtiter plates).

A protein of interest, or a variant thereof, can also be immobilized via being bound to a solid support. Non-limiting examples of suitable solid supports include glass or plastic slides, tissue culture plates, microtiter wells, tubes, silicon chips, or particles such as beads (including, but not limited to, latex, polystyrene, or glass beads). Any method known in the art can be used to attach a polypeptide (or polynucleotide) or a variant thereof, or test compound to a solid support, including use of covalent and non-covalent linkages, or passive absorption.

The screening methods of the invention can also involve monitoring the expression of a protein of interest, such as CaMKII, IP3R, including but not limited to, IP3R1, IP3R2, IP3R3, calcineurin, p38, MK2/3, HDAC4, Dach1, or Dach2, or a variant thereof. For example, regulators of the expression of a protein of interest can be identified via contacting a cell with a test compound and determining the expression of a protein of interest in the cell. The expression level of a protein of interest in the cell in the presence of the test compound is compared to the expression level of a protein of interest in the absence of the test compound. The test compound can then be identified as a regulator of the expression of a protein of interest based on this comparison. For example, when expression of a protein of interest in the cell is statistically or significantly greater in the presence of the test compound than in its absence, the test compound is identified as a stimulator/enhancer of expression of a protein of interest in the cell. Alternatively, when expression of a protein of interest in the cell is statistically or significantly less in the presence of the test compound than in its absence, the compound is identified as an inhibitor of the expression of a protein of interest in the cell. The test compound can also be said to be an antagonist. The methods to determine the expression level of a protein encoded by a gene or mRNA of interest in the cell are well known in the art.

For binding assays, the test compound can be a small molecule which binds to and occupies the binding site of a polypeptide encoded by a gene of interest, or a variant thereof. This can make the ligand binding site inaccessible to substrate such that normal biological activity is prevented. Examples of such small molecules include, but are not limited to, small peptides or peptide-like molecules. In binding assays, either the test compound or a polypeptide encoded by a gene of interest can comprise a detectable label, such as a fluorescent, radioisotopic, chemiluminescent, or enzymatic label (for example, alkaline phosphatase, horseradish peroxidase, or luciferase). Detection of a test compound which is bound to a polypeptide encoded by a gene of interest can then be determined via direct counting of radioemmission, by scintillation counting, or by determining conversion of an appropriate substrate to a detectable product.

Determining the ability of a test compound to bind to a protein of interest also can be accomplished using real-time Biamolecular Interaction Analysis (BIA) [McConnell et al., 1992, *Science* 257, 1906-1912; Sjolander, Urbaniczky, 1991, *Anal. Chem.* 63, 2338-2345]. BIA is a technology for studying biospecific interactions in real time, without labeling any of the interactants (for example, BIA-Core™). Changes in the optical phenomenon surface plasmon resonance (SPR) can be used as an indication of real-time reactions between biological molecules.

To identify other proteins which bind to or interact with a protein of interest and modulate its activity, a polypeptide encoded by a gene of interest can be used as a bait protein in a two-hybrid assay or three-hybrid assay (Szabo et al., 1995, *Curr. Opin. Struct. Biol.* 5, 699-705; U.S. Pat. No. 5,283,317), according to methods practiced in the art. The two-hybrid system is based on the modular nature of most transcription factors, which consist of separable DNA-binding and activation domains.

Functional Assays.

Compounds can be tested for the ability to increase or decrease the activity of a protein of interest, such as CaMKII, IP3R, including but not limited to, IP3R1, IP3R2, IP3R3, calcineurin, p38, MK2/3, HDAC4, Dach1, or Dach2, or a variant thereof. Activity can be measured after contacting a purified protein of interest, a cell membrane preparation, or an intact cell with a test compound. A test compound that decreases the activity of a protein of interest by at least about 10%, at least about 20%, at least about 30%, at least about 40%, at least about 50%, at least about 60%, at least about 70%, at least about 75%, at least about 80%, at least about 90%, at least about 95% or 100% is identified as a potential agent for decreasing the activity of a protein of interest, for example an antagonist. A test compound that increases the activity of a protein of interest by at least about 10%, at least about 20%, at least about 30%, at least about 40%, at least about 50%, at least about 60%, at least about 70%, at least about 75%, at least about 80%, at least about 90%, at least about 95% or 100% is identified as a potential agent for increasing the activity of a protein of interest, for example an agonist.

Compounds

The present disclosure provides methods for the treatment and/or prevention of a metabolic disorder in a subject. The disclosure also provides methods for the treatment and/or prevention of coronary artery disease in a subject with a metabolic disorder. In one embodiment, the disorder is induced by obesity. In another embodiment, the disorder is not induced by obesity. The disclosure also provides methods for reducing hepatic glucose production in a subject. The disclosure also provides methods for reducing the activity or inhibiting the activity of CaMKII, IP3R, including, but not limited to, IP3R1, IP3R2, and IP3R3, calcineurin, p38, MK2/3, HDAC4, Dach1 or Dach2. The disclosure also provides methods for reducing the phosphorylation and/or activation of CaMKII, IP3R, including, but not limited to, IP3R1, IP3R2, and IP3R3, calcineurin, p38, MK2/3, HDAC4, Dach1 or Dach2. The disclosure also provides methods for increasing the activity or activating CaMKII, IP3R, including, but not limited to, IP3R1, IP3R2, and IP3R3, calcineurin, p38, MK2/3, HDAC4, Dach1 or Dach2. The disclosure also provides methods for increasing the phosphorylation and/or activation of CaMKII, IP3R, including, but not limited to, IP3R1, IP3R2, and IP3R3, calcineurin, p38, MK2/3, HDAC4, Dach1 or Dach2.

In one aspect, the present disclosure provides a method of treating or preventing a metabolic disorder in a subject in need thereof, the method comprising administering to the subject a therapeutically effective amount of a compound, thereby treating or preventing the disorder.

In one embodiment, the compound is an inhibitor of CamKII. In another embodiment, the compound is an inhibitor of IP3R, including, but not limited to, IP3R1, IP3R2, and IP3R3. In one embodiment, the compound is an inhibitor of calcineurin. In one embodiment, the compound is an inhibitor of p38. In another embodiment, the compound is an inhibitor of MK2/3. In one embodiment, the compound is an inhibitor of HDAC4. In another embodiment, the compound is an inhibitor of Dach1. In one embodiment, the compound is an inhibitor of Dach2. In another embodiment, the compound is an inhibitor of CamKII, IP3R, including, but not limited to, IP3R1, IP3R2, and/or IP3R3, calcineurin, p38, MK2/3, HDAC4, Dach1, Dach2, or any combination thereof.

In one embodiment, the compound is an activator of CaMKII. In another embodiment, the compound is an activator of IP3R, including, but not limited to, IP3R1, IP3R2, and IP3R3. In one embodiment, the compound is an activator of calcineurin. In one embodiment, the compound is an activator of p38. In another embodiment, the compound is an activator of MK2/3. In one embodiment, the compound is an activator of HDAC4. In another embodiment, the compound is an activator of Dach1. In one embodiment, the compound is an activator of Dach2. In another embodiment, the compound is an activator of CamKII, IP3R, including, but not limited to, IP3R1, IP3R2, and/or IP3R3, calcineurin, p38, MK2/3, HDAC4, Dach1, Dach2, or any combination thereof.

Any suitable compound, either an inhibitor or activator of the CaMKII protein, IP3R, including, but not limited to, IP3R1, IP3R2, and IP3R3, calcineurin, p38, MK2/3, HDAC4, Dach1, and/or Dach2, may be used in the methods of the invention. Such compounds may be, for example, small molecule drugs, peptide agents, peptidomimetic agents, antibodies (including, but not limited to monoclonal, polyclonal, humanized, and fully human antibodies, as well as antibody fragments), inhibitory RNA molecules (such as siRNA) and the like. One of skill in the art will understand that these and other types of agents may be used to inhibit or reduce or increase the activity of CaMKII, IP3R, including, but not limited to, IP3R1, IP3R2, and IP3R3, calcineurin, p38, MK2/3, HDAC4, Dach1, Dach2, or any combination thereof, or reduce or increase the phosphorylation and/or activation of CaMKII, IP3R, including, but not limited to, IP3R1, IP3R2, and IP3R3, calcineurin, p38, MK2/3, HDAC4, Dach1, Dach2, or any combination thereof.

In one embodiment, a compound of the invention is a small molecule inhibitor of CaMKII. Such inhibitors include, but are not limited to, KN-93 (N-[2-[[[3-(4-Chlorophenyl)-2-propenyl]methylamino]methyl]phenyl]-N-(2-hydroxyethyl)-4-methoxybenzenesulphonamide); lavendustin C (5-((2,5-Dihydroxybenzyl)amino)-2-hydroxybenzoic acid); CK59 (2-(2-Hydroxyethylamino)-6-aminohexylcarbamic acid tert-butyl ester-9-isopropylpurine); KN62 (see Clyne et al., 1995); DY9760e (see Sugimura et al., 1997); K-252a *Nocardiopsis* sp. (see Kase et al., 1987); H89 dihydrochloride (N-[2-[[3-(4-Bromophenyl)-2-propenyl]amino]ethyl]-5-isoquinolinesulfonamide dihydrochloride); PP1 Analog II, 1NM-PP1 (Mutant Kinases Inhibitor II, 4-Amino-1-tert-butyl-3-(1'-naphthylmethyl)pyrazolo[3,4-d]pyrimidine, NM); eEF-2 kinase inhibitor NH125 (1-Benzyl-3-cetyl-2-methylimidazolium iodide, 1-Cetyl-3-benzyl-2-methylimidazolium iodide, CaM-Dependent Kinase III Inhibitor, NH125), and STO-609 (see Tokumitsu et al., 2002).

In another embodiment, a compound of the invention is a peptide or peptidomimetic inhibitor or activator of CaMKII. Such peptides or peptidomimetic inhibitors or activators include, but are not limited to, Ant-CaMKIINtide, [Ala$^{286}$]-Ca$^{2+}$/Calmodulin Kinase II inhibitor 281-301, [Ala$^{286}$]-Ca$^{2+}$/Calmodulin Kinase II inhibitor 281-309 and CaM Kinase II (290-309) calmodulin antagonist.

In another embodiment, a compound of the invention is a protein or polypeptide inhibitor or activator of CaMKII. Such a protein or polypeptide inhibitor may be a recombinant protein or polypeptide, such as, but not limited to, oncomodulin/MDP14.

In another embodiment, a compound of the invention is an antibody inhibitor or activator of a component of the CaMKII protein. In yet another embodiment, a compound of the invention is a nucleotide-based inhibitor or activator of CaMKII. Such inhibitors include, but are not limited to siRNAs, shRNAs, dsRNAs, microRNAs, antisense RNA molecules, and ribozymes, that inhibit the expression or activity of CaMKII, or a variant thereof. Such nucleotide-based inhibitors may comprise ribonucleotides, deoxyribonucleotides, or various artificial nucleotide derivatives.

Other compounds that may inhibit the activity of CaMKII or reduce the activation of CaMKII are further described in U.S. Pat. No. 7,205,298 (Kuo et al.,), U.S. Publication No. 2004/0086973 (Duecker K.), U.S. Publication No. 2010-0056494 (Winzeler et al.), U.S. Pat. No. 5,386,019 (Danishefsky et al.) and U.S. Pat. No. 6,828,327 (Kuo et al.), which are incorporated by reference in their entireties.

In one embodiment, a compound of the invention is a small molecule inhibitor of IP3R, including, but not limited to, IP3R1, IP3R2, and IP3R3. Such inhibitors include, but are not limited to, Xestospongin C from Calbiochem (EMD Millipore) cat#682160. Xestospongin C is an oxaquinolizidine alkaloid isolated from a marine sponge and a very potent, reversible, and membrane-permeable blocker of IP$_3$-mediated Ca$^{2+}$ release (IC$_{50}$=358 nM) that does not interact with the IP$_3$-binding site. It displays high selectivity over the skeletal isoform of the ryanodine receptor type 1 (RyR-1). It also blocks bradykinin- and carbamylcholine-induced Ca$^{2+}$ efflux from the endoplasmic reticulum stores in a reversible manner. Other small molecule inhibitors of IP3R include aminoethoxydiphenyl borate (also called 2-APB), from Tocris, Bristol, UK (see Sugawara et al., 1997, EMBO J., 16:3078-88, herein incorporated by reference in its entirety), and caffeine. In another embodiment, a compound of the invention is a small molecule activator of IP3R, including, but not limited to, IP3R1, IP3R2, and IP3R3.

In another embodiment, a compound of the invention is a peptide or peptidomimetic inhibitor or activator of IP3R, including, but not limited to, IP3R1, IP3R2, and IP3R3. In another embodiment, a compound of the invention is a protein or polypeptide inhibitor or activator of IP3R, including, but not limited to, IP3R1, IP3R2, and IP3R3. Such a protein or polypeptide inhibitor may be a recombinant protein or polypeptide.

In another embodiment, a compound of the invention is an antibody inhibitor or activator of IP3R, including, but not limited to, IP3R1, IP3R2, and IP3R3. In yet another embodiment, a compound of the invention is a nucleotide-based inhibitor or activator of IP3R, including, but not limited to, IP3R1, IP3R2, and IP3R3. Such inhibitors include, but are not limited to siRNAs, shRNAs, dsRNAs, microRNAs, antisense RNA molecules, and ribozymes, that inhibit the expression or activity of IP3R, including, but not limited to, IP3R1, IP3R2, and IP3R3, or a variant thereof. Such nucleotide-based inhibitors may comprise ribonucleotides, deoxyribonucleotides, or various artificial nucleotide derivatives.

In one embodiment, a compound of the invention is a small molecule inhibitor of calcineurin. Such inhibitors include, but are not limited to, pimecrolimus and tacrolimus. In another embodiment, a compound of the invention is a small molecule activator of calcineurin.

In another embodiment, a compound of the invention is a peptide or peptidomimetic inhibitor or activator of calcineurin. Such a peptide or peptidomimetic inhibitor includes the calcineurin (PP2B) inhibitor cyclosporin A from Calbiochem (EMD Millipore) cat#239835. This compound is a cyclic oligopeptide with immunosuppressant properties that induces apoptosis in rat thymocytes and in the murine B cell lymphoma cell line, WEH1-231. It prevents anti-IgM and ionomycin-induced apoptosis in BLB cell lines. The complex of cyclosporin A with cyclophilin inhibits protein phosphatase 2B with nanomolar affinity and inhibits nitric oxide synthesis induced by interleukin-1α, lipopolysaccharides, and TNF-α. It also induces cardiomyocytes from embryonic stem cells.

In another embodiment, a compound of the invention is a protein or polypeptide inhibitor or activator of calcineurin. Such a protein or polypeptide inhibitor may be a recombinant protein or polypeptide.

In another embodiment, a compound of the invention is an antibody inhibitor or activator of calcineurin. In yet another embodiment, a compound of the invention is a nucleotide-based inhibitor or activator of calcineurin. Such inhibitors include, but are not limited to siRNAs, shRNAs, dsRNAs, microRNAs, antisense RNA molecules, and ribozymes, that inhibit the expression or activity of calcineurin, or a variant thereof. Such nucleotide-based inhibitors may comprise ribonucleotides, deoxyribonucleotides, or various artificial nucleotide derivatives.

In one embodiment, a compound of the invention is a small molecule inhibitor of p38. Such inhibitors include, but are not limited to, SB 202190, SB203580 and SB 239063. SB203580 is a compound available from Calbiochem (EMD Millipore) cat#559389. It is a highly specific, potent, cell-permeable, selective, reversible, and ATP-competitive inhibitor of p38 MAP kinase (IC50=34 nM in vitro, 600 nM in cells). It does not significantly inhibit the JNK and p42 MAP kinase at 100 μM. It reduces epirubicin-induced cell injury and caspase-3/7 activity and inhibits IL-1 and TNF-α production from LPS-stimulated human monocytes and the human monocyte cell line THP-1 (IC50=50-100 nM). It inhibits bone morphogenetic protein-2-induced neurite out-growth in PC12 cells. In another embodiment, a compound of the invention is a small molecule activator of p38.

In another embodiment, a compound of the invention is a peptide or peptidomimetic inhibitor or activator of p38.

In another embodiment, a compound of the invention is a protein or polypeptide inhibitor or activator of p38. Such a protein or polypeptide inhibitor may be a recombinant protein or polypeptide.

In another embodiment, a compound of the invention is an antibody inhibitor or activator of p38. In yet another embodiment, a compound of the invention is a nucleotide-based inhibitor or activator of p38. Such inhibitors include, but are not limited to siRNAs, shRNAs, dsRNAs, microRNAs, antisense RNA molecules, and ribozymes, that inhibit the expression or activity of p38, or a variant thereof. Such nucleotide-based inhibitors may comprise ribonucleotides, deoxyribonucleotides, or various artificial nucleotide derivatives.

In one embodiment, a compound of the invention is a small molecule inhibitor of MK2/3. In another embodiment, a compound of the invention is a small molecule activator of MK2/3. Such small molecule inhibitors of MK2/3 include, but are not limited, aminocyoanopyridine compounds, pyrrolopyridines, and carboline-based MK2 inhibitors (see Fyhrquist et al., 2010, *J. Investig, Dermatol.*, 130: 342-344, which is incorporated by reference herein in its entirety).

In another embodiment, a compound of the invention is a peptide or peptidomimetic inhibitor or activator of MK2/3. Such peptide inhibitors include, but are not limited to, Hsp25 Kinase Inhibitor, available from Calbiochem (EMD Millipore) cat#385880. The inhibitor is a 13-residue, cell-permeable peptide that acts as a potent and selective inhibitor of mammalian heat-shock protein (Hsp25) kinase [also called mitogen-activated protein kinase-activated protein kinase-2 (MAPKAP kinase-2)]. Inhibition is competitive with respect to the substrate peptide ($K_i$=8.1 µM) and non-competitive with respect to ATP ($K_i$=134 µM).

In another embodiment, a compound of the invention is a protein or polypeptide inhibitor or activator of MK2/3. Such a protein or polypeptide inhibitor may be a recombinant protein or polypeptide.

In another embodiment, a compound of the invention is an antibody inhibitor or activator of MK2/3. In yet another embodiment, a compound of the invention is a nucleotide-based inhibitor or activator of MK2/3. Such inhibitors include, but are not limited to siRNAs, shRNAs, dsRNAs, microRNAs, antisense RNA molecules, and ribozymes, that inhibit the expression or activity of MK2/3, or a variant thereof. Such nucleotide-based inhibitors may comprise ribonucleotides, deoxyribonucleotides, or various artificial nucleotide derivatives.

In one embodiment, a compound of the invention is a small molecule inhibitor of HDAC4. In another embodiment, a compound of the invention is a small molecule activator of HDAC4.

In another embodiment, a compound of the invention is a peptide or peptidomimetic inhibitor or activator of HDAC4.

In another embodiment, a compound of the invention is a protein or polypeptide inhibitor or activator of HDAC4. Such a protein or polypeptide inhibitor or activator may be a recombinant protein or polypeptide.

In another embodiment, a compound of the invention is an antibody inhibitor or activator of HDAC4. In yet another embodiment, a compound of the invention is a nucleotide-based inhibitor or activator of HDAC4. Such inhibitors and activators include, but are not limited to siRNAs, shRNAs, dsRNAs, microRNAs, antisense RNA molecules, and ribozymes, that inhibit or increase the expression or activity of HDAC4, or a variant thereof. Such nucleotide-based inhibitors and activators may comprise ribonucleotides, deoxyribonucleotides, or various artificial nucleotide derivatives.

In one embodiment, a compound of the invention is a small molecule inhibitor of Dach1 In another embodiment, a compound of the invention is a small molecule activator of Dach1.

In another embodiment, a compound of the invention is a peptide or peptidomimetic inhibitor or activator of Dach1.

In another embodiment, a compound of the invention is a protein or polypeptide inhibitor or activator of Dach1. Such a protein or polypeptide inhibitor or activator may be a recombinant protein or polypeptide.

In another embodiment, a compound of the invention is an antibody inhibitor or activator of Dach1. In yet another embodiment, a compound of the invention is a nucleotide-based inhibitor or activator of Dach1. Such inhibitors and activators include, but are not limited to siRNAs, shRNAs, dsRNAs, microRNAs, antisense RNA molecules, and ribozymes, that inhibit or increase the expression or activity of Dach1, or a variant thereof. Such nucleotide-based inhibitors and activators may comprise ribonucleotides, deoxyribonucleotides, or various artificial nucleotide derivatives.

In one embodiment, a compound of the invention is a small molecule inhibitor of Dach2 In another embodiment, a compound of the invention is a small molecule activator of Dach2.

In another embodiment, a compound of the invention is a peptide or peptidomimetic inhibitor or activator of Dach2.

In another embodiment, a compound of the invention is a protein or polypeptide inhibitor or activator of Dach2. Such a protein or polypeptide inhibitor or activator may be a recombinant protein or polypeptide.

In another embodiment, a compound of the invention is an antibody inhibitor or activator of Dach2. In yet another embodiment, a compound of the invention is a nucleotide-based inhibitor or activator of Dach2. Such inhibitors and activators include, but are not limited to siRNAs, shRNAs, dsRNAs, microRNAs, antisense RNA molecules, and ribozymes, that inhibit or increase the expression or activity of Dach2, or a variant thereof. Such nucleotide-based inhibitors and activators may comprise ribonucleotides, deoxyribonucleotides, or various artificial nucleotide derivatives.

One of skill in the art will understand that other agents may be useful as inhibitors or activators of CaMKII, IP3R, including, but not limited to, IP3R1, IP3R2, and IP3R3, calcineurin, p38, MK2/3, HDAC4, Dach1, and/or Dach2, and may be used in conjunction with the methods of the invention.

Pharmaceutical Compositions and Administration for Therapy

Compounds of the invention can be administered to the subject once (e.g., as a single injection or deposition). Alternatively, compounds of the invention can be administered once or twice daily to a subject in need thereof for a period of from about two to about twenty-eight days, or from about seven to about ten days. Compounds of the invention can also be administered once or twice daily to a subject for a period of 1, 2, 3, 4, 5, 6, 7, 8, 9, 10, 11, 12 times per year, or a combination thereof. Furthermore, compounds of the invention can be co-administered with another therapeutic. Where a dosage regimen comprises multiple administrations, the effective amount of the compound(s) administered to the subject can comprise the total amount of the compound(s) administered over the entire dosage regimen.

Compounds can be administered to a subject by any means suitable for delivering the compounds to cells of the subject. For example, compounds can be administered by methods suitable to transfect cells. Transfection methods for eukaryotic cells are well known in the art, and include direct injection of a nucleic acid into the nucleus or pronucleus of a cell; electroporation; liposome transfer or transfer mediated by lipophilic materials; receptor mediated nucleic acid delivery, bioballistic or particle acceleration; calcium phosphate precipitation, and transfection mediated by viral vectors.

The compositions of this invention can be formulated and administered to reduce the symptoms associated with a metabolic disorder, or coronary artery disease, or elevated hepatic glucose production, by any means that produces contact of the active ingredient with the agent's site of action in the body of a subject, such as a human or animal (e.g., a dog, cat, or horse). They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

The compounds of the invention may be administered to a subject in an amount effective to treat or prevent a metabolic disorder, or coronary artery disease, or to reduce hepatic glucose production. One of skill in the art can readily determine what will be an effective amount of the compounds of the invention to be administered to a subject, taking into account whether the compound is being used prophylactically or therapeutically, and taking into account other factors such as the age, weight and sex of the subject, any other drugs that the subject may be taking, any allergies or contraindications that the subject may have, and the like. For example, an effective amount can be determined by the skilled artisan using known procedures, including analysis of titration curves established in vitro or in vivo. Also, one of skill in the art can determine the effective dose from performing pilot experiments in suitable animal model species and scaling the doses up or down depending on the subjects weight etc. Effective amounts can also be determined by performing clinical trials in individuals of the same species as the subject, for example starting at a low dose and gradually increasing the dose and monitoring the effects on a metabolic disorder, or coronary artery disease. Appropriate dosing regimens can also be determined by one of skill in the art without undue experimentation, in order to determine, for example, whether to administer the agent in one single dose or in multiple doses, and in the case of multiple doses, to determine an effective interval between doses.

A therapeutically effective dose of a compound that treats or prevents a metabolic disorder or coronary artery disease, or reduces hepatic glucose production, can depend upon a number of factors known to those of ordinary skill in the art. The dose(s) of the compounds can vary, for example, depending upon the identity, size, and condition of the subject or sample being treated, further depending upon the route by which the composition is to be administered, if applicable, and the effect which the practitioner desires the compound to have upon the target of interest. These amounts can be readily determined by a skilled artisan. These amounts include, for example, mg or microgram (µg) amounts per kilogram (kg) of subject weight, such as about 0.25 mg/kg, 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg or about 10 mg/kg, or between about 0.25 mg/kg to about 0.5 mg/kg, 0.5 mg/kg to 1 mg/kg, 1 mg/kg to 2 mg/kg, 2 mg/kg to 3 mg/kg, 3 mg/kg to 4 mg/kg, 4 mg/kg to 5 mg/kg, 5 mg/kg to 6 mg/kg, 6 mg/kg to 7 mg/kg, 7 mg/kg to 8 mg/kg, 8 mg/kg to 9 mg/kg, or 9 mg/kg to 10 mg/kg, or any range in between. These amounts also include a unit dose of a compound, for example, at least about 0.5 mg, 1 mg, 2 mg, 3 mg, 5 mg, 10 mg, 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 750 mg, 800 mg, 850 mg, 900 mg, or more. Any of the therapeutic applications described herein can be applied to any subject in need of such therapy, including, for example, a mammal such as a dog, a cat, a cow, a horse, a rabbit, a monkey, a pig, a sheep, a goat, or a human.

Pharmaceutical compositions for use in accordance with the invention can be formulated in conventional manner using one or more physiologically acceptable carriers or excipients. The therapeutic compositions of the invention can be formulated for a variety of routes of administration, including systemic and topical or localized administration. Techniques and formulations generally can be found in *Remington's Pharmaceutical Sciences*, Meade Publishing Co., Easton, Pa. (20$^{th}$ Ed., 2000), the entire disclosure of which is herein incorporated by reference. For systemic administration, an injection is useful, including intramuscular, intravenous, intraperitoneal, and subcutaneous. For injection, the therapeutic compositions of the invention can be formulated in liquid solutions, for example in physiologically compatible buffers such as Hank's solution or Ringer's solution. In addition, the therapeutic compositions can be formulated in solid form and redissolved or suspended immediately prior to use. Lyophilized forms are also included. Pharmaceutical compositions of the present invention are characterized as being at least sterile and pyrogen-free. These pharmaceutical formulations include formulations for human and veterinary use.

According to the invention, a pharmaceutically acceptable carrier can comprise any and all solvents, dispersion media, coatings, antibacterial and antifungal agents, isotonic and absorption delaying agents, and the like, compatible with pharmaceutical administration. The use of such media and agents for pharmaceutically active substances is well known in the art. Any conventional media or agent that is compatible with the active compound can be used. Supplementary active compounds can also be incorporated into the compositions.

The invention also provides for a kit that comprises a pharmaceutically acceptable carrier and a compound identified using the screening assays of the invention packaged with instructions for use.

A pharmaceutical composition containing a compound of the invention can be administered in conjunction with a pharmaceutically acceptable carrier, for any of the therapeutic effects discussed herein. Such pharmaceutical compositions can comprise, for example antibodies directed to polypeptides encoded by genes of interest or variants thereof, or agonists and antagonists of a polypeptide encoded by a gene of interest. The compositions can be administered alone or in combination with at least one other agent, such as a stabilizing compound, which can be administered in any sterile, biocompatible pharmaceutical carrier including, but not limited to, saline, buffered saline, dextrose, and water. The compositions can be administered to a patient alone, or in combination with other agents, drugs or hormones.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EM™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyethylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it can be useful to include isotonic agents, for example, sugars, polyalcohols such as mannitol, sorbitol, sodium chloride in the composition. Prolonged absorption of injectable compositions can be brought about by incorporating an agent which delays absorption, for example, aluminum monostearate and gelatin.

Sterile injectable solutions can be prepared by incorporating the compound (e.g., a small molecule, peptide or antibody) in the required amount in an appropriate solvent with one or a combination of ingredients enumerated herein, as required, followed by filtered sterilization. Generally, dispersions are prepared by incorporating the active compound into a sterile vehicle which contains a basic dispersion medium and the required other ingredients from those enumerated herein. In the case of sterile powders for the preparation of sterile injectable solutions, examples of useful preparation methods are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. In some embodiments, the compound can be applied via transdermal delivery systems, which slowly releases the active compound for percutaneous absorption. Permeation enhancers can be used to facilitate transdermal penetration of the active factors in the conditioned media. Transdermal patches are described in for example, U.S. Pat. No. 5,407,713; U.S. Pat. No. 5,352,456; U.S. Pat. No. 5,332,213; U.S. Pat. No. 5,336,168; U.S. Pat. No. 5,290,561; U.S. Pat. No. 5,254,346; U.S. Pat. No. 5,164,189; U.S. Pat. No. 5,163,899; U.S. Pat. No. 5,088,977; U.S. Pat. No. 5,087,240; U.S. Pat. No. 5,008,110; and U.S. Pat. No. 4,921,475.

Administration of the compound is not restricted to a single route, but may encompass administration by multiple routes. For instance, exemplary administrations by multiple routes include, among others, a combination of intradermal and intramuscular administration, or intradermal and subcutaneous administration. Multiple administrations may be sequential or concurrent. Other modes of application by multiple routes will be apparent to the skilled artisan.

The compounds of the invention may be formulated into compositions for administration to subjects for the treatment and/or prevention of a metabolic disorder or coronary artery disease, or the reduction of hepatic glucose production. Such compositions may comprise the compounds of the invention in admixture with one or more pharmaceutically acceptable diluents and/or carriers and optionally one or more other pharmaceutically acceptable additives. The pharmaceutically-acceptable diluents and/or carriers and any other additives must be "acceptable" in the sense of being compatible with the other ingredients of the composition and not deleterious to the subject to whom the composition will be administered. One of skill in the art can readily formulate the compounds of the invention into compositions suitable for administration to subjects, such as human subjects, for example using the teaching a standard text such as Remington's Pharmaceutical Sciences, 18th ed, (Mack Publishing Company: Easton, Pa., 1990), pp. 1635-36), and by taking into account the selected route of delivery.

Examples of diluents and/or carriers and/or other additives that may be used include, but are not limited to, water, glycols, oils, alcohols, aqueous solvents, organic solvents, DMSO, saline solutions, physiological buffer solutions, peptide carriers, starches, sugars, preservatives, antioxidants, coloring agents, pH buffering agents, granulating agents, lubricants, binders, disintegrating agents, emulsifiers, binders, excipients, extenders, glidants, solubilizers, stabilizers, surface active agents, suspending agents, tonicity agents, viscosity-altering agents, carboxymethyl cellulose, crystalline cellulose, glycerin, gum arabic, lactose, magnesium stearate, methyl cellulose, powders, saline, sodium alginate. The combination of diluents and/or carriers and/or other additives used can be varied taking into account the nature of the active agents used (for example the solubility and stability of the active agents), the route of delivery (e.g. oral, parenteral, etc.), whether the agents are to be delivered over an extended period (such as from a controlled-release capsule), whether the agents are to be co-administered with other agents, and various other factors. One of skill in the art will readily be able to formulate the compounds for the desired use without undue experimentation.

The compounds of the invention may be administered to a subject by any suitable method that allows the agent to exert its effect on the subject in vivo. For example, the compositions may be administered to the subject by known procedures including, but not limited to, by oral administration, sublingual or buccal administration, parenteral administration, transdermal administration, via inhalation, via nasal delivery, vaginally, rectally, and intramuscularly. The compounds of the invention may be administered parenterally, or by epifascial, intracapsular, intracutaneous, subcutaneous, intradermal, intrathecal, intramuscular, intraperitoneal, intrasternal, intravascular, intravenous, parenchymatous, or sublingual delivery. Delivery may be by injection, infusion, catheter delivery, or some other means, such as by tablet or spray. In one embodiment, the compounds of the invention are administered to the subject by way of delivery directly to the heart tissue, such as by way of a catheter inserted into, or in the proximity of the subject's heart, or by using delivery vehicles capable of targeting the drug to the heart. For example, the compounds of the invention may be conjugated to or administered in conjunction with an agent that is targeted to the heart, such as an antibody or antibody fragment. In one embodiment, the compounds of the invention are administered to the subject by way of delivery directly to the muscle tissue of interest, such as by way of a catheter inserted into, or in the proximity of the subject's muscle of interest, or by using delivery vehicles capable of targeting the drug to the muscle, such as an antibody or antibody fragment.

For oral administration, a formulation of the compounds of the invention may be presented as capsules, tablets, powders, granules, or as a suspension or solution. The formulation may contain conventional additives, such as lactose, mannitol, cornstarch or potato starch, binders, crystalline cellulose, cellulose derivatives, acacia, cornstarch, gelatins, disintegrators, potato starch, sodium carboxymethylcellulose, dibasic calcium phosphate, anhydrous or sodium starch glycolate, lubricants, and/or or magnesium stearate.

For parenteral administration (i.e., administration by through a route other than the alimentary canal), the compounds of the invention may be combined with a sterile aqueous solution that is isotonic with the blood of the subject. Such a formulation may be prepared by dissolving the active ingredient in water containing physiologically-compatible substances, such as sodium chloride, glycine and the like, and having a buffered pH compatible with physiological conditions, so as to produce an aqueous solution, then rendering the solution sterile. The formulation may be presented in unit or multi-dose containers, such as sealed ampoules or vials. The formulation may be delivered by injection, infusion, or other means known in the art.

For transdermal administration, the compounds of the invention may be combined with skin penetration enhancers, such as propylene glycol, polyethylene glycol, isopropanol, ethanol, oleic acid, N-methylpyrrolidone and the like, which increase the permeability of the skin to the compounds of the invention and permit the compounds to penetrate through the skin and into the bloodstream. The compounds of the invention also may be further combined with a polymeric substance, such as ethylcellulose, hydroxypropyl cellulose, ethylene/vinylacetate, polyvinyl pyrrolidone, and the like, to provide the composition in gel form, which are dissolved in a solvent, such as methylene chloride, evaporated to the desired viscosity and then applied to backing material to provide a patch.

In some embodiments, the compounds of the invention are provided in unit dose form such as a tablet, capsule or single-dose injection or infusion vial.

Combination Therapy

According to the methods of the invention, a compound of the invention can be administered to a subject either as a single agent, or in combination with one or more other agents. In one embodiment, a compound of the invention is administered to a subject as a single agent. In one embodiment, a compound of the invention is administered to a subject alone. In one embodiment, a compound of the invention is administered to a subject in combination with one or more other agents.

In certain embodiments, a compound of the invention may be used in combination with other agents that are used for the treatment or prevention of a metabolic disorder or coronary artery disease, or the reduction of hepatic glucose in a subject. In certain embodiments, a compound of the invention may be used in combination with other agents that are not used for the treatment or prevention of a metabolic disorder or coronary artery disease, or the reduction of hepatic glucose in a subject. In one embodiment, a compound of the invention may be delivered to a subject as part of the same pharmaceutical composition or formulation containing one or more additional active agents. In another embodiment, a compound of the invention may be delivered to a subject in a composition or formulation containing only that active agent, while one or more other agents are administered to the subject in one or more separate compositions or formulations. In one embodiment, the other agents are not used for the treatment or prevention of a metabolic disorder or coronary artery disease, or the reduction of hepatic glucose in a subject. In another embodiment, the other agents are used for the treatment or prevention of a metabolic disorder or coronary artery disease, or the reduction of hepatic glucose in a subject.

A compound of the invention and the other agents that are used for the treatment or prevention of a metabolic disorder or coronary artery disease, or the reduction of hepatic glucose in a subject, may be administered to the subject at the same time, or at different times. A compound of the invention and the other agents that are not used for the treatment or prevention of a metabolic disorder or coronary artery disease, or the reduction of hepatic glucose, may be administered to the subject at the same time, or at different times. For example, a compound of the invention and the other agents may be administered within minutes, hours, days, weeks, or months of each other, for example as part of the overall treatment regimen of a subject. In some embodiments, a compound of the invention may be administered prior to the administration of other agents. In other embodiments, a compound of the invention may be administered subsequent to the administration of other agents.

Compounds of the invention, as described above, including, but not limited to, inhibitors or activators of CaMKII, IP3R, including, but not limited to, IP3R1, IP3R2, IP3R3, calcineurin, p38, MK2/3, HDAC4, Dach1, and/or Dach2, may be used in combination with each other for the treatment or prevention of a metabolic disorder or coronary artery disease, or the reduction of hepatic glucose in a subject.

In some embodiments, the administration of a compound of the invention in combination with one or more other agents has an additive effect, in comparison with administration of the compound of the invention alone, or administration of the one or more other agents alone. In other embodiments, the administration of a compound of the invention in combination with one or more other agents has a synergistic effect, in comparison with administration of the compound of the invention alone, or administration of the one or more other agents alone. In some embodiments, the administration of a compound of the invention in combination with one or more other agents can help reduce side effects, in comparison with administration of the compound of the invention alone, or administration of the one or more other agents alone.

In some embodiments, the compound of the invention is used as an adjuvant therapy. In other embodiments, the compound of the invention is used in combination with an adjuvant therapy.

Subjects

According to the methods of the invention, the subject or patient can be any animal that has or is diagnosed with a metabolic disorder or coronary artery disease, or that has elevated hepatic glucose. According to the methods of the invention, the subject or patient can be any animal that is predisposed to or is at risk of developing a metabolic disorder or coronary artery disease, or elevated hepatic glucose. In preferred embodiments, the subject is a human subject. In some embodiments, the subject is a rodent, such as a mouse. In some embodiments, the subject is a cow, pig, sheep, goat, cat, horse, dog, and/or any other species of animal used as livestock or kept as pets.

In some embodiments, the subject is already suspected to have a metabolic disorder, coronary artery disease or elevated hepatic glucose. In other embodiments, the subject is being treated for a metabolic disorder, coronary artery disease or elevated hepatic glucose, before being treated according to the methods of the invention. In other embodiments, the subject is not being treated for a metabolic disorder, coronary artery disease or elevated hepatic glucose, before being treated according to the methods of the invention.

EXAMPLES

The following examples illustrate the present invention, and are set forth to aid in the understanding of the invention, and should not be construed to limit in any way the scope of the invention as defined in the claims which follow thereafter.

Example 1: Regulation of Hepatocyte Glucose Production by a Calcium Sensing Enzyme, CaMKII Hepatic glucose production is crucial for glucose homeostasis. Several transcription factors and co-activators have been shown to regulate this process, however, the underlying mechanisms have not been fully elucidated. As described herein, a calcium sensing enzyme, CaMKII, is activated in a calcium- and IP3R-dependent manner by cAMP and glucagon in primary hepatocytes and by glucagon and fasting in vivo. Genetic deficiency or inhibition of CaMKII blocks nuclear translocation of FoxO1, impairs fasting- and glucagon/cAMP-induced glycogenolysis and gluconeogenesis, and lowers blood glucose levels. Conversely, adenoviral expression of constitutively active CaMKII induces genes involved in gluconeogenesis and glycogenolysis, stimulates glucose production both in vitro and in vivo, and raises blood glucose levels. The suppressive effect of CaMKII deficiency on glucose metabolism is abrogated by transduction with constitutively nuclear FoxO1, indicating that the effect of CaMKII deficiency requires nuclear exclusion of FoxO1. These results reveal a new, calcium-sensing molecular pathway in the control of hepatic glucose homeostasis by glucagon and fasting.

Example 2: Regulation of Hepatocyte Glucose Production by a Calcium Sensing Enzyme, CaMKII Hepatic glucose production is crucial for glucose homeostasis. Several transcription factors and co-activators have been shown to regulate this process, however, the underlying mechanisms have not been fully elucidated. As described herein, a calcium sensing enzyme, CaMKII, is activated in a calcium- and IP3R-dependent manner by cAMP and glucagon in primary hepatocytes and by glucagon and fasting in vivo. Genetic deficiency or inhibition of CaMKII blocks nuclear translocation of FoxO1, impairs fasting- and glucagon/cAMP-induced glycogenolysis and gluconeogenesis, and lowers blood glucose levels. Conversely, adenoviral expression of constitutively active CaMKII induces genes involved in gluconeogenesis and glycogenolysis, stimulates glucose production both in vitro and in vivo, and raises blood glucose levels. Importantly, the suppressive effect of CaMKII deficiency on glucose metabolism is abrogated by transduction with constitutively nuclear FoxO1, indicating that the effect of CaMKII deficiency requires nuclear exclusion of FoxO1. The results described herein show a calcium-sensing molecular pathway in the control of hepatic glucose homeostasis by glucagon and fasting.

Example 3: Regulation of Hepatocyte Glucose Production by a Calcium Sensing Enzyme, CaMKII Liver is the main organ responsible for maintaining euglycemia under conditions of nutrient deprivation. During the early stages of fasting, liver uses glycogen stores to mobilize glucose (Radziuk and Pye, 2001). As fasting progresses, de novo synthesis of glucose from non-carbohydrate precursors, gluconeogenesis, becomes the main contributor to hepatic glucose production (Klover and Mooney, 2004). Glucose production is also regulated by substrate flux through glycolysis, glycogen synthesis, and glycogenolysis.

These changes occur rapidly in response to direct hormonal signaling. In addition, both insulin and glucagon affect transcription of glycogenolytic and gluconeogenic enzymes, glucose-6-phosphatase (G6pc) and phosphoenolpyruvate carboxykinase (Pck1), respectively (Pilkis and Granner, 1992). During fasting, glucagon and its downstream effector, cAMP, induce changes in the subcellular localization of "glucogenic" transcription factors, such as FoxO (1, 3, and 4) and Crct2, which activate expression of these genes (Lin and Accili, 2011). In addition, different co-activators, such as peroxisome proliferator-activated receptor-γ coactivator-1α (PGC-1α) and CBP, are thought to interact with different components of the cAMP response, including CREB, hepatic nuclear factor 4α (HNF4α), Sirt1, and Clock genes, leading to an increase in transcription of gluconeogenic genes (Hall et al., 1995; Matsumoto et al., 2007; Puigserver et al., 2003; Rhee et al., 2003).

Calcium (Ca+2) has been linked to the regulation of gluconeogenesis, however the underlying mechanisms have not been fully elucidated (Friedmann and Rasmussen, 1970; Kraus-Friedmann and Feng, 1996; Marques-da-Silva et al., 1997). Evidence indicates that glucagon and cAMP alter Ca+2 fluxes in the liver. Stimulation by glucagon leads to calcium influx which is then followed by the release of Ca+2 from intracellular stores, and as a result of these changes, cytosolic Ca+2 concentration increases (Bygrave and Benedetti, 1993; Staddon and Hansford, 1989). Noteworthy, intracellular Ca+2 chelation has been shown to reduce glucagon induced glucose production (Mine et al., 1993). However the mechanism of how Ca+2 regulates this phenomenon is not known. Based on these previous studies showing the importance of intracellular Ca+2, the results described herein show that CaMKII, the activity of which is increased by Ca+2, can play a role in glucagon-induced hepatic glucose production.

Calcium calmodulin-dependent kinase II (CaMKII) is a serine-threonine kinase that is an important mediator of cellular Ca+2 signaling in cells. There are four genes for different CaMKII isoforms: α, β, γ and δ. The α and β isoforms are mostly neuronal, while CaMKIIγ and δ are expressed in a wide variety of tissues. After binding Ca+2/calmodulin complex, autophosphorylation on Thr287 results in Ca+2/calmodulin independent activity (Couchonnal and Anderson, 2008). Most studies on CaMKII have been carried out in neurons and cardiomyocytes and there is only a limited understanding of CaMKII in other tissues, and the specific role of CaMKII in metabolism remains unknown. The results described herein show that CaMKII activity is increased by cAMP and glucagon and also in response to fasting in vivo. The results described herein demonstrate that CaMKII plays a role in the regulation of glycogenolysis and gluconeogenesis. In particular, these results show that CaMKII has a profound effect on FoxO1 nuclear localization in a manner that regulates the expression of two key enzymes, G6pc and Pck1 in vitro and in vivo.

Results

Fed-to-Fasting Metabolic Switch Leads to Activation of Hepatic CaMKII

Figures 1A, 1B, 1C:
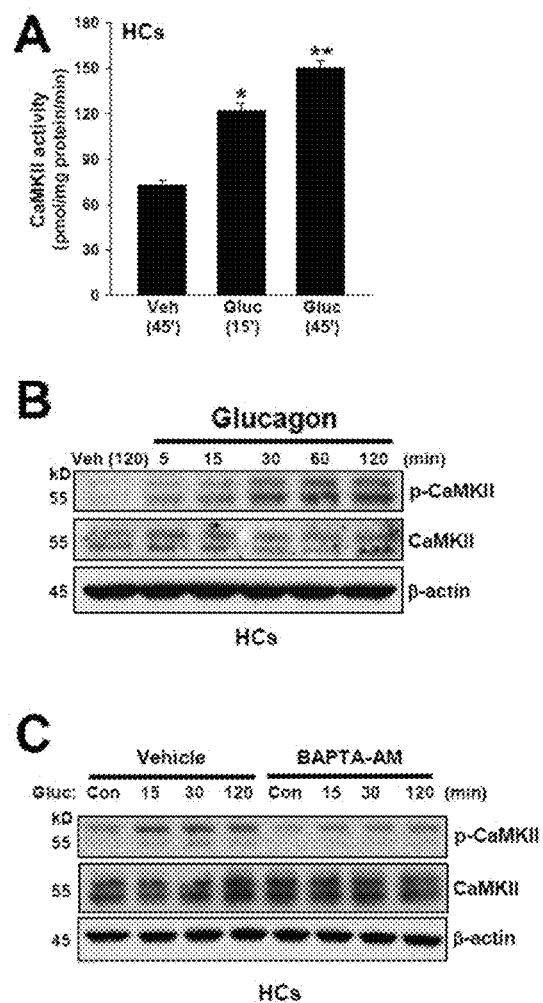
FIGS. 1A-J. Glucagon and fasting activates hepatic CaMKII.

Fasting leads to an increase in circulating levels of glucagon, which has been shown to increase intracellular calcium (Staddon and Hansford, 1989). The results described herein show that CaMKII, the activity of which is increased by a rise in intracellular Ca+2, might be activated by fasting. To test this idea, a CaMKII activity assay from primary mouse hepatocytes challenged with glucagon for various times showed that CaMKII activity increased steadily as a function of time (FIG. 1A). The activation state of CaMKII by immunoblotting with anti-pThr287-CaMKII antibody. Consistent with the kinase assay results, phosphorylation at Thr287 was induced by glucagon treatment (FIG. 1B).

Figure 1D:
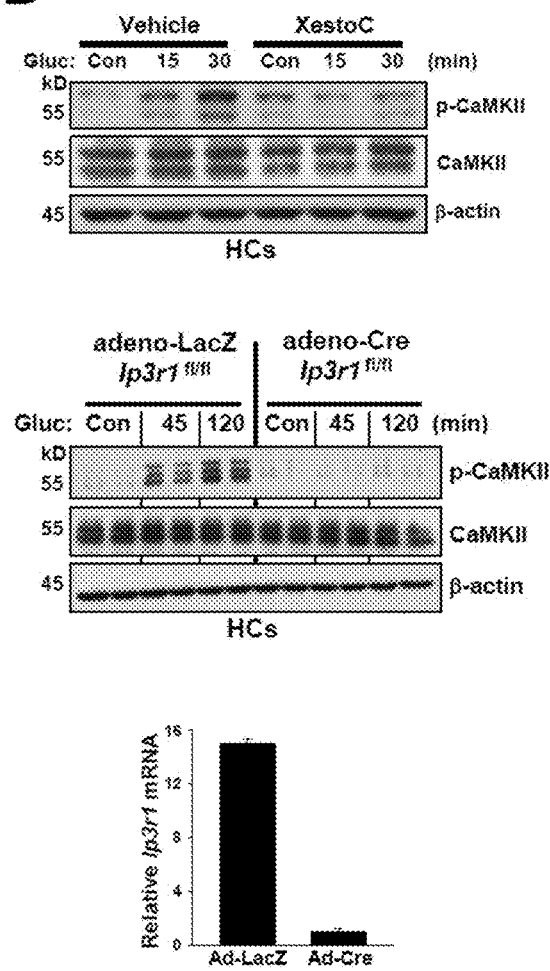

To determine the role of cytosolic Ca+2 on CaMKII activation, the effect of cytosolic Ca+2 chelator, 1,2-bis[2-aminophenoxy]ethane-N,N,N',N'-tetraacetic acid tetrakis [acetoxymethyl ester] (BAPTA-AM), which markedly decreased glucagon-induced CaMKII phosphorylation, was tested. (FIG. 1C). Inositol 1,4,5-trisphosphate receptor (IP3R) channels, located in the endoplasmic reticulum (ER), release Ca2+ in response to binding of the second messenger, IP3, and play a major role in intracellular Ca+2 homeostasis. Glucagon-induced PKA phosphorylates and activates IP3R activity and that this event is important in hepatic glucose production. To investigate the contribution of IP3Rs in glucagon-induced CaMKII activation, pretreatment with the IP3R inhibitor, xestospongin C. Xestospongin C led to a significant decrease in glucagon-induced CaMKII phosphorylation, demonstrating the critical role of IP3Rs in this process (FIG. 1D).

Figures 1E, 1F, 1G:
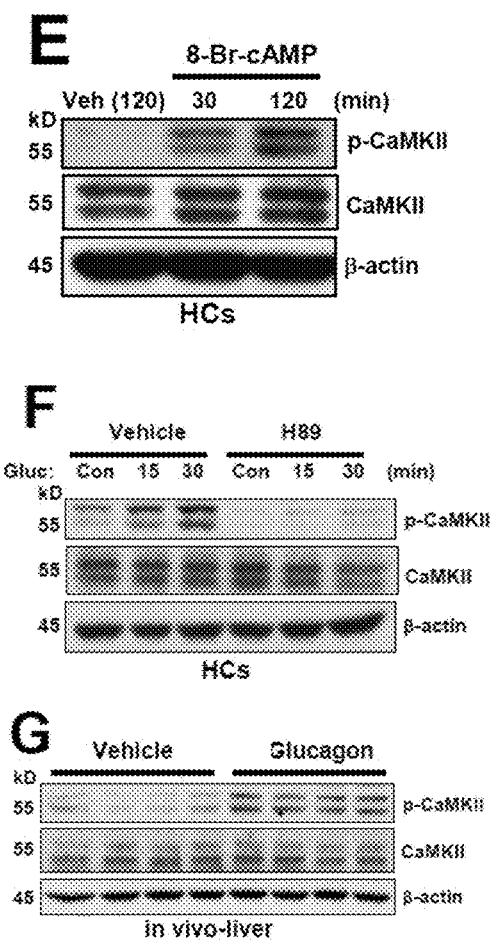

The increase in cAMP levels in response to glucagon increases the activity of PKA, a key enzyme involved in gluconeogenesis. In this context, treatment of hepatocytes with a membrane permeant analog of cAMP, 8-bromo-cAM, mimicked the effect of glucagon and led to a marked increase in phospho-CaMKII (FIG. 1E). To investigate whether CaMKII phosphorylation is causally related to PKA activation, hepatocytes were treated with a PKA inhibitor, H89, prior to the addition of glucagon Inhibition of PKA markedly inhibited the glucagon-mediated increase in phospho-CaMKII (FIG. 1F). These data support the existence of a pathway in which glucagon promotes phosphorylation/activation of CaMKII through its effects on IP3R-mediated intracellular Ca+2 release in a cAMP-PKA-dependent manner.

Figures 1H, 1I, 1J:
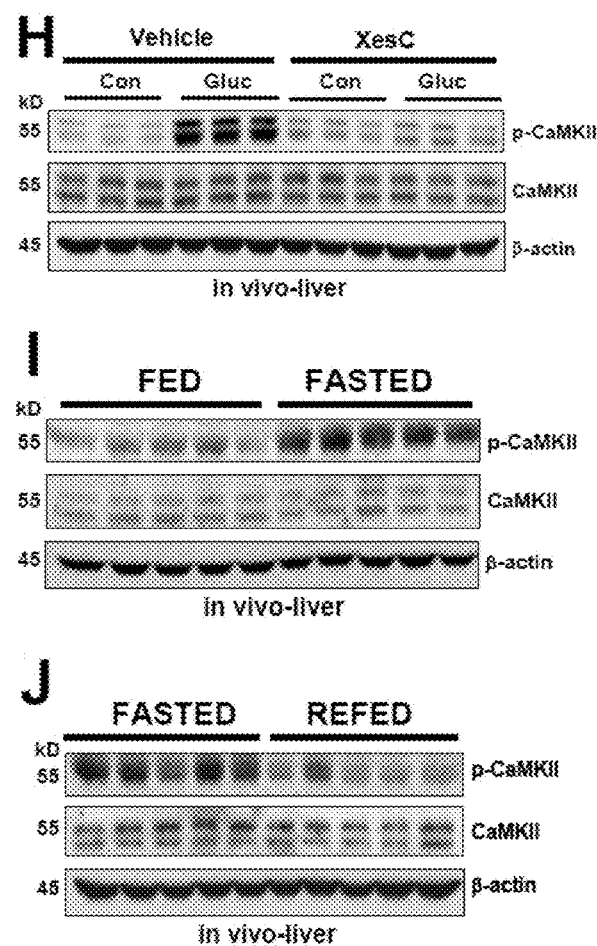
Figures 2A, 2B:
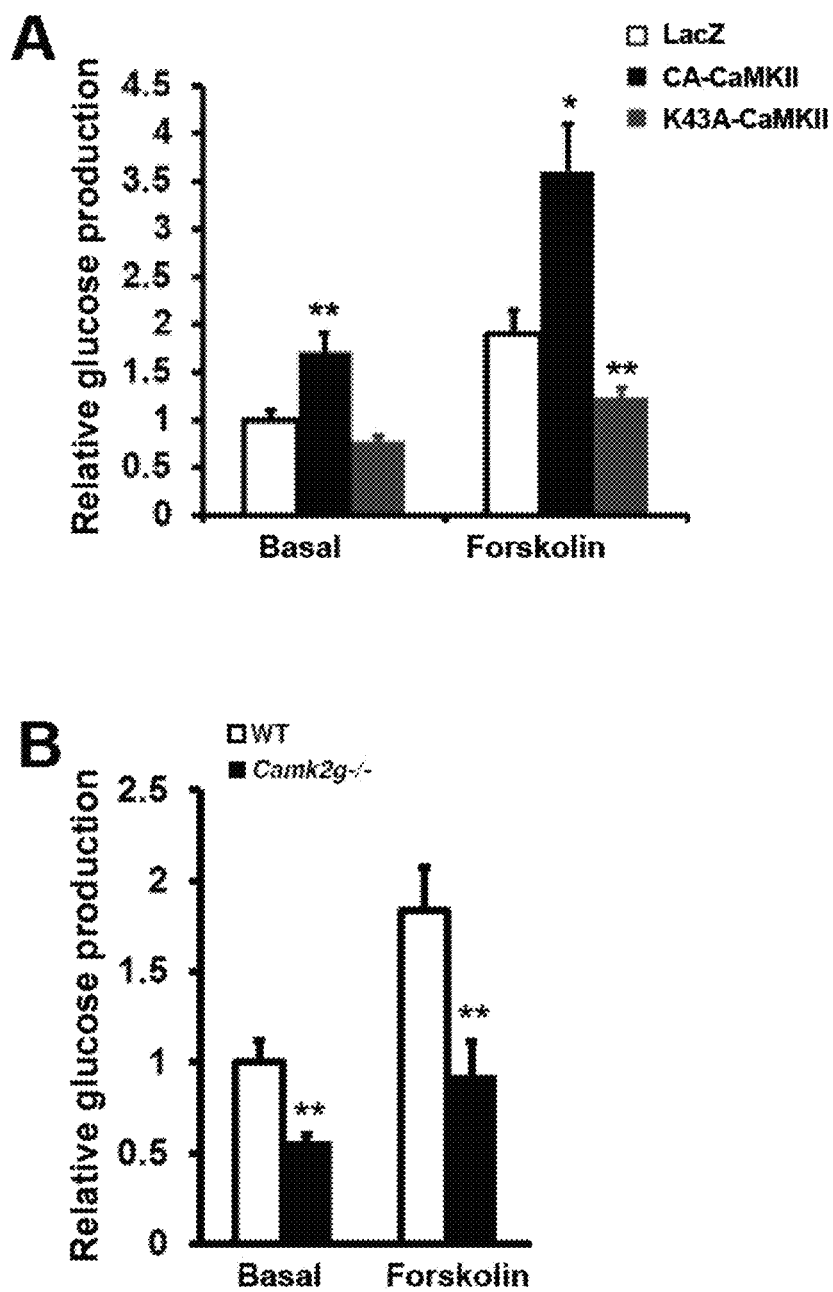
FIGS. 2A-E. CaMKII regulates glucose production and hepatic G6Pc and Pck1 expression in primary hepatocytes.

To examine whether CaMKII is regulated by glucagon in vivo, mice were challenged with a bolus of intraperitoneal (i.p.) glucagon. Consistent with the effects observed in cultured hepatocytes, hepatic CaMKII phosphorylation was induced by glucagon treatment (FIG. 1G). A glucagon dose as low as 1 μg kg−1 was capable of phosphorylating CaMKII in the liver. To gain in vivo evidence that IP3Rs are important in the regulation of glucagon-mediated CaMKII phosphorylation, mice were treated with i.p. xestospongin C for 4 days. The mice were then challenged with glucagon, and liver extracts were assayed for p-CaMKII. As shown in FIG. 1H, xestospongin C treatment reduced glucagon-induced CaMKII phosphorylation. Next, hepatic CaMKII phosphorylation during the transition from a fed to fasting state was compared. The hepatic CaMKII phosphorylation was significantly increased upon fasting, whereas the total amount of CaMKII appeared to be unaffected by nutrient status (FIG. 1I). Moreover, upon re-feeding, the level of p-CaMKII in liver diminished (FIG. 1J). These data show that activity of hepatic CaMKII is regulated by nutrient status in a manner that is consistent with its role in fasting-induced hepatic glucose production CaMKII Promotes Hepatic Glucose Production, the Expression of G6pc and Pck1, and FoxO1 Nuclear Localization in Primary Hepatocytes The regulation of hepatic CaMKII activity in response to fasting/re-feeding in vivo lead to directly testing its role in glucose production by hepatocytes. Glucose production was examined from pyruvate and lactate in primary hepatocytes transduced with adenoviruses expressing constitutively active CaMKII (adeno-CA-CaMKII), a kinase-inactive, dominant negative form of CaMKII (adeno-K43A-CaM-KII), or control adeno-LacZ. The CA-CaMKII construct possesses an amino acid substitution at T287D, which mimics autophosphorylation at that site and results in autonomous activity in the absence of bound Ca+2/calmodulin (Pfleiderer et al., 2004). The cells were examined under basal conditions and after stimulation with forskolin, a glucagon mimetic and a potent adenylate cyclase activator. An increase in both basal and forskolin-induced glucose release was observed in cells transduced with adeno-CA-CaMKII (FIG. 2A). Conversely, infection of cells with adeno-K43A-CaMKII decreased both basal and forskolin-induced glucose production (FIG. 2A). To further substantiate these results, glucose production in hepatocytes was assayed from WT mice and from mice lacking CaMKIIγ, the major isoform of the enzyme expressed in hepatocytes. Glucose production was suppressed in CaMKIIγ-deficient hepatocytes (FIG. 2B). Thus, CaMKII plays an important role in the hormonal regulation of glucose production in hepatocytes.

Figure 2C:
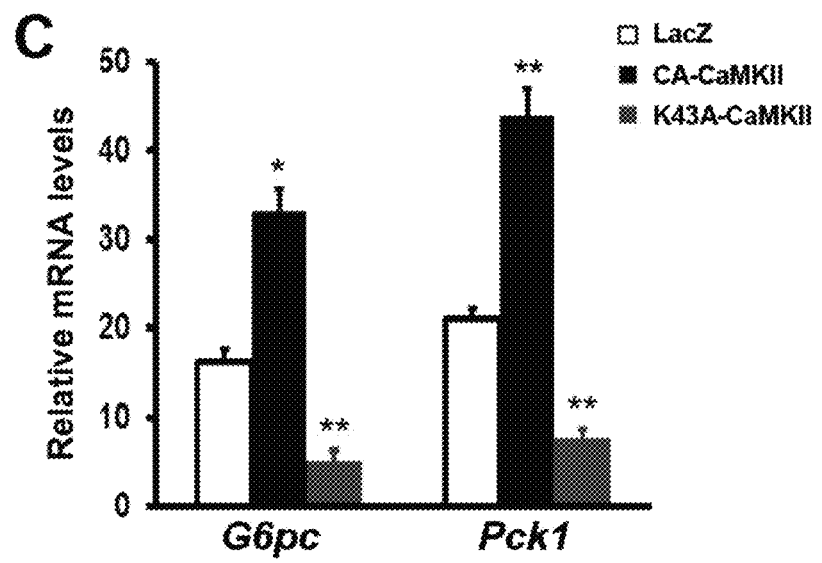
Figure 2D:
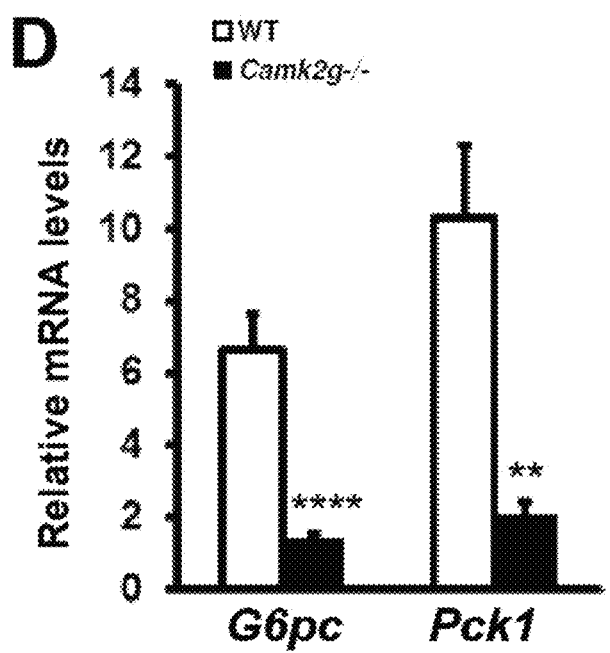
Figure 2E:
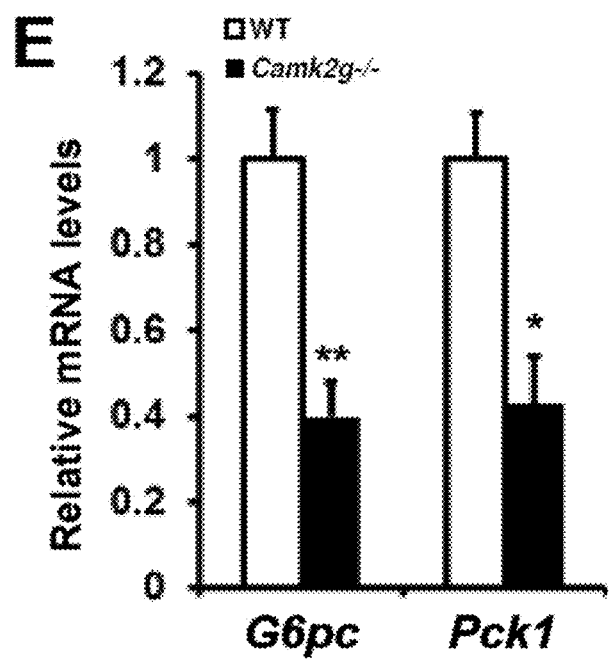

The role of CaMKII on hepatic glucose production prompted an investigation of transcriptional effects on genes encoding the rate-limiting enzymes in glycogenolysis and gluconeogenesis. To this end, primary hepatocytes were transduced with adeno-LacZ, CA-CaMKII, or K43A-CaMKII and measured forskolin-induced G6pc and Pck1 gene expression. Both G6pc and Pck1 mRNA levels were significantly higher in hepatocytes transduced with adeno-CA-CaMKII compared with adeno-LacZ, while transduction with adeno-K43A-CaMKII decreased the mRNA levels for these two genes (FIG. 2C). The effect of CaMKII on gluconeogenesis is further supported by the observation that forskolin-induced G6pc and Pck1 mRNA levels were significantly lower in Camk2g−/− versus WT hepatocytes (FIG. 2D). Similar results were obtained with glucagon treatment (FIG. 2E). Thus, CaMKII is necessary for the expression of G6Pc and Pck1.

Figure 3A:
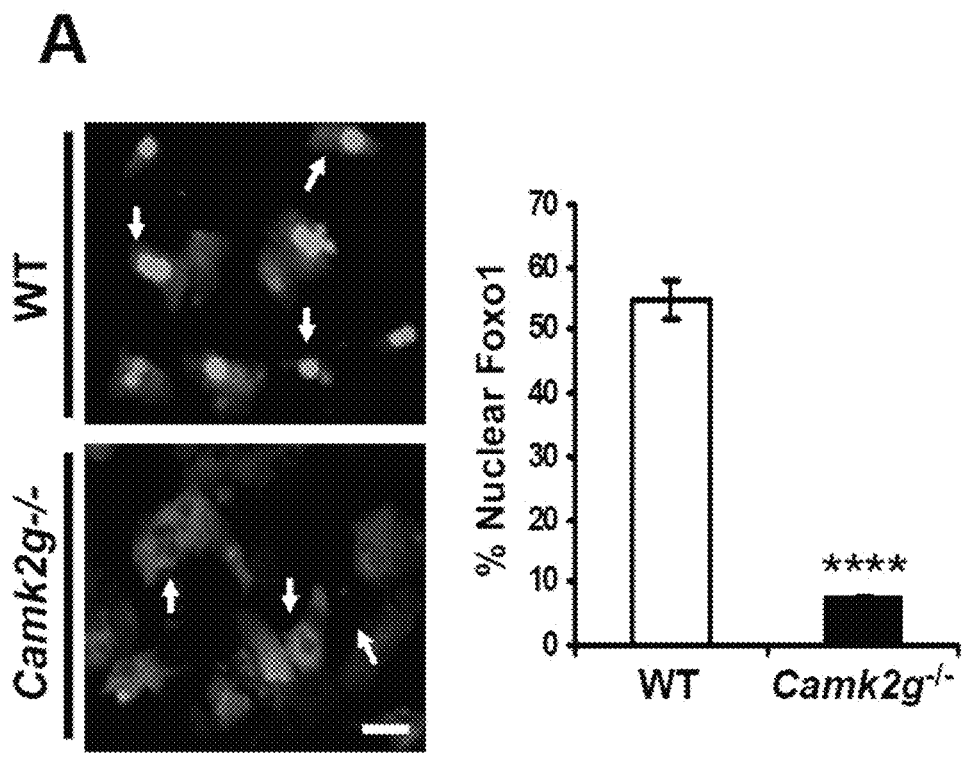
FIGS. 3A-C. CaMKII regulates hepatic FoxO1 subcellular localization in primary hepatocytes.
Figure 3B:
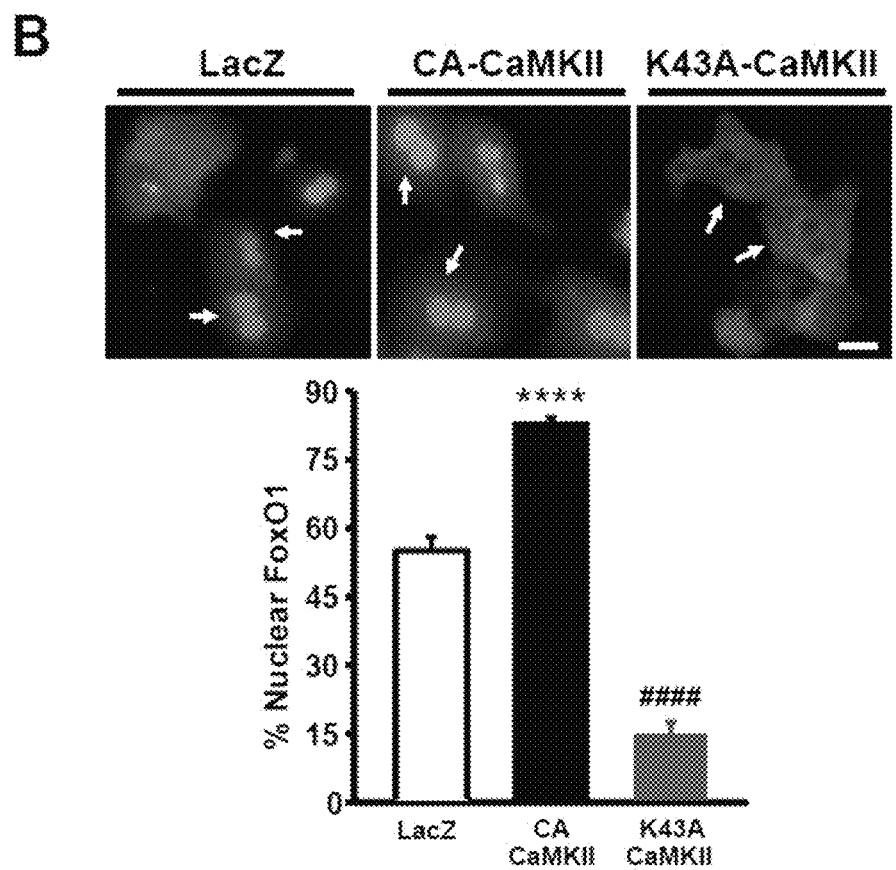
Figure 3C:
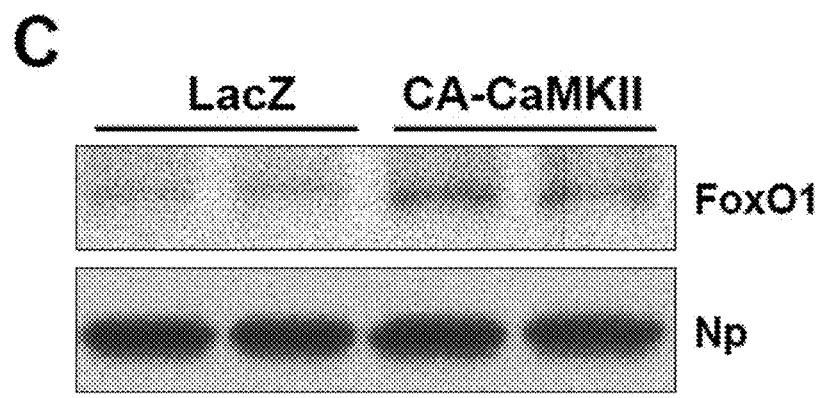

A major transcription factor involved in the induction of G6pc and Pck1 is FoxO1, whose activity is primarily regulated by changes in its cytoplasmic vs. nuclear localization (Greer and Brunet, 2005). The distribution of GFP-tagged FoxO1 was assayed in hepatocytes from WT vs. Camk2g−/− mice. Under serum-starved conditions in WT hepatocytes, the majority of GFP-FoxO1 was in the nucleus (FIG. 3A). In contrast, Camk2g−/− hepatocytes displayed primarily cytosolic localization of GFP-FoxO1. Moreover, when hepatocytes were transduced with constitutively active CaMKII, FoxO1 became predominantly nuclear (FIG. 3B-C). Consistent with the Camk2g−/− data, FoxO1 was located mostly in cytoplasm WT hepatocytes transduced with dominant-negative adeno-K43A-CaMKII (FIG. 3B). These data indicate that CaMKII facilitates FoxO1 subcellular localization in serum-starved hepatocytes.

Figures 4A, 4B:
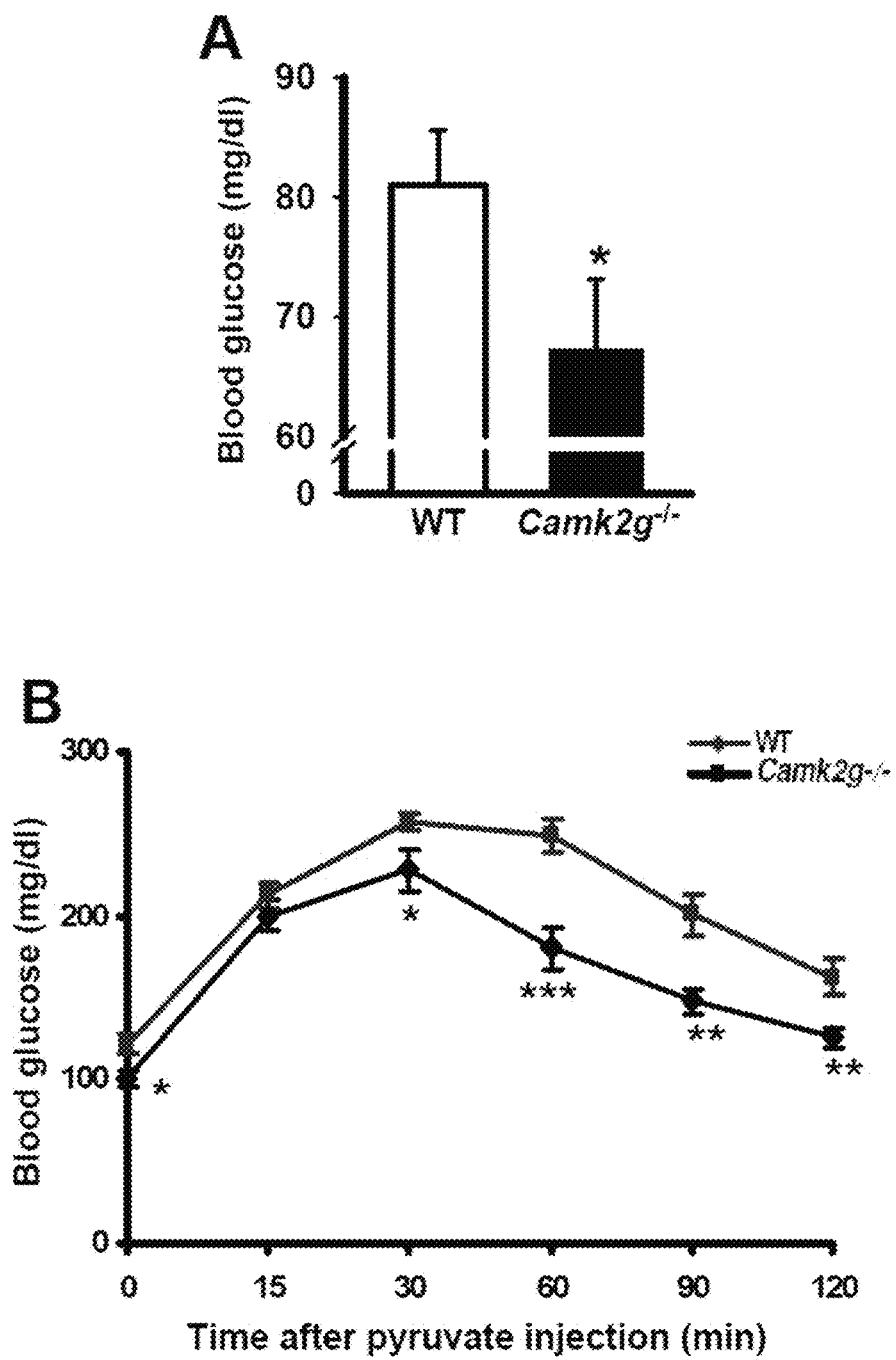
FIGS. 4A-D. CaMKIIγ deficiency decreases blood glucose, G6pc and Pck1 expression, and nuclear FoxO1.
Figure 4C:
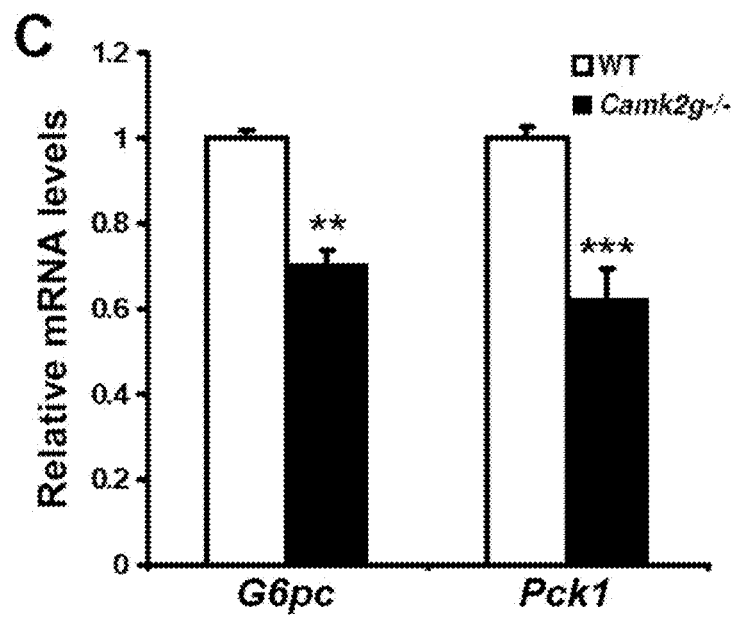
Figure 4D:
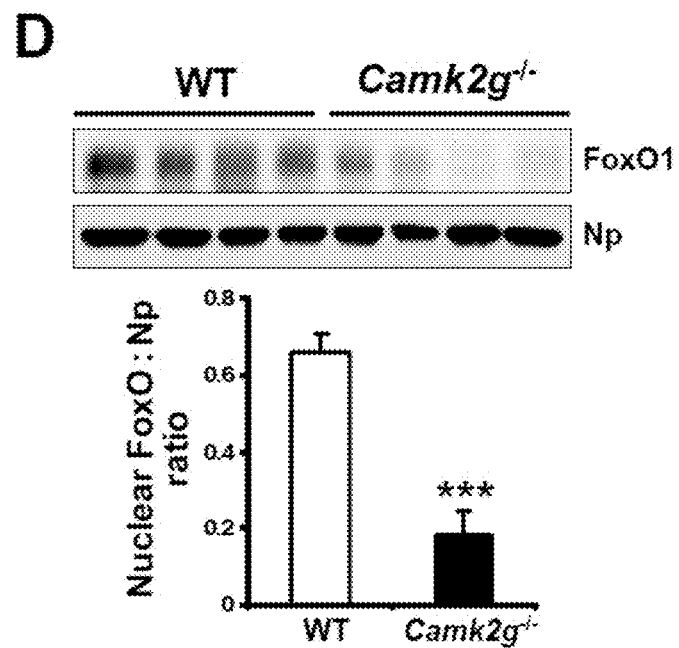

CaMKIIγ Deficiency Impairs and Constitutively Active Hepatic CaMKII Stimulates Hepatic Glucose Production In Vivo To assess the functional role of CaMKII in hepatic glucose metabolism in vivo, fasting blood glucose levels in WT and Camk2g−/− mice were examined. Consistent with in vitro data, a modest but statistically significant decrease in blood glucose levels in fasted Camk2g−/− vs. WT mice was observed (FIG. 4A). The difference in fasting glucose concentration was not associated with an increase in circulating insulin concentration in knockout vs. WT mice. The mutant mice also showed lower plasma glucose in response to a pyruvate challenge test (FIG. 4B). Consistent with the primary hepatocyte data, there was a decrease in G6pc and Pck1 mRNA levels and nuclear FoxO1 in the livers of Camk2g−/− mice (FIGS. 4C-D).

Figure 5A:
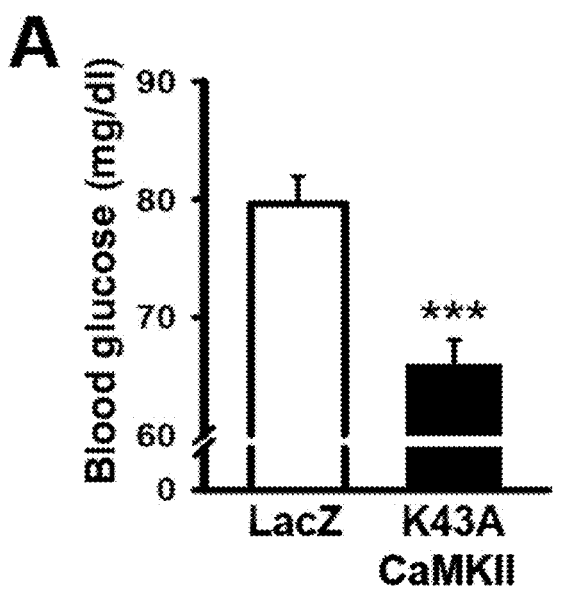
FIGS. 5A-F. Acute inhibition of CaMKII decreases blood glucose, G6pc and Pck1 expression, and nuclear FoxO1. 9 wk-old WT mice were injected through the tail vein with 1.5×109 pfu of adenovirus containing either control LacZ (n=5) or K43A-CaMKII (n=5).
Figure 5B:
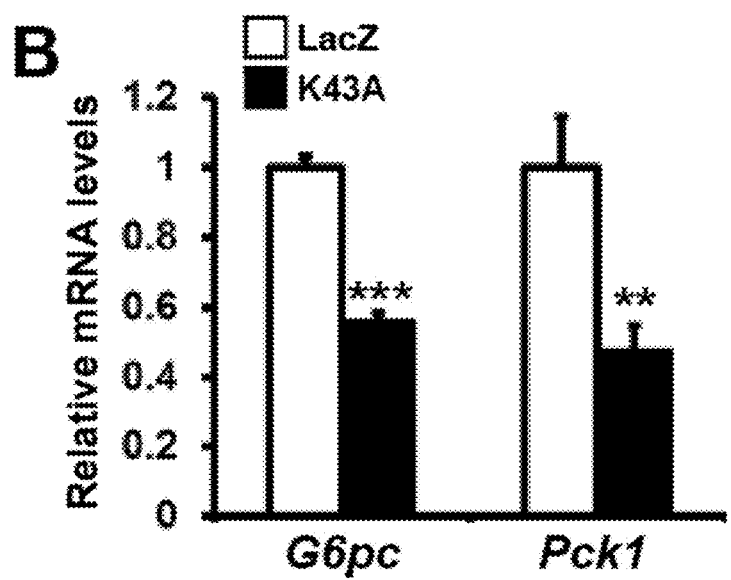
Figures 5C, 5D:
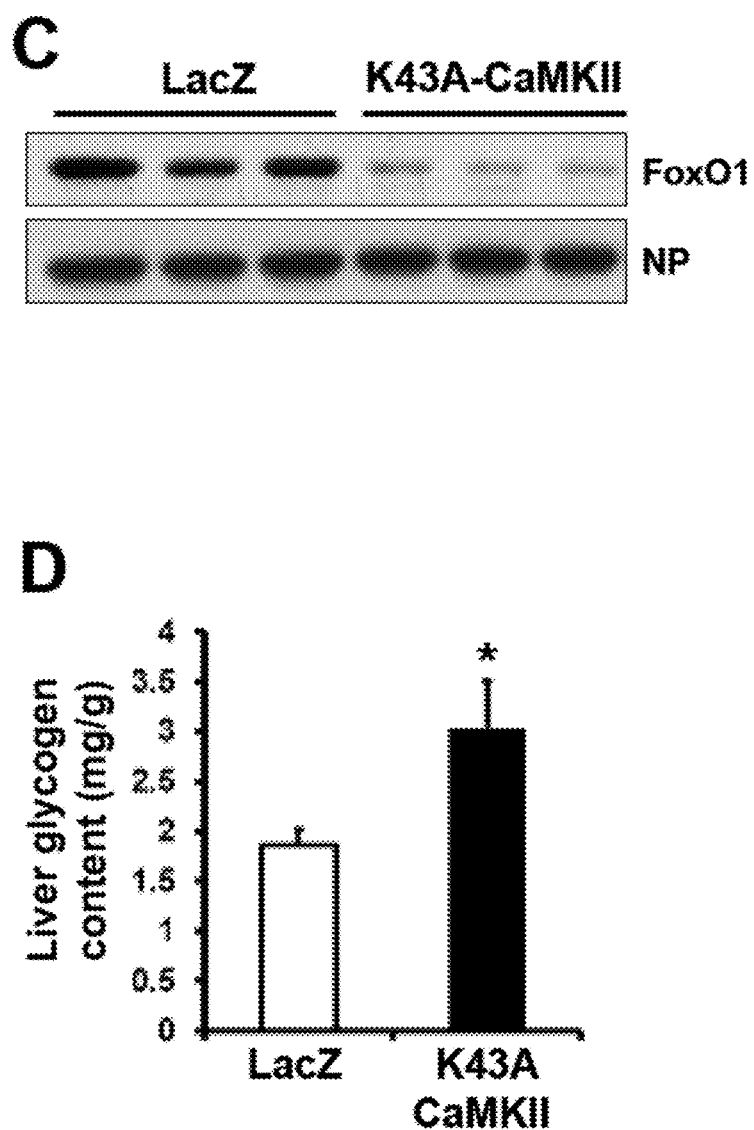
Figure 5E:
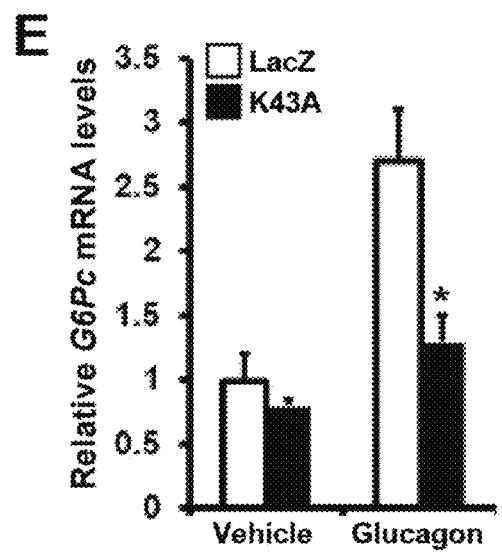
Figure 5F:
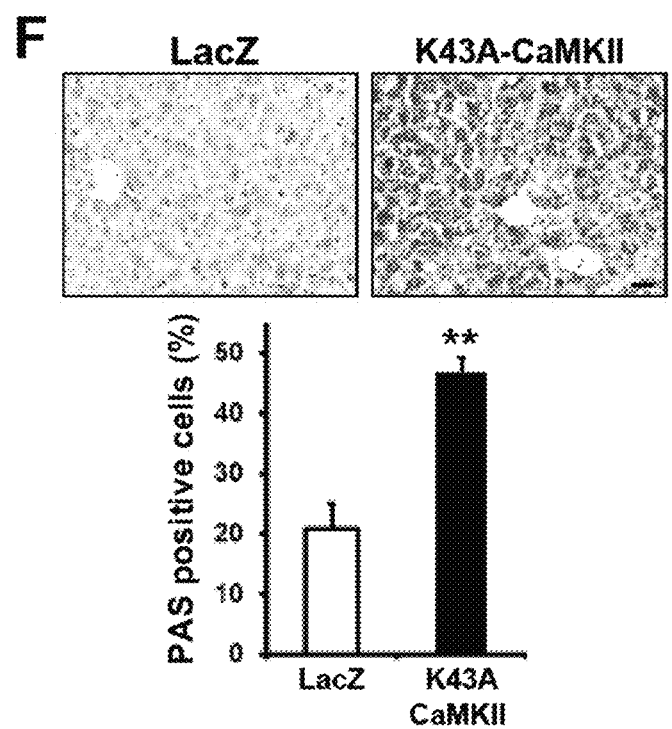

To further substantiate this important result, an adenoviral approach to inhibit hepatic CaMKII in vivo was used. Treatment of C57BL/6 mice with adeno-K43A-CaMKII led to a decrease in fasting blood glucose levels compared with mice treated with adeno-LacZ (FIG. 5A). In line with this finding, hepatic expression of G6pc and Pck1 mRNA and nuclear FoxO1 levels were lower in mice injected with K43A-CaMKII (FIG. 5B-C). Because FoxO1 ablation impairs both fasting gluconeogenesis and glycogenolysis, and CaMKII inhibition has a profound effect on the key glycogenolytic enzyme G6pc, the effect of acute CaMKII inhibition on hepatic glycogen content was examined. The data show a 60% increase in hepatic glycogen content in the mice treated with adeno-K43A-CaMKII (FIG. 5D). To directly link these findings to glucagon, mice treated with adeno-LacZ or adeno-K43A-CaMKII were injected i.p. with a bolus of glucagon and then the livers were analyzed 30 min later. G6pc was induced markedly in the livers of LacZ treated mice after glucagon injection but much less so in the livers of K43A-CaMKII-treated mice (FIG. 5E). Moreover, the K43A-CaMKII-treated mice had higher levels of hepatic glycogen as visualized by Periodic acid-Schiff (PAS) stain (FIG. 5F). These results further substantiate the role of CaMKII in hepatic glucose production.

Figures 6A, 6B:
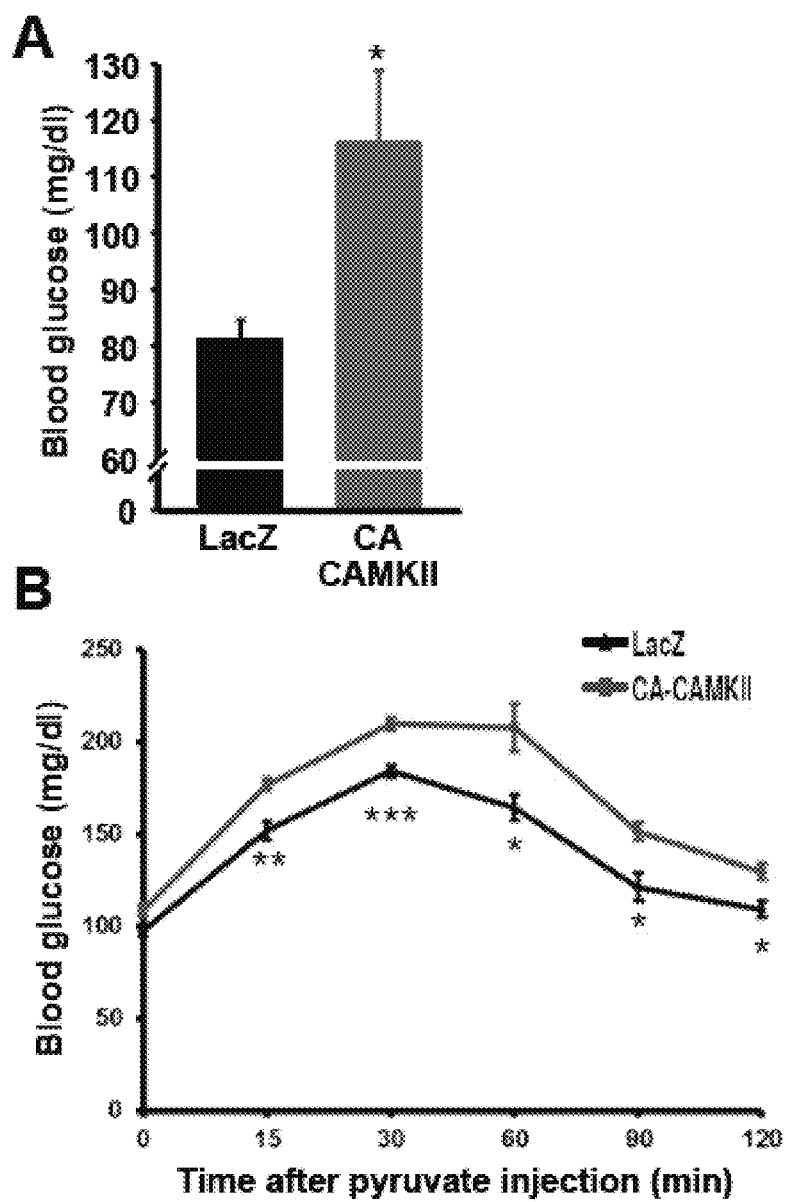
FIGS. 6A-D. Constitutively active CaMKII increases blood glucose, G6pc and Pck1 expression, and nuclear FoxO1. 9 week-old WT mice were injected with 1.5×109 pfu of adenoviruses containing either control LacZ (n=5) or CA-CaMKII (n=5).
Figure 6C:
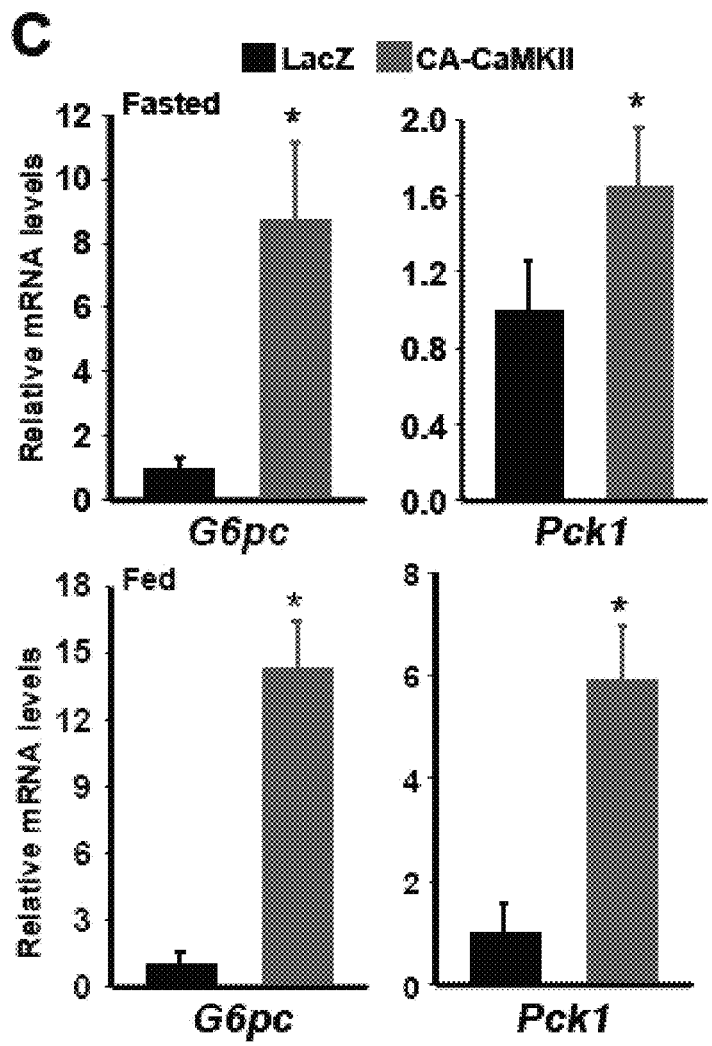
Figure 6D:
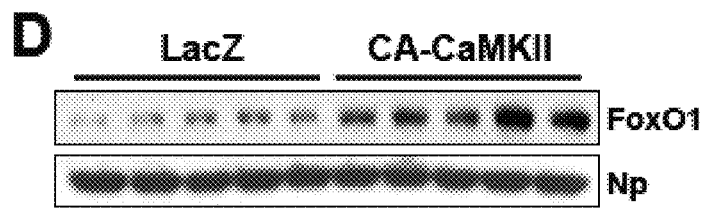

The effect of constitutively active hepatic CaMKII in mice by treating mice with adeno-CA-CAMKII was examined. This treatment led to an increase in fasting glucose levels (FIG. 6A). There was also a slight increase in fed blood glucose levels, but it did not reach statistically significance. Furthermore, mice overexpressing CA-CaMKII showed a significant increase in blood glucose levels in response to pyruvate administration (FIG. 6B). Consistent with these observations, there was an increase in hepatic mRNA levels of G6pc and Pck1 and in nuclear FoxO1 in mice treated with adeno-CA-CAMKII (FIG. 6C-D). These combined in vivo data show that CaMKII affects plasma glucose levels, pyruvate conversion into glucose, nuclear FoxO1, and the expression of hepatic glucose metabolism genes.

Impairment of Glucose Metabolism in Camk2g−/− Hepatocytes and CaMKII-Inhibited Mice is Rescued by Transduction with Constitutively Nuclear FoxO1

Figures 7A, 7B:
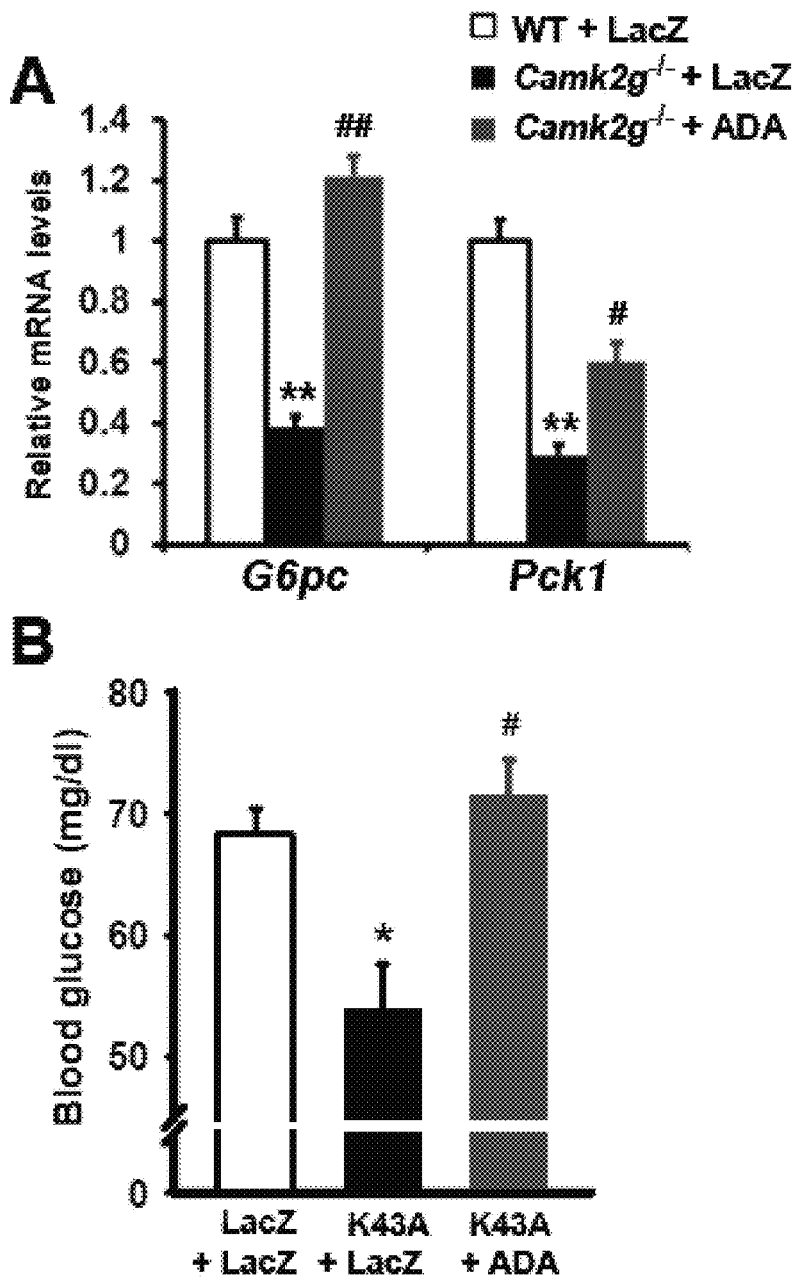
FIGS. 7A-D. Glucose metabolism impairment in Camk2g–/– hepatocytes and in vivo is rescued by transduction with constitutively nuclear FoxO1-ADA.
Figures 7C, 7D:
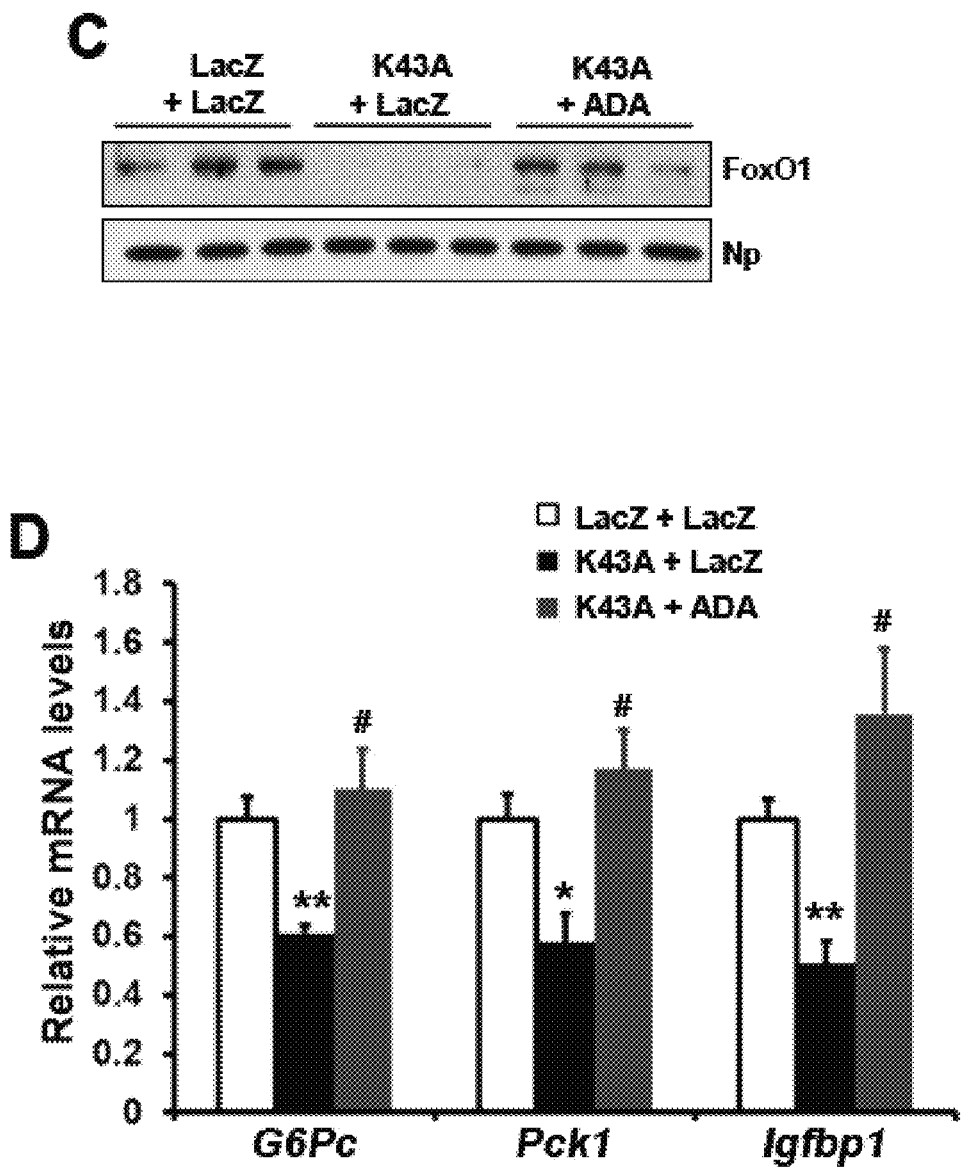

To validate the importance of FoxO1 in the control of hepatic glucose metabolism by CaMKII, hepatocytes were transduced from Camk2g−/− mice with adenovirus containing a phosphorylation-defective, constitutively nuclear FoxO1 mutant (FoxO1-ADA) (Nakae et al., 2001) such that the level of nuclear FoxO1 was similar to that in WT hepatocytes. The suppressive effect of CaMKIIγ deficiency on G6pc and Pck1 mRNAs was abrogated by transduction with adeno-FoxO1-ADA (FIG. 7A). Treatment of mice with adeno-FoxO1-ADA adenovirus rescued the impairment in glucose homeostasis in adeno-K43A-CaMKII-treated mice (FIG. 7B-D). Taken together, these results are consistent with a model in which CaMKII contributes to hepatic glucose production through promoting nuclear localization of FoxO1.

Discussion

Glucose metabolism in the liver is tightly regulated by the opposing actions of insulin and glucagon. A number of signaling molecules and transcription factors have been implicated in the control of glycogenolysis and gluconeogenesis during periods of food deprivation. The in vitro and in vivo data herein add CaMKII to this list and, by doing so, provide a molecular link to the role of intracellular calcium in hepatic glucose metabolism. In particular, the data herein show that hepatic CaMKII is activated in response to fasting, leading to nuclear translocation of FoxO1 and the induction of glycogenolytic and gluconeogenic genes. The role of FoxO1 in CaMKII action is supported by the finding that the suppressive effect of CaMKII deficiency on glucose production is abrogated when constitutively nuclear FoxO1 is introduced into CaMKIIγ-deficient hepatocytes.

The glucagon-cAMP-PKA pathway not only leads to CaMKII activation, as shown here, but also directly phosphorylates cAMP response element binding (CREB) protein on Ser133. Phosphorylated CREB transcriptionally induces PGC1α, which acts with FoxO1 to promote the transcription of G6pc1 and Pck1 (Herzig et al., 2001). Previous work has shown that CREB from brain tissue can also be phosphorylated on Ser133 by CaMKII in vitro (Dash et al., 1991; Sheng et al., 1991), and a drug inhibitor of CaMKII blocked CREB transcriptional activity in a cell culture model of osteoclastogenesis (Ang et al., 2007). A difference in either nuclear CREB or phospho-CREB in WT vs. CaMKII-deficient hepatocytes was not observed, excluding the possibility that CaMKII exerts its actions on hepatic glucose metabolism through modifying CREB.

FoxO1 activity is primarily regulated by post-translational modifications including phosphorylation and acetylation (van der Horst and Burgering, 2007). It is well documented that FoxO1 is phosphorylated at Thr24, Ser256, and Ser319 by growth factors via Akt to promote its nuclear exclusion. CaMKII promotes FoxO1 nuclear localization. Indeed, CaMKIIγ deficiency did not affect the phosphorylation of these three residues. There is evidence that FoxO phosphorylation on non-Akt sites by other kinases, such as JNK and AMPK, might actually promote its nuclear retention. Thus, the balance of FoxO activity can result from a combination of stimulatory and inhibitory phosphorylation events, and, without being bound by theory, CaMKII can affect this balance either through direct kinase action or through affecting a FoxO phosphatase activity. FoxO1 de-acetylation can also promote its nuclear localization (Frescas et al., 2005), but FoxO1 acetylation was also not affected by CaMKII deficiency. Alternatively, CaMKIIγ might somehow affect the import or export machinery involved in FoxO1 translocation or the expression or activity of FoxO1-interacting molecules in the cytoplasm or nucleus that might affect this process. Future studies will be directed toward the elucidation of this mechanism.

The discovery of a new molecule involved in hepatic glucose production not only provides insight into the physiologic defense against fasting hypoglycemia but may also reveal new therapeutic targets for the disturbed glucose metabolism that occurs in the setting of insulin resistance. Indeed, in type 2 diabetes, disproportionate hepatic glucose output and an imbalance of glucagon vs. insulin signaling contributes to fasting hyperglycemia (Saltiel, 2001). In this context, future studies will address whether inhibition of hepatic CaMKII ameliorates the metabolic abnormalities of obesity and insulin resistance.

Example 4: Experimental Procedures Suitable for Use with the Methods Described Herein Reagents and Antibodies Glucagon, pyruvate, forskolin, H89, and 8-bromo-cAMP were from Sigma. BAPTA-AM, and anti-nucleophosmin (Np) antibody were from Invitrogen. Xestospongin C was from EMD Chemicals. Anti-phospho-Thr287 CaMKII antibody was from Imgenex and Novus; anti-total CaMKII and anti-FoxO1 antibodies were from Santa Cruz Biotechnology Inc, anti-β-actin antibody was from Abcam.

Cell Culture

Primary mouse hepatocytes were isolated from 8- to 12-week-old mice as described previously (Matsumoto et al., 2002). Cells were serum depleted overnight and were then incubated with forskolin (10 µm) for 5 h in serum-free media.

Measurement of CaMKII Activity

CaMKII activity was assayed using a CaMKII assay kit from Promega according to the manufacturer's instructions. After the hepatocytes were treated as indicated in the figure legends, they were lysed by a 5-min exposure to 1% Triton-X in 50 mM HEPES, 150 mM NaCl, 10 mM Na pyrophosphate, 10 mM EDTA, 10 mM EGTA, 1 mM Na3VO4, 50 mM NaF, 1 mM PMSF, and 5 µg/ml leupeptin. Next, [γ-32P]ATP and CaMKII biotinylated peptide substrate were added to the lysate and after incubation for 10 minutes at 30° C., the [32P]-phosphorylated substrate was separated from the residual [32P]ATP using SAM biotin capture membrane and quantitated using a scintillation counter.

Adenovirus Infection

Adenoviruses encoding LacZ, CA-CaMKII, K43A-CaMKII and GFP-FoxO1 were described previously (Pfleiderer et al., 2004; Tanaka et al., 2009) and amplified by Viraquest, Inc. (North Liberty, Iowa). Primary hepatocytes were transduced 12 h after plating. RNA and protein isolation and glucose production were carried out 24 h after transduction.

Glucose Production in Primary Hepatocytes

Glucose production assays were carried out as described (Backs et al., 2010; Yoon et al., 2001). Briefly, after primary mouse hepatocytes were harvested and cultured as described above, cell culture medium was switched to glucose- and phenol-free DMEM (pH 7.4) supplemented with 20 mM sodium lactate and 2 mM sodium pyruvate. After 16 h of culture, 500 µl medium was collected, and the glucose content was measured using a colorimetric glucose assay kit (Abcam). The readings were then normalized to the total protein amount in the whole-cell lysates.

Mouse Experiments

Camk2g−/− mice were generated as described previously (Backs et al., 2010) and crossed onto the C57BL6/J background. Mice were fed a standard chow diet and maintained on a 12-h light-dark cycle. Recombinant adenovirus (1.5× 109 plaque-forming unit/mice) was delivered by tail vein injection. Fasting blood glucose was measured in mice that were fasted for 12-14 h, with free access to water, using a glucose meter (One Touch Ultra, Lifescan). Pyruvate-tolerance tests were carried out with an intraperitoneal injection of 2 g kg−1 body weight pyruvate after 17 h of fasting. Blood glucose levels were measured over the following 2 h. Xestospongin C was administered by daily i.p. injections to mice at a dose of 10 pmol g−1 for 4 days.

Hepatic Glycogen Measurement 50-100 mg of frozen livers were homogenized in 1 mL of H2O with protease and phosphatase inhibitors. Samples were then mixed with KOH (1:2), boiled for 25 minutes and washed with 70% ethanol. The pellet was dried and dissolved in 100 µl H2O and the glycogen content was assessed using Glycogen Assay Kit (Abcam) according to manufacturer's instructions. Data represent the mean±SEM.

PAS Staining of Mouse Liver Sections

Liver samples were fixed in 10% neutral-buffered formalin for 24 h and embedded in paraffin. Sections (5 micron) were stained for glycogen using Periodic acid-Schiff (PAS) stain (Sigma) according to manufacturer's instructions. The sections were then counterstained with hematoxylin and examined by light microscopy. For the quantification of PAS staining, 5 fields from 4 different sections were chosen randomly and the number of PAS-positive cells was counted and expressed as a percentage of the total number of cells, as described before (Raza Asim et al., 2010). Two independent investigators, blinded to the identity of the samples, performed the analysis.

Immunoblotting and Quantitative RT-PCR

Total RNA was extracted from hepatocytes using the RNeasy kit (Qiagen). cDNA was synthesized from 2 µg total RNA using oligo (dT) and Superscript II (Invitrogen). Real-time qPCR analysis and western blotting were performed as previously described (Timmins et al., 2009). Nuclear extraction from liver was performed using the Nuclear Extraction Kit from Panomics according to the manufacturer's instructions.

Statistical Analysis

All results are presented as mean±SEM. P values were calculated using the student's t-test.

REFERENCES

Ang, E. S., Zhang, P., Steer, J. H., Tan, J. W., Yip, K., Zheng, M. H., Joyce, D. A., and Xu, J. (2007). Calcium/calmodulin-dependent kinase activity is required for efficient induction of osteoclast differentiation and bone resorption by receptor activator of nuclear factor kappa B ligand (RANKL). J Cell Physiol 212, 787-795.

Backs, J., Stein, P., Backs, T., Duncan, F. E., Grueter, C. E., McAnally, J., Qi, X., Schultz, R. M., and Olson, E. N. (2010). The gamma isoform of CaM kinase II controls mouse egg activation by regulating cell cycle resumption. Proc Natl Acad Sci USA 107, 81-86.

Bygrave, F. L., and Benedetti, A. (1993). Calcium: its modulation in liver by cross-talk between the actions of glucagon and calcium-mobilizing agonists. Biochem J 296 (Pt 1), 1-14.

Couchonnal, L. F., and Anderson, M. E. (2008). The role of calmodulin kinase II in myocardial physiology and disease. Physiology (Bethesda) 23, 151-159.

Dash, P. K., Karl, K. A., Colicos, M. A., Prywes, R., and Kandel, E. R. (1991). cAMP response element-binding protein is activated by Ca2+/calmodulin—as well as cAMP-dependent protein kinase. Proc Natl Acad Sci USA 88, 5061-5065.

Frescas, D., Valenti, L., and Accili, D. (2005). Nuclear trapping of the forkhead transcription factor FoxO1 via Sirt-dependent deacetylation promotes expression of glucogenetic genes. J Biol Chem 280, 20589-20595.

Friedmann, N., and Rasmussen, H. (1970). Calcium, manganese and hepatic gluconeogenesis. Biochim Biophys Acta 222, 41-52.

Greer, E. L., and Brunet, A. (2005). FOXO transcription factors at the interface between longevity and tumor suppression. Oncogene 24, 7410-7425.

Hall, R. K., Sladek, F. M., and Granner, D. K. (1995). The orphan receptors COUP-TF and HNF-4 serve as accessory factors required for induction of phosphoenolpyruvate carboxykinase gene transcription by glucocorticoids. Proc Natl Acad Sci USA 92, 412-416.

Herzig, S., Long, F., Jhala, U. S., Hedrick, S., Quinn, R., Bauer, A., Rudolph, D., Schutz, G., Yoon, C., Puigserver, P., Spiegelman, B., and Montminy, M. (2001). CREB regulates hepatic gluconeogenesis through the coactivator PGC-1. Nature 413, 179-183.

Klover, P. J., and Mooney, R. A. (2004). Hepatocytes: critical for glucose homeostasis. Int J Biochem Cell Biol 36, 753-758.

Kraus-Friedmann, N., and Feng, L. (1996). The role of intracellular Ca2+ in the regulation of gluconeogenesis. Metabolism 45, 389-403.

Lin, H. V., and Accili, D. (2011). Hormonal regulation of hepatic glucose production in health and disease. Cell Metab 14, 9-19.

Marques-da-Silva, A. C., D'Avila, R. B., Ferrari, A. G., Kelmer-Bracht, A. M., Constantin, J., Yamamoto, N. S., and Bracht, A. (1997). Ca2+ dependence of gluconeogenesis stimulation by glucagon at different cytosolic NAD (+)-NADH redox potentials. Braz J Med Biol Res 30, 827-836.

Matsumoto, M., Ogawa, W., Teshigawara, K., Inoue, H., Miyake, K., Sakaue, H., and Kasuga, M. (2002). Role of the insulin receptor substrate 1 and phosphatidylinositol 3-kinase signaling pathway in insulin-induced expression of sterol regulatory element binding protein 1c and glucokinase genes in rat hepatocytes. Diabetes 51, 1672-1680.

Matsumoto, M., Pocai, A., Rossetti, L., Depinho, R. A., and Accili, D. (2007). Impaired regulation of hepatic glucose production in mice lacking the forkhead transcription factor Foxo1 in liver. Cell Metab 6, 208-216.

Mine, T., Kojima, I., and Ogata, E. (1993). Role of calcium fluxes in the action of glucagon on glucose metabolism in rat hepatocytes. Am J Physiol 265, G35-42.

Nakae, J., Kitamura, T., Silver, D. L., and Accili, D. (2001). The forkhead transcription factor Foxo1 (Fkhr) confers insulin sensitivity onto glucose-6-phosphatase expression. J Clin Invest 108, 1359-1367.

Pfleiderer, P. J., Lu, K. K., Crow, M. T., Keller, R. S., and Singer, H. A. (2004). Modulation of vascular smooth muscle cell migration by calcium/calmodulin-dependent protein kinase II-delta 2. Am J Physiol Cell Physiol 286, C1238-1245.

Pilkis, S. J., and Granner, D. K. (1992). Molecular physiology of the regulation of hepatic gluconeogenesis and glycolysis. Annu Rev Physiol 54, 885-909.

Puigserver, P., Rhee, J., Donovan, J., Walkey, C. J., Yoon, J. C., Oriente, F., Kitamura, Y., Altomonte, J., Dong, H., Accili, D., and Spiegelman, B. M. (2003). Insulin-regulated hepatic gluconeogenesis through FOXO1-PGC-1alpha interaction. Nature 423, 550-555.

Radziuk, J., and Pye, S. (2001). Hepatic glucose uptake, gluconeogenesis and the regulation of glycogen synthesis. Diabetes Metab Res Rev 17, 250-272.

Raza Asim, M. B., Shahzad, M., Yang, X., Sun, Q., Zhang, F., Han, Y., and Lu, S. (2010). Suppressive effects of black seed oil on ovalbumin induced acute lung remodeling in E3 rats. Swiss Med Wkly 140, w13128.

Rhee, J., Inoue, Y., Yoon, J. C., Puigserver, P., Fan, M., Gonzalez, F. J., and Spiegelman, B. M. (2003). Regulation of hepatic fasting response by PPARgamma coactivator-1alpha (PGC-1): requirement for hepatocyte nuclear factor 4alpha in gluconeogenesis. Proc Natl Acad Sci USA 100, 4012-4017.

Saltiel, A. R. (2001). New perspectives into the molecular pathogenesis and treatment of type 2 diabetes. Cell 104, 517-529.

Sheng, M., Thompson, M. A., and Greenberg, M. E. (1991). CREB: a Ca(2+)-regulated transcription factor phosphorylated by calmodulin-dependent kinases. Science 252, 1427-1430.

Staddon, J. M., and Hansford, R. G. (1989). Evidence indicating that the glucagon-induced increase in cytoplasmic free Ca2+ concentration in hepatocytes is mediated by an increase in cyclic AMP concentration. Eur J Biochem 179, 47-52.

Tanaka, J., Qiang, L., Banks, A. S., Welch, C. L., Matsumoto, M., Kitamura, T., Ido-Kitamura, Y., DePinho, R. A., and Accili, D. (2009). Foxo1 links hyperglycemia to LDL oxidation and endothelial nitric oxide synthase dysfunction in vascular endothelial cells. Diabetes 58, 2344-2354.

Timmins, J. M., Ozcan, L., Seimon, T. A., Li, G., Malagelada, C., Backs, J., Backs, T., Bassel-Duby, R., Olson, E. N., Anderson, M. E., and Tabas, I. (2009). Calcium/calmodulin-dependent protein kinase II links ER stress with Fas and mitochondrial apoptosis pathways. J Clin Invest 119, 2925-2941.

van der Horst, A., and Burgering, B. M. (2007). Stressing the role of FoxO proteins in lifespan and disease. Nat Rev Mol Cell Biol 8, 440-450.

Yoon, J. C., Puigserver, P., Chen, G., Donovan, J., Wu, Z., Rhee, J., Adelmant, G., Stafford, J., Kahn, C. R., Granner, D. K., Newgard, C. B., and Spiegelman, B. M. (2001). Control of hepatic gluconeogenesis through the transcriptional coactivator PGC-1. Nature 413, 131-138.

Example 5: The Role of Hepatic CaMKII in Glucagon-Mediated Hepatic Glucose Production (HGP)

Obesity-induced insulin resistance and disturbances in liver glucose and fat metabolism increase the risk for heart disease, cancer, and other widespread and devastating diseases. Current treatments options are severely limited, leading to a critical unmet clinical need affecting hundreds of millions of overweight people in the current obesity epidemic. Over the last 2 years, several discoveries, including validation in models of obesity, indicate that inhibitors of a unique drug target—a liver enzyme called CaMKII—can be invaluable in this niche. Thus, the overall goal of this invention is to develop and test CaMKII inhibitors for the purpose of drug development to improve the metabolic disturbances and their consequences in obesity, metabolic syndrome, and type 2 diabetes.

It was shown that CaMKII is activated by glucagon in primary hepatocytes and by glucagon and fasting in vivo (FIG. 1). Genetic deficiency or inhibition of hepatic CaMKII lowered blood glucose levels, suppressed the HGP genes G6pc and Pck1, decreased glycogen depletion, and blocked nuclear translocation of the HGP transcription factor FoxO1 (data with dominant-negative CaMKII shown in FIG. 5). Conversely, constitutively active CaMKII induced G6pc and Pck1, stimulated glucose production, and raised blood glucose levels. Importantly, the suppressive effect of CaMKII deficiency on glucose metabolism was abrogated by constitutively nuclear FoxO1, indicating that the effect of CaMKII deficiency requires nuclear exclusion of FoxO1 (FIG. 7). These results reveal a new molecular pathway regulated by CaMKII in the control of HGP.

Figure 8A:
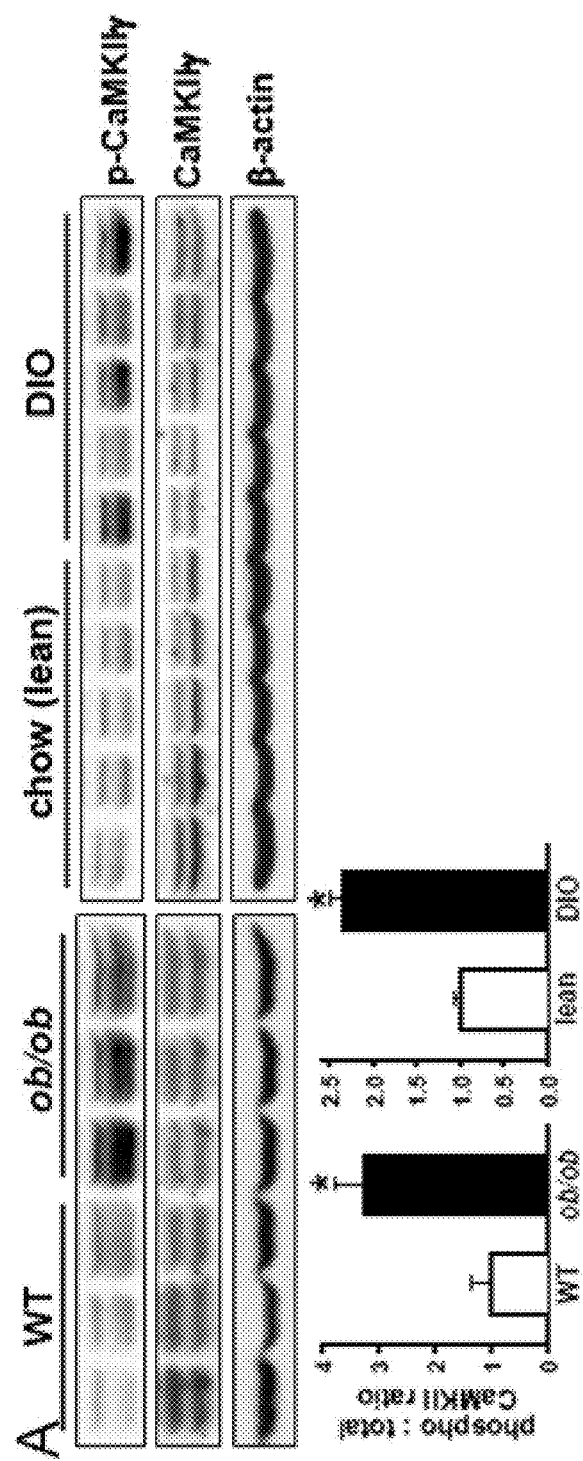
FIGS. 8A-B. P-CaMKIIγ in obese liver Immunoblots of liver extracts from FIG. 8A 10-wk/oWT or ob/ob mice and mice fed chow or high-calorie (DIO) diet for 20 wks.
Figure 8B:
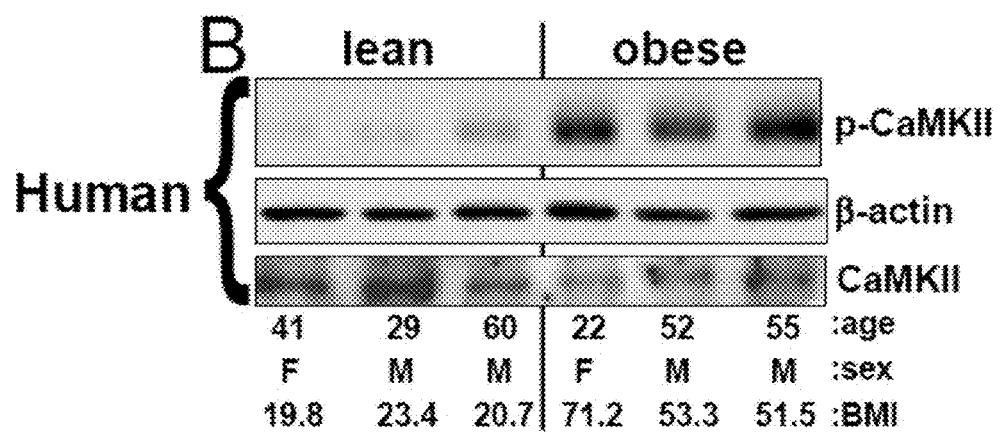

Obesity was examined because an imbalance of glucagon over insulin signaling contributes to hyperglycemia and insulin resistance in obesity. CaMKII is activated in the livers of leptin-deficient (ob/ob) and diet-induced obese (DIO) mice but not in the livers of lean mice (FIG. 8A). CaMKII is also activated in the livers of obese but not lean humans (FIG. 8B). Most important, genetic or pharmacologic inhibition of hepatic CaMKII in obese mice lowered fasting blood glucose; improved insulin resistance; decreased the expression of key genes involved in HGP; decreased fatty liver and inflammation, and improved dyslipidemia (FIGS. 9-10). These data support the concept that therapeutic targeting of CaMKII will improve hyperglycemia and insulin resistance in obese subjects.

CaMKIIγ Anti-Sense Oligonucleotides (ASO's) Will be Tested in a Mouse Model of Obesity ASOs directed against Camk2g will be tested in a mouse model of obesity. Isis has a control ASO and 4 different Camk2g ASO's, which will be used to treat DIO obese mice (i.p. injection once a week for 6 weeks). The level of Camk2g mRNA in the liver and other tissue will be measured and overall tolerance including liver weight, liver function tests, and tolerance to fasting will be assessed. Efficacy in improving the following parameters will be tested: fasting and fed plasma glucose and insulin; HGP gene expression and FoxO1 nuclear localization; HGP and peripheral insulin sensitivity via a hyperinsulinemic euglycemic clamp study; fatty liver; and plasma triglycerides and fatty acids.

Screen for and Test Novel Chemical Inhibitors of CaMKII:

"Druggable" chemical libraries will be screened using a high-throughput fluorescence-based assay of CaMKII activity that relies on changes in fluorescence emission ratio when the enzyme is inactivated. Structure-activity relationships will be defined and potency and specificity of CaMKII inhibitors that already exist and are commercially available for in vitro and pre-clinical studies will be optimized. The most promising hits will then be secondarily screened in a model of insulin-resistant primary hepatocytes, which involves treating the cells with saturated fatty acids in a manner that mimics the increase in glucose production and insulin resistance seen in liver in obese mice. Using this model, the most potent inhibitors of CaMKII, glucose production, and insulin resistance will be examined. The most promising drugs, prepared in gram quantities, will be tested in vivo according to the strategy outlined above for the ASO's, with vigilance on monitoring the activity of CaMKII and consequences of inhibition in non-liver tissues. Orally available drugs will be assessed for ease of delivery and delivery to the liver, i.e., via the portal circulation. Drugs can be altered to achieve oral availability if that becomes necessary.

Example 6

Figure 11:
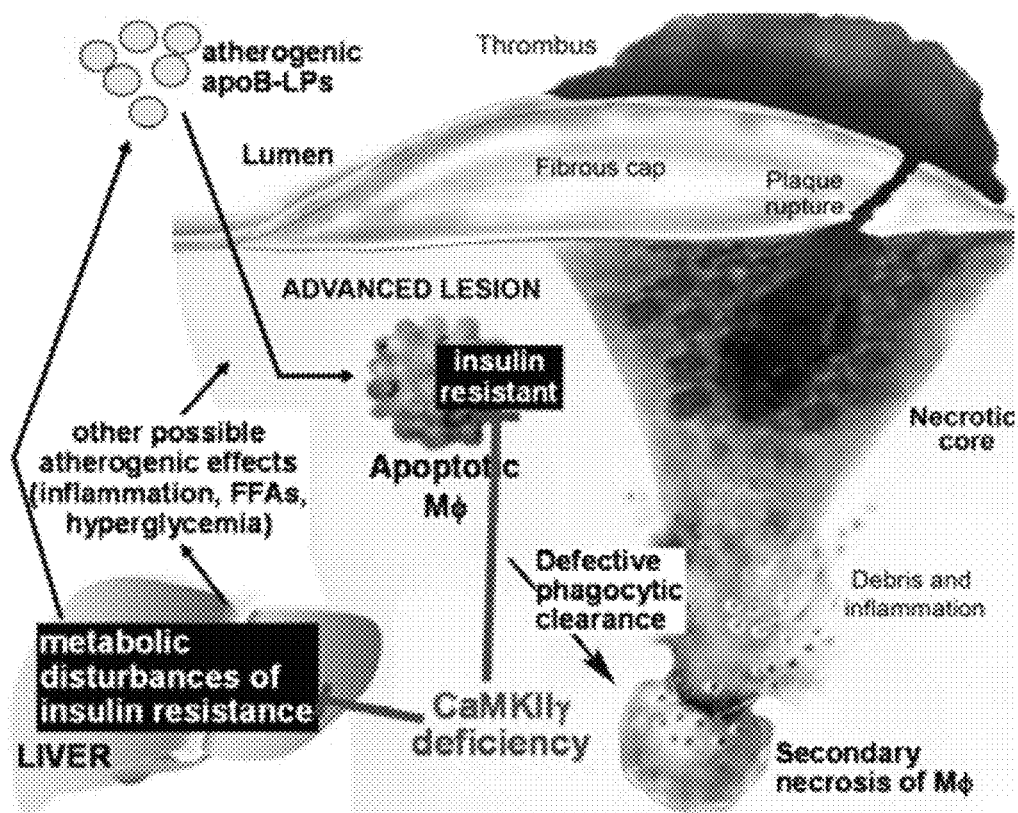
FIG. 11. CaMKII γ deficiency mediated suppression of atherosclerosis by complementary mechanisms.

Two major factors contributing to the increased risk of coronary artery disease (CAD) in obesity/insulin resistance are pro-atherogenic processes in the plaques themselves and an increase in systemic risk factors, notably hepatic-derived dyslipidemia. Human diabetic plaques are characterized by especially large necrotic areas, which promote inflammation, plaque disruption, and acute CAD. Plaque necrosis develops as a consequence of macrophage (Mφ) apoptosis in the setting of defective clearance of the dead cells. The mechanisms by which prolonged endoplasmic reticulum (ER) stress in advanced plaques triggers Mφ death and plaque necrosis will be examined. These processes are amplified in Mφs with defective insulin signaling. Prolonged ER stress promotes elevated cytoplasmic calcium (Ca2+), which triggers apoptosis through activation of Ca2+/calmodulin-dependent protein kinase II-γ (CaMKIIγ). Deletion or inhibition of CaMKIIγ in obese mice was protective against hyperinsulinemia, gluconeogenesis, dyslipidemia, fatty liver, and ER stress. These new findings indicate that one enzyme may have critical effects on two complementary processes that promote CAD in insulin-resistant subjects (FIG. 11). Thus, Mϕ CaMKIIγ deficiency can lessen advanced lesional Mϕ apoptosis and plaque necrosis in a murine model of Mϕ insulin resistance and that hepatic CaMKIIγ deficiency will improve atherogenic metabolic disturbances in obese mice.

Mϕ CaMKIIγ Deficiency Will Lessen Advanced Lesional Mϕ Apoptosis and Plaque Necrosis in Insulin-Resistant Mice In vitro data shows that CaMKIIγ orchestrates a number of critical apoptotic pathways in ER-stressed Mϕs. PPG data shows perturbed Ca2+ metabolism and activated CaMKIIγ in insulin-resistant Mϕs. Thus, CaMKIIγ can play a particularly important role in apoptosis of ER-stressed insulin-resistant Mϕs. It will be first determined whether siRNA-mediated silencing of Camk2g in Mϕs isolated from Insr−/− and ob/ob, two proof-of-concept models of defective Mϕ insulin signaling, suppresses the very high level of ER stress-induced apoptosis in these cells and then explore the molecular/cellular mechanisms of protection. p-CaMKII, a measure of CaMKII activation, will be measured to determine if it is higher in lesional Mϕs in advanced vs. earlier stage atherosclerotic lesions in humans and mice. To test causation, bone marrow cells from Camg2gfl/flLysmcre+/− Insr−/− mice, as well as from WT mice and from mice lacking Mϕ CaMKIIγ or insulin receptors will be transplanted separately, into Ldlr−/− mice, and then place on the Western diet. The high level of advanced lesional Mϕ apoptosis and plaque necrosis in Insr−/−→Ldlr−/− mice will be markedly ameliorated by Mϕ CaMKII deficiency.

Mechanisms Whereby Liver CaMKIIγ Deficiency Improves the Metabolic Disturbances of Obesity and Liver-Specific CaMKIIγ Deficiency Will Suppress Atherosclerosis in Obese Mice.

Camk2gfl/fl X α1-antitrypsin-Cre mice will be used to test whether hepatic-specific CaMKIIγ deficiency improves glucose, lipid, and lipoprotein metabolism in obesity. The idea that obesity activates hepatic CaMKIIγ through a mechanism involving the ER stress effector CHOP will be tested. One mechanism underlying the beneficial effects of hepatic CaMKIIγ deficiency on glucose and lipid metabolism will be explored, namely, nuclear exclusion of FoxO1 and suppression of hepatic glucose production/gluconeogenesis. CaMKII activation and related mechanisms in liver specimens from obese vs. lean human subjects will be probed. The LysMCre model will be used to investigate whether CaMKIIγ deficiency in liver Mϕs, by suppressing ER stress and/or inflammation, and whether it can also contribute to the suppression of liver-mediated metabolic disturbances in obesity. The following will be tested: (a) whether liver CaMKIIγ deficiency in Western diet-fed Ldlr−/− mice will suppress atherogenesis; and (b) whether combined hepatic and Mϕ CaMKIIγ deficiency will have marked beneficial effect on all stages of atherosclerosis.

Example 7: Plaque Necrosis

The 2-3% of lesions that cause acute CAD are distinguished not by their larger size but by the presence of plaque necrosis 1,2, which promotes plaque disruption, acute lumenal thrombosis, and tissue infarction (3). Plaque necrosis is caused by the combination of Mϕ apoptosis and defective clearance, or "efferocytosis," of the dead Mϕs, resulting in post-apoptotic necrosis (4-6). This concept is particularly important in considering how diabetes and insulin resistance promotes CAD, because advanced atherosclerotic lesions in diabetic subjects are characterized by particularly large necrotic cores when compared with similarly sized lesions from non-diabetic individuals (7-12). A prospective study of subjects with CAD found that only diabetes and age were associated positively with necrotic core size (12). These data raise the issue as to whether advanced lesional Mϕ apoptosis is enhanced in the setting of diabetes.

Prolonged ER Stress as a Mechanism of Advanced Lesional Mϕ Apoptosis

Mechanistic and in vivo data support a role for prolonged ER stress in advanced lesional Mϕ apoptosis and plaque necrosis {4997, 5081}. ER stress-induced Mϕ apoptosis is largely dependent on the CHOP branch of the so-called the Unfolded Protein Response (UPR) (15,16). In human coronary arteries, there is a very strong correlation among CHOP expression, apoptosis, and advanced plaque stage (17). CHOP-deficient atherosclerosis-susceptible mice have suppressed advanced plaque progression (16), which was then confirmed by another group who used bone marrow transfer to implicate the role of Mϕ CHOP (18). A third study showed an atheroprotective effect of a "chemical chaperone" that is thought to relieve ER stress (19). CHOP-induced apoptosis can be modeled in cultured Mϕs by: (a) potent inducers of ER stress, such as 7-ketocholesterol (16,20), which is the most abundant oxysterol in advanced atherosclerotic lesions (17); or (b) the combination of more subtle ER stress plus an athero-relevant "2nd hit," notably, pattern recognition receptor (PRR) activation by modified lipoproteins or saturated fatty acids, which amplifies pro-apoptotic signaling and suppresses cell-survival signaling (21,22). The 2-hit concept also applies to another model of advanced lesional Mϕs, namely, Mϕs loaded with lipoprotein-derived free cholesterol (FC) (23-26), because excess FC in the ER membrane activates the UPR, while modified lipoproteins activate PRRs. Most importantly for this proposal, the PPG has shown that ER stress-induced apoptosis is markedly enhanced in Mϕs with defective insulin signaling.

Pro-Atherogenic Roles of the Liver in Obesity and Insulin Resistance.

The liver plays a major role in the increased CAD risk in insulin resistance (27,28). A major link is through increased VLDL apoB and triglyceride (TG) secretion, which is triggered by de novo lipogenesis coupled with increased hepatic delivery of adipose-derived free fatty acids; suppression of apoB degradation; and enhancement of apoB translation28. SREBP1c-mediated lipogenesis and VLDL secretion are stimulated by the activation of "residual" insulin receptor signaling pathways by hyperinsulinemia (29-33). An insulin receptor-mTORC1 pathway suppresses sortilin-1-mediated apoB degradation. Two other potential links among obesity, insulin resistance, and metabolic disturbances are hepatic ER stress and inflammation. Hepatic ER stress in obesity can suppress insulin signaling by IRE1-JNK-mediated phosphorylation of IRS-1 on Ser30734 or by activation of GSK-3β, which inhibits rictor-mediated AKT activation (35,36). Manipulations that relieve hepatic ER stress in animal models improve insulin resistance (37,38), and studies in humans have shown that weight loss decreases hepatic ER stress (39). Hepatic ER stress promotes SREBP-1c activation and steatosis (34, 38, 40), but the effects on VLDL secretion per se remain to be fully explored (41-43). In terms of inflammation, cytokines can enter the liver from the blood or through secretion by resident Kupffer cells or newly recruited macrophages, which have been implicated in obesity-induced insulin resistance (28, 44, 45). Inflammatory cytokines activate JNK, which has been linked to insulin resistance by disrupting insulin receptor signaling (above) and through activation of the kinase PKR46.

CaMKII.

CaMKII is a Ca2+-activated Ser/Thr kinase whose active form is a homo-multimer of 12-14 subunits encoded by one of 4 genes, α, β, γ, or δ47. (NB: CaMKII is distinct from CaMKK, which activates AMPK). The α and β isoforms are neuronal, while CaMKIIγ and δ are expressed in a wide variety of tissues. Mφs and HCs express the γ form 48. In the basal state, a regulatory domain interacts with and inhibits the catalytic domain. When cytosolic Ca2+ is increased, Ca2+-calmodulin complex disrupts this interaction, thus relieving auto-inhibition and promoting auto-phosphorylation of Thr287. This process increases the affinity of Ca2+-CaM binding and results in Ca2+-independent kinase activation. Most studies on CaMKII have been carried out in neurons and cardiomyocytes. In Mφs, in vitro inhibitor studies have reported roles in phagolysosomal killing of bacteria; LPS-mediated adenylyl cyclase activation and HIF-1α induction; PKR-mediated p38 activation; auto-immune induced apoptosis; and de-repression of inflammatory genes (49-54). Published data with CaMKII in hepatocytes is very limited. As explained in the following sections, genetic targeting of Camk2g was used to show new roles in ER stress-induced Mφ apoptosis (48) and in liver-driven metabolic disturbances in the setting of obesity.

The role of Mφ CaMKIIγ in atherosclerosis has never before been explored, and its importance in the setting of insulin resistance because of altered calcium dynamics in insulin-resistant Mφs is a new concept. A new cre-lox model will be used to test these ideas. The role of hepatocyte CaMKIIγ in the metabolic disturbances of obesity can reveal additional new principles in this critical area. The cre-lox model will also be ideal to test this idea. Finally, the proposed integrated role of this single molecule in mediating atherosclerosis in the setting of obesity and insulin resistance, through effects on lesional Mφs, hepatocytes, and possibly hepatic Mφs, represents a novel concept that can have important therapeutic implications.

CAD risk factors associated with the epidemic of obesity and insulin resistance will be the major drivers of CAD over the next decades (55). This finding addresses new mechanisms and in vivo consequences of two critical processes in this area, one centered on plaque Mφ apoptosis and the other on metabolic processes in the liver that promote CAD risk. The Mφ studies are focused on advanced plaque morphology, notably necrosis, which is the most important feature of the small minority of human plaques that actually cause acute CAD (56). Moreover, the finding includes future studies using human plaque specimens at various stages of progression and liver specimens from obese vs. lean human subjects. Upon completion of the proposed studies, new therapeutic strategies for obese/insulin-resistant subjects that target common pro-atherogenic signaling pathways in the arterial wall and liver will be obtained. Of note, CaMKII inhibitors have been tested successfully in animal models in other scenarios in which CaMKII is thought to contribute to disease progression (57,58). As described herein, partial inhibition of the enzyme has a significant effect on protecting Mφs and HCs, which further increases the feasibility of a therapeutic approach. Specificity can be obtained through selective inhibition of the gamma isoform and by using strategies that target drugs to atherosclerotic lesions and the liver (59,60). However, this specificity may not be needed given the benefit of CaMKII inhibition in other aspects of diabetes, such as heart failure (61), hypertension and renal disease (62), and retinal disease (63).

Testing Whether Mφ CaMKIIγ Deficiency Will Lessen Advanced Lesional Mφ Apoptosis and Plaque Necrosis in Insulin-Sensitive and Especially Mφ-Insulin-Resistant Mice.

Figure 12:
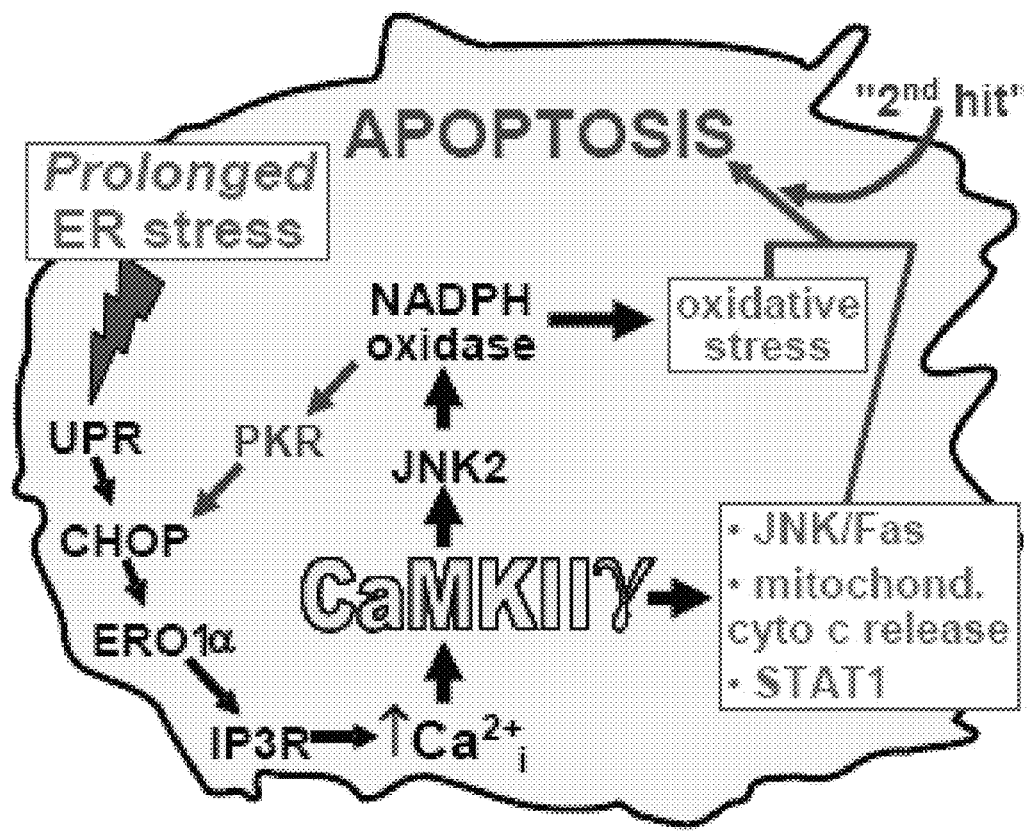
FIG. 12. Role of CaMKIIγ in UPR-induced Mϕapoptosis
Figure 13:
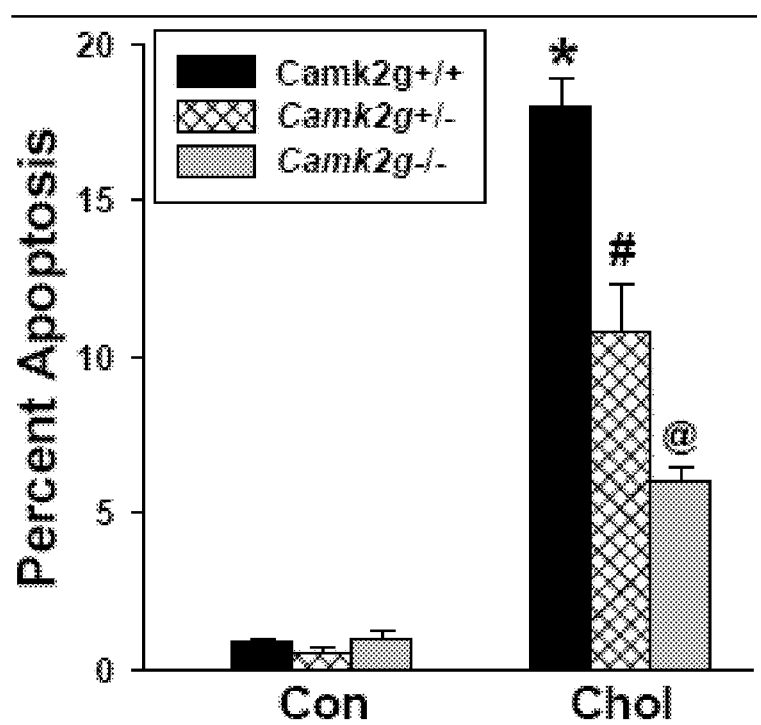
FIG. 13. CaMKIIγ haploinsufficency protects Mϕs from ER stress-induced apoptosis. Mϕs from WT, Camk2g+/−, or Camk2g−/− mice were treated under control or FC-loading (Chol) conditions and then assayed for apoptosis. *, #, @=P<0.01 vs. each other.

There is in vitro and in vivo evidence for the aforementioned "2-hit" mechanism of Mφ apoptosis involving prolonged ER stress in combination with PRR signaling (22, 48, 64-72). A key ER stress pathway involves CHOP-mediated induction of the ER oxidase ERO1α, which then activates the ER Ca2+ release channel IP3R. The released Ca2+ activates CaMKIIγ, which in turn triggers downstream apoptosis pathways, including INK-mediated induction of the Fas death receptor; permeabilization of the outer mitochondrial membrane and release of cytochrome c; and induction of NADPH oxidase-mediated ROS, which also amplifies CHOP through an upstream kinase called PKR (FIG. 12). With regard to the therapeutic potential mentioned above, partial inhibition of CaMKIIγ is adequate to protect Mφs (FIG. 13). Importantly, ER-stressed CaMKIIγ-deficient mice are protected from apoptosis in peritoneal and splenic Mφs and renal epithelial cells in vivo. However, the role of Mφ-CaMKIIγ in advanced atherosclerotic lesional Mφ apoptosis and plaque necrosis is not known.

Application of these concepts to Mφs in the setting of insulin resistance has been a major goal of the PPG. Mφs enhances ER-stress-induced apoptosis by at least 3 mechanisms: (a) up-regulation of scavenger receptors (74); (b) suppression of the AKT and NF-κB cell-survival pathways (66); and (c) down-regulation of the ER Ca2+ pump SERCA75. Most importantly, advanced lesional Mφ apoptosis and plaque necrosis are increased in lesions in which Mφs have defective insulin signaling 76, which is consistent with the very large necrotic cores of human diabetic lesions. Another study showed that mixed-genetic-background Apoe−/− mice fed a very-high-cholesterol/cholate ("Paigen") diet had a modest decrease in lesion area when Mφs were Insr−/− or Irs2−/−77. This can be related to anti-inflammatory effect in the setting of the pro-inflammatory Paigen diet (77-79), consistent with the above NF-κB study (66). Most importantly, the critical endpoints of advanced lesional Mφ apoptosis and plaque necrosis, which are the focus of the PPG, were not included.

Figure 14:
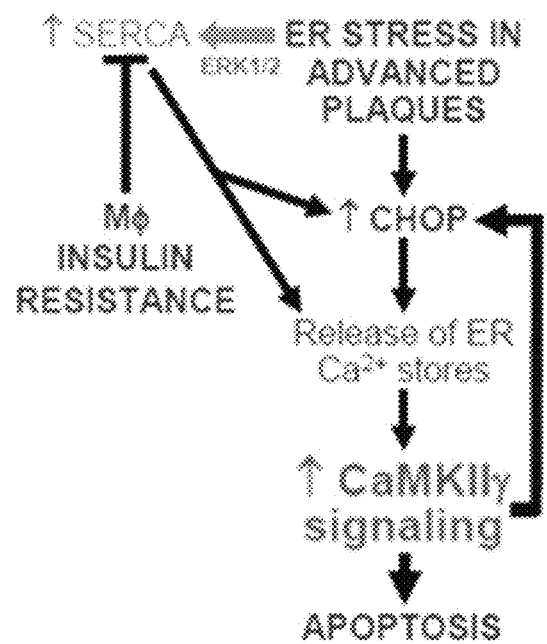
FIG. 14. Overview of key role of CaMKIIγ in ER stress-induced Mϕapoptosis in the setting of insulin resistance.
Figure 15A:
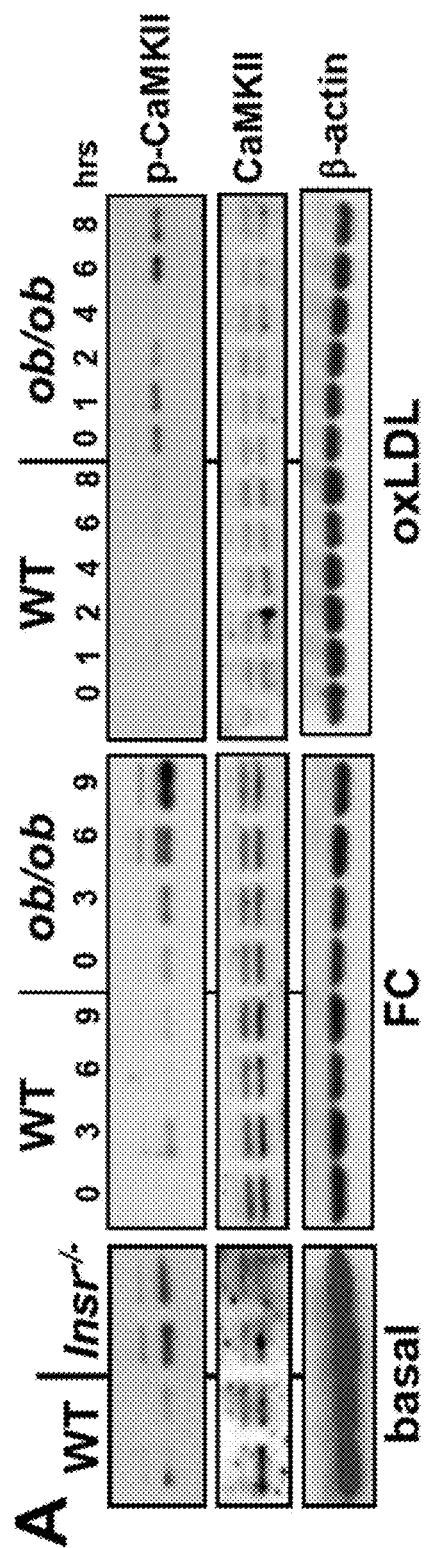
FIGS. 15A-B. Mϕinsulin resistance and ERK1/2 inhibition increase p-CaMKII. Immunoblots of pThr287-CaMKII in FIG. 15A WT, Insr−/−, and ob/obMϕs±FC loading or oxLDL and FIG. 15B WT Mϕs±4 h treatment with 5 μM U0126 ERK inhibitor.
Figure 15B:
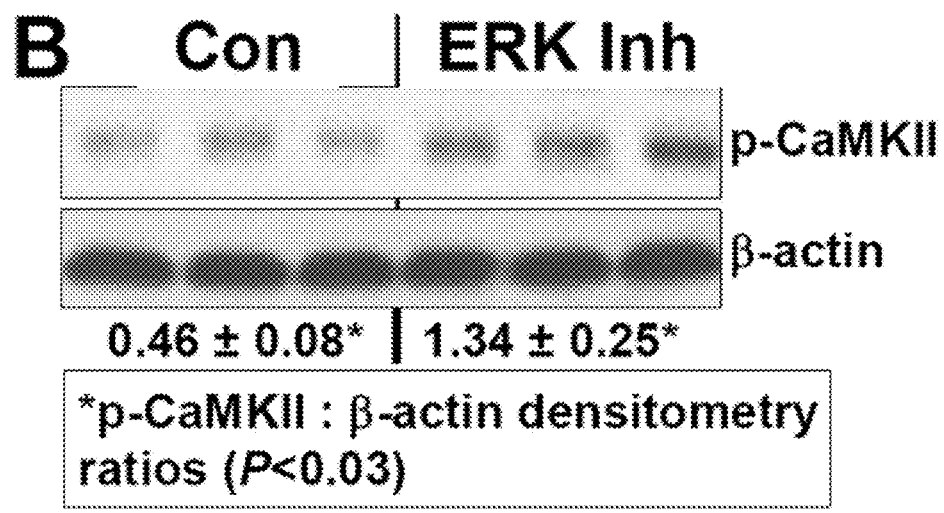

Without being bound by theory, links between these 3 mechanisms and the ER stress/PRR 2-hit model are readily apparent based upon these mechanisms and new data (FIG. 14): (a) in insulin-resistant Mφs, an ERK1/2-SERCA pathway is inhibited, which increases release of ER Ca2+ into the cytosol (75). The results described herein show increased p-CaMKII, a marker of its activation, in Insr−/− and ob/ob Mφs and, consistent with the above mechanism (75), in ERK-inhibited WT Mφs (FIG. 15); (b) inhibition of SERCA can prolong ER stress (80), and CaMKII activation amplifies ER stress through a feed-forward cycle (FIG. 16)—all consistent with the finding of increased CHOP in Mφs freshly isolated from ob/ob mice (68).

Mechanistic Studies.

CaMKII activity will be assayed in control vs. insulin-resistant ER-stressed Mφs. To broaden significance, different sources of Mφs, inducers of insulin resistance, activators of ER stress, and methods for silencing CaMKIIγ will be used. Peritoneal Mφs from Insr−/− mice (76), which is based on the marked down-regulation of insulin receptors by hyperinsulinemia (81-84), including on monocytes from insulin-resistant humans (85,86) will be used. These Mφs vWT Mφs will be challenged with athero-relevant ER stress activators (13): FC loading; 7-ketocholesterol; or low-dose ER stress plus a PRR activator, e.g., the peroxynitrite donor SIN-1 plus oxidized phospholipids (oxPLs) 72. Lipoprotein Lp(a) which is a risk factor for CAD (87-91), a carrier of oxPLs in humans (92), and a potent stimulator oapoptosis in ER-stressed Mφs (72) will be tested. CaMKII activation will be assayed by pThr287 immunoblot (FIG. 15) or by direct CaMKII kinase assay (48).

The level of apoptosis in ER-stressed insulin-resistant Mφs consists of two components: "basal" (i.e., that seen in ER-stressed WT Mφs) plus the increment afforded by insulin resistance, with each contributing ~50% to the final apoptotic response (76). In ob/ob Mφs, partial CaMKII inhibition resulted in a ~40% decrease in the basal component of ER stress-induced apoptosis and a ~65% inhibition in the ob/ob-induced incremental portion, i.e., total apoptosis was decreased the inhibitor to a greater extent in ob/ob than in WT ER-stressed Mφs (5.0±0.4→3.1±0.2% in WT vs. 11.9±1.1→5.6±0.5% in ob/ob). These experiments will be repeated using (a) Camk2g siRNA in ob/oMφs; (b) ob/ob vs. ob/obCamk2g-/-Mφs; and (c) Mφs from the atherosclerosis study below, i.e., Ldlr-/- mice transplanted with marrowWT, Camk2g KO, Insr KO, or Camk2gInsr DKO mice. Mechanism will be probed by determining which of the effectors of CAMKIIgamma-induced pro-apoptotic signaling are increased in insulin-resistant Mφs and decreased by CaMKIIγ deficiency: Fas death receptor induction; STAT1 activation; mitochondrial Ca2+ uptake and cytochrome c release; Nox2 induction/ROS48; UPR amplification; and PKR activation. Four groups of Mφs—con-WT; insulin-resistant-WT; con-Camk2g-/-; and insulin-resistant-Camk2g-/-—will be assayed as follows (48, 68, 93, 94): RT-QPCR for Fas mRNA and FACS analysis for Fas cell-surface expression; immunoblot for p-STAT1; rhodamine-2 staining and mt-pericam fluorescence (95) for mitochondrial Ca2+; immunoblot for mitochondrial and cytosolic cytochrome c and caspase-9 activity assay; RT-QPCR for Nox2 mRNA and DCF staining for cellular peroxide accumulation; immunoblots for p-PERK and CHOP; and immunoblot for p-PKR. These effector endpoints will be increased in insulin-resistant vs. -sensitive ER-stressed Mφs and that both the basal ER stress-induced component and the further increment in insulin-resistant Mφs will be decreased in the absence of CaMKIIγ, leading to an overall dramatic decrease the Camk2g-/- Mφs. However, insulin resistance causes a selective increase in specific endpoints or if the data indicate that factors other than CaMKIIγ can be involved in the insulin resistance-induced increment, mechanistic experiments driven by the data will be conceived and executed.

Figure 16:
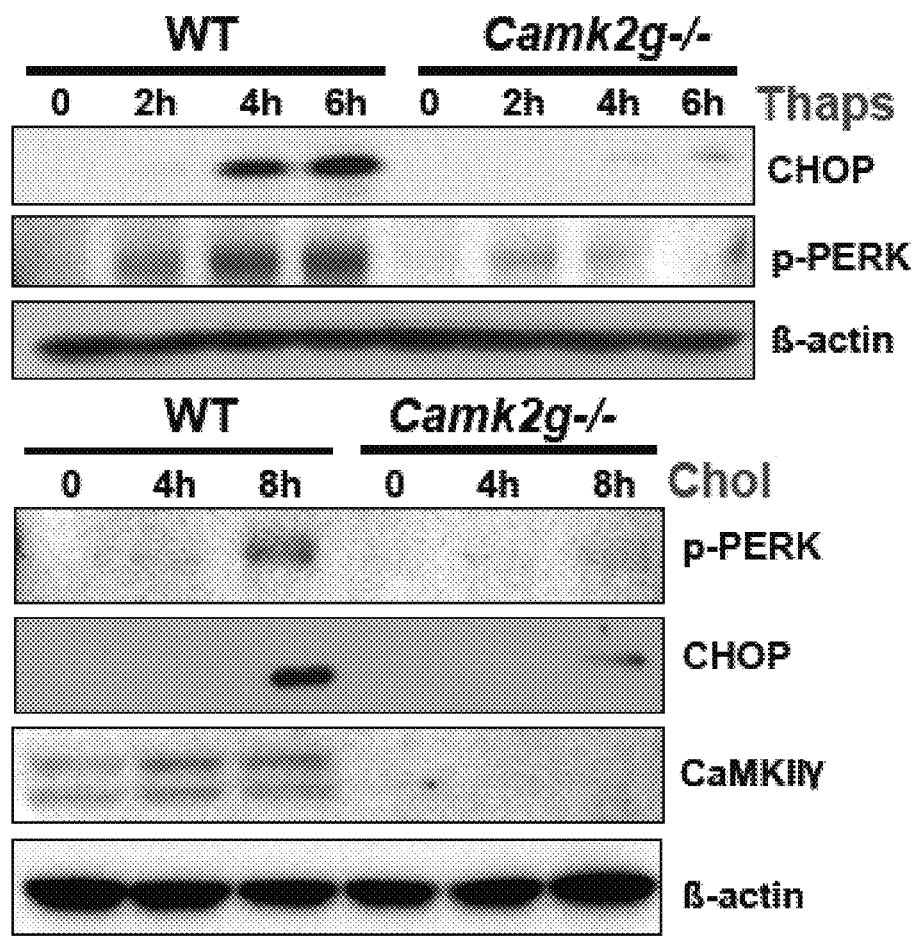
FIG. 16. CaMKIIγ deficiency suppresses the UPR. Mϕs from WT or Camk2g−/− mice were incubated with thapsigargin (Thaps) or under FC-loading conditions (Chol) and then immuno-blotted for UPR proteins, CaMKIIγ, and β-actin.

Without being bound by theory, insulin resistance (IR) enhances the pro-apoptotic effects of CaMKIIγ in ER-stressed Mφs (IR→CaMKII). Positive-feedback cycles are often involved in ER stress-induced apoptotic signaling pathways (93) (FIG. 16). Thus, whether CaMKIIγ can feedback-enhance insulin resistance (IR↔CaMKII) will be explored. If so, CaMKIIγ-deficiency can have the following protective effects in insulin-resistant Mφs based on previous studies (66, 72, 74, 75, 75): (a) ↓ SRA and CD36, ↑ p-Akt, ↑ p-ERK, ↑ SERCA2b, and ↑ p-FoxO1 (immunoblot); (b) ↑ Serca2b, ↓ Ikbe, and ↑ Bcl2, an NF-κB target decreased in insulin-resistant Mφs66 (RT-QPCR); (c) ↓ ER Ca2+ (Fluo-3-thapsigargin fluorescence microscopy assay); and (d) ↓ nuclear FoxO (immunofluorescence in adeno-GFP-FoxO1-transduced Mφs). The latter assay is of particular interest given that CaMKIIγ is necessary for FoxO1 nuclear localization in fasting and insulin-resistant hepatocytes. Together, these studies will provide a comprehensive view of the roles of CaMKIIγ in the pro-apoptotic effects of insulin resistance in ER-stressed Mφs.

Human Atherosclerosis.

Figure 17:
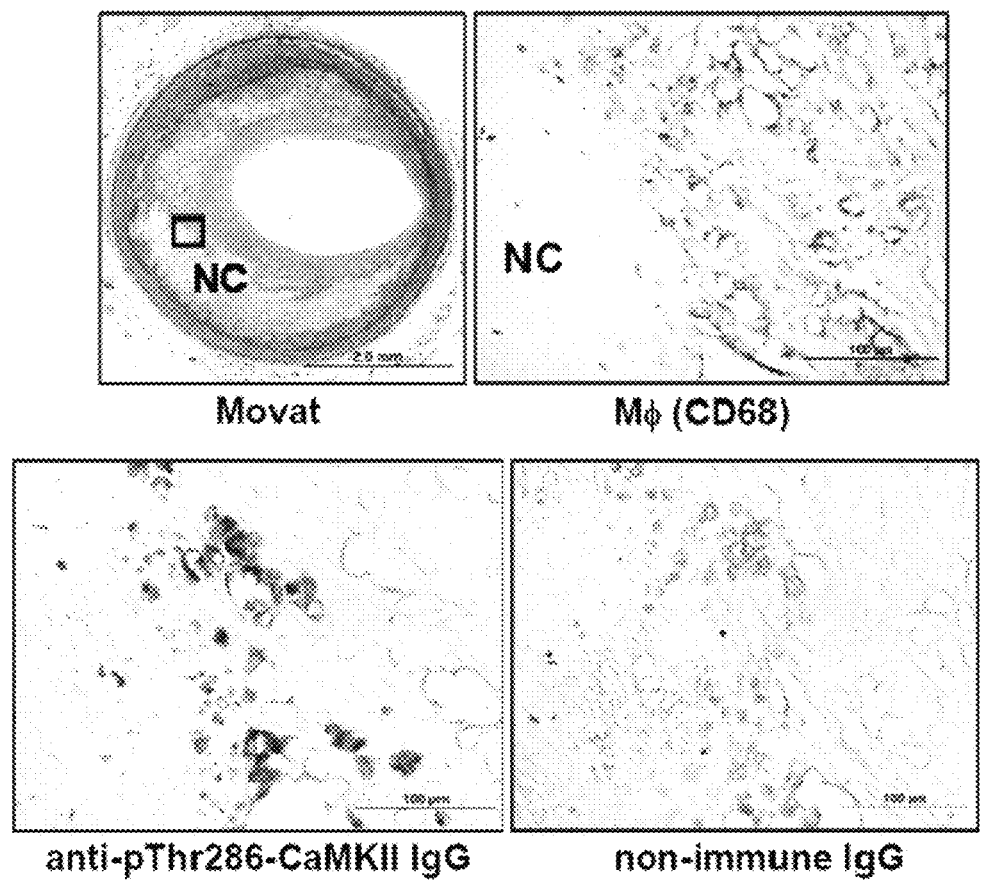
FIG. 17. p-CaMKI in macrophages in advanced human coronary artery plaque. The area examined is depicted by the box in the Movat Pentachrome stained plaque specimen; NC, necrotic core; Bar, 2 mm. The antibody reaction yields a reddish-brown product if positive and is light blue if negative. Bar, 100 μm for enlarged images.

Whereas causation studies will be conducted in mice (next section), whether activation of CaMKIIγ in plaque Mφs increases will be tested (a) as a function of advanced plaque stage; and (b) in the setting of defective Mφ insulin signaling. Freshly isolated/flash-frozen carotid plaque specimens will be divided into 3 small, adjacent sections in the middle of the plaque. The middle section will be used for anti-p-CaMKII immunoblot analysis and quantified by densitometric ratio with total CaMKIIγ and β-actin loading controls. The immediate flanking regions will be microtome-sectioned and then (a) stained with Movat pentachrome for necrotic area measurement (quantified as percent of total area); and (b) immunostained for Mφs, p-CaMKII (FIG. 17), and TUNEL for apoptosis (quantified as percent of Mφs that are positive). The goal is to show that the correlation between p-CaMKII and necrotic area (and Mφ TUNEL) is significant at P=0.05. In addition, these specimens will be classified in a blinded manner into 5 stages using the Virmani-AHA scheme (96): 1=diffuse intimal thickening; 2=fibrous plaques; 3=thick-cap atheroma; 4=thin-cap atheroma; and 5=ruptured plaques. The goal is to test whether if p-CaMKII is enriched in stages 4+5 vs. 1+2. n=15 will be sufficient with 80% power to show at least a 2-fold difference in p-CaMKII at P=0.05 between 4+5 lesions and 1+2 lesions. Finally, all data will be analyzed for correlations with the presence of type 2 diabetes, corrected for lesion stage, and positive correlations between p-CaMKII and both lesion stage and the presence of type 2 diabetes.

Murine Atherosclerosis Study.

The two objectives are: (a) to test the whether CaMKIIγ activation and its pro-apoptotic effects are increased as a function of advanced plaque stage and in the setting of Mφ insulin resistance; and (b) as a causation study, to test the effect and mechanisms of CaMKIIγ deficiency on advanced lesional Mφ apoptosis and plaque necrosis. Using the same overall strategy as previously described (76), 4 groups of mice will be used as bone marrow transplantation (BMT) donors into male Ldlr-/- mice: Camk2gfl/flInsr+/+ (WT→Ldlr-/-); Camk2gfl/flLysmcre+/-Insr+/+(Mφ-CK KO→Ldlr-/-); Camk2gfl/flInsr-/- (Mφ-InsR KO→Ldlr-/-); and Camk2gfl/flLysmcre+/-Insr-/-(Mφ-CK/InsR DKO→Ldlr-/-). All genotypes have been backcrossed onto the C57BL6/J background for >8 generations, and all experiments will use littermate controls. Previous studies have shown that there is almost complete deletion of floxed genes in lesional Mφs on the Lysmcre+/- background (67,97). Six wks after BMT, the mice will be fed the Western diet (WD) for 8, 12, 16, and 20 weeks, which will enable an analysis of early, mid-stage, and advanced/necrotic lesions (16, 65, 67, 71, 97-102). Previous atherosclerosis studies with similar strategies and goals (16, 65, 71, 97, 101, 102), together with the statistics from the previous in vivo study (76), allow an estimate that n=30 male mice per group will give us an 80% chance of detecting a 33% difference in these endpoints among the four groups of mice.

The overall protocols for the mouse atherosclerosis studies, including Mφ apoptosis and necrotic core quantification, have been detailed in publications in this area (16, 65, 67, 71, 72, 97, 101-103). Briefly, plasma is obtained for lipid/lipoprotein analysis, fasting glucose, and insulin. The aortic root and brachiocephalic artery are analyzed for lesion and necrotic area; apoptosis (TUNEL and activated caspase-3); and in-situ efferocytosis. In situ efferocytosis in lesions will be assayed (103). Necrotic areas are defined as acellular areas with Mφ debris (Mφ-specific antigens in the absence of cells) and by the absence of collagen staining. Mφs, SMCs, ECs, and T cells will be identified by IHC, and fibrous caps are quantified for thickness using Verhoeff's and Masson's trichrome stains for elastin and collagen (97). The latter assays will be complemented by probing the 20-wk lesions for complete degradation of medial elastic fibers ("medial erosion") in Verhoeff-stained samples, as described (104), because suppression of Mφ secondary necrosis may lead to less leakage of MMPs, which can be causative for this endpoint (105). The data will be quantified as number of mice in each group whose lesions show medial erosions, as described (104). Positive results would be followed by assaying lesion sections for active MMPs by zymography and near-infrared fluorescence using MMP gelatinase (MMP2/9) substrates, as described (106). The advanced plaque property of intraplaque hemorrhage (107,108) will be assayed using Perl's iron stain (109) and inspection of H&E section and 560-nm fluorescence for RBCs (107,110). IHC using anti-F4/80 (Mφs) and anti-p-CaMKII to will be used evaluate whether p-CaMKII is increased as a function of advanced plaque stage and in the setting of defective Mφ insulin signaling. The anti-p-CaMKII antibody gives no signal above background in Mφs from Camk2g−/− mice. As with human lesions (FIG. 17), a staining pattern that is consistent with the presence of p-CaMKII has been obtained in advanced lesional Mφs, and this signal will be validated using the Mφ-CK KO groups. The IHC data will be quantified as area of p-CaMKII staining per lesion area; percent of CaMKIIγ-stained cells that are Mφs; and percent of Mφs that stain with p-CaMKII. Immunoblots will be conducted on aortic root and arch segments from which the adventitia has been removed so that p-CaMKII (and total CaMKII) can be precisely identified. This analysis does not exclude the contribution of other arterial-wall cells, but IHC studies should allow us to assess whether or not these other cells even express the gamma isoform of the enzyme. Pro-inflammatory (TNFα and IL-6) and anti-inflammatory (TGFβ and IL-10) cytokine mRNA expression laser-capture microdissection (LCM)-RT-QPCR will be conducted, because a decrease in Mφ apoptosis and ER stress would likely decrease plaque inflammation (70,111), and absence of CaMKIIγ may decrease the transcription of inflammatory genes by stabilizing NCoR corepressor function (53,54). The captured RNA will also be used to explore in vivo mechanisms, as guided by cell culture studies. Pro-apoptotic transcriptional targets of activated CaMKIIγ, notably Fas, Nox2, and Chop (Ddit3) mRNA48 will be assessed. mRNA for Serca2b, Ikbe, and Bcl2 (an NF-κB target decreased in insulin-resistant Mφs66) will also be assayed. Mφ Tlr4 and Tlr2 mRNA expression, which are FoxO1 targets (112) will be assayed. With regard to Nox2 and oxidative stress (93), lesional ROS will be assayed using DHE. These results will show that (a) advanced lesional Mφ apoptosis and plaque necrosis, and markers of the CaMKII-apoptosis pathway, will be lower in the CKO vs. WT group, and particularly in the CK/InsR DKO vs. WT group; (b) Mφ Fas, Nox2, and Chop mRNA and ROS will be lower in the CKO vs. WT group, and particularly the CK/InsR DKO vs. WT group; and (c) Serca2b and Bcl2 will be lower, and Ikbe higher, in the insulin-resistant vs. WT group, and it will be interesting to see whether these trends are reversed in the CK/InsR DKO group.

TABLE 1

Summary of mouse models and predictions for endpoints

| Model | Mφ apoptosis | Plaque necrosis | Mφ-p-CaMKII | Pro-apoptotic effects of activated CaMKII (Fas, Nox2, Chop, ROS) | Serca2b Bcl2 | Ikbe |
|---|---|---|---|---|---|---|
| WT → Ldlr−/− | ++ | ++ | ++ | ++ | ++ | + |
| Mφ-CK KO → Ldlr−/− | + | + | + | + | ? | ? |
| Mφ-InsR KO → Ldlr−/− | ++++ | ++++ | ++++ | ++++ | + | ++ |
| Mφ-CK/InsR DKO → Ldlr−/− | + | + | + | + | ?++ | ?+ |

Necrosis, and markers of the CaMKII-apoptosis pathway, will be lower in the CKO vs. WT group, and particularly in the CK/InsR DKO vs. WT group; (b) Mφ Fas, Nox2, and Chop mRNA and ROS will be lower in the CKO vs. WT group, and particularly the CK/InsR DKO vs. WT group; and (c) Serca2b and Bcl2 will be lower, and Ikbe higher, in the insulin-resistant vs. WT group, and it will be interesting to see whether these trends are reversed in the CK/InsR DKO group.

Characterization of the Mechanisms Whereby Liver CaMKIIγ Deficiency Improves the Metabolic Disturbances of Obesity and Assaying Whether Liver-Specific CaMKIIγ Deficiency Will Suppress Atherosclerosis in Obese Mice.

Figures 9A, 9B, 9C, 9D:
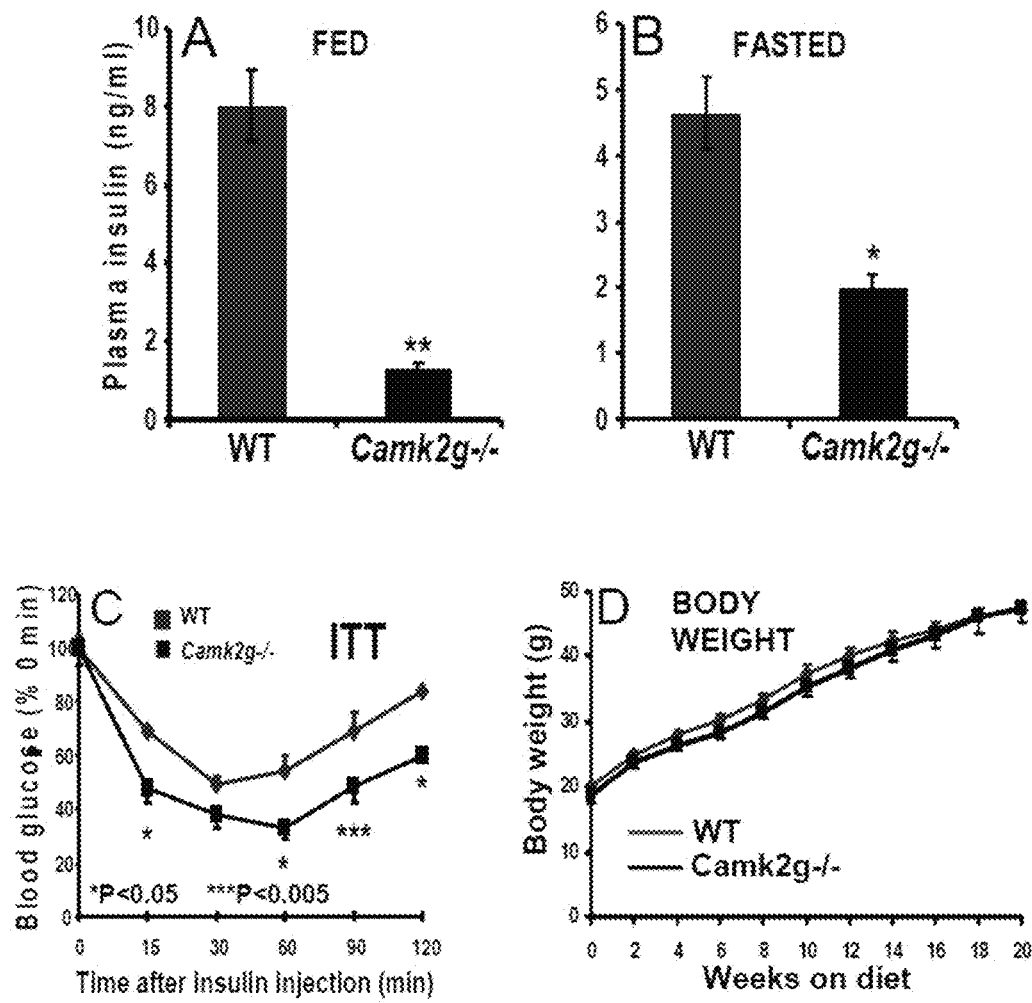
FIGS. 9A-I. CaMKIIγ deficiency reduces hyperinsulinemia and improves insulin and glucose metabolism in obese mice.
Figures 9E, 9F:
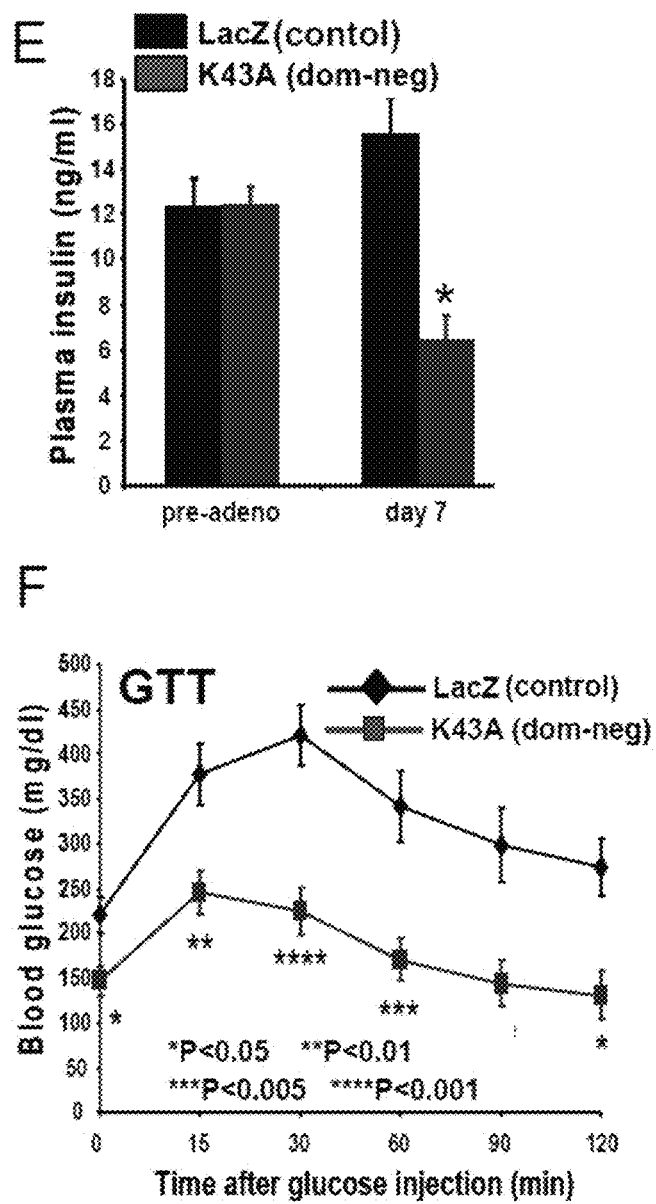
Figures 9G, 9H:
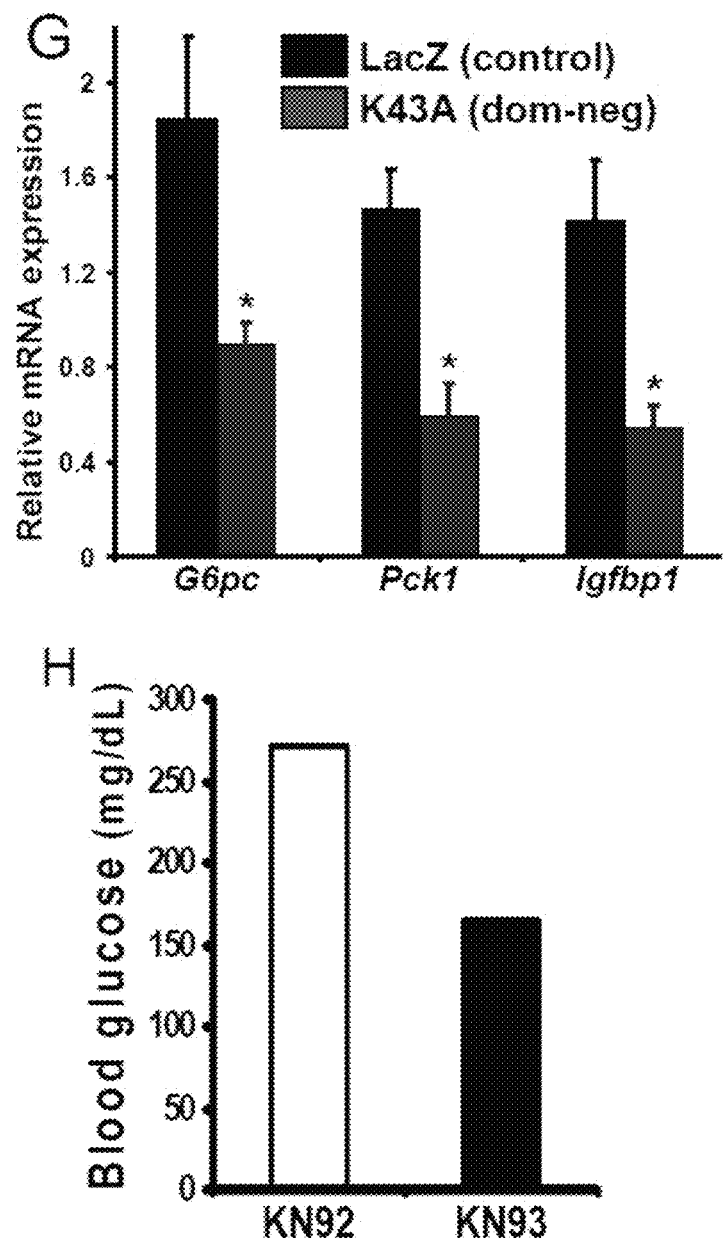
Figure 9I:
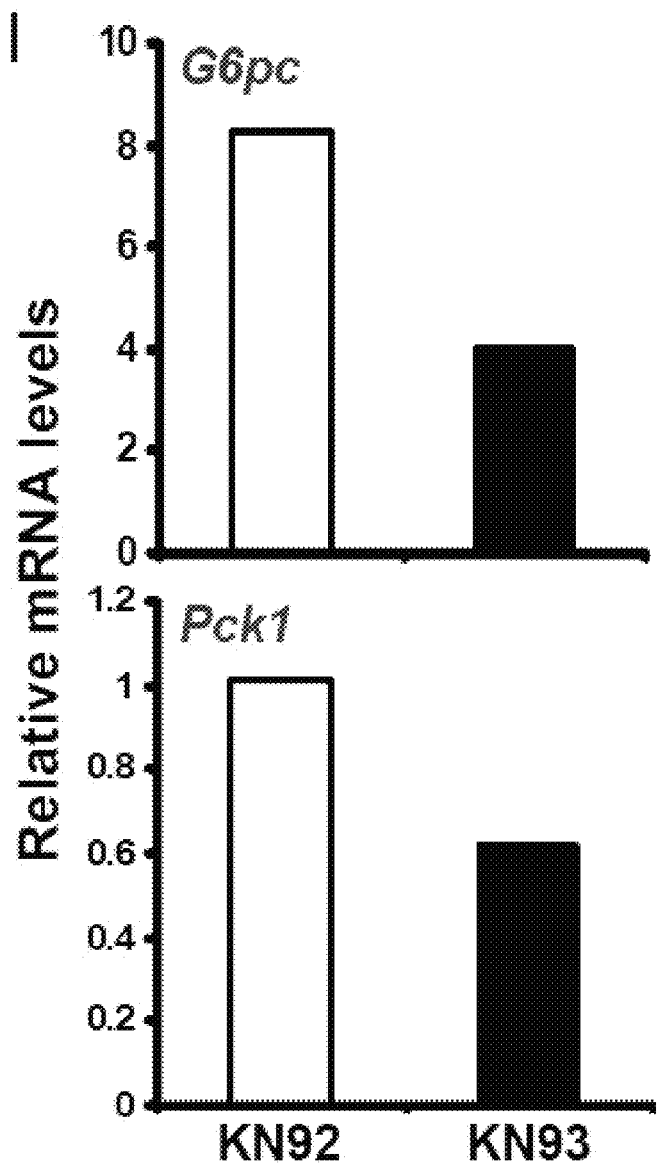

Deficiency of HC CaMKIIγ—the same enzyme that plays a critical role in ER stress-induced Mφ apoptosis—improves atherogenic metabolic disturbances in obesity. CaMKIIγ was the major isoform of CaMKII in mouse and human liver and that p-CaMKIIγ, a measure of its activation state, was increased in the livers of ob/ob mice, diet-induced (DIO) mice (5.24 kcal/g, 60% cals from fat, ×20 wks), and morbidly obese humans compared with lean controls (FIGS. 8A-B). Consistent with these data and the fact that obesity leads to hepatic ER stress (34), ER stress activation by azetidine or palmitate increased p-CaMKIIγ in HCs, and CaMKIIγ deficiency in DIO mice suppressed UPR activation, suggesting that CaMKIIγ participates in a UPR positive feedback cycle in HCs like it does in Mφs (see FIG. 16). The functional importance CaMKIIγ in obesity was shown by finding that CaMKIIγ-deficient DIO michave markedly lower plasma insulin and are more responsive to insulin-mediated glucose lowering than DIO WT mice despite no difference in weight (FIG. 9A-D). The mice also had an improvement in blood glucose during a glucose tolerance test. Similar results were found using acute inhibition of liver CaMKII through the use of adeno-K43A-CaMKII (FIG. 9E-F), which is a kinase-inactive, dominant-negative form of CaMKII123 that were verified inhibits hepatic CaMKII. The mRNAs for the gluconeogenic (GNG) genes G6Pase and PEPCK were decreased in the livers of adeno-K43A-CaMKII-treated ob/ob mice (FIG. 9G).

Figures 10A, 10B:
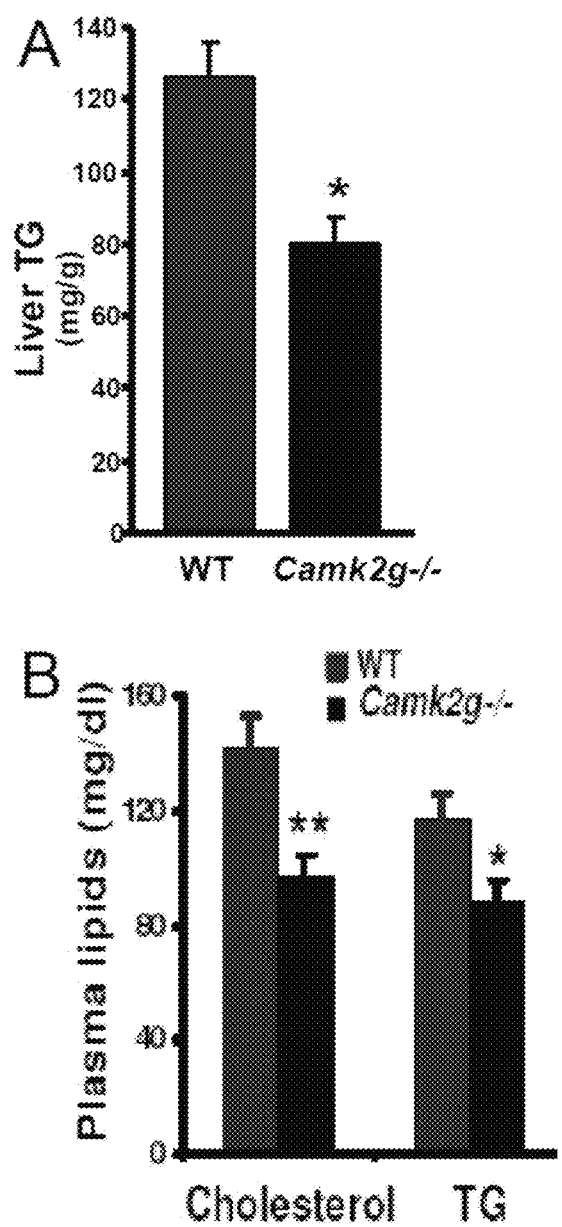
FIGS. 10A-D. CaMKIIγ deficiency improves steatosis, dyslipidemia, and inflammation in obese mice.
Figures 10C, 10D:
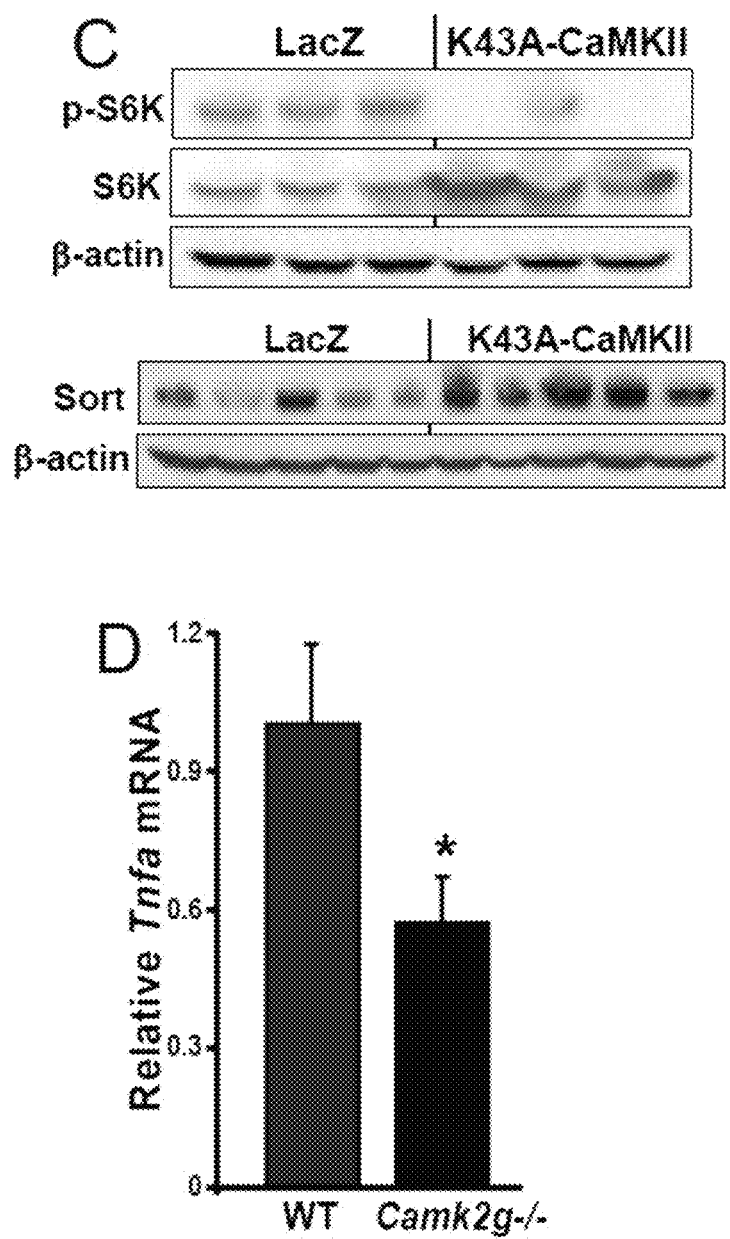

Both genes are targets of FoxO1, as is Igfbp1, which was also decreased in CaMKII-inhibited livers. These data are consistent with CaMKII inhibition suppressing FoxO1 nuclear localization (see below). CaMKIIγ-deficient DIO mice also had decreased (a) liver triglyceride (TG) content (FIG. 10A); (b) SERBP-1c-induced lipogenic mRNAs but not mRNAs associated with fatty acid oxidation; and (c) plasma cholesterol and TG (FIG. 10B). High fat diet-induced dyslipidemia involves stimulation of an mTORC1-pS6K pathway by hyperinsulinemia acting on residual hinsulin receptors, leading to suppression of Sortilin 1 (Sort). Decreased Sort has been linked genetically to human dyslipidemia, and the mechanism appears to be decreased Sort-mediated degradation of LDL apoB-100, perhaps through a Sort chaperone-mediated lysosomal degradation pathway 124. This pathway is partially prevented by CaMKII inhibition (FIG. 10C). Finally, hepatic Tnfa mRNA was decreased ~50% in Camkg2g−/− vs. WT DIO liver (FIG. 10D).

Hepatocyte CaMKIIγ Deficiency Lessens Hyperinsulinemia and Subsequent Dyslipidemia by Decreasing Gluconeogenesis (GNG) and Hepatic Glucose Production (HGP) Via a Mechanism Involving Nuclear Exclusion of FoxO1 (FIG. 18).

This analysis is based on (a) the role of elevated HGP in promoting hyperinsulinemia in obesity and the importance of hyperinsulinemia in driving dyslipidemia; (b) the finding that CaMKII inhibition in obese mice decreases FoxO1-induced GNG genes and the FoxO1 target, Igfbp1 (FIG. 8G); and (c) data on links among hepatic CaMKIIγ, FoxO1, and GNG in fasting lean mice.

The Camk2g mice described herein, which are now being crossed with α1-antitrypsin Cre (A1atcre+/−) mice to delete CaMKIIγ in HCs125 will be used. Four groups of male mice will be fed the DIO diet for 20 wks starting at 4 wks of age: DIO/Camk2gfl/fl (DIO/WT) and chow-fed control (lean/WT); and DIO/Camk2gfl/flA1atcre+/−(DIO/Li-CK KO); and chow-fed control (lean/Li-CK KO). To rule out compensatory effects of germline knockout, a cohort of DIO/Li-CK KO mice will be "restored" with adeno-T287D-CaMKII (vs. adeno-LacZ control), which is a constitutively active form of the kinase (123) that should reverse the predicted beneficial metabolic effects in the DIO/Li-CK KO mice. Food intake and body weight will be monitored, and fasting plasma glucose and insulin will be obtained every 4 wks. At the end of the feeding period, the mice will be fasted for 6 h, weighed, and sacrificed. In view of links between circadian rhythm and metabolism (126-128), there will be strict adherence to a 12-h light/dark cycle, and all mice will be sacrificed at the same time of day. Although Camk2g−/− mice develop to adulthood without obvious morphological or functional abnormalities, including those related to the liver 48, plasma will be obtained for the metabolic and lipid parameters described below and for alanine transaminase (ALT) and aspartate transaminase (AST) as a measure of HC dysfunction. The liver will then be removed immediately, snap-frozen in liquid nitrogen, and stored at −80° C. Deletion of CaMKIIγ will be confirmed by RT-PCR and immunoblot, and specificity for liver deletion will be determined by similar analysis on snap-frozen samples of brain, heart, kidney, adipose tissue, skeletal muscle, and intestine. The liver will also be analyzed for p-CaMKII, p-JNK134, and UPR markers (34) by immunoblot, and, in the context of liver inflammation, for Tnfa by QPCR. Without being bound by theory, these endpoints will be elevated in the DIO/WT group vs. lean-WT but suppressed in the DIO/Li-CK KO group.

HC CaMKIIγ Deficiency Improvement of Glucose and Lipid Metabolism 8 mice in each groups will undergo a complete hyperinsulinemic-euglycemic clamp study, which will further assess insulin sensitivity and quantify basal and insulin-stimulated hepatic glucose production (HGP) and insulin-stimulated glucose uptake, glycolysis, and glycogen synthesis in peripheral tissues (e.g., skeletal muscle, adipose tissue) (129). The DIO/WT group vs. lean-WT group should show decreased glucose infusion, increased HGP, and decreased peripheral tissue glucose disposal, reflective of insulin resistance in these mice. These parameters will be improved (i.e., increased glucose infusion and reduced HGP) in DIO/Li-CK KO vs. DIO/WT mice. 8 mice per group may have 80% power to show statistically significant differences between the DIO/Li-CK KO and DIO/WT groups ($P<0.05$).

DIO/Li-CK KO mice will have a less atherogenic lipid profile compared with DIO/WT mice, which will be tested by assaying plasma TG, total cholesterol, HDL-cholesterol, FPLC lipoprotein profile, and atherogenic and are elevated in insulin-resistant states (130). To complement the plasma studies, liver samples from the mice will be analyzed for TG content, LDL receptor protein and mRNA, and mRNA for Srebp1c and its transcriptional targets. The predicted decrease in plasma TG-rich lipoproteins in the DIO/Li-CK KO vs. DIO/mice can be due to decreased hepatic secretion or increased hepatic clearance. To assay TG secretion, a Triton WR-1339 study will be conducted (131). Briefly, fasted mice will be injected with [35S]-methionine to metabolically label apoB and with Triton WR-1339 to block lipoprotein clearance. Plasma will be collected throughout a 2-h post-injection period and analyzed for TG content and VLDL, and apoB100 and apoB48 will be assayed by SDS-PAGE followed by autoradiography. The rate of rise of labeled apoB-labeled lipoproteins during the 2-h period is a measure of secretion rate. CaMKIIγ deficiency increases (de-represses) hepatic Sort expression in the setting of insulin resistance (FIG. 10C). The goal is to determine if silencing hepatic Sort in DIO/Li-CK KO mice increases VLDL secretion. Fatty liver of DIO mice is markedly improved by CaMKIIγ deficiency (FIG. 10A). TG content will be measured and stained for Oil Red 0-positive lipid droplets in liver specimens of the 4 groups of mice. If DIO/Li-CK KO mice show decreased liver TG accumulation, mechanism will be probed by assaying the expression of lipogenic genes, including Srebf1, Fasn, Acaca, Scd1; genes involved in fatty acid oxidation, including Ppara, and Acox1; and Nampt in view of its role in steatosis in liver-FoxO KO mice (132). Follow-up studies will explore the molecular mechanisms linking CaMKII to the positive findings, as guided by the results of the above experiments. For example, preliminary data support a link between the UPR effector ATF3 and the mTORC1-SORT suppression pathway, and thus, given the ability of CaMKIIγ to amplify the UPR.

Obesity is Promoted by CaMKIIγ Phosphorylation

In Mφs, ER stress activates CaMKIIγ through a pathway involving CHOP-induced release of ER Ca2+ stores (48,68). In view of the induction of hepatic ER stress and CHOP in obesity (34) (above) and the causative role for CHOP in ER stress-induced hepatic steatosis (94), whether CHOP is necessary for CaMKIIγ activation in obesity will be tested. Chopfl/fl mice on a pure C57BL6/J background have been made. CHOP deletion occurs when the mice were crossed with a deletor-Cre mouse. These mice will be crossed with A1atcre+/− mice to test whether these mice, compared with control Chopfl/fl mice, have less hepatic p-CaMKIIγ on the DIO diet (see FIG. 8). If so, and if glucose and lipid metabolism are improved in these mice using the above assays, they will be transduced with constitutively active adeno-T287D-CaMKII to show that the beneficial effects of hepatic CHOP deficiency are reversed. Follow-up metabolic and mechanistic experiments will follow pending the results.

GNG is Promoted by CaMKII.

Figure 19A:
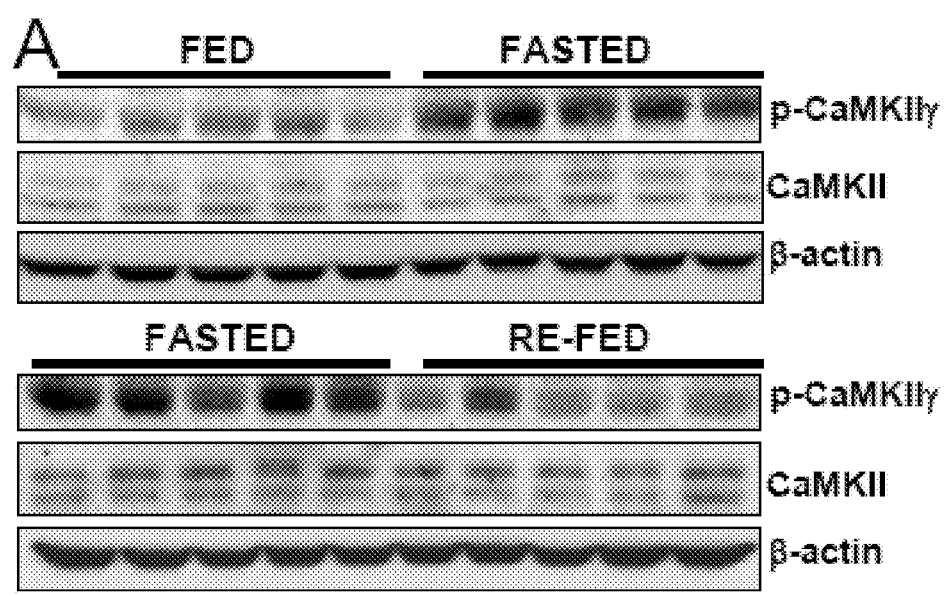
FIGS. 19A-H. Fasting activates hepatic CaMKII, and CaMKII deficiency or inhibition suppresses GNG and nuclear FoxO1.
Figure 19B:
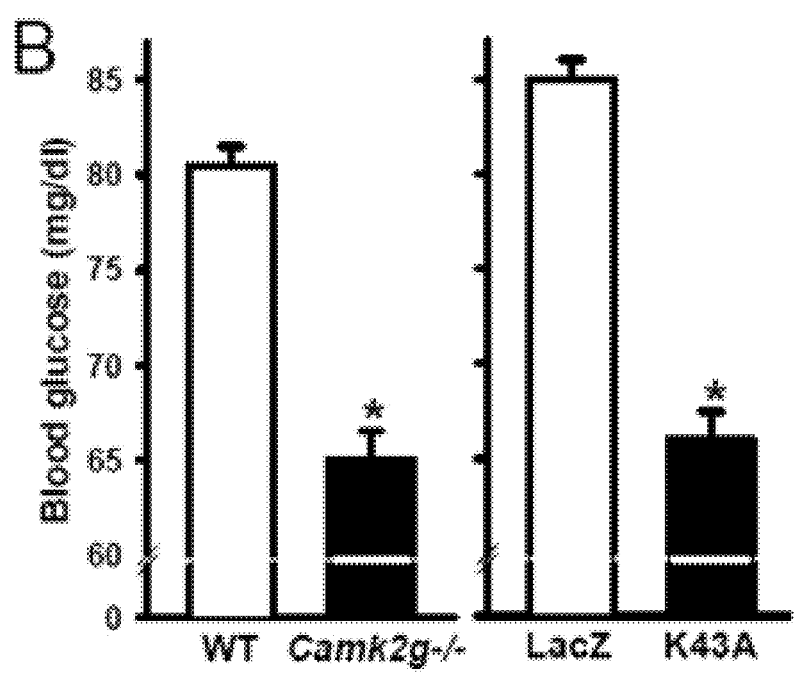
Figure 19C:
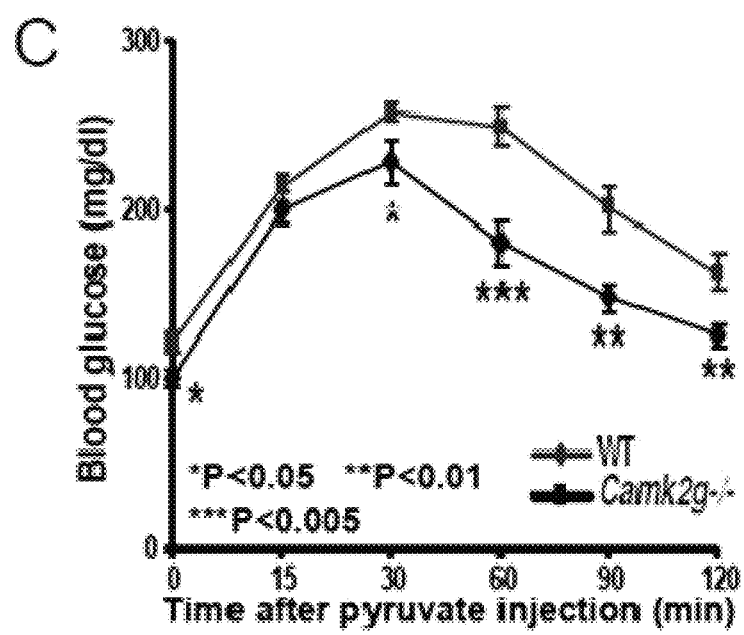
Figure 19D:
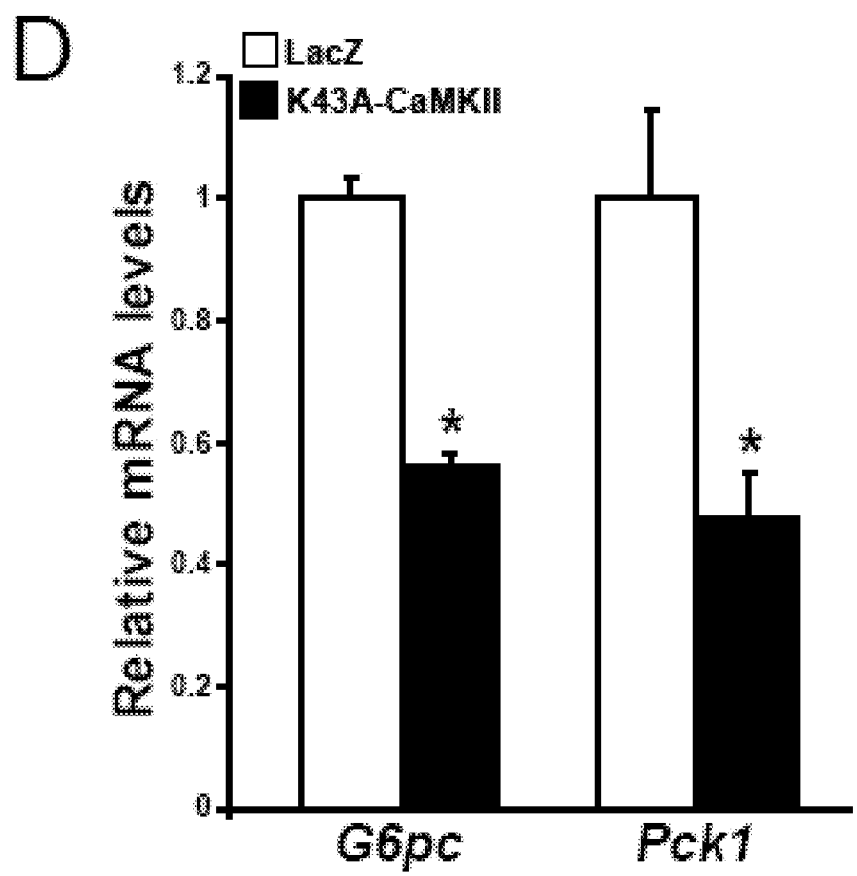
Figures 19E, 19F:
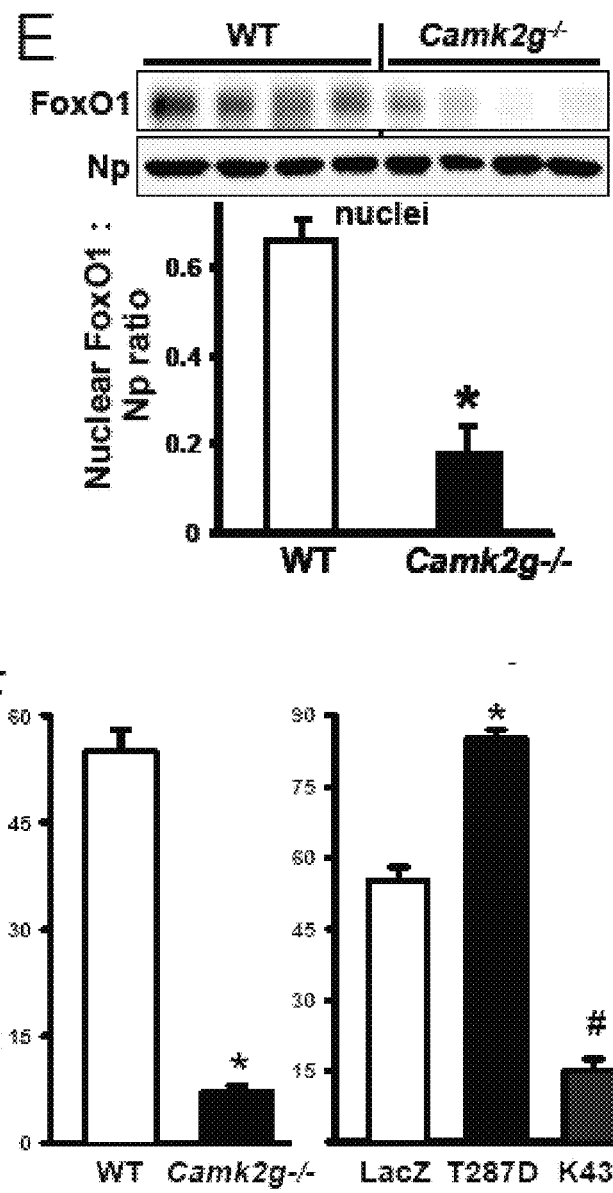
Figure 19G:
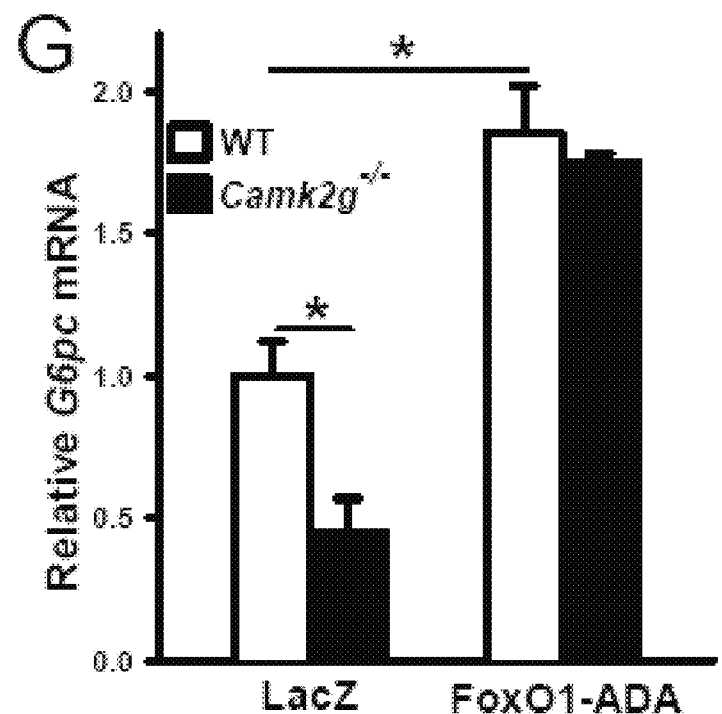
Figure 19H:
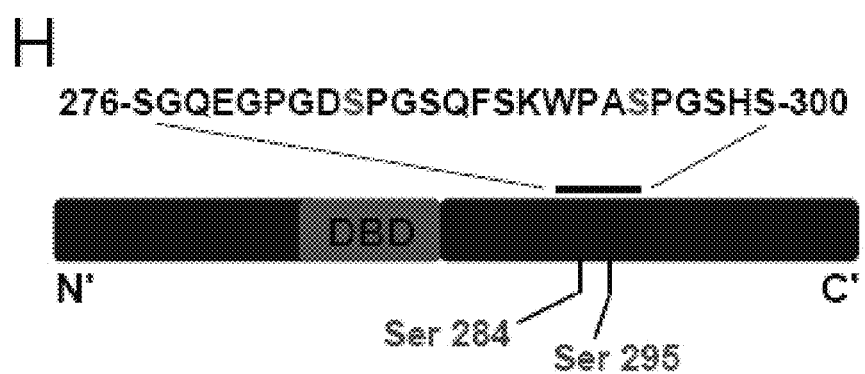

Fasting promoted phosphorylation of CaMKIIγ and that this was decreased by re-feeding (FIG. 19A). Consistent with these data, glucagon (and forskolin) promoted CaMKIIγ phosphorylation in primary HCs. Functional importance in vivo was shown by decreases in fasting and pyruvate-stimulated blood glucose and in liver G6pc and Pck1 mRNA in fasting Camk2g−/− mice or in WT mice treated with adeno-K43A-CaMKII to more acutely inhibit liver CaMKII (FIG. 19B-D). CaMKIIγ deficiency or inhibition in fasting liver or in serum-starved HCs also led to a dramatic decrease in nuclear FoxO1 (FIGS. 19E-F), and constitutively active T287D CaMKII increased nuclear FoxO1 (FIG. 19F), plasma glucose and insulin, and hepatic G6pc and Pck1 mRNA. The suppressive effect of CaMKIIγ deficiency on G6pc mRNA was abrogated by transduction with constitutively nuclear FoxO1-ADA (FIG. 19G), consistent with the idea that the effect of CaMKII deficiency requires nuclear exclusion of FoxO1. It may seem inconsistent that a kinase can promote nuclear FoxO1 given that Akt-induced FoxO1 phosphorylation at T24, S316, and S253 does the opposite (133). Indeed, CaMKIIγ deficiency did not promote phosphorylation at these sites. However, LC-MS phospho-peptide mapping studies (134) showed that two other sites in FoxO1—Ser284 and 295—were phosphorylated in serum-starved HCs from WT mice but were completely unphosphorylated in HCs from Camk2g−/− mice (FIG. 19H). Thus, without being bound by theory, the absence of pSer284/295 in CaMKII-deficient HCs promotes FoxO1 nuclear exclusion and thus suppresses GNG.

G6pc and Pck1 mRNA and nuclear FoxO1 in the 4 groups of mice will be assayed. Both will be suppressed in DIO/Li-CK KO vs. DIO/WT mice. FoxO1 from the mice will be immunoprecipitated for phospho-peptide mapping. CaMKII deficiency will be associated with absent pSer284/295-FoxO1. S284/295A-FoxO1 can mimic the effect of CaMKIIγ inhibition (↑, nuclear FoxO1 and G6pc and Pck1 mRNA), while S284/295D FoxO1 should be resistant to the effects of CaMKIIγ inhibition. HCs of liver-specific FoxO1 KO mice, which have decreased GNG125, will be transduced with GFP-tagged WT or mutant FoxO1 constructs, ±adeno-K43A-CaMKII to inhibit CaMKII, and then FoxO1 localization and G6pc & Pck1 mRNA will be assayed. To complement the use of K43A-CaMKII to inhibit CaMKII, HCs from Li-CK KO will be transduced with adeno-WT-FoxO1 vs. adeno-S284/295D-FoxO1. Without being bound by theory, this mutant will be constitutively nuclear and have a dominant negative effect on the ability of CaMKIIγ deficiency to suppress GNG. To summarize:

These predictions will be translated to DIO-fed L-FoxO1 mice transduced with the above adenoviral constructs. The endpoints will be hepatic G6pc and Pck1 mRNA; nuclear FoxO1 where applicable; plasma glucose (including post-pyruvate challenge) and insulin; and the lipid and lipoprotein parameters described above. The predictions are similar to those in the table, where decreases in the GNG genes will be accompanied by improvements in glucose and lipid/lipoprotein metabolism. In the unlikely situation that HGP is affected but G6pc and Pck1 are not, the GNG genes Pdk4, Fbp1, and Gck will be assayed.

Activation of CaMKIIγ in the Liver of Obese Humans.

Flash-frozen fresh liver biopsy specimens from obese subjects undergoing bariatric surgery and from lean subjects undergoing general surgery will be examined There will be no patient identifiers, but there will be a coded list for each subject that includes weight, waist:hip ratio, age, and sex; diabetic/metabolic medicines; fasting plasma glucose, insulin, HbA1c, and free fatty acids; and based on histological analysis, degree of steatosis and steatohepatitis (graded on a scale from 1 to 5). The specimens will be immunoblotted for p- and total CaMKIIγ and for ER stress markers, including CHOP and Sort. The data will be quantified by densitometric analysis relative to loading controls. The primary goal is to determine whether p-CaMKII is higher in liver from obese vs. lean subjects and whether within the obese group there is an increase of p-CaMKII as a function of worsening insulin resistance. A secondary goal is to determine whether high levels of p-CaMKII correlate with high levels of CHOP and a low level or Sort. The results described herein (FIG. 8B) show that every lean liver sample has a lower p-CaMKII level than of every obese sample, and so the planned sample size of n=20 for obese and lean livers should have a >95% power to show statistically significant differences in level of p-CaMKII between lean- and obese-derived specimens (P<0.05). For the associations within obese livers between p-CaMKII and insulin resistance and between p-CaMKII and CHOP and Sort expression, the 20 obese liver samples will provide 80% power to find a correlation coefficient of 0.6 to be statistically significant. Further studies will be guided by mechanistic studies, e.g., those related to FoxO in the previous section.

CaMKIIγ in Liver Mφs Plays a Role in Insulin Resistance and Glucose and Lipid Metabolism in the Setting of Obesity.

HCs in obese mice express the chemokine CCL2 (MCP-1), which attracts new myeloid cells that subsequently play an important role in hepatosteatosis by promoting the transcription of genes involved in fatty acid esterification and TG accumulation (45). In addition, activated liver Mφs, including Kupffer cells, may suppress HC fatty acid oxida-

TABLE 2

| HCs lacking FoxO1 | | Predictions | | |
|---|---|---|---|---|
| adeno-CaMKII | adeno-FoxO1 | nucl FoxO1 | G6pc, Pck1 | Explanation of Predictions |
| control | control | N/A | ↓ | GNG requires FoxO1[125] |
| control | WT | nucl | ↑ | FoxO1 should restore GNG mL1-FoxO1 HCs[125] |
| K43A | WT | cytopl | ↓ | CaMKII inhibition should suppress GNG-see FIG. 8 |
| control | $S^{284/295}A$ | cytopl | ↓ | $S^{284/295}A$-FoxO1 should mimic CaMKIIγ deficiency if pSer284/295 is important |
| control | $S^{284/295}D$ | nucl | ↑ | $S^{284/295}D$-FoxO1 may be constitutively nuclear |
| K43A | $S^{284/295}D$ | nucl | ↑ | $S^{284/295}D$-FoxO1 should block the GNG-suppressive effect dom-neg CaMKII | ad, adenovirus;
control, ad-LacZ;
K43A, dom. neg. CaMKII, S→A FoxO1, constitutively de-phos model; S→D FoxO1, constitutively 'phos' model tion through a paracrine mechanism (44). While HC CaMKIIγ can be instrumental in attracting new Mφs, without being bound by theory, Mφ CaMKIIγ can play an important role in Mφ-mediated effects on HC lipid metabolism. In particular, saturated fatty acids, which Mφs can be exposed to in obese liver, activate the UPR in Mφs and that UPR activation is linked to Mφ inflammation (72,111). If so, and given the role of CaMKIIγ in mediating and amplifying ER stress processes in Mφs (FIG. 16), liver Mφ CaMKIIγ can have important effects on HC lipid metabolism and insulin resistance in the setting of obesity. As described herein, TNFα is decreased in obese liver with inhibited CaMKII (FIG. 10D), and CaMKIIγ deficiency is linked to decreased Mφ inflammation (53,54). A DIO study similar will be performed wherein LysMCre mice will be used instead of A1at-Cre mice. If Mφ CaMKIIγ deficiency improves metabolic parameters, including steatosis, in the setting of obesity, mechanism will be examined. The primary concept is that ER stress-induced inflammation of Mφs can be lower, and so liver Mφ UPR and cytokine mRNAs by LCM-RT-QPCR will be assayed. In theory, there can also be a decrease in the number of liver Mφs if, for example, Mφ accumulation will be assayed. These are processes that have been linked to dyslipidemia (136), hyperglycemia (137), and the effect of increased FFAs and insulin resistance on the endothelium (130, 138, 139). For plaque progression, inflammatory cytokine expression will be assayed in plaque cells, especially Mφs28; Mφ apoptosis, which can be triggered by saturated FAs and insulin resistance (72,73); defective efferocytosis, which can be worsened by saturated FAs in obesity (140); and intraplaque hemorrhage in advanced plaques, which has been linked to the dyslipidemia of diabetes (141).

Absence of CaMKIIγ in liver Mφs can improve insulin sensitivity and glucose and lipid metabolism. In that case, the LysMCre model can have two mechanisms for improvement in atherosclerosis. Thus, whether deficiency of both Mφ and HC CaMKIIγ will have marked protective effects on all stages of atherosclerosis will be tested. For this purpose, 2 additional groups will be added to the study described herein in which the Li-CK LDLR DKO mice are transplanted with bone marrow from WT vs. Camk2gfl/flLysmcre+/− mice. This will be evaluated by testing all aspects of atherosclerosis and metabolism.

TABLE 3

Summary of mouse models and predictions for endpoints:

| Model | Plasma glucose | Plasma insulin | Insulin resistance (clamp) | Dyslipidemia | Fatty liver | Model | Atherosclerosis |
|---|---|---|---|---|---|---|---|
| lean/WT | normal | normal | normal | normal | normal | LDLR KO | +++ |
| DIO/WT | ↑ | ↑ | ↑ | ↑ | ↑ | Li-CK LDLR DKO | ++ |
| lean/Li-CK KO | normal | normal | normal | normal | normal | Mφ CK → Li-CK LDLR DKO | + |
| DIO/Li-CK KO | normal | normal | normal | normal | normal | | |
| ad-T287D → DIO/Li-CK KO | ↑ | ↑ | ↑ | ↑ | ↑ | | |

CaMKIIγ deficiency deceased monocyte chemokine receptor expression. Thus, liver Mφ content will be quantified using Mφ IHC. Further mechanistic studies will be driven by the data. For example, there is evidence that PPARδ activation can be an ameliorating process in liver Mφs in the setting of obesity (44), which will prompt experiments investigating links among CaMKII, ER stress, inflammation, and PPARδ pathways in liver Mφs from the different groups of mice.

Atherosclerosis Studies Related to Liver CaMKIIγ.

Figure 20A:
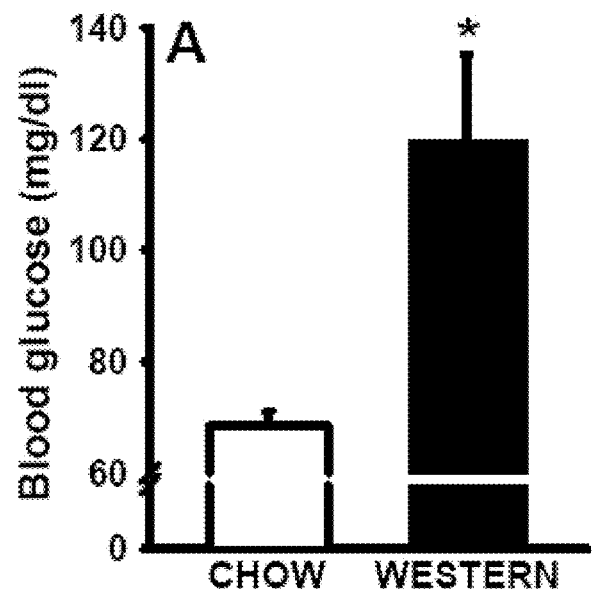
FIGS. 20A-B. CaMKIIgamma is phosphorylated in the livers of WD-fed Ldlr−/− mice. Ldlr−/− mice on a chow or Western diet for 11 wks were assayed for blood glucose FIG. 20A; P<0.001) and hepatic p-CaMKII, total CaMKII, and beta-actin by immunoblot (FIG. 20B).
Figure 20B:
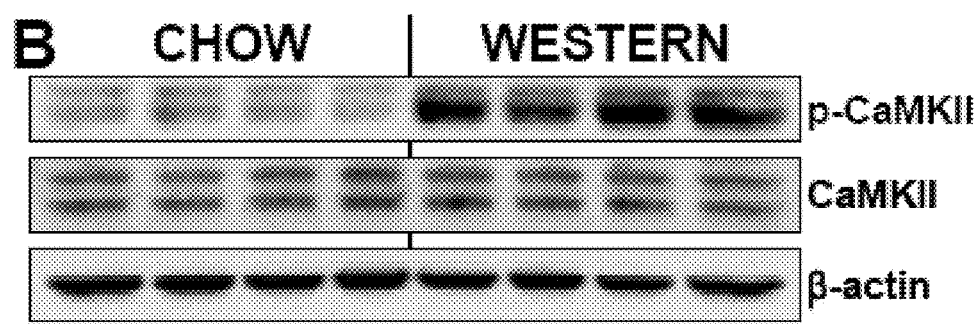
Figure 21A:
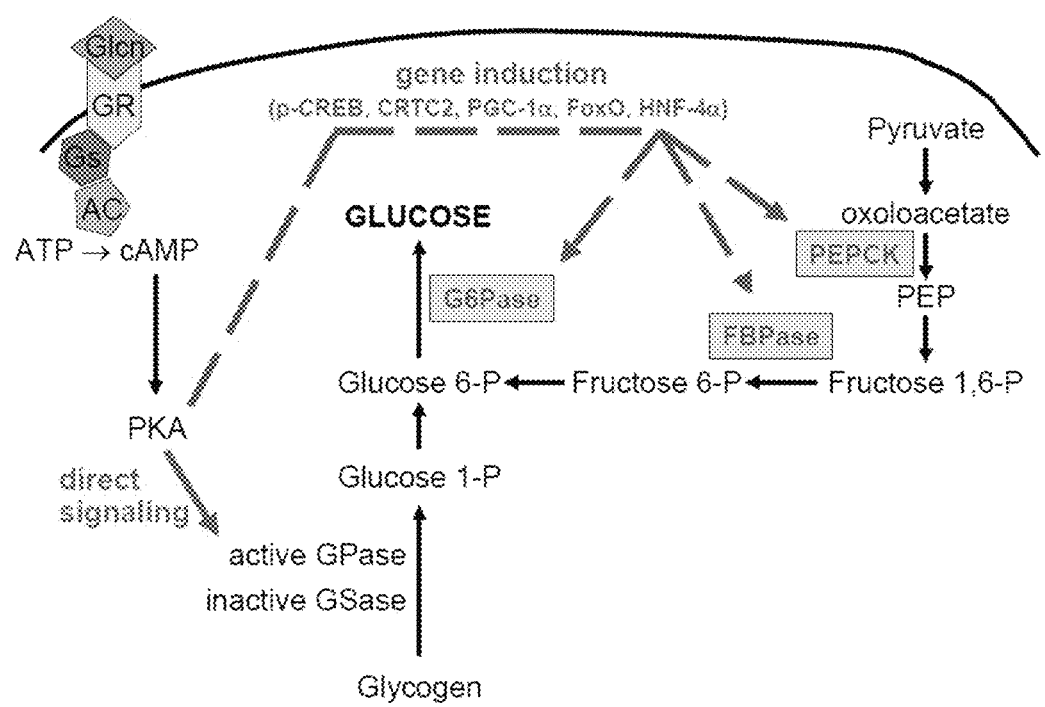
FIGS. 21A-21AV show a molecular link in glucagon-induced hepatic glucose production in fasting and obesity.
Figure 21B:
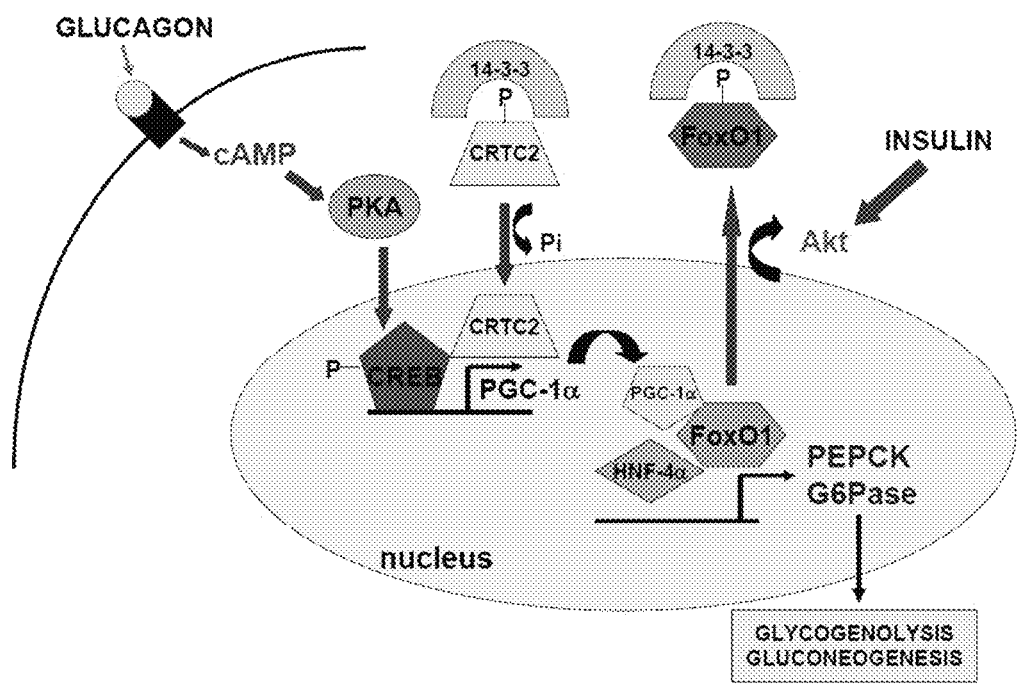
FIG. 21B shows transcriptional control of hepatic glucose production (HGP).
Figure 21C:
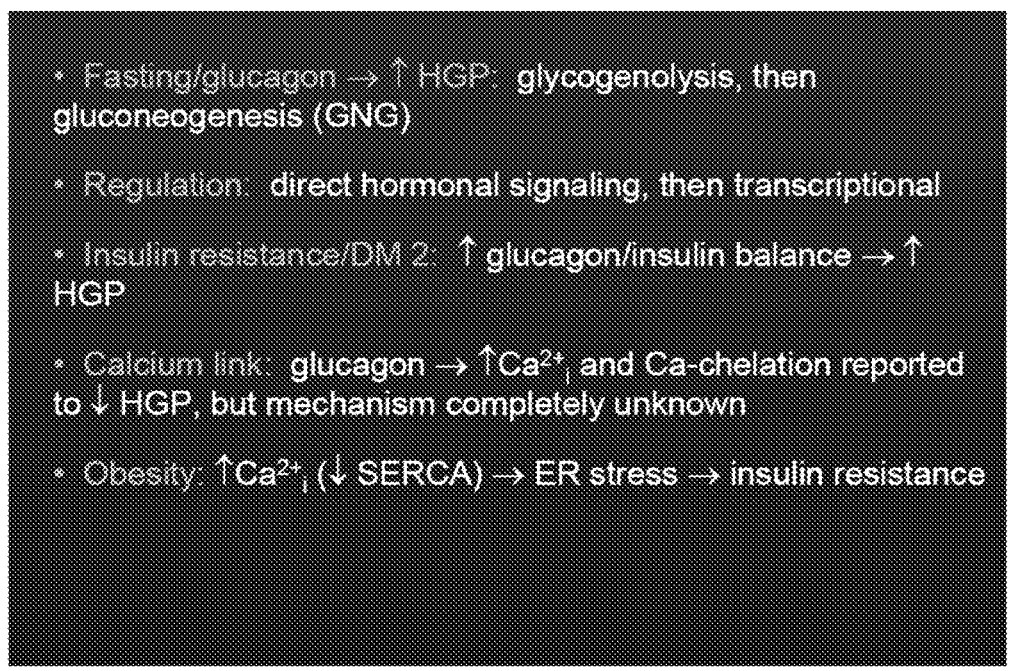
FIG. 21C shows a link between hepatic glucose production, fasting/glucagon, insulin resistance/DM2 and calcium and obesity. The link between an increase in calcium and HGP will be studied.
Figure 21D:
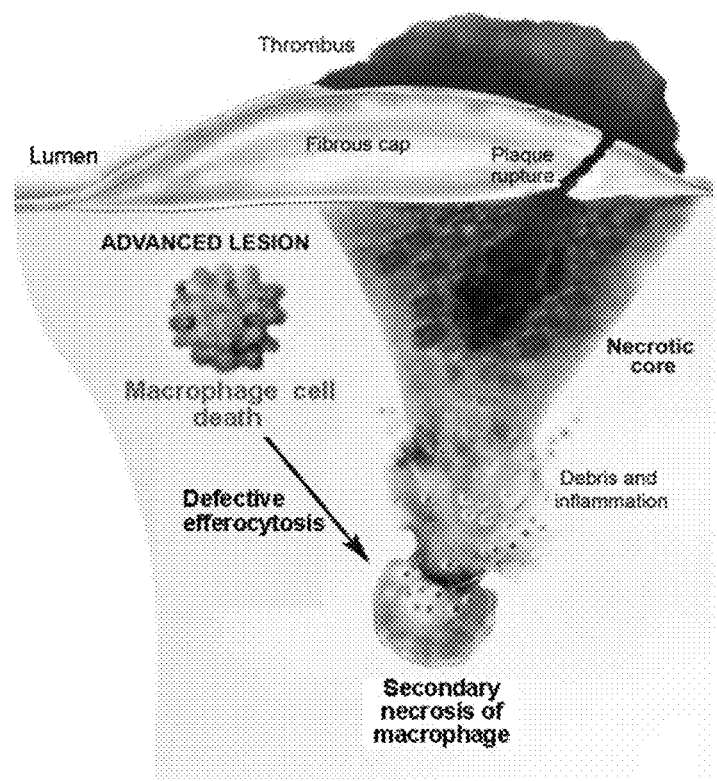
FIGS. 21D-F show a brief historical perspective of the link between calcium, hepatic glucose production and apoptosis.
Figure 21E:
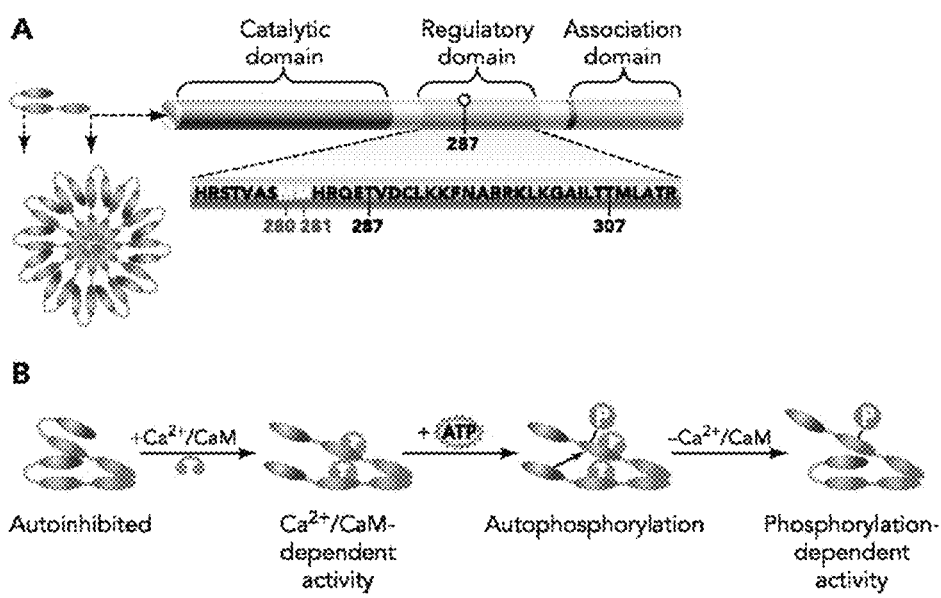
Figure 21F:
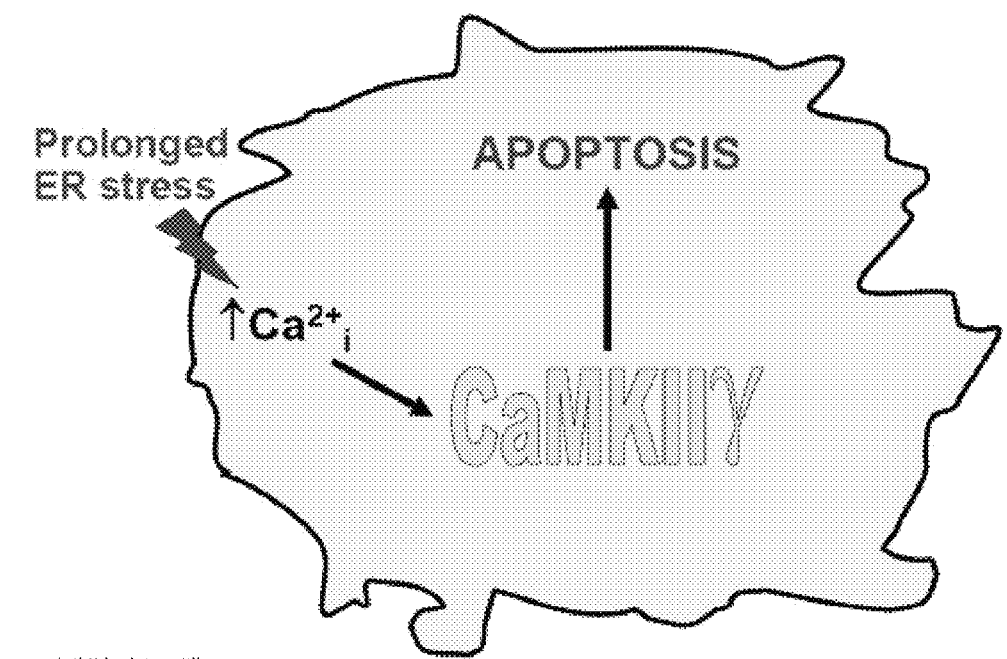
Figure 21G:
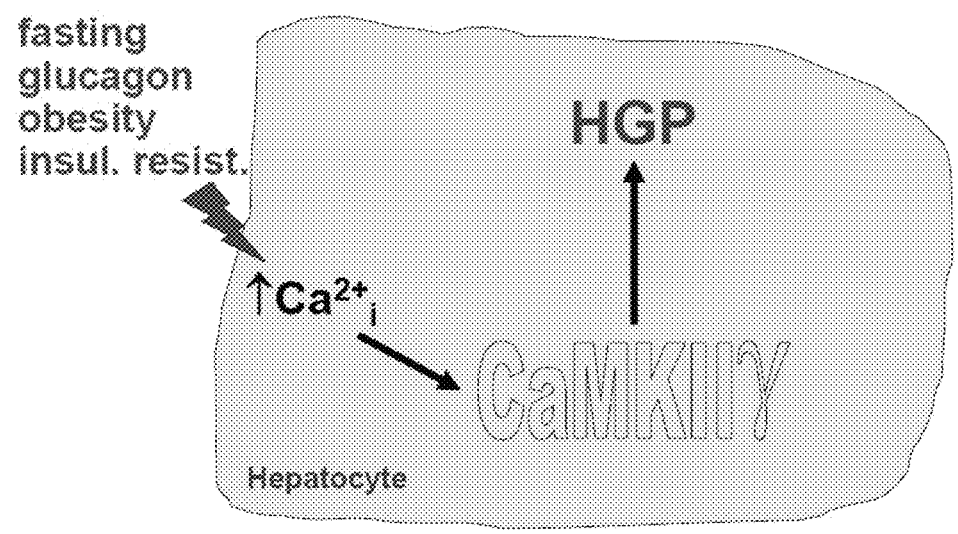
FIG. 21G is a diagram showing that, without being bound by theory, CaMKII-γ can regulate HGP.
Figure 21H:
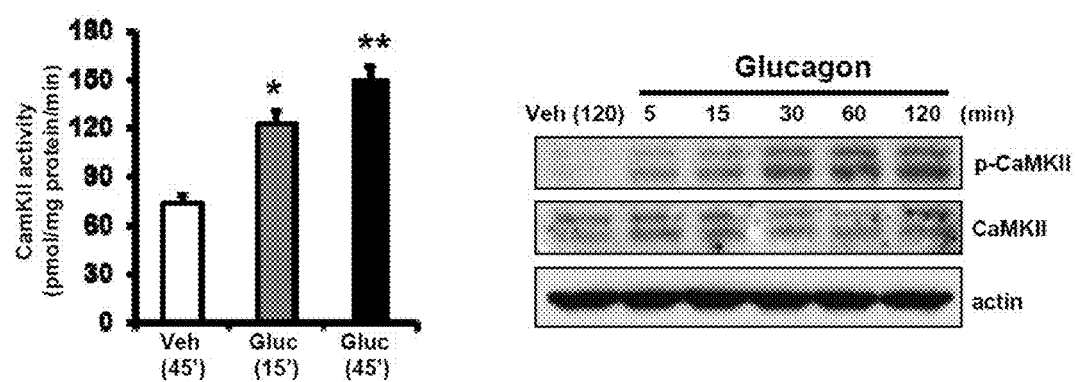
Figure 21I:
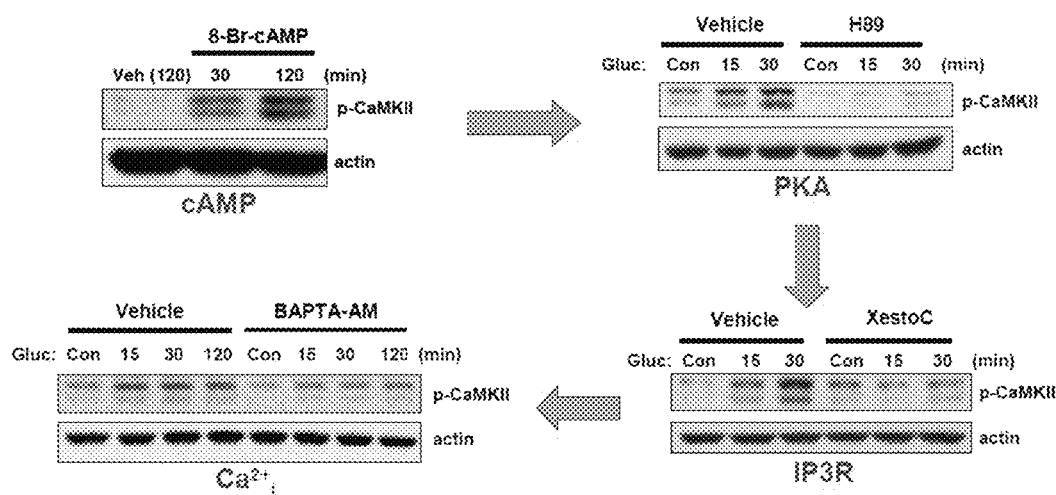
Figure 21K:
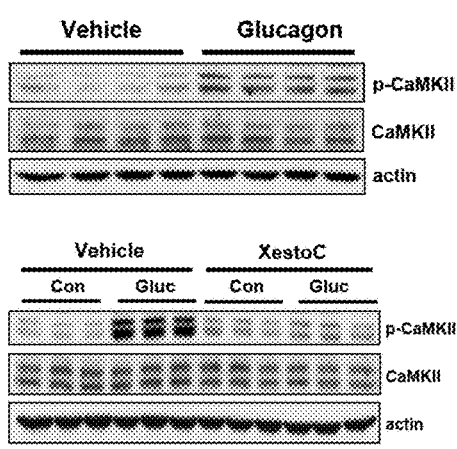
Figure 21L:
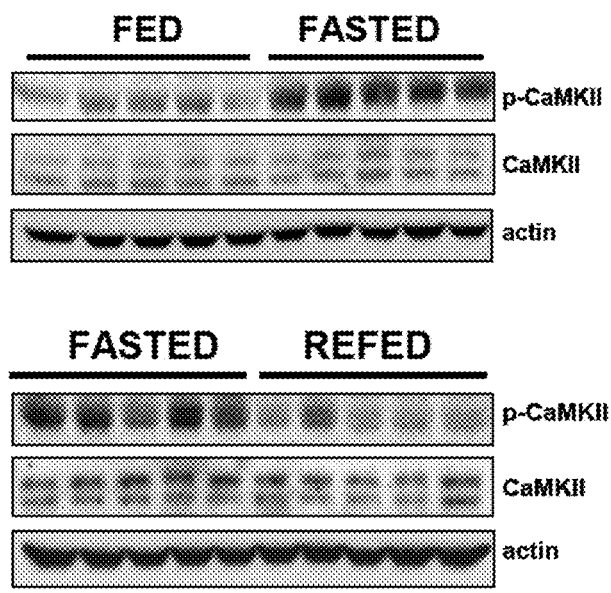
Figure 21M:
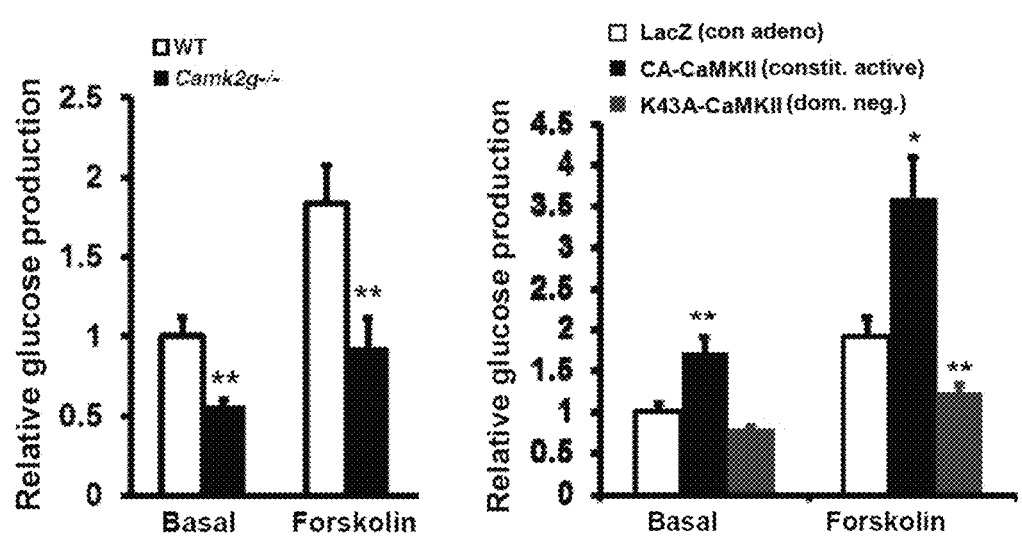
FIG. 21M shows that CaMKII plays an important role in PKA-induced glucose production by primary hepatocytes.
Figure 21N:
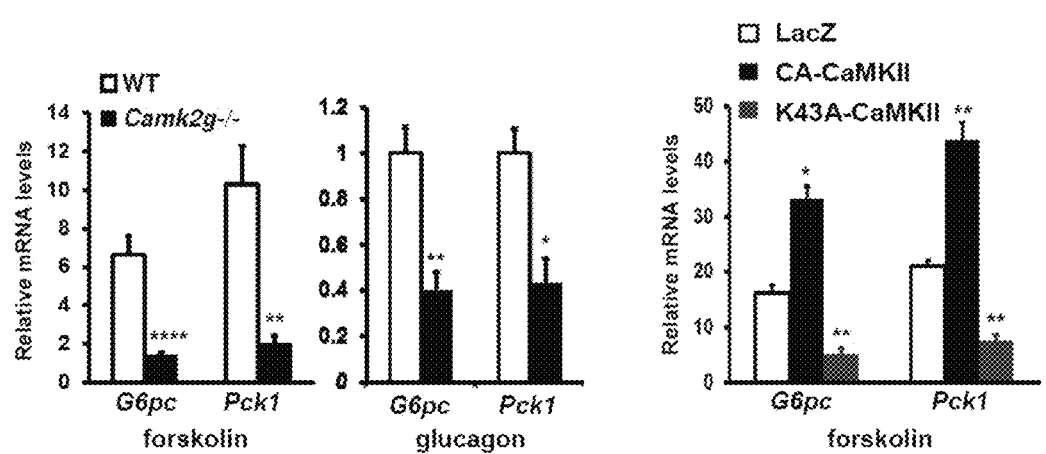
FIG. 21N shows that CamKII plays an important role in PKA and glucagon-mediated Gcpc and Pck1 induction in primary hepatocytes.
Figure 21O:
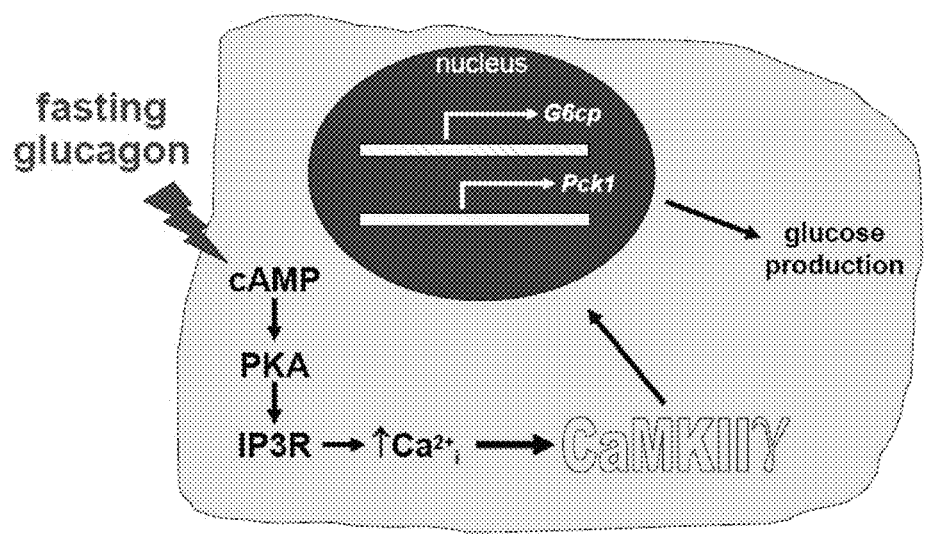
FIG. 21O is a diagram showing the link between fasting and glucagon, CaMKII and glucose production through a mechanism of gene induction.
Figure 21P:
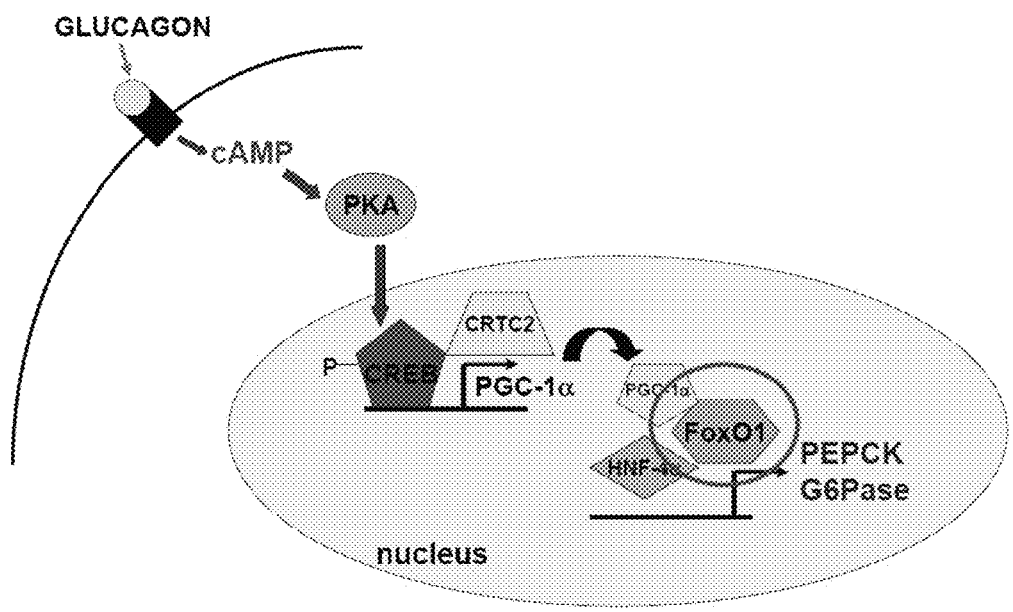
FIG. 21P is a diagram showing the transcriptional control of HGP.
Figure 21Q:
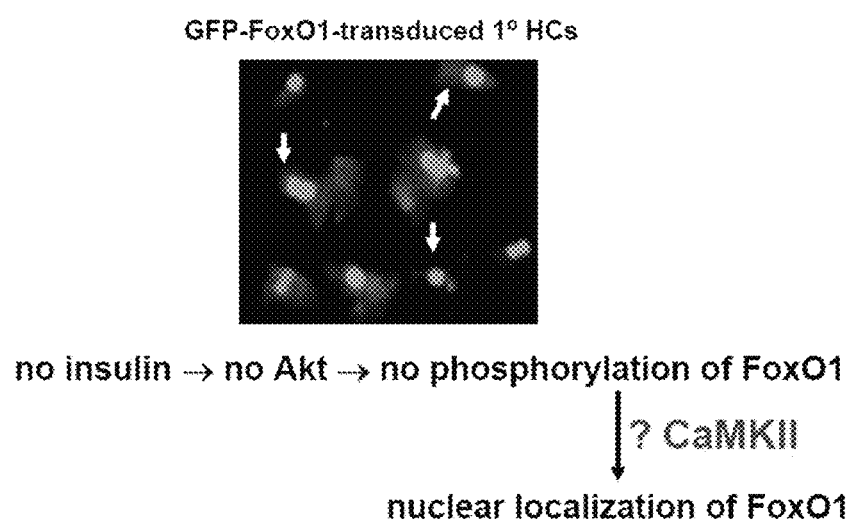
FIG. 21Q shows that FoxO1 is nuclear in serum-starved primary hepatocytes.
Figure 21R:
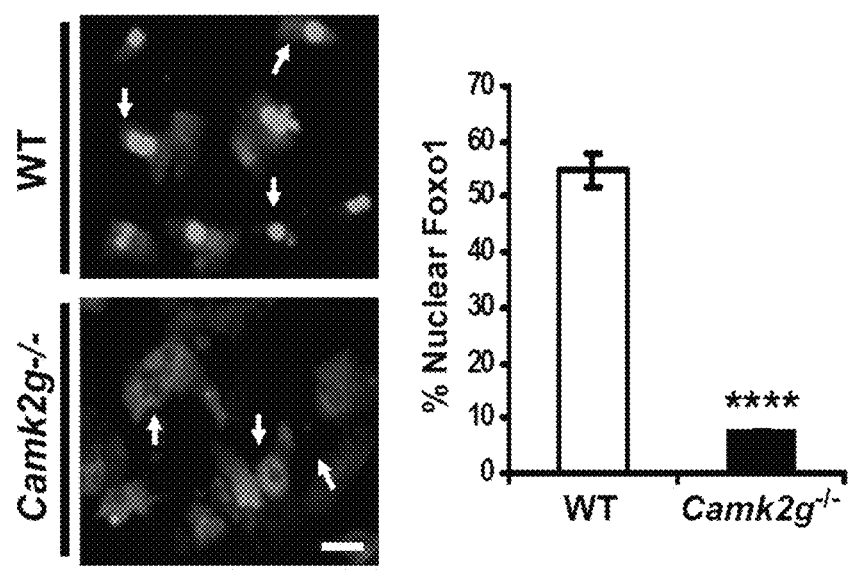
FIG. 21R shows that CamKII plays an important role in FoxO1 nuclear localization in serum-starved primary hepatocytes.
Figure 21S:
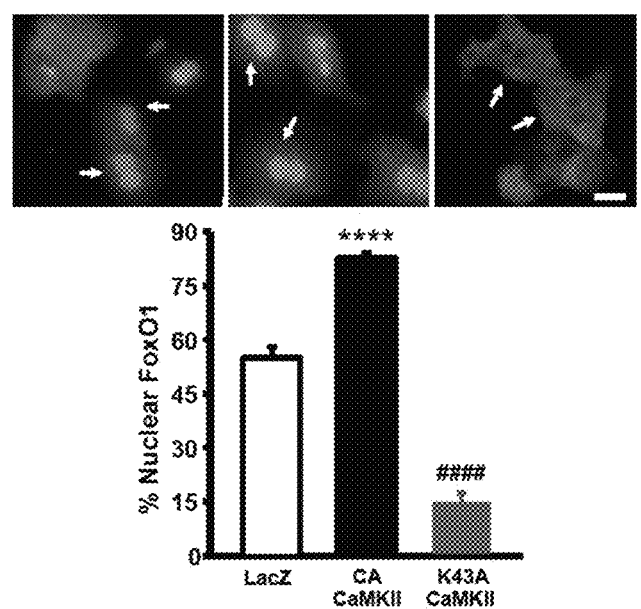
FIG. 21S shows that CaMKII plays an important role in FoxO1 nuclear localization in serum-starved primary hepatocytes.
Figure 21T:
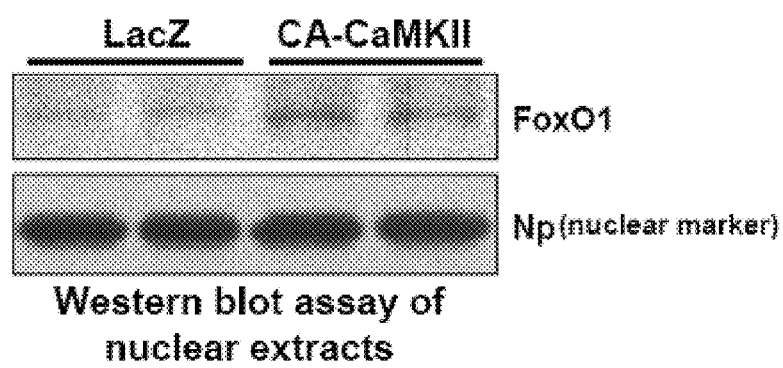
FIG. 21T shows a Western blot assay of nuclear extracts that shows that CaMKII plays an important role in FoxO1 nuclear localization in serum-starved primary hepatocytes.
Figure 21U:
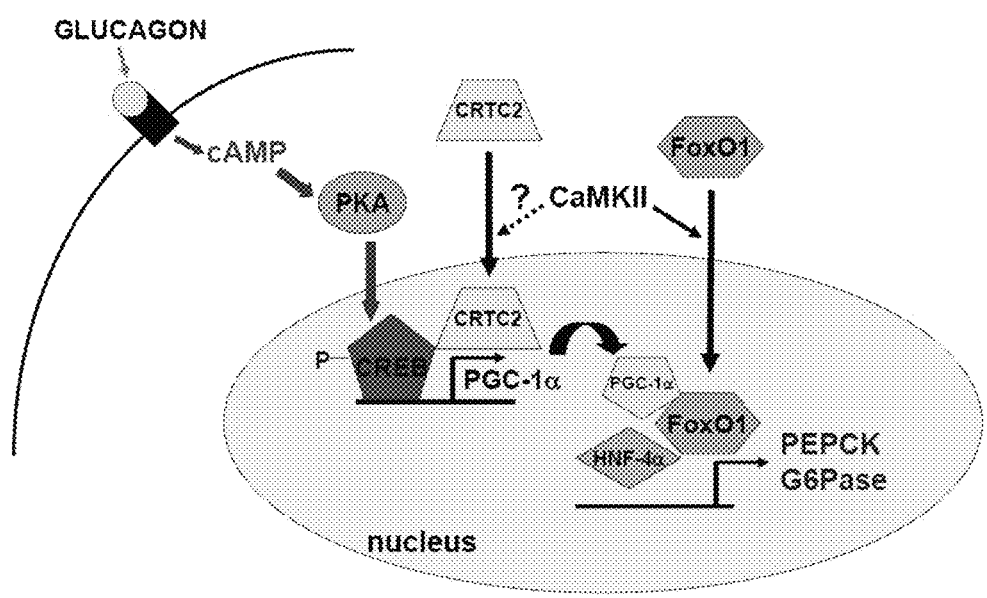
FIG. 21U is a diagram showing the transcriptional control of HGP, including the CRTC2-PGC1α pathway.
Figure 21V:
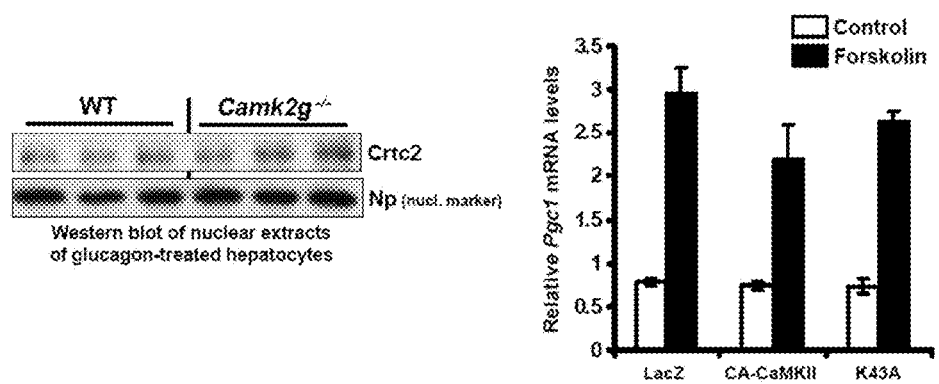
FIG. 21V shows that CaMKII does not play a role in CRTC2 nuclear localization of Pgc1 induction in primary hepatocytes.
Figure 21W:
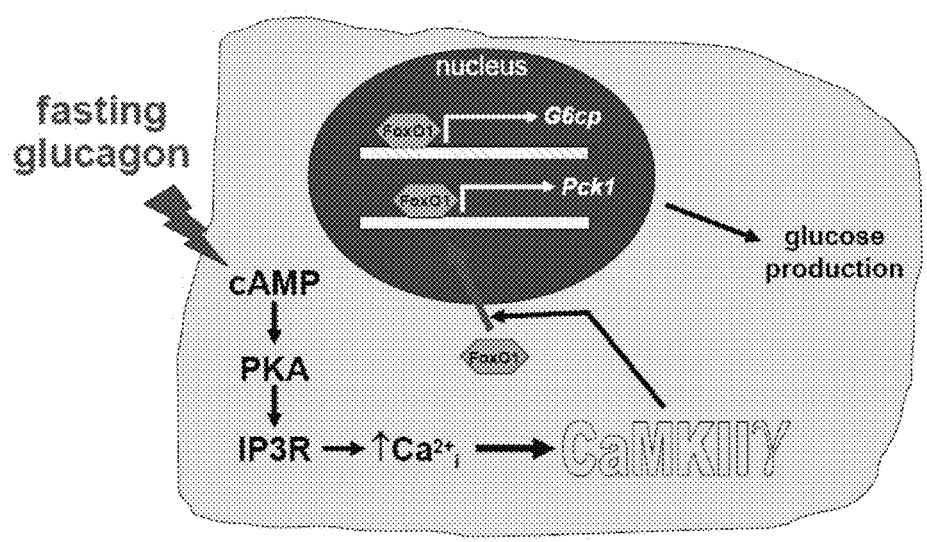
FIG. 21W is a diagram that shows the link between fasting and glucagon production, CaMKII, FoxO1 and glucose production.
Figure 21X:
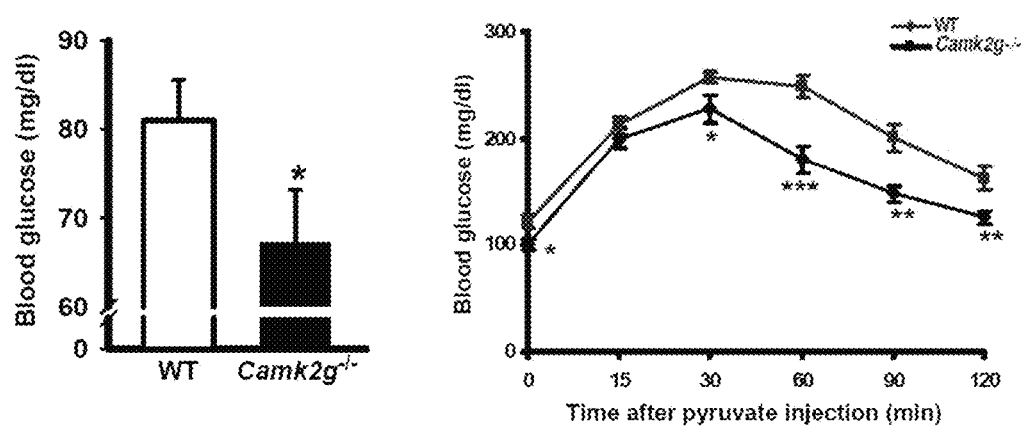
FIG. 21X presents in vivo evidence in fasting CaMKIIγ−/− mice of a blood glucose and pyruvate challenge test.
Figure 21Y:
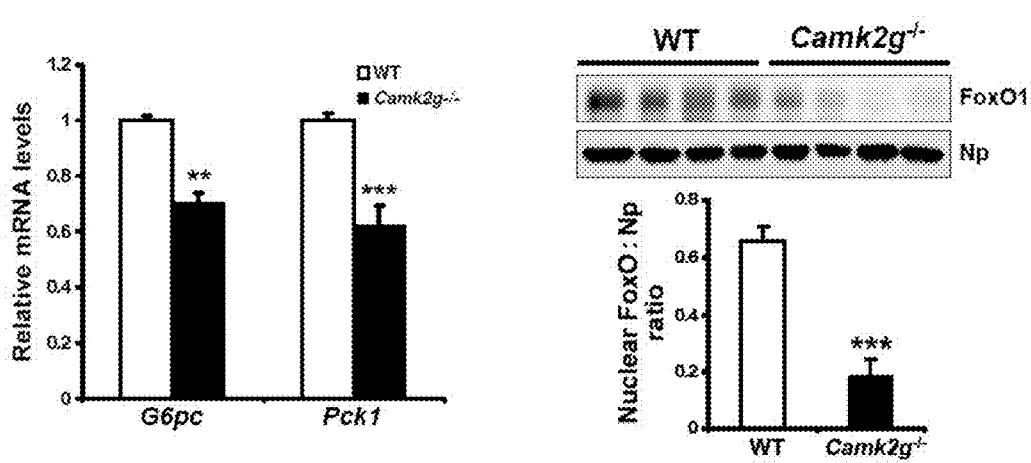
FIG. 21Y presents in vivo evidence in fasting CaMKIIγ−/− mice of hepatic Gcpc/Pck1 mRNA and nuclear FoxO1.
Figure 21Z:
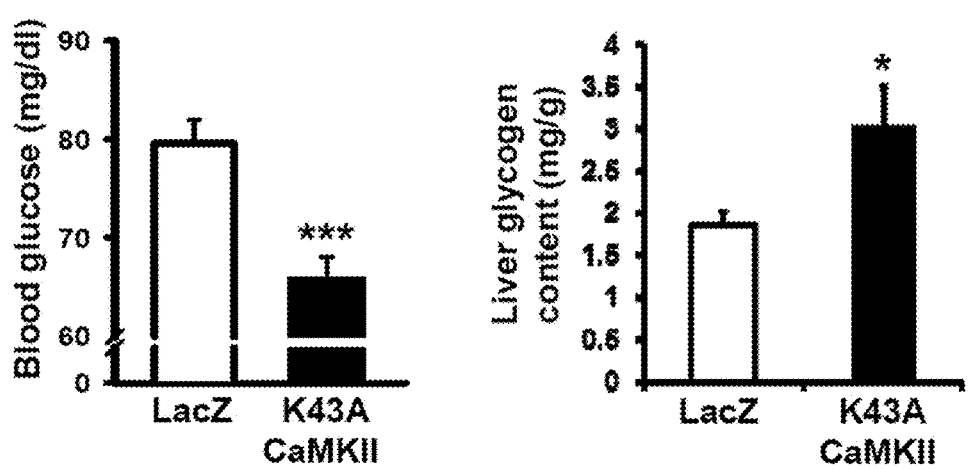
FIG. 21Z presents in vivo evidence in fasting adeno-K43A CaMKII-transduced WT mice of blood glucose and glycogen stores.
Figure 21A:
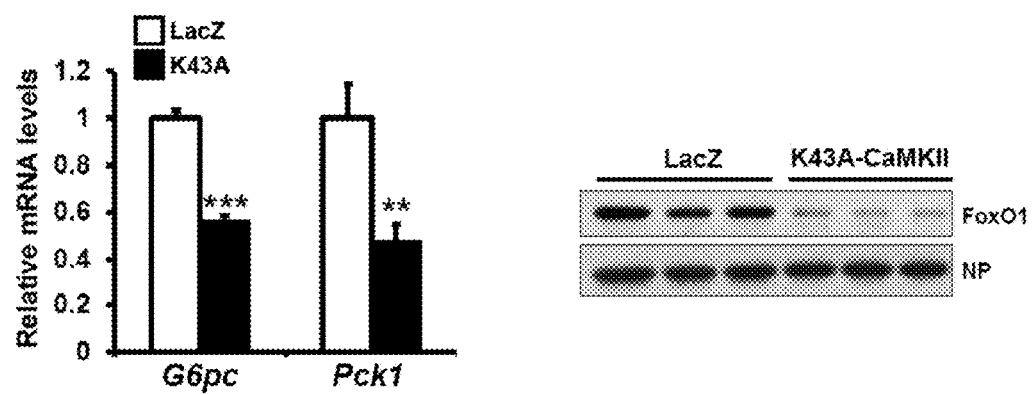
Figure 21A:
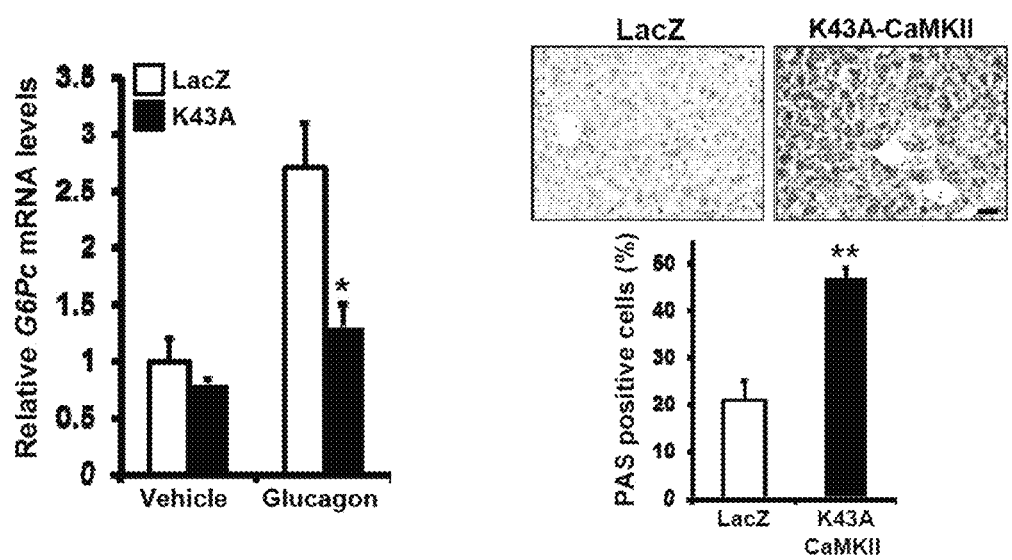
Figure 21A:
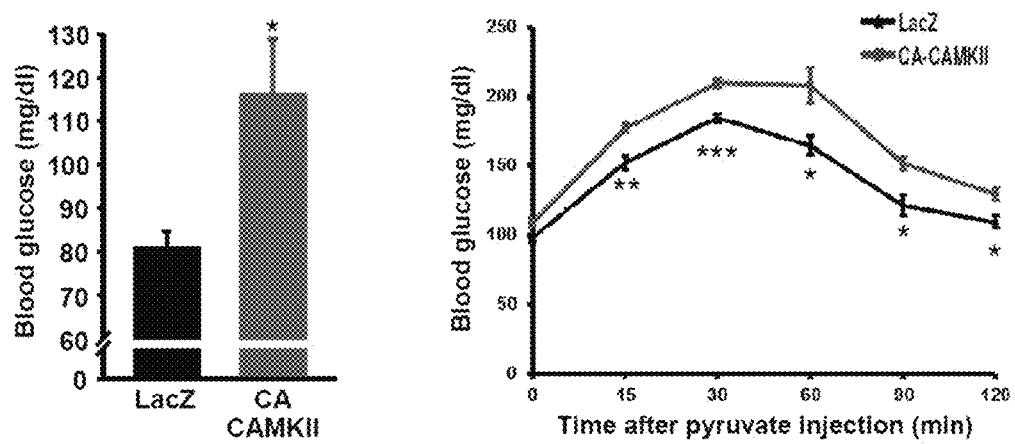
Figure 21A:
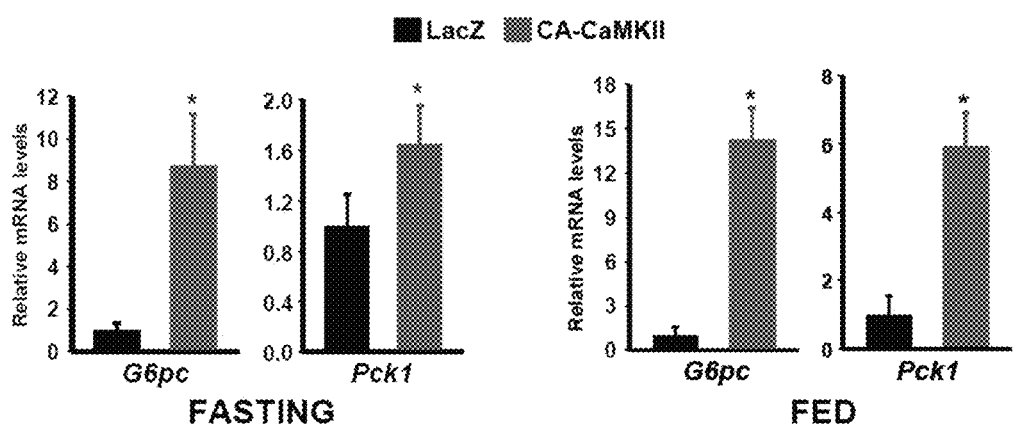
Figure 21A:
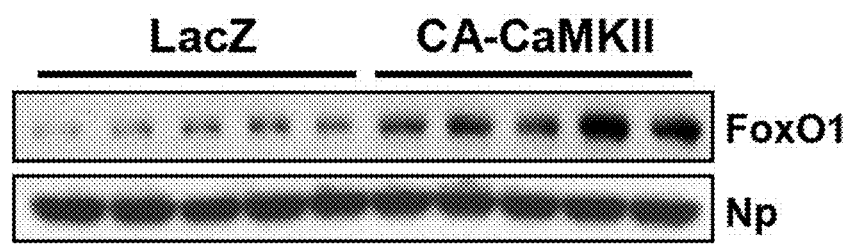
Figure 21A:
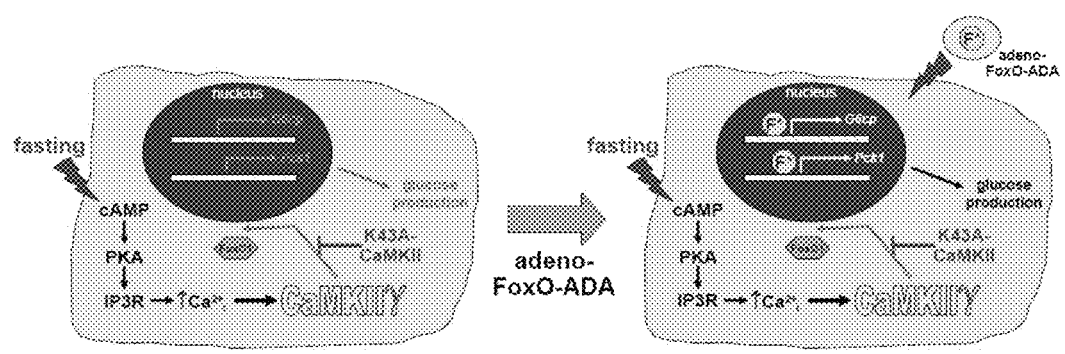
Figure 21A:
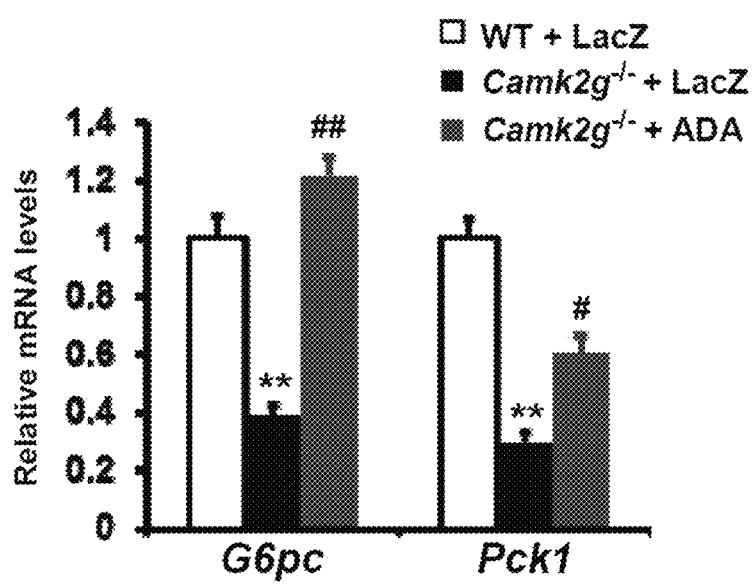
Figure 21A:
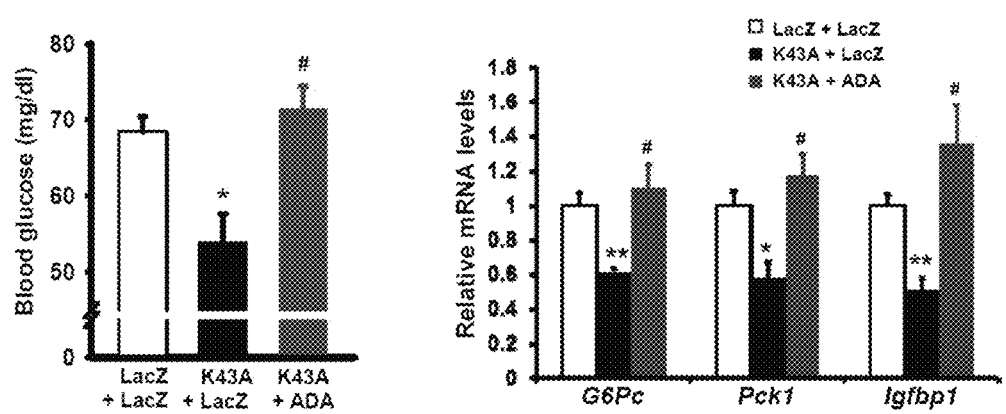
Figure 21A:
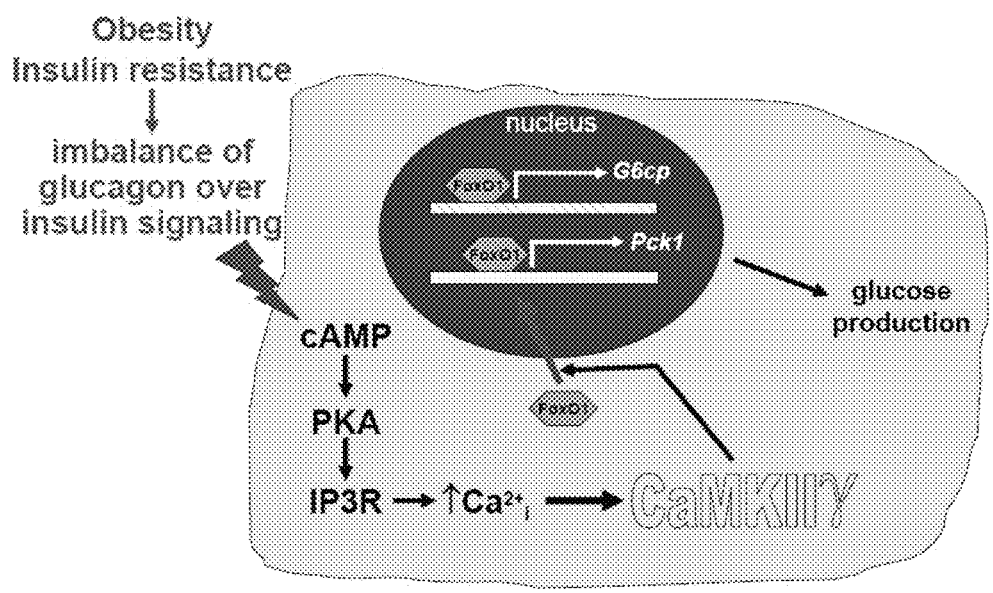
Figure 21A:
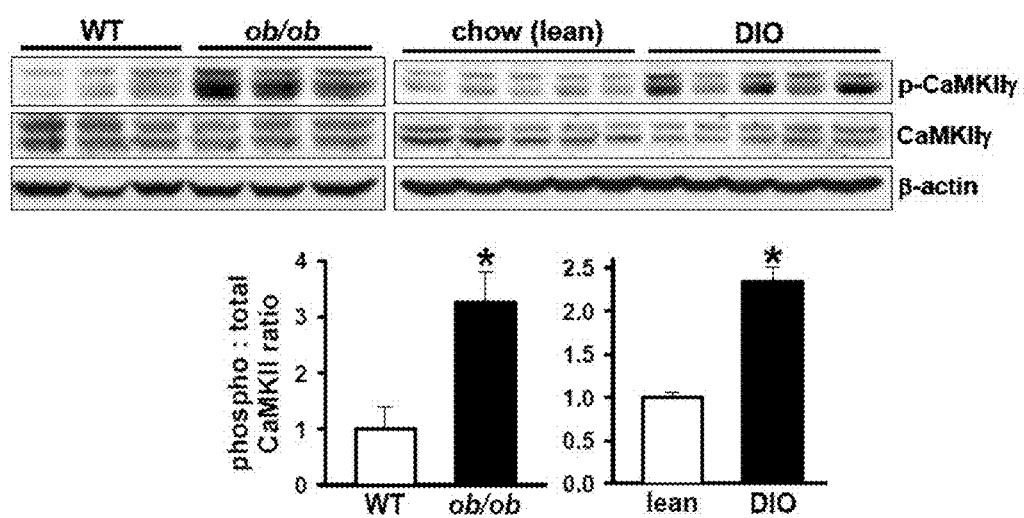
Figure 21A:
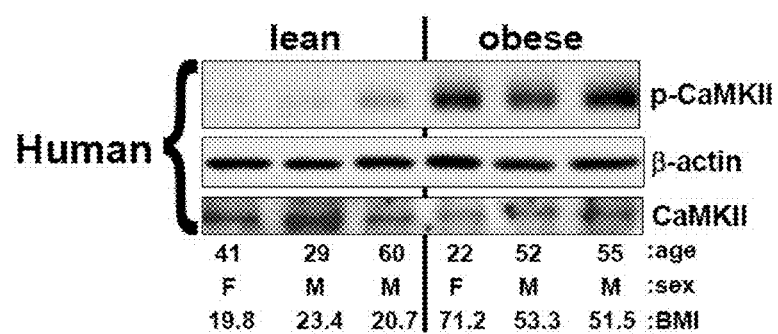
Figure 21A:
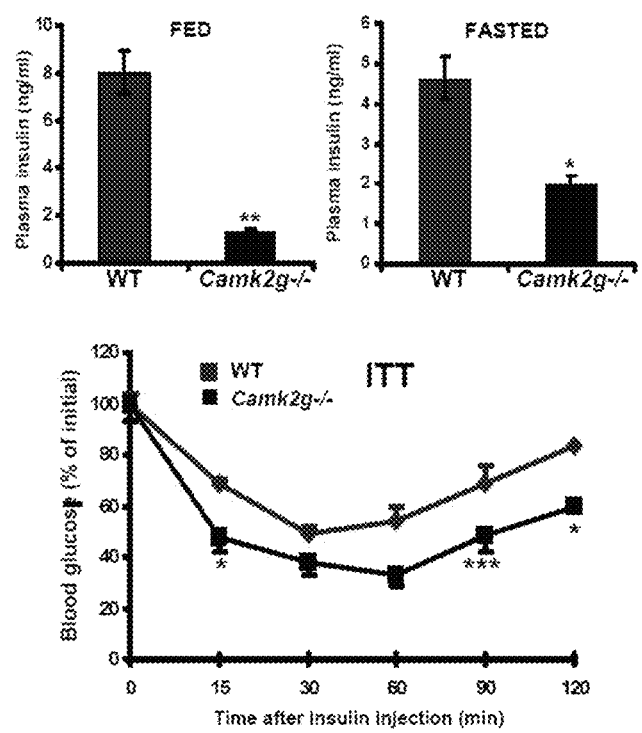
Figure 21A:
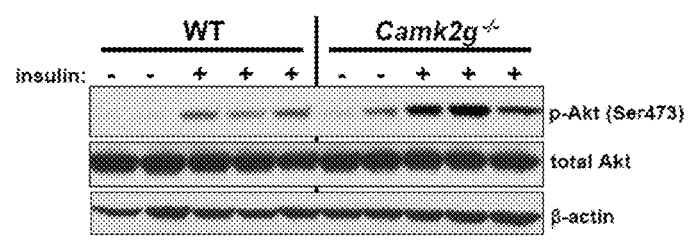
Figure 21A:
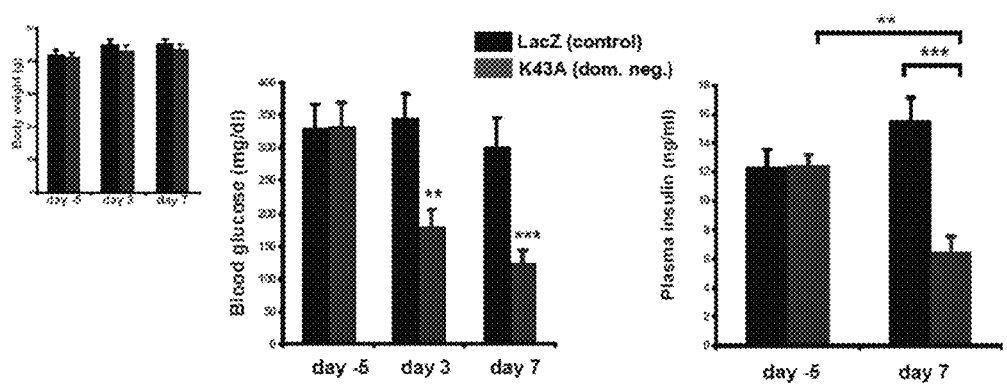
Figure 21A:
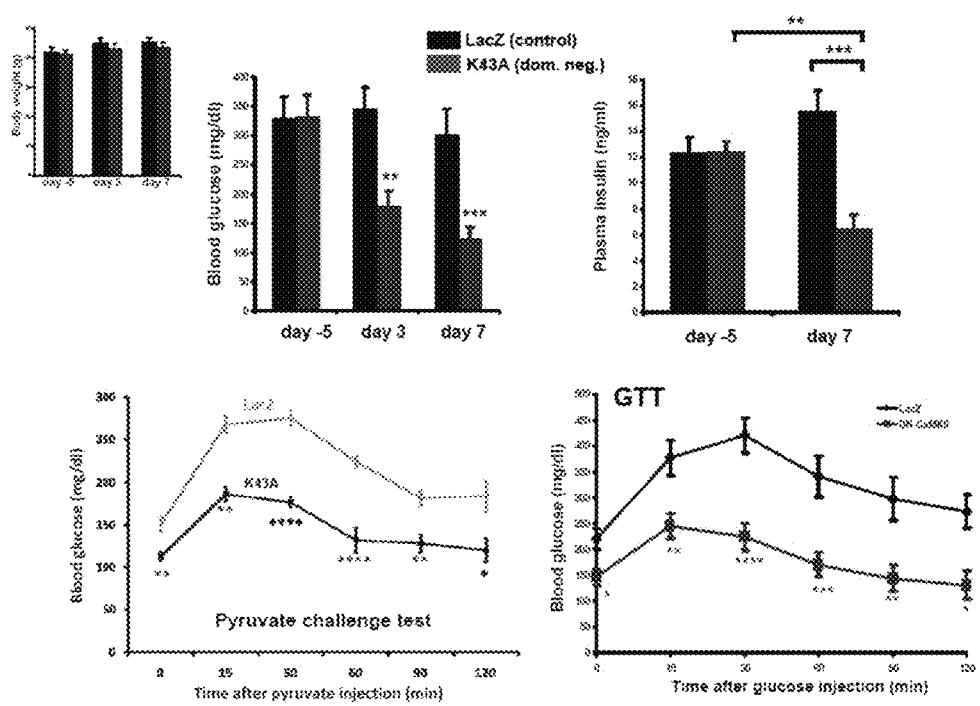
Figure 21A:
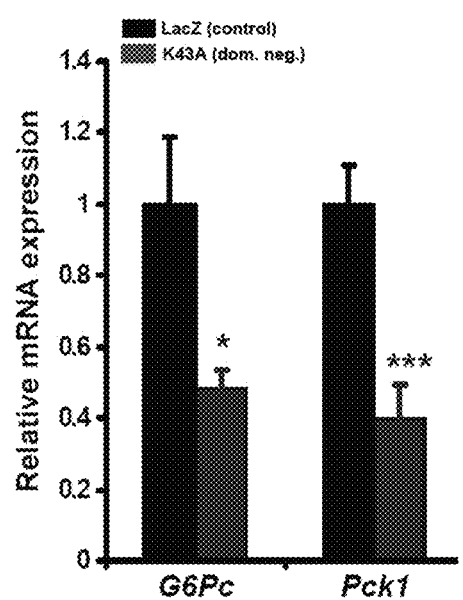
Figure 21A:
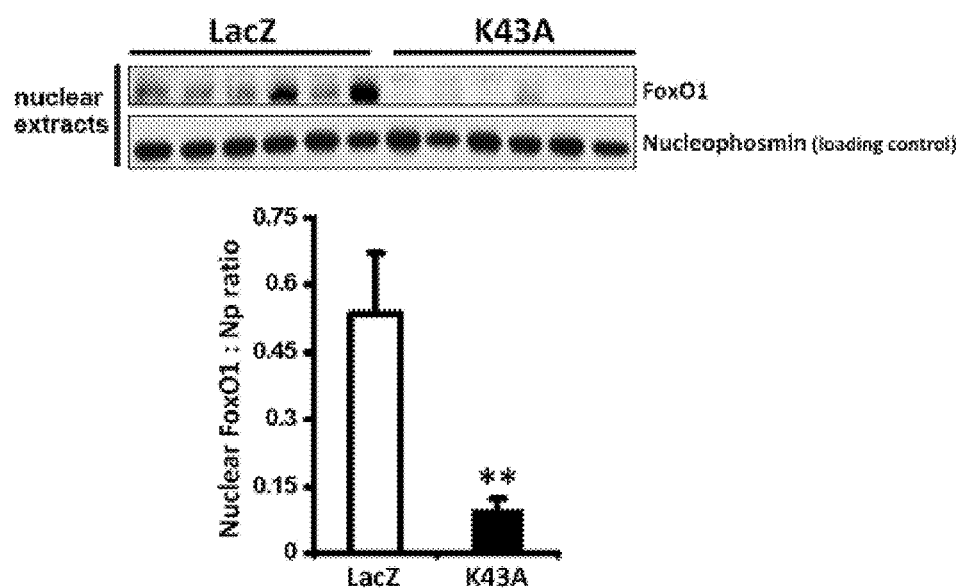
Figure 21A:
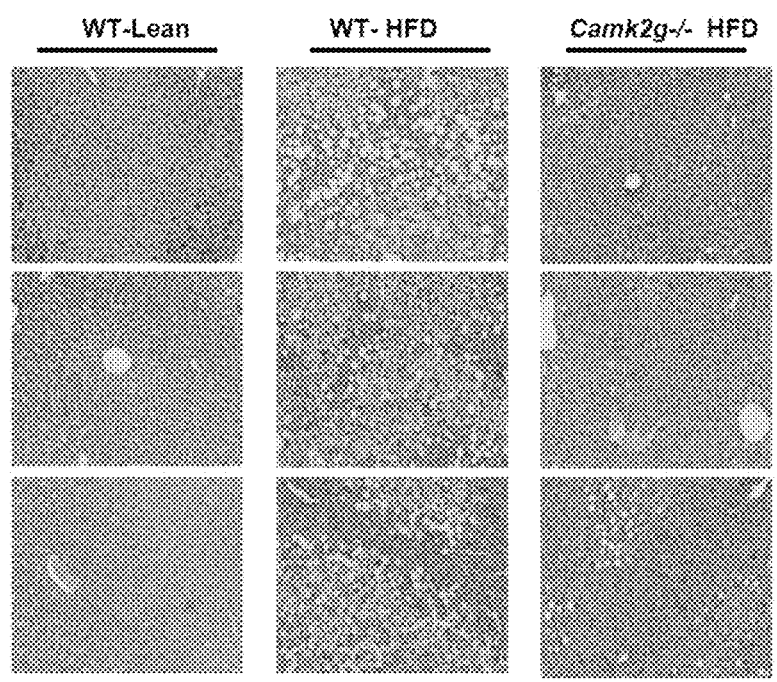
Figure 21A:
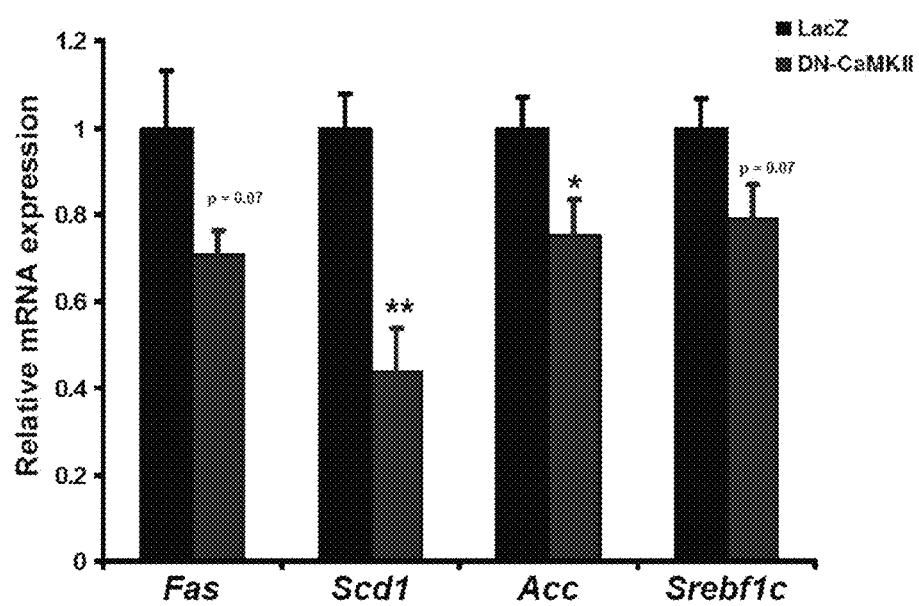
Figure 21A:
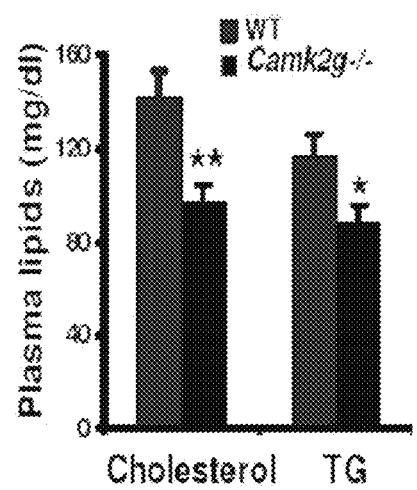
Figure 21A:
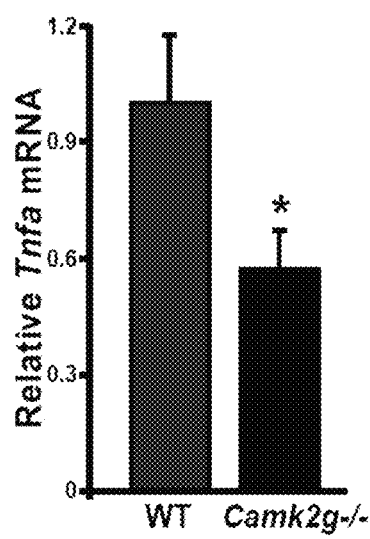
Figure 21A:
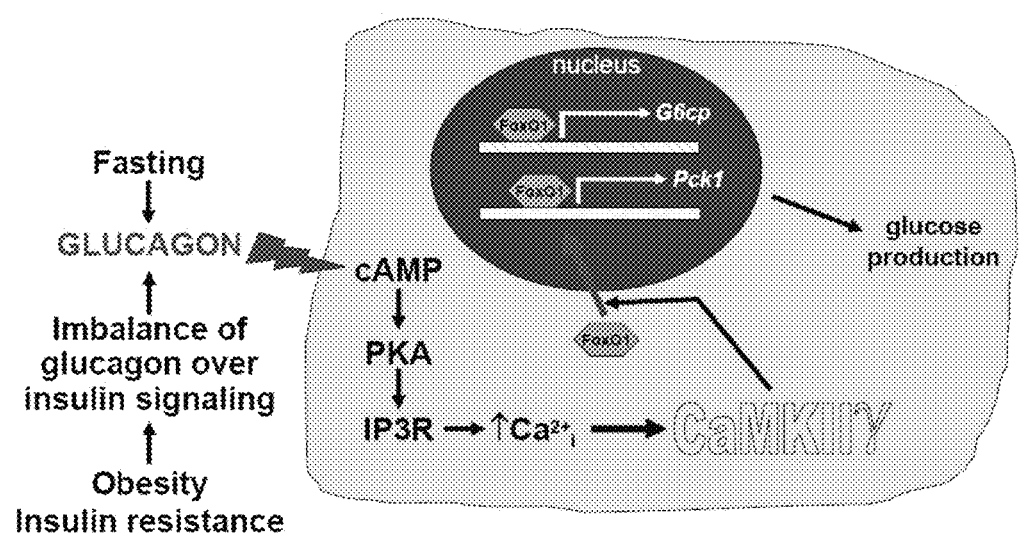

Hepatic CaMKIIγ deficiency, by improving dyslipidemia and possibly other parameters, e.g., inflammation, circulating FFAs, arterial wall effects of hyperinsulinemia, and hyperglycemia, will lessen atherosclerosis in the setting of insulin resistance. Western diet (WD) feeding of Ldlr−/− mice is required for the atherogenic lipoprotein phenotype. On the C57BL/6 background, feeding the WD, whose fat content is only modestly lower than the DIO diet, leads to insulin resistance 135 and, as shown in FIG. 20, phosphorylation of hepatic CaMKIIγ. To evaluate this model, mice will be bred to obtain the following 2 groups: Camk2gfl/flLdlr−/−(LDLR KO) and Camk2gfl/flA1atcre+/−Ldlr−/− (Li-CK LDLR DKO). After 8, 12, 16 and 20 wks on WD, metabolic parameters, plasma and inflammatory cytokines and FFAs will be assayed. 8 wks on WD is sufficient time to develop insulin resistance in this model (135). There will be a focus on lesion endpoints that may be exacerbated by these factors. For lesion initiation, endothelial activation (e.g., acetylchdependent vasodilation, VCAM-1 expression, p-eNOS, ROS, and monocyte adhesion to endothelium) and With regard to the KO model, controls will be added through inclusion of the adeno-T287D-CaMKII→DIO/Li-CK KO group. If phosphorylation of FoxO1 Ser284/295 is not involved in mediating the metabolic effects of CaMKII, parameters will be explored including those that affect the nuclear import/export machinery involved in FoxO1 localization, such as interaction with 14-3-3 sites (142), and those related to possible effects of CaMKIIγ on the hepatic insulin receptor signaling pathway. If Ser284/295 phosphorylation is important, future studies will investigate (a) whether CaMKIIγ is directly involved or whether it induces another kinase for this purpose (143); and (b) how defective phosphorylation of these sites can promote nuclear export of FoxO1. A FoxO1-S284/293A mouse will be created to study the role of these p-Ser residues in liver glucose and lipid metabolism. Relief of ER stress in the setting of CaMKIIγ deficiency may improve the response of HCs to acute insulin. For example, suppression of ER stress can decrease Ser207 phosphorylation of IRS1, which improves insulin signaling (34).

Example 8: Calcium Signaling Through CaMKII Regulates Hepatic Glucose Production in Fasting and Obesity Hepatic glucose production (HGP) is crucial for glucose homeostasis, but the underlying mechanisms have not been fully elucidated. Here it is shown that a calcium-sensing enzyme, CaMKII, is activated in a calcium- and IP3R-dependent manner by cAMP and glucagon in primary HCs and by glucagon and fasting in vivo. Genetic deficiency or inhibition of CaMKII blocks nuclear translocation of FoxO1 by affecting its phosphorylation, impairs fasting- and glucagon/cAMP-induced glycogenolysis and gluconeogenesis, and lowers blood glucose levels, while constitutively active CaMKII has the opposite effects. Importantly, the suppressive effect of CaMKII deficiency on glucose metabolism is abrogated by transduction with constitutively nuclear FoxO1, indicating that the effect of CaMKII deficiency requires nuclear exclusion of FoxO1. This same pathway is also involved in excessive HGP in the setting of obesity. These results reveal a calcium-mediated signaling pathway involved in FoxO1 nuclear localization and hepatic glucose homeostasis.

Highlights Include:
Fasting and glucagon activate hepatic CaMKII in a PKA-IP3R1-Ca2+i-dependent manner
CaMKII promotes fasting/glucagon-induced hepatic glucose production (HGP)
CaMKII promotes nuclear FoxO1, which is required for CaMKII-mediated stimulation of HGP.
The CaMKII-FoxO1 pathway is also involved in excessive HGP in the setting of obesity.

Liver is the main organ responsible for maintaining euglycemia under conditions of nutrient deprivation. During the early stages of fasting, liver uses glycogen stores to mobilize glucose (Radziuk and Pye, 2001). As fasting progresses, de novo synthesis of glucose from non-carbohydrate precursors, gluconeogenesis, becomes the main contributor to hepatic glucose production (HGP) (Lin and Accili, 2011). These changes occur rapidly in response to direct hormonal signaling. In addition, both insulin and glucagon affect transcription of glucose-6-phosphatase (G6pc), which is involved in both gluconeogenesis and glycogenolysis, and phosphoenolpyruvate carboxykinase (Pck1), which also regulates HGP (Pilkis and Granner, 1992; Burgess et al., 2007). During fasting, changes in the subcellular localization of "glucogenic" transcription factors, such as FoxO (1, 3, and 4) and Crct2, activate expression of these genes (Lin and Accili, 2011). In addition, different co-activators, such as peroxisome proliferator-activated receptor-γ coactivator-1α (PGC-1α) and CBP, are thought to interact with components of the cAMP response, including CREB, hepatic nuclear factor 4α (HNF4α), Sirt1, and Clock genes, leading to an increase in transcription of gluconeogenic genes (Hall et al., 1995; Matsumoto et al., 2007; Puigserver et al., 2003; Rhee et al., 2003). In addition to its role in stimulating HGP during fasting, excessive glucagon signaling is thought to play an important role in hyperglycemia in type 2 diabetes (Sorensen et al., 2006; Unger and Cherrington, 2012; Saltiel, 2001).

The intracellular signal transduction pathways through which glucagon stimulates the nuclear translocation of HGP transcription factors in general, and FoxO1 in particular, to stimulate HGP is not well understood. In this context, previous reports that linked intracellular calcium ($Ca^{2+}_i$) to the regulation of gluconeogenesis were of interest (Friedmann and Rasmussen, 1970; Kraus-Friedmann and Feng, 1996; Marques-da-Silva et al., 1997). For example, glucagon and cAMP can increase $Ca^{2+}_i$, and $Ca^{2+}_i$ chelation has been shown to reduce glucagon induced HGP gene expression and glucose production (Bygrave and Benedetti, 1993; Staddon and Hansford, 1989; Mine et al., 1993). Based on these previous studies, which did not offer a molecular mechanism linking $Ca^{2+}_i$ to hepatic glucose metabolism, without being bound by theory, a role for the $Ca^{2+}_i$-sensing enzyme CaMKII is implicated.

Calcium calmodulin-dependent kinase II (CaMKII) is a serine-threonine kinase that is an important mediator of $Ca^{2+}_i$ signaling in cells (Couchonnal and Anderson, 2008; Singer, 2011). There are four CaMKII isoforms—α, β, γ and δ—each encoded by a separate gene. The α and β isoforms are mostly neuronal, while CaMKIIγ and δ are expressed in a wide variety of tissues. After binding calcium/calmodulin complex, autophosphorylation on Thr287 results in calcium/calmodulin independent activity (Couchonnal and Anderson, 2008; Singer, 2011). Most studies on CaMKII have been carried out in neurons and cardiomyocytes, and there is only a limited understanding of CaMKII in other tissues, with none to date related to glucose metabolism. In the present study, it is shown that CaMKII activity is increased by cAMP and glucagon and also in response to fasting in vivo. It is further demonstrated that CaMKII plays an essential role in the regulation of glycogenolysis and gluconeogenesis. In particular, evidence is provided that CaMKII has a profound effect on FoxO1 nuclear localization in a manner that regulates the expression of two key enzymes, G6pc and Pck1, in vitro and in vivo. Finally, evidence indicating that this same pathway is involved in excessive HGP in the setting of obesity is presented.

Results

Glucagon and Fasting Activate Hepatic CaMKII in a IP3R- and $Ca^{2+}_i$-Dependent Manner Glucagon has been shown to increase intracellular calcium ($Ca^{2+}_i$) in hepatocytes (HCs) (Staddon and Hansford, 1989), which was recently verified (Y. Wang, G. Li, J. Goode, J. C. Paz, R. Screaton, W. H. Fischer, I. Tabas, and M. Montminy, manuscript submitted for publication). To determine whether glucagon activates the $Ca^{2+}_i$-sensing enzyme, CaMKII, primary murine HCs were treated with glucagon for various periods of time and then assayed CaMKII enzymatic activity and CaMKII phosphorylation at Thr287, which is a measure of its activation state (Couchonnal and Anderson, 2008; Singer, 2011). The results of both assays show that CaMKII activity increases as a function of time of glucagon treatment (FIG. 1A-B). The cytosolic calcium chelator, 1,2-bis[2-aminophenoxy]ethane-N,N,N', N'-tetraacetic acid tetrakis[acetoxymethyl ester] (BAPTA-AM), was used to determine the role of $Ca^{2+}_i$ on CaMKII activation and it was found that BAPTA-AM markedly decreased glucagon-induced CaMKII phosphorylation (FIG. 1C).

Inositol 1,4,5-trisphosphate receptor ($IP_3R$) channels, located in the endoplasmic reticulum (ER), release $Ca^{2+}$ in response to $IP_3$ binding and play a major role in intracellular $Ca^{2+}_i$ homeostasis. Additional studies have revealed that glucagon-induced PKA phosphorylates and increases IP3R activity, leading to an increase in $Ca^{2+}_i$ (Y. Wang, G. Li, J. Goode, J. C. Paz, R. Screaton, W. H. Fischer, I. Tabas, and M. Montminy, manuscript submitted for publication). Glucagon has also been shown to induce phospholipase C-mediated IP3 release (Hansen et al., 1998). To investigate the contribution of IP3Rs in glucagon-induced CaMKII activation, the IP3R inhibitor xestospongin C and, as a complementary approach, adeno-Cre-treated HCs from Ip3r1$^{fl/fl}$ mice, were used. Both xestospongin C treatment and Cre-mediated deletion of IP3R1 led to a significant decrease in glucagon-induced CaMKII phosphorylation, demonstrating the critical role of IP3Rs in this process (FIG. 1D).

Glucagon receptor signaling, including that involved in the increase in $Ca^{2+}_i$ (Staddon and Hansford, 1989), is mediated by activation of adenylate cyclase to produce cAMP, followed by activation of protein kinase A (PKA), a key enzyme involved in HGP. In this context, it was found that treatment of HCs with 8-bromo-cAMP mimicked the effect of glucagon and led to a marked increase in phospho-CaMKII (FIG. 1E). Moreover, when HCs were treated with the PKA inhibitor H89 prior to the addition of glucagon, glucagon-mediated increase in phospho-CaMKII was markedly inhibited (FIG. 1F). These data support the existence of a pathway in which glucagon-cAMP-PKA signaling promotes phosphorylation/activation of CaMKII through its effects on IP3R-mediated intracellular $Ca^{2+}$ release.

To examine whether CaMKII is regulated by glucagon in vivo, mice were challenged with a bolus of intraperitoneal (i.p.) glucagon. Consistent with the effects observed in cultured HCs, hepatic CaMKII phosphorylation was induced by glucagon treatment (FIG. 1G). It was found that a glucagon dose as low as 1 µg $kg^{-1}$ was capable of phosphorylating CaMKII in the liver (FIG. 28A). To gain in vivo evidence that IP3Rs are important in the regulation of glucagon-mediated CaMKII phosphorylation, mice were treated with i.p. xestospongin C for 4 days. The mice were then challenged with glucagon, and liver extracts were assayed for p-CaMKII. As shown in FIG. 1H, xestospongin C treatment markedly reduced glucagon-induced CaMKII phosphorylation. Next, hepatic CaMKII phosphorylation was compared during the transition from a fed to fasting state, which is known to elevate plasma glucagon (Lin and Accili, 2011) (FIG. 28B). The data show that hepatic CaMKII phosphorylation was significantly increased upon fasting, whereas the total amount of CaMKII appeared to be unaffected by nutrient status (FIG. 1I). Moreover, upon re-feeding, the level of p-CaMKII in liver diminished (FIG. 1J). As with glucagon treatment, fasting-induced phosphorylation of CaMKII was suppressed by xestospongin C treatment of the mice (FIG. 28C). These data show that activity of hepatic CaMKII is regulated by nutrient status in a manner that is consistent with a potential role in fasting-induced HGP.

CaMKII Promotes Glucose Production in Primary HCs

Figures 22A, 22B, 22C:
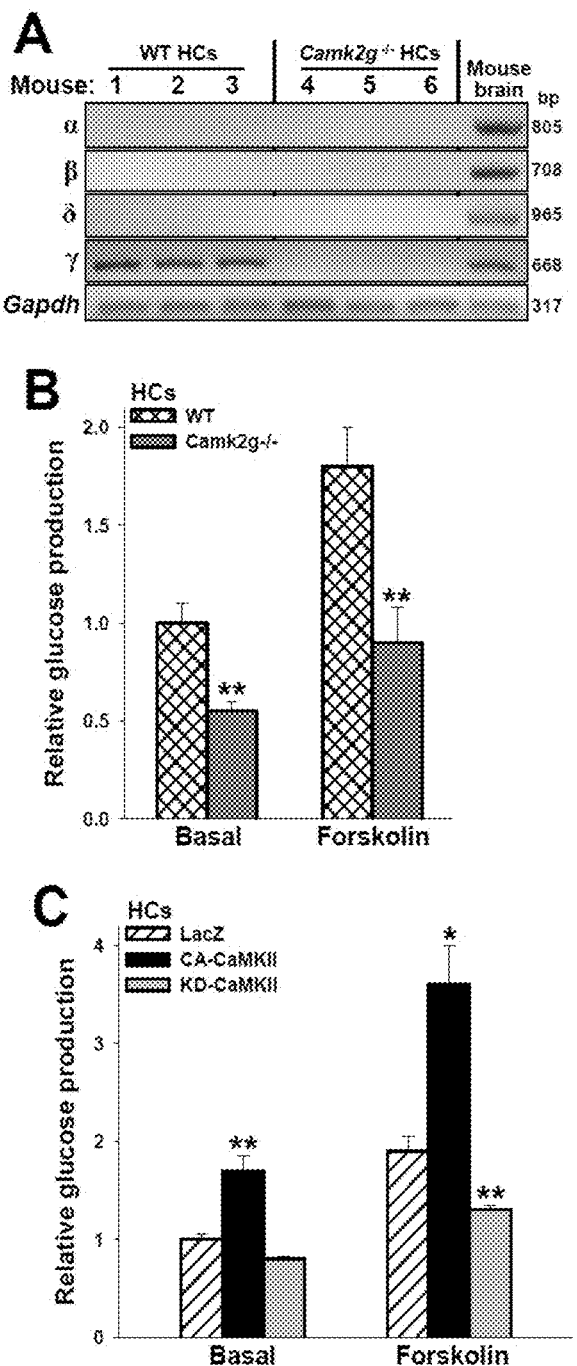
FIGS. 22A-E. CaMKII regulates glucose production and hepatic G6Pc and Pck1 expression in primary HCs.

CaMKIIγ is the major CaMKII isoform in HCs, and the other isoforms are not induced in HCs lacking the γ isoform (FIG. 22A). In view of the regulation of hepatic CaMKII activity by glucagon and fasting in vivo, glucose production was assayed in HCs from WT and $Camk2g^{-/-}$ mice. The cells were examined under basal conditions and after stimulation with forskolin, a glucagon mimetic and a potent adenylate cyclase activator (Harano et al., 1985). The data show that both basal and forskolin-induced glucose production was suppressed in CaMKIIγ-deficient HCs (FIG. 22B). Glucose production was next examined in WT HCs transduced with adenoviruses expressing constitutively active CaMKII (adeno-CA-CaMKII), "kinase-dead" dominant-negative CaMKII (adeno-KD-CaMKII) (Pfleiderer et al., 2004), or LacZ control. CA-CaMKII possesses an amino acid substitution, T287D, which mimics autophosphorylation at T287 and results in autonomous activity in the absence of bound calcium/calmodulin, while KD-CaMKII has a disabling mutation in the kinase domain (Pfleiderer et al., 2004). An increase in both basal and forskolin-induced glucose release was observed in cells transduced with adeno-CA-CaMKII (FIGS. 22C and 28D). HCs transduced with adeno-KD-CaMKII, which resulted in ~40% decrease in CaMKII activity (FIG. 28E), showed decreased forskolin-induced glucose production (FIG. 22C).

Figures 22D, 22E:
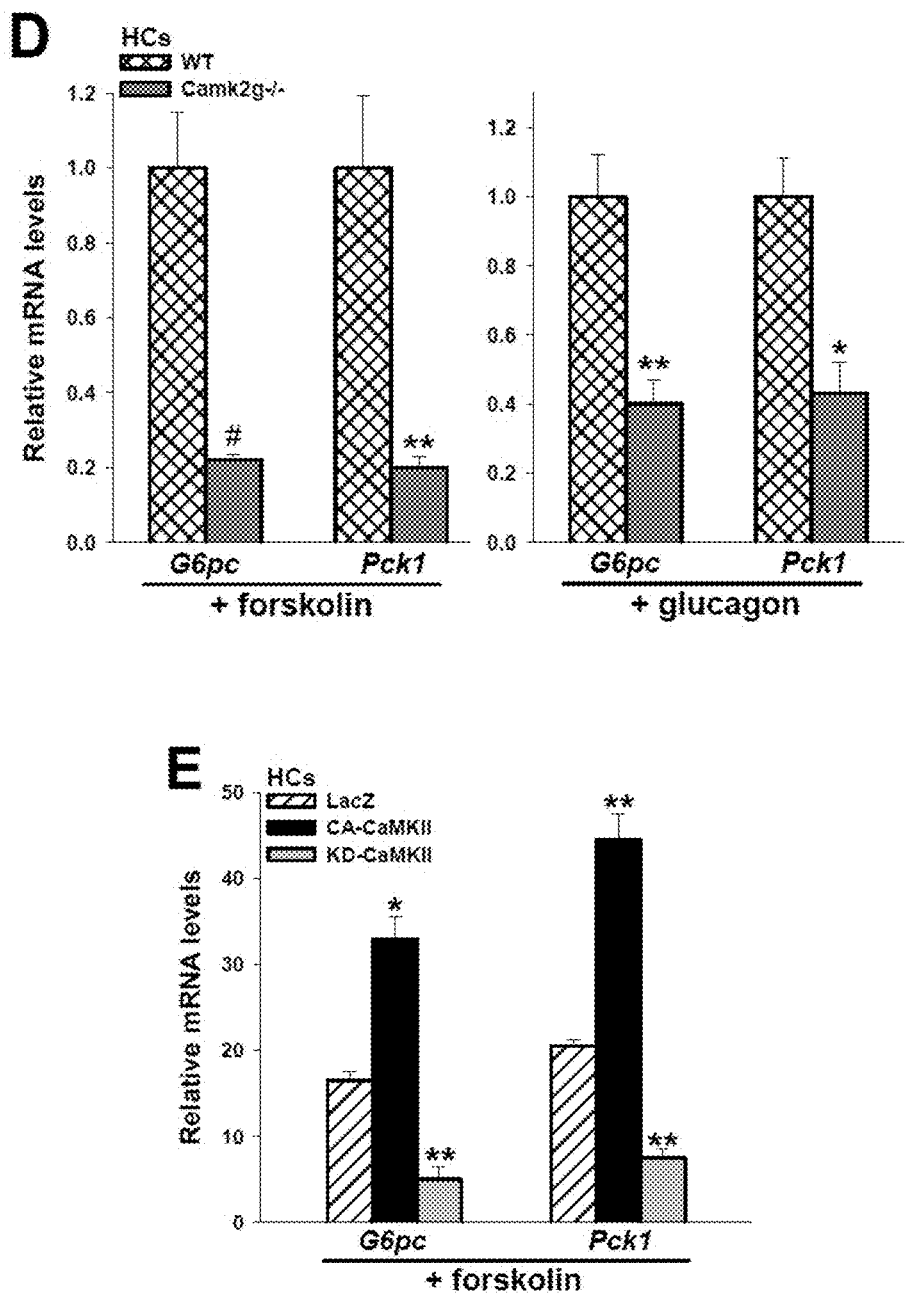

The role of CaMKII on HGP prompted us to investigate transcriptional effects on two genes encoding enzymes that regulate HGP, glucose-6-phosphatase and phosphoenolpyruvate carboxykinase. To this end, G6pc and Pck1 mRNA levels were assayed in the models described above (FIG. 22D-E). In all cases, knockout or KD-CaMKII-mediated inhibition of CaMKII lowered forskolin- or glucagon-induced gene expression, whereas CA-CaMKII increased gene expression. In the absence of forskolin or glucagon, expression levels of G6pc and Pck1 mRNA in WT HCs were much lower than those in hormone-treated WT HCs, but even under these conditions CaMKIIγ deficiency led to a lowering of gene expression (FIG. 28F). Moreover, adeno-KD-CaMKII did not decrease the low but detectable level of forskolin-induced G6pc mRNA in HCs lacking CaMKIIγ (FIG. 28G), consistent with the premise that the suppressive effect of KD-CaMKII on G6pc in FIG. 22E is due to CaMKII inhibition.

In summary, the CaMKII deficiency and inhibition data show the importance of endogenous CaMKII in glucose production and Pck1/G6pc gene expression, while the data with CA-CaMKII show that when the enzyme is expressed at a high level, it can force these processes in the absence of hormones or increase them in the presence of hormones.

Figures 23A, 23B:
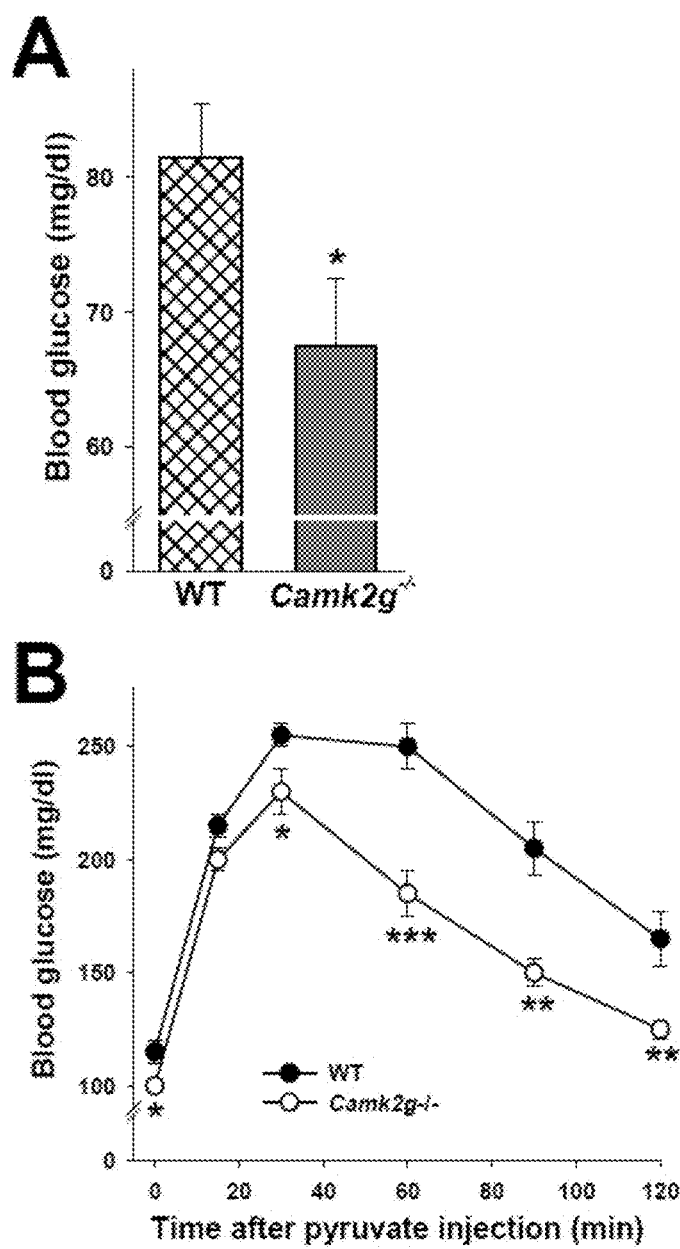
FIGS. 23A-G. CaMKIIγ deficiency or acute inhibition in vivo decreases blood glucose and hepatic G6pc and Pck1.
Figures 23C, 23D:
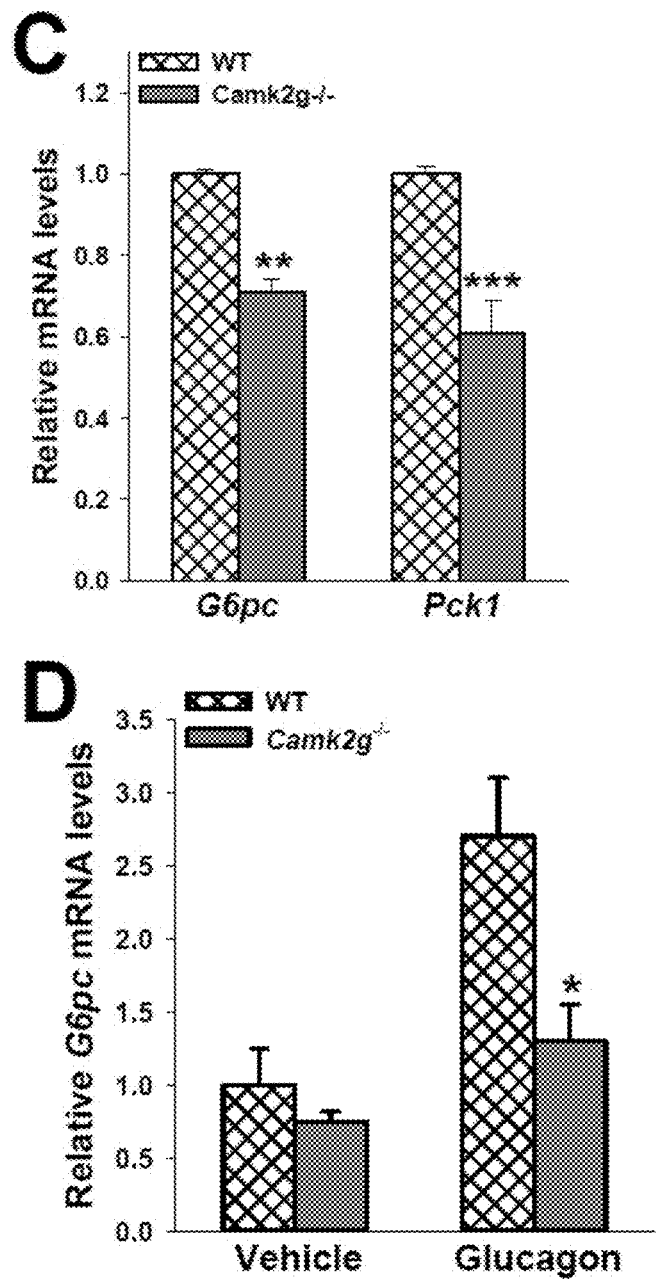

Hepatic Glucose Production In Vivo is Impaired by CaMKIIγ Deficiency and Stimulated by Constitutively Active CaMKII To assess the functional role of CaMKII in hepatic glucose metabolism in vivo, fasting blood glucose levels were examined in WT and $Camk2g^{-/-}$ mice. Consistent with the in vitro data, a modest but statistically significant decrease in blood glucose levels was observed in fasted $Camk2g^{-/-}$ vs. WT mice (FIG. 23A). The difference in fasting glucose concentration was not associated with an increase in circulating insulin or a decrease in glucagon concentrations in knockout vs. WT mice (FIG. 29A, left). The mutant mice also showed lower plasma glucose in response to a pyruvate challenge test (FIG. 23B). Consistent with the primary HC data, there was a decrease in G6pc and Pck1 mRNA levels in the livers of fasting $Camk2g^{-/-}$ mice (FIG. 23C). Similar data were obtained in mice treated with glucagon (FIG. 23D).

Figures 23E, 23F:
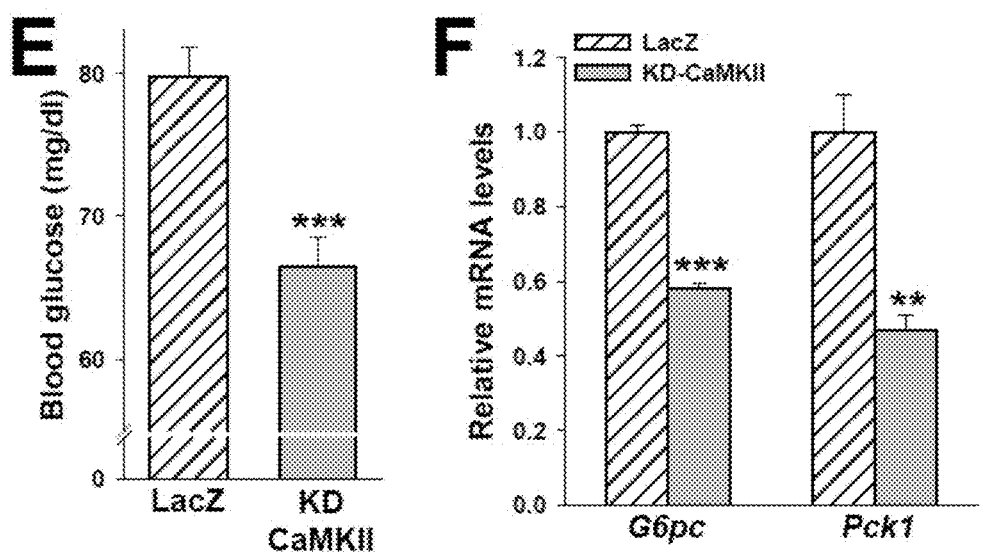
Figure 23G:
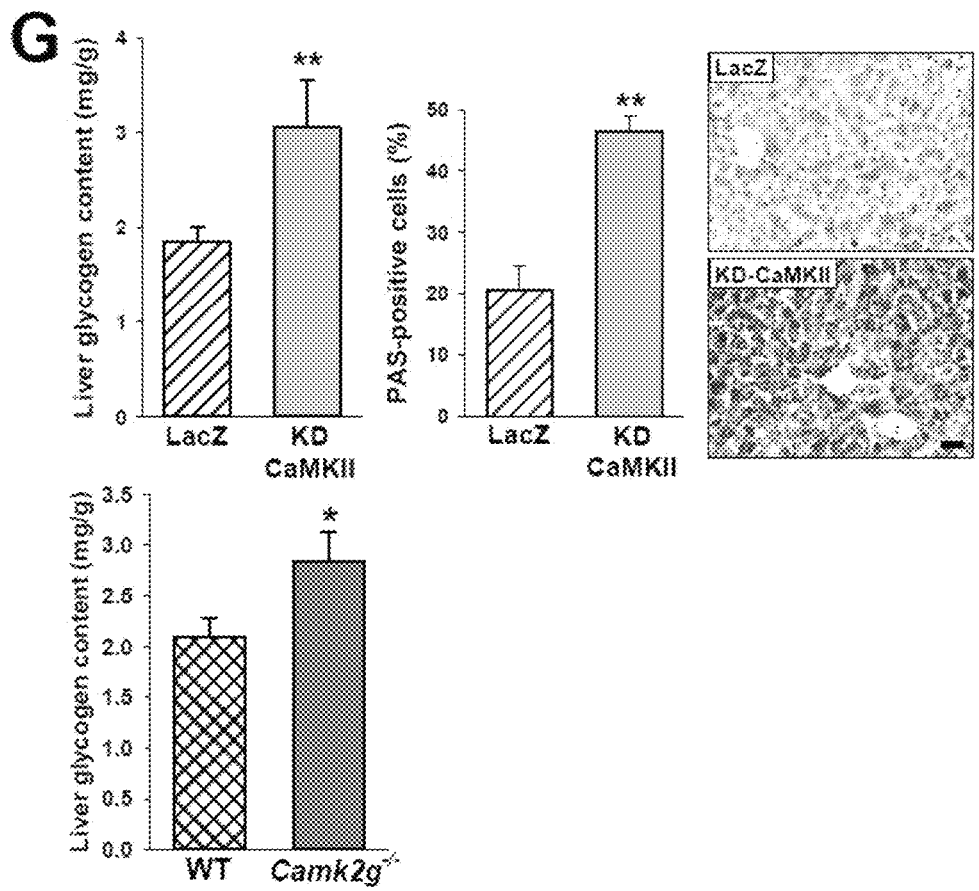

Consistent with these data, treatment of C57BL/6 mice with adeno-KD-CaMKII, which inhibited liver CaMKII activity by ~45% (FIG. 29B), decreased fasting blood glucose (FIG. 23E). As above, plasma glucagon and insulin were not different between the control and experimental groups (FIG. 29A, right). In line with blood glucose data, hepatic expression of G6pc and Pck1 mRNA was lower in mice injected with KD-CaMKII (FIG. 23F). Because CaMKII inhibition lowers the level the mRNA for the key glycogenolytic enzyme glucose-6-phosphatase, the effect of acute and chronic CaMKII inhibition on liver glycogen content was examined and, as another indicator of glycogen, the percent of periodic acid-Schiff (PAS)—positive cells was also examined. The data show that adeno-KD-CaMKII or CaMKII gene targeting increases hepatic glycogen in fasting mice (FIG. 23G).

The effect of constitutively active hepatic CaMKII was next examined in mice by treating mice with adeno-CA-CAMKII. The CA-CaMKII group had elevated blood glucose levels after pyruvate challenge, increased liver G6pc and Pck1 mRNA levels, and increased liver glycogen content (FIG. 29C-E). CA-CaMKII administration did not alter plasma glucagon or insulin. These combined in vivo data show that CaMKII affects plasma glucose levels, pyruvate conversion into glucose, and the expression of hepatic glucose metabolism genes.

CaMKII Promotes Nuclear Localization of FoxO1

Figures 24A, 24B:
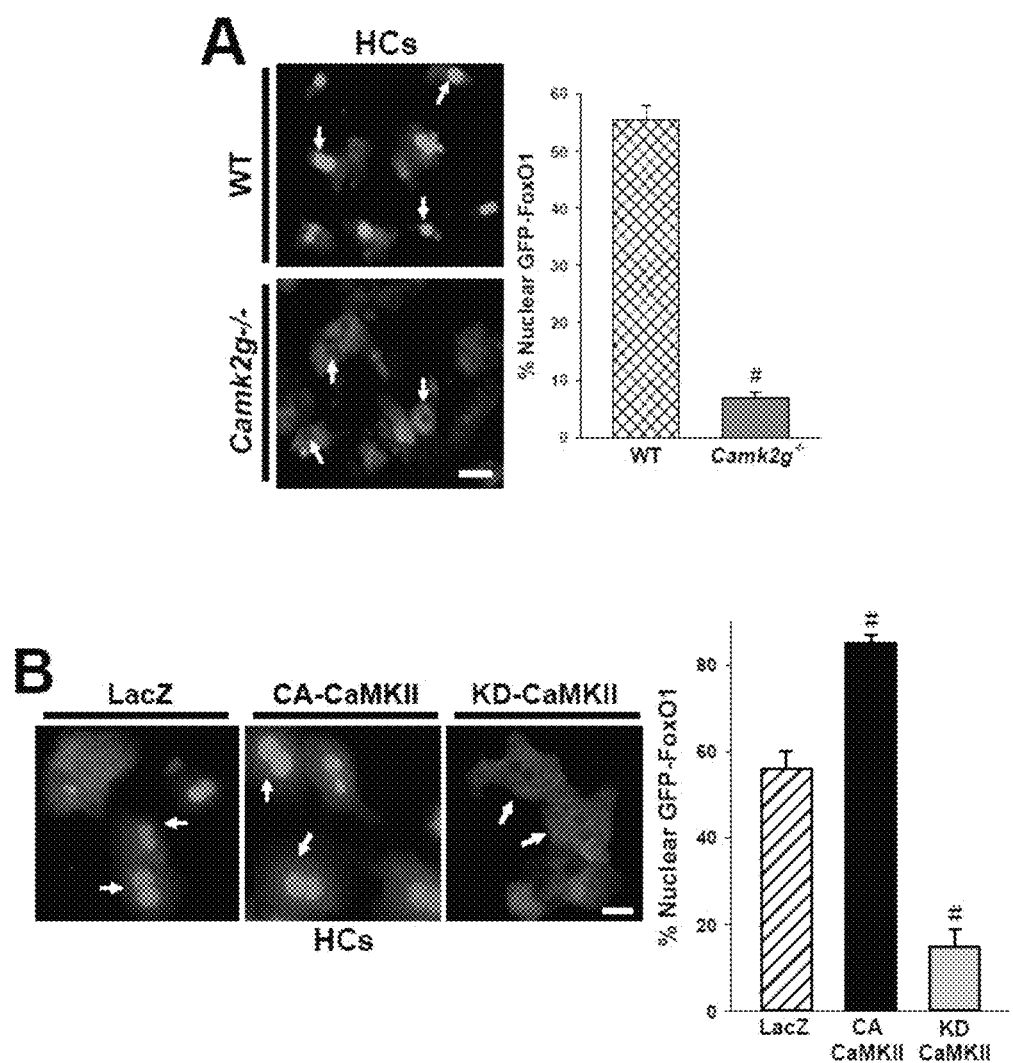
FIGS. 24A-D. CaMKII regulates hepatic FoxO1 subcellular localization.
Figure 24C:
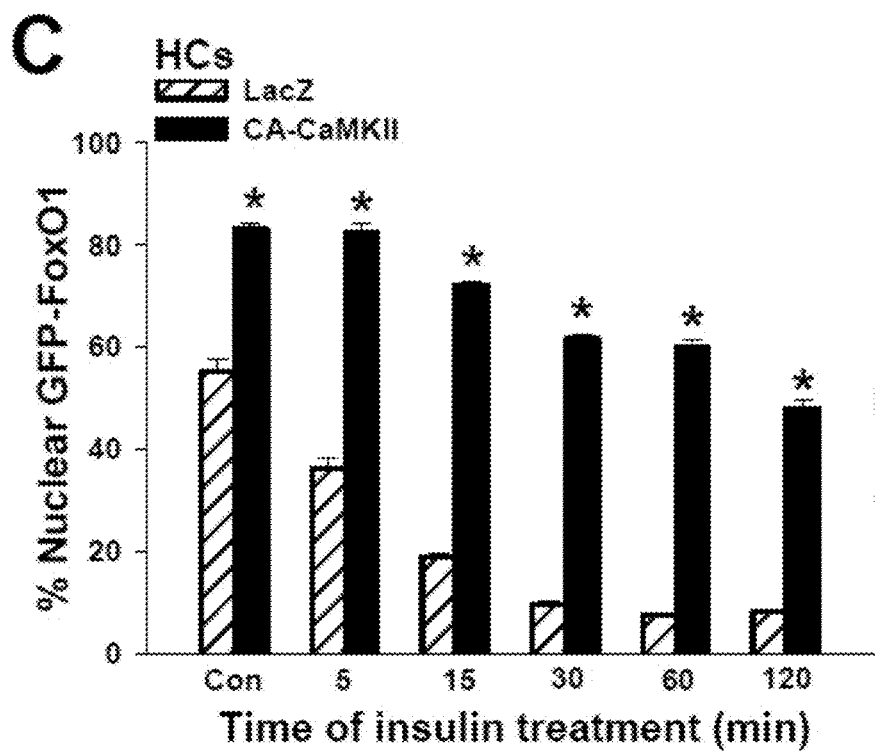
Figure 24D:
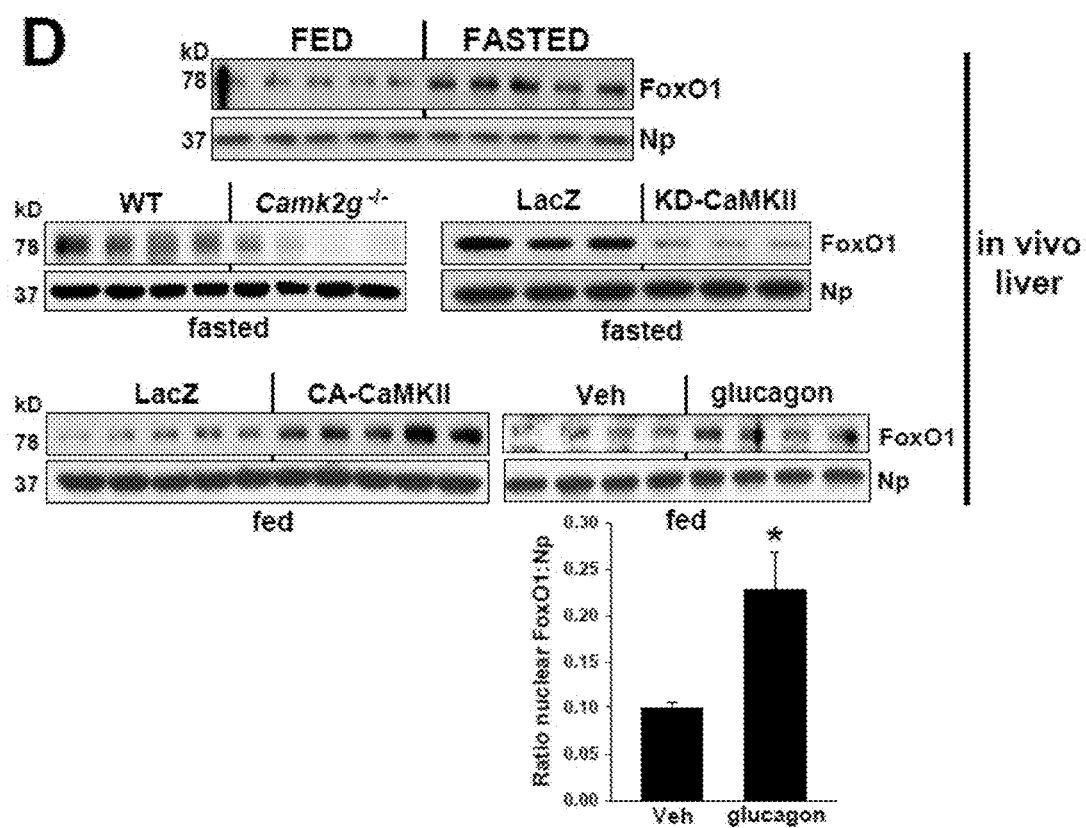
Figures 25A, 25B:
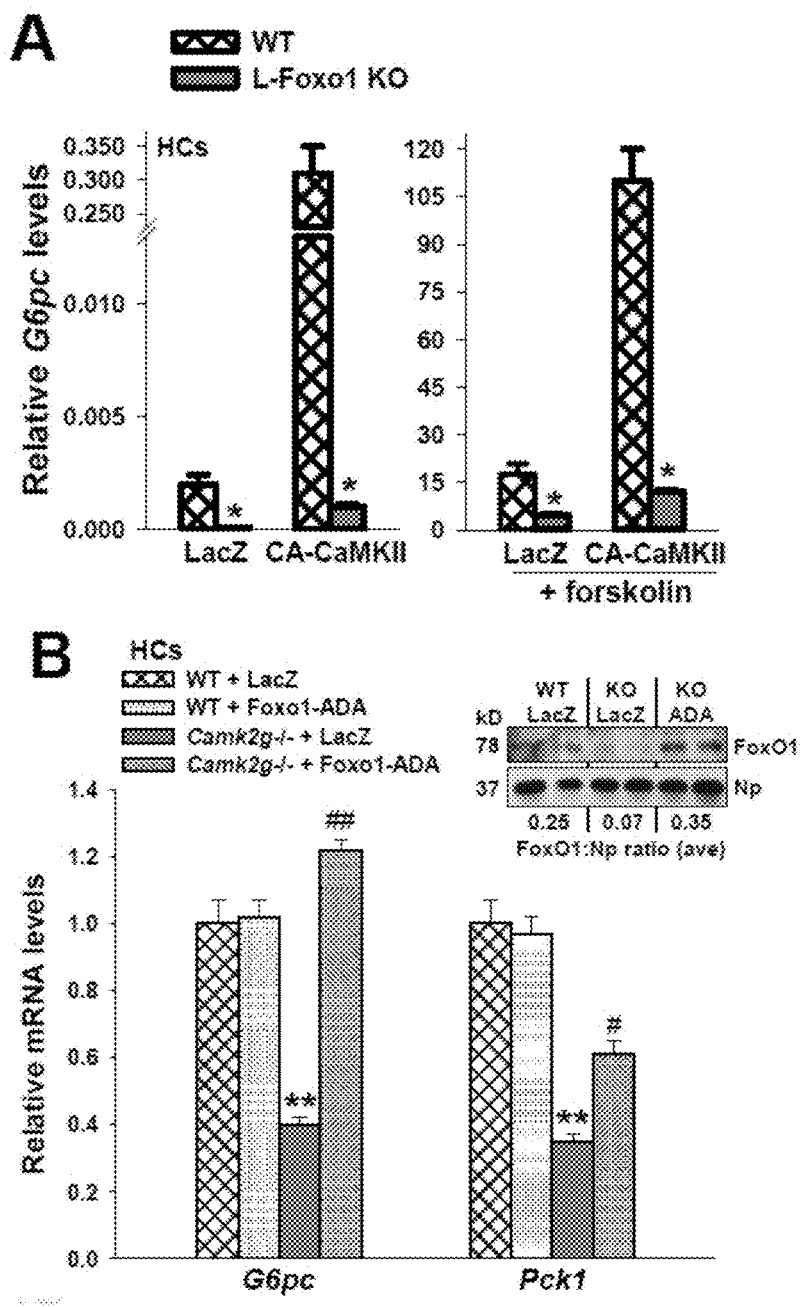
FIGS. 25A-E. Impairment of glucose metabolism by CaMKII inhibition is rescued by transduction with constitutively nuclear FoxO1-ADA.

A major transcription factor involved in HGP is FoxO1, which is regulated primarily by changes in its localization between the cytoplasm and nucleus (Accili and Arden, 2004). The distribution of GFP-tagged FoxO1 that was transduced into HCs isolated from WT vs. Camk2g$^{-/-}$ mice was assayed. Under serum-starved conditions, the majority of GFP-FoxO1 was in the nucleus in WT HCs, whereas Camk2g$^{-/-}$ HCs displayed primarily cytosolic localization of GFP-FoxO1 (FIG. 24A). Moreover, when HCs were transduced with adeno-CA-CaMKII, FoxO1 became predominantly nuclear, while transduction with adeno-KD-CaMKII caused mostly cytoplasmic FoxO1 (FIG. 24B). It was noted that nuclear FoxO1 was substantial in cultured HCs under the "basal" cell culture conditions used here, and so the fold increase with CA-CaMKII was limited. Basal nuclear FoxO1 was therefore lowered using short incubations with insulin, which then revealed a marked increase in nuclear FoxO1 with CA-CaMKII (FIG. 24C). Although this experiment was done using a high level of total CaMKII protein expression (see FIG. 28D), a similar experiment using a lower MOI of CA-CaMKII showed an increase in nuclear FoxO1 at a level of total CaMKII protein that was similar to endogenous CaMKII (FIG. 30A). To show relevance in vivo, the effect of CaMKIIγ deficiency or inhibition was tested in fasting mice. Nuclear FoxO1 in liver was prominent under fasting conditions (FIG. 24D, top blot), and it was markedly diminished in Camk2g$^{-/-}$ mice or mice transduced with adeno-KD-CaMKII (FIG. 24D, middle 2 blots). Feeding diminished nuclear FoxO1, and nuclear FoxO1 was increased under these conditions by both CA-CaMKII and glucagon (FIG. 24D, bottom blots).

cAMP-mediated induction of G6pc mRNA in primary hepatocytes is suppressed >50% by FoxO1 shRNA, indicating an important role for FoxO1 in the endogenous setting (Matsumoto et al., 2007). Consistent with these data, it was found that induction of luciferase downstream of the human G6PC promoter was blunted when three consensus FoxO-binding sites were mutated (Ayala et al., 1999; von Groote-Bidlingmaier et al., 2003) (FIG. 30B). However, this hepatoma cell line—reporter construct experiment does not distinguish between cAMP and dexamethasone effects and cannot accurately reflect the endogenous situation. For example, reporter induction here was much less robust than actual G6pc mRNA induction in primary hepatocytes (Matsumoto et al., 2007), and the identified promoter element may not be the only site required for regulation. Therefore, rather than pursue this model further as a way to assess the functional importance of FoxO1 in CaMKII-mediated G6pc expression, the induction of endogenous G6pc in primary hepatocytes and, most importantly, in vivo, was studied. To begin, the ability of CA-CaMKII to induce G6pc in HCs from WT vs. L-Foxo1 KO mice, which lack FoxO1 in liver, was compared (Matsumoto et al., 2007). Consistent with previous studies (Puigserver et al., 2003; Matsumoto et al., 2007), forskolin-induced expression of G6pc was suppressed in the absence of FoxO1 (FIG. 25A, right graph). Most importantly, the increase in G6pc mRNA expression by CA-CaMKII was markedly blunted by FoxO1 deficiency. In the absence of forskolin, gene expression was much lower as expected (FIG. 25A, left graph; note Y-axis scale), but even here CA-CaMKII-induced gene expression was almost completely dependent on FoxO1. Finally, the fact that the nuclear localization of two other transcription factors involved in HGP, CREB and Crtc2, were not decreased by CaMKII inhibition of deficiency, was documented (FIG. 30C-D). These combined data are consistent with a model in which CaMKII promotes FoxO1 nuclear localization, which then leads to induction of G6pc.

Figures 25C, 25D:
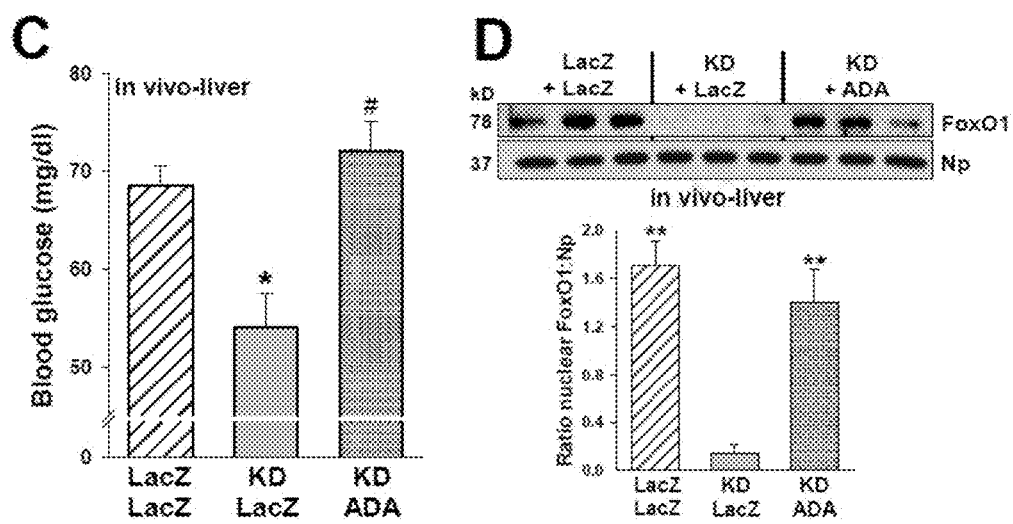
Figure 25E:
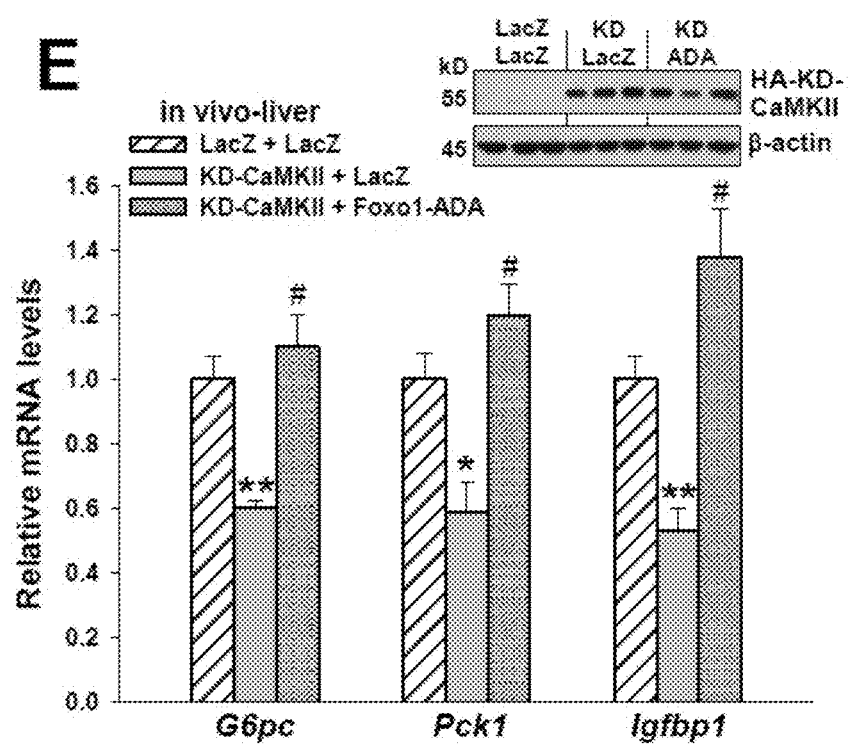

To further validate the importance of FoxO1 in the impairment of HGP by CaMKII deficiency or inhibition, HCs were transduced from Camk2g$^{-/-}$ mice with adenovirus containing a phosphorylation-defective, constitutively nuclear FoxO1 mutant (FoxO1-ADA) (Nakae et al., 2001). It was observed that the suppressive effect of CaMKIIγ deficiency on forskolin-induced G6pc and Pck1 mRNA expression was abrogated by transduction with adeno-FoxO1-ADA (FIG. 25B). Note that the level of FoxO1-ADA used here was low enough so as not to increase G6pc or Pck1 in forskolin-treated WT HCs, and the level of nuclear FoxO1 in the Camk2g$^{-/-}$+ADA group was similar to the endogenous level in the WT+LacZ group (inset, FIG. 25B). The Pck1 results in FIG. 25B, as well as those in FIGS. 22-23, are interesting in view of the finding that germline knockdown of FoxO1 does not affect Pck1 induction (Nakae et al., 2002; Barthel et al., 2001). However, more acute silencing of FoxO1 does suppress Pck1 (Matsumoto et al., 2007), and so manipulations of CaMKII may be more parallel to that setting. Consistent with the effect of FoxO1-ADA on HGP gene expression, treatment of mice with adeno-FoxO1-ADA adenovirus rescued the impairment of glucose homeostasis in adeno-KD-CaMKII-treated mice (FIG. 25C-E). Note that this result cannot be explained by defective transduction with adeno-KD in the ADA group (inset, FIG. 25E). Taken together, these results are consistent with a model in which CaMKII contributes to HGP through promoting nuclear localization of FoxO1.

The Role of Non-AKT-Phospho-FoxO1 Sites and p38 MAP Kinase in CaMKIIγ-Mediated FoxO1 Nuclear Localization Insulin/Akt promotes FoxO1 nuclear exclusion through phosphorylation of T24, S253, and S316 (murine residues) (Brunet et al., 1999). Although CaMKII is a kinase, it can activate a phosphatase and thereby promote nuclear localization of FoxO1 by indirectly decreasing the phosphorylation at these sites. However, it was found that phosphorylation at these three sites was not altered in liver from Camk2g$^{-/-}$ mice (FIG. 31A). FoxO1 acetylation, which can also affect FoxO1 localization and activity in HCs (Accili and Arden, 2004), was also not affected by CaMKII deficiency (FIG. 31B).

FoxO1 can also be phosphorylated at other Ser/Thr residues by other kinases, such as p38 MAP kinase (Asada et al., 2007), and these phosphorylation events might promote FoxO1 nuclear localization, not exclusion. To assess the possible role of CaMKII in the phosphorylation of non-Akt sites, the model displayed in FIG. 24A was used, i.e., serum-starved WT and Camk2g$^{-/-}$ (KO) HCs transduced with GFP-FoxO1, which also carries a FLAG tag. FoxO1 was immunopurified using anti-FLAG, followed by reduction, alkylation, and proteolytic digestion using a triple protease protocol developed by MacCoss et al. (MacCoss et al., 2002). Phosphorylated peptides were enriched by TiO$_2$ chromatography and then analyzed by LC-MS/MS (Cantin et al., 2007) using MS-based shotgun proteomic methods and label-free quantitation by spectral counting (Cantin et al., 2007). The FoxO1 protein was identified with ~70% sequence coverage, and a total of 57 phosphopeptides for WT and 63 phosphopeptides for KO samples were identified (Tables S1 and S2 at http://fields.scripps.edu/published/foxo1_Tabas_2012/, which are incorporated by reference in their entireties). The peptide false discovery rate (FDR) was less than one percent. Stringent selection criteria were used so that all identified phosphopeptides would have high confidence.

These criteria, with further validation using the phosphopeptide analysis tools Debunker and Ascore (Lu et al., 2007; Beausoleil et al., 2006), enabled the identification of 11 phosphorylation sites: S284, S295, S326, S467, S475, T24, S246, S253, S413, S415 and T553 (see FIG. 31C for murine FoxO1 sequence). FIG. 26A shows the spectral counts, the Debunker score, and Ascore of each of these 11 FoxO1 phosphopeptides from the KO and WT samples. Most phosphorylation sites are well above the high confidence cut-off values of 0.5 and 12 for Debunker and Ascore, respectively. Five sites with slightly lower values of Debunker or A scores were subjected to manual verification, and their annotated tandem mass spectra are shown in FIG. 32D-E for KO peptides 4 and 5 and the aforementioned website for WT peptides 7, 10, and 11. The characteristic b- and/or y-ions for the phospho-sites are all identified. The lower scores are most likely due to the low-abundance fragment ions or lack of neutral losses of phosphoric acid because of the nature of the amino acid sequence for these peptides.

The ratio of spectral KO:WT counts, which was calculated only for peptides with a combined spectral count in KO and WT samples above 10, was used to obtain a measure of the relative expression of identified phosphorylated peptides. By this analysis, only phosphorylation of S295, S467, S475 (peptides 2, 4, and 5) were significantly lower in the KO based on a cut-off value of <0.5, with the ratio of spectral counts in KO vs. WT of 0.45, 0.38 and 0.5, respectively. Although the peptide containing p-S246 had a combined spectral count of 7, and thus did not reach the pre-specified criterion of >10, it showed a lower trend in the KO vs. WT (2 vs. 5, 0.4). In contrast, S326 (peptide 3) had a ratio of 1.65, indicating upregulation in KO vs. WT.

As an initial test of function for the some of the sites lower in the KO, an available plasmid encoding FoxO1 with S-A mutations at seven Ser residues (7A-FoxO1), including Ser295 and 475, as well as Ser246, was used (Asada et al., 2007). When transfected to a similar levels in Foxo1$^{-/-}$ HCs, 7A-FoxO1 showed strikingly less nuclear localization than WT FoxO1 in response to glucagon, while cytoplasmic FoxO1 was higher in the cells transfected with the mutant FoxO1 (FIG. 26B). A construct that had the same seven S-A mutations as in 7A plus 2 additional S-A mutations in S326 and S467 (mutant 9A) was also tested (Asada et al., 2007). This mutant showed similarly defective nuclear localization (FIG. 31F). Moreover, whereas adeno-CA-CaMKII transduction increased nuclear WT-FoxO1, consistent with the data in FIG. 24D, CA-CaMKII did not increase nuclear 7A-FoxO1 (FIG. 26C). These combined data are consistent with a model in which CaMKII directly or indirectly alters the phosphorylation of certain Ser residues in FoxO1 in a manner that promotes its nuclear localization.

Asada et al. (Asada et al., 2007) found evidence of FoxO1 phosphorylation at several sites, including Ser284, 295, 467, and 475, in HEK293T cells transfected with the upstream p38 kinase MKK6. Because p38 has been implicated in the stimulation of HGP (Cao et al., 2005), and CaMKII can activate p38 when studied in neurons (Blanquet, 2000), a CaMKII→p38→FoxO1 phosphorylation/nuclear localization pathway involved in HGP was considered. It was first confirmed that p38 was phosphorylated, which is a measure of its activation, in the livers of fasting mice (FIG. 32A) and that inhibition of p38 by the high-affinity competitive inhibitor SB202190 blocked the expression of G6pc and Pck1 in glucagon-stimulated HC (FIG. 32B, left). The inhibitor data were confirmed using adeno-Cre-transduced HCs isolated from the livers of from P38a$^{fl/fl}$ mice (FIG. 32B, right). To test a potential link between CaMKII and p38, serum-starved HCs from WT and Camk2g$^{-/-}$ mice were compared and a striking decrease in phospho-p38 in the CaMKIIγ-deficient HCs was found (FIG. 32C). It was then determined whether p38 was involved in hepatic FoxO1 nuclear localization in vivo by comparing fasting mice treated with SB202190 vs. vehicle control. Among the 7 mice in each group, there was a certain degree of variability in both the basal level of p-MK2, a p38 kinase target that reflects p38 activity, and in the level of inhibition of MK2 phosphorylation by SB202190. Nuclear FoxO1 for all 14 mice was therefore plotted as a function of p-MK2. The data show a clear decrease in nuclear FoxO1 in mice as a function of p38 inhibition, i.e., as indicated by lower p-MK2 (FIG. 32D). Moreover, the p38 inhibitor decreased nuclear GFP-FoxO1 in HCs treated with glucagon (FIG. 32E). These combined data are consistent with a model in which CaMKII promotes FoxO1 nuclear localization through p38 activation. Whether p38 functions in CaMKII-induced FoxO1 nuclear localization by directly phosphorylating the aforementioned Ser residues in FoxO1 (Asada et al., 2007) remains to be determined.

The Role of CaMKII in Hepatic Glucose Metabolism in Obesity

Elevated HGP, in part due to an imbalance of glucagon-to-insulin signaling, contributes to fasting hyperglycemia in obesity and other insulin-resistant states (Sorensen et al., 2006; Unger and Cherrington, 2012; Saltiel, 2001). To test the role of CaMKIIγ in hepatic glucose metabolism in the setting of obesity, evidence of hepatic CaMKIIγ activation was sought in two mouse models of obesity. It was found that the level of p-CaMKII, but not total CaMKII, was markedly higher in the livers of both ob/ob mice and WT mice placed on a high-fat, high-calorie diet for 20 wks (diet-induced obesity; DIO) (FIG. 27A). Antibody specificity for both anti-p-CaMKII and anti-CaMKII in obese liver is shown by the absence of the immunoblot bands in obese Camk2g$^{-/-}$ mice. The functional importance was next tested by comparing fasting plasma glucose and hepatic FoxO1-target gene expression in ob/ob mice transduced with adeno-KD-CaMKII vs. adeno-LacZ control. The mice treated with adeno-KD-CaMKII had lower fasting glucose, lower blood glucose after pyruvate challenge, and lower expression of three FoxO1-target genes, including G6pc and Pck1 (FIG. 27B-D) These changes were not associated with either higher plasma insulin or lower weight in the adeno-KD-CaMKII-treated mice. Thus, hepatic CaMKII is activated in the livers of obese mice and regulates hepatic glucose metabolism and FoxO1-target gene expression.

Discussion

The data in this report provide evidence for calcium-mediated regulation of HGP as part of a pathway that can be summarized as follows: glucagon/fasting→cAMP/PKA→IP3R1→Ca$^{2+}_f$→CaMKII→nuclear FoxO1→HGP. CaMKII also mediates elevated HGP in obese mice (FIG. 27), and although more work is needed in this area, it is possible that driving force here is also glucagon (Sorensen et al., 2006; Unger and Cherrington, 2012; Saltiel, 2001). As such, the present findings have implications for three fundamental areas related to HGP: the molecular mechanisms whereby glucagon and fasting, as well as obesity/insulin resistance, stimulate HGP; the molecular links between intracellular calcium and HGP; and the regulation of FoxO1 nuclear transport. The latter issue is of particular interest, because while there have been many reports on how insulin/AKT-mediated phosphorylation of FoxO1, as well as FoxO1 acetylation, promote nuclear exclusion of FoxO1 (Lin and Accili, 2011; van der Horst and Burgering, 2007), there has been little emphasis on the regulation of FoxO1 nuclear entry that occurs in the absence of insulin or in the setting of insulin resistance.

The CaMKII pathway is downstream of cAMP/PKA, and so it would naturally complement other glucagon-PKA pathways that stimulate HGP. Thus far, the data herein indicate that these other pathways occur in parallel with the CaMKII pathway rather than also being downstream of CaMKII. For example, glucagon-PKA directly phosphorylates cAMP response element binding (CREB) protein, which transcriptionally induces the FoxO1 transcriptional co-factor PGC1α (Herzig et al., 2001), but there was no difference in nuclear CREB in livers from adeno-LacZ vs. KD-CaMKII mice (FIG. 30B). This was an important finding, because there are in vitro data in neurons and in RANKL-treated RAW264.7 cells that CaMKII can activate/phosphorylate CREB in certain settings (Dash et al., 1991; Sheng et al., 1991; Ang et al., 2007). It was also found that CaMKII deficiency did not affect nuclear Crtc2 (FIG. 30C), which is another transcriptional activator involved in HGP. These data indicate that CaMKII in liver works in parallel with these other pathways, which together effect the nuclear localization of the proper array of transcriptional factors to mediate HGP. The case with Crtc2 is particularly interesting, because glucagon/PKA-mediated IP3R activation and ER calcium release promotes Crtc2 nuclear localization through another calcium-sensing enzyme, calcineurin. Indeed, it was found that inhibition of CaMKII and calcineurin are additive in terms of suppressing forskolin-induced G6pc mRNA. Thus, a common proximal signaling pathway leads to the coordinated nuclear entry of two key HGP transcription factors, Crtc2 and FoxO1, by different distal mechanisms. In this regard, it is interesting to note a previous study showing that drugs that promote calcium entry through the plasma membrane actually decrease Pck1 mRNA in HCs (Valera et al., 1993), which can indicate that the route of calcium entry into the cytoplasm is a factor in determining downstream events.

FoxO1 is phosphorylated at Thr24, Ser253, and Ser316 (murine sequence numbers) by insulin/growth factors via Akt to promote its nuclear exclusion. CaMKII promotes FoxO1 nuclear localization, but, without being bound by theory, CaMKII can activate a phosphatase that de-phosphorylates these sites. However, CaMKIIγ deficiency did not affect the phosphorylation of these three residues, and it also did not affect FoxO1 acetylation (FIG. 31A-B). Instead, evidence that CaMKII mediates the phosphorylation of other Ser residues on FoxO1 was found, and the Ser-Ala FoxO1 mutant experiments indicate that this action plays a role in CaMKII-mediated FoxO1 nuclear localization.

The link between CaMKII and FoxO1 phosphorylation can be direct or indirect. An indirect mechanism, i.e., whereby CaMKII activates another kinase, can be linked to previous findings that other kinases can phosphorylate FoxO on non-Akt sites in a manner that promotes their nuclear retention (Essers et al., 2004; Chiacchiera and Simone, 2010). Based on the p38 inhibitor and gene-targeting data herein and the study of Asada et al. (Asada et al., 2007), without being bound by theory, p38 MAPK can also be able to carry out this function and, indeed, can be the mediator of CaMKII-induced FoxO1 nuclear localization. In support of this are reports of links between CaMKII and p38 and between p38 and HGP (Cao et al., 2005; Blanquet, 2000). While there is no direct evidence yet that p38 phosphorylates and thereby activates FoxO1, the ability of glucocorticoids to promote FoxO1 nuclear localization in rat cardiomyocytes correlated with activation/phosphorylation of nuclear p38, and immunofluorescence microscopy and IP/immunoblot data indicated that p-P38 and FoxO1 can interact with each other (Puthanveetil et al., 2010). Interestingly, there is evidence that FoxO1 can be able to activate p38 in HCs (Naimi et al., 2007), and so it is possible that a FoxO1-p38 feed-forward pathway can amplify the effect the CaMKII-p38 pathway indicated here on FoxO1 nuclear localization. However, more work is needed to establish the role of p38 and to further elucidate the mechanisms whereby CaMKII promotes FoxO1 nuclear localization.

The discovery of the role of calcium-CaMKII in HGP not only provides insight into the physiologic defense against fasting hypoglycemia but can also reveal therapeutic targets for the disturbed glucose metabolism that occurs in the setting of insulin resistance, as indicated by the data in FIG. 27. Indeed, in type 2 diabetes, disproportionate HGP and an imbalance of glucagon vs. insulin signaling contributes to fasting hyperglycemia (Sorensen et al., 2006; Saltiel, 2001). Moreover, glucagon signaling has also been implicated in type 1 diabetes (Unger and Cherrington, 2012). In this context, future studies will further address the pathophysiologic role(s) and mechanisms of hepatic CaMKIIγ in obesity, insulin resistance, and diabetes and thereby evaluate its potential as a therapeutic target in these disorders.

Experimental Procedures

Measurement of CaMKII Activity

CaMKII activity was assayed using a CaMKII assay kit from Promega according to the manufacturer's instructions. After the HCs were treated as indicated in the figure legends, they were lysed by a 5-min exposure to 1% Triton-X100 in 50 mM HEPES, 150 mM NaCl, 10 mM Na pyrophosphate, 10 mM EDTA, 10 mM EGTA, 1 mM $Na_3VO_4$, 50 mM NaF, 1 mM PMSF, and 5 μg ml$^{-1}$ leupeptin. Next, [γ-$^{32}$P]ATP and biotinylated CaMKII peptide substrate were added to the lysate or to the immunoprecipitated complexes (see below). After incubation for 10 min at 30° C., the [$^{32}$P]-phosphorylated substrate was separated from the residual [$^{32}$P]ATP using SAM biotin-capture membrane and then quantitated using a scintillation counter. Assays were conducted ±calmodulin, and the activity value in the absence of calmodulin was subtracted from those obtained in the presence of calmodulin.

Glucose Production in Primary HCs

Glucose production assays were carried out as described (Yoon et al., 2001). Briefly, after primary mouse HCs were harvested and cultured as described above, the cell culture medium was switched to glucose- and phenol-free DMEM (pH 7.4) supplemented with 20 mM sodium lactate and 2 mM sodium pyruvate. After 16 h of culture, 500 μl medium was collected, and the glucose content was measured using a colorimetric glucose assay kit (Abcam). The readings were then normalized to the total protein amount in the whole-cell lysates.

Mouse Experiments

Camk2g$^{-/-}$ mice were generated as described previously (Backs et al., 2010) and crossed onto the C57BL6/J background. ob/ob mice were obtained from Jackson Labs. Mice were fed a standard chow diet, or a high-fat diet with 60% kcal from fat for the experiments in FIG. 27, and maintained on a 12-h light-dark cycle. Recombinant adenovirus (1.5× 10$^9$ plaque-forming unit/mice) was delivered by tail vein injection, and experiments were commenced after 5 days. Fasting blood glucose was measured in mice that were fasted for 12-14 h, with free access to water, using a glucose meter (One Touch Ultra, Lifescan). Pyruvate-tolerance tests were carried out with an intraperitoneal injection of 2 g kg$^{-1}$ body weight pyruvate after 17 h of fasting. Blood glucose levels were measured over the following 2 h. Xestospongin C was administered by daily i.p. injections to mice at a dose of 10 pmol g$^{-1}$ for 4 days. P38a$^{fl/fl}$ mice were generated as described previously (Engel et al., 2005).

Hepatic Glycogen Measurement 50-100 mg of frozen livers were homogenized in 1 ml of H$_2$O with protease and phosphatase inhibitors. Samples were then mixed with KOH (1:2), boiled for 25 min and washed with 70% ethanol. The pellet was dried and dissolved in 100 µl H$_2$O, and the glycogen content was assessed using the Glycogen Assay Kit (Abcam) according to the manufacturer's instructions. Data represent the mean±SEM.

PAS Staining of Mouse Liver Sections

Liver samples were fixed in 10% neutral-buffered formalin for 24 h and embedded in paraffin. Sections (5 micron) were stained for glycogen using Periodic acid-Schiff (PAS) stain (Sigma) according to manufacturer's instructions. The sections were then counterstained with hematoxylin and examined by light microscopy. For the quantification of PAS staining, 5 fields from 4 different sections were chosen randomly, and the number of PAS-positive cells was counted and expressed as the percentage of the total number of cells (Hammad et al., 1982). Two independent investigators, blinded to the identity of the samples, performed the analysis.

Analysis of Mass Spectrometric Data

Protein and phosphopeptide identification, quantification, and phospho analysis were performed with Integrated Proteomics Pipeline—IP2 (Integrated Proteomics Applications, Inc., San Diego, Calif. http://www.integratedproteomics.com/) using ProLuCID, DTASelect2, Census, DeBunker and Ascore. Spectrum raw files were extracted into ms1 and ms2 files (McDonald et al., 2004) from raw files using RawExtract 1.9.9 (http://fields.scripps.edu/downloads.php), and the tandem mass spectra were searched against EBI IPI mouse protein database (http://www.ebi.ac.uk/IPI/IPI-mouse.html, released on Mar. 24, 2010). In order to accurately estimate peptide probabilities and false discovery rates, a decoy database containing the reversed sequences of all the proteins appended to the target database was used (Peng et al., 2003). Tandem mass spectra were matched to sequences using the ProLuCID (Xu et al., 2006) algorithm with 50 ppm peptide mass tolerance. ProLuCID searches were done on an Intel Xeon cluster running under the Linux operating system. The search space included all fully- and half-tryptic peptide candidates that fell within the mass tolerance window. Carbamidomethylation (+57.02146 Da) of cysteine was considered as a static modification, while phosphorylation (+79.9663) on serine, threonine, and tyrosine were considered as variable modifications.

The validity of peptide/spectrum matches (PSMs) was assessed in DTASelect (Tabb et al., 2002; Cociorva et al., 2007) using two SEQUEST (Eng et al., 1994) defined parameters, the cross-correlation score (XCorr), and normalized difference in cross-correlation scores (DeltaCN). The search results were grouped by charge state (+1, +2, +3, and greater than +3) and tryptic status (fully tryptic, half-tryptic, and non-tryptic), resulting in 12 distinct sub-groups. In each one of these sub-groups, the distribution of Xcorr, DeltaCN, and DeltaMass values for (a) direct and (b) decoy database PSMs was obtained, and then the direct and decoy subsets were separated by discriminant analysis. Full separation of the direct and decoy PSM subsets is not generally possible; therefore, peptide match probabilities were calculated based on a nonparametric fit of the direct and decoy score distributions. A peptide confidence of 99.5% was set as the minimum threshold, and only phosphopeptides with delta mass less than 10 ppm were accepted. The false discovery rate was calculated as the percentage of reverse decoy PSMs among all the PSMs that passed the 99.5% confidence threshold. After this last filtering step, it is estimated that both the protein and peptide false discovery rates were both below 0.1%. After database searching and DTASelect2 filtering, phosphopeptides were analyzed with IP2 phospho analysis tool that uses Ascore (Beausoleil et al., 2006) and Debunker (Lu et al., 2007). Peptides and phosphopeptides were quantified using the Spectral Count method (Liu et al., 2004).

Statistical Analysis

All results are presented as mean±SEM. P values were calculated using the student's t-test for normally distributed data and the Mann-Whitney rank sum test for non-normally distributed data.

Supplemental Experimental Procedures

Reagents and Antibodies

Glucagon, pyruvate, forskolin, H89, 8-bromo-cAMP and SB202190 were from Sigma. BAPTA-AM and anti-nucleophosmin (Np) antibody were from Invitrogen. Xestospongin C was from EMD Chemicals. Anti-phospho-Thr287 CaMKII antibody was from Imgenex and Novus; anti-total CaMKII, anti-FoxO1 and anti-Ac-FoxO1 antibodies were from Santa Cruz Biotechnology Inc. Anti-β-actin and anti-phospho-S316 FoxO1 antibodies were from Abcam. Anti-phospho-p38, anti-phospho-MK2, anti-phospho-CREB, anti-p38, anti-MK2, anti-CREB, anti-phospho-T24 FoxO1, anti-phospho-S253 FoxO1, anti-HA and anti-FLAG antibodies were from Cell Signaling. Anti-CRTC2 antibody was a gift from Dr. Marc Montminy. Adenoviruses encoding LacZ, CA-CaMKII, KD-CaMKII, GFP-FoxO1, and Cre were described previously (Pfleiderer et al., 2004; Tanaka et al., 2009; Akagi et al., 1997) and amplified by Viraquest, Inc. (North Liberty, Iowa). Plasmids encoding FoxO1 mutants 7A and 9A were constructed as described (Asada et al., 2007).

Primary Hepatocytes

Primary mouse HCs were isolated from 8- to 12-week-old mice as described previously (Matsumoto et al., 2002). For most experiments, the HCs were serum-depleted overnight by incubation in medium containing 0.5% fetal calf serum and were then incubated for 5 h in serum-free media, with individual treatments noted in the figure legends. HCs were transduced with adenoviral constructs 12 h after plating, and experiments were conducted 24 h after transduction. Transfections with WT, 7A- and 9A-Foxo1 were carried out using jetPEI™-hepatocyte DNA transfection reagent (Polyplus-transfection, Inc.) according to manufacturer's instructions.

Immunoprecipitation

Cells were lysed by a 5-min exposure to 1% Triton-X in 50 mM HEPES, 150 mM NaCl, 10 mM Na pyrophosphate, 10 mM EDTA, 10 mM EGTA, 1 mM Na3VO4, 50 mM NaF, 1 mM PMSF, and 5 µg/ml leupeptin. The lysate (500 µg of protein) was brought to a total volume of 1 ml with lysis buffer containing 0.3-0.6 µg antibody and 80 µl Sepharose beads. The mixture was rotated in a 1.5-ml microfuge tube at 4° C. for 14 h Immune complexes were collected by centrifugation at 16,000 g and washed 3 times with chilled lysis buffer.

Generation of Ip3r1$^{flox}$ Mice

The Ip3r1$^{flox}$ mouse line was created as follows: a targeting construct was generated by recombineering using the BAC clone RP24-245H16 (CHORI), containing a fragment of chromosome 6, encompassing exons 1 through 9 of IP$_3$R1 from C57Bl/6J mice (Liu et al., 2003; Warming et al., 2005).

Plasmids pL451, pL452 & pL253 were kindly provided by Dr. Neal Copeland (NCI, NIH). Briefly, a Frt-Neo-Frt-loxP cassette (from plasmid pL451) was inserted upstream of exon 4 (second coding exon), then the Neo cassette was removed by agarose-induced flp recombination. The second and third loxP sites were introduced downstream of exon 4 by inserting loxP-Neo-loxP cassette (from vector pL452). Finally, a DTA cassette (from plasmid pL253), containing thymidine kinase, was inserted further downstream of the third loxP site. All intermediate BAC constructs and the final construct were screened by PCR, and the final construct was "fingerprinted" by Acc65I digestion and tested for loxP functionality. Crucial junction sites were confirmed by sequencing. The resulting modified BAC was electroporated into chimeric ES cells (CSL3 cell line, derived from 12956/SvEvTac mouse line). The correct recombinant ES cells were injected into C57BL/6 blastocysts-stage mouse embryos. Chimeric male mice were bred to C57BL/6 female mice to establish a hybrid line. Germ-line transmission generated $Ip3r1^{3xflox}$ mice, and females were crossed with EIIa-cre males to create $Ip3r1^{flox}$ mice in which the floxed Neo cassette was eliminated. These mice were subsequently crossed with C57BL/6J mice to breed out the EIIa-cre allele. The final $Ip3r1^{fl/fl}$ line was derived through heterozygous breeding.

Immunoblotting and RT-qPCR

Immunoblot and RT-qPCR assays were performed as previously described (Timmins et al., 2009). Total RNA was extracted from HCs using the RNeasy kit (Qiagen). cDNA was synthesized from 2 μg total RNA using oligo (dT) and Superscript II (Invitrogen). Nuclear extraction from liver was performed using the Nuclear Extraction Kit from Panomics according to the manufacturer's instructions. With regard to anti-Thr287-p and total CaMKII immunoblots, 2 bands and occasionally 3 bands, which were absent in CaMKIIγ-deficient HCs, were routinely seen. Whether their origin is alternative splicing or post-translational modification remains to be determined.

Mass Spectrometry of FoxO1 Phosphopeptides

HCs from WT and $Camk2g^{-/-}$ mice were transduced with adeno-FLAG-FoxO1 at an MOI of 2. Cells were serum-depleted overnight and then incubated for 5 h in serum-free media. FoxO1 was immunopurified using anti-FLAG. FLAG-FoxO1 in ice-cold Tris-buffered saline was precipitated by mixing 1 volume of the sample solution (cold) with ⅓ volume of 100% (w/v) TCA (6.1 N, Sigma). After 3 h on ice, the samples were centrifuged for 30 min at 4° C., and the supernate was aspirated leaving ~5-10 μl in the tube so as to not disturb the pellet. The pellet was washed twice with ice-cold acetone (500 μl each). After each wash, the solution was centrifuged for 10 min. The final pellet was then dried on a Speed-vac for 1-2 min.

Peptides were generated by proteolysis as described (Delahunty and Yates, III, 2005; MacCoss et al., 2002). The TCA pellets were solubilized in 60 μl of 100 mM Tris-HCl, pH 8.5, containing 8 M urea, and then the proteins were reduced by the addition of 500 mM Tris(2-carboxyethyl) phosphine (TCEP) to a final concentration of 5 mM. After a 20-min incubation at room temperature, cysteine residues were carboxymethylated by the addition of 500 mM iodo-acetamide to achieve a final concentration of 10 mM. The solution was incubated for 30 min at room temperature in the dark and then split equally into three tubes. In one of the tubes, the concentration of urea was then diluted 2-fold (to 4 M) by the addition of an equal volume of 100 mM Tris-HCl, pH 8.5, and then subtilisin (Promega) was added at ~1:100 enzyme:substrate ratio (wt:wt) and incubated at 37° C. for 4 h in the dark. The other two samples were diluted 4-fold (to 2 M), and elastase and trypsin (Promega) were added at ~1:100 enzyme:substrate ratio (wt:wt), and then both samples were incubated at 37° C. overnight in the dark. The resulting peptides from the three digests were combined into one tube and dissolved in 90% formic acid to a final concentration of 2% in 10% acetonitrile. The samples were stored at −20° C. prior to TiO2 enrichment and LC-MS/MS analysis.

TiO2 enrichment for phosphopeptides was done as described by Cantin et al. (Cantin et al., 2007). A TiO2 column was made by pressure-slurry packing TiO2 (5-μ partisphere, Whatman, Clifton, N.J.) into fused-silica capillary (250-μm i.d.) to a length of 5 cm, and the peptide mixtures were pressure-loaded onto the column. The column was washed with buffer A and B (see the following section for buffer compositions) in succession, and then phosphopeptides were eluted using 250 mM ammonium bicarbonate (pH 9) directly into 100-μm-i.d. Kasil-fritted end packed column with 5 cm of 5-nm reversed phase (Gemini C18, Phenomenex, Torrance, Calif.), which was linked to a pulled-tip analytical column with a bed volume of 15 cm of the same reversed phase. This second column was in-line with an Agilent 1200 quaternary HPLC pump (Palo Alto, Calif.) for mass spectrometry analysis.

The HPLC buffer solutions used were water/acetonitrile/formic acid (95:5:0.1, v/v/v) as buffer A and water/acetonitrile/formic acid (20:80:0.1, v/v/v) as buffer B. The elution gradient was as follows: 10 min of 100% buffer A, a 5-min gradient from 0 to 15% buffer B, a 65-min gradient from 15 to 45% buffer B, a 15-min gradient from 45 to 100% buffer B, and 5 min of 100% buffer B. Data-dependent tandem mass spectrometry (MS/MS) analysis was performed with a LTQ-Velos-Orbitrap mass spectrometer (ThermoFisher, San Jose, Calif.). Peptides eluted from the LC column were directly electrosprayed into the mass spectrometer with the application of a distal 2.5-kV spray voltage. A cycle of one full-scan MS spectrum (m/z 300-1800) was acquired followed by twenty MS/MS events, sequentially generated on the first to the twentieth most intense ions selected from the full MS spectrum at a 35% normalized collision energy. The number of microscans was one for both MS and MS/MS scans, and the maximum ion injection time was 25 and 50 ms respectively. The dynamic exclusion settings used were as follows: repeat count, 1; repeat duration, 30 second; exclusion list size, 500; and exclusion duration, 120 second. MS scan functions and HPLC solvent gradients were controlled by the Xcalibur data system (ThermoFisher).

G6PC Promoter-Luciferase Assay

FAO hepatocytes were transfected with a construct encoding nucleotides −1227 to +57 of the human G6PC promoter fused to luciferase (−1227 WT) or the same construct with three consensus FoxO binding sites mutated (−1227 Mut): −187 to −183 (GTTT→CGAG); −171 (G→C); and −164 (A→C), disrupting the consensus IRS sequences T(G/A)TTT in the G6PC promoter (Ayala et al., 1999; von Groote-Bidlingmaier et al., 2003). The final mutation at position −164 is upstream of the cAMP-response element (CRE; −161 to −152), leaving the CRE unaffected (Barthel et al., 2001). Hepatocytes were treated for 16 h with 0.1 mM cAMP and 1 μM dexamethasone in serum-free medium with 1% BSA prior to lysis and analysis of luciferase activity. The luciferase units (RLU) were normalized to the untreated cells in each group.

Example 9: InsP3 Receptor Regulates Hepatic Gluconeogenesis in Fasting and Diabetes In the fasted state, increases in circulating glucagon promote hepatic glucose production through induction of the gluconeogenic program. Triggering of the cAMP pathway increases gluconeogenic gene expression via the dephosphorylation of the CREB coactivator CRTC2 (1). Glucagon promotes CRTC2 dephosphorylation in part through the PKA-mediated inhibition of the CRTC2 kinase SIK2. A number of Ser/Thr phosphatases appear capable of dephosphorylating CRTC2 (2,3), but the mechanisms by which hormonal cues regulate these enzymes remain unclear. Here it is shown that glucagon stimulates CRTC2 dephosphorylation in hepatocytes by mobilizing intracellular calcium stores and activating the calcium/calmodulin dependent Ser/Thr phosphatase calcineurin/PP2B. Glucagon increased cytosolic calcium through the PKAmediated phosphorylation of inositol 1,4,5-trisphosphate receptors (InsP3Rs), which is shown here to associate with CRTC2. Following their activation, InsP3Rs enhanced gluconeogenic gene expression by promoting the calcineurin-mediated dephosphorylation of CRTC2. During feeding, increases in insulin signaling reduced CRTC2 activity via the AKT-mediated inactivation of InsP3Rs. InsP3R activity was increased in diabetes, leading to upregulation of the gluconeogenic program. As hepatic down-regulation of InsP3Rs and calcineurin improved circulating glucose levels in insulin resistance, these results demonstrate how cross-talk between cAMP and calcium pathways at the level of the InsP3 receptor modulates hepatic glucose production under fasting conditions and in diabetes.

Results and Discussion

A series of Ser/Thr protein phosphatase (PP) inhibitors were tested for their ability to block CRTC2 activation in response to glucagon. Exposure to the PP2B/calcineurin inhibitor cyclosporine A (CsA) disrupted the glucagon-induced dephosphorylation and nuclear translocation of CRTC2, but okadaic acid (OA), an inhibitor of PP1, PP2A, and PP4 did not (FIG. 33A, FIG. 37A). CsA and other calcineurin inhibitors also reduced CRE-luciferase (luc) reporter activity (FIG. 33A, FIG. 37B), but they had no effect in cells expressing phosphorylation-defective (Ser171, 275 Ala) and therefore active forms of CRTC2 (FIGS. 37C-E).

Based on the ability for CsA to interfere with CRTC2 activation, it was considered whether calcineurin can promote the dephosphorylation of CRTC2 in response to glucagon. Supporting this idea, CRTC2 contains two consensus (PXIXIT) motifs that mediate an association with calcineurin (3, 4) (FIG. 38A, B). Moreover, mutation of both motifs disrupted the glucagon-dependent dephosphorylation of CRTC2 (FIG. 33B) and prevented its nuclear translocation (FIG. 38C), thereby down-regulating CRE-luc activation (FIG. 33B).

Based on these results, whether calcineurin modulates expression of the gluconeogenic program was tested. Adenoviral over-expression of the calcineurin catalytic subunit in hepatocytes augmented CRTC2 dephosphorylation, CRE-luc activity, and glucose secretion in response to glucagon, whereas calcineurin knockdown had the opposite effect (FIG. 33C). Although calcineurin can, in principle, modulate CRTC2 activity indirectly through effects on cAMP signaling, calcineurin over-expression or knockdown did not alter the phosphorylation of cellular PKA substrates in cells exposed to glucagon (FIG. 38D).

Whether calcineurin modulates hepatic gluconeogenesis in vivo was next examined Modest (2-fold) over-expression of calcineurin in liver increased gluconeogenic gene expression, hepatic CRE-luc activity, and fasting blood glucose concentrations (FIG. 33D, FIG. 39A). Conversely, knockdown of hepatic calcineurin reduced expression of the gluconeogenic program and lowered circulating glucose levels (FIG. 33D, FIG. 39B), demonstrating that this phosphatase contributes to the fasting adaptation in liver. Calcineurin appeared to stimulate gluconeogenesis via the CREB pathway; depletion of CRTC2 blocked effects of calcineurin over-expression in this setting (FIG. 40).

Realizing that calcineurin activity is dependent on increases in intracellular calcium, whether the cAMP pathway stimulates calcium mobilization was tested. Exposure of primary hepatocytes to glucagon triggered a rapid increase in cellular free calcium (FIG. 34A, FIG. 41A); these effects were partially reversed by co-treatment with the PKA inhibitor H89 (FIG. 41B). The rise in intracellular calcium appears critical for CRTC2 activation because co-incubation with the calcium chelator BAPTA disrupted CRTC2 dephosphorylation and CRE-luc activation in response to glucagon (FIG. 34B). Arguing against an effect of calcium on cAMP signaling, exposure to BAPTA did not block the PKA-mediated phosphorylation of CREB in response to glucagon.

Without being bound by theory, cAMP can increase calcium mobilization through the PKA-dependent phosphorylation of an intracellular calcium channel. In mass spectrometry studies to identify proteins that undergo phosphorylation by PKA in response to glucagon, the inositol 1,4,5-trisphosphate receptor 1 (InsP3R1) was recovered from immunoprecipitates of phospho-PKA substrate antiserum (FIG. 41C). InsP3R1 and its related family members (InsP3R2, InsP3R3) are calcium release channels that promote the mobilization of endoplasmic reticulum (ER) calcium stores following their activation in response to extracellular signals (5-9). Moreover, cAMP agonists have also been shown to enhance InsP3R receptor activity through PKA-mediated phosphorylation.

Inhibiting InsP3Rs, either by exposure of hepatocytes to Xestospongin C (Xc) or by knockdown of all three InsP3Rs, disrupted cytosolic calcium mobilization and calcineurin activation in response to glucagon and forskolin (FIG. 34A, FIG. 42A). Moreover, Xc treatment and InsP3R knockdown also blocked glucagon effects on CRTC2 dephosphorylation, CRE-luc activation, and induction of the gluconeogenic program (FIG. 34C, FIG. 42A, B). Effects of InsP3R depletion using hepatocytes from mice with a knockout of InsP3R2 (10), the predominant InsP3R isoform in these cells, were confirmed (FIGS. 42C-E).

Based on these results, without being bound by theory, InsP3Rs can also modulate fasting glucose production in vivo. Decreasing hepatic InsP3R expression, either by knockdown of all three Insp3Rs in liver or by targeted disruption of the InsP3R2 gene, reduced fasting CRE-luc activity, gluconeogenic gene expression, and circulating glucose concentrations, demonstrating the importance of these receptors in glucose homeostasis (FIG. 34D, FIG. 43).

It was tested whether glucagon modulates InsP3R activity through PKA-mediated phosphorylation. Exposure of hepatocytes to glucagon increased the phosphorylation of InsP3R1 as well as InsP3R2 and InsP3R3 by immunoblot assay with phospho-PKA substrate antiserum; these effects were blocked by the PKA inhibitor H89 (FIG. 35A, FIG. 44A). Moreover, mutation of serine residues at consensus PKA sites in InsP3R1 (Ser1589, Ser1756) to alanine completely disrupted InsP3R1 phosphorylation in response to glucagon (FIG. 35B). As a result, over-expression of PKA-defective (S1589,1756A) InsP3R1 interfered with calcium mobilization and calcineurin activation, and it reduced CRE-luc activation and glucose secretion from hepatocytes exposed to glucagon (FIGS. 35B-D).

Similar to glucagon, fasting also stimulated hepatic InsP3R1 phosphorylation at Ser1589 and Ser1756 (FIG. 44B). And over-expression of PKA-defective InsP3R1 reduced fasting CRE-luc induction, calcineurin activation, and gluconeogenic gene expression, leading to lower circulating glucose concentrations (FIG. 35E, FIG. 44C, D). Taken together, these results support an important role for the PKA-mediated phosphorylation of InsP3R in hepatic gluconeogenesis.

Without being bound by theory, the proximity of CRTC2 to the calcium signaling machinery can be important for its activation. Supporting this notion, CRTC2 was found to associate with InsP3R1 via its N-terminal CREB binding domain (CBD) in co-immunoprecipitation assays (FIG. 35F, FIGS. 45A-D). Moreover, CRTC2 was enriched in ER-containing high density microsomal (HDM) fractions, which also contain the InsP3Rs (FIG. 45E). The InsP3R:CRTC2 association appears critical for CRTC2 localization in the perinuclear space because RNA-mediated knockdown of the InsP3Rs led to redistribution of CRTC2 in the cytoplasm (FIG. 45F). Disrupting the CRTC2:InsP3R interaction, by deletion of the CBD in CRTC2 or by addition of an N-terminal myristoylation signal that targets CRTC2 to the plasma membrane, blocked CRTC2 dephosphorylation and CRE-reporter activation in response to glucagon (FIGS. 45G-I). Taken together, these results indicate that the association of CRTC2 with InsP3Rs enhances its sensitivity to fasting signals.

Under feeding conditions, insulin inhibits gluconeogenesis in part by increasing CRTC2 phosphorylation. Whether insulin interferes with InsP3R effects on CRTC2 activation was examined Supporting this idea, AKT has been shown to block calcium mobilization by phosphorylating InsP3Rs at Ser 2682 (in InsP3R1) (11). Indeed, exposure of hepatocytes to insulin increased InsP3R phosphorylation by immunoblot analysis with phospho-AKT substrate antiserum (FIG. 46A); mutation of Ser 2682 (in InsP3R1) to alanine blocked these effects. Insulin treatment also reduced glucagon-dependent increases in calcium mobilization and calcineurin activation in cells expressing wild-type InsP3R1, but it had no effect in cells expressing AKT-defective (S2682A) InsP3R1 (FIG. 46B). As a result, CRTC2 dephosphorylation, CRE-luc activity, and glucose output were elevated in hepatocytes expressing (S2682A)-InsP3R compared to wild-type (FIG. 46C).

Whether InsP3R1 phosphorylation by AKT is important in regulating hepatic glucose production in vivo was next examined Feeding increased hepatic InsP3R1 phosphorylation at Ser2682 (FIG. 44B). Moreover, over-expression of AKT-defective InsP3R1 partially suppressed feeding-induced decreases in CRE-luc activity and gluconeogenic gene expression, leading to elevations in circulating glucose concentrations (FIG. 46D). Taken together, these results indicate that the AKT-mediated phosphorylation of InsP3Rs during feeding inhibits hepatic gluconeogenesis by blocking the calcineurin-dependent dephosphorylation of CRTC2.

Whether hepatic InsP3R signaling contributes to increases in gluconeogenesis in the setting of insulin resistance was examined. Hepatic calcineurin activity was enhanced in both ob/ob and db/db diabetic animals, leading to increases in CRE-luc activity (FIG. 36A, FIG. 47A,B). Pointing to a role for InsP3R, hepatic amounts of PKA-phosphorylated, active InsP3Rs were increased in these diabetic mice, while amounts of AKT-phosphorylated, inactive InsP3R were reduced (FIG. 36B). Correspondingly, knockdown of either calcineurin or InsP3Rs in db/db mice reduced CRE-luc activity, gluconeogenic gene expression, and hepatic gluconeogenesis (FIG. 36C, FIG. 47C).

Collectively, the results herein demonstrate that glucagon promotes CRTC2 dephosphorylation during fasting by triggering increases in cytoplasmic calcium that lead to calcineurin activation (FIG. 48). The ability for glucagon to increase calcium signaling via the PKA-mediated phosphorylation of InsP3Rs demonstrates an important regulatory node for cross-talk between cAMP and calcium signaling pathways in liver and perhaps other insulin sensitive tissues. The partial inhibition of calcium entry by the PKA inhibitor H89 also points to additional regulatory inputs (12,13) that may function with PKA to increase InsP3R activity in response to glucagon. CRTC2 has also been found to stimulate metabolic gene expression by upregulating the nuclear hormone receptor coactivator PGC1α in liver (14,15) and muscle (16). Based on the well-recognized role of calcium signaling in PGC1α dependent transcription, InsP3Rs can also function importantly in this setting.

Methods

Adenoviruses were delivered by tail vein injection (17). Hepatic CRE-luc activity was visualized using an IVIS Imaging system. Mice were imaged 3-5 days after injection of CRE-luc adenovirus. Pyruvate tolerance testing was performed on mice fasted overnight and injected intraperitoneally with pyruvate (2g kg-1). Insp3r2 knockout mice have been described (10). Cultured primary mouse hepatocytes were prepared as reported (18). Cellular fractionation studies were conducted using primary mouse hepatocytes (18). Calcium imaging experiments were performed using a CCD camera on primary hepatocytes loaded with fura-2 dye. Mass spectrometry studies were performed on CRTC2 immunoprecipitates prepared from HEK293T cells and on immunoprecipitates of phospho-PKA substrate antiserum prepared from primary hepatocytes exposed to glucagon. Anti-InsP3R1 (A302-158A) and InsP3R3 (A302-160A) antibodies were purchased from Bethyl Laboratories, anti-InsP3R2 (ab77838) antiserum was from Abcam, anti-Calcineurin (610260) from BD Biosciences, anti-GRP78 (ADISPA-826-F) from Enzo Life Sciences, anti-phospho-PKA substrate (RRXS/T, 9624), anti-phospho-AKT substrate (RXXS/T, 9614) and CRTC2 (pS171, 2892) from Cell Signaling. Phospho (Ser275) CRTC2 antibody was used as described (19). Details are included below.

Mouse Strains and Adenovirus

Adenoviruses ($1 \times 10^8$ plaque forming units (pfu) GFP, Calcineurin, InsP3R1, InsP3R1 DM (S1589A/S1756A), unspecific (US) RNAi, Calcineurin RNAi, Insp3r1 RNAi, Insp3r2 RNAi, Insp3r3 RNAi, Crtc2 RNAi, $1 \times 10^9$ pfu CRE-luc reporter, $5 \times 107$ pfu RSV β-gal) were delivered to 8-10 week old male C57BL/6J, B6.V-lep<ob>/J, B6.Cg-m+/+Lepr<db>/J by tail vein injection (17). Insp3r2 knockout mice were described previously (10). All mice were adapted to their environment for 1 week before study and were housed in colony cages with 12 h light/dark cycle in a temperature-controlled environment. For in vivo imaging experiments, mice were imaged on day 3-5 after adenovirus delivery. Wild-type CRTC2, CRTC2 (S171A), GFP, unspecific RNAi, Crtc2 RNAi, CRE-luc, and RSV β-gal adenoviruses have been described previously (17,20). The adenoviruses containing rat InsP3R1, InsP3R1 DM and InsP3R1 (52682A) were generated from the InsP3R1 plasmid. Calcineurin adenovirus was constructed using a mouse Calcineurin plasmid (Addgene). CRTC2 ACBD (51-692aa), S275A and S171A/S275A adenoviruses were made from mouse CRTC2. Myristoylated-CRTC2 (Myr-CRTC2) adenovirus was generated with mouse CRTC2 fused to an N-terminal myristoylation tag (MGSSKSKPKDPSQR) (SEQ ID NO: 1) from Src. Calcineurin RNAi, Insp3r1 RNAi, Insp3r2 RNAi, Insp3r3 RNAi adenoviruses were constructed using the sequence 5'-GGGTACCGCATGTA-CAGGAAAA-3' (SEQ ID NO: 2), 5'-GGGTACTG-GAATAGCCTCTTCC-3' (SEQ ID NO: 3), 5'-GGG-TAACAAGCACCACCATCCC-3' (SEQ ID NO: 4) and 5'-GGGCAAGCTGCAGGTGTTCCTG-3' (SEQ ID NO: 5), respectively. All expressed constructs used in this study were confirmed by sequencing.

In Vivo Analysis

For in vivo imaging, mice were imaged as described (17,20) under ad libitum feeding conditions or after fasting for 6 hours. For pyruvate challenge experiments, mice were fasted overnight and injected intraperitoneally with pyruvate (2g kg$^{-1}$). Blood glucose values were determined using a LifeScan automatic glucometer. For immunoblot, mouse tissues were sonicated, centrifuged and supernatants were reserved for protein determinations, and SDS-PAGE analysis.

Cell Culture, Cellular Fractionation, Luciferase Assay, Calcineurin Activity and cAMP Measurement HEK293T (ATCC) cells were cultured in DMEM containing 10% FBS (HyClone), 100 mg ml$^{-1}$ penicillin-streptomycin. Mouse primary hepatocytes were isolated and cultured as previously described (18). Cellular fractionation studies were conducted as previously reported (18). For reporter studies, Ad-CRE-luc infected hepatocytes (1 pfu per cell) were exposed to glucagon (Gcg, 100 nM) for 2~4 h. For cyclosporine A (CsA, 10 µM) or okadaic acid (OA, 100 nM) or cell permeable calcineurin autoinhibitory peptide (10 µM) or CN585 (100 µM) or Calyculin A (10 nM) or Xestospongin C (Xc, 2 µM) or H89 (30 µM) or BAPTA (50 µM) inhibition, hepatocytes were pre-treated with the inhibitors for one hour. Luciferase activities were normalized to β-galactosidase activity from adenoviral-encoded RSV β-gal. Calcineurin activity (test kit from Enzo Life Sciences) and cellular cAMP levels (test kit from Cayman Chemical Company) were measured according to manufacturer's instructions.

Calcium Imaging

Mouse primary hepatocytes were plated on glass coverslips and loaded with 5 µM Fura-2 acetoxymethyl ester (Molecular Probes) in the presence of 0.025% (w/v) pluronic F127 (Sigma-Aldrich) in Media 199 (Mediatech) for 30 minutes. Coverslips were mounted on a laminar flow perfusion chamber (Warner Instruments Corp.) and perfused with Media 199 or a solution of 100 nM glucagon in Media 199. Images of Fura-2 loaded cells were collected with a cooled CCD camera while the excitation wavelength was alternated between 340 nm and 380 nm. The ratio of fluorescence intensity at the two excitation wavelengths was calculated after subtracting background fluorescence. [Ca2+]I (cytosolic free calcium concentration) was calculated using a Fura-2 calcium imaging calibration kit (Invitrogen). Images were collected and analyzed using the MetaFluor software package (Universal Imaging Corp.). Graphs represent average responses from groups of 30-40 individual cells from representative single experiments. Bar graphs represent average responses (fold over average baseline) from 150-200 cells per condition. All experiments were repeated at least three times with similar results.

Immunoblot, Immunoprecipitation, Immunostaining

Immunoblot, immunoprecipitation, and immunostaining assays were performed as described (18). CRTC2, pCREB (Ser133), CREB, pAKT (Thr308), AKT, tubulin, HA, and FLAG antibodies were previously described (18). The antibodies anti-InsP3R1 (A302-158A) and InsP3R3 (A302-160A) were purchased from Bethyl Laboratories, anti-InsP3R2 (ab77838) from Abcam, anti-Calcineurin (610260) from BD Biosciences, anti-GRP78 (ADI-SPA-826-F) from Enzo Life Sciences, anti-phospho-PKA substrate (RRXS/T, 9624), anti-phospho-AKT substrate (RXXS/T, 9614) and CRTC2 (pS171, 2892) from Cell Signaling. CRTC2 (pS275) antibody was employed as described (19).

Quantitative PCR

Total cellular RNAs from whole liver or from primary hepatocytes were extracted using the RNeasy kit (Qiagen) and used to generate cDNA with SuperScript II enzyme (Invitrogen). cDNA were analyzed by quantitative PCR as described (18).

Mass Spectrometry

Immunoprecipitates of endogenous CRTC2 from HEK293T cells and of phospho-PKA substrate antiserum from glucagon stimulated hepatocytes were prepared for mass spectrometric studies as previously reported (21), and analyzed by electrospray ionization tandem mass spectrometry on a Thermo LTQ Orbitrap instrument.

Statistical Analyses

All studies were performed on at least three independent occasions. Results are reported as mean±s.e.m. The comparison of different groups was carried out using two-tailed unpaired Student's t-test. Differences were considered statistically significant at P<0.05.

REFERENCES

1. Altarejos, J. Y. & Montminy, M. CREB and the CRTC co-activators: sensors for hormonal and metabolic signals. *Nat Rev Mol Cell Biol* 12, 141-51 (2011).
2. Yoon, Y. S. et al. Suppressor of MEK null (SMEK)/protein phosphatase 4 catalytic subunit (PP4C) is a key regulator of hepatic gluconeogenesis. *Proc Natl Acad Sci USA* 107, 17704-9 (2010).
3. Screaton, R. A. et al. The CREB coactivator TORC2 functions as a calcium- and cAMP-sensitive coincidence detector. *Cell* 119, 61-74 (2004).
4. Hogan, P. G., Chen, L., Nardone, J. & Rao, A. Transcriptional regulation by calcium, calcineurin, and NFAT. *Genes Dev* 17, 2205-32 (2003).
5. Ferris, C. D., Huganir, R. L., Bredt, D. S., Cameron, A. M. & Snyder, S. H. Inositol trisphosphate receptor: phosphorylation by protein kinase C and calcium calmodulin-dependent protein kinases in reconstituted lipid vesicles. *Proc Natl Acad Sci USA* 88, 2232-5 (1991).
6. Volpe, P. & Alderson-Lang, B. H. Regulation of inositol 1,4,5-trisphosphate-induced Ca2+ release. II. Effect of cAMP-dependent protein kinase. *Am J Physiol* 258, C1086-91 (1990).
7. Bird, G. S., Burgess, G. M. & Putney, J. W., Jr. Sulfhydryl reagents and cAMP-dependent kinase increase the sensitivity of the inositol 1,4,5-trisphosphate receptor in hepatocytes. *J Biol Chem* 268, 17917-23 (1993).
8. Patterson, R. L., Boehning, D. & Snyder, S. H. Inositol 1,4,5-trisphosphate receptors as signal integrators. *Annu Rev Biochem* 73, 437-65 (2004).
9. Futatsugi, A. et al. IP3 receptor types 2 and 3 mediate exocrine secretion underlying energy metabolism. *Science* 309, 2232-4 (2005).
10. Cruz, L. N. et al. Regulation of multidrug resistance-associated protein 2 by calcium signaling in mouse liver. *Hepatology* 52, 327-37 (2010).

11. Szado, T. et al. Phosphorylation of inositol 1,4,5-trisphosphate receptors by protein kinase B/AKT inhibits Ca2+ release and apoptosis. *Proc Natl Acad Sci USA* 105, 2427-32 (2008).
12. Tovey, S. C. et al. Regulation of inositol 1,4,5-trisphosphate receptors by cAMP independent of cAMP-dependent protein kinase. *J Biol Chem* 285, 12979-89 (2010).
13. Wakelam, M. J., Murphy, G. J., Hruby, V. J. & Houslay, M. D. Activation of two signal-transduction systems in hepatocytes by glucagon. *Nature* 323, 68-71 (1986).
14. Yoon, J. et al. Control of hepatic gluconeogenesis through the transcriptional coactivator PGC-1. *Nature* 413, 131-138 (2001).
15. Herzig, S. et al. CREB Regulates Hepatic Gluconeogenesis via the Coactivator PGC-1. *Nature* 413, 179-183 (2001).
16. Wu, Z. et al. Transducer of regulated CREB-binding proteins (TORCs) induce PGC-1alpha transcription and mitochondrial biogenesis in muscle cells. *Proc Natl Acad Sci USA* 103, 14379-84 (2006).
17. Dentin, R. et al. Insulin modulates gluconeogenesis by inhibition of the coactivator TORC2. *Nature* 449, 366-9 (2007).
18. Wang, Y., Vera, L., Fischer, W. H. & Montminy, M. The CREB coactivator CRTC2 links hepatic ER stress and fasting gluconeogenesis. *Nature* 460, 534-7 (2009).
19. Jansson, D. et al. Glucose controls CREB activity in islet cells via regulated phosphorylation of TORC2. *Proc Natl Acad Sci USA* 105, 10161-6 (2008).
20. Liu, Y. et al. A fasting inducible switch modulates gluconeogenesis via activator/coactivator exchange. *Nature* 456, 269-73 (2008).
21. Wang, B. et al. A hormone-dependent module regulating energy balance. *Cell* 145, 596-606 (2011).

Example 10: p38 and MK2/3 Inhibitors for Treatment and Prevention of Metabolic Diseases There are two kinases downstream of CaMKII that can mediate the adverse effects of CaMKII—p38 and MK2 (see FIG. 51). While drugs blocking the more upstream targets like IP3 receptor and CaMKII can cover more pathways, they also can be more toxic. In contrast, targeting the more downstream mediators can lead to less off-target effects. MK2 and MK3 are very similar, and reagents that block MK2 (DN-MK2 and MK2 inhibitor) block both MK2 and MK3. If one blocked only one of them, the other would compensate.

Thus, p38 inhibitors and MK2/3 inhibitors can also be used to treat metabolic diseases induced by obesity, such as Type 1 diabetes, Type 2 diabetes, insulin resistance and metabolic syndrome.

The studies described in FIGS. 52-56 use primary murine hepatocytes (HCs). For p38 experiments, p38 is deleted in samples labeled as "Cre" or "adeno-Cre" or "ad-Cre" and the control for this is adeno-LacZ (sometimes labeled ad-LacZ or LacZ). (The HCs have a form of the p38 gene that is deleted when exposed to Cre recombinase, which is delivered using an adenoviral vector. The control is an adenoviral vector encoding an irrelevant protein called LacZ.)

FIG. 52 directly relates p38 to the key distal consequence of CaMKII, namely, FoxO1 nuclear localization: in normal HCs with p38 present (LacZ), constitutively active (CA) CaMKII pushes FoxO1 into the nucleus, but it cannot do this HCs lacking p38 (Cre).

FIG. 53 uses an MK2 inhibitor to show the importance of MK2 in both nuclear FoxO1 and in induction of genes involved in hepatic glucose production. MK-2 Inhibitor is from Calbiochem (cat#475864): 2-(2-Quinolin-3-ylpyridin-4-yl)-1,5,6,7-tetrahydro-4H-pyrrolo-[3,2-c]pyridin-4-one.

FIG. 54 uses an experimental model (an inducer of protein misfolding called tunicamycin) that mimics a process in obesity and type 2 diabetes in which liver cells are subjected to endoplasmic reticulum (ER) stress. ER stress is represented by 'PERK/PKR' and 'ATF4/CHOP' (lower right branch) (see FIG. 51). What is shown in FIG. 54 is that p38 is needed for the tunicamycin (ER stress)-induced increase in p-PERK (its active form) and CHOP. One will also see that p58IPK is slightly but consistently elevated in the HCs lacking p38 (Cre)—this also fits the lower right branch of FIG. 51.

FIG. 55 uses another experimental model (a fatty acid called palmitate) that mimics liver ER stress in obesity and diabetes. As in FIG. 54, p38 is needed for the increase in CHOP and p-PERK.

FIG. 56 If one looks at the bottom of the right branch of FIG. 51, one will see that the readout is p-Akt response to insulin. All the HCs in FIG. 56 received an acute dose of insulin to test insulin's ability to activate (phosphorylate) Akt. The model used here to mimic obesity/diabetes is the palmitate model used in FIG. 55. One can see that in HCs with normal p38 (Ad-LacZ), insulin gave a robust p-Akt signal (first 2 lanes) but this was lowered by palmitate ("palm"). This "insulin resistance" in the face of palmitate mimics what happens in obesity and type 2 diabetes. If one then looks at HCs without p38 (Ad-Cre), the ability of insulin to activate Akt (p-Aid) is improved. This is consistent with the p38-p-Akt link shown in FIG. 51.

FIGS. 86, 87 and 88 relate to how inhibition of CaMKII, p38, or MK2/3 causes an improvement in insulin signaling, i.e., how these inhibitors prevent insulin resistance. The data therein support the following mechanism: Inhibitors of CaMKII, p38, or MK2/3 lower Tribble3 (Trb3), which then improves the ability of insulin to phosphorylate AKT (Trb3 is an endogenous inhibitor of AKT phosphorylation).

REFERENCES

Accili, D. and Arden, K. C. (2004). FoxOs at the crossroads of cellular metabolism, differentiation, and transformation. Cell. 117, 421-426.

Ang, E. S., Zhang, P., Steer, J. H., Tan, J. W., Yip, K., Zheng, M. H., Joyce, D. A., and Xu, J. (2007). Calcium/calmodulin-dependent kinase activity is required for efficient induction of osteoclast differentiation and bone resorption by receptor activator of nuclear factor kappa B ligand (RANKL). J. Cell Physiol. 212, 787-795.

Asada, S., Daitoku, H., Matsuzaki, H., Saito, T., Sudo, T., Mukai, H., Iwashita, S., Kako, K., Kishi, T., Kasuya, Y., and Fukamizu, A. (2007). Mitogen-activated protein kinases, Erk and p38, phosphorylate and regulate Foxo1. Cell Signal. 19, 519-527.

Ayala, J. E., Streeper, R. S., Desgrosellier, J. S., Durham, S. K., Suwanichkul, A., Svitek, C. A., Goldman, J. K., Barr, F. G., Powell, D. R., and O'Brien, R. M. (1999). Conservation of an insulin response unit between mouse and human glucose-6-phosphatase catalytic subunit gene promoters: transcription factor FKHR binds the insulin response sequence. Diabetes. 48, 1885-1889.

Backs, J., Stein, P., Backs, T., Duncan, F. E., Grueter, C. E., McAnally, J., Qi, X., Schultz, R. M., and Olson, E. N. (2010). The gamma isoform of CaM kinase II controls mouse egg activation by regulating cell cycle resumption. Proc. Natl. Acad. Sci. U.S.A 107, 81-86.

Barthel, A., Schmoll, D., Kruger, K. D., Bahrenberg, G., Walther, R., Roth, R. A., and Joost, H. G. (2001). Differential regulation of endogenous glucose-6-phosphatase and phosphoenolpyruvate carboxykinase gene expression by the forkhead transcription factor FKHR in H4IIE-hepatoma cells. Biochem. Biophys. Res. Commun. 285, 897-902.

Beausoleil, S. A., Villen, J., Gerber, S. A., Rush, J., and Gygi, S. P. (2006). A probability-based approach for high-throughput protein phosphorylation analysis and site localization. Nat. Biotechnol. 24, 1285-1292.

Blanquet, P. R. (2000). Identification of two persistently activated neurotrophin-regulated pathways in rat hippocampus. Neuroscience. 95, 705-719.

Brunet, A., Bonni, A., Zigmond, M. J., Lin, M. Z., Juo, P., Hu, L. S., Anderson, M. J., Arden, K. C., Blenis, J., and Greenberg, M. E. (1999). Akt promotes cell survival by phosphorylating and inhibiting a Forkhead transcription factor. Cell. %19; 96, 857-868.

Burgess, S. C., He, T., Yan, Z., Lindner, J., Sherry, A. D., Malloy, C. R., Browning, J. D., and Magnuson, M. A. (2007). Cytosolic phosphoenolpyruvate carboxykinase does not solely control the rate of hepatic gluconeogenesis in the intact mouse liver. Cell Metab. 5, 313-320.

Bygrave, F. L. and Benedetti, A. (1993). Calcium: its modulation in liver by cross-talk between the actions of glucagon and calcium-mobilizing agonists. Biochem. J. 296, 1-14.

Cantin, G. T., Shock, T. R., Park, S. K., Madhani, H. D., and Yates, J. R., III (2007). Optimizing TiO2-based phosphopeptide enrichment for automated multidimensional liquid chromatography coupled to tandem mass spectrometry. Anal. Chem. 79, 4666-4673.

Cao, W., Collins, Q. F., Becker, T. C., Robidoux, J., Lupo, E. G., Jr., Xiong, Y., Daniel, K. W., Floering, L., and Collins, S. (2005). p38 Mitogen-activated protein kinase plays a stimulatory role in hepatic gluconeogenesis. J. Biol Chem. 280, 42731-42737.

Chiacchiera, F. and Simone, C. (2010). The AMPK-FoxO3A axis as a target for cancer treatment. Cell Cycle. 9, 1091-1096.

Cociorva, D., Tabb, L., and Yates, J. R. (2007). Validation of tandem mass spectrometry database search results using DTASelect. Curr. Protoc. Bioinformatics. Chapter 13:Unit 13.4., Unit.

Couchonnal, L. F. and Anderson, M. E. (2008). The role of calmodulin kinase II in myocardial physiology and disease. Physiology. (Bethesda.) 23, 151-159.

Dash, P. K., Karl, K. A., Colicos, M. A., Prywes, R., and Kandel, E. R. (1991). cAMP response element-binding protein is activated by Ca2+/calmodulin—as well as cAMP-dependent protein kinase. Proc Natl Acad Sci USA. 88, 5061-5065.

Eng, J. K., McCormack, A. L., and Yates, J. R., III (1994). An approach to correlate tandem mass spectral data of peptides with amino acid sequences in a protein database. J. Am. Soc. Mass Spectrometry 5, 976-989.

Engel, F. B., Schebesta, M., Duong, M. T., Lu, G., Ren, S., Madwed, J. B., Jiang, H., Wang, Y., and Keating, M. T. (2005). p38 MAP kinase inhibition enables proliferation of adult mammalian cardiomyocytes. Genes Dev. 19, 1175-1187.

Essers, M. A., Weijzen, S., de Vries-Smits, A. M., Saarloos, I., de Ruiter, N. D., Bos, J. L., and Burgering, B. M. (2004). FOXO transcription factor activation by oxidative stress mediated by the small GTPase Ral and JNK. EMBO J. 23, 4802-4812.

Friedmann, N. and Rasmussen, H. (1970). Calcium, manganese and hepatic gluconeogenesis. Biochim. Biophys. Acta. 222, 41-52.

Hall, R. K., Sladek, F. M., and Granner, D. K. (1995). The orphan receptors COUP-TF and HNF-4 serve as accessory factors required for induction of phosphoenolpyruvate carboxykinase gene transcription by glucocorticoids. Proc Natl Acad Sci USA. 92, 412-416.

Hammad, E. S., Striffler, J. S., and Cardell, R. R., Jr. (1982). Morphological and biochemical observations on hepatic glycogen metabolism in genetically diabetic (db/db) mice. Diabete Metab. 8, 147-153.

Hansen, L. H., Gromada, J., Bouchelouche, P., Whitmore, T., Jelinek, L., Kindsvogel, W., and Nishimura, E. (1998). Glucagon-mediated Ca2+ signaling in BHK cells expressing cloned human glucagon receptors. Am. J. Physiol. 274, C1552-C1562.

Harano, Y., Kashiwagi, A., Kojima, H., Suzuki, M., Hashimoto, T., and Shigeta, Y. (1985). Phosphorylation of carnitine palmitoyltransferase and activation by glucagon in isolated rat hepatocytes. FEBS Lett. 188, 267-272.

Herzig, S., Long, F., Jhala, U. S., Hedrick, S., Quinn, R., Bauer, A., Rudolph, D., Schutz, G., Yoon, C., Puigserver, P., Spiegelman, B., and Montminy, M. (2001). CREB regulates hepatic gluconeogenesis through the coactivator PGC-1. Nature. 413, 179-183.

Kraus-Friedmann, N. and Feng, L. (1996). The role of intracellular Ca2+ in the regulation of gluconeogenesis. Metabolism. 45, 389-403.

Lin, H. V. and Accili, D. (2011). Hormonal regulation of hepatic glucose production in health and disease. Cell Metab. 14, 9-19.

Liu, H., Sadygov, R. G., and Yates, J. R., III (2004). A model for random sampling and estimation of relative protein abundance in shotgun proteomics. Anal. Chem. 76, 4193-4201.

Lu, B., Ruse, C., Xu, T., Park, S. K., and Yates, J., III (2007). Automatic validation of phosphopeptide identifications from tandem mass spectra. Anal. Chem. 79, 1301-1310.

MacCoss, M. J., McDonald, W. H., Saraf, A., Sadygov, R., Clark, J. M., Tasto, J. J., Gould, K. L., Wolters, D., Washburn, M., Weiss, A., Clark, J. I., and Yates, J. R., III (2002). Shotgun identification of protein modifications from protein complexes and lens tissue. Proc Natl Acad Sci USA. 99, 7900-7905.

Marques-da-Silva, A. C., D'Avila, R. B., Ferrari, A. G., Kelmer-Bracht, A. M., Constantin, J., Yamamoto, N. S., and Bracht, A. (1997). Ca2+ dependence of gluconeogenesis stimulation by glucagon at different cytosolic NAD(+)-NADH redox potentials. Braz. J. Med. Biol Res. 30, 827-836.

Matsumoto, M., Pocai, A., Rossetti, L., Depinho, R. A., and Accili, D. (2007). Impaired regulation of hepatic glucose production in mice lacking the forkhead transcription factor Foxo1 in liver. Cell Metab 6, 208-216.

McDonald, W. H., Tabb, D. L., Sadygov, R. G., MacCoss, M. J., Venable, J., Graumann, J., Johnson, J. R., Cociorva, D., and Yates, J. R., III (2004). MS1, MS2, and SQT-three unified, compact, and easily parsed file formats for the storage of shotgun proteomic spectra and identifications. Rapid Commun. Mass Spectrom. 18, 2162-2168.

Mine, T., Kojima, I., and Ogata, E. (1993). Role of calcium fluxes in the action of glucagon on glucose metabolism in rat hepatocytes. Am. J. Physiol. 265, G35-G42.

Naimi, M., Gautier, N., Chaussade, C., Valverde, A. M., Accili, D., and Van, O. E. (2007). Nuclear forkhead box O1 controls and integrates key signaling pathways in hepatocytes. Endocrinology. 148, 2424-2434.

Nakae, J., Biggs, W. H., III, Kitamura, T., Cavenee, W. K., Wright, C. V., Arden, K. C., and Accili, D. (2002). Regulation of insulin action and pancreatic beta-cell function by mutated alleles of the gene encoding forkhead transcription factor Foxo1. Nat. Genet. 32, 245-253.

Nakae, J., Kitamura, T., Silver, D. L., and Accili, D. (2001). The forkhead transcription factor Foxo1 (Fkhr) confers insulin sensitivity onto glucose-6-phosphatase expression. J. Clin. Invest. 108, 1359-1367.

Peng, J., Elias, J. E., Thoreen, C. C., Licklider, L. J., and Gygi, S. P. (2003). Evaluation of multidimensional chromatography coupled with tandem mass spectrometry (LC/LC-MS/MS) for large-scale protein analysis: the yeast proteome. J. Proteome. Res. 2, 43-50.

Pfleiderer, P. J., Lu, K. K., Crow, M. T., Keller, R. S., and Singer, H. A. (2004). Modulation of vascular smooth muscle cell migration by calcium/calmodulin-dependent protein kinase II-delta 2. Am J Physiol Cell Physiol 286, C1238-C1245.

Pilkis, S. J. and Granner, D. K. (1992). Molecular physiology of the regulation of hepatic gluconeogenesis and glycolysis. Annu. Rev. Physiol. 54:885-909., 885-909.

Puigserver, P., Rhee, J., Donovan, J., Walkey, C. J., Yoon, J. C., Oriente, F Kitamura, Y., Altomonte, J., Dong, H., Accili, D., and Spiegelman, B. M. (2003). Insulin-regulated hepatic gluconeogenesis through FOXO1-PGC-1alpha interaction. Nature. 423, 550-555.

Puthanveetil, P., Wang, Y., Wang, F., Kim, M. S., Abrahani, A., and Rodrigues, B. (2010). The increase in cardiac pyruvate dehydrogenase kinase-4 after short-term dexamethasone is controlled by an Akt-p38-forkhead box other factor-1 signaling axis. Endocrinology. 151, 2306-2318.

Radziuk, J. and Pye, S. (2001). Hepatic glucose uptake, gluconeogenesis and the regulation of glycogen synthesis. Diabetes Metab Res. Rev. 17, 250-272.

Rhee, J., Inoue, Y., Yoon, J. C., Puigserver, P., Fan, M., Gonzalez, F. J., and Spiegelman, B. M. (2003). Regulation of hepatic fasting response by PPARgamma coactivator-1alpha (PGC-1): requirement for hepatocyte nuclear factor 4alpha in gluconeogenesis. Proc Natl Acad Sci USA. 100, 4012-4017.

Saltiel, A. R. (2001). New perspectives into the molecular pathogenesis and treatment of type 2 diabetes. Cell. 104, 517-529.

Sheng, M., Thompson, M. A., and Greenberg, M. E. (1991). CREB: a Ca(2+)-regulated transcription factor phosphorylated by calmodulin-dependent kinases. Science. 252, 1427-1430.

Singer, H. A. (2011). Ca2+/calmodulin-dependent protein kinase II Function in Vascular Remodeling. J. Physiol.

Sorensen, H., Brand, C. L., Neschen, S., Holst, J. J., Fosgerau, K., Nishimura, E., and Shulman, G. I. (2006) Immunoneutralization of endogenous glucagon reduces hepatic glucose output and improves long-term glycemic control in diabetic ob/ob mice. Diabetes. 55, 2843-2848.

Staddon, J. M. and Hansford, R. G. (1989). Evidence indicating that the glucagon-induced increase in cytoplasmic free Ca2+ concentration in hepatocytes is mediated by an increase in cyclic AMP concentration. Eur. J. Biochem. 179, 47-52.

Tabb, D. L., McDonald, W. H., and Yates, J. R., III (2002). DTASelect and Contrast: tools for assembling and comparing protein identifications from shotgun proteomics. J. Proteome. Res. 1, 21-26.

Unger, R. H. and Cherrington, A. D. (2012). Glucagonocentric restructuring of diabetes: a pathophysiologic and therapeutic makeover. J. Clin. Invest. 122, 4-12.

Valera, A., Solanes, G., and Bosch, F. (1993). Calcium-mobilizing effectors inhibit P-enolpyruvate carboxykinase gene expression in cultured rat hepatocytes. FEBS Lett. 333, 319-324.

van der Horst, A. and Burgering, B. M. (2007). Stressing the role of FoxO proteins in lifespan and disease. Nat. Rev. Mol. Cell Biol. 8, 440-450.

von Groote-Bidlingmaier, F., Schmoll, D., Orth, H. M., Joost, H. G., Becker, W., and Barthel, A. (2003). DYRK1 is a co-activator of FKHR (FOXO1a)-dependent glucose-6-phosphatase gene expression. Biochem. Biophys. Res. Commun 300, 764-769.

Xu, T., Venable, J. D., Park, S. K., Cociorva, D., Lu, B., Liao, L., Wohlschlegel, J., Hewel, J., and Yates, J. R. (2006). ProLuCID, a fast and sensitive tandem mass spectra-based protein identification program. Mol. Cell Proteomics 5, 5174.

Yoon, J. C., Puigserver, P., Chen, G., Donovan, J., Wu, Z., Rhee, J., Adelmant, G., Stafford, J., Kahn, C. R., Granner, D. K., Newgard, C. B., and Spiegelman, B. M. (2001). Control of hepatic gluconeogenesis through the transcriptional coactivator PGC-1. Nature. 413, 131-138

Akagi, K., Sandig, V., Vooijs, M., van, d., V, Giovannini, M., Strauss, M., and Berns, A. (1997). Cre-mediated somatic site-specific recombination in mice. Nucleic Acids Res. 25, 1766-1773.

Asada, S., Daitoku, H., Matsuzaki, H., Saito, T., Sudo, T., Mukai, H., Iwashita, S., Kako, K., Kishi, T., Kasuya, Y., and Fukamizu, A. (2007). Mitogen-activated protein kinases, Erk and p38, phosphorylate and regulate Foxo1. Cell Signal. 19, 519-527.

Ayala, J. E., Streeper, R. S., Desgrosellier, J. S., Durham, S. K., Suwanichkul, A., Svitek, C. A., Goldman, J. K., Barr, F. G., Powell, D. R., and O'Brien, R. M. (1999). Conservation of an insulin response unit between mouse and human glucose-6-phosphatase catalytic subunit gene promoters: transcription factor FKHR binds the insulin response sequence. Diabetes. 48, 1885-1889.

Barthel, A., Schmoll, D., Kruger, K. D., Bahrenberg, G., Walther, R., Roth, R. A., and Joost, H. G. (2001). Differential regulation of endogenous glucose-6-phosphatase and phosphoenolpyruvate carboxykinase gene expression by the forkhead transcription factor FKHR in H4IIE-hepatoma cells. Biochem. Biophys. Res. Commun. 285, 897-902.

Cantin, G. T., Shock, T. R., Park, S. K., Madhani, H. D., and Yates, J. R., III (2007). Optimizing TiO2-based phosphopeptide enrichment for automated multidimensional liquid chromatography coupled to tandem mass spectrometry. Anal. Chem. 79, 4666-4673.

Delahunty, C. and Yates, J. R., III (2005). Protein identification using 2D-LC-MS/MS. Methods. 35, 248-255.

Liu, P., Jenkins, N. A., and Copeland, N. G. (2003). A highly efficient recombineering-based method for generating conditional knockout mutations. Genome Res. 13, 476-484.

MacCoss, M. J., McDonald, W. H., Saraf, A., Sadygov, R., Clark, J. M., Tasto, J. J., Gould, K. L., Wolters, D., Washburn, M., Weiss, A., Clark, J. I., and Yates, J. R., III (2002). Shotgun identification of protein modifications from protein complexes and lens tissue. Proc Natl Acad Sci USA. 99, 7900-7905.

Matsumoto, M., Ogawa, W., Teshigawara, K., Inoue, H., Miyake, K., Sakaue, H., and Kasuga, M. (2002). Role of the insulin receptor substrate 1 and phosphatidylinositol 3-kinase signaling pathway in insulin-induced expression of sterol regulatory element binding protein 1c and glucokinase genes in rat hepatocytes. Diabetes. 51, 1672-1680.

Pfleiderer, P. J., Lu, K. K., Crow, M. T., Keller, R. S., and Singer, H. A. (2004). Modulation of vascular smooth muscle cell migration by calcium/calmodulin-dependent protein kinase II-delta 2. Am J Physiol Cell Physiol 286, C1238-C1245.

Tanaka, J., Li, Q., Banks, A. S., Welch, C. L., Matsumoto, M., Kitamura, T., Ido-Kitamura, Y., Depinho, R. A., and Accili, D. (2009). Foxo1 links hyperglycemia to LDL oxidation and eNOS dysfunction in vascular endothelial cells. Diabetes.

Timmins, J M, Ozcan, L., Seimon, T. A., Li, G., Malagelada, C., Backs, J., Backs, T., Bassel-Duby, R., Olson, E. N., Anderson, M. E., and Tabas, I. (2009). Calcium/calmodulin-dependent protein kinase II links endoplasmic reticulum stress with Fas and mitochondrial apoptosis pathways. J. Clin. Invest. 119, 2925-2941.

von Groote-Bidlingmaier, F., Schmoll, D., Orth, H. M., Joost, H. G., Becker, W., and Barthel, A. (2003). DYRK1 is a co-activator of FKHR (FOXO1a)-dependent glucose-6-phosphatase gene expression. Biochem. Biophys. Res. Commun 300, 764-769.

Warming, S., Costantino, N., Court D L, Jenkins, N. A., and Copeland, N. G. (2005). Simple and highly efficient BAC recombineering using galK selection. Nucleic Acids Res. 33, e36.

Clyne C D, Nguyen A, Rainey W E, (1995) The effects of KN62, a Ca2+/calmodulin-dependent protein kinase II inhibitor, on adrenocortical cell aldosterone production. Endocr Res., 21(1-2):259-65.

Takao K., et al., (2005), Visualization of synaptic Ca2+/calmodulin-dependent protein kinase II activity in living neurons, J. Neurosci., 25(12): 3107-3112.

Kwok et al., (2008), Genetically encoded probe for fluorescence lifetime imaging of CaMKII activity, Biochem Biophys Res Commun, 369(2):519-25.

Tokumitsu et al., 2002, STO-609, a Specific Inhibitor of the Ca2+/Calmodulin-dependent Protein Kinase Kinase, J Biol Chem., 277(18):15813-15818.

Sugimura et al., 1997, DY-9760e, a novel calmodulin antagonist with cytoprotective action, Eur J. Pharm., 336:99-106.

Kase et al., 1987, K-252 compounds, novel and potent inhibitors of protein kinase C and cyclic nucleotide-dependent protein kinases, Biochem Biophys Res Commun, 142:436-440.

Example 11: Activation of Calcium/Calmodulin-Dependent Protein Kinase II in Obesity Mediates Suppression of Hepatic Insulin Signaling A hallmark of obesity is selective suppression of hepatic insulin signaling ("insulin resistance"), but critical gaps remain in the understanding of the molecular mechanisms. A major role for hepatic CaMKII, a calcium-responsive kinase that is activated in obesity, is now reported. Genetic targeting of hepatic CaMKII, its downstream mediator p38, or the p38 substrate and stabilizer MK2 enhances insulin-induced p-Akt in palmitate-treated hepatocytes and obese mouse liver, leading to metabolic improvement. The mechanism of improvement begins with induction of ATF6 and the ATF6 target p58$^{IPK}$, a chaperone that suppresses the PERK—p-eIF2α—ATF4 branch of the UPR. The result is a decrease in the ATF target TRB3, an inhibitor of insulin-induced p-Aid, leading to enhanced activation of Akt and its downstream metabolic mediators. These findings increase the understanding of the molecular mechanisms linking obesity to selective insulin resistance and indicate new therapeutic targets for type 2 diabetes and metabolic syndrome.

Introduction

Obesity is the leading cause of insulin resistance, metabolic syndrome, and type 2 diabetes (T2D), but therapeutic options are limited due to critical gaps in knowledge of molecular mechanisms linking obesity with the metabolic disturbances of insulin resistance and T2D (Samuel and Shulman, 2012). A key factor in T2D is an inappropriate increase in hepatic glucose production (HGP), which results from selective hepatic insulin resistance together with impaired suppression of glucagon signaling (Lin and Accili, 2011). In addition to elevated HGP, selective insulin resistance contributes to other critical maladies associated with T2D, including cardiovascular disease, the leading cause of death in these patients (Bornfeldt and Tabas, 2011; Leavens and Birnbaum, 2011).

A new pathway through which glucagon stimulates HGP in fasting and in obesity was elucidated, and in obesity, this pathway contributes to hyperglycemia (Ozcan et al., 2012; Wang et al., 2012). The pathway is triggered downstream of the glucagon receptor by PKA-mediated activation of the endoplasmic reticulum (ER) calcium release channel, inositol 1,4,5-trisphosphate receptor (IP3R). Channel opening, which is also promoted by a glucagon receptor-phospholipase C pathway that generates IP3, results in release of calcium from ER stores, which then activates the cytoplasmic calcium-sensitive kinase, calcium/calmodulin dependent-protein kinase II (CaMKII). CaMKII then activates the MAPK p38α, which phosphorylates FoxO1 in a manner that promotes FoxO1 nuclear translocation. Nuclear FoxO1 induces target genes that are rate-limiting for glycogenolysis and gluconeogenesis, notably, G6pc and Pck1. This CaMKII-FoxO1 pathway is complemented by the activation of the calcium-sensitive phosphatase calcineurin, which promotes CRTC2-mediated induction of the FoxO1 transcriptional partner, PGC1α (Wang et al., 2012). Moreover, recent studies have shown that calcium transport back into the ER, mediated by sarcoplasmic/endoplasmic reticulum calcium ATPase (SERCA), is dysfunctional in obesity (Fu et al., 2011; Park et al., 2010), which can contribute to both the amplitude and duration of the pathological calcium response. Collectively, these data point to the importance of intracellular calcium metabolism and CaMKII in enhanced HGP in obesity. However, a critical remaining question in this area was whether CaMKII plays a role in the other major pathological process in obesity and T2D, namely, selective insulin resistance.

Defective insulin signaling is a major feature of selective hepatic insulin resistance in obesity (Brown and Goldstein, 2008; Konner and Bruning, 2012). In normal physiology, insulin stimulates insulin autophosphorylation of the insulin receptor (IR), which promotes to Tyr-phosphorylation of insulin receptor substrates 1 and 2 (IRS-1/2). Through a series of downstream processes involving lipid mediators and protein kinases, p-IRS-1/2 leads to Ser/Thr-phosphorylation and activation of Akt (also known as protein kinase B) (Saltiel and Kahn, 2001). Akt-induced phosphorylation of a number of substrates is critically involved in promoting the anabolic effects of insulin on glucose and lipid metabolism. In obesity and T2D, insulin-induced phosphorylation of Akt is defective, which disables the pathway that normally suppresses HGP (Lin and Accili, 2011). In theory, defective Akt phosphorylation can occur at the level of the insulin receptor, IRS1/2, signal transducers downstream of IRS-1/2, or Akt phosphorylation itself. Studies in obese mouse models have shown evidence for defects in each of these steps, depending on the model used and the focus of the investigation, and there is also evidence for defects in insulin-induced p-Akt in humans with T2D (Brozinick et al., 2003; Krook et al., 1998; Saad et al., 1992). Moreover, the resulting hyperinsulinemia excessively stimulates non-resistant insulin pathways that mediate hepatic lipid synthesis and storage (Brown and Goldstein, 2008) and is associated with other maladies associated with T2D, such as atherosclerosis (Bornfeldt and Tabas, 2011; Leavens and Birnbaum, 2011). Because perturbation of proximal insulin signaling is one of the earliest hallmarks of T2D and is responsible for the most important complications of obesity and T2D, identification of the molecular mechanisms responsible for this defect has the potential to aid in the development of new and more specific anti-diabetic drugs.

In this report, a CaMKII/p38-mediated pathway that plays a critical role in obesity-associated insulin resistance in the liver was identified. This pathway is independent of the aforementioned CaMKII/p38-FoxO1 pathway involved in HGP in obesity. Evidence that obesity-activated CaMKII/p38 suppresses insulin-induced Akt phosphorylation by activating the ER stress effector ATF4, which in turn induces the Akt inhibitor, TRB3, is provided. Thus, an integrated, calcium-based paradigm in hepatocytes involved in the two cardinal features of T2D, hyperglycemia and defective insulin signaling, is beginning to emerge, providing new potential therapeutic targets.

Results

Inhibition of Liver CaMKII, p38α, or MAPKAPK2 (MK2) in Obese Mice Lowers Plasma Insulin and Improves the Response to Glucose Challenge The role of CaMKII on plasma insulin levels and response to glucose in three models of obese mice was first evaluated. In the first model, liver CaMKII in ob/ob mice was inhibited through the use of an adenoviral vector expressing K43A-CaMKII (Pfleiderer et al., 2004), which is a kinase-inactive, dominant-negative form that has been shown to inhibit hepatic CaMKII (Ozcan et al., 2012). It was shown previously that adeno-K43A-CaMKII treatment of ob/ob mice, as compared with ob/ob mice treated with adeno-LacZ control vector, lowered blood glucose (Ozcan et al., 2012). This effect occurred in the absence of any change in body weight (44.8±1.9 vs. 43.5±1.6 g), food intake (5.3±0.3 vs. 5±0.2 g per mouse per day), or epididymal fat pad mass (3.2±0.2 vs. 3±0.1 g). Moreover, K43A-CaMKII-treated mice displayed a more than twofold reduction in plasma insulin concentration compared with control adeno-LacZ-treated mice (FIG. 89A), consistent with an increase in insulin sensitivity. In support of this conclusion, adeno-K43A-CaMKII treated ob/ob mice exhibited significantly lower glucose levels during glucose and insulin tolerance tests (FIG. 89B-C).

In the second model, liver CaMKIIγ, which is the CaMKII isoform in hepatocytes, was deleted in diet-induced obese (DIO) mice by injecting DIO Camk2g$^{fl/fl}$ mice with adeno-associated virus-8 encoding Cre recombinase driven by the hepatocyte-specific thyroxin-binding globulin promoter (AAV8-TBG-Cre) (Sun et al., 2012). This treatment successfully silenced Camk2g in the hepatocytes (FIG. 89D) without changing body weight (44.6±2.29 vs. 43±0.7 g), food intake (3.13±0.17 vs. 2.92±0.19 g per mouse per day), or epididymal fat pad mass (2.4±0.14 vs. 2.24±0.07 g). Consistent with the ob/ob data, DIO mice that lack hepatocyte CaMKIIγ had lower fasting insulin levels (FIG. 89E), lower blood glucose levels (FIG. 89F), and an improved blood glucose response to glucose challenge (FIG. 89G). Similar results were found using a third model in which holo-CaMKIIγ KO (Camk2g$^{-/-}$) mice were placed on the high fat diet (FIGS. 96A-B).

Consistent with an improvement insulin resistance, targeting hepatocyte CaMKIIγ in obese mice (AAV8-TBG-Cre) led to a decrease in hepatic steatosis (FIG. 96C); hepatocyte TG content was also decreased in the Cre-treated mice (79.13±7.21 vs. 59.6±7.27 mg/g liver). The decrease in hepatic steatosis was not due to an increase in triglyceride secretion, as the Cre-treated mice had a decrease in plasma triglyceride levels (266.78±28.08 vs. 193.34±13.01 mg/dl). These combined data indicate that hepatic CaMKIIγ plays a central role in the manifestations of obesity-induced insulin resistance.

Although hepatic p38 activation has been implicated in insulin resistance in obese mice (Hemi et al., 2011), the upstream and downstream mechanisms remain incompletely understood. It was previously shown that CaMKII regulates p38α MAPK activity in hepatocytes (Ozcan et al., 2012), and so the possibility that p38 can also function as a downstream mediator of CaMKII in the pathogenesis of insulin resistance was explored. To this end, the gene encoding p38α (Mapk14) was silenced in hepatocytes by injecting DIO Mapk14$^{fl/fl}$ mice with AAV-TBG-Cre, which led to more than 90% silencing of p38α protein levels in liver (below) without affecting body weight (41±2.36 vs. 39±1.04 g), food intake (2.62±0.09 vs. 2.24±0.06 g per mouse per day) or epididymal fat pad mass (1.92±0.15 vs. 1.83±0.14 g). Compared with control mice (AAV-TBG-LacZ), mice deficient in hepatocyte p38α had lower fasting blood glucose (FIG. 90A), lower plasma insulin levels (FIG. 90B), improved blood glucose response to glucose challenge and enhanced glucose disposal upon insulin stimulation (FIGS. 90C&D).

MAPK-activating protein kinase 2 (MK2) is a well-characterized downstream effector of p38 (Freshney et al., 1994; Rouse et al., 1994). Moreover, activated MK2 forms a tight complex with p38α and thus reciprocally stabilizes p38α (Gaestel, 2006). To investigate the role of MK2, ob/ob mice were injected i.v. with adenovirus encoding MK2 with a mutation in its p38 phosphorylation site (T222A), which acts as a dominant negative (DN) form of the enzyme (Streicher et al., 2010). This treatment resulted in lowering of blood glucose (FIG. 90E), plasma insulin levels (FIG. 90F), and a marked improvement in glucose tolerance (FIG. 90G), without changing body weight (49.4±2.01 vs. 51.4±0.67 g) or food intake (5.37±0.44 vs. 5.52±0.23 g per mouse per day). Thus, liver p38α and MK2, like CaMKII, play an important role in the development of hyperglycemia and hyperinsulinemia in obese mice and the response of these mice to exogenous glucose.

Deletion or Inhibition of CaMKII, p38α, or MK2 Improves Insulin-Induced Akt Phosphorylation in Obese Mice In view of the above data, attention was focused on hepatocyte insulin signaling, where defects contribute to insulin resistance in obesity (Brown and Goldstein, 2008). As a measure of hepatic insulin signaling, pSer$^{473}$-Akt was assayed in the livers of mice injected with insulin through the portal vein. The data show a significant increase in insulin-induced p-Akt in the livers of Camk2g$^{-/-}$ DIO mice compared with WT DIO mice (FIG. 91A, top 2 blots). Improvements in Akt phosphorylation are often associated with increased tyrosine phosphorylation of IR and/or IRS-1/2. However, in the case of DIO CaMKII KO mice, neither phosphorylation of IR nor IRS-1 was increased (FIG. 91A, bottom 2 blots). Similar results were found in DIO Camk2g$^{fl/fl}$ mice injected with AAV-TBG-Cre and in ob/ob mice treated with dominant-negative adeno-K43A-CaMKII: insulin-induced phosphorylation of Akt was increased but phosphorylation of IR and IRS-1 was not (FIGS. 91B and 97A). Note that inhibition of CaMKII in chow-fed lean mice did not induce significant changes in p-Akt levels (FIG. 97B), indicating a specific role of CaMKII in defective insulin-induced p-Akt in obese mice.

The data in FIG. 90 showed that liver-directed silencing of either p38, which is a downstream target of CaMKII, or MK2, which is a substrate and stabilizer of p38, improved plasma insulin and response to glucose and insulin. To link these findings to hepatic insulin signaling, DIO Mapk14$^{fl/fl}$ mice were treated with AAV-TBG-Cre and then assayed insulin-induced p-Akt. As with CaMKII silencing, there was enhanced insulin-stimulated Akt phosphorylation without an increase in IR or IRS-1/2 phosphorylation (FIG. 91C). Similarly, Akt activation was increased in ob/ob mice injected with dominant-negative adeno-T222A-MK2 (FIG. 97C) without an increase in the phosphorylation of IR or IRS proteins. These combined data indicate that CaMKII, p38α, and MK2 participate in defective insulin-p-Akt signaling in the livers of obese mice at a step to distal to IRS phosphorylation.

Inhibition of CaMKII or p38α Improves Insulin-Induced Akt Phosphorylation Distal to IR and IRS and in a FoxO1-Independent Manner To further probe mechanism, a primary murine hepatocyte (HC) model in which insulin-induced Akt phosphorylation is suppressed by treatment with the saturated fatty acid palmitate was used (Achard and Laybutt, 2012). Using transduction with adeno-K43A-CaMKII, it was first shown that this model recapitulates the improvement in insulin-induced Akt phosphorylation conferred by inhibition of CaMKII (FIG. 92A, top 3 blots), whereas adeno-K43A-CaMKII transduction did not evoke any significant changes under control, BSA treated group. Moreover, consistent with the in vivo findings, CaMKII inhibition did not enhance Tyr-phosphorylation of IRS-1 (FIG. 92A, right panel), IR, or IRS-2. Similar data were obtained using p38α-deficient hepatocytes in terms of p-Akt (FIG. 92B, upper panel, top 3 blots) and p-IR and p-IRS-1 (FIG. 92B, left lower panel). Consistent with improved Akt activation, insulin-stimulated phosphorylation of the downstream Akt targets, FoxO1 and GSK-3β, were also significantly improved (FIG. 92B, right lower panel, bottom 4 blots) and glucose output was significantly inhibited (49.97±2.76 vs. 82.78±4.66 nmol per hour per mg protein). Furthermore, in order to acquire information about the human relevance of the murine HC studies, the effect of CaMKII inhibition was tested in metabolism-qualified human HCs using the palmitate model. Consistent with the murine HC data, palmitate-induced suppression of insulin-induced p-Akt was prevented by CaMKII inhibition using adeno-K43A-CaMKII (FIG. 92C).

It was next examined whether a constitutively active mutant of CaMKII (CA-CaMKII) is sufficient to interfere with insulin action in the absence of palmitate. This mutant possesses an amino acid substitution, T287D, which mimics autophosphorylation at T287 and results in autonomous activity in the absence of bound calcium/calmodulin (Ozcan et al., 2012; Pfleiderer et al., 2004). The data show that CA-CaMKII resulted in a decrease in insulin-induced Akt phosphorylation without decreasing either p-IRS-1, which was actually increased, or p-IRS-2 (FIG. 92D). Thus, CaMKII is both necessary and sufficient for the palmitate-induced insulin signaling defect in primary HCs.

It was recently demonstrated that CaMKII mediates glucagon-induced hepatic glucose production (HGP) through p38-induced phosphorylation of FoxO1 (Ozcan et al., 2012). In particular, phosphorylation of FoxO1 by p38 promotes nuclear localization of FoxO1 and transcription of FoxO1 target genes involved in HGP, and inhibition of CaMKII or p38 leads to cytoplasmic localization of FoxO1 and inhibition of HGP. Because FoxO1 has been implicated in the regulation of Akt action (Lin and Accili, 2011), the contribution of FoxO1 nuclear exclusion in the enhancement of insulin signaling by CaMKII deficiency was investigated. A series of experiments were begun using nuclear FoxO1 restoration in palmitate-treated HCs. First, a nuclear FoxO1 bioassay—induction of the FoxO1 gene target Igfb1—was used to verify the pervious data (Ozcan et al., 2012) that deletion of CaMKIIγ caused a decrease in nuclear FoxO1 activity that can be restored by transduction with constitutively nuclear adeno-FoxO1-ADA (FIG. 98A). This model was then used to ask whether FoxO1 restoration can abrogate the benefit of CaMKII deletion on insulin-induced p-Akt. As before, deletion of CaMKII improved insulin-induced p-Aid, and this improvement was not diminished by FoxO1 restoration (FIG. 98B). These data indicate the distinct nature of the two CaMKII pathways.

This important point was next investigated in vivo. As in lean mice, adeno-K43A-CaMKII treatment markedly diminished nuclear FoxO1 in the livers of obese mice (FIG. 98C). However, as was the case with HCs, restoration of nuclear FoxO1 did not reverse the benefit of CaMKII inhibition (K43A) on insulin-induced p-Akt (FIG. 98D). Thus, the improvement in insulin-induced p-Akt by CaMKII deficiency is not due to nuclear exclusion of FoxO1. Rather, there appear to be two separate CaMKII pathways, one involved in CaMKII-p38-FoxO1 dependent HGP (Ozcan et al., 2012) and the other involved in defective insulin-induced p-Akt.

Inhibition of CaMKII or p38α Improves Insulin-Induced Akt Phosphorylation by Suppressing TRB3

In considering mechanisms of how insulin-induced p-Akt signaling distal to IRS proteins is regulated, the role of the pseudokinase tribble 3 (TRB3), a molecule that is increased in the livers of obese mice and humans and previously shown to bind to Akt and thereby prevent its phosphorylation by insulin, was tested (Du et al., 2003). The effect of CaMKII and p38 deficiency on TRB3 levels in HCs was first investigated. Palmitate treatment of control HCs led to an increase in TRB3 levels, consistent with a previous report (Cunha et al., 2012). Most importantly, CaMKII deficiency markedly decreased TRB3 protein and mRNA under both basal and palmitate-treated conditions (FIGS. 93A and 99A). To show relevance in vivo, the effect of CaMKII deficiency or inhibition on TRB3 levels was tested in obese mice. Consistent with the HC data, TRB3 levels were markedly suppressed in DIO Camk2g$^{-/-}$ mice or in ob/ob mice transduced with adeno-K43A-CaMKII (FIG. 93B).

To test the importance of TRB3 in the enhancement of insulin-induced p-Akt conferred by CaMKII deficiency, DIO Camk2g$^{fl/fl}$ mice were transduced with TRB3 in order to bring TRB3 protein to a level similar to that in WT. TRB3 overexpression abrogated the improvement in insulin-induced p-Akt conferred by CaMKII deficiency (FIG. 99B), indicating that the suppression of TRB3 by CaMKII deficiency is causally important in the improvement in insulin signaling. A similar experiment was conducted, except physiologic re-feeding (16 h fasting followed by 4 h of a high-fat diet) was used instead of portal vein insulin injection to activate Akt. Similar to the case with portal vein insulin injections, TRB3 overexpression abolished the improvement in re-feeding-induced p-Akt conferred by CaMKII inhibition (FIG. 93C). In line with the effect of TRB3 restoration on insulin signaling, treatment of mice with adeno-TRB3 abrogated the lowering of blood glucose (FIG. 93D) and plasma insulin (FIG. 93E) by CaMKII inhibition in DIO mice under both fasting and re-feeding conditions. Next, the effect of CaMKII deletion in TRB3-inhibited HCs was examined RNAi mediated knock down of TRB3 in CaMKII-deficient HCs did not further improve insulin-induced p-Akt (FIG. 99C), consistent with the idea that TRB3 is the downstream effector of CaMKII in the regulation of insulin-induced p-Akt.

The data in a previous report (Ozcan et al., 2012) and here indicate that, in the setting of obesity, CaMKIIγ deficiency lowers HGP by suppressing p38-mediated FoxO1 nuclear localization and improves insulin signaling by suppressing hepatic TRB3 expression, which then leads to improvement in insulin/Akt signaling. Although it was shown above that nuclear FoxO1 does not affect insulin-induced p-Aid, an interesting question is whether the improvement in p-Akt (new pathway here) contributes, via Akt phosphorylation sites on FoxO1 (Lin and Accili, 2011), to nuclear exclusion of FoxO1 in obese mice lacking CaMKII or p38, which is promoted by decreased p38-mediated phosphorylation of FoxO1 (Ozcan et al., 2012). To address this issue, the improvement in p-Akt in CaMKII-deficient obese mice was disabled through TRB3 restoration (above). Without being bound by theory, both pathways can contribute to the exclusion of nuclear FoxO1 by CaMKII deficiency in the setting of obesity, and TRB3 restoration in CaMKII-deficient mice led to a partial increase in nuclear FoxO1 (FIG. 99D). Without being bound by theory, no effect of TRB3 on nuclear FoxO1 can be shown, if one chose a non-insulin resistant model, i.e., a model where TRB3 would be irrelevant in terms of the Akt-FoxO1 pathway. For this purpose, non-insulin-resistant forskolin-treated HCs were used (Ozcan et al., 2012). Nuclear FoxO1 biological activity was assayed by quantifying the mRNA levels of the FoxO1 target genes, G6pc and Pck1. In this case, the suppressive effect of CaMKIIγ deficiency on forskolin-induced G6Pc and Pck1 mRNA was not abrogated by transduction with adeno-TRB3 (FIG. 99E). Thus, in the absence of a defect in insulin signaling, TRB3 restoration does not affect the ability of CaMKII deficiency to suppress HGP gene induction. These data further establish the separateness of the two CaMKII/p38 pathways, although in the setting of insulin resistance, FoxO1 nuclear localization is promoted by both pathways.

CaMKII Deficiency Suppresses TRB3 by Decreasing ER Stress-Induced ATF4

TRB3 expression has been reported to be increased in cancer cells and pancreatic islets undergoing endoplasmic reticulum (ER) stress (Bromati et al., 2011; Corcoran et al., 2005). Moreover, in HEK293 embryonic kidney cells treated with tunicamycin, a glycosylation inhibitor that activates the UPR, TRB3 was shown to be a direct transcriptional target of the ER stress-inducible transcription factor ATF4 (Ohoka et al., 2005). Because hepatic ER stress is increased obesity and can act as a link between obesity and insulin resistance (Gregor et al., 2009; Ozcan et al., 2004), without being bound by theory, a CaMKII-ATF4-TRB3 pathway can be upstream of defective insulin-induced p-Akt in obese liver. ATF4 levels in WT vs. CaMKIIγ-deficient HCs were measured under various conditions. Exposure to tunicamycin increased ATF4 in control HCs but not in CaMKII-deficient HCs (FIG. 94A). Similarly, the livers of obese mice deficient in hepatic CaMKIIγ had lower ATF4 levels compared with obese WT mice (FIG. 94B), indicating that CaMKII can suppress TRB3 by first suppressing ATF4. To test this and link it to insulin-induced p-Akt, palmitate-treated CaMKIIγ-deficient HCs were transduced with adeno-ATF4 to restore the level of this protein to the WT level. ATF4 restoration resulted in an increase in TRB3 mRNA and protein levels and abrogation of the improvement in p-Akt seen with CaMKII deficiency (FIGS. 94C-D). To further validate the importance of ATF4 suppression in the improvement of insulin signaling by CaMKII deficiency, ATF4 was restored in adeno-K43A-CaMKII-treated DIO mice. It was observed that the beneficial effect of CaMKIIγ inhibition on insulin-induced p-Akt was abrogated by transduction with adeno-ATF4 (FIG. 94E). Consistent with the effect of ATF4 restoration on insulin signaling, the blood glucose- and plasma insulin-lowering effect of CaMKII inhibition in DIO mice was also abrogated by adeno-ATF4 (FIG. 94F). These data support a signaling pathway in which CaMKII promotes ATF4 expression, which in turn induces TRB3, leading to suppression of insulin-induced p-Akt.

ATF4 is translationally up-regulated when the PERK branch of the ER stress unfolded protein response (UPR) is activated (Tabas and Ron, 2011; Walter and Ron, 2011). Whether CaMKII deficiency suppresses the PERK branch of UPR as a mechanism for reduced ATF-4 and TRB3 expression was investigated. When exposed to tunicamycin, HCs lacking CaMKIIγ showed a marked decrease in PERK phosphorylation, which is a measure of its activation, as well as decreased expression of the ATF4 gene target CEBP/β-homologous protein (CHOP) (FIG. 100A). Similar results were seen with tunicamycin- or palmitate-treated HCs deficient in CaMKIIγ or p38α (FIGS. 100B and 100C). To explore a possible role of CaMKII in the regulation of PERK branch of UPR in vivo, Chop mRNA levels in obese mice were analyzed. Consistent with the in vitro data, obese mice deficient in hepatic CaMKII had lower Chop mRNA levels in liver compared with WT mice (FIG. 100D). Interestingly, the IRE1α branch of the UPR, as measured by Xbp1 mRNA splicing, was not activated in either palmitate-treated HCs or in obese mouse liver (FIGS. 100E-F). Thus, CaMKII deficiency selectively suppresses the PERK branch of the UPR in the setting of obesity, leading to decreased ATF4 and TRB3 and increased insulin-induced p-Akt.

Evidence that an ATF6-p58$^{IPK}$ Pathway is Upstream of the ATF4-TRB3-Akt Pathway How silencing of CaMKII can suppress the PERK branch of the UPR was next addressed. Without being bound by theory, global suppression of ER stress can be a possibility and CaMKII deficiency can increase the expression of a widely studied inhibitor of PERK kinase called p58$^{IPK}$ (Yan et al., 2002). Initial support for this came from the finding that p58$^{IPK}$ mRNA and protein levels were increased by CaMKIIγ or p38α deficiency in ER-stressed HCs and obese mice liver (FIGS. 95A and 101A-C). Most importantly, siRNA-mediated silencing of p58$^{IPK}$ increased Trb3 and abrogated the improvement in insulin-Akt signaling in CaMKII-deficient, palmitate-treated HCs (FIGS. 95B-C), demonstrating a casual link between the proposed upstream role of p58$^{IPK}$ and the key functional endpoint of the CaMKII pathway, insulin-induced p-Akt.

Finally, to explore how CaMKII deficiency can increase p58$^{IPK}$ in obese mice liver, the role of a known inducer of the molecule, ATF6, which has been shown to be decreased in the livers of obese mice, was explored (Wang et al., 2009; Wu et al., 2007). Without being bound by theory, CaMKII deficiency can increase ATF6 levels, which indeed was the case in obese liver, in tunicamycin-treated HCs, and in palmitate-treated HCs (FIGS. 95D, 101D, and 95F). To determine causation, Atf6 was silenced in palmitate-treated CaMKII-deficient HCs using siRNA and it was found that this treatment lowered P58$^{ipk}$, increased Trb3, and reduced insulin-induced p-Akt to the level of palmitate-treated control HCs (FIGS. 95E-F). Thus, inhibition of hepatic CaMKII improves insulin signaling in the setting of obesity through induction of ATF6 and p58$^{IPK}$, which suppresses a PERK-ATF4-TRB3 pathway.

Discussion

The epidemic of obesity and T2D demands a precise understanding of the molecular events that link obesity to the two cardinal features of T2D, hyperglycemia and insulin resistance. The current findings, viewed together with two recent studies (Ozcan et al., 2012; Wang et al., 2012), present a unified scheme in which cytosolic calcium working through CaMKII in the liver plays a central role (FIG. 95G). Cytosolic calcium in the liver is elevated in obesity through at least two mechanisms: lipid-induced de-activation of the calcium pump SERCA (Fu et al., 2011; Park et al., 2010) and opening of the IP3R ER calcium channel by two processes triggered by glucagon receptor activation: formation of IP3 by phospholipase C (Hansen et al., 1998) and direct activation of the channel by PKA-mediated phosphorylation of IP3R (Wang et al., 2012). With regard to excessive HGP as a cause of hyperglycemia, the released calcium activates both calcineurin, which promotes nuclear localization of CRTC2 (Wang et al., 2012), and CaMKII, which, through p38, promotes nuclear by localization of FoxO1 (Ozcan et al., 2012). The current report reveals that a separate pathway in the liver, also mediated by CaMKII-p38, disrupts insulin-induced Akt phosphorylation, which is a key process in the pathogenesis of insulin resistance (Brozinick et al., 2003; Cho et al., 2001; Krook et al., 1998). From a translational viewpoint, this scheme indicates that a single pathway can be therapeutically inhibited to achieve improvement in both hyperglycemia and insulin resistance in obesity and T2D.

The key downstream step through which CaMKII deficiency improves insulin-induced p-Akt is suppression of TRB3, which binds Akt, prevents its membrane association, and thus block its phosphorylation (Du et al., 2003). TRB3 levels are increased in the livers of obese mice and humans, and it can play a major role in hepatic insulin resistance in this setting (Du et al., 2003; Lima et al., 2009). Notably, when TRB3 is expressed in WT mouse liver to a level similar to that in obese mouse liver, insulin resistance occurs, whereas silencing its expression in obesity improves glucose tolerance (Du et al., 2003). Moreover, a common gain-of-function polymorphism in TRB3 (Q48R) that increases the ability of TRB3 to suppress insulin-induced p-Akt is associated with increased insulin resistance in T2D in several independent cohorts (Prudente et al., 2005). TRB3 can also play a role in adipose tissue, because TRB3 antisense oligonucleotide (ASO) treatment of obese rats was reported to improve insulin sensitivity through a mechanism that involved activation of PPAR-γ and changes in adipogenesis rather than an increase in p-Akt (Weismann et al., 2011). In the case of the CaMKII pathway, the hepatic p-Akt mechanism is clearly important, but whether changes in PPARγ and adipogenesis also occur remains to be investigated.

An important finding in the study is that CaMKII induces TRB3 through activation of the PERK-ATF4 branch of UPR, providing a novel link between CaMKII and ER stress. In the context of previous findings linking P58IPK to suppression of PERK activation (Yan et al., 2002), the data indicate that the obesity-induced CaMKII/P38 pathway activates PERK through suppression of p58$^{IPK}$. Interestingly, p58$^{IPK}$-deficient mice exhibit glucosuria and hyperglycemia through a mechanism attributed to β-cell dysfunction (Ladiges et al., 2005). The results now reveal another beneficial effect of p58$^{IPK}$ in metabolism, namely, improvement in hepatic insulin signaling through suppression of CaMKII-induced ATF4 and TRB3.

It was shown that a key link between CaMKII/p38 deficiency and de-activation of the PERK branch of the UPR is activation of an ATF6-p58$^{IPK}$ pathway. CaMKII-deficient obese mice have higher nuclear ATF6 levels, and silencing ATF6 in these mice lowers p58$^{IPK}$ and suppresses insulin-induced p-Akt. How inhibition of the CaMKII/p38 pathway leads to increased ATF6 expression remains to be elucidated, but it is interesting to consider previous studies linking CaMKII/p38 activation with changes in gene expression (Backs et al., 2006; Raingeaud et al., 1996). As with p58$^{IPK}$ induction and TRB3 suppression, ATF6 activation can have additional and independent beneficial effects in obesity and T2D. In particular, others have provided evidence that ATF6 could suppress HGP through disruption of CREB-CRTC2 interaction (Wang et al., 2009).

The discovery of a common pathway that independently affects the two cardinal features of T2D raises the possibility of new therapeutic targets. To the extent that excessive glucagon signaling is at least one mechanism that likely activates the CaMKII-p38-MK2 pathway in T2D, relevance to humans is indicated by the ability of glucagon receptor antagonists (GRAs) to markedly lower blood sugar in human subjects (Petersen and Sullivan, 2001). However, there can be an advantage to targeting a more downstream branch of the glucagon pathway in order to avoid the possible adverse effects of GRAs (Yang et al., 2011). In terms of the "druggability" of the molecules in the pathway, CaMKII inhibitors are in development for heart failure (Rokita and Anderson, 2012), and MK2 inhibitors are being explored as a more effective alternative than p38 inhibitors for inflammatory diseases (Huang et al., 2012). Because all new diabetes drugs must pass safety tests for coronary artery disease, the applications of these inhibitors to T2D can be particularly advantageous: CaMKII inhibition in liver lowers plasma cholesterol and triglycerides in obese mice; CaMKII inhibition in macrophages protects the cells from ER stress-induced apoptosis, a key step in advanced plaque progression (Timmins et al., 2009); and MK2-deficient Ldlr$^{-/-}$ mice are protected against atherosclerosis (Jagavelu et al., 2007).

Experimental Procedures

Mouse Experiments

Camk2g$^{-/-}$ were generated as described previously (Backs et al., 2010) and crossed onto the C57BL6/J background. Camk2g$^{fl/fl}$ mice were generated by flanking exon 1-2 with loxP sites, which will be described in detail elsewhere (M. Kreuβer et al., submitted manuscript), and then crossed onto the C57BL6/J background. Ob/ob mice were obtained from Jackson Labs. Mapk14$^{fl/fl}$ mice were generated as described previously (Engel et al., 2005). Male mice were fed a standard chow diet or a high-fat diet with 60% kcal from fat (Research Diets) and maintained on a 12-h-light-dark cycle. Recombinant adenovirus ($0.5-3 \times 10^9$ plaque-forming units/mice) was delivered by tail vein injection, and experiments were commenced after 5-7 days. Fasting blood glucose was measured in mice that were fasted for 4-6 h, with free access to water, using a glucose meter. Glucose tolerance tests were performed in overnight-fasted mice by assaying blood glucose at various times after i.p. injection of glucose (0.5 g/kg for ob/ob and 1.5 g/kg for DIO). Plasma insulin levels were measured using ultrasensitive mouse insulin ELISA Kit (Crystal Chem). Insulin tolerance tests were performed in 5 h-fasted mice by assaying blood glucose at various times after i.p. injection of insulin (2 IU/kg for ob/ob and 0.75-1 IU/kg for DIO).

Portal Vein Insulin Infusion and Protein Extraction from Tissues

Following 6 h food withdrawal, mice were anesthetized, and insulin (1-2 IU/kg) or PBS was injected into mice through the portal vein. Three minutes after injection, tissues were removed, frozen in liquid nitrogen, and kept at −80° C. until processing. For protein extraction, tissues were placed in a cold lysis buffer (25 mM Tris-HCl pH 7.4, 1 mM EGTA, 1 mM EDTA, 10 mM $Na_4P_2O_7$, 10 mM NaF, 2 mM $Na_3VO_4$, 1% NP-40, 2 mM PMSF, 5 µg/ml leupeptin, 10 nM okadaic acid, and 5 µg/ml aprotinin). After homogenization on ice, the tissue lysates were centrifuged, and the supernatant fractions were used for immunoblot blot analysis.

Primary Hepatocytes (HCs)

Primary mouse HCs were isolated from 8- to 12-week-old mice as described previously (Ozcan et al., 2012). For most experiments, the HCs were cultured in DMEM containing 10% fetal bovine serum, treated as described in the figure legends, and then incubated for 5 h in serum-free DMEM. HCs were transduced with adenoviral constructs 4 h after plating, and experiments were conducted 12 h after transduction. Transfections with scrambled RNA and siRNAs targeting $p58^{ipk}$ and Atf6 were carried out using Lipofectamine™ RNAiMAX transfection reagent (Life Technologies, Inc.) according to manufacturer's instructions. Metabolism-qualified human HCs were purchased from Life Technologies and cultured according to the manufacturer's instructions.

Statistical Analysis

All results are presented as mean±SEM. P values were calculated using the Student's t-test for normally distributed data and the Mann-Whitney rank sum test for non-normally distributed data.

REFERENCES

1. Achard, C. S., and Laybutt, D. R. (2012). Lipid-induced endoplasmic reticulum stress in liver cells results in two distinct outcomes: adaptation with enhanced insulin signaling or insulin resistance. Endocrinology 153, 2164-2177.
2. Backs, J., Song, K., Bezprozvannaya, S., Chang, S., and Olson, E. N. (2006). CaM kinase II selectively signals to histone deacetylase 4 during cardiomyocyte hypertrophy. J. Clin. Invest. 116, 1853-1864.
3. Backs, J., Stein, P., Backs, T., Duncan, F. E., Grueter, C. E., McAnally, J., Qi, X., Schultz, R. M., and Olson, E. N. (2010). The gamma isoform of CaM kinase II controls mouse egg activation by regulating cell cycle resumption. Proc. Natl. Acad. Sci. U.S.A. 107, 81-86.
4. Bornfeldt, K. E., and Tabas, I. (2011). Insulin resistance, hyperglycemia, and atherosclerosis. Cell Metab. 14, 575-585.
5. Bromati, C. R., Lellis-Santos, C., Yamanaka, T. S., Nogueira, T. C., Leonelli, M., Caperuto, L. C., Gorjao, R., Leite, A. R., Anhe, G. F., and Bordin, S. (2011). UPR induces transient burst of apoptosis in islets of early lactating rats through reduced AKT phosphorylation via ATF4/CHOP stimulation of TRB3 expression. Am. J. Physiol. Regul. Integr. Comp. Physiol. 300, R92-100.
6. Brown, M. S., and Goldstein, J. L. (2008). Selective versus total insulin resistance: a pathogenic paradox. Cell Metab. 7, 95-96.
7. Brozinick, J. T., Jr., Roberts, B. R., and Dohm, G. L. (2003). Defective signaling through Akt-2 and -3 but not Akt-1 in insulin-resistant human skeletal muscle: potential role in insulin resistance. Diabetes 52, 935-941.
8. Cho, H., Mu, J., Kim, J. K., Thorvaldsen, J. L., Chu, Q., Crenshaw, E. B., 3rd, Kaestner, K. H., Bartolomei, M. S., Shulman, G. I., and Birnbaum, M. J. (2001). Insulin resistance and a diabetes mellitus-like syndrome in mice lacking the protein kinase Akt2 (PKB beta). Science 292, 1728-1731.
9. Corcoran, C. A., Luo, X., He, Q., Jiang, C., Huang, Y., and Sheikh, M. S. (2005). Genotoxic and endoplasmic reticulum stresses differentially regulate TRB3 expression. Cancer Biol. Ther. 4, 1063-1067.
10. Cunha, D. A., Igoillo-Esteve, M., Gurzov, E. N., Germano, C. M., Naamane, N., Marhfour, I., Fukaya, M., Vanderwinden, J. M., Gysemans, C., Mathieu, C., Marselli, L., Marchetti, P., Harding, H. P., Ron, D., Eizirik, D. L., and Cnop, M. (2012). Death protein 5 and p53-upregulated modulator of apoptosis mediate the endoplasmic reticulum stress-mitochondrial dialog triggering lipotoxic rodent and human beta-cell apoptosis. Diabetes 61, 2763-2775.
11. Du, K., Herzig, S., Kulkarni, R. N., and Montminy, M. (2003). TRB3: a tribbles homolog that inhibits Akt/PKB activation by insulin in liver. Science 300, 1574-1577.
12. Engel, F. B., Schebesta, M., Duong, M. T., Lu, G., Ren, S., Madwed, J. B., Jiang, H., Wang, Y., and Keating, M. T. (2005). p38 MAP kinase inhibition enables proliferation of adult mammalian cardiomyocytes. Genes Dev. 19, 1175-1187.
13. Freshney, N. W., Rawlinson, L., Guesdon, F., Jones, E., Cowley, S., Hsuan, J., and Saklatvala, J. (1994). Interleukin-1 activates a novel protein kinase cascade that results in the phosphorylation of Hsp27. Cell 78, 1039-1049.
14. Fu, S., Yang, L., Li, P., Hofmann, O., Dicker, L., Hide, W., Lin, X., Watkins, S. M., Ivanov, A. R., and Hotamisligil, G. S. (2011). Aberrant lipid metabolism disrupts calcium homeostasis causing liver endoplasmic reticulum stress in obesity. Nature 473, 528-531.
15. Gaestel, M. (2006). MAPKAP kinases—MKs—two's company, three's a crowd. Nat. Rev. Mol. Cell Biol. 7, 120-130.
16. Gregor, M. F., Yang, L., Fabbrini, E., Mohammed, B. S., Eagon, J. C., Hotamisligil, G. S., and Klein, S. (2009). Endoplasmic reticulum stress is reduced in tissues of obese subjects after weight loss. Diabetes 58, 693-700.
17. Hansen, L. H., Gromada, J., Bouchelouche, P., Whitmore, T., Jelinek, L., Kindsvogel, W., and Nishimura, E. (1998). Glucagon-mediated Ca2+ signaling in BHK cells expressing cloned human glucagon receptors. Am. J. Physiol. 274, C1552-1562.
18. Hemi, R., Yochananov, Y., Barhod, E., Kasher-Meron, M., Karasik, A., Tirosh, A., and Kanety, H. (2011). p38 mitogen-activated protein kinase-dependent transactivation of ErbB receptor family: a novel common mechanism for stress-induced IRS-1 serine phosphorylation and insulin resistance. Diabetes 60, 1134-1145.
19. Huang, X., Zhu, X., Chen, X., Zhou, W., Xiao, D., Degrado, S., Aslanian, R., Fossetta, J., Lundell, D., Tian, F., Trivedi, P., and Palani, A. (2012). A three-step protocol for lead optimization: quick identification of key conformational features and functional groups in the SAR studies of non-ATP competitive MK2 (MAPKAPK2) inhibitors. Bioorg. Med. Chem. Lett. 22, 65-70.
20. Jagavelu, K., Tietge, U. J., Gaestel, M., Drexler, H., Schieffer, B., and Bavendiek, U. (2007). Systemic deficiency of the MAP kinase-activated protein kinase 2 reduces atherosclerosis in hypercholesterolemic mice. Circ. Res. 101, 1104-1112.
21. Kerouz, N. J., Horsch, D., Pons, S., and Kahn, C. R. (1997). Differential regulation of insulin receptor substrates-1 and -2 (IRS-1 and IRS-2) and phosphatidylinositol 3-kinase isoforms in liver and muscle of the obese diabetic (ob/ob) mouse. J. Clin. Invest. 100, 3164-3172.
22. Konner, A. C., and Bruning, J. C. (2012). Selective insulin and leptin resistance in metabolic disorders. Cell Metab. 16, 144-152.
23. Krook, A., Roth, R. A., Jiang, X. J., Zierath, J. R., and Wallberg-Henriksson, H. (1998). Insulin-stimulated Akt kinase activity is reduced in skeletal muscle from NIDDM subjects. Diabetes 47, 1281-1286.
24. Ladiges, W. C., Knoblaugh, S. E., Morton, J. F., Korth, M. J., Sopher, B. L., Baskin, C. R., MacAuley, A., Goodman, A. G., LeBoeuf, R. C., and Katze, M. G. (2005). Pancreatic beta-cell failure and diabetes in mice with a deletion mutation of the endoplasmic reticulum molecular chaperone gene P58IPK. Diabetes 54, 1074-1081.
25. Leavens, K. F., and Birnbaum, M. J. (2011). Insulin signaling to hepatic lipid metabolism in health and disease. Crit. Rev. Biochem. Mol. Biol. 46, 200-215.
26. Lima, A. F., Ropelle, E. R., Pauli, J. R., Cintra, D. E., Frederico, M. J., Pinho, R. A., Velloso, L. A., and De Souza, C. T. (2009). Acute exercise reduces insulin resistance-induced TRB3 expression and amelioration of the hepatic production of glucose in the liver of diabetic mice. J. Cell. Physiol. 221, 92-97.
27. Lin, H. V., and Accili, D. (2011). Hormonal regulation of hepatic glucose production in health and disease. Cell Metab. 14, 9-19.
28. Ohoka, N., Yoshii, S., Hattori, T., Onozaki, K., and Hayashi, H. (2005). TRB3, a novel ER stress-inducible gene, is induced via ATF4-CHOP pathway and is involved in cell death. EMBO J. 24, 1243-1255.
29. Ozcan, L., Wong, C. C., Li, G., Xu, T., Pajvani, U., Park, S. K., Wronska, A., Chen, B. X., Marks, A. R., Fukamizu, A., Backs, J., Singer, H. A., Yates, J. R., 3rd, Accili, D., and Tabas, I. (2012). Calcium Signaling through CaMKII Regulates Hepatic Glucose Production in Fasting and Obesity. Cell Metab. 15, 739-751.
30. Ozcan, U., Cao, Q., Yilmaz, E., Lee, A. H., Iwakoshi, N. N., Ozdelen, E., Tuncman, G., Gorgun, C., Glimcher, L. H., and Hotamisligil, G. S. (2004). Endoplasmic reticulum stress links obesity, insulin action, and type 2 diabetes. Science 306, 457-461.
31. Park, S. W., Zhou, Y., Lee, J., Lee, J., and Ozcan, U. (2010). Sarco(endo)plasmic reticulum Ca2+-ATPase 2b is a major regulator of endoplasmic reticulum stress and glucose homeostasis in obesity. Proc. Natl. Acad. Sci. U.S.A. 107, 19320-19325.
32. Petersen, K. F., and Sullivan, J. T. (2001). Effects of a novel glucagon receptor antagonist (Bay 27-9955) on glucagon-stimulated glucose production in humans. Diabetologia 44, 2018-2024.
33. Pfleiderer, P. J., Lu, K. K., Crow, M. T., Keller, R. S., and Singer, H. A. (2004). Modulation of vascular smooth muscle cell migration by calcium/calmodulin-dependent protein kinase II-delta 2. Am. J. Physiol. Cell Physiol. 286, C1238-1245.
34. Prudente, S., Hribal, M. L., Flex, E., Turchi, F., Morini, E., De Cosmo, S., Bacci, S., Tassi, V., Cardellini, M., Lauro, R., Sesti, G., Dallapiccola, B., and Trischitta, V. (2005). The functional Q84R polymorphism of mammalian Tribbles homolog TRB3 is associated with insulin resistance and related cardiovascular risk in Caucasians from Italy. Diabetes 54, 2807-2811.
35. Raingeaud, J., Whitmarsh, A. J., Barrett, T., Derijard, B., and Davis, R. J. (1996). MKK3- and MKK6-regulated gene expression is mediated by the p38 mitogen-activated protein kinase signal transduction pathway. Mol. Cell. Biol. 16, 1247-1255.
36. Rokita, A. G., and Anderson, M. E. (2012). New therapeutic targets in cardiology: arrhythmias and Ca2+/calmodulin-dependent kinase II (CaMKII). Circulation 126, 2125-2139.
37. Rouse, J., Cohen, P., Trigon, S., Morange, M., Alonso-Llamazares, A., Zamanillo, D., Hunt, T., and Nebreda, A. R. (1994). A novel kinase cascade triggered by stress and heat shock that stimulates MAPKAP kinase-2 and phosphorylation of the small heat shock proteins. Cell 78, 1027-1037.
38. Saad, M. J., Araki, E., Miralpeix, M., Rothenberg, P. L., White, M. F., and Kahn, C. R. (1992). Regulation of insulin receptor substrate-1 in liver and muscle of animal models of insulin resistance. J. Clin. Invest. 90, 1839-1849.
39. Saltiel, A. R., and Kahn, C. R. (2001). Insulin signalling and the regulation of glucose and lipid metabolism. Nature 414, 799-806.
40. Samuel, V. T., and Shulman, G. I. (2012). Mechanisms for insulin resistance: common threads and missing links. Cell 148, 852-871.
41. Streicher, J. M., Ren, S., Herschman, H., and Wang, Y. (2010). MAPK-activated protein kinase-2 in cardiac hypertrophy and cyclooxygenase-2 regulation in heart. Circ Res 106, 1434-1443.
42. Sun, Z., Miller, R. A., Patel, R. T., Chen, J., Dhir, R., Wang, H., Zhang, D., Graham, M. J., Unterman, T. G., Shulman, G. I., Sztalryd, C., Bennett, M. J., Ahima, R. S., Birnbaum, M. J., and Lazar, M. A. (2012). Hepatic Hdac3 promotes gluconeogenesis by repressing lipid synthesis and sequestration. Nat. Med. 18, 934-942.
43. Tabas, I., and Ron, D. (2011). Integrating the mechanisms of apoptosis induced by endoplasmic reticulum stress. Nat. Cell Biol. 13, 184-190.
44. Timmins, J. M., Ozcan, L., Seimon, T. A., Li, G., Malagelada, C., Backs, J., Backs, T., Bassel-Duby, R., Olson, E. N., Anderson, M. E., and Tabas, I. (2009). Calcium/calmodulin-dependent protein kinase II links ER stress with Fas and mitochondrial apoptosis pathways. J. Clin. Invest. 119, 2925-2941.
45. Walter, P., and Ron, D. (2011). The unfolded protein response: from stress pathway to homeostatic regulation. Science 334, 1081-1086.
46. Wang, Y., Li, G., Goode, J., Paz, J. C., Ouyang, K., Screaton, R., Fischer, W. H., Chen, J., Tabas, I., and Montminy, M. (2012). Inositol-1,4,5-trisphosphate receptor regulates hepatic gluconeogenesis in fasting and diabetes. Nature 485, 128-132.

47. Wang, Y., Vera, L., Fischer, W. H., and Montminy, M. (2009). The CREB coactivator CRTC2 links hepatic ER stress and fasting gluconeogenesis. Nature 460, 534-537.

48. Weismann, D., Erion, D. M., Ignatova-Todorava, I., Nagai, Y., Stark, R., Hsiao, J. J., Flannery, C., Birkenfeld, A. L., May, T., Kahn, M., Zhang, D., Yu, X. X., Murray, S. F., Bhanot, S., Monia, B. P., Cline, G. W., Shulman, G. I., and Samuel, V. T. (2011). Knockdown of the gene encoding Drosophila tribbles homologue 3 (Trib3) improves insulin sensitivity through peroxisome proliferator-activated receptor-gamma (PPARgamma) activation in a rat model of insulin resistance. Diabetologia 54, 935-944.

49. Wu, J., Rutkowski, D. T., Dubois, M., Swathirajan, J., Saunders, T., Wang, J., Song, B., Yau, G. D., and Kaufman, R. J. (2007). ATF6alpha optimizes long-term endoplasmic reticulum function to protect cells from chronic stress. Dev. Cell 13, 351-364.

50. Yan, W., Frank, C. L., Korth, M. J., Sopher, B. L., Novoa, I., Ron, D., and Katze, M. G. (2002). Control of PERK eIF2alpha kinase activity by the endoplasmic reticulum stress-induced molecular chaperone P58IPK. Proc. Natl. Acad. Sci. U.S.A. 99, 15920-15925.

51. Yang, J., MacDougall, M. L., McDowell, M. T., Xi, L., Wei, R., Zavadoski, W. J., Molloy, M. P., Baker, J. D., Kuhn, M., Cabrera, O., and Treadway, J. L. (2011). Polyomic profiling reveals significant hepatic metabolic alterations in glucagon-receptor (GCGR) knockout mice: implications on anti-glucagon therapies for diabetes. BMC Genomics 12, 281.

Supplemental Experimental Procedures

Reagents and Antibodies

Sodium palmitate, tunicamycin, and insulin were from Sigma. Anti-ATF-4, anti-CHOP, anti-phosphotyrosine, and anti-IR antibodies were from Santa Cruz Biotechnology, Inc. Anti-β-actin and anti-p58$^{fl/fl}$ from Abcam. Anti-phospho-S473-Akt, anti-phospho-T308-Akt, anti-Akt, anti-IRS2, anti-nucleophosmin (Np), anti-FoxO1, anti-phospho-S253-FoxO1, anti-phospho-S9-GSK3l3, anti-GSK3l3, anti-HA, anti-phospho-PERK, and anti-PERK antibodies were from Cell Signaling. Anti-ATF6 antibody was from Imgenex. Adenoviruses encoding LacZ, T287A-CaMKII, and K43A-CaMKII were gifts; TRB3 and TRB3 RNAi adenoviruses, and adeno-ATF-4 were gifts, and adeno-FoxO1-ADA was also a gift. All adenoviruses were amplified by Viraquest, Inc. Adeno-associated viruses (AAV) containing either hepatocyte-specific TBG-Cre recombinase (AAV8-TBG-Cre) or the control vector (AAV8-TBG-LacZ) were purchased from the Penn Vector Core. Adeno-T222A-MK2 was purchased from Cell Biolabs Inc.

Immunoprecipitation

Cell lysate from tissues (~1 mg total protein) or cells (~350 μg total protein) were brought to a total volume of 1 ml with lysis buffer. Antibodies (0.3-0.6 μg) and protein A Sepharose beads (80 μl) were added to the tube, which was then rotated at 4° C. overnight. Immune complexes were collected by centrifugation at 16,000×g and washed 3 times with chilled lysis buffer.

Immunoblot and RT-qPCR Assays

Immunoblot and RT-qPCR assays were performed as previously described (Timmins et al., 2009). Total RNA was extracted from HCs using the RNeasy kit (Qiagen). cDNA was synthesized from 1 μg total RNA using oligo (dT) and Superscript II (Invitrogen). Nuclear extraction from liver was performed using the Nuclear Extraction Kit from Panomics according to the manufacturer's instructions.

XBP1 Splicing

Total RNA was reverse-transcribed into cDNA. A segment of XBP-1 mRNA was amplified using the forward primer AAC TCC AGC TAG AAA ATC AGC (SEQ ID NO: 31) and the reverse primer ACC ACC ATG GAG AAG GCT GG (SEQ ID NO: 32). Spliced and unspliced XBP-1 were resolved by electrophoresis in a 2.5% agarose gel and visualized using ethidium bromide under UV light. GAPDH, using CCA TGG GAA GAT GTT CTG GG (SEQ ID NO: 33) and CTC AGT GTA GCC CAG GAT GC (SEQ ID NO: 34) as forward and reverse primers, respectively, was used as an internal standard to verify equal RT product loading for each experiment.

Liver Triglyceride Measurement

Lipid extraction was performed using a modification of the Bligh-Dyer method (Bligh and Dyer, 1959). Briefly, livers were homogenized in chloroform:MeOH:H2O (1:2: 0.8) at room temperature and then centrifuged. Equal volumes of chloroform and water were added to the supernatant fraction, which was then vortexed and centrifuged. The chloroform layer was collected and dried under nitrogen. The dried lipids were then resuspended in 90% isopropanol: 10% Triton-X and then assayed for triglyceride using a kit from Wako and cholesterol using a kit from Life Technologies.

Glucose Production in Primary HCs

After primary mouse HCs were harvested and cultured as described above, the cell culture medium was switched to glucose- and phenol-free DMEM (pH 7.4) supplemented with 20 mM sodium lactate and 2 mM sodium pyruvate. After 20 h of culture, 500 ml medium was collected, and the glucose content was measured using a colorimetric glucose assay kit (Abcam). The readings were then normalized to the total protein amount in the whole-cell lysates.

REFERENCES

1. Bligh, E. G., and Dyer, W. J. (1959). A rapid method of total lipid extraction and purification. Can. J. Biochem. Physiol. 37, 911-917.

2. Timmins, J. M., Ozcan, L., Seimon, T. A., Li, G., Malagelada, C., Backs, J., Backs, T., Bassel-Duby, R., Olson, E. N., Anderson, M. E., and Tabas, I. (2009), Calcium/calmodulin-dependent protein kinase II links ER stress with Fas and mitochondrial apoptosis pathways. J. Clin. Invest. 119, 2925-2941.

Example 12: Study of the CaMKII-p38-MK2 Pathway in Human Liver Tissue and Hepatocytes The studies conducted in FIGS. 102 and 103 use human liver tissue. The studies conducted in FIGS. 104 and 105 use human hepatocytes (HC).

FIGS. 102 and 103 show that the CaMKII-p38-MK2 pathway is induced in obese human liver. In FIG. 102, frozen liver biopsy samples from human subjects with different BMIs were lysed and total liver extracts were then assayed for p-CaMKII, ox-CaMKII, CaMKII, p-38, p38, p-MK2, p58$^{IPK}$ and β-actin by immunoblot. In FIG. 103, frozen liver biopsy samples from human subjects from another cohort, with different BMIs were lysed and total liver extracts were then assayed for p-CaMKII, p-38, p38, p-MK2, p-hsp27, p58$^{IPK}$ and β-actin by immunoblot.

FIG. 104 shows that CaMKII regulates G6Pc and Pck1 expression in primary human hepatocytes (HCs). Primary human HCs (metabolism-qualified) were transduced with adeno-LacZ or -K43A-CaMKII at an MOI of 30. 24 h later, cells were serum-depleted overnight and then incubated for 5 h with 10 µM forskolin. RNA was assayed for G6pc and Pck1 mRNA by RT-qPCR (Differing symbols indicate p<0.05; mean±S.E.M.).

FIG. 105 shows that MK2 regulates G6Pc expression in primary human hepatocytes (HCs). Primary human HCs (metabolism-qualified) were transduced with adeno-LacZ or -DN-MK2 at an MOI of 20. 24 h later cells were serum-depleted overnight and then incubated for 5 h with 10 µM forskolin. RNA was assayed for G6pc mRNA by RT-qPCR (**P<0.05; mean±S.E.M.).

Example 13: HDAC4, Dach 1 and Dach2 Inhibitors and Activators for Treatment and Prevention of Metabolic Diseases The studies conducted in FIGS. 106 to 120 explore a new upstream-pathway mechanism involving two molecules that play an important role in transmitting the signal from CaMKII-P238-MK2 to the insulin signaling pathway in hepatocytes, HDAC4 and Dach1. The studies in FIGS. 106 to 120 also explore the role of Dach2.

FIG. 106 shows that CaMKII or p38 deficiency increases nuclear HDAC4. Primary HCs from Camk2g$^{fl/fl}$ or Mapk14$^{fl/fl}$ mice were transduced with adeno-LacZ or -Cre at an MOI of 10. 36 h later nuclear and cytoplasmic proteins were isolated and HDAC4, β-actin and nucleophosmin (Np) levels were assayed by immunoblotting.

FIG. 107 shows an improvement in insulin-mediated Akt phosphorylation by CaMKII deficiency is partially abrogated by HDAC4 inhibition. HCs from Camk2γ$^{fl/fl}$ mice were pretreated with either scrambled RNA (scr) or siRNA targeting HDAC4 (si-HDAC4). After 12 h, the cells were transduced with adeno-LacZ or -Cre. After an additional 24 h, the cells were incubated with BSA control or palmitate (0.2 mM) for 19 h, with the last 5 h in serum-free media and subsequently treated with ±100 nM insulin for 5 min. Lysates were immunoblotted for p-Akt and Akt by immunoblot. Densitometric quantification of the immunoblot data is shown in the graph (Bars with different symbols are different from each other and control, p<0.05; mean±S.E.M.).

FIG. 108 shows that increased ATF6 and p58 levels in CaMKII deficient HCs are partially abrogated by HDAC4 inhibition. HCs from Camk2g$^{fl/fl}$ mice were pretreated with either scrambled RNA or siRNA targeting HDAC4 (si-HDAC4). After 12 h, the cells were transduced with adeno-LacZ or -Cre. After an additional 24 h, the cells were incubated with BSA control or palmitate (0.2 mM) for 14 h. RNA was assayed for Atf6 and p58$^{ipk}$ mRNA by RT-qPCR (Bars with different symbols are different from each other and control, p<0.05; mean±S.E.M.).

FIG. 109 shows that constitutively nuclear (CN) HDAC4 improves insulin-induced Akt phosphorylation in palmitate-treated primary hepatocytes. Primary HCs from WT mice were transduced with adeno-LacZ or -CN-HDAC4 at different MOI's as indicated. 24 h later cells were incubated with either BSA control or 0.2 mM palmitate for 19 h, with the last 5 h in serum-free media and subsequently treated with ±100 nM insulin for 5 min. Lysates were immunoblotted for p-Akt, Akt and β-actin by immunoblot.

FIG. 110 shows that CN-HDAC4 increases Atf6 and p58 mRNA levels. Primary HCs from WT mice were transduced with adeno-LacZ or -CN-HDAC4 at an MOI of 0.1. 24 h later cells were incubated with either BSA control or 0.2 mM palmitate for 14 h. RNA was assayed for Atf6 and p58$^{ipk}$ mRNA by RT-qPCR (Bars with different symbols are different from each other and control, p<0.05; mean±S.E.M.).

FIGS. 111A-C shows that CN-HDAC4 improves hyperglycemia in diet-induced obese (DIO) mice. 18 wk-old DIO mice were injected with adeno-LacZ (n=6) or -CN-HDAC4 (n=6). Body weight, fasting blood glucose and plasma insulin levels of DIO mice 2 weeks after treatment (*p<0.05; mean±S.E.M.) are shown.

FIG. 112 shows that CN-HDAC4 overexpression improves insulin-induced Akt phosphorylation in obese mice liver. 18 wk-old DIO mice injected with adeno-LacZ or -CN-HDAC4. 3 weeks after the treatment, mice were fasted for 5 h and then injected with 1.5 IU/kg insulin through the portal vein. Total liver extracts were then assayed for p-Akt and Akt by immunoblot. Densitometric quantification of the immunoblot data is shown in the graph (*p<0.05; mean±S.E.M.).

FIG. 113 shows that hepatic dach1 and dach2 levels are increased in obesity. Liver extracts from 10-week-old WT or ob/ob mice, or WT mice fed a chow or high fat-high calorie diet for 15 wks (DIO), were probed for dach1, dach2 and β-actin by immunoblot.

FIG. 114 shows that CaMKII deficiency decreases hepatic dach1 and dach2 levels. Dach1, dach2 and β-actin were probed in livers from DIO Camk2g$^{fl/fl}$ mice treated with TBG-LacZ or TBG-Cre or ob/ob mice treated with adeno-LacZ or adeno-K43A-CaMKII.

FIG. 115 shows that palmitate induces dach1 and dach2 mRNA levels. Primary HCs from WT mice were treated with 0.5 mM palmitate for 6 h. RNA was assayed for dach1 and dach2 mRNA by RT-qPCR (*p<0.05; mean±S.E.M.).

FIG. 116 shows that CaMKII inhibition decreases palmitate-induced dach1 and dach2 levels. Primary HCs from Camk2γ$^{fl/fl}$ mice were treated with adeno-LacZ or adeno-Cre. 36 h later, cell were treated with 0.5 mM palmitate for 6 h. RNA was assayed for dach1 and dach2 mRNA by RT-qPCR (*p<0.05; mean±S.E.M.).

FIG. 117 shows that Dach1 is induced in obese human liver. Frozen liver biopsy samples from human subjects with different BMIs were lysed and total liver extracts were then assayed for dach1 and β-actin by immunoblot.

FIG. 118 shows that CaMKII inhibition decreases palmitate-induced dach1 and dach2 levels in human hepatocytes. Primary human HCs (metabolism-qualified) were transduced with adeno-LacZ or -K43A-CaMKII at an MOI of 30. 24 h later cells were treated with 0.3 mM palmitate for 14 h. Lysates were probed for dach1, dach2 and β-actin by immunoblot. Densitometric quantification of the immunoblot data is shown in the graph (Bars with different symbols are different from each other and control, p<0.05; mean±S.E.M.).

FIG. 119 shows that Dach1&2 inhibition increases ATF6 levels. Primary HCs from WT mice were treated with either scrambled RNA (scr) or siRNAs targeting both dach1 and dach2 (si-dach1&2). 60 h later, cells were treated with 0.5 mM palmitate for 5 and RNA was assayed for Atf6, dach1 and dach2 mRNA by RT-qPCR (Bars with different symbols are different from each other and control, p<0.05; mean±S.E.M.).

FIG. 120 shows that Dach1&2 silencing improves insulin-induced Akt phosphorylation in palmitate-treated primary hepatocytes. Primary HCs from WT mice were treated with either scrambled RNA (scr) or siRNAs targeting both dach1 and dach2 (si-dach1&2). 48 h later, cells were treated with 0.3 mM palmitate for 19 h, with the last 5 h in serum-free media and subsequently treated with ±100 nM insulin for 5 min. Lysates were immunoblotted for p-Akt, Akt and β-actin by immunoblot. Densitometric quantification of the immunoblot data is shown in the graph (Bars with different symbols are different from each other and control, $p<0.05$; mean±S.E.M.).

FIG. 121 shows that hepatic CaMKIIγ deletion suppresses visceral adipose tissue (VAT) inflammation. 15 wk-old DIO Camk2g$^{fl/fl}$ mice were injected with AAV-TBG-LacZ or -TBG-Cre. 4 weeks after the treatment, VAT was assayed for inflammatory cell infiltration via H&E staining.

FIG. 122 shows that hepatic CaMKIIγ deletion suppresses expression of inflammatory genes in VAT. 15 wk-old DIO Camk2g$^{fl/fl}$ mice were injected with AAV-TBG-LacZ or -TBG-Cre. 4 weeks after the treatment, RNA from VAT was assayed for F4/80, Mcp1 and Tnfα mRNA by RT-qPCR (*$p<0.05$; mean±S.E.M.).

The invention claimed is:

1. A method of treating a metabolic disorder in a subject in need thereof, wherein the metabolic disorder is induced by obesity and is selected from the group consisting of Type 2 diabetes, insulin resistance, and metabolic syndrome, the method comprising reducing the activity of MAP kinase activated protein kinase 2/MAP kinase activated protein kinase 3 (MK2/3) by administering to the subject an inhibitor of MK2/3, thereby treating the disorder, wherein the inhibitor of MK2/3 is a small molecule.

2. The method of claim 1, wherein the treating affects glycogenolysis or gluconeogenesis in the subject.

3. The method of claim 1, wherein the treating reduces hepatic glucose production, hyperglycemia, hyperinsulinemia, fatty liver, insulin resistance, insulin resistance-associated inflammation, insulin resistance-associated dyslipidemia, or any combination thereof, in the subject.

4. A method of treating hyperinsulinemia associated with a metabolic disorder in a subject in need thereof, wherein the metabolic disorder is induced by obesity and selected from the group consisting of Type 2 diabetes, insulin resistance, and metabolic syndrome, the method comprising reducing the activity of MK2/3 by administering to the subject an inhibitor of MK2/3, thereby treating the hyperinsulinemia associated with the disorder, wherein the inhibitor of MK2/3 is a small molecule.

5. The method of claim 4, wherein the treating affects glycogenolysis or gluconeogenesis in the subject.

6. A method of treating hyperglycemia associated with a metabolic disorder in a subject in need thereof, wherein the metabolic disorder is induced by obesity and selected from the group consisting of Type 2 diabetes, insulin resistance, and metabolic syndrome, the method comprising reducing the activity of MK2/3 by administering to the subject an inhibitor of MK2/3, thereby treating the hyperglycemia associated with the disorder, wherein the inhibitor of MK2/3 is a small molecule.

7. The method of claim 6, wherein the treating affects glycogenolysis or gluconeogenesis in the subject.

* * * * *

UNITED STATES PATENT AND TRADEMARK OFFICE
CERTIFICATE OF CORRECTION

| | | |
|---|---|---|
| PATENT NO. | : 9,771,430 B2 | Page 1 of 1 |
| APPLICATION NO. | : 14/197173 | |
| DATED | : September 26, 2017 | |
| INVENTOR(S) | : Ira Tabas et al. | |

It is certified that error appears in the above-identified patent and that said Letters Patent is hereby corrected as shown below:

In the Specification

At Column 1, Line number 20, please delete "This invention was made with government support under Grant No. P01 HL087123 awarded by the National Institute of Health and the National Heart, Lung and Blood Institute, and Grant Nos. R01-DK049777, R01-DK083834 and R01-DK091618 awarded by the National Institute of Health and the National Institute of Diabetes and Digestive and Kidney Diseases. Thus, the United States Government has certain rights in the present invention." and insert --This invention was made with government support under grants HL087123, DK049777, DK083834, and DK091618 awarded by the National Institutes of Health. The Government has certain rights in this invention.--

Signed and Sealed this
Seventh Day of November, 2017

Joseph Matal
*Performing the Functions and Duties of the*
*Under Secretary of Commerce for Intellectual Property and*
*Director of the United States Patent and Trademark Office*